United States Patent
Yamamoto et al.

(10) Patent No.: US 10,000,488 B2
(45) Date of Patent: Jun. 19, 2018

(54) HETEROCYCLIC COMPOUND

(71) Applicant: TAKEDA PHARMACEUTICAL COMPANY LIMITED, Osaka (JP)

(72) Inventors: Satoshi Yamamoto, Kanagawa (JP); Junya Shirai, Kanagawa (JP); Tsuneo Oda, Kanagawa (JP); Takashi Imada, Kanagawa (JP); Mitsunori Kono, Kanagawa (JP); Ayumu Sato, Kanagawa (JP); Yoshihide Tomata, Kanagawa (JP); Atsuko Ochida, Kanagawa (JP); Naoki Ishii, Kanagawa (JP); Yusuke Sasaki, Kanagawa (JP); Yoshiyuki Fukase, New York, NY (US); Tomoya Yukawa, Kanagawa (JP); Shoji Fukumoto, Hyogo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days. days.

(21) Appl. No.: 15/510,225

(22) PCT Filed: Sep. 10, 2015

(86) PCT No.: PCT/JP2015/075692
§ 371 (c)(1),
(2) Date: Mar. 9, 2017

(87) PCT Pub. No.: WO2016/039408
PCT Pub. Date: Mar. 17, 2016

(65) Prior Publication Data
US 2017/0253591 A1    Sep. 7, 2017

(30) Foreign Application Priority Data

Sep. 11, 2014   (JP) .................................. 2014-184778

(51) Int. Cl.
| | | |
|---|---|---|
| *C07D 471/04* | (2006.01) | |
| *C07D 401/14* | (2006.01) | |
| *C07D 413/12* | (2006.01) | |
| *C07D 405/12* | (2006.01) | |
| *C07D 405/14* | (2006.01) | |
| *C07D 413/14* | (2006.01) | |
| *C07D 239/96* | (2006.01) | |
| *C07D 409/14* | (2006.01) | |
| *C07D 403/12* | (2006.01) | |
| *C07D 401/12* | (2006.01) | |
| *C07D 417/14* | (2006.01) | |
| *C07D 417/12* | (2006.01) | |

(52) U.S. Cl.
CPC ......... *C07D 471/04* (2013.01); *C07D 239/96* (2013.01); *C07D 401/12* (2013.01); *C07D 401/14* (2013.01); *C07D 403/12* (2013.01); *C07D 405/12* (2013.01); *C07D 405/14* (2013.01); *C07D 409/14* (2013.01); *C07D 413/12* (2013.01); *C07D 413/14* (2013.01); *C07D 417/12* (2013.01); *C07D 417/14* (2013.01)

(58) Field of Classification Search
CPC .................................................... C07D 471/04
See application file for complete search history.

(56) References Cited

U.S. PATENT DOCUMENTS

| | | |
|---|---|---|
| 9,365,520 B2 | 6/2016 | Yamamoto et al. |
| 9,573,903 B2 | 4/2017 | Yamamoto et al. |
| 2002/0193377 A1 | 12/2002 | Andrianjara et al. |

(Continued)

FOREIGN PATENT DOCUMENTS

| | | |
|---|---|---|
| JP | 2004-523546 | 8/2004 |
| WO | 2001/44228 | 6/2001 |

(Continued)

OTHER PUBLICATIONS

Intrnational Search Report and Written Opinion for Application No. PCT/JP2015/075692 dated Oct. 13, 2015 (16 pages).

*Primary Examiner* — Paul V Ward
(74) *Attorney, Agent, or Firm* — Anne M. Reynolds; Casimir Jones, S.C.

(57) ABSTRACT

The problem of the present invention is to provide a compound having a superior RORγt inhibitory action, and useful as a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus, chronic obstructive pulmonary disease or the like. The present invention relates to a compound represented by the formula (I):

(I)

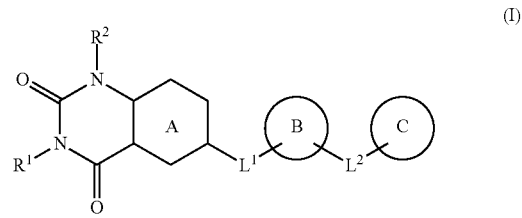

[wherein each symbol is as described in the DESCRIPTION] or a salt thereof, which has an RORγt inhibitory action, and useful as a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus, chronic obstructive pulmonary disease or the like.

13 Claims, No Drawings

(56) References Cited

U.S. PATENT DOCUMENTS

| | | |
|---|---|---|
| 2014/0163001 A1 | 6/2014 | Yamamoto et al. |
| 2014/0228409 A1 | 8/2014 | Yamamoto et al. |
| 2015/0141400 A1 | 5/2015 | Murata et al. |
| 2016/0002169 A1 | 1/2016 | Yamamoto et al. |
| 2016/0176873 A1 | 6/2016 | Yamamoto et al. |
| 2017/0050974 A1 | 2/2017 | Yamamoto et al. |
| 2017/0107240 A1 | 4/2017 | Yamamoto et al. |

FOREIGN PATENT DOCUMENTS

| | | |
|---|---|---|
| WO | 2002/064572 | 8/2002 |
| WO | 2013/018695 | 2/2013 |
| WO | 2013/042782 | 3/2013 |
| WO | 2013/100027 | 7/2013 |
| WO | 2013/161853 | 10/2013 |
| WO | 2014/142255 | 9/2014 |
| WO | 2015/002230 | 1/2015 |
| WO | 2015/002231 | 8/2015 |
| WO | 2016/002968 | 1/2016 |

HETEROCYCLIC COMPOUND

CROSS-REFERENCE TO RELATED APPLICATION(S)

This is a U.S. national stage entry of International Patent Application No. PCT/JP2015/075692, filed on Sep. 10, 2015, which claims priority to Japanese Patent Application No. 2014-184778, filed on Sep. 11, 2014, the entire contents of all of which are fully incorporated herein by reference.

TECHNICAL FIELD

The present invention relates to a heterocyclic compound having an RORγt inhibitory activity, a medicament containing the compound, and the like.

BACKGROUND OF THE INVENTION

Th17 cell and inflammatory cytokines (IL-17A, IL-17F and the like) produced thereby cause a decrease in QOL as a severe etiology cell and factor accompanying enhancement of a systemic new immune response, in various autoimmune diseases such as inflammatory bowel disease (IBD), rheumatoid arthritis, multiple sclerosis and psoriasis. However, the existing therapeutic drugs show only limited effects, and therefore, the earliest possible development of a novel therapeutic drug has been desired.

Involvement of T cells, inter alia, Th17 cell and inflammatory cytokines (IL-17A, IL-17F and the like) produced thereby, in the pathology of these immune diseases has been drawing attention in recent years.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation.

Therefore, a medicament that inhibits the action of RORγt is expected to show a treatment effect on various immune diseases by suppressing differentiation and activation of Th17 cells.

WO 2002/064572A1 (patent document 1) discloses the following compound

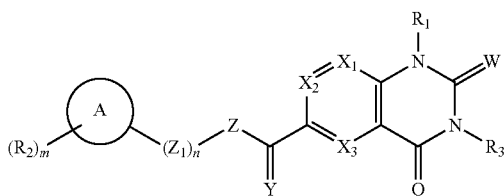

wherein each symbol is as defined in the document, as a compound having MMP-13 inhibitory activity and effective for irritable bowel syndrome (IBS), psoriasis, multiple sclerosis and the like.

WO 2013/042782A1 (patent document 2) discloses the following compound.

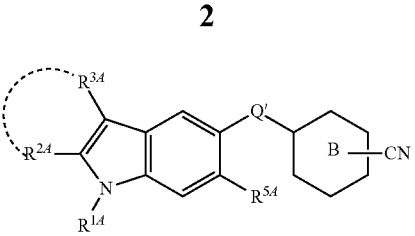

wherein each symbol is as defined in the document, as a compound having RORγt inhibitory activity and effective for inflammatory bowel disease (IBD) and the like.

WO 2013/018695A1 (patent document 3) discloses the following compound

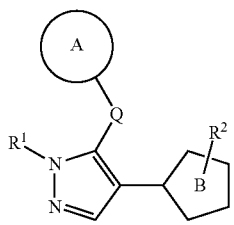

wherein each symbol is as defined in the document, as a compound having RORγt inhibitory activity and effective for inflammatory bowel disease (IBD), ulcerative colitis (UC), Crohn's disease (CD), rheumatoid arthritis, multiple sclerosis, psoriasis and the like.

WO 2013/100027A1 (patent document 4) discloses the following compound

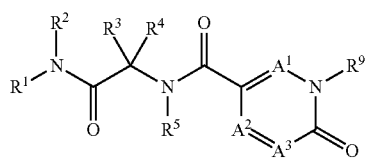

wherein each symbol is as defined in the document, as a compound having RORγt inhibitory activity and effective for inflammatory bowel disease (IBD), ulcerative colitis (UC), Crohn's disease (CD), rheumatoid arthritis, multiple sclerosis, psoriasis and the like.

DOCUMENT LIST

Patent Documents patent document 1: WO 2002/064572A1
patent document 2: WO 2013/042782A1
patent document 3: WO 2013/018695A1
patent document 4: WO 2013/100027A1

SUMMARY OF THE INVENTION

Problems to be Solved by the Invention

The present invention aims to provide a compound having a superior RORγt inhibitory action, and is useful as a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus, chronic obstructive pulmonary disease or the like.

Means of Solving the Problems

The present inventors have found that a compound represented by the following formula (I) or a salt thereof has a superior RORγt inhibitory action based on its specific chemical structure, and shows superior efficacy as a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus, chronic obstructive pulmonary disease or the like. Based on this finding, the present inventors have conducted intensive studies and completed the present invention.

Accordingly, the present invention relates to the following.

[1] A compound represented by the following formula (I):

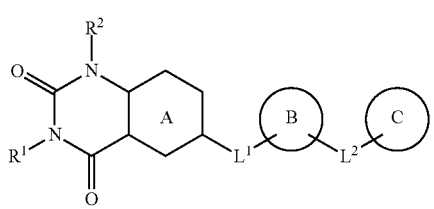

wherein

R$^1$ and R$^2$ are each independently (1) a methyl group substituted by one substituent selected from (a) an optionally substituted C$_{3-6}$ cycloalkyl group and (b) an optionally substituted 5- or 6-membered non-aromatic heterocyclic group, (2) an optionally substituted C$_{2-6}$ alkyl group, or (3) an optionally substituted C$_{2-6}$ alkenyl group;

ring A is an optionally further substituted 6-membered aromatic ring;

L$^1$ is a bond, or a spacer having a main chain having 1-3 atoms;

ring B is a non-aromatic ring optionally further substituted by 1 to 3 substituents selected from: (a) an acyl group, (b) an optionally substituted C$_{1-6}$ alkyl group, (c) an optionally substituted C$_{1-6}$ alkoxy group, (d) a hydroxy group, (e) a halogen atom and (f) an oxo group;

L$^2$ is a bond, or a spacer having a main chain having 1-4 atoms; and ring C is a optionally further substituted ring] or a salt thereof (hereinafter compound (I) sometimes to be referred to as);

[1A] the compound of [1], wherein R$^1$ and R$^2$ are each independently (1) a methyl group substituted by one substituent selected from (a) a C$_{3-6}$ cycloalkyl group optionally substituted by 1 to 3 halogen atoms and (b) a 5- or 6-membered non-aromatic heterocyclic group, (2) a C$_{2-6}$ alkyl group optionally substituted by 1 to 3 substituents selected from a halogen atom, a C$_{1-6}$ alkoxy group and an acyl group, or (3) a C$_{2-6}$ alkenyl group, or a salt thereof;

[2] the compound of [1] above, wherein L$^1$ is a bond, or a spacer having a main chain of 1-2 atoms, or a salt thereof;

[3] the compound of [1] or [2] above, wherein R$^2$ is an optionally substituted C$_{3-6}$ alkyl group or an optionally substituted C$_{3-6}$ alkenyl group, each of which is branched at a carbon atom bonded to a nitrogen atom, or a salt thereof;

[4] the compound of [1] or [2] above, wherein R$^1$ is a C$_{2-6}$ alkyl group optionally substituted by 1 to 3 substituents selected from (1) a methyl group substituted by one substituent selected from (a) a C$_{3-6}$ cycloalkyl group optionally substituted by 1 to 3 halogen atoms and (b) a 5- or 6-membered non-aromatic heterocyclic group, or (2) a halogen atom, a C$_{1-6}$ alkoxy group and a C$_{1-6}$ alkoxy-carbonyl group;

R$^2$ is (1) a methyl group substituted by a C$_{3-6}$ cycloalkyl group, (2) a C$_{2-6}$ alkyl group optionally substituted by 1 to 3 halogen atoms, or (3) a C$_{2-6}$ alkenyl group;

ring A is (1) a benzene ring optionally further substituted by 1 to 3 halogen atoms, or (2) 6-membered aromatic heterocycle;

L$^1$ is a bond, —C(=O)—, —O—C(=O)—, —CH$_2$—C(=O)—, —C(=O)—NH—, or —NH—C(=O)—;

ring B is C$_{3-10}$ cycloalkane or non-aromatic heterocycle, each of which is optionally further substituted by 1 to 3 substituents selected from (a) an acyl group selected from (i) a carboxy group, (ii) a C$_{1-6}$ alkyl-carbonyl group optionally substituted by a carboxy group, (iii) a C$_{1-6}$ alkoxy-carbonyl group optionally substituted by a carboxy group or a C$_{7-16}$ aralkyloxy-carbonyl group, (iv) a C$_{7-16}$ aralkyloxy-carbonyl group, (v) a carbamoyl group and (vi) a C$_{1-6}$ alkyl-sulfonyl group, (b) a C$_{1-6}$ alkyl group optionally substituted by a hydroxy group, (c) a hydroxy group and (d) an oxo group;

L$^2$ is a bond, —O—, —C(=O)—, —CH$_2$—O—, —C(=O)—CH$_2$—, —C(=O)—NH— optionally substituted by a C$_{1-6}$ alkyl group optionally substituted by 1 to 3 halogen atoms, —NH—C(=O)— optionally substituted by a C$_{1-6}$ alkyl group optionally substituted by 1 to 3 halogen atoms, —NH—S(=O)$_2$—, —CH$_2$—C(=O)—NH—, —CH$_2$—NH—C(=O)—, —O—C(=O)—NH—, —NH—C(=O)—NH—, —NH—C(=O)—CH$_2$— optionally substituted by a hydroxy group, —CH$_2$—NH—CH$_2$— optionally substituted by a C$_{1-6}$ alkyl group optionally substituted by 1 to 3 halogen atoms, —NH—C(=O)—CH$_2$—CH$_2$— or —CH$_2$—NH—C(=O)—NH—; and ring C is a C$_{6-14}$ aromatic hydrocarbon ring, a 5- or 6-membered monocyclic aromatic heterocycle, a 8- to 14-membered fused polycyclic aromatic heterocycle, a 3- to 8-membered monocyclic non-aromatic heterocycle or a 9- to 14-membered fused polycyclic non-aromatic heterocycle, each of which is optionally further substituted by 1 to 3 substituents selected from (1) a cyano group, (2) a hydroxy group, (3) an oxo group, (4) a halogen atom, (5) a C$_{1-6}$ alkyl group optionally substituted by 1 to 3 substituents selected from a cyano group, a hydroxy group, a halogen atom, a C$_{1-6}$ alkoxy group, an amino group, a C$_{1-6}$ alkoxy-carbonylamino group, a C$_{1-6}$ alkyl-carbonylamino group optionally substituted by a halogen atom, a C$_{2-6}$ alkenyl-carbonylamino group and a C$_{1-6}$ alkyl-aminocarbonyloxy group, (6) a C$_{2-6}$ alkenyl group optionally substituted by a C$_{1-6}$ alkyl-carbonyl group, (7) a C$_{3-6}$ cycloalkyl group, (8) a C$_{6-14}$ aryl group, (9) a C$_{1-6}$ alkoxy group optionally substituted by 1 to 3 substituents selected from a halogen atom and a C$_{1-6}$ alkoxy group, (10) a C$_{1-6}$ alkyl-carbonyl group, (11) a carboxy group, (12) a C$_{2-6}$ alkenyl-carbonyl group, (13) a C$_{1-6}$ alkoxy-carbonyl group, (14) a carbamoyl group, (15) an amino group, (16) a C$_{1-6}$ alkyl-carbonylamino group optionally substituted by a halogen atom, (17) a $C_{1-6}$ alkoxy-carbonylamino group, (18) a $C_{1-6}$ alkyl-sulfonyl group, (19) a $C_{2-6}$ alkenyl-carbonylamino group optionally substituted by a mono- or di-$C_{1-6}$ alkylamino group, (20) a $C_{2-6}$ alkenyl-sulfonylamino group and (21) a 3- to 8-membered monocyclic non-aromatic heterocycle; or a salt thereof;

[5] the compound of [1] or [2] above, wherein
$R^1$ is a methyl group substituted by one substituent selected from (a) a $C_{3-6}$ cycloalkyl group optionally substituted by 1 to 3 halogen atoms and (b) a 5- or 6-membered non-aromatic heterocyclic group;
$R^2$ is a $C_{2-6}$ alkyl group;
ring A is a benzene ring optionally further substituted by 1 to 3 halogen atoms;
$L^1$ is —NH—C(=O)—;
ring B is a $C_{3-10}$ cycloalkane or a 3- to 8-membered monocyclic non-aromatic heterocycle;
$L^2$ is a bond, —C(=O)—NH—, —NH—C(=O)— or —NH—C(=O)—NH—; and
ring C is a $C_{6-14}$ aromatic hydrocarbon ring, a 5- or 6-membered monocyclic aromatic heterocycle, a 8- to 14-membered fused polycyclic aromatic heterocycle or a 9- to 14-membered fused polycyclic non-aromatic heterocycle, each of which is optionally further substituted by 1 to 3 substituents selected from (1) a cyano group, (2) an oxo group, (3) a halogen atom, (4) a $C_{1-6}$ alkyl group optionally substituted by 1 to 3 substituents selected from a $C_{1-6}$ alkoxy-carbonylamino group and a $C_{1-6}$ alkyl-aminocarbonyloxy group, (5) a $C_{1-6}$ alkoxy group and (6) a $C_{1-6}$ alkoxy-carbonyl group;
or a salt thereof;

[6] (2R)—$N^2$-(3-chloro-4-cyanophenyl)-$N^4$-(3-(cyclopropylmethyl)-7-fluoro-1-isopropyl-2,4-dioxo-1,2,3,4-tetrahydroquinazolin-6-yl)morpholine-2,4-dicarboxamide or a salt thereof;

[7] (3R)-3-(7-cyano-4-oxoquinazolin-3(4H)-yl)-N-(3-(cyclopropylmethyl)-7-fluoro-1-isopropyl-2,4-dioxo-1,2,3,4-tetrahydroquinazolin-6-yl)piperidine-1-carboxamide or a salt thereof;

[8] 4-cyano-N-((1S,2R)-2-((3-(cyclopropylmethyl)-1-isopropyl-2,4-dioxo-1,2,3,4-tetrahydroquinazolin-6-yl)carbamoyl)cyclopentyl)benzamide or a salt thereof;

[9] a medicament comprising the compound of [1] or [2] above, or a salt thereof;

[10] the medicament of [9] above, which is an RORγt inhibitor;

[11] the medicament of [9] above, which is a prophylactic or therapeutic drug of psoriasis, inflammatory bowel disease, ulcerative colitis, Crohn's disease, rheumatoid arthritis, multiple sclerosis, uveitis, asthma, ankylopoietic spondylarthritis, systemic lupus erythematosus or chronic obstructive pulmonary disease;

[12] a method of inhibiting RORγt, comprising administering an effective amount of the compound of [1] or [2] above or a salt thereof to a mammal;

[13] a method for the prophylaxis or treatment of psoriasis, inflammatory bowel disease, ulcerative colitis, Crohn's disease, rheumatoid arthritis, multiple sclerosis, uveitis, asthma, ankylopoietic spondylarthritis, systemic lupus erythematosus or chronic obstructive pulmonary disease, comprising administering an effective amount of the compound of [1] or [2] above or a salt thereof to a mammal;

[14] use of the compound of [1] or [2] above or a salt thereof in the production of a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus or chronic obstructive pulmonary disease a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus or chronic obstructive pulmonary disease;

[15] the compound of [1] or [2] above or a salt thereof for use in the prophylaxis or treatment of psoriasis, inflammatory bowel disease, ulcerative colitis, Crohn's disease, rheumatoid arthritis, multiple sclerosis, uveitis, asthma, ankylopoietic spondylarthritis, systemic lupus erythematosus or chronic obstructive pulmonary disease.

Effect of the Invention

The compound of the present invention has a superior RORγt inhibitory action, and is useful as a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus, chronic obstructive pulmonary disease or the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),

(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclyl-sulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents of the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5-to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constitution atom.

In the present specification, examples of the "optionally substituted heterocyclic group" include a heterocyclic group optionally having substituent(s) selected from the aforementioned substituent group A.

The number of the substituents of the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbonsulfonyl group, a heterocyclyl-sulfonyl group, a hydrocarbon-sulfinyl group and a heterocyclyl-sulfinyl group.

Here, the hydrocarbon-sulfonyl group means a hydrocarbon group-bonded sulfonyl group, the heterocyclyl-sulfonyl group means a heterocyclic group-bonded sulfonyl group, the hydrocarbon-sulfinyl group means a hydrocarbon group-bonded sulfinyl group and the heterocyclyl-sulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., alkylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and a 8- to 14-membered fused polycyclic (preferably bi or tricyclic) aromatic heterocycle such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include a 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, as the "ring" of the "optionally substituted ring", the above-mentioned "hydrocarbon ring" and "heterocycle" can be mentioned and, as the substituent thereof, the above-mentioned "substituent" can be mentioned.

In the present specification, as the "6-membered aromatic ring" of the "optionally further substituted 6-membered aromatic ring", benzene ring and the above-mentioned 6-membered "aromatic heterocycle" can be mentioned, and as the substituent thereof, the above-mentioned "substituent" can be mentioned.

In the present specification, as the "non-aromatic ring", the above-mentioned "$C_{3-10}$ cycloalkane", "$C_{3-10}$ cycloalkene" and "non-aromatic heterocycle" can be mentioned.

The definition of each symbol in the formula (I) is described in detail below.

$R^1$ is (1) a methyl group substituted by one substituent selected from (a) an optionally substituted $C_{3-6}$ cycloalkyl group and (b) an optionally substituted 5- or 6-membered non-aromatic heterocyclic group, (2) an optionally substituted $C_{2-6}$ alkyl group, or (3) an optionally substituted $C_{2-6}$ alkenyl group.

As the "substituent" of the above-mentioned "(1) (a) optionally substituted $C_{3-6}$ cycloalkyl group", a halogen atom (e.g., fluorine atom) can be mentioned.

As the "substituent" of the above-mentioned "(2) optionally substituted $C_{2-6}$ alkyl group", a halogen atom (e.g., fluorine atom), a $C_{1-6}$ alkoxy group (e.g., methoxy), and a $C_{1-6}$ alkoxy-carbonyl group (e.g., tert-butoxycarbonyl) can be mentioned.

$R^1$ is preferably (1) a methyl group substituted by one substituent selected from (a) an optionally substituted $C_{3-6}$ cycloalkyl group (e.g., cyclopropyl, cyclobutyl) and (b) an optionally substituted 5- or 6-membered non-aromatic heterocyclic group (e.g., tetrahydrofuryl) or (2) an optionally substituted $C_{2-6}$ alkyl group (e.g., ethyl), more preferably, (1) a methyl group substituted by one substituent selected from (a) a $C_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl) or (2) a $C_{2-6}$ alkyl group (e.g., ethyl) optionally substituted by 1 to 3 substituents selected from a halogen atom (e.g., fluorine atom), a $C_{1-6}$ alkoxy group (e.g., methoxy) and a $C_{1-6}$ alkoxy-carbonyl group (e.g., tert-butoxycarbonyl).

$R^1$ is particularly preferably a methyl group substituted by one substituent selected from (a) a $C_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl).

$R^2$ is (1) a methyl group substituted by one substituent selected from (a) an optionally substituted $C_{3-6}$ cycloalkyl group and (b) an optionally substituted 5- or 6-membered non-aromatic heterocyclic group, (2) an optionally substituted $C_{2-6}$ alkyl group, or (3) an optionally substituted $C_{2-6}$ alkenyl group.

As the "substituent" of the above-mentioned "(2) optionally substituted $C_{2-6}$ alkyl group", a halogen atom (e.g., fluorine atom) can be mentioned.

$R^2$ is preferably (1) a methyl group substituted by an optionally substituted $C_{3-6}$ cycloalkyl group (e.g., cyclopropyl, cyclobutyl), (2) an optionally substituted $C_{2-6}$ alkyl group (e.g., ethyl, isopropyl, isobutyl, 1-methylpropyl, isopentyl, neopentyl), or (3) an optionally substituted $C_{2-6}$ alkenyl group (e.g., 3-methylbut-2-en-1-yl), more preferably, (1) a methyl group substituted by a $C_{3-6}$ cycloalkyl group (e.g., cyclopropyl, cyclobutyl), (2) a $C_{2-6}$ alkyl group (e.g., ethyl, isopropyl, isobutyl, 1-methylpropyl, isopentyl, neopentyl) optionally substituted by 1 to 3 halogen atoms (e.g., fluorine atom), or (3) a $C_{2-6}$ alkenyl group (e.g., 3-methylbut-2-en-1-yl).

$R^2$ is particularly preferably a $C_{2-6}$ alkyl group (e.g., isopropyl).

In another preferable embodiment, $R^2$ is an optionally substituted $C_{3-6}$ alkyl group (e.g., isopropyl, 1-methylpropyl) or an optionally substituted $C_{3-6}$ alkenyl group, each of which is branched at carbon atom bonded to nitrogen atom, particularly preferably, $R^2$ is a $C_{3-6}$ alkyl group (e.g., isopropyl) optionally substituted by 1 to 3 halogen atoms (e.g., fluorine atom).

Ring A is a further optionally substituted 6-membered aromatic ring.

As the "6-membered aromatic ring" of the "further optionally substituted 6-membered aromatic ring" for ring A, a benzene ring and a 6-membered aromatic heterocycle (e.g., a pyridine ring) can be mentioned.

The "further optionally substituted 6-membered aromatic ring" for ring A is optionally further substituted by 1-3 (preferably 1-2, more preferably 1) substituent other than a group: -$L^1$-ring B-$L^2$-ring C at substitutable position(s). As such "substituent", a halogen atom (e.g., fluorine atom) can be mentioned.

Ring A is preferably a benzene ring or a 6-membered aromatic heterocycle (e.g., a pyridine ring), each of which is optionally further substituted by 1 to 3 halogen atoms (e.g., fluorine atom), more preferably, (1) a benzene ring optionally further substituted by 1 to 3 halogen atoms (e.g., fluorine atom), or (2) a 6-membered aromatic heterocycle (e.g., a pyridine ring).

Ring A is particularly preferably a benzene ring optionally further substituted by 1 to 3 halogen atoms (e.g., fluorine atom).

$L^1$ is a bond, or a spacer having a main chain of 1-3 atoms.

The "spacer having a main chain of 1-3 atoms" for $L^1$ is a divalent group shown by —$X^1$—$X^2$—$X^3$—, $X^1$, $X^2$ and $X^3$ are each independently selected from a bond, —CH$_2$—, —O—, —C(=O)— and —NH— (provided that $X^1$, $X^2$ and $X^3$ are not each a bond at the same time).

—CH$_2$— and —NH— shown by $X^1$, $X^2$ or $X^3$ are optionally substituted. As such substituent, a hydroxy group and a $C_{1-6}$ alkyl group (e.g., methyl) optionally substituted by 1 to 3 halogen atoms (e.g., fluorine atom) can be mentioned.

$L^1$ is preferably a bond, —C(=O)—, —O—C(=O)—, optionally substituted —CH$_2$—C(=O)—, optionally substituted —C(=O)—NH—, optionally substituted —NH—C(=O)—, optionally substituted —NH—C(=O)—CH$_2$— or optionally substituted —C(=O)—NH—CH$_2$—, more preferably, a bond, —C(=O)—, —O—C(=O)—, —CH$_2$—C(=O)—, —C(=O)—NH—, —NH—C(=O)—, —NH—C(=O)—CH$_2$— or —C(=O)—NH—CH$_2$—.

$L^1$ is particularly preferably —NH—C(=O)—.

In another preferable embodiment, $L^1$ is a spacer having a main chain of 1-2 atoms, more preferably a spacer having a main chain of 2 atoms, particularly preferably —NH—C(=O)—.

In still another preferable embodiment, $L^1$ is a bond or a spacer having a main chain of 1-2 atoms, more preferably a bond or —C(=O)—, —O—C(=O)—, —CH$_2$—C(=O)—, —C(=O)—NH—, or —NH—C(=O)—, particularly preferably —NH—C(=O)—.

Ring B is a non-aromatic ring optionally further substituted by 1 to 3 substituents selected from the following: (a) an acyl group, (b) an optionally substituted $C_{1-6}$ alkyl group, (c) an optionally substituted $C_{1-6}$ alkoxy group, (d) a hydroxy group, (e) a halogen atom and (f) an oxo group.

As the "non-aromatic ring" of the "non-aromatic ring optionally further substituted by 1 to 3 substituents selected from the following" for ring B, $C_{3-10}$ cycloalkane (e.g., cyclopropane, cyclopentane, cyclohexane), non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring) can be mentioned.

Ring B is optionally further substituted by 1 to 3 (preferably 1-2, more preferably 1) substituents selected from the above-mentioned (a)-(f), other than groups: -$L^1$-ring A and -$L^2$-ring C, at substitutable position(s).

As the above-mentioned "(a) acyl group", a carboxy group, an optionally substituted $C_{1-6}$ alkyl-carbonyl group, an optionally substituted $C_{1-6}$ alkoxy-carbonyl group, an optionally substituted $C_{7-16}$ aralkyloxy-carbonyl group, a carbamoyl group, and a $C_{1-6}$ alkyl-sulfonyl group can be mentioned.

Ring B is preferably a $C_{3-10}$ cycloalkane (e.g., cyclopropane, cyclopentane, cyclohexane) or a non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally further substituted by 1 to 3 substituents selected from (a) an acyl group selected from (i) a carboxy group, (ii) an optionally substituted $C_{1-6}$ alkyl-carbonyl group (e.g., methylcarbonyl, propylcarbonyl), (iii) an optionally substituted $C_{1-6}$ alkoxy-carbonyl group (e.g., methoxycarbonyl, tert-butoxycarbonyl), (iv) an optionally substituted $C_{7-16}$ aralkyloxy-carbonyl group (e.g., benzyloxycarbonyl), (v) a carbamoyl group and (vi) a $C_{1-6}$ alkyl-sulfonyl group (e.g., methylsulfonyl), (b) an optionally substituted $C_{1-6}$ alkyl group (e.g., methyl), (c) a hydroxy group and (d) an oxo group, more preferably a $C_{3-10}$ cycloalkane (e.g., cyclopropane, cyclopentane, cyclohexane) or a non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally further substituted by 1 to 3 substituents selected from (a) (i) a carboxy group, (ii) a $C_{1-6}$ alkyl-carbonyl group (e.g., methylcarbonyl, propylcarbonyl) optionally substituted by a carboxy group, (iii) a $C_{1-6}$ alkoxy-carbonyl group (e.g., methoxycarbonyl, tert-butoxycarbonyl) optionally substituted by a carboxy group or a $C_{7-16}$ aralkyloxy-carbonyl group (e.g., benzyloxycarbonyl), (iv) a $C_{7-16}$ aralkyloxy-carbonyl group (e.g., benzyloxycarbonyl), (v) a carbamoyl group or (vi) a $C_{1-6}$ alkyl-sulfonyl group (e.g., methylsulfonyl), (b) a $C_{1-6}$ alkyl group (e.g., methyl) optionally substituted by a hydroxy group, (c) a hydroxy group and (e) an oxo group.

Ring B is particularly preferably $C_{3-10}$ cycloalkane (e.g., cyclopentane) or non-aromatic heterocycle (preferably, 3- to 8-membered monocyclic non-aromatic heterocycle, such as piperidine ring, piperazine ring, a morpholine ring, thiomorpholine ring).

$L^2$ is a bond, or a spacer having a main chain having 1-4 atoms.

The "spacer having a main chain having 1-4 atoms" for $L^2$ is a divalent group shown by —$Y^1$—$Y^2$—$Y^3$—$Y^4$—, and $Y^1$, $Y^2$, $Y^3$ and $Y^4$ are each independently selected from a bond, —$CH_2$—, —O—, —C(=O)—, —NH— and —S(=O)$_2$— (provided that $Y^1$, $Y^2$, $Y^3$ and $Y^4$ are not each a bond at the same time).

—$CH_2$— and —NH— shown by $Y^1$, $Y^2$, $Y^3$ or $Y^4$ are optionally substituted. As such substituent, a hydroxy group, and a $C_{1-6}$ alkyl group (e.g., methyl) optionally substituted by 1 to 3 halogen atoms (e.g., fluorine atom) can be mentioned.

$L^2$ is preferably a bond, —O—, —C(=O)—, optionally substituted —$CH_2$—O—, optionally substituted —C(=O)—$CH_2$—, optionally substituted —C(=O)—NH—, optionally substituted —NH—C(=O)—, optionally substituted —NH—S(=O)$_2$—, optionally substituted —$CH_2$—C(=O)—NH—, optionally substituted —$CH_2$—NH—C(=O)—, optionally substituted —O—C(=O)—NH—, optionally substituted —NH—C(=O)—NH—, optionally substituted —NH—C(=O)—$CH_2$—, optionally substituted —$CH_2$—NH—$CH_2$—, optionally substituted —NH—C(=O)—$CH_2$—$CH_2$— or optionally substituted —$CH_2$—NH—C(=O)—NH—, more preferably a bond, —O—, —C(=O)—, —$CH_2$—O—, —C(=O)—$CH_2$—, —C(=O)—NH— (e.g., —C(=O)—NH—, —C(=O)—N(CH$_3$)—) optionally substituted by a $C_{1-6}$ alkyl group (e.g., methyl) optionally substituted by 1 to 3 halogen atoms (e.g., fluorine atom), —NH—C(=O)— (e.g., —NH—C(=O)—, —N(CH$_3$)—C(=O)—) optionally substituted by a $C_{1-6}$ alkyl group (e.g., methyl) optionally substituted by 1 to 3 halogen atoms (e.g., fluorine atom), —NH—S(=O)$_2$—, —$CH_2$—C(=O)—NH—, —$CH_2$—NH—C(=O)—, —O—C(=O)—NH—, —NH—C(=O)—NH—, —NH—C(=O)—$CH_2$— (e.g., —NH—C(=O)—$CH_2$—, —NH—C(=O)—CH(OH)—) optionally by a hydroxy group optionally substituted by a hydroxy group, —$CH_2$—NH—$CH_2$— (e.g., —$CH_2$—NH—CH(CF$_3$)—) optionally substituted by a $C_{1-6}$ alkyl group (e.g., methyl) optionally substituted by 1 to 3 halogen atoms (e.g., fluorine atom), —NH—C(=O)—$CH_2$—$CH_2$— or —$CH_2$—NH—C(=O)—NH—.

$L^2$ is particularly preferably a bond, —C(=O)—NH—, —NH—C(=O)— or —NH—C(=O)—NH—.

One end of $L^1$ and $L^2$ substitutes ring B at a substitutable position. Therefore, one end of $L^1$ and $L^2$ optionally substitutes the same atom or optionally substitutes different atoms on ring B.

Ring C is a ring optionally further substituted.

As the "ring" of the "optionally substituted ring" for ring C, a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring), and a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring) can be mentioned.

The "ring" of the "optionally further substituted ring" for ring C is optionally further substituted by 1-3 (preferably 1-2, more preferably 1) substituents other than a group: -$L^2$-ring B-$L^1$-ring A at substitutable position(s).

As such "substituent", a cyano group, a hydroxy group, an oxo group, a halogen atom (e.g., fluorine atom, chlorine atom, bromine atom), an optionally substituted $C_{1-6}$ alkyl group (e.g., methyl, ethyl), an optionally substituted $C_{2-6}$ alkenyl group (e.g., vinyl), a $C_{3-6}$ cycloalkyl group (e.g., cyclopropyl), $C_{6-14}$ aryl group (e.g., phenyl), an optionally substituted $C_{1-6}$ alkoxy group (e.g., methoxy, ethoxy), a $C_{1-6}$ alkyl-carbonyl group (e.g., methylcarbonyl), a carboxy group, a $C_{2-6}$ alkenyl-carbonyl group (e.g., vinylcarbonyl), a $C_{1-6}$ alkoxy-carbonyl group (e.g., methoxycarbonyl, ethoxycarbonyl, tert-butoxycarbonyl), a carbamoyl group, an amino group, an optionally substituted $C_{1-6}$ alkyl-carbonylamino group (e.g., methylcarbonylamino, ethylcarbonylamino), a $C_{1-6}$ alkoxy-carbonylamino group (e.g., tert-butoxycarbonylamino), a $C_{1-6}$ alkyl-sulfonyl group (e.g., methylsulfonyl), an optionally substituted $C_{2-6}$ alkenyl-carbonylamino group (e.g., vinylcarbonylamino, 1-propenylcarbonylamino), a $C_{2-6}$ alkenyl-sulfonylamino group (e.g., vinylsulfonylamino), and a 3- to 8-membered monocyclic non-aromatic heterocycle (e.g., oxiranyl) can be mentioned.

Ring C is preferably a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) an optionally substituted $C_{1-6}$ alkyl group (e.g., methyl, ethyl), (6) an optionally substituted $C_{2-6}$ alkenyl group (e.g., vinyl), (7) a $C_{3-6}$ cycloalkyl group (e.g., cyclopropyl), (8) a $C_{6-14}$ aryl group (e.g., phenyl), (9) an optionally substituted $C_{1-6}$ alkoxy group (e.g., methoxy, ethoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) an optionally substituted $C_{1-6}$ alkyl-carbonylamino group (e.g., methylcarbonylamino, ethylcarbonylamino), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) an optionally substituted $C_{2-6}$ alkenyl-carbonylamino group (e.g., vinylcarbonylamino, 1-propenylcarbonylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

Ring C is more preferably a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3-to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) a $C_{1-6}$ alkyl group (e.g., methyl, ethyl) optionally substituted by 1 to 3 substituents selected from a cyano group, a hydroxy group, a halogen atom (e.g., fluorine atom, bromine atom), a $C_{1-6}$ alkoxy group (e.g., methoxy), an amino group, a $C_{1-6}$ alkoxy-carbonylamino group (e.g., methoxycarbonylamino, tert-butoxycarbonylamino), a $C_{1-6}$ alkyl-carbonylamino group (e.g., methylcarbonylamino) optionally substituted by a halogen atom (e.g., chlorine atom), a $C_{2-6}$ alkenyl-carbonylamino group (e.g., vinylcarbonylamino) and a $C_{1-6}$ alkyl-aminocarbonyloxy group (e.g., ethylaminocarbonyloxy), (6) a $C_{2-6}$ alkenyl group (e.g., vinyl) optionally substituted by a $C_{1-6}$ alkyl-carbonyl group (e.g., methylcarbonyl), (7) a $C_{3-6}$ cycloalkyl group (e.g., cyclopropyl), (8) a $C_{6-14}$ aryl group (e.g., phenyl), (9) a $C_{1-6}$ alkoxy group (e.g., methoxy, ethoxy) optionally substituted by 1 to 3 substituents selected from a halogen atom (e.g., fluorine atom) and a $C_{1-6}$ alkoxy group (e.g., methoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) a $C_{1-6}$ alkyl-carbonylamino group (e.g., methylcarbonylamino, ethylcarbonylamino) optionally substituted by a halogen atom (e.g., chlorine atom), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) a $C_{2-6}$ alkenyl-carbonylamino group (e.g., vinylcarbonylamino, 1-propenylcarbonylamino) optionally substituted by a mono- or di-$C_{1-6}$ alkylamino group (e.g., dimethylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

Ring C is particularly preferably a $C_{6-14}$ aromatic hydrocarbon ring (e.g., benzene ring), a 5- or 6-membered monocyclic aromatic heterocycle (e.g., thiophene ring, pyridine ring), a 8- to 14-membered fused polycyclic (preferably bi- or tricyclic) aromatic heterocycle (e.g., benzoxazole ring, quinazoline ring) or a 9- to 14-membered fused polycyclic (preferably bi- or tricyclic) non-aromatic heterocycle (e.g., dihydroisoindole ring, dihydrobenzofuran ring, tetrahydroisoquinoline ring), each of which is optionally substituted by 1 to 3 substituents selected from (1) a cyano group, (2) an oxo group, (3) a halogen atom (e.g., fluorine atom, chlorine atom), (4) a $C_{1-6}$ alkyl group (e.g., methyl) optionally substituted by 1 to 3 substituents selected from a $C_{1-6}$ alkoxy-carbonylamino group (e.g., methoxycarbonylamino, tert-butoxycarbonylamino) and a $C_{1-6}$ alkyl-aminocarbonyloxy group (e.g., ethylaminocarbonyloxy), (5) a $C_{1-6}$ alkoxy group (e.g., methoxy) and (6) a $C_{1-6}$ alkoxy-carbonyl group (e.g., methoxycarbonyl, tert-butoxycarbonyl).

Preferable examples of compound (I) include the following compounds.

[Compound I-1]

Compound (I) wherein $R^1$ is (1) a methyl group substituted by one substituent selected from (a) an optionally substituted $C_{3-6}$ cycloalkyl group (e.g., cyclopropyl, cyclobutyl) and (b) an optionally substituted 5- or 6-membered non-aromatic heterocyclic group (e.g., tetrahydrofuryl), or (2) an optionally substituted $C_{2-6}$ alkyl group (e.g., ethyl);

$R^2$ is (1) a methyl group substituted by an optionally substituted $C_{3-6}$ cycloalkyl group (e.g., cyclopropyl, cyclobutyl), (2) an optionally substituted $C_{2-6}$ alkyl group (e.g., ethyl, isopropyl, isobutyl, 1-methylpropyl, isopentyl, neopentyl), or (3) an optionally substituted $C_{2-6}$ alkenyl group (e.g., 3-methylbut-2-en-1-yl);

ring A is a benzene ring or a 6-membered aromatic heterocycle (e.g., pyridine ring), each of which is optionally further substituted by 1 to 3 halogen atoms (e.g., fluorine atom);

$L^1$ is a bond, —C(=O)—, —O—C(=O)—, optionally substituted —CH₂—C(=O)—, optionally substituted —C(=O)—NH—, optionally substituted —NH—C(=O)—, optionally substituted —NH—C(=O)—CH₂— or optionally substituted —C(=O)—NH—CH₂—;

ring B is $C_{3-10}$ cycloalkane (e.g., cyclopropane, cyclopentane, cyclohexane) or non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally substituted by 1 to 3 substituents selected from (a) an acyl group selected from (i) a carboxy group, (ii) an optionally substituted $C_{1-6}$ alkyl-carbonyl group (e.g., methylcarbonyl, propylcarbonyl), (iii) an optionally substituted $C_{1-6}$ alkoxy-carbonyl group (e.g., methoxycarbonyl, tert-butoxycarbonyl), (iv) an optionally substituted $C_{7-16}$ aralkyloxy-carbonyl group (e.g., benzyloxycarbonyl), (v) a carbamoyl group and (vi) a $C_{1-6}$ alkyl-sulfonyl group (e.g., methylsulfonyl), (b) an optionally substituted $C_{1-6}$ alkyl group (e.g., methyl), (c) a hydroxy group and (d) an oxo group;

$L^2$ is a bond, —O—, —C(=O)—, optionally substituted —CH$_2$—O—, optionally substituted —C(=O)—CH$_2$—, optionally substituted —C(=O)—NH—, optionally substituted —NH—C(=O)—, optionally substituted —NH—S(=O)$_2$—, optionally substituted —CH$_2$—C(=O)—NH—, optionally substituted —CH$_2$—NH—C(=O)—, optionally substituted —O—C(=O)—NH—, optionally substituted —NH—C(=O)—NH—, optionally substituted —NH—C(=O)—CH$_2$—, optionally substituted —CH$_2$—NH—CH$_2$—, optionally substituted —NH—C(=O)—CH$_2$—CH$_2$— or optionally substituted —CH$_2$—NH—C(=O)—NH—; and ring C is a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, a pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) an optionally substituted $C_{1-6}$ alkyl group (e.g., methyl, ethyl), (6) an optionally substituted $C_{2-6}$ alkenyl group (e.g., vinyl), (7) a $C_{3-6}$ cycloalkyl group (e.g., cyclopropyl), (8) a $C_{6-14}$ aryl group (e.g., phenyl), (9) an optionally substituted $C_{1-6}$ alkoxy group (e.g., methoxy, ethoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) an optionally substituted $C_{1-6}$ alkyl-carbonylamino group (e.g., methylcarbonylamino, ethylcarbonylamino), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) an optionally substituted $C_{2-6}$ alkenyl-carbonylamino group (e.g., vinylcarbonylamino, 1-propenylcarbonylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

[Compound I-2]

Compound (I) wherein $R^1$ is (1) a methyl group substituted by one substituent selected from (a) a $C_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl), or (2) a $C_{2-6}$ alkyl group (e.g., ethyl) optionally substituted by 1 to 3 substituents selected from a halogen atom (e.g., fluorine atom), a $C_{1-6}$ alkoxy group (e.g., methoxy) and a $C_{1-6}$ alkoxy-carbonyl group (e.g., tert-butoxycarbonyl);

$R^2$ is (1) a methyl group substituted by a $C_{3-6}$ cycloalkyl group (e.g., cyclopropyl, cyclobutyl), (2) a $C_{2-6}$ alkyl group (e.g., ethyl, isopropyl, isobutyl, 1-methylpropyl, isopentyl, neopentyl) optionally substituted by 1 to 3 halogen atoms (e.g., fluorine atom), or (3) a $C_{2-6}$ alkenyl group (e.g., 3-methylbut-2-en-1-yl);

ring A is (1) a benzene ring optionally further substituted by 1 to 3 halogen atoms (e.g., fluorine atom), or (2) a 6-membered aromatic heterocycle (e.g., a pyridine ring);

$L^1$ is a bond, —C(=O)—, —O—C(=O)—, —CH$_2$—C(=O)—, —C(=O)—NH—, —NH—C(=O)—, —NH—C(=O)—CH$_2$— or —C(=O)—NH—CH$_2$—;

ring B is a $C_{3-10}$ cycloalkane (e.g., cyclopropane, cyclopentane, cyclohexane) or a non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally substituted by 1 to 3 substituents selected from (a) an acyl group selected from (i) a carboxy group, (ii) a $C_{1-6}$ alkyl-carbonyl group (e.g., methylcarbonyl, propylcarbonyl) optionally substituted by a carboxy group, (iii) a $C_{1-6}$ alkoxy-carbonyl group (e.g., methoxycarbonyl, tert-butoxycarbonyl) optionally substituted by a carboxy group or a $C_{7-16}$ aralkyloxy-carbonyl group (e.g., benzyloxycarbonyl), (iv) a $C_{7-16}$ aralkyloxy-carbonyl group (e.g., benzyloxycarbonyl), (v) a carbamoyl group and (vi) a $C_{1-6}$ alkyl-sulfonyl group (e.g., methylsulfonyl), (b) a $C_{1-6}$ alkyl group (e.g., methyl) optionally substituted by a hydroxy group, (c) a hydroxy group and (d) an oxo group;

$L^2$ is a bond, —O—, —C(=O)—, —CH$_2$—O—, —C(=O)—CH$_2$—, —C(=O)—NH— (e.g., —C(=O)—NH—, —C(=O)—N(CH$_3$)—) optionally substituted by a $C_{1-6}$ alkyl group (e.g., methyl) optionally substituted by 1 to 3 halogen atoms (e.g., fluorine atom), —NH—C(=O)— (e.g., —NH—C(=O)—, —N(CH$_3$)—C(=O)—) optionally substituted by a $C_{1-6}$ alkyl group (e.g., methyl) optionally substituted by 1 to 3 halogen atoms (e.g., fluorine atom), —NH—S(=O)$_2$—, —CH$_2$—C(=O)—NH—, —CH$_2$—NH—C(=O)—, —O—C(=O)—NH—, —NH—C(=O)—NH—, —NH—C(=O)—CH$_2$— (e.g., —NH—C(=O)—CH$_2$—, —NH—C(=O)—CH(OH)—) optionally substituted by a hydroxy group, —CH$_2$—NH—CH$_2$— (e.g., —CH$_2$—NH—CH(CF$_3$)—) optionally substituted by a $C_{1-6}$ alkyl group (e.g., methyl) optionally substituted by 1 to 3 halogen atoms (e.g., fluorine atom), —NH—C(=O)—CH$_2$—CH$_2$— or —CH$_2$—NH—C(=O)—NH—; and ring C is a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, a pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) a $C_{1-6}$ alkyl group (e.g., methyl, ethyl) optionally substituted by 1 to 3 substituents selected from a cyano group, a hydroxy group, a halogen atom (e.g., fluorine atom, bromine atom), a $C_{1-6}$ alkoxy group (e.g., methoxy), an amino group, a $C_{1-6}$ alkoxy-carbonylamino group (e.g., methoxycarbonylamino, tert-butoxycarbonylamino), a $C_{1-6}$ alkyl-carbonylamino group (e.g., methylcarbonylamino) optionally substituted by a halogen atom (e.g., chlorine atom), a $C_{2-6}$ alkenyl-carbonylamino group (e.g., vinylcarbonylamino) and a $C_{1-6}$ alkyl-aminocarbonyloxy group (e.g., ethylaminocarbonyloxy), (6) a $C_{2-6}$ alkenyl group (e.g., vinyl) optionally substituted by a $C_{1-6}$ alkyl-carbonyl group (e.g., methylcarbonyl), (7) a $C_{3-6}$ cycloalkyl group (e.g., cyclopropyl), (8) a $C_{6-14}$ aryl group (e.g., phenyl), (9) a $C_{1-6}$ alkoxy group (e.g., methoxy, ethoxy) optionally substituted by 1 to 3 substituents selected from a halogen atom (e.g., fluorine atom) and a $C_{1-6}$ alkoxy group (e.g., methoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) a $C_{1-6}$ alkyl-carbonylamino group (e.g., methylcarbonylamino, ethylcarbonylamino) optionally substituted by a halogen atom (e.g., chlorine atom), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) a $C_{2-6}$ alkenyl-carbonylamino group (e.g., vinylcarbonylamino, 1-propenylcarbonylamino) optionally substituted by a mono- or di-$C_{1-6}$ alkylamino group (e.g., dimethylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

[Compound I-3]

Compound (I) wherein $R^1$ is a methyl group substituted by one substituent selected from (a) a $C_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl);

$R^2$ is a $C_{2-6}$ alkyl group (e.g., isopropyl);

ring A is a benzene ring optionally further substituted by 1 to 3 halogen atoms (e.g., fluorine atom);

$L^1$ is —NH—C(=O)—;

ring B is $C_{3-10}$ cycloalkane (e.g., cyclopentane) or non-aromatic heterocycle (preferably, a 3- to 8-membered monocyclic non-aromatic heterocycle, such as piperidine ring, piperazine ring, morpholine ring, thiomorpholine ring);

$L^2$ is a bond, —C(=O)—NH—, —NH—C(=O)— or —NH—C(=O)—NH—; and ring C is a $C_{6-14}$ aromatic hydrocarbon ring (e.g., benzene ring), a 5- or 6-membered monocyclic aromatic heterocycle (e.g., thiophene ring, a pyridine ring), a 8- to 14-membered fused polycyclic (preferably bi- or tricyclic) aromatic heterocycle (e.g., benzoxazole ring, quinazoline ring) or a 9- to 14-membered fused polycyclic (preferably bi- or tricyclic) non-aromatic heterocycle (e.g., dihydroisoindole ring, dihydrobenzofuran ring, tetrahydroisoquinoline ring), each of which is optionally substituted by 1 to 3 substituents selected from (1) a cyano group, (2) an oxo group, (3) a halogen atom (e.g., fluorine atom, chlorine atom), (4) a $C_{1-6}$ alkyl group (e.g., methyl) optionally substituted by 1 to 3 substituents selected from a $C_{1-6}$ alkoxy-carbonylamino group (e.g., methoxycarbonylamino, tert-butoxycarbonylamino) and a $C_{1-6}$ alkyl-aminocarbonyloxy group (e.g., ethylaminocarbonyloxy), (5) a $C_{1-6}$ alkoxy group (e.g., methoxy) and (6) a $C_{1-6}$ alkoxy-carbonyl group (e.g., methoxycarbonyl, tert-butoxycarbonyl).

As other preferable examples of compound (I), the following compounds can be mentioned.

[Compound I-0A]

Compound (I) wherein $R^1$ and $R^2$ is (1) a methyl group substituted by one substituent selected from (a) an optionally substituted $C_{3-6}$ cycloalkyl group and (b) an optionally substituted 5- or 6-membered non-aromatic heterocyclic group, (2) an optionally substituted $C_{2-6}$ alkyl group, or (3) an optionally substituted $C_{2-6}$ alkenyl group;

ring A is an optionally further substituted 6-membered aromatic ring;

$L^1$ is a bond, or a spacer having a main chain having 1-2 atoms;

ring B is a non-aromatic ring optionally further substituted by 1 to 3 substituents selected from (a) an acyl group, (b) an optionally substituted $C_{1-6}$ alkyl group, (c) an optionally substituted $C_{1-6}$ alkoxy group, (d) a hydroxy group, (e) a halogen atom and (f) an oxo group:

$L^2$ is a bond, or a spacer having a main chain having 1-4 atoms; and ring C is an optionally further substituted ring.

[Compound I-1A]

Compound (I) wherein $R^1$ is (1) a methyl group substituted by one substituent selected from (a) an optionally substituted $C_{3-6}$ cycloalkyl group (e.g., cyclopropyl, cyclobutyl) and (b) an optionally substituted 5- or 6-membered non-aromatic heterocyclic group (e.g., tetrahydrofuryl) or (2) an optionally substituted $C_{2-6}$ alkyl group (e.g., ethyl);

$R^2$ is (1) a methyl group substituted by an optionally substituted $C_{3-6}$ cycloalkyl group (e.g., cyclopropyl, cyclobutyl), (2) an optionally substituted $C_{2-6}$ alkyl group (e.g., ethyl, isopropyl, isobutyl, 1-methylpropyl, isopentyl, neopentyl), or (3) an optionally substituted $C_{2-6}$ alkenyl group (e.g., 3-methylbut-2-en-1-yl);

ring A is a benzene ring or a 6-membered aromatic heterocycle (e.g., a pyridine ring), each of which is optionally further substituted by 1 to 3 halogen atoms (e.g., fluorine atom);

$L^1$ is a bond, —C(=O)—, —O—C(=O)—, optionally substituted —CH$_2$—C(=O)—, optionally substituted —C(=O)—NH— or optionally substituted —NH—C(=O)—;

ring B is $C_{3-10}$ cycloalkane (e.g., cyclopropane, cyclopentane, cyclohexane) or non-aromatic heterocycle (preferably 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally substituted by 1 to 3 substituents selected from (a) an acyl group selected from (i) a carboxy group, (ii) an optionally substituted $C_{1-6}$ alkyl-carbonyl group (e.g., methylcarbonyl, propylcarbonyl), (iii) an optionally substituted $C_{1-6}$ alkoxy-carbonyl group (e.g., methoxycarbonyl, tert-butoxycarbonyl), (iv) an optionally substituted $C_{7-16}$ aralkyloxy-carbonyl group (e.g., benzyloxycarbonyl), (v) a carbamoyl group and (vi) a $C_{1-6}$ alkyl-sulfonyl group (e.g., methylsulfonyl), (b) an optionally substituted $C_{1-6}$ alkyl group (e.g., methyl), (c) a hydroxy group and (d) an oxo group;

$L^2$ is a bond, —O—, —C(=O)—, optionally substituted —CH$_2$—O—, optionally substituted —C(=O)—CH$_2$—, optionally substituted —C(=O)—NH—, optionally substituted —NH—C(=O)—, optionally substituted —NH—S(=O)$_2$—, optionally substituted —CH$_2$—C(=O)—NH—, optionally substituted —CH$_2$—NH—C(=O)—, optionally substituted —O—C(=O)—NH—, optionally substituted —NH—C(=O)—NH—, optionally substituted —NH—C(=O)—CH$_2$—, optionally substituted —CH$_2$—NH—CH$_2$—, optionally substituted —NH—C(=O)—CH$_2$—CH$_2$— or optionally substituted —CH$_2$—NH—C(=O)—NH—; and ring C is a C$_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) an optionally substituted C$_{1-6}$ alkyl group (e.g., methyl, ethyl), (6) an optionally substituted C$_{2-6}$ alkenyl group (e.g., vinyl), (7) a C$_{3-6}$ cycloalkyl group (e.g., cyclopropyl), (8) a C$_{6-14}$ aryl group (e.g., phenyl), (9) an optionally substituted C$_{1-6}$ alkoxy group (e.g., methoxy, ethoxy), (10) a C$_{1-6}$ alkyl-carbonyl group (e.g., methylcarbonyl), (11) a carboxy group, (12) a C$_{2-6}$ alkenyl-carbonyl group (e.g., vinylcarbonyl), (13) a C$_{1-6}$ alkoxy-carbonyl group (e.g., methoxycarbonyl, ethoxycarbonyl, tert-butoxycarbonyl), (14) a carbamoyl group, (15) an amino group, (16) an optionally substituted C$_{1-6}$ alkyl-carbonylamino group (e.g., methylcarbonylamino, ethylcarbonylamino), (17) a C$_{1-6}$ alkoxy-carbonylamino group (e.g., tert-butoxycarbonylamino), (18) a C$_{1-6}$ alkyl-sulfonyl group (e.g., methylsulfonyl), (19) an optionally substituted C$_{2-6}$ alkenyl-carbonylamino group (e.g., vinylcarbonylamino, 1-propenylcarbonylamino), (20) a C$_{2-6}$ alkenyl-sulfonylamino group (e.g., vinylsulfonylamino) and (21) a 3- to 8-membered monocyclic non-aromatic heterocycle (e.g., oxiranyl).

[Compound I-2A]

Compound (I) wherein $R^1$ is (1) a methyl group substituted by one substituent selected from (a) a C$_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl), or (2) a C$_{2-6}$ alkyl group (e.g., ethyl) optionally substituted by 1 to 3 substituents selected from a halogen atom (e.g., fluorine atom), a C$_{1-6}$ alkoxy group (e.g., methoxy) and a C$_{1-6}$ alkoxy-carbonyl group (e.g., tert-butoxycarbonyl);

$R^2$ is (1) a methyl group substituted by a C$_{3-6}$ cycloalkyl group (e.g., cyclopropyl, cyclobutyl), (2) a C$_{2-6}$ alkyl group (e.g., ethyl, isopropyl, isobutyl, 1-methylpropyl, isopentyl, neopentyl) optionally substituted by 1 to 3 halogen atoms (e.g., fluorine atom), or (3) a C$_{2-6}$ alkenyl group (e.g., 3-methylbut-2-en-1-yl);

ring A is (1) a benzene ring optionally further substituted by 1 to 3 halogen atoms (e.g., fluorine atom), or (2) a 6-membered aromatic heterocycle (e.g., pyridine ring);

$L^1$ is a bond, —C(=O)—, —O—C(=O)—, —CH$_2$—C(=O)—, —C(=O)—NH— or —NH—C(=O)—;

ring B is a C$_{3-10}$ cycloalkane (e.g., cyclopropane, cyclopentane, cyclohexane) or a non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally substituted by 1 to 3 substituents selected from (a) an acyl group selected from (i) a carboxy group, (ii) a C$_{1-6}$ alkyl-carbonyl group (e.g., methylcarbonyl, propylcarbonyl) optionally substituted by a carboxy group, (iii) a C$_{1-6}$ alkoxy-carbonyl group (e.g., methoxycarbonyl, tert-butoxycarbonyl) optionally substituted by a carboxy group or a C$_{7-16}$ aralkyloxy-carbonyl group (e.g., benzyloxycarbonyl), (iv) a C$_{7-16}$ aralkyloxy-carbonyl group (e.g., benzyloxycarbonyl), (v) a carbamoyl group and (vi) a C$_{1-6}$ alkyl-sulfonyl group (e.g., methylsulfonyl), (b) a C$_{1-6}$ alkyl group (e.g., methyl) optionally substituted by a hydroxy group, (c) a hydroxy group and (d) an oxo group;

$L^2$ is a bond, —O—, —C(=O)—, —CH$_2$—O—, —C(=O)—CH$_2$—, —C(=O)—NH— (e.g., —C(=O)—NH—, —C(=O)—N(CH$_3$)—) optionally substituted by a C$_{1-6}$ alkyl group (e.g., methyl) optionally substituted by 1 to 3 halogen atoms (e.g., fluorine atom), —NH—C(=O)— (e.g., —NH—C(=O)—, —N(CH$_3$)—C(=O)—) optionally substituted by a C$_{1-6}$ alkyl group (e.g., methyl) optionally substituted by 1 to 3 halogen atoms (e.g., fluorine atom), —NH—S(=O)$_2$—, —CH$_2$—C(=O)—NH—, —CH$_2$—NH—C(=O)—, —O—C(=O)—NH—, —NH—C(=O)—NH—, —NH—C(=O)—CH$_2$— (e.g., —NH—C(=O)—CH$_2$—, —NH—C(=O)—CH(OH)—) optionally substituted by a hydroxy group, —CH$_2$—NH—CH$_2$— (e.g., —CH$_2$—NH—CH(CF$_3$)—) optionally substituted by a C$_{1-6}$ alkyl group (e.g., methyl) optionally substituted by 1 to 3 halogen atoms (e.g., fluorine atom), —NH—C(=O)—CH$_2$—CH$_2$— or —CH$_2$—NH—C(=O)—NH—; and ring C is a C$_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) a C$_{1-6}$ alkyl group (e.g., methyl, ethyl) optionally substituted by 1 to 3 substituents selected from a cyano group, a hydroxy group, a halogen atom (e.g., fluorine atom, bromine atom), a C$_{1-6}$ alkoxy group (e.g., methoxy), an amino group, a C$_{1-6}$ alkoxy-carbonylamino group (e.g., methoxycarbonylamino, tert-butoxycarbonylamino), a C$_{1-6}$ alkyl-carbonylamino group (e.g., methylcarbonylamino) optionally substituted by a halogen atom (e.g., chlorine atom), a C$_{2-6}$ alkenyl-carbonylamino group (e.g., vinylcarbonylamino) and a C$_{1-6}$ alkylaminocarbonyloxy group (e.g., ethylaminocarbonyloxy), (6) a C$_{2-6}$ alkenyl group (e.g., vinyl) optionally substituted by a C$_{1-6}$ alkyl-carbonyl group (e.g., methylcarbonyl), (7) a C$_{3-6}$ cycloalkyl group (e.g., cyclopropyl), (8) a C$_{6-14}$ aryl group (e.g., phenyl), (9) a C$_{1-6}$ alkoxy group (e.g., methoxy, ethoxy) optionally substituted by 1 to 3 substituents selected from a halogen atom (e.g., fluorine atom) and a $C_{1-6}$ alkoxy group (e.g., methoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) a $C_{1-6}$ alkyl-carbonylamino group (e.g., methylcarbonylamino, ethylcarbonylamino) optionally substituted by a halogen atom (e.g., chlorine atom), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) a $C_{2-6}$ alkenyl-carbonylamino group (e.g., vinylcarbonylamino, 1-propenylcarbonylamino) optionally substituted by a mono- or di-$C_{1-6}$ alkylamino group (e.g., dimethylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

As still other preferable examples of compound (I), the following compounds can be mentioned.

[Compound I-1B]

Compound (I) wherein $R^1$ is (1) a methyl group substituted by one substituent selected from (a) an optionally substituted $C_{3-6}$ cycloalkyl group (e.g., cyclopropyl, cyclobutyl) and (b) an optionally substituted 5- or 6-membered non-aromatic heterocyclic group (e.g., tetrahydrofuryl), or (2) an optionally substituted $C_{2-6}$ alkyl group (e.g., ethyl);

$R^2$ is an optionally substituted $C_{3-6}$ alkyl group (e.g., isopropyl, 1-methylpropyl) or an optionally substituted $C_{3-6}$ alkenyl group, each of which is branched at a carbon atom bonded to a nitrogen atom;

$L^1$ is a bond, —C(=O)—, —O—C(=O)—, optionally substituted —CH$_2$—C(=O)—, optionally substituted —C(=O)—NH— or optionally substituted —NH—C(=O)—;

ring B is a $C_{3-10}$ cycloalkane (e.g., cyclopropane, cyclopentane, cyclohexane) or a non-aromatic heterocycle (preferably a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally substituted by 1 to 3 substituents selected from (a) an acyl group selected from (i) a carboxy group, (ii) an optionally substituted $C_{1-6}$ alkyl-carbonyl group (e.g., methylcarbonyl, propylcarbonyl), (iii) an optionally substituted $C_{1-6}$ alkoxy-carbonyl group (e.g., methoxycarbonyl, tert-butoxycarbonyl), (iv) an optionally substituted $C_{7-16}$ aralkyloxy-carbonyl group (e.g., benzyloxycarbonyl), (v) a carbamoyl group and (vi) a $C_{1-6}$ alkyl-sulfonyl group (e.g., methylsulfonyl), (b) an optionally substituted $C_{1-6}$ alkyl group (e.g., methyl), (c) a hydroxy group and (d) an oxo group;

$L^2$ is a bond, —O—, —C(=O)—, optionally substituted —CH$_2$—O—, optionally substituted —C(=O)—CH$_2$—, optionally substituted —C(=O)—NH—, optionally substituted —NH—C(=O)—, optionally substituted —NH—S(=O)$_2$—, optionally substituted —CH$_2$—C(=O)—NH—, optionally substituted —CH$_2$—NH—C(=O)—, optionally substituted —O—C(=O)—NH—, optionally substituted —NH—C(=O)—NH—, optionally substituted —NH—C(=O)—CH$_2$—, optionally substituted —CH$_2$—NH—CH$_2$—, optionally substituted —NH—C(=O)—CH$_2$—CH$_2$— or optionally substituted —CH$_2$—NH—C(=O)—NH—; and ring C is a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) an optionally substituted $C_{1-6}$ alkyl group (e.g., methyl, ethyl), (6) an optionally substituted $C_{2-6}$ alkenyl group (e.g., vinyl), (7) a $C_{3-6}$ cycloalkyl group (e.g., cyclopropyl), (8) a $C_{6-14}$ aryl group (e.g., phenyl), (9) an optionally substituted $C_{1-6}$ alkoxy group (e.g., methoxy, ethoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) an optionally substituted $C_{1-6}$ alkyl-carbonylamino group (e.g., methylcarbonylamino, ethylcarbonylamino), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) an optionally substituted $C_{2-6}$ alkenyl-carbonylamino group (e.g., vinylcarbonylamino, 1-propenylcarbonylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

[Compound I-2B]

Compound (I) wherein $R^1$ is (1) a methyl group substituted by one substituent selected from (a) a $C_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl), or (2) a $C_{2-6}$ alkyl group (e.g., ethyl) optionally substituted by 1 to 3 substituents selected from a halogen atom (e.g., fluorine atom), a $C_{1-6}$ alkoxy group (e.g., methoxy) and a $C_{1-6}$ alkoxy-carbonyl group (e.g., tert-butoxycarbonyl);

$R^2$ is a $C_{3-6}$ alkyl group (e.g., isopropyl, 1-methylpropyl) optionally substituted by 1 to 3 halogen atoms (e.g., fluorine atom), each of which is branched at a carbon atom bonded to a nitrogen atom;

ring A is (1) a benzene ring optionally further substituted by 1 to 3 halogen atoms (e.g., fluorine atom), or (2) a 6-membered aromatic heterocycle (e.g., pyridine ring);

$L^1$ is a bond, —C(=O)—, —O—C(=O)—, —CH$_2$—C(=O)—, —C(=O)—NH— or —NH—C(=O)—;

ring B is a $C_{3-10}$ cycloalkane (e.g., cyclopropane, cyclopentane, cyclohexane) or a non-aromatic heterocycle (preferably, a 3- to 8-membered monocyclic non-aromatic heterocycle, such as pyrrolidine ring, tetrahydrofuran ring, piperidine ring, piperazine ring, morpholine ring, thiomorpholine ring, tetrahydropyran ring, azepane ring, 1,4-diazepane ring), each of which is optionally substituted by 1 to 3 substituents selected from (a) an acyl group selected from (i) a carboxy group, (ii) a $C_{1-6}$ alkyl-carbonyl group (e.g., methylcarbonyl, propylcarbonyl) optionally substituted by a carboxy group, (iii) a $C_{1-6}$ alkoxy-carbonyl group (e.g., methoxycarbonyl, tert-butoxycarbonyl) optionally substituted by a carboxy group or a $C_{7-16}$ aralkyloxy-carbonyl group (e.g., benzyloxycarbonyl), (iv) a $C_{7-16}$ aralkyloxycarbonyl group (e.g., benzyloxycarbonyl), (v) a carbamoyl group and (vi) a $C_{1-6}$ alkyl-sulfonyl group (e.g., methylsulfonyl), (b) a $C_{1-6}$ alkyl group (e.g., methyl) optionally substituted by a hydroxy group, (c) a hydroxy group and (d) an oxo group;

$L^2$ is a bond, —O—, —C(=O)—, —CH$_2$—O—, —C(=O)—CH$_2$—, —C(=O)—NH— (e.g., —C(=O)—NH—, —C(=O)—N(CH$_3$)—) optionally substituted by a $C_{1-6}$ alkyl group (e.g., methyl) optionally substituted by 1 to 3 halogen atoms (e.g., fluorine atom), —NH—C(=O)— (e.g., —NH—C(=O)—, —N(CH$_3$)—C(=O)—) optionally substituted by a $C_{1-6}$ alkyl group (e.g., methyl) optionally substituted by 1 to 3 halogen atoms (e.g., fluorine atom), —NH—S(=O)$_2$—, —CH$_2$—C(=O)—NH—, —CH$_2$—NH—C(=O)—, —O—C(=O)—NH—, —NH—C(=O)—NH—, —NH—C(=O)—CH$_2$— (e.g., —NH—C(=O)—CH$_2$—, —NH—C(=O)—CH(OH)—) optionally substituted by a hydroxy group, —CH$_2$—NH—CH$_2$— (e.g., —CH$_2$—NH—CH(CF$_3$)—) optionally substituted by a $C_{1-6}$ alkyl group (e.g., methyl) optionally substituted by 1 to 3 halogen atoms (e.g., fluorine atom), —NH—C(=O)—CH$_2$—CH$_2$— or —CH$_2$—NH—C(=O)—NH—; and ring C is a $C_{6-14}$ aromatic hydrocarbon ring (e.g., benzene ring), a 5- or 6-membered monocyclic aromatic heterocycle (e.g., oxazole ring, isoxazole ring, pyrazole ring, furan ring, thiophene ring, thiazole ring, oxadiazole ring, pyridine ring), a 8- to 14-membered fused polycyclic (preferably bi- or tricyclic) aromatic heterocycle (e.g., benzimidazole ring, benzothiazole ring, imidazopyridine ring, benzoxazole ring, indazole ring, quinazoline ring), a 3- to 8-membered monocyclic non-aromatic heterocycle (e.g., piperidine ring, tetrahydropyran ring) or a 9- to 14-membered fused polycyclic (preferably bi- or tricyclic) non-aromatic heterocycle (e.g., dihydroindole ring, dihydroisoindole ring, dihydrobenzofuran ring, tetrahydroquinazoline ring, dihydroindene ring, dihydroisoquinoline ring, dihydroquinazoline ring, tetrahydroisoquinoline ring), each of which is optionally substituted by 1 to 3 substituents selected from (1) a cyano group, (2) a hydroxy group, (3) an oxo group, (4) a halogen atom (e.g., fluorine atom, chlorine atom, bromine atom), (5) a $C_{1-6}$ alkyl group (e.g., methyl, ethyl) optionally substituted by 1 to 3 substituents selected from a cyano group, a hydroxy group, a halogen atom (e.g., fluorine atom, bromine atom), a $C_{1-6}$ alkoxy group (e.g., methoxy), an amino group, a $C_{1-6}$ alkoxy-carbonylamino group (e.g., methoxycarbonylamino, tert-butoxycarbonylamino), a $C_{1-6}$ alkyl-carbonylamino group (e.g., methylcarbonylamino) optionally substituted by a halogen atom (e.g., chlorine atom), a $C_{2-6}$ alkenyl-carbonylamino group (e.g., vinylcarbonylamino) and a $C_{1-6}$ alkyl-aminocarbonyloxy group (e.g., ethylaminocarbonyloxy), (6) a $C_{2-6}$ alkenyl group (e.g., vinyl) optionally substituted by a $C_{1-6}$ alkyl-carbonyl group (e.g., methylcarbonyl), (7) a $C_{3-6}$ cycloalkyl group (e.g., cyclopropyl), (8) a $C_{6-14}$ aryl group (e.g., phenyl), (9) a $C_{1-6}$ alkoxy group (e.g., methoxy, ethoxy) optionally substituted by 1 to 3 substituents selected from a halogen atom (e.g., fluorine atom) and a $C_{1-6}$ alkoxy group (e.g., methoxy), (10) a $C_{1-6}$ alkyl-carbonyl group (e.g., methylcarbonyl), (11) a carboxy group, (12) a $C_{2-6}$ alkenyl-carbonyl group (e.g., vinylcarbonyl), (13) a $C_{1-6}$ alkoxy-carbonyl group (e.g., methoxycarbonyl, ethoxycarbonyl, tert-butoxycarbonyl), (14) a carbamoyl group, (15) an amino group, (16) a $C_{1-6}$ alkyl-carbonylamino group (e.g., methylcarbonylamino, ethylcarbonylamino) optionally substituted by a halogen atom (e.g., chlorine atom), (17) a $C_{1-6}$ alkoxy-carbonylamino group (e.g., tert-butoxycarbonylamino), (18) a $C_{1-6}$ alkyl-sulfonyl group (e.g., methylsulfonyl), (19) a $C_{2-6}$ alkenyl-carbonylamino group (e.g., vinylcarbonylamino, 1-propenylcarbonylamino) optionally substituted by a mono- or di-$C_{1-6}$ alkylamino group (e.g., dimethylamino), (20) a $C_{2-6}$ alkenyl-sulfonylamino group (e.g., vinylsulfonylamino) and (21) a 3- to 8-membered monocyclic non-aromatic heterocycle (e.g., oxiranyl).

[Compound I-3B]

Compound (I) wherein $R^1$ is (1) a methyl group substituted by one substituent selected from (a) a $C_{3-6}$ cycloalkyl group (e.g., cyclopropyl, cyclobutyl) optionally substituted by 1 to 3 halogen atoms (e.g., fluorine atom) and (b) a 5- or 6-membered non-aromatic heterocyclic group (e.g., tetrahydrofuryl);

$R^2$ is a $C_{3-6}$ alkyl group (e.g., isopropyl, 1-methylpropyl) optionally substituted by 1 to 3 halogen atoms (e.g., fluorine atom), each of which is branched at a carbon atom bonded to a nitrogen atom;

ring A is a benzene ring optionally further substituted by 1 to 3 halogen atoms (e.g., fluorine atom);

$L^1$ is —NH—C(=O)—;

ring B is a $C_{3-10}$ cycloalkane (e.g., cyclopentane) or a non-aromatic heterocycle (preferably, a 3- to 8-membered monocyclic non-aromatic heterocycle, such as piperidine ring, piperazine ring, morpholine ring, thiomorpholine ring);

$L^2$ is a bond, —C(=O)—NH—, —NH—C(=O)— or —NH—C(=O)—NH—;

ring C is a $C_{6-14}$ aromatic hydrocarbon ring (e.g., benzene ring), a 5- or 6-membered monocyclic aromatic heterocycle (e.g., thiophene ring, a pyridine ring), a 8- to 14-membered fused polycyclic (preferably bi- or tricyclic) aromatic heterocycle (e.g., benzoxazole ring, quinazoline ring) or a 9- to 14-membered fused polycyclic (preferably bi- or tricyclic) non-aromatic heterocycle (e.g., dihydroisoindole ring, dihydrobenzofuran ring, tetrahydroisoquinoline ring), each of which is optionally substituted by 1 to 3 substituents selected from (1) a cyano group, (2) an oxo group, (3) a halogen atom (e.g., fluorine atom, chlorine atom), (4) a $C_{1-6}$ alkyl group (e.g., methyl) optionally substituted by 1 to 3 substituents selected from a $C_{1-6}$ alkoxy-carbonylamino group (e.g., methoxycarbonylamino, tert-butoxycarbonylamino) and a $C_{1-6}$ alkyl-aminocarbonyloxy group (e.g., ethylaminocarbonyloxy), (5) a $C_{1-6}$ alkoxy group (e.g., methoxy) and (6) a $C_{1-6}$ alkoxy-carbonyl group (e.g., methoxycarbonyl, tert-butoxycarbonyl).

Specific examples of compound (I) include the compounds of Examples 1-376.

When compound (I) is a salt, examples of such salt include salts with inorganic base, ammonium salts, salts with organic base, salts with inorganic acid, salts with organic acid, salts with basic or acidic amino acids, and the like.

Preferable examples of the salt with inorganic base include alkaline metal salts such as sodium salt and potassium salt; alkaline earth metal salts such as calcium salt, magnesium salt and barium salt; and aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salt with aspartic acid, glutamic acid and the like.

Of these salts, a pharmaceutically acceptable salt is preferable. As the pharmaceutically acceptable preferable salt, when the compound has a basic functional group therein, examples of the salt thereof include salts with inorganic acids such as hydrochloric acid, hydrobromic acid, nitric acid, sulfuric acid and phosphoric acid, and salts with organic acids such as acetic acid, phthalic acid, fumaric acid, oxalic acid, tartaric acid, maleic acid, citric aid, succinic acid, methanesulfonic acid, p-toluenesulfonic acid and the like. When an acidic functional group is contained in the compound, examples thereof include inorganic salts such as alkali metal salt (e.g., sodium salt, potassium salt etc.), alkaline earth metal salt (e.g., calcium salt, magnesium salt, barium salt etc.) and the like, ammonium salt, and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate etc.) and non-solvates (e.g., non-hydrate etc.) within the scope thereof. Compound (I) may be a compound labeled or substituted with an isotope (e.g., $^2H$, $^3H$, $^{11}C$, $^{14}C$, $^{18}F$, $^{35}S$, $^{125}I$). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are also encompassed in compound (I) of the present invention.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

The compound (I) of the present invention can be produced by the following Method A to Method U.

[Method A]

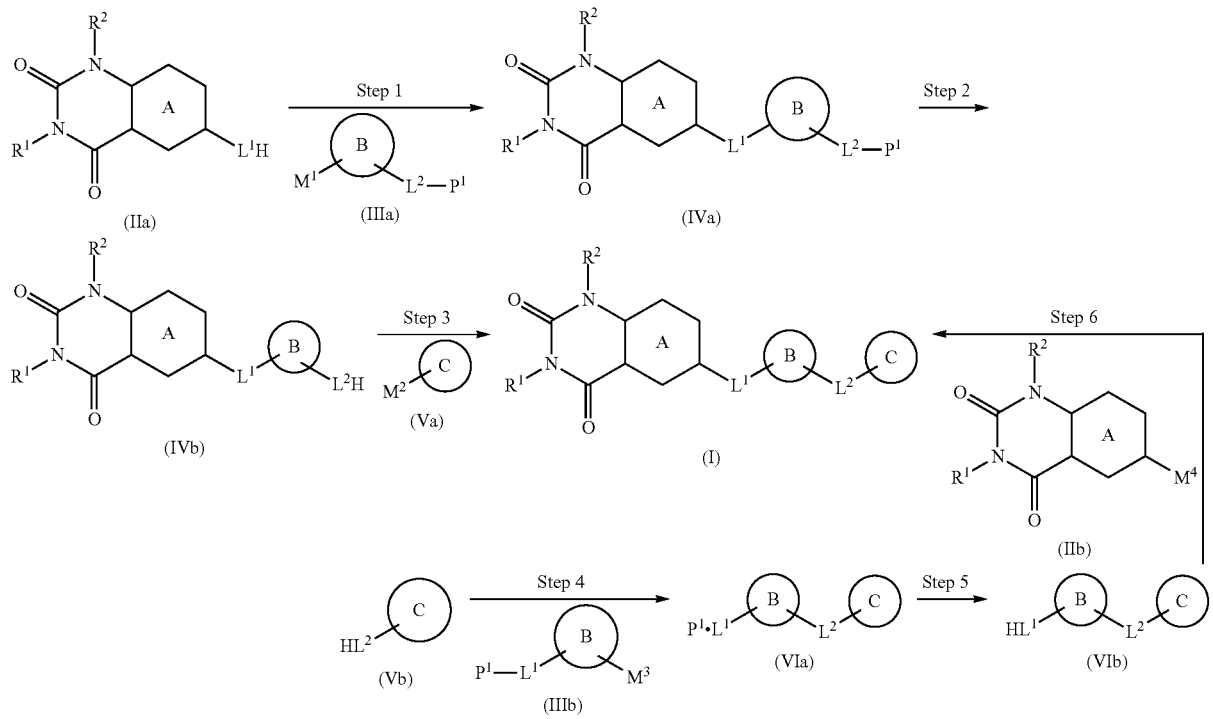

wherein $M^1$, $M^2$, $M^3$, $M^4$ are each a leaving group, $P^1$ is a protecting group, and other symbols are as defined above.

As the leaving group for $M^1$, $M^2$, $M^3$, $M^4$, a halogen atom (a chlorine atom, a bromine atom, an iodine atom and the like), a substituted sulfonyloxy group ($C_{1-6}$ alkylsulfonyloxy group such as methanesulfonyloxy, ethanesulfonyloxy and the like; a $C_{6-14}$ arylsulfonyloxy group such as benzenesulfonyloxy, p-toluenesulfonyloxy and the like; a $C_{7-16}$ aralkylsulfonyloxy group such as benzylsulfonyloxy group and the like, and the like), acyloxy (acetoxy, benzoyloxy and the like), an oxy group substituted by a heterocycle or an aryl group (succinimide, benzotriazole, quinoline, 4-nitrophenyl and the like), a heterocycle (imidazole and the like) and the like are used.

As the protecting group for $P^1$, a protecting group known per se, for example, an optionally substituted alkyl group (methyl, ethyl, benzyl and the like), an optionally substituted aryl group (phenyl and the like), an optionally substituted silyl group (trimethylsilyl, tert-butyldimethylsilyl and the like), an optionally substituted acyl group (acetyl, benzyloxycarbonyl, methylsulfonyl and the like) and the like are used.

(Step 1)

In this step, compound (IIa) or a salt thereof is reacted with compound (IIIa) to produce compound (IVa) or a salt thereof.

Compound (IIa) and compound (IIIa) may be commercially available products, or can also be produced according to a method known per se or a method analogous thereto. Compound (IIa) can also be produced by the method described in the below-mentioned Method M, N or O or a method analogous thereto, and compound (IIIa) can also be produced according to a method known per se or a method analogous thereto.

The amount of compound (IIIa) to be used is generally about 1-10 molar equivalents, preferably about 1-2 molar equivalents, per 1 mol of compound (IIa).

This reaction is generally performed in a solvent that does not adversely influence the reaction, and an acid, a base, a salt, a transition metal catalyst and the like may be added as necessary to promote the reaction. Examples of the solvent include alcohols (methanol, ethanol and the like), nitriles (acetonitrile and the like), hydrocarbons (benzene, toluene and the like), ethers (diethyl ether, dioxane, tetrahydrofuran and the like), acids (acetic acid and the like), esters (ethyl acetate and the like), halogenated hydrocarbons (chloroform, dichloromethane and the like), amides (N,N-dimethylformamide and the like), aromatic amines (pyridine and the like), water and the like, which may be mixed as appropriate.

Examples of the acid include mineral acids (hydrochloric acid, hydrobromic acid, sulfuric acid, hydrogen chloride and the like), carboxylic acids (acetic acid, trifluoroacetic acid, trichloroacetic acid and the like), sulfonic acids (methanesulfonic acid, p-toluenesulfonic acid and the like), Lewis acids (aluminum chloride, tin chloride, zinc bromide and the like) and the like, and two or more kinds thereof may be used in a mixture as necessary. While the amount of the acid to be used varies depending on the kind of the solvent and other reaction conditions, it is generally not less than about 0.1 mol equivalents per 1 mol of compound (IIa)), and it can also be used as a solvent.

Examples of the base or salt include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine, diisopropylethylamine and the like), aromatic amines (pyridine, picoline, N,N-dimethylaniline, 4-dimethylaminopyridine and the like), inorganic salts (alkali metal salt such as sodium fluoride, potassium fluoride and the like, and the like) and the like. The amount of the base to be used is generally about 1-100 molar equivalents, preferably about 1-5 molar equivalents, per 1 mol of compound (IIa).

Examples of the transition metal catalyst include palladium catalyst (palladium acetate, palladium chloride, tetrakistriphenylphosphine palladium and the like), nickel catalyst (nickel chloride and the like) and the like, and a ligand (triphenylphosphine, tri-t-butylphosphine, S-Phos, BINAP and the like) may also be used as necessary. While the amount of the transition metal catalyst to be used varies depending on the kind thereof and other reaction conditions, it is generally about 0.001-1 mol equivalents, preferably about 0.1-0.5 molar equivalents, per 1 mol of compound (IIa), and the amount of the ligand to be used is generally about 0.001-1 mol equivalents per 1 mol of compound (IIa).

The reaction temperature is generally about −80-200° C., preferably about −80-150° C., and the reaction time is generally about 0.1-100 hr, preferably about 0.1-48 hr.
(Step 2)

In this step, compound (IVa) or a salt thereof is subjected to deprotection reaction to produce compound (IVb) or a salt thereof.

Such deprotection reaction can be performed according to a known method. For example, while subject to variation depending on the kind of compound (IVa), it is performed by a method using an acid or base, a method using a transition metal catalyst, or reduction by catalytic hydrogenation using a transition metal catalyst, each in a solvent that does not adversely influence the reaction.

Examples of the solvent include alcohols (methanol, ethanol and the like), nitriles (acetonitrile and the like), hydrocarbons (benzene, toluene and the like), ethers (diethyl ether, dioxane, tetrahydrofuran and the like), acids (acetic acid and the like), esters (ethyl acetate and the like), halogenated hydrocarbons (chloroform, dichloromethane and the like), amides (N,N-dimethylformamide and the like), aromatic amines (pyridine and the like), water and the like, which may be mixed as appropriate.

Examples of the acid include mineral acids (hydrochloric acid, hydrobromic acid, sulfuric acid, hydrogen chloride and the like), carboxylic acids (acetic acid, trifluoroacetic acid, trichloroacetic acid and the like), sulfonic acids (methanesulfonic acid, p-toluenesulfonic acid and the like), Lewis acids (aluminum chloride, tin chloride, zinc bromide and the like) and the like, and two or more kinds thereof may be used in a mixture as necessary. While the amount of the acid to be used varies depending on the kind of the solvent and other reaction conditions, it is generally not less than about 0.1 mol equivalent per 1 mol of compound (IVa), and it can also be used as a solvent.

Examples of the base include alkali metal hydroxide (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine, diisopropylethylamine and the like), aromatic amines (pyridine, picoline, N,N-dimethylaniline, 4-dimethylaminopyridine and the like. While the amount of the base to be used varies depending on the kind of the solvent and other reaction conditions, it is generally about 1-10 molar equivalents, preferably about 1-5 molar equivalents, per 1 mol of compound (IVa).

Examples of the transition metal catalyst include palladiums (palladium carbon, palladium hydroxide, palladium oxide and the like), nickels (Raney-nickel and the like), platinums (platinum oxide, platinum carbon and the like), rhodiums (rhodium acetate, rhodium carbon and the like) and the like. The amount thereof to be used is, for example, about 0.001-1 equivalents, preferably about 0.01-0.5 equivalents, per 1 mol of compound (IVa).

For catalytic hydrogenation using a transition metal catalyst, the hydrogen pressure at which the reaction is performed is generally about 1-500 atm, preferably about 1-100 atm.

The reaction temperature is, for example, about −50-200° C., preferably about 0-100° C. While the reaction time varies depending on the kind of compound (IVa) or additive, reaction temperature and the like, it is, for example, about 5 min-100 hr, preferably about 0.5-40 hr.
(Step 3)

In this step, compound (IVb) or a salt thereof is reacted with compound (Va) or a salt thereof to produce compound (I).

Compound (Va) may be commercially available products, or can also be produced according to a method known per se or a method analogous thereto, as well as the method described in the below-mentioned Method Q, Method R or Method S or a method analogous thereto.

This step can be performed according to the method described in step 1 or a method analogous thereto.
(Step 4)

In this step, compound (Vb) or a salt thereof is reacted with compound (IIIb) or a salt thereof to produce compound (VIa) or a salt thereof.

Compound (Vb) may be commercially available products, or can also be produced according to a method known per se or a method analogous thereto, as well as the method described in the below-mentioned Method Q, Method R or Method S or a method analogous thereto. Compound (IIIb) can also be produced according to a method known per se or a method analogous thereto.

This step can be performed according to the method described in step 1 or a method analogous thereto.
(Step 5)

In this step, compound (VIa) or a salt thereof is subjected to deprotection reaction to produce compound (VIb) or a salt thereof.

This step can be performed according to the method described in step 2 or a method analogous thereto.
(Step 6)

In this step, compound (VIb) or a salt thereof is reacted with compound (IIb) or a salt thereof to produce compound (I).

Compound (IIb) can be produced according to a method known per se or a method analogous thereto.

This step can be performed according to the method described in step 1 or a method analogous thereto.

[Method B]

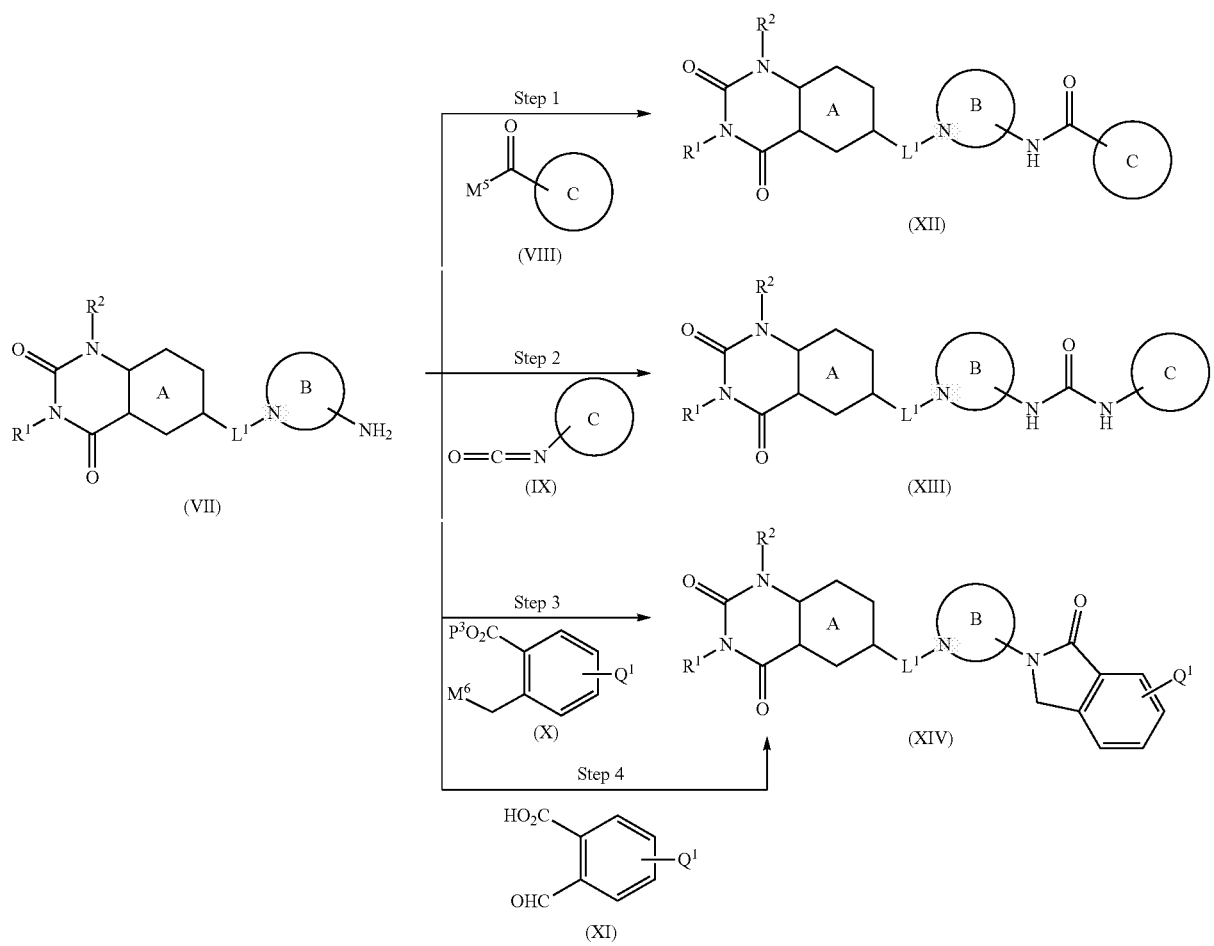

wherein $M^5$ is a halogen atom or hydroxy group, $M^6$ is a leaving group, $Q^1$ is, in the definition of ring C in the aforementioned formula (I), any substituent in the substituents mentioned above as the substituents optionally further substituted at substitutable position(s) of ring C, and other symbols are as defined above.

As the leaving group for $M^6$, a halogen atom (a chlorine atom, a bromine atom, an iodine atom and the like), a substituted sulfonyloxy group ($C_{1-6}$ alkylsulfonyloxy group such as methanesulfonyloxy, ethanesulfonyloxy and the like; a $C_{6-14}$ arylsulfonyloxy group such as benzenesulfonyloxy, p-toluenesulfonyloxy and the like; a $C_{7-16}$ aralkylsulfonyloxy group such as benzylsulfonyloxy group and the like, and the like), acyloxy (acetoxy, benzoyloxy and the like), an oxy group substituted by a heterocycle or an aryl group (succinimide, benzotriazole, quinoline, 4-nitrophenyl and the like), a heterocycle (imidazole and the like) and the like are used.

(Step 1)

In this step, compound (VII) or a salt thereof is reacted with compound (VIII) or a salt thereof to produce compound (XII) or a salt thereof.

Compound (VII) can be produced according to a method known per se or a method analogous thereto, or the method described in the below-mentioned Method J or a method analogous thereto.

When $M^5$ is a hydroxy group, compound (VIII) or a salt thereof may be commercially available products, or can also be produced according to a method known per se or a method analogous thereto, as well as the method described in the below-mentioned Method Q or Method S.

When $M^5$ is a halogen atom, compound (VIII) or a salt thereof may be commercially available products, or can also be produced according to a method known per se or a method analogous thereto.

The amount of compound (VIII) to be used is generally about 1-10 molar equivalents, preferably about 1-2 molar equivalents, per 1 mol of compound (VII).

The above-mentioned reaction is generally performed in a solvent that does not adversely influence the reaction, and a convenient base may be added to promote the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, and they may be mixed as appropriate. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine, diisopropylethylamine and the like), aromatic amines (pyridine, picoline, N,N-dimethylaniline, 4-dimethylaminopyridine and the like) and the like. The amount of the base to be used is generally about 1-100 molar equivalents, preferably about 1-5 molar equivalents, per 1 mol of compound (VII).

The reaction temperature is generally about −80-150° C., preferably about 0-50° C. The reaction time is generally about 0.5-48 hr, preferably 0.5-16 hr.

When $M^5$ is a hydroxy group, compound (VII) or a salt thereof is reacted with compound (VIII) or a salt thereof in the presence of a condensing agent to produce compound (XII) or a salt thereof.

Examples of the condensing agent used in this step include dicyclohexylcarbodiimide (DCC), diisopropylcarbodiimide (DIC), $N^1$-((ethylimino)methylene)-$N^3$,$N^3$-dimethylpropane-1,3-diamine hydrochloride (WSC), benzotriazol-1-yl-tris(dimethylamino)phosphonium hexafluorophosphate (BOP), diphenylphosphoryl azide (DPPA), (1-cyano-2-ethoxy-2-oxoethylideneaminooxy)dimethylamino-morpholino-carbenium hexafluorophosphate (COMU), ethyl (hydroxyimino)cyanoacetate (Oxyma), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 2-(1H-7-azabenzotriazol-1-yl)-1,1,3,3-tetramethyluronium hexafluorophosphate (HATU), O-[(ethoxycarbonyl)cyanomethyleneamino]-N, N, N',N'-tetramethyluronium hexafluorophosphate (HOTU) or 2,4,6-tripropyl-1,3,5,2,4,6-trioxatriphosphorinane-2,4,6-trioxide (T3P) and the like. These may be used alone, or can also be used in combination with an additive (e.g., N-hydroxysuccinimide (HOSu), 1-hydroxybenzotriazole (HOBt), 6-chloro-1-hydroxybenzotriazole (Cl-HOBt), 1-hydroxy-7-azabenzotriazole (HOAt) or 3-hydroxy-4-oxo-3,4-dihydro-1,2,3-benzotriazine and the like). The amount of the condensing agent to be used is generally about 1-10 molar equivalents, preferably about 1-2 molar equivalents, per 1 mol of compound (VIII). The amount of the additive to be used is generally about 1-10 molar equivalents, preferably about 1-2 molar equivalents, per 1 mol of compound (VIII).

The amount of compound (VII) to be used is generally about 1-10 molar equivalents, preferably about 1-2 molar equivalents, per 1 mol of compound (VIII).

The above-mentioned reaction is generally performed in a solvent that does not adversely influence the reaction, and a base may be added to promote the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like) and the like, which may be mixed as appropriate. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, diisopropylethylamine, N-methylmorpholine and the like), aromatic amines (pyridine, picoline, N,N-dimethylaniline and the like) and the like. The amount of the base to be used is generally about 1-100 molar equivalents, preferably about 1-5 molar equivalents, per 1 mol of compound (VIII).

While the reaction temperature varies depending on the kind of the solvent, it is generally about −80-150° C., preferably about 0-50° C., and the reaction time is generally about 0.5-100 hr, preferably about 0.5-60 hr.

(Step 2)

In this step, compound (VII) or a salt thereof is reacted with compound (IX) or a salt thereof to produce compound (XIII) or a salt thereof.

Compound (IX) or a salt thereof may be a commercially available product, or can be produced according to a method known per se or a method analogous thereto.

The amount of compound (IX) to be used is generally about 1-10 molar equivalents, preferably about 1-2 molar equivalents, per 1 mol of compound (VII).

The above-mentioned reaction is generally performed in a solvent that does not adversely influence the reaction, and a base may be added to promote the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like) and the like, which may be mixed as appropriate. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, diisopropylethylamine, N-methylmorpholine and the like), aromatic amines (pyridine, picoline, N,N-dimethylaniline and the like) and the like. The amount of the base to be used is generally about 1-100 molar equivalents, preferably about 1-5 molar equivalents, per 1 mol of compound (VII).

While the reaction temperature varies depending on the kind of the solvent, it is generally about −80-150° C., preferably about 0-50° C., and the reaction time is generally about 0.5-100 hr, preferably about 0.5-60 hr.

(Step 3)

In this step, compound (VII) or a salt thereof is reacted with compound (X) or a salt thereof in the presence of a base or a salt to produce compound (XIV) or a salt thereof.

Compound (X) may be commercially available products, or can also be produced according to a method known per se or a method analogous thereto.

Examples of the base or salt include inorganic base (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, and the like), inorganic salts (alkali metal salts such as sodium fluoride, potassium fluoride and the like, and the like) and the like. While the amount of the base or salt to be used varies depending on the kind of the solvent and other reaction conditions, it is generally about 1-10 molar equivalents, preferably about 1-5 molar equivalents, per 1 mol of compound (VII).

This reaction is performed in a solvent that does not adversely influence the reaction. Examples of the solvent that does not adversely influence the reaction include aromatic hydrocarbons (benzene, toluene, xylene and the like), alcohols (methanol, ethanol, propanol and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), aprotic polar solvent (N,N-dimethylformamide, dimethyl sulfoxide, hexamethylphosphoramide and the like) and the like. Two or more kinds of these solvents may be used in a mixture in an appropriate ratio.

The reaction temperature varies depending on the kind of the solvent, for example, about 0-200° C., preferably about 10-100° C. While the reaction time varies depending on the kind of compound (VII) or a salt thereof, reaction temperature and the like, it is, for example, about 0.1-48 hr.

(Step 4)

In this step, compound (VII) or a salt thereof is reacted with compound (XI) or a salt thereof to produce compound (XIV) or a salt thereof.

Compound (XI) may be commercially available products, or can also be produced according to a method known per se or a method analogous thereto.

While this step includes a condensation reaction and a reductive alkylation reaction in the presence of a reducing agent, these may be performed separately or simultaneously.

The condensation reaction can be performed by a method similar to that described in Method A, step 1 when $M^5$ is a hydroxy group.

Examples of the reducing agent in the reductive alkylation reaction include metal hydrides (sodium borohydride, lithium borohydride, zinc borohydride, sodium cyanoborohydride, sodium triacetoxyborohydride, lithium cyanoborohydride, dibutyl aluminum hydride, aluminum hydride, lithium aluminum hydride and the like), borane complex (borane-THF complex, catechol borane etc.) and the like. The amount of the reducing agent to be used is generally about 1-50 mol, preferably about 1-5 mol, per 1 mol of compound (VII).

This reaction is performed in a solvent inert to the reaction. Examples of such solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), alcohols (methanol, ethanol, 2-propanol, butanol, benzyl alcohol and the like), nitriles (acetonitrile and the like), N,N-dimethylformamide, dimethyl sulfoxide and the like, and these solvents may be used in a mixture at an appropriate ratio. In addition, to advantageously perform the reaction, acids (acetic acid, hydrochloric acid and the like) may be added.

While the reaction temperature varies depending on the kind of the solvent, it is generally about −80-80° C., preferably about −40-40° C. The reaction time is generally about 5 min-48 hr, preferably about 1-24 hr.

The amount of compound (XI) to be used is generally about 2-50 mol, preferably about 2-5 mol, per 1 mol of compound (VII).

[Method C]

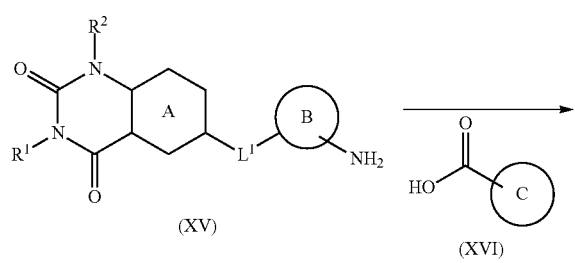

(XV)

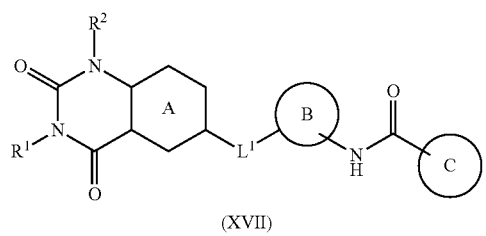

(XVII)

wherein each symbol is as defined above.

In this step, compound (XV) or a salt thereof is reacted with compound (XVI) or a salt thereof in the presence of a condensing agent to produce compound (XVII) or a salt thereof.

Compound (XV) can be produced according to a method known per se or a method analogous thereto, or by the method described in the below-mentioned Method J or a method analogous thereto. Compound (XVI) may be commercially available products, or can also be produced according to a method known per se or a method analogous thereto, as well as the method described in the below-mentioned Method Q or Method S. This step can be performed by a method similar to that described in Method A, step 1 when $M^5$ is a hydroxy group.

[Method D]

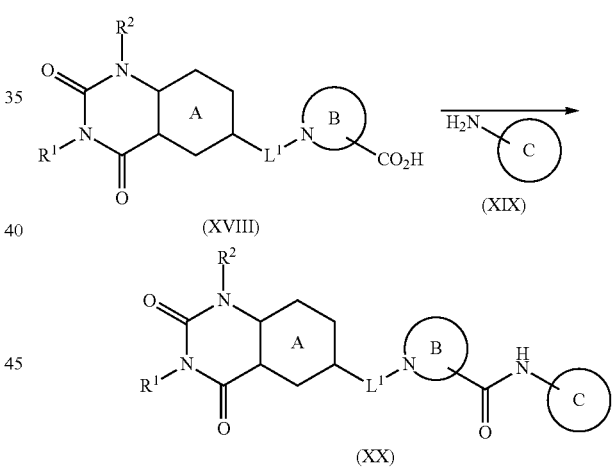

(XVIII)

(XX)

wherein each symbol is as defined above.

In this step, compound (XVIII) or a salt thereof is reacted with compound (XIX) or a salt thereof in the presence of a condensing agent to produce compound (XX) or a salt thereof.

Compound (XVIII) can be produced according to the method described in the below-mentioned Method J or a method analogous thereto.

Compound (XIX) may be commercially available products, or can also be produced according to a method known per se or a method analogous thereto, as well as the method described in the below-mentioned Method R or a method analogous thereto. This step can be performed by a method similar to that described in Method A, step 1 when $M^5$ is a hydroxy group.

[Method E]

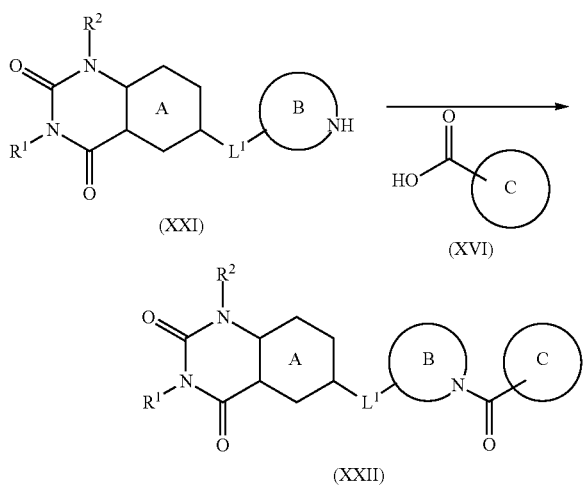

wherein each symbol is as defined above.

In this step, compound (XXI) or a salt thereof is reacted with compound (XVI) or a salt thereof in the presence of a condensing agent to produce compound (XXII) or a salt thereof.

Compound (XXI) can be produced according to a method known per se or a method analogous thereto, or the method described in the below-mentioned Method J, or a method analogous thereto. Compound (XVI) may be a commercially available product, or can also be produced according to a method known per se or a method analogous thereto, as well as the method described in the below-mentioned Method Q or a method analogous thereto. This step can be performed by a method similar to that described in Method A, step 1 when $M^5$ is a hydroxy group.

[Method F]

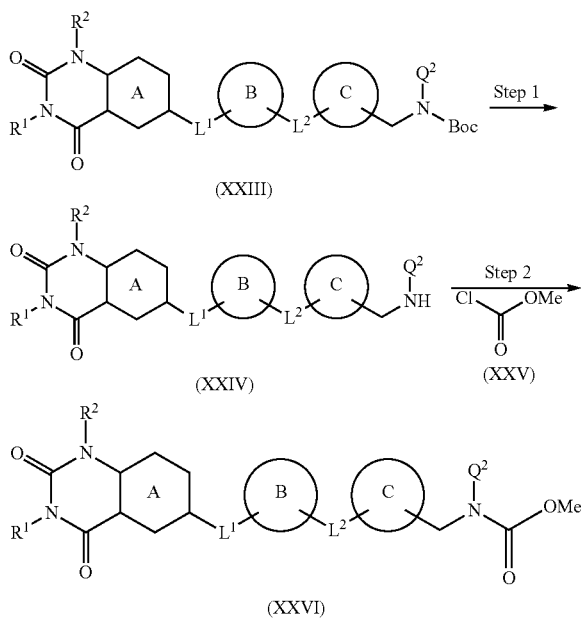

wherein $Q^2$ is a hydrocarbon group that may form a ring together with the substituent on ring C or a hydrogen atom, and other symbols are as defined above.

(Step 1)

In this step, compound (XXIII) or a salt thereof is subjected to deprotection reaction to produce compound (XXIV) or a salt thereof.

Compound (XXIII) can be produced according to the method described in the synthetic method of compound (I), for example, Method B, or a method analogous thereto.

Such deprotection can be performed according to a known method. For example, while subject to variation depending on the kind of compound (XXIII), it is generally performed in the presence of an acid and in a solvent as necessary that does not adversely influence the reaction.

Examples of the acid include mineral acids (hydrochloric acid, hydrobromic acid, sulfuric acid, hydrogen chloride and the like), carboxylic acids (acetic acid, trifluoroacetic acid, trichloroacetic acid and the like), sulfonic acids (methanesulfonic acid, p-toluenesulfonic acid and the like), Lewis acids (aluminum chloride, tin chloride, zinc bromide and the like) and the like, and two or more kinds thereof may be used in a mixture as necessary. While the amount of the acid to be used varies depending on the kind of the solvent and other reaction conditions, it is generally not less than about 0.1 mol equivalent per 1 mol of compound (XXIII), and it can also be used as a solvent.

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like), water and the like, and a mixed solvent thereof can be mentioned.

The reaction temperature varies depending on the kind of the solvent, and it is, for example, about −50-200° C., preferably about 0-100° C. While the reaction time varies depending on the kind of compound (XXIII), reaction temperature and the like, it is, for example, about 0.5-100 hr, preferably about 0.5-24 hr. [0122]

(Step 2)

In this step, compound (XXIV) or a salt thereof is reacted with compound (XXV) to produce compound (XXVI) or a salt thereof.

Compound (XXV) can be a commercially available product.

The amount of compound (XXV) to be used is generally about 1-10 molar equivalents, preferably about 1-2 molar equivalents, per 1 mol of compound (XXIV).

The above-mentioned reaction is generally performed in a solvent that does not adversely influence the reaction, and a convenient base may be added to promote the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, and they may be mixed as appropriate. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine, diisopropylethylamine and the like), aromatic amines (pyridine, picoline, N,N-dimethylaniline, 4-dimethylaminopyridine and the like) and the like. The amount of the base to be used is generally about 1-100 molar equivalents, preferably about 1-5 molar equivalents, per 1 mol of compound (XXIV).

The reaction temperature is generally about −80-150° C., preferably about 0-50° C., and the reaction time is generally about 0.5-48 hr, preferably about 0.5-16 hr.

[Method G]

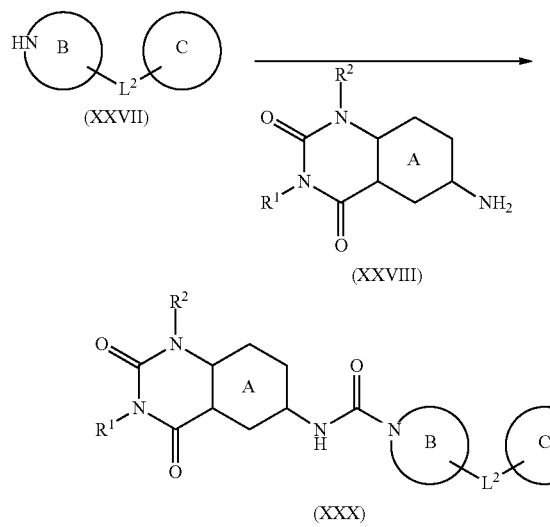

wherein each symbol is as defined above.

(Step 1)

In this step, compound (XXX) or a salt thereof is produced from compound (XXVII) or a salt thereof and compound (XXVIII) or a salt thereof by using a carbonylation reagent.

Compound (XXVII) can be produced by a method known per se or a method analogous thereto, or by the method described in the below-mentioned Method K or a method analogous thereto, and compound (XXVIII) is a commercially available product, or can also be produced by a method known per se or a method analogous thereto, or the method described in the below-mentioned Method M, N or O or a method analogous thereto.

Examples of the carbonylation reagent include phosgene, triphosgene, carbodiimides (e.g., carbodiimidazole), phenyl halocarbonates (e.g., 4-nitrophenyl chloroformate) and the like. In addition, to advantageously perform the reaction, a base may be added.

The amount of the carbonylation reagent to be used is varies depending on the kind of the solvent, and other reaction conditions, and it is generally about 1-10 molar equivalents, preferably about 1-5 molar equivalents, per 1 mol of compound (XXVII) and compound (XXVIII).

As the base, an organic base (amines such as trimethylamine, triethylamine, diisopropylethylamine and the like, pyridine and the like) and the like are used.

The amount of the base to be used varies depending on the kind of the solvent, and other reaction conditions, and it is generally about 1-10 molar equivalents, preferably about 1-5 molar equivalents, per 1 mol of compound (XXVII) and compound (XXVIII).

This reaction is performed in a solvent that does not adversely influence the reaction. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, 1,2-dichloroethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (N,N-dimethylformamide and the like) and the like. Two or more kinds of these solvents may be used in a mixture in an appropriate ratio.

The reaction temperature varies depending on the kind of the solvent, and it is, for example, about −50-200° C., preferably about 0-100° C. While the reaction time varies depending on the kind of compound (XXVIII) or a salt thereof, reaction temperature and the like, it is, for example, about 0.5-100 hr, preferably about 0.5-24 hr.

[Method H]

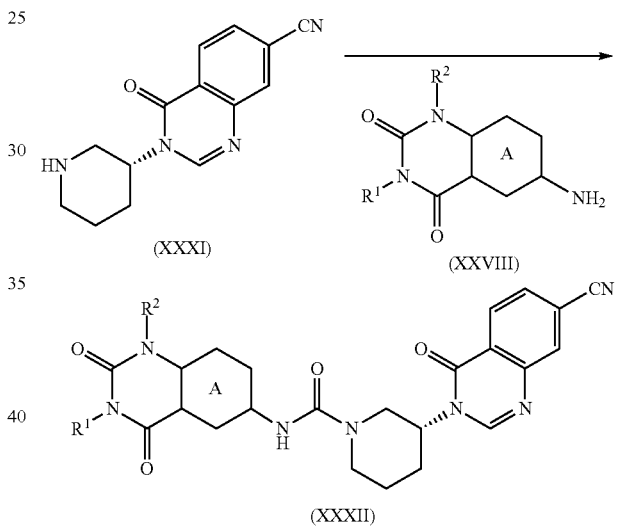

wherein each symbol is as defined above.

In this step, compound (XXXII) or a salt thereof is produced from compound (XXXI) or a salt thereof and compound (XXVIII) or a salt thereof, by using a carbonylation reagent step.

Compound (XXXI) can be produced according to the method described in the below-mentioned Method L or a method analogous thereto. This step can be performed by a method similar to that described in Method G.

[Method I]

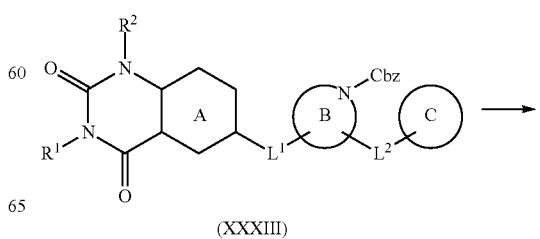

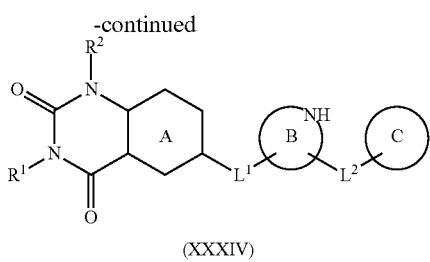

(XXXIV)

wherein Cbz is a benzyloxycarbonyl group, and each symbol is as defined above.

In this step, compound (XXXIII) or a salt thereof is subjected to deprotection reaction to produce compound (XXXIV) or a salt thereof.

Compound (XXXIII) can also be produced according to the production method of compound (I), for example, the method described in Method E or a method analogous thereto.

Such deprotection reaction can be performed according to a known method. For example, while subject to variation depending on the kind of compound (XXXIII), it is performed by reduction by catalytic hydrogenation using a transition metal catalyst, in a solvent that does not adversely influence the reaction.

Examples of the transition metal catalyst to be used in this step include palladiums (palladium carbon, palladium hydroxide, palladium oxide and the like), nickels (Raney-nickel and the like), platinums (platinum oxide, platinum carbon and the like), rhodiums (rhodium acetate, rhodium carbon and the like) and the like. The amount thereof to be used is, for example, about 0.001-1 equivalents, preferably about 0.01-0.5 equivalents, per 1 mol of compound (XXXIII). The hydrogenation reaction is generally performed in a solvent inert to the reaction. Examples of the solvent include alcohols (methanol, ethanol, propanol, butanol and the like), hydrocarbons (benzene, toluene, xylene and the like), halogenated hydrocarbons (dichloromethane, chloroform and the like), ethers (diethyl ether, dioxane, tetrahydrofuran and the like), esters (ethyl acetate and the like), amides (N,N-dimethylformamide and the like), carboxylic acids (acetic acid and the like), water and a mixture thereof. The reaction is performed at a hydrogen pressure of generally about 1-500 atm, preferably about 1-100 atm.

While the reaction temperature varies depending on the kind of the solvent, it is generally about 0-150° C., preferably about 20-100° C., and the reaction time is generally 5 min.-72 hr, preferably about 0.5-40 hr.

[Method J]

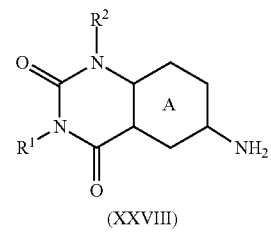

(XXVIII)

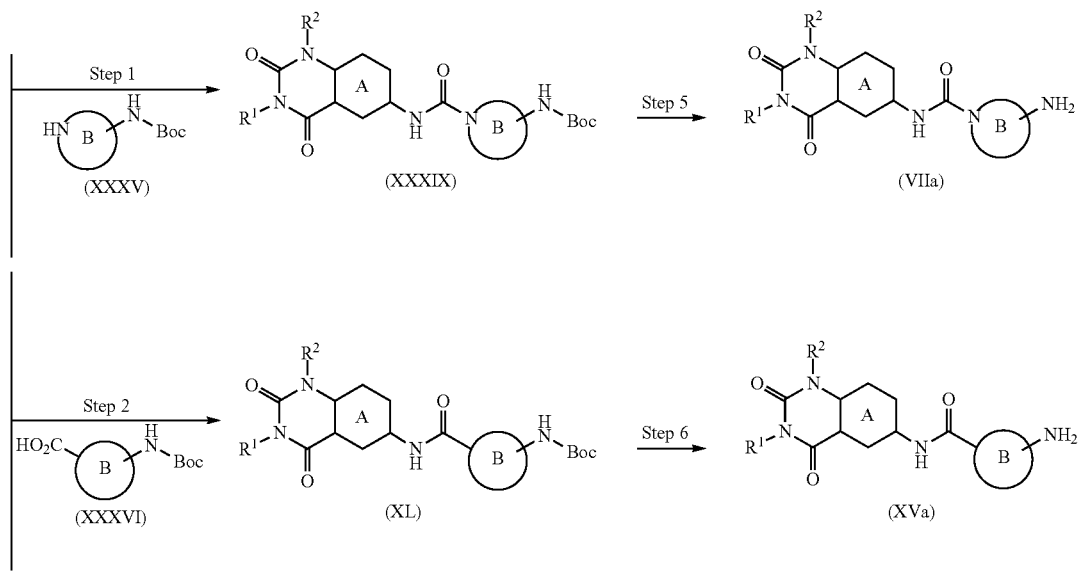

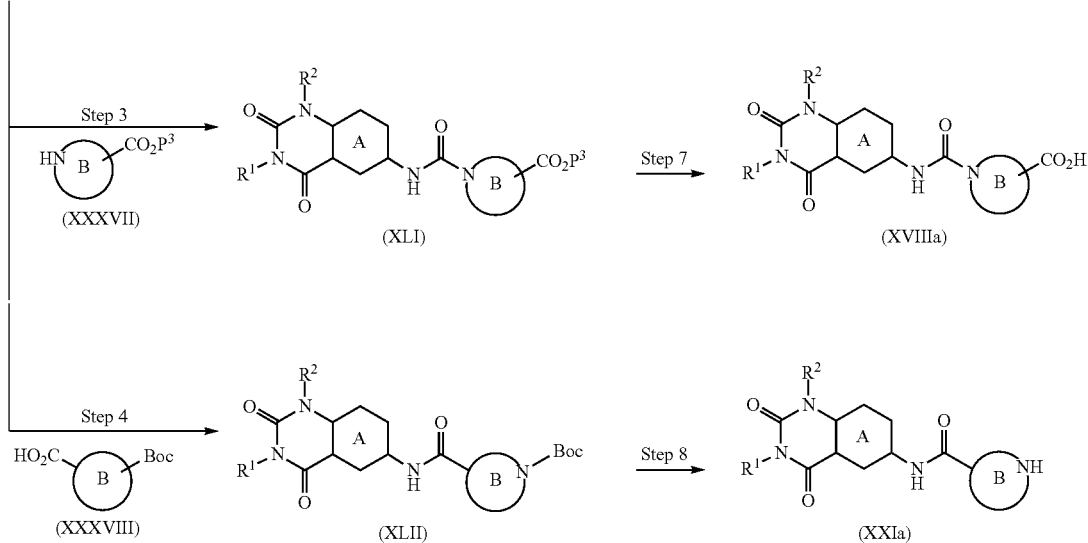

wherein $P^3$ is an alkyl group optionally having substituent(s) (e.g., methyl group, an ethyl group), and other symbols are as defined above.

(Step 1)

In this step, compound (XXXIX) or a salt thereof is produced from compound (XXVIII) or a salt thereof and compound (XXXV) or a salt thereof by using a carbonylation reagent.

Compound (XXXV) may be a commercially available product, or can also be produced according to a method known per se or a method analogous thereto. This step can be performed by a method similar to that described in Method G.

(Step 2)

In this step, compound (XXVIII) or a salt thereof is reacted with compound (XXXVI) or a salt thereof in the presence of a condensing agent to produce compound (XL) or a salt thereof.

Compound (XXXVI) may be a commercially available product, or can also be produced according to a method known per se or a method analogous thereto. This step can be performed by a method similar to that described in Method A, step 1 when $M^5$ is a hydroxy group.

(Step 3)

In this step, compound (XLI) or a salt thereof is produced from compound (XXVIII) or a salt thereof and compound (XXXVII) or a salt thereof by using a carbonylation reagent.

Compound (XXXVII) may be a commercially available product, or can also be produced according to a method known per se or a method analogous thereto. This step can be performed by a method similar to that described in Method G.

(Step 4)

In this step, compound (XXVIII) or a salt thereof is reacted with compound (XXXVIII) or a salt thereof in the presence of a condensing agent to produce compound (XLII) or a salt thereof.

Compound (XXXVIII) may be a commercially available product, or can also be produced according to a method known per se or a method analogous thereto or Method P. This step can be performed by a method similar to that described in Method A, step 1 when $M^5$ is a hydroxy group.

(Step 5)

In this step, compound (XXXIX) or a salt thereof is subjected to deprotection reaction to produce compound (VIIa) or a salt thereof. This step can be performed by a method similar to that described in Method F, step 1.

(Step 6)

In this step, compound (XL) or a salt thereof is subjected to deprotection reaction to produce compound (XVa) or a salt thereof. This step can be performed by a method similar to that described in Method F, step 1.

(Step 7)

In this step, compound (XLI) or a salt thereof is subjected to hydrolysis reaction to be converted to compound (XVIIIa) or a salt thereof. While this reaction can be performed by a method known per se, it is generally performed in the presence of an acid or a base and, where necessary, in a solvent that does not adversely influence the reaction.

As the acid, mineral acids (hydrochloric acid, hydrobromic acid, sulfuric acid and the like), carboxylic acids (acetic acid, trifluoroacetic acid, trichloroacetic acid and the like), sulfonic acids (methanesulfonic acid, p-toluenesulfonic acid and the like), Lewis acids (aluminum chloride, tin chloride, zinc bromide and the like) and the like are used, and two or more kinds thereof may be mixed as necessary. The amount of the acid to be used varies depending on the kind of the solvent, and other reaction conditions, and is generally about 0.1 mol or more equivalents per 1 mol of compound (XLI). It can also be used as a solvent.

As the base, for example, inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkali metal alkoxides such as sodium methoxide, sodium ethoxide and the like, and the like), organic bases (amines such as trimethylamine, triethylamine, diisopropylethylamine and the like, cyclic amines such as pyridine, 4-dimethylaminopyridine and the like, and the like) and the like are used. Of these, sodium hydroxide is preferable. The amount of the base to be used varies depending on the kind of the solvent, and other reaction conditions, and is generally about 1-10 molar equivalents, preferably about 1-5 molar equivalents, per 1 mol of compound (XLI).

Examples of the solvent that does not adversely influence the reaction include alcohols (methanol, ethanol, propanol, 2-propanol, butanol, isobutanol, t-butanol and the like), hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), carboxylic acids (acetic acid and the like), amides (N,N-dimethylformamide, dimethylacetamide and the like), sulfoxides (dimethyl sulfoxide and the like), water and the like. Two or more kinds of these solvents may be used in a mixture in an appropriate ratio.

The reaction temperature is, for example, about −50-200° C., preferably about 0-100° C., and the reaction time varies depending on the kind of compound (XLI) or a salt thereof, reaction temperature and the like, and it is, for example, about 0.5-100 hr, preferably about 0.5-24 hr.

(Step 8)

In this step, compound (XLII) or a salt thereof is subjected to deprotection reaction to produce compound (XXIa) or a salt thereof. This step can be performed by a method similar to that described in Method F, step 1.

[Method K]

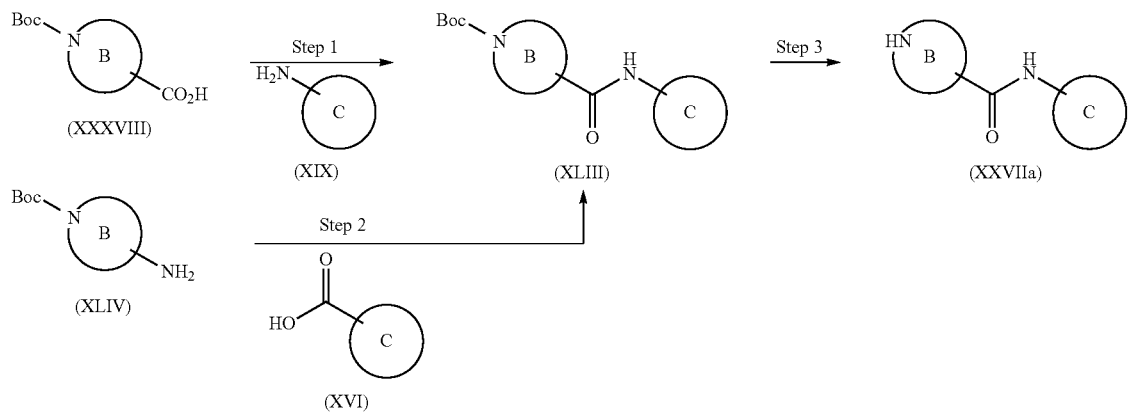

[Method L]

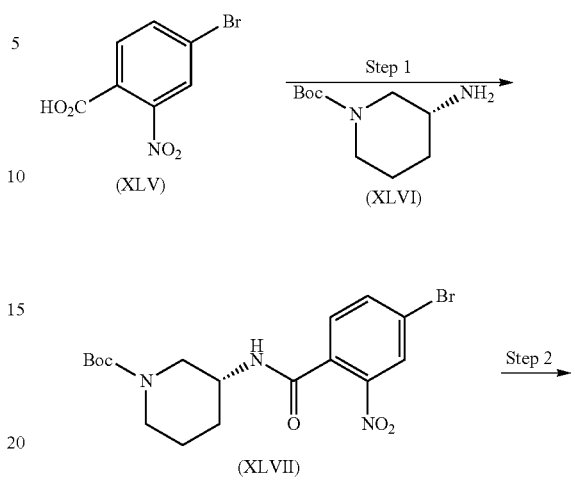

wherein each symbol is as defined above.

(Step 1)

In this step, compound (XXXVIII) or a salt thereof is reacted with compound (XIX) or a salt thereof in the presence of a condensing agent to produce compound (XLIII) or a salt thereof.

This step can be performed by a method similar to that described in Method A, step 1 when $M^5$ is a hydroxy group.

(Step 2)

In this step, compound (XLIV) or a salt thereof is reacted with compound (XVI) or a salt thereof in the presence of a condensing agent to produce compound (XLIII) or a salt thereof.

Compound (XLIV) may be a commercially available product, or can also be produced according to a method known per se or a method analogous thereto. This step can be performed by a method similar to that described in Method A, step 1 when $M^5$ is a hydroxy group.

(Step 3)

In this step, compound (XLIII) or a salt thereof is subjected to deprotection reaction to produce compound (XXVIIa) or a salt thereof. This step can be performed by a method similar to that described in Method F, step 1.

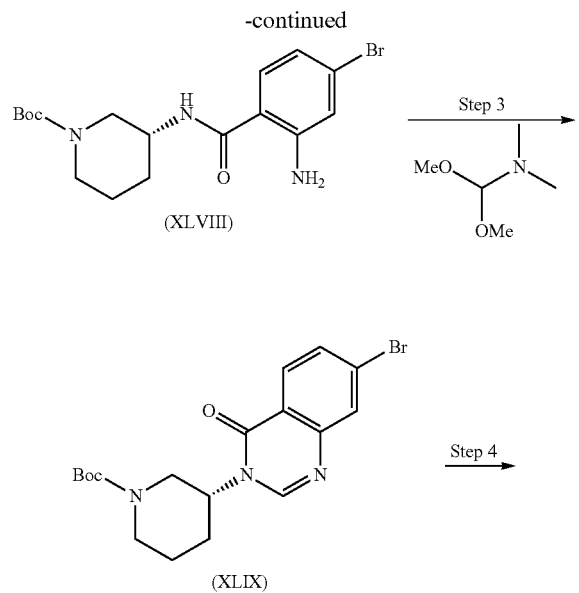

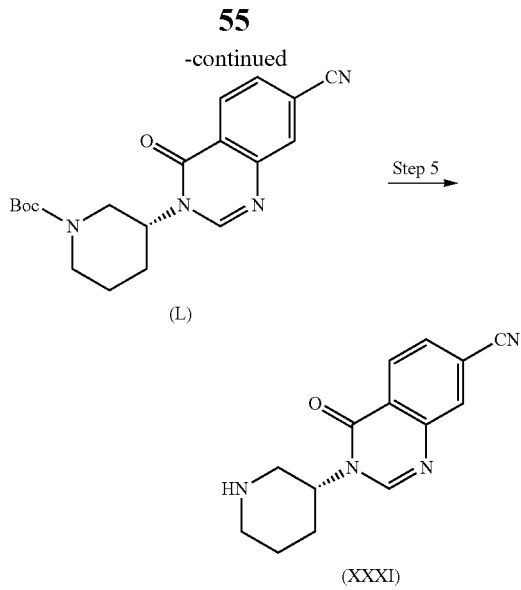

wherein each symbol is as defined above.

(Step 1)

In this step, compound (XLV) or a salt thereof is reacted with compound (XLVI) or a salt thereof in the presence of a condensing agent to produce compound (XLVII).

Compound (XLV) and compound (XLVI) are each commercially available products, or can also be produced according to a method known per se or a method analogous thereto. This step can be performed by a method similar to that described in Method A, step 1 when $M^5$ is a hydroxy group.

(Step 2)

In this step, compound (XLVII) is subjected to a reduction reaction to produce compound (XLVIII) or a salt thereof.

The reduction reaction can be performed by reduction using a metal or a metal salt or reduction by catalytic hydrogenation using a transition metal catalyst, in a solvent that does not adversely influence the reaction.

As the metal or metal salt to be used for the "reduction using a metal or a metal salt", for example, alkali metals (lithium, sodium, potassium and the like), alkaline earth metals (magnesium, calcium and the like), other metals (zinc, chrome, titanium, iron, samarium, selenium and the like), metal salts (zinc-amalgam, zinc-copper alloy, aluminum-amalgam, sodium hydrosulfite and the like) and the like are preferable. The amount of the metal or metal salt to be used is, for example, 1-50 molar equivalents, preferably 1-5 molar equivalents, per 1 mol of compound (XLVII).

Examples of the solvent to be used for the reaction include alcohols (methanol, ethanol, 2-propanol, t-butanol, benzyl alcohol and the like), amines (liquid ammonia, methylamine, ethylamine, ethylenediamine and the like), ethers (diethyl ether, tetrahydrofuran, dioxane, dimethoxyethane and the like), mineral acids (hydrochloric acid, hydrobromic acid, sulfuric acid and the like), carboxylic acids (acetic acid and the like), amides (hexamethylphosphoramide), water and the like, and these solvents can be used alone or in a mixture.

The reaction temperature varies depending on the kind of the solvent, is generally about −80-150° C., preferably about −80-100° C. The reaction time is generally 5 min-48 hr, preferably 1-24 hr.

Examples of the transition metal catalyst to be used for the "reduction by catalytic hydrogenation using a transition metal catalyst" include palladiums (palladium carbon, palladium hydroxide, palladium oxide and the like), nickels (Raney-nickel and the like), platinums (platinum oxide, platinum carbon and the like), rhodiums (rhodium acetate, rhodium carbon and the like) and the like. The amount thereof to be used is, for example, about 0.001-1 equivalents, preferably about 0.01-0.5 equivalents, per 1 mol of compound (XLVII). The hydrogenation reaction is generally performed in a solvent inert to the reaction. Examples of the solvent include alcohols (methanol, ethanol, propanol, butanol and the like), hydrocarbons (benzene, toluene, xylene and the like), halogenated hydrocarbons (dichloromethane, chloroform and the like), ethers (diethyl ether, dioxane, tetrahydrofuran and the like), esters (ethyl acetate and the like), amides (N,N-dimethylformamide and the like), carboxylic acids (acetic acid and the like), water and a mixture thereof. The reaction is performed at a hydrogen pressure of generally about 1-500 atm, preferably about 1-100 atm.

The reaction temperature varies depending on the kind of the solvent, and it is generally about 0-150° C., preferably about 20-100° C. The reaction time is generally 5 min-72 hr, preferably 0.5-40 hr.

(Step 3)

In this step, compound (XLVIII) or a salt thereof is reacted with N,N-dimethylformamide dimethyl acetal to produce compound (XLIX) or a salt thereof.

N,N-dimethylformamide dimethyl acetal is a commercially available product.

This step can be performed in a solvent that does not adversely influence the reaction. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (N,N-dimethylformamide and the like), sulfoxides (dimethyl sulfoxide and the like), carboxylic acids (acetic acid and the like) and the like. Two or more kinds of these solvents may be used in a mixture in an appropriate ratio.

The reaction temperature is, for example, about 0-200° C., and the reaction time varies depending on the kind of compound (XLVIII) or a salt thereof, reaction temperature and the like, it is, for example, about 0.5-100 hr, preferably about 0.5-24 hr.

(Step 4)

In this step, compound (XLIX) or a salt thereof is subjected to a cyanation reaction to produce compound (L) or a salt thereof.

This reaction can be performed in the presence or absence of a transition metal catalyst by using a cyanation reagent in a solvent that does not adversely influence the reaction.

Examples of the transition metal catalyst to be used in this reaction include palladium catalysts (palladium acetate, palladium chloride, tetrakistriphenylphosphine palladium and the like), nickel catalysts (nickel chloride and the like) and the like, and a ligand (triphenylphosphine, tri-t-butylphosphine, S-Phos, BINAP and the like) may also be used as necessary. While the amount of the transition metal catalyst to be used varies depending on the kind of the solvent and other reaction conditions, it is generally about 0.001-1 mol equivalent, preferably about 0.1-0.5 molar equivalent, per 1 mol of compound (XLIX). The amount of the ligand to be used is generally about 0.001-1 mol equivalent per 1 mol of compound (XLIX).

Examples of the cyanation reagent to be used in this reaction include zinc cyanide, copper cyanide and the like. While the amount thereof to be used varies depending on the kind of the solvent and other reaction conditions, it is generally about 0.5-10 molar equivalents, preferably about 0.5-2 molar equivalents, per 1 mol of compound (XLIX).

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (N,N-dimethylformamide and the like), sulfoxides (dimethyl sulfoxide and the like) and the like. Two or more kinds of these solvents may be used in a mixture in an appropriate ratio.

The reaction temperature is, for example, about −10-200° C. The reaction time varies depending on the kind of compound (XLIX) or a salt thereof, reaction temperature and the like, and it is, for example, about 0.5-100 hr, preferably about 0.5-24 hr. The reaction may be performed under microwave irradiation as necessary.

(Step 5)

In this step, compound (L) or a salt thereof is subjected to deprotection reaction to produce compound (XXXI) or a salt thereof. This step can be performed by a method similar to that described in Method F, step 1.

[Method M]

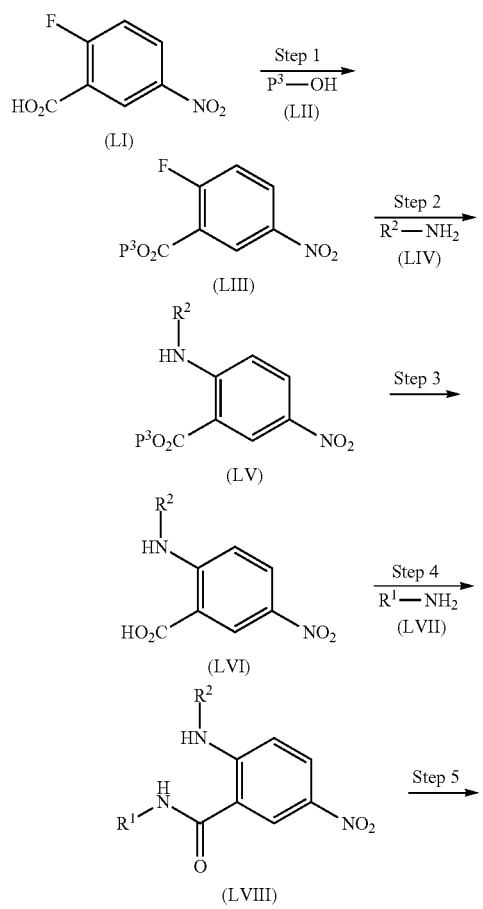

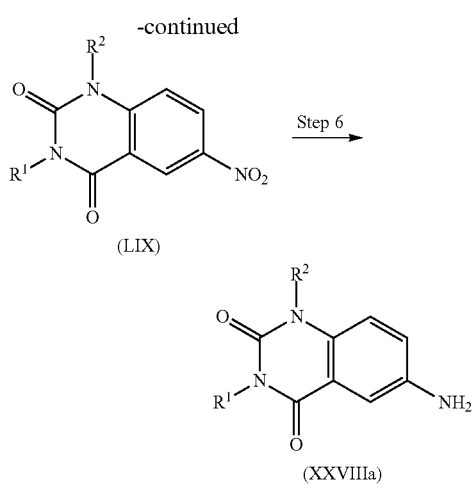

wherein each symbol is as defined above.

(Step 1)

In this step, compound (LI) or a salt thereof is esterified to produce compound (LIII).

Compound (LI) and compound (LII) are commercially available products, or can also be produced by a method known per se or a method analogous thereto.

This reaction can be performed according to a known method. For example, compound (LIII) can be produced by heating in the presence of an acid catalyst and using compound (LI) as a solvent.

Examples of the acid catalyst to be used in this reaction include mineral acids (hydrochloric acid, sulfuric acid and the like), organic sulfonic acids (methanesulfonic acid, p-toluenesulfonic acid and the like), Lewis acids (boron fluoride etherate and the like), thionyl chloride and the like. The amount of the acid catalyst to be used varies depending on the kind of the solvent and other reaction conditions, and it is generally about 0.0001-10 molar equivalents, preferably about 0.01-0.1 mol equivalent, per 1 mol of compound (LI).

While the reaction temperature varies depending on the kind of compound (LI), it is, for example, about 20-200° C., preferably about 50-150° C., and the reaction time is, for example, about 0.5-100 hr, preferably about 0.5-24 hr.

(Step 2)

In this step, compound (LIII) or a salt thereof is reacted with compound (LIV) or a salt thereof in the presence of a base to produce compound (LV) or a salt thereof.

Compound (LIV) may be a commercially available product, or can also be produced according to a method known per se or a method analogous thereto.

Examples of the base to be used in this step include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1-100 molar equivalents, preferably about 1-5 molar equivalents, per 1 mol of compound (LIII).

The above-mentioned reaction is performed in a solvent that does not adversely influence the reaction. Examples of the solvent to be used include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like) and the like, and they may be mixed as appropriate.

The reaction temperature varies depending on the kind of the solvent, and is, for example, about 0-200° C., preferably about 25-100° C., and the reaction time is, for example, about 0.5-100 hr, preferably about 0.5-24 hr.
(Step 3)

In this step, compound (LV) or a salt thereof is subjected to hydrolysis reaction to be converted to compound (LVI) or a salt thereof. This step can be performed by a method similar to that described in Method J, step 7.
(Step 4)

In this step, compound (LVI) is reacted with compound (LVII) or a salt thereof in the presence of a condensing agent to produce compound (LVIII) or a salt thereof.

Compound (LVII) may be a commercially available product, or can also be produced according to a method known per se or a method analogous thereto. This step can be performed by a method similar to that described in Method A, step 1 when $M^5$ is a hydroxy group.
(Step 5)

In this step, compound (LIX) or a salt thereof is produced from compound (LVIII) or a salt thereof by triphosgene in the presence of a base.

The amount of triphosgene to be used varies depending on the kind of the solvent, and other reaction conditions, and it is generally about 1-10 molar equivalents, preferably about 1-5 molar equivalents, per 1 mol of compound (LVIII).

As the base, organic bases (amines such as trimethylamine, triethylamine, diisopropylethylamine and the like, pyridine and the like) and the like are used.

The amount of the base to be used varies depending on the kind of the solvent, and other reaction conditions, and it is generally about 1-10 molar equivalents, preferably about 1-5 molar equivalents, per 1 mol of compound (LVIII).

This reaction is performed in a solvent that does not adversely influence the reaction. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, 1,2-dichloroethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (N,N-dimethylformamide and the like) and the like can be mentioned. Two or more kinds of these solvents may be used in a mixture in an appropriate ratio.

The reaction temperature varies depending on the kind of the solvent, and is, for example, about −50-200° C., preferably about 0-100° C. The reaction time varies depending on the kind of compound (LVIII) or a salt thereof, the reaction temperature and the like, and it is, for example, about 0.5-100 hr, preferably about 0.5-24 hr.
(Step 6)

In this step, compound (LIX) or a salt thereof is subjected to a reduction reaction to produce compound (XXVIIIa) or a salt thereof.

Compound (LIX) can also be produced by, besides the above-mentioned step 5, the method described in the below-mentioned Method N or a method analogous thereto. This step can be performed by a method similar to that described in Method L, step 2.

[Method N]

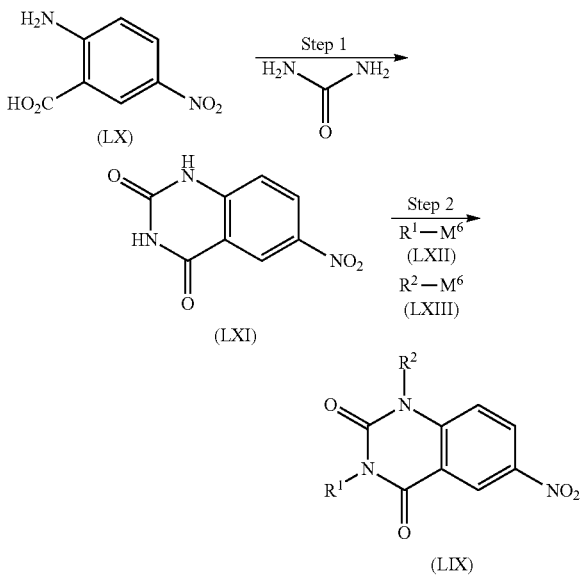

wherein each symbol is as defined above.
(Step 1)

In this step, compound (LX) or a salt thereof is reacted with urea to produce compound (LXI) or a salt thereof.

Compound (LX) is a commercially available product.

This step is performed in a solvent that does not adversely influence the reaction. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylacetamide and the like), sulfoxides (dimethyl sulfoxide and the like) and the like. Of these, dimethylacetamide is preferable. Two or more kinds of these solvents may be used in a mixture in an appropriate ratio. In addition, the reaction an also be performed without using a solvent. When a solvent is used, the amount of urea to be used is generally about 1-10 molar equivalents, preferably about 1-5 molar equivalents, per 1 mol of compound (LX), and when a solvent is not used, it is generally about 1-500 molar equivalents, preferably about 1-50 molar equivalents, per 1 mol of compound (LX).

When a solvent is used, the reaction temperature varies depending on the kind of the solvent, and is, for example, about 0-200° C., preferably about 100-200° C. In this case, microwave may be irradiated to accelerate the reaction. The reaction time is, for example, about 0.1-100 hr, preferably about 0.1-24 hr.

When a solvent is not used, the reaction temperature is, for example, about 0-300° C., preferably about 100-200° C. The reaction time is, for example, about 0.1-100 hr, preferably about 0.1-24 hr.
(Step 2)

In this step, when compound (LXII) and compound (LXIII) are the same, they are reacted with compound (LXI) to produce compound (LIX) or a salt thereof.

In this step, a base may be added to promote the reaction. Examples of the base to be used include alkali metal hydroxides (sodium hydroxide, potassium hydroxide and the like), alkali metal hydrides (sodium hydride, lithium hydride and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, diisopropylethylamine, N-methylmorpholine and the like), aromatic amines (pyridine, picoline, N,N-dimethylaniline and the like) and the like can be mentioned. The amount of the base to be used is generally about 1-100 molar equivalents, preferably about 1-5 molar equivalents, per 1 mol of compound (LXI).

This reaction is performed in a solvent that does not adversely influence the reaction. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (N,N-dimethylformamide and the like), sulfoxides (dimethyl sulfoxide and the like) and the like. Two or more kinds of these solvents may be used in a mixture in an appropriate ratio.

The reaction temperature varies depending on the kind of the solvent, and is, for example, about −50-200° C., preferably about 0-100° C. While the reaction time varies depending on the kind of compound (LXI) or a salt thereof, reaction temperature and the like, it is, for example, about 0.5-100 hr, preferably about 0.5-24 hr.

Compound (LXII) and compound (LXIII) may be commercially available products, or can also be produced according to a method known per se or a method analogous thereto. The amount of compound (LXII) or compound (LXIII) to be used is each generally about 1-10 molar equivalents, preferably about 1-5 molar equivalents, per 1 mol of compound (LXI).

[O Method]

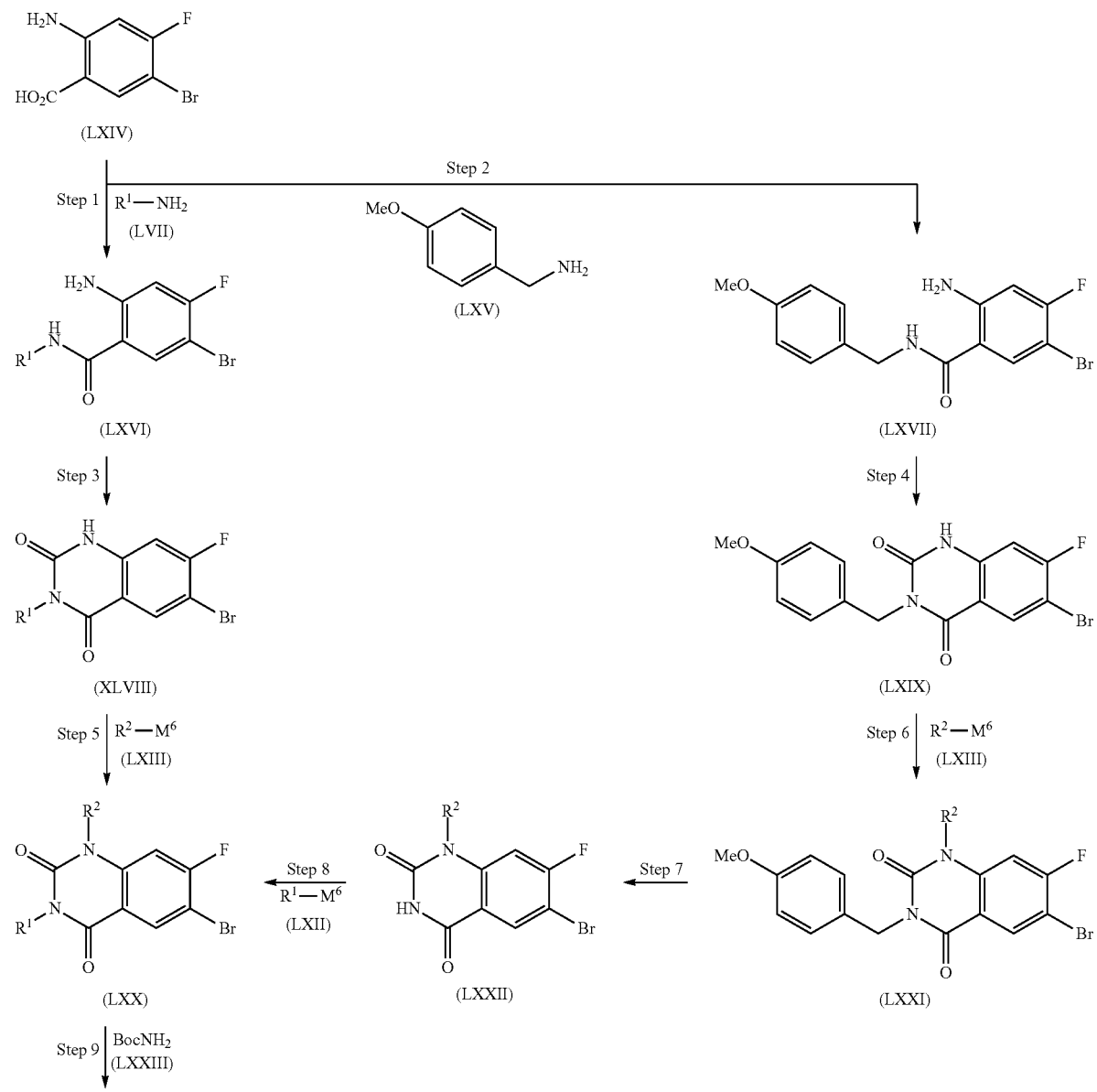

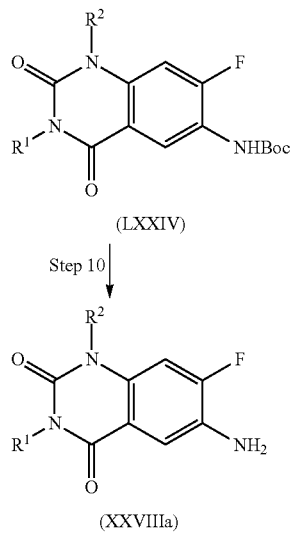

(LXXIV)

Step 10

(XXVIIIa)

wherein each symbol is as defined above.

(Step 1)

In this step, compound (LXIV) or a salt thereof is reacted with compound (LVII) or a salt thereof in the presence of a condensing agent to produce compound (LXVI) or a salt thereof.

Compound (LXIV) may be a commercially available product, or can also be produced according to a method known per se or a method analogous thereto. This step can be performed by a method similar to that described in Method A, step 1 when M⁵ is a hydroxy group.

(Step 2)

In this step, compound (LXIV) or a salt thereof is reacted with compound (LXV) or a salt thereof in the presence of a condensing agent to produce compound (LXVII) or a salt thereof.

Compound (LXV) may be a commercially available product, or can also be produced according to a method known per se or a method analogous thereto. This step can be performed by a method similar to that described in Method A, step 1 when M⁵ is a hydroxy group.

(Step 3)

In this step, compound (LXVIII) or a salt thereof is produced from compound (LXVI) or a salt thereof by a carbonylation reagent. This step can be performed by a method similar to that described in Method M, step 5.

(Step 4)

In this step, compound (LXIX) or a salt thereof is produced from compound (LXVII) or a salt thereof by a carbonylation reagent. This step can be performed by a method similar to that described in Method M, step 5.

(Step 5)

In this step, compound (LXVIII) is reacted with compound (LXIII) to produce compound (LXX) or a salt thereof. This step can be performed by a method similar to that described in Method N, step 2.

(Step 6)

In this step, compound (LXIX) is reacted with compound (LXIII) to produce compound (LXXI) or a salt thereof. This step can be performed by a method similar to that described in Method N, step 2.

(Step 7)

In this step, compound (LXXI) or a salt thereof is subjected to deprotection reaction to produce compound (LXXII) or a salt thereof. This step can be performed by a method similar to that described in Method F, step 1.

(Step 8)

In this step, compound (LXXII) or a salt thereof is reacted with compound (LXII) to produce compound (LXX) or a salt thereof. This step can be performed by a method similar to that described in Method N, step 2.

(Step 9)

In this step, compound (LXX) or a salt thereof is reacted with compound (LXXIII) in the presence of a transition metal catalyst and a base to produce compound (LXXIV) or a salt thereof.

Examples of the transition metal catalyst to be used in this reaction include palladium catalysts (palladium acetate, palladium chloride, tetrakistriphenylphosphine palladium, tris(dibenzylideneacetone)dipalladium(0) and the like), nickel catalysts (nickel chloride and the like) and the like and, where necessary, a ligand (triphenylphosphine, tri-t-butylphosphine, S-Phos, XPhos, BINAP, 2'-(di-tert-butylphosphino)-N, N-dimethyl-[1,1'-biphenyl]-2-amine and the like), a base (e.g., organic amines (trimethylamine, triethylamine, diisopropylethylamine, N-methylmorpholine, 1,8-diazabicyclo[5,4,0]undeca-7-ene, pyridine, N,N-dimethylaniline and the like), an alkali metal salt (sodium hydrogen carbonate, potassium hydrogen carbonate, sodium carbonate, potassium carbonate, cesium carbonate, sodium phosphate, potassium phosphate, sodium hydroxide, potassium hydroxide, lithium acetate and the like), metal hydride (potassium hydride, sodium hydride and the like), alkali metal alkoxide (sodium methoxide, sodium ethoxide, sodium-t-butoxide, potassium-t-butoxide and the like), alkali disilazide (lithium disilazide, sodium disilazide, potassium disilazide and the like)) may be added, or metal oxide (copper oxide, silver oxide and the like) and the like may be used as a cocatalyst. The amount of the catalyst to be used is generally about 0.0001-1 mol equivalents, preferably about 0.01-0.5 molar equivalents, per 1 mol of compound (LXX). The amount of the ligand to be used is generally about 0.0001-4 molar equivalents, preferably about 0.01-2 molar equivalents, per 1 mol of compound (LXX). The amount of the base to be used is generally about 1-10 molar equivalents, preferably about 1-2 molar equivalents, per 1 mol of compound (LXX). The amount of the cocatalyst to be used is generally about 0.0001-4 molar equivalents, preferably about 0.01-2 molar equivalents, per 1 mol of compound (LXX).

The solvent to be used may be any as long as it does not adversely influence the reaction and, for example, hydrocarbons (benzene, toluene, xylene and the like), halogenated hydrocarbons (chloroform, 1,2-dichloroethane and the like), nitriles (acetonitrile and the like), ethers (dimethoxyethane, tetrahydrofuran), alcohols (methanol, ethanol and the like), aprotic polar solvents (N,N-dimethylformamide, dimethyl sulfoxide, hexamethylphosphoramide and the like), water and a mixture thereof can be used.

The reaction temperature is generally about −100-200° C., preferably about −80-150° C., and the reaction time is generally about 0.5-48 hr, preferably about 0.5-24 hr. the reaction may be performed under microwave irradiation as necessary.

Compound (LXXIII) may be a commercially available product, or can also be produced according to a method known per se or a method analogous thereto. The amount of this compound to be used is generally about 1-5 molar equivalents, preferably about 1-2 molar equivalents, per 1 mol of compound (LXX).

(Step 10)

In this step, compound (LXXIV) or a salt thereof is subjected to deprotection reaction to produce compound (XXVIIIa) or a salt thereof. This step can be performed by a method similar to that described in Method F, step 1.

[Method P]

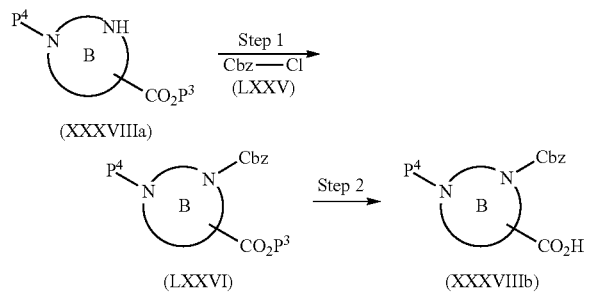

wherein each symbol is as defined above.

(Step 1)

In this step, compound (XXXVIIIa) or a salt thereof is subjected to a reaction for protecting with a Cbz group to produce compound (LXXVI) or a salt thereof.

Compound (XXXVIIIa) may be a commercially available product, or can also be produced according to a method known per se or a method analogous thereto. Compound (LXXV) may be a commercially available product.

Such Cbz protection reaction can be performed according to a known method. For example, while subject to variation depending on the kind of compound (XXXVIIIa), it can be performed in the presence of a base where necessary and in a solvent that does not adversely influence the reaction where necessary.

As the base, for example, inorganic bases (alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate and the like, alkali metal alkoxides such as sodium methoxide, sodium ethoxide and the like, and the like), organic bases (amines such as trimethylamine, triethylamine, diisopropylethylamine and the like, cyclic amines such as pyridine, 4-dimethylaminopyridine and the like, and the like) and the like are used. Of these, sodium hydroxide is preferable. The amount of the base to be used varies depending on the kind of the solvent, and other reaction conditions, and is generally about 0.1-10 molar equivalents, preferably about 1-5 molar equivalents, per 1 mol of compound (XXXVIIIa).

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like), water and the like, and a mixed solvent thereof.

Compound (LXXV) to be used in this step is generally about 1-10 molar equivalents, preferably about 1-2 molar equivalents, per 1 mol of compound (XXXVIIIa).

The reaction temperature varies depending on the kind of the solvent, and it is, for example, about −50-200° C., preferably about 0-100° C. While the reaction time varies depending on the kind of compound (XXXVIIIa), reaction temperature and the like, it is, for example, about 0.5-100 hr, preferably about 0.5-24 hr.

(Step 2)

In this step, compound (LXXVI) or a salt thereof is subjected to hydrolysis reaction to be converted to compound (XXXVIIIb) or a salt thereof. This step can be performed by a method similar to that described in Method J, step 7.

[Method Q]

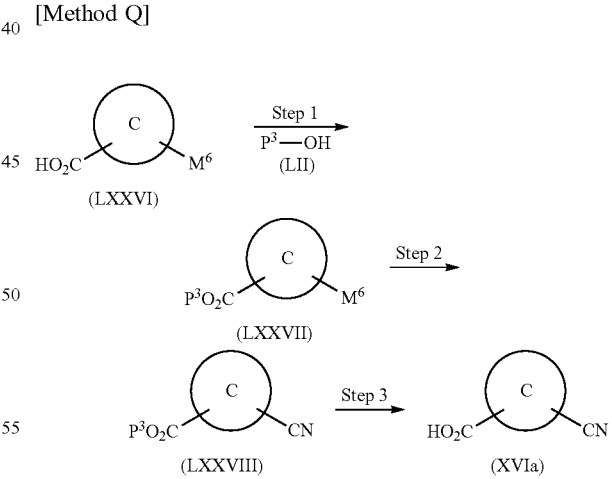

wherein each symbol is as defined above.

(Step 1)

In this step, compound (LXXVI) or a salt thereof is esterified to produce compound (LXXVII).

Compound (LXXVI) may be a commercially available product, or can also be produced according to a method known per se or a method analogous thereto. This step can be performed by a method similar to that described in Method M, step 1.

(Step 2)

In this step, compound (LXXVII) or a salt thereof is subjected to a cyanation reaction to produce compound (LXXVIII) or a salt thereof. This step can be performed by a method similar to that described in Method L, step 4.

(Step 3)

In this step, compound (LXXVIII) or a salt thereof is subjected to hydrolysis reaction to be converted to compound (XVIa) or a salt thereof. This step can be performed by a method similar to that described in Method J, step 7.

[Method R]

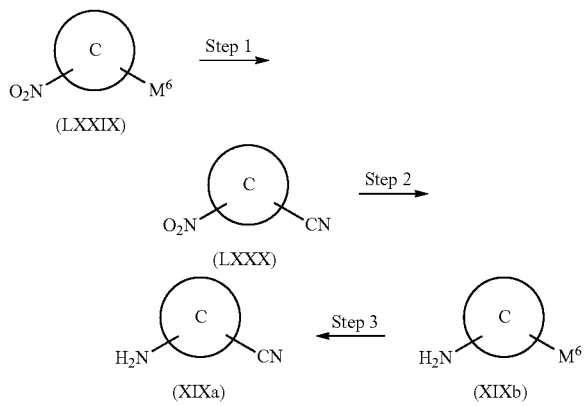

wherein each symbol is as defined above.

(Step 1)

In this step, compound (LXXIX) or a salt thereof is subjected to a cyanation reaction to produce compound (LXXX) or a salt thereof.

Compound (LXXIX) may be a commercially available product, or can also be produced according to a method known per se or a method analogous thereto. This step can be performed by a method similar to that described in Method L, step 4.

(Step 2)

In this step, compound (LXXX) is subjected to a reduction reaction to produce compound (XIXa) or a salt thereof. This step can be performed by a method similar to that described in Method L, step 2.

(Step 3)

In this step, compound (XIXb) or a salt thereof is subjected to a cyanation reaction to produce compound (XIXa) or a salt thereof.

Compound (XIXb) may be a commercially available product, or can also be produced according to a method known per se or a method analogous thereto. This step can be performed by a method similar to that described in Method L, step 4.

[Method S]

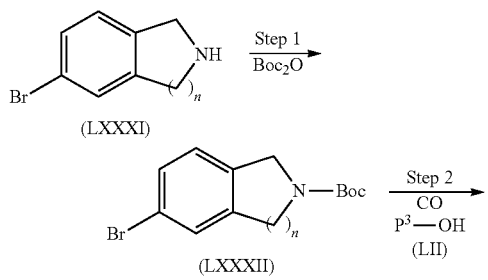

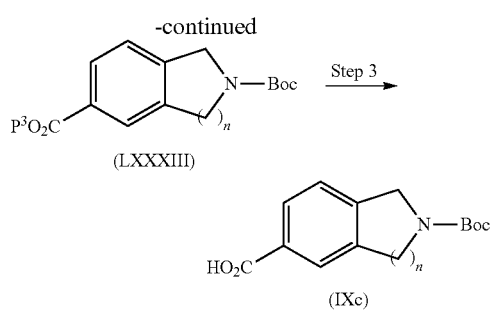

wherein each symbol is as defined above.

(Step 1)

In this step, compound (LXXXII) is produced by a reaction to protect compound (LXXXI) with a Boc group.

Compound (LXXXI) may be a commercially available product, or can also be produced according to a method known per se or a method analogous thereto or the following Method T or Method U.

In this reaction, compound (LXXXI) is reacted with di-tert-butyl dicarbonate ($Boc_2O$) in the presence of a base in a solvent that does not adversely influence the reaction.

As the base to be used in this step, for example, inorganic bases (alkali metal hydrides such as sodium hydride, lithium hydride and the like, alkali metal hydroxides such as lithium hydroxide, sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, alkali metal alkoxides such as sodium methoxide, sodium ethoxide, etc. and the like), organic base (amines such as trimethylamine, triethylamine, diisopropylethylamine and the like, cyclic amines such as pyridine, 4-dimethylaminopyridine, etc. and the like) and the like are used and, of these, sodium hydride and trimethylamine are preferable. The amount of the base to be used varies depending on the kind of the solvent, and other reaction conditions, and is generally about 1-10 molar equivalents, preferably about 1-5 molar equivalents, per 1 mol of compound (LXXXI).

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (N,N-dimethylformamide and the like), sulfoxides (dimethyl sulfoxide and the like), and water and the like. Two or more kinds of these solvents may be used in a mixture in an appropriate ratio.

$Boc_2O$ to be used in this step is generally about 1-10 molar equivalents, preferably about 1-2 molar equivalents, per 1 mol of compound (LXXXI).

The reaction temperature is, for example, about $-10$-$100°$ C. The reaction time varies depending on the kind of compound (LXXXI) or a salt thereof, the reaction temperature and the like, and it is, for example, about 0.5-100 hr, preferably about 0.5-24 hr.

(Step 2)

In this step, compound (LXXXIII) or a salt thereof is produced from compound (LXXXII) or a salt thereof by using a transition metal catalyst and compound (LII) under a carbon monoxide atmosphere.

Examples of the transition metal catalyst include palladium catalyst (palladium acetate, palladium chloride, tetrakis(triphenylphosphine)palladium and the like), nickel catalyst (nickel chloride and the like) and the like and, where necessary, an organophosphorus reagent such as triphenylphosphine, 1,1'-bis(diphenylphosphino)ferrocene (dppf) and the like can be used. The amount of the catalyst to be used varies depending on the kind of the catalyst, and is generally about 0.0001-1 mol, preferably about 0.01-0.5 mol, per 1 mol of compound (LXXXII), and the amount of the organophosphorus reagent is preferably about 0.01-2 mol.

As compound (LII), alkylalcohol optionally having substituent(s) is preferably used, and an excess amount of methanol or ethanol is generally used.

This reaction is generally performed in a solvent that does not adversely influence the reaction. Examples of the solvent that does not adversely influence the reaction include aromatic hydrocarbons (benzene, toluene, xylene and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), aprotic polar solvent (N,N-dimethylformamide, dimethyl sulfoxide or hexamethylphosphoramide and the like) and the like. Two or more kinds of these solvents may be used in a mixture in an appropriate ratio.

In addition, the reaction can be advantageously performed by adding a base or a salt. Examples of such base or salt include inorganic bases (alkali metal hydroxides such as sodium hydroxide, potassium hydroxide and the like, alkali metal hydrogen carbonates such as sodium hydrogen carbonate, potassium hydrogen carbonate and the like, alkali metal carbonates such as lithium carbonate, sodium carbonate, potassium carbonate, cesium carbonate and the like, and the like) or organic bases (amines such as trimethylamine, triethylamine, diisopropylethylamine and the like, cyclic amines such as pyridine and the like and the like) and the like. The amount of the base or salt to be used is generally about 1-100 molar equivalents, preferably about 1-10 molar equivalents, per 1 mol of compound (LXXXII).

While the reaction is generally performed under a carbon monoxide atmosphere at normal pressure, where necessary, it can be performed under pressurization (e.g., about 3-10 atm).

The reaction temperature varies depending on the kind of the solvent and it is, for example, about −50-200° C., preferably about 20-150° C. The reaction time varies depending on the kind of compound (LXXXII) or a salt thereof, the reaction temperature and the like, and it is, for example, about 0.5-100 hr, preferably about 0.5-24 hr.

(Step 3)

In this step, compound (LXXXIII) or a salt thereof is subjected to hydrolysis reaction to be converted to compound (IXc) or a salt thereof. This step can be performed by a method similar to that described in Method J, step 7.

[Method T]

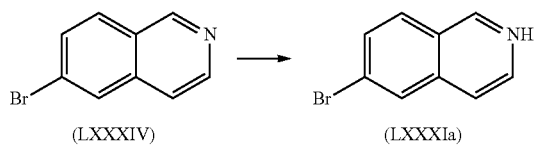 [SMILES: Brc1ccc2cnccc2c1 ; Brc1ccc2cnccc2c1]

(LXXXIV)          (LXXXIa)

wherein each symbol is as defined above.

In this step, compound (LXXXIV) or a salt thereof is subjected to a reduction reaction to produce compound (LXXXIa) or a salt thereof.

Compound (LXXXIV) may be a commercially available product, or can also be produced according to a method known per se or a method analogous thereto.

The reduction reaction can be performed by reduction with a metal hydride in a solvent that does not adversely influence the reaction.

Examples of the metal hydride include sodium borohydride, diisobutylaluminum hydride, aluminum hydride, lithium aluminum hydride, borane complex (borane-THF complex, catechol borane etc.) and the like, and sodium borohydride and the like are preferable. The amount of metal hydride to be used is, for example, about 1-50 mol, preferably about 1-10 mol, per 1 mol of compound (LXXXIV).

The reduction reaction with metal hydride is generally performed in a solvent inert to the reaction. Examples of such solvent include aromatic hydrocarbons (toluene, xylene etc.), aliphatic hydrocarbons (heptane, hexane etc.), halogenated hydrocarbons (chloroform, dichloromethane etc.), ethers (diethyl ether, tetrahydrofuran, dioxane etc.), alcohols (methanol, ethanol, 2-propanol, butanol, benzyl alcohol etc.), nitriles (acetonitrile etc.), N,N-dimethylformamide, dimethyl sulfoxide and the like. These solvent may be used in a mixture at an appropriate ratio.

While the reaction temperature varies depending on the kind of the solvent, it is generally about −80-80° C., preferably about −40-40° C. The reaction time is generally about 5 min-48 hr, preferably about 1-24 hr.

[U Method]

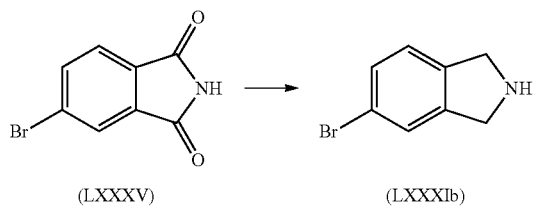 [SMILES: O=C1NC(=O)c2cc(Br)ccc21 ; Brc1ccc2c(c1)CNC2]

(LXXXV)          (LXXXIb)

wherein each symbol is as defined above.

In this step, compound (LXXXV) or a salt thereof is subjected to a reduction reaction to produce compound (LXXXIb) or a salt thereof.

Compound (LXXXV) may be a commercially available product, or can also be produced according to a method known per se or a method analogous thereto. This step can be performed by a method similar to that described in Method T.

When compound (I) has an optical isomer, a stereoisomer, a regioisomer or a rotamer, these are also encompassed in compound (I), and can be obtained as a single product according to a synthetic method and separation method known per se. For example, when compound (I) has an optical isomer, the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer.

3) Diastereomer Method

A method wherein a racemic mixture is converted to a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to separate an optically active reagent moiety, whereby an optical isomer is obtained. For example, when compound (I) contains hydroxy group or primary or secondary amino group in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When the compound (I) is obtained as a free compound, it can be converted into a desired salt by a method known per se or a modification thereof; conversely, when it is obtained as a salt, it can be converted into a free form or another desired salt by a method known per se or a modification thereof.

Compound (I) may be used as a prodrug. The prodrug of compound (I) means a compound which can be converted into compound (I) by reaction with an enzyme, gastric acid, or the like under physiological conditions in the living body. In other words, it means a compound which can be converted into compound (I) by enzymatic oxidation, reduction, hydrolysis or the like, or a compound which can be converted into compound (I) by hydrolysis with gastric acid or the like.

Examples of the prodrug of compound (I) include a compound in which amino of compound (I) is acylated, alkylated, or phosphorylated (e.g., the amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which hydroxyl group of compound (I) is acylated, alkylated, phosphorylated, or borated (e.g., hydroxy group of compound (I) is acetylated, palmitoylated, propanoylated, pivaloylated, succinylated, fumarylated, alanylated, or dimethylaminomethylcarbonylated); a compound in which carboxy group of compound (I) is esterified or amidated (e.g., a compound in which carboxy group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated). These compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The prodrug of compound (I) may also be one which is converted to compound (I) under physiological conditions as described in "IYAKUHIN no KAIHATSU (Development of Pharmaceuticals)", Vol. 7 (Design of Molecules), p. 163-198 (HIROKAWA SHOTEN).

Compound (I) may be a crystal, and both single crystal form and a crystalline mixture are encompassed in the compound (I) of the present invention. The crystal can be produced by crystallization by a crystallization method known per se.

Since compound (I) and a prodrug thereof [hereinafter sometimes to be abbreviated as the compound of the present invention] show superior RORγt inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt related diseases, Th17 cell related diseases and IL-17A or IL-17F related diseases, more specifically, the diseases described in (1)-(4) below.

(1) inflammatory diseases (e.g., rheumatoid arthritis, acute pancreatitis, chronic pancreatitis, asthma, bronchial asthma, adult respiratory distress syndrome, chronic obstructive pulmonary disease (COPD), inflammatory bone disease, pulmonary sarcoidosis, inflammatory bowel disease, celiac disease, Behcet's syndrome, hepatitis, alcoholic hepatic fibrosis, alcoholic hepatitis, alcoholic cirrhosis, hepatitis B viral hepatopathy, primary biliary cirrhosis (PBC), primary sclerosing cholangitis (PSC), transient cerebral ischemic attack (TIA), systemic inflammatory response syndrome (SIRS), dry eye, glaucoma, uveitis, orbital cellulitis, idiopathic orbital inflammation, age-related macular degeneration, postoperative or post-traumatic inflammation, hepatopathy, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, autoimmune anemia, Good Basucha syndrome, Graves' disease, hashimoto's thyroiditis, vasculitis, Basedow's disease, sinusitis, allergic rhinitis, chronic hypertrophic rhinitis etc.), (2) autoimmune diseases (e.g., rheumatoid arthritis, ankylopoietic spondylarthritis, psoriasis, multiple sclerosis (MS), polymyositis, optic nervemyelitis (NMO), chronic inflammatory demyelinating polyneuropathy (CIDP), dermatomyositis (DM), polyarteritis *nodosa* (PN), mixed connective tissue disease (MCTD), amyotrophic lateral sclerosis (ALS), Guillain-Barré syndrome, myasthenia gravis, Parkinson's disease, spinal muscular atrophy, spinocerebellar atrophy, progressive supranuclear palsy, Fisher syndrome, central nervous system lupus, acute disseminated encephalomyelitis, multiple system atrophy, Huntington's disease, Alzheimer's disease, cerebrovascular dementia, diffuse Lewy body disease, cerebrovascular diseases, cerebral infarction, transient cerebral ischemic attack, cerebral hemorrhage, spinal cord vascular disorder, spinal cord infarction, polyneuritis, Lambert-Eaton syndrome, muscular dystrophy, metabolic myopathy, inflammatory myopathy, inclusion body myositis, encephalitis, meningitis, Sjogren's syndrome, systemic lupus erythematosus, scleroderma, pemphigus, *profundus* lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis (UC), Crohn's disease, graft versus host disease, Addison's disease, abnormal immunoresponse, arthritis, dermatitis, radiodermatitis, sarcoidosis, type 1 diabetes etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile Hemangioma, multiple myeloma, acute myeloblastic leukemia, chronic sarcoma, multiple myeloma, chronic myeloid leukemia, metastasis melanoma, Kaposi's sarcoma, vascular proliferation, cachexia, metastasis of the breast cancer, cancer (e.g., colorectal cancer (e.g., familial colorectal cancer, hereditary non-polyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, hormone-independent prostate cancer and the like), liver cancer (e.g., primary liver cancer, extrahepatic bile duct cancer and the like), thyroid cancer (e.g., medullary thyroid carcinoma and the like), renal cancer (e.g., renal cell carcinoma, transitional cell carcinoma in kidney and ureter and the like), uterine cancer, uterine body cancer, brain tumor (e.g., pineal astrocytoma, pilocytic astrocytoma, diffuse astrocytoma, anaplastic astrocytoma and the like), melanoma (melanoma), sarcoma, urinary bladder cancer, hematologic cancer and the like including multiple myeloma, hypophyseal adenoma, glioma, acoustic schwannoma, retinoblastoma, head and neck carcinoma, pharyngeal cancer, laryngeal cancer, tongue cancer, thymoma, esophagus cancer, duodenal cancer, colorectal cancer, rectal cancer, hepatoma, pancreatic endocrine tumor, bile duct cancer, gall bladder cancer, penile cancer, ureter cancer, testis tumor, vulvar cancer, cervical cancer, uterine body cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary).

The medicament of the present invention can be preferably used as a prophylactic or therapeutic agent for psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE), chronic obstructive pulmonary disease and the like.

In another embodiment, the medicament of the present invention can be used as a prophylactic or therapeutic agent for preferably autoimmune disease, inflammatory disease, bone or articular disease or neoplastic disease, particularly preferably, psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE), chronic obstructive pulmonary diseases, ovarian cancer, non-small cell lung cancer, breast cancer, gastric cancer, head and neck carcinoma, prostate cancer or uterine body cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I)) for one day, which is administered once to several times, preferably once to 2 or 3 times per day.

The pharmacologically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can also be used as appropriate in an appropriate amount.

When the compound of the present invention is used as an ointment, it is produced by mixing the compound of the present invention with a general ointment base to a concentration of about 0.001-3% (W/W), preferably about 0.01-1% (W/W). In the production of an ointment, a powderizing step of the compound of the present invention, or a sterilization step of a preparation is preferably included. An ointment is administered 1-4 times per day according to the condition of the patients.

As an ointment base, purified lanolin, white petrolatum, macrogol, plastibase, liquid paraffin and the like are appropriately used.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.

(1) Non-steroidal Anti-inflammatory Drug (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor, COX-2 selective inhibitor and the like)
salicylic acid derivatives (e.g., celecoxib, aspirin), etoricoxib, valdecoxib, diclofenac, indomethacin, loxoprofen and the like.
(iii) nitric oxide-releasing NSAIDs
(2) Disease-modifying Anti-rheumatic Drugs (DMARDs)
(i) Gold preparation
auranofin and the like.
(ii) penicillamine
D-penicillamine.
(iii) aminosalicylic acid preparation
sulfasalazine, mesalamine, olsalazine, balsalazide.
(iv) antimalarial drug
chloroquine and the like.
(v) pyrimidine synthesis inhibitor
leflunomide and the like.
(vi) tacrolimus
(3) Anti-cytokine Drug
(I) protein drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
anakinra (interleukin-1 receptor antagonist), soluble interleukin-1 receptor and the like.

(iii) interleukin-6 inhibitor
  tocilizumab (anti-interleukin-6 receptor antibody), anti-interleukin-6 antibody and the like.
(iv) interleukin-10 drug
  interleukin-10 and the like.
(v) interleukin-12/23 inhibitor
  ustekinumab, briakinumab (anti-interleukin-12/23 antibody) and the like.
(vi) B cell activation inhibitor
  Rituxan, Benlysta and the like.
(vii) costimulatory molecule-related protein drug
  Abatacept and the like.
(II) non-protein drug
(i) MAPK inhibitor
  BMS-582949 and the like.
(ii) gene modulator
  inhibitor of molecule involved in signal transduction, such as NF-κ, NF-κB, IKK-1, IKK-2, AP-1 and the like, and the like.
(iii) cytokine production inhibitor
  iguratimod, tetomilast and the like.
(iv) TNF-α converting enzyme inhibitor
(v) interleukin-1β converting enzyme inhibitor
  Belnacasan and the like.
(vi) interleukin-6 antagonist
  HMPL-004 and the like.
(vii) interleukin-8 inhibitor
  IL-8 antagonist, CXCR1 & CXCR2 antagonist, reparixin and the like.
(viii) chemokine antagonist
  CCR9 antagonist (Vercirnon sodium), CCX025, N-{4-chloro-2-[(1-oxidepyridin-4-yl)carbonyl]phenyl}-4-(propan-2-yloxy)benzenesulfonamide), MCP-1 antagonist and the like.
(ix) interleukin-2 receptor antagonist
  denileukin, diftitox and the like.
(x) therapeutic vaccines
  TNF-α vaccine and the like.
(xi) gene therapy drug
  gene therapy drugs aiming at promoting the expression of gene having an anti-inflammatory action such as interleukin-4, interleukin-10, soluble interleukin-1 receptor, soluble TNF-α receptor and the like.
(xii) antisense compound
  ISIS-104838 and the like.
(4) Integrin Inhibitor
  natalizumab, vedolizumab, AJM300, TRK-170, E-6007 and the like.
(5) Immunomodulator (Immunosuppressant)
  methotrexate, cyclophosphamide, MX-68, atiprimod dihydrochloride, Abatacept, CKD-461, rimexolone, cyclosporine, tacrolimus, gusperimus, azathioprine, anti-lymphocyte serum, freeze-dried sulfonated normal immunoglobulin, erythropoietin, colony stimulating factor, interleukin, interferon and the like.
(6) Proteasome Inhibitor
  Velcade and the like.
(7) JAK Inhibitor
  tofacitinib and the like.
(8) Steroid
  dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(9) Angiotensin Converting Enzyme Inhibitor
  enalapril, captopril, ramipril, lisinopril, cilazapril, perindopril and the like.
(10) Angiotensin II Receptor Antagonist
  candesartan cilexetil, valsartan, irbesartan, olmesartan, eprosartan and the like.
(11) Diuretic Drug
  hydrochlorothiazide, spironolactone, furosemide, indapamide, bendrofluazide, cyclopenthiazide and the like.
(12) Cardiotonic Drug
  digoxin, dobutamine and the like.
(13) β Receptor Antagonist
  carvedilol, metoprolol, atenolol and the like.
(14) Ca Sensitizer
  Caldaret hydrate and the like.
(15) Ca Channel Antagonist
  nifedipine, diltiazem, verapamil and the like.
(16) Anti-platelet Drug, Anticoagulant
  heparin, aspirin, warfarin and the like.
(17) HMG-CoA Reductase Inhibitor
  atorvastatin, simvastatin and the like.
(18) Contraceptive
(i) sex hormone or derivatives thereof
  gestagen or a derivative thereof (progesterone, 17α-hydroxyprogesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Tosagestin, TX-525, ethinylestradiol/TX525 or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
  ormeloxifene, mifepristone, Org-33628 and the like.
(iii) spermatocide
  ushercell and the like.
(19) Others
(i) T cell inhibitors
(ii) inosine monophosphate dehydrogenase (IMPDH) inhibitor
  mycophenolate mofetil and the like.
(iii) adhesion molecule inhibitor
  Alicaforsen sodium, selectin inhibitor, ELAM-1 inhibitor, VCAM-1 inhibitor, ICAM-1 inhibitor and the like.
(iv) thalidomide
(v) cathepsin inhibitor
(vi) matrix metalloprotease (MMPs) inhibitor
  V-85546 and the like.
(vii) glucose-6-phosphate dehydrogenase inhibitor
(viii) Dihydroorotate dehydrogenase (DHODH) inhibitor
(ix) phosphodiesterase IV(PDE IV) inhibitor
  roflumilast, apremilast, CG-1088 and the like.
(x)) phospholipase $A_2$ inhibitor
(xi) iNOS inhibitor
  VAS-203 and the like.
(xii) microtubule stimulating drug
  paclitaxel and the like.
(xiii) microtuble inhibitor
  reumacon and the like.
(xiv) MHC class II antagonist
(xv) prostacyclin agonist
  iloprost and the like.

(xvi) CD4 antagonist
  zanolimumab and the like.
(xvii) CD23 antagonist
(xviii) LTB4 receptor antagonist
  DW-1350 and the like.
(xix) 5-lipoxygenase inhibitor
  zileuton and the like.
(xx) cholinesterase inhibitor
  galanthamine and the like.
(xxi) tyrosine kinase inhibitor
  Tyk2 inhibitor (WO 2010/142752) and the like.
(xxii) carepsin B inhibitor
(xxiii) adenosine deaminase inhibitor
  pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
  synvisc (hylan G-F 20), orthovisc and the like.
(xxix) glucosamine sulfate
(xxx) amiprilose
(xxxi) CD-20 inhibitor
  rituximab, ibritumomab, tositumomab, ofatumumab and the like.
(xxxii) BAFF inhibitor
  belimumab, tabalumab, atacicept, Blisibimod and the like.
(xxxiii) CD52 inhibitor
  alemtuzumab and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiotonic drug, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent
(i) sulfa drug
  sulfamethizole, sulfisoxazole, sulfamonomethoxine, salazosulfapyridine, silver sulfadiazine and the like.
(ii) quinolone antibacterial agent
  nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
  isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
  diaphenylsulfone, rifampicin and the like.
(v) antiviral drug
  idoxuridine, acyclovir, vidarabine, gancyclovir and the like.
(vi) anti-HIV agent
  zidovudine, didanosine, zalcitabine, indinavir sulfate ethanolate, ritonavir and the like.
(vii) antispirochetele
(viii) antibiotic
  tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) Antifungal Agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) Antiprotozoal Agent
  metronidazole, tinidazole, diethylcarbamazine citrate, quinine hydrochloride, quinine sulfate and the like.

(4) Antitussive and Expectorant Drug
  ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terputaline, oxypetebanol, morphine hydrochloride, dextropethorfan hydrobromide, oxycodone hydrochloride, dimorphan phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocysteine and the like.

(5) Sedative
  chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic
(6-1) Local Anesthetic
  cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.
(6-2) General Anesthetic
(i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) Antiulcer Drug histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin and the like.

(8) Antiarrhythmic Agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug

6-O-(N-chloroacetylcarbamoyl) fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796(1990)], pravastatin, simvastatin, probucol, bezafibrate, clinofibrate, nicomol, cholestyramine, dextran sulfate sodium and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Antiepileptic Drug phenytoin, ethosuximide, acetazolamide, chlordiazepoxide, tripethadione, carbamazepine, phenobarbital, primidone, sulthiame, sodium valproate, clonazepam, diazepam, nitrazepam and the like.

(17) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiotonic Drug trans-π-oxocamphor, terephyllol, aminophylline, etilefrine, dopamine, dobutamine, denopamine, aminophylline, vesinarine, amrinone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine denopamine and the like.

(22) Hypotensive Diuretic hexamethonium bromide, pentolinium, mecamylamine, ecarazine, clonidine, diltiazem, nifedipine and the like.

(23) Therapeutic Drug for Diabetes tolbutamide, chlorpropamide, acetohexamide, glibenclamide, tolazamide, acarbose, epalrestat, troglitazone, glucagon, glymidine, glipuzide, phenformin, puformin, metformin and the like.

(24) Antinarcotic levallorphan, nalorphine, naloxone or a salt thereof and the like.

(25) Liposoluble Vitamins (i) vitamin A: vitamin $A_1$, vitamin $A_2$ and retinol palmitate (ii) vitamin D: vitamin $D_1$, $D_2$, $D_3$, $D_4$ and $D_5$ (iii) vitamin E: α-tocopherol, β-tocopherol, γ-tocopherol, δ-tocopherol, dl-α-tocopherol nicotinate (iv) vitamin K: vitamin $K_1$, $K_2$, $K_3$ and $K_4$ (v) folic acid (vitamin M) and the like.

(26) Vitamin Derivative various derivatives of vitamins, for example, vitamin $D_3$ derivatives such as 5,6-trans-cholecalciferol, 2,5-hydroxycholecalciferol, 1-α-hydroxycholecalciferol, calcipotriol and the like, vitamin $D_2$ derivatives such as 5,6-trans-ergocalciferol and the like, and the like.

(27) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, predonisolone, hydrocortisone, hydrocortisone sodium succinate, beclometasone dipropionate, ciclesonide and the like.

(28) Therapeutic Agent for Pollakisuria/Anischuria
flavoxate hydrochloride and the like.

(29) Therapeutic Agent for Atopic Dermatitis
sodium cromoglicate and the like.

(30) Therapeutic Agent for Allergic Rhinitis
sodium cromoglicate, chlorpheniramine maleate, alimemazine tartrate, clemastine fumarate, homochlorcyclizine hydrochloride, fexofenadine, mequitazine, ketotifen fumarate, cetirizine hydrochloride, oxatomide, azelastine, ebastine, epinastine hydrochloride, loratadine and the like.

(31) Hypertensor
dopamine, dobutamine, denopamine, digitoxin, digoxin, methyldigoxin, lanatoside C, G-strophanthin and the like.

(32) Others
hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 99.99% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose varies depending on the kind of the compound of the present invention, administration route, symptom, age of patients and the like. For example, for oral administration to patients (body weight about 60 kg) with inflammatory bowel disease (IBD), about 0.1 mg/kg body weight-about 30 mg/kg body weight, preferably about 1 mg/kg body weight-20 mg/kg body weight, of compound (I) can be administered once to several portions per day.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from for 1 minute to 3 days, preferably from for 10 minutes to 1 day, more preferably from for 15 minutes to 1 hour, after administration of the concomitant drug is included. When the compound of the present invention is administered first, a method in which the concomitant drug is administered within time range of from for 1 minute to 1 day, preferably from for 10 minutes to 6 hours, more preferably from for 15 minutes to 1 hour after administration of the compound of the present invention is included.

EXAMPLES

The present invention is explained in more detail in the following by referring to Examples, preparation Examples and Experimental Examples, which are not to be construed as limitative and may be modified without departing from the scope of the invention.

Unless particularly indicated, the elution in column chromatography in the Examples was performed under observation by TLC (Thin Layer Chromatography). For TLC observation, 60F254 manufactured by Merck was used as a TLC plate, and the solvent used as an elution solvent for column chromatography was used. For detection, moreover, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), C18 means use of octadecyl-bonded silica gel. The elution solvents show volume mixing ratios, unless otherwise specified. The room temperature generally means a temperature about 10° C. to 35° C. For drying extracts, sodium sulfate or magnesium sulfate was used.

In the chemical structural formulas described in the Examples, a solid line bonded to an asymmetric carbon ——— shows a mixture of two stereochemistries, except when a compound name contains description relating to the stereochemistry.

The abbreviations in the present specification or Examples mean as follows.
LC: liquid chromatography
MS: mass spectrometry spectrum
API: atmospheric pressure ionization method
M: molecular weight of the compound
NMR: nuclear magnetic resonance spectrum
Hz: hertz
J: coupling constant
m: multiplet
q: quartet
t: triplet
d: doublet
d like: doublet like
dd: double doublet
dd like: double doublet like
s: singlet
dt: double triplet
spt: septet
sxt: sextet
brs: broad singlet
quant.: quantitatively
Boc: tert-butyloxycarbonyl group
Boc$_2$O: di-tert-butyl dicarbonate
COMU: 1-[(1-(cyano-2-ethoxy-2-oxoethylideneaminooxy)-dimethylamino-morpholino)]carbenium hexafluorophosphate
CPME: cyclopentyl methyl ether
DIEA: diisopropylethylamine
DMAP: 4-dimethylaminopyridine
DMF: N,N-dimethylformamide
DMSO: dimethyl sulfoxide
EtOH: ethanol
HATU: 2-(1H-7-azabenzotriazol-1-yl)-1,1,3,3-tetramethyluronium hexafluorophosphate
HOBt: 1H-benzo[d][1,2,3]triazol-1-ol hydrate
IPE: diisopropyl ether
MeOH: methanol
M: mol concentration
N: normal concentration
NaBH$_4$: sodium borohydride
NaBH(OAc)$_3$: sodium triacetoxyborohydride
NMP: N-methyl-2-pyrrolidone
Pd(PPh$_3$)$_4$: tetrakis(triphenylphosphine)palladium(0)
Pd$_2$(dba)$_3$: tris(dibenzylideneacetone)dipalladium(0)
PPh$_3$: triphenylphosphine
t-: tert-
T3P: 1.6 M 2,4,6-tripropyl-1,3,5,2,4,6-trioxatriphorinane-2,4,6-trioxide/ethyl acetate solution, or DMF solution
TEA: triethylamine
TFA: trifluoroacetic acid
THF: tetrahydrofuran
tR$_1$: retention time 1
tR$_2$: retention time 2
WSC: N$^1$-((ethylimino)methylene)-N$^3$,N$^3$-dimethylpropane-1,3-diamine hydrochloride
XPhos: dicyclohexyl(2',4',6'-triisopropyl-[1,1'-biphenyl]-2-yl)phosphine Example 1

N-(cis-2-((1,3-bis(cyclopropylmethyl)-2,4-dioxo-1,2,3,4-tetrahydroquinazolin-6-yl)carbamoyl)cyclopentyl)-3-chloro-4-cyanobenzamide (Step 1)

A mixture of 2-amino-5-nitro-benzoic acid (30 g, 164.71 mmol) and urea (99 g, 1647.14 mmol) was heated at 160° C. with stirring overnight. The mixture was cooled, water (300 mL) was added thereto, and the precipitate was collected by filtration. The precipitate was washed with AcOH (50 mL) and MeOH (100 mL) to give 6-nitroquinazoline-2,4(1H, 3H)-dione (33.8 g, 163 mmol, 99%) as a yellow solid.

$^1$H NMR (300 MHz, DMSO-d$_6$): δ 7.32(1H,d,J=9.1 Hz), 8.45(1H,dd,J=9.1,2.6 Hz), 8.58(1H,d,J=2.6 Hz), 11.65(2H,brs).

(Step 2)

Potassium carbonate (2.502 g, 18.10 mmol) was added to a mixture of 6-nitroquinazoline-2,4(1H, 3H)-dione (2.00 g, 9.66 mmol) and (bromomethyl)cyclopropane (2.341 mL, 24.14 mmol) in DMF (20 mL), and the mixture was stirred at 70° C. overnight. The reaction mixture was cooled and insoluble materials were filtered off. The filtrate was concentrated under reduced pressure to give crude 1,3-bis(cyclopropylmethyl)-6-nitroquinazoline-2,4(1H, 3H)-dione (3.28 g, 10.40 mmol, 108%) as a pale-brown oil. The resultant product was used for the next step without purification.

$^1$H NMR (300 MHz, DMSO-d$_6$): δ 0.21-0.57(6H,m), 0.96-1.36(2H,m), 2.69-2.78(1H,m), 2.80-3.19(1H,m), 3.75-3.99(2H,m), 4.13(2H,d,J=7.2 Hz), 7.84(1H,d,J=9.4 Hz), 8.52(1H,dd,J=9.3, 2.8 Hz), 8.74(1H,d,J=2.6 Hz).

(Step 3)

A mixture of crude 1,3-bis(cyclopropylmethyl)-6-nitroquinazoline-2,4(1H, 3H)-dione (3.00 g, 9.51 mmol) and 10% palladium-carbon (300 mg, 2.82 mmol, 50% wet) in MeOH (30 mL) and ethyl acetate (30 mL) was stirred under a hydrogen atmosphere at 1 atm at room temperature overnight. The catalyst was removed by filtration, and the filtrate was concentrated under reduced pressure. The residue was purified by silica gel column chromatography (solvent gradient; 5→75% ethyl acetate/hexane) to give 6-amino-1,3-bis(cyclopropylmethyl)quinazoline-2,4(1H, 3H)-dione (1.930 g, 6.76 mmol, 71.1%) as a white amorphous solid.

$^1$H NMR (300 MHz, CDCl$_3$): δ 0.30-0.65(8H,m), 1.09-1.45(2H,m), 3.76(2H,brs), 3.98(2H,d,J=6.6 Hz), 4.03(2H,d,J=6.9 Hz), 7.04(1H,dd,J=8.9, 2.8 Hz), 7.16(1H,d,J=8.7 Hz), 7.52(1H,d,J=2.6 Hz).

(Step 4)

T3P (0.329 mL, 0.56 mmol) was added to a mixture of 6-amino-1,3-bis(cyclopropylmethyl)quinazoline-2,4(1H, 3H)-dione (145 mg, 0.51 mmol), cis-2-(tert-butoxycarbonylamino)-1-cyclopentane carboxylic acid (128 mg, 0.56 mmol) and DIEA (0.098 mL, 0.56 mmol) in ethyl acetate (10 mL) at room temperature, and the mixture was stirred at 50° C. overnight. To the reaction mixture was added brine, and the mixture was extracted with ethyl acetate. The organic layer was washed with brine, dried over magnesium sulfate, and the solvent was evaporated under reduced pressure. The residue was purified by silica gel column chromatography (solvent gradient; 10→50% ethyl acetate/hexane) to give tert-butyl (cis-2-((1,3-bis(cyclopropylmethyl)-2,4-dioxo-1,2,3,4-tetrahydroquinazolin-6-yl)carbamoyl)cyclopentyl) carbamate (183 mg, 0.369 mmol, 72.5%) as a white solid.

$^1$H NMR (300 MHz, CDCl$_3$): δ 0.23-0.66(8H,m), 1.10-1.46(9H,m), 1.61(5H,s), 1.83-2.43(3H,m), 3.10(1H,d,J=7.2 Hz), 3.71-4.39(5H,m), 4.94(1H,d,J=7.2 Hz), 7.27-7.32(2H, m), 8.09(2H,s).

(Step 5)

A mixture of tert-butyl (cis-2-((1,3-bis(cyclopropylmethyl)-2,4-dioxo-1,2,3,4-tetrahydroquinazolin-6-yl)carbamoyl)cyclopentyl)carbamate (183 mg, 0.37 mmol) and TFA (3 mL) was stirred at room temperature for 3 hr, and basified with 1N aqueous sodium hydroxide solution. The mixture was extracted with ethyl acetate. The organic layer was washed with brine, dried over magnesium sulfate, and the solvent was evaporated under reduced pressure to give crude cis-2-amino-N-(1,3-bis(cyclopropylmethyl)-2,4-dioxo-1,2,3,4-tetrahydroquinazolin-6-yl)cyclopentane carboxamide as an oil. The resultant product was used for the next step without purification.

$^1$H NMR (300 MHz, CDCl$_3$): δ 0.27-0.67(9H,m), 1.26 (4H,t,J=7.2 Hz), 1.56-1.82(1H,m), 2.09(4H,brs), 2.85(1H,d, J=6.4 Hz), 3.70(1H,d,J=5.7 Hz), 3.86-4.26(4H,m), 7.22-7.25(1H,m), 8.02(1H,d,J=2.6 Hz), 8.26(1H,dd,J=9.1, 2.3 Hz), 10.53(1H,brs).

(Step 6)

T3P (0.264 mL, 0.45 mmol) was added to a mixture of crude cis-2-amino-N-(1,3-bis(cyclopropylmethyl)-2,4-dioxo-1,2,3,4-tetrahydroquinazolin-6-yl)cyclopentane carboxamide (162 mg, 0.41 mmol), 3-chloro-4-cyanobenzoic acid (82 mg, 0.45 mmol) and DIEA (0.078 mL, 0.45 mmol) in ethyl acetate (5 mL) at room temperature, and the mixture was stirred at 70° C. overnight. To the reaction mixture was added brine, and the mixture was extracted with ethyl acetate. The organic layer was washed with brine, dried over magnesium sulfate, and the solvent was evaporated under reduced pressure. The residue was purified by silica gel column chromatography (solvent gradient; 10→100% ethyl acetate/hexane) to give the title compound (20.00 mg, 0.036 mmol, 8.74%) as a white solid.

Example 71

N$^2$-(3-chloro-4-cyanophenyl)-N$^4$-(3-(cyclopropylmethyl)-1-isopropyl-2,4-dioxo-1,2,3,4-tetrahydroquinazolin-6-yl)morpholine-2,4-dicarboxamide (Step 1)

Sulfuric acid (5 mL, 93.80 mmol) was added to a solution of 2-fluoro-5-nitrobenzoic acid (25.55 g, 138.03 mmol) in MeOH (250 mL) with stirring. The mixture was heated under reflux for 16 hr, concentrated under reduced pressure to a half volume, and ethyl acetate (about 300 mL) was added. The mixture was washed with water, aqueous sodium hydrogen carbonate solution and brine, and dried over magnesium sulfate to give methyl 2-fluoro-5-nitrobenzoate (24.32 g, 122 mmol, 88%) as a grayish white solid.

$^1$H NMR (300 MHz, CDCl$_3$): δ 4.00(3H,s), 7.33(1H,t, J=9.3 Hz), 8.38-8.45(1H,m), 8.86(1H,dd,J=6.2, 2.8 Hz).

(Step 2)

Isopropylamine (32.4 mL, 377.53 mmol) was added to a solution of 2-fluoro-5-nitrobenzoate (25.06 g, 125.84 mmol) in acetonitrile (250 mL) at 0° C. The mixture was stirred at room temperature for 1 hr, poured into water (800 mL), stirred at room temperature for 10 min. The precipitate was collected by filtration, and successively washed with water, IPA and IPE to give methyl 2-(isopropylamino)-5-nitrobenzoate (28.64 g, 120 mmol, 96%) as pale-yellow crystals.

$^1$H NMR (300 MHz, CDCl$_3$): δ 1.33(6H,d,J=6.4 Hz), 3.81(1H,spt), 3.91(3H,s), 6.69(1H,d,J=9.4 Hz), 8.19(1H,dd, J=9.4, 2.3 Hz), 8.56(1H,brs), 8.87(1H,d,J=2.6 Hz).

(Step 3)

2N Aqueous sodium hydroxide solution (174 mL, 347.30 mmol) was added to a solution of methyl 2-(isopropylamino)-5-nitrobenzoate (27.58 g, 115.77 mmol) in EtOH (120 mL) and THF (120 mL) at room temperature. The mixture was stirred at 75° C. for 2.5 hr, poured into water (600 mL), and concentrated hydrochloric acid was added up to pH 3. The mixture was extracted 3 times with ethyl acetate/THF mixed solution (3:1, v/v). The organic layer was washed with brine, dried over magnesium sulfate, and the solvent was evaporated under reduced pressure. The precipitate was washed with IPE and hexane to give 2-(isopropylamino)-5-nitrobenzoic acid (25.32 g, 113 mmol, 98%) as pale-yellow crystals.

$^1$H NMR (300 MHz, CDCl$_3$): δ 1.36(6H,d,J=6.4 Hz), 3.84(1H, spt), 6.73(1H,d,J=9.4 Hz), 8.24(1H,dd,J=9.4, 2.6 Hz), 8.35(1H, d, J=6.8 Hz), 8.95(1H,d,J=2.6 Hz), 11.04(1H, brs).

(Step 4)

WSC (24.81 mL, 135.51 mmol) was added to a solution of 2-(isopropylamino)-5-nitrobenzoic acid (25.32 g, 112.93 mmol), cyclopropylmethanamine (8.83 g, 124.22 mmol) and HOBt (16.79 g, 124.22 mmol) in DMF (300 mL) at 0° C. The mixture was stirred at room temperature for 18 hr, poured into aqueous sodium hydrogen carbonate solution (1200 mL), and extracted 3 times with ethyl acetate/THF mixed solution (3:1, v/v). The organic layer was washed with brine, dried over magnesium sulfate, and the solvent was evaporated under reduced pressure. The precipitate was washed with hexane to give N-(cyclopropylmethyl)-2-(isopropylamino)-5-nitrobenzamide (28.68 g, 103 mmol, 92%) as pale-yellow crystals.

$^1$H NMR (300 MHz, CDCl$_3$): δ 0.26-0.33(2H,m), 0.57-0.65(2H,m), 1.03-1.14(1H,m), 1.30(6H,d,J=6.4 Hz), 3.27 (2H,dd,J=7.2, 5.3 Hz), 3.77(1H,spt,J=6.5 Hz), 6.32(1H,brs), 6.65(1H,d,J=9.4 Hz), 8.16 (1H,dd,J=9.1, 2.3 Hz), 8.36(1H, d,J=2.6 Hz), 8.75(1H,d,J=7.2 Hz).

(Step 5)

Triphosgene (20.56 g, 69.29 mmol) was added to a solution of N-(cyclopropylmethyl)-2-(isopropylamino)-5-nitrobenzamide (28.68 g, 103.42 mmol) and TEA (31.7 mL, 227.52 mmol) in THF (280 mL) at 0° C. The mixture was stirred at 0° C. for 15 min and at 65° C. for 4.5 hr, poured into aqueous sodium hydrogen carbonate solution (700 mL), and the mixture was extracted 3 times with ethyl acetate. The organic layer was washed with brine, dried over magnesium sulfate, and the solvent was evaporated under reduced pressure. The residue was dissolved in THF (280 mL), and triphosgene (15.34 g, 51.71 mmol) and TEA (23.78 mL, 170.64 mmol) were added at 0° C. The mixture was stirred at 0° C. for 15 min and at 65° C. for 15 hr, poured into aqueous sodium hydrogen carbonate solution (700 mL), and the mixture was extracted 3 times with ethyl acetate. The organic layer was washed with brine, dried over magnesium sulfate, and the solvent was evaporated under reduced pressure. The residue was purified by silica gel column chromatography (solvent gradient; 5→20% ethyl acetate/hexane), and the precipitate was washed with hexane to give 3-(cyclopropylmethyl)-1-isopropyl-6-nitroquinazoline-2,4 (1H, 3H)-dione (18.62 g, 61.4 mmol, 59.4%) as pale-yellow crystals.

$^1$H NMR (300 MHz, CDCl$_3$): δ 0.42-0.54(4H,m), 1.24-1.37(1H,m), 1.65(6H,d,J=6.8 Hz), 3.98(2H,d,J=7.2 Hz), 5.11(1H,brs), 7.48(1H,d,J=9.1 Hz), 8.46(1H,dd,J=9.4, 3.0 Hz), 9.10(1H,d,J=3.0 Hz).

(Step 6)

A mixture of 3-(cyclopropylmethyl)-1-isopropyl-6-nitroquinazoline-2,4(1H, 3H)-dione (18.62 g, 61.39 mmol) and 10% palladium-carbon (4.5 g, 38.00 mmol, 50% wet) in MeOH (300 mL) and THF (150 mL) was stirred under a hydrogen atmosphere at 1 atm at room temperature for 4 hr. The catalyst was removed by filtration, and the filtrate was concentrated under reduced pressure. To the residue was added ethyl acetate (about 500 mL), and the mixture was treated with activated carbon (5.0 g). The mixture was filtrated, and the filtrate was concentrated under reduced pressure. The precipitate was washed with IPE and hexane to give 6-amino-3-(cyclopropylmethyl)-1-isopropylquinazoline-2,4(1H, 3H)-dione (15.02 g, 55.0 mmol, 90%) as pale-yellow crystals.

$^1$H NMR (300 MHz, CDCl$_3$): δ 0.42-0.48(4H,m), 1.23-1.36(1H,m), 1.59(6H,d,J=7.2 Hz), 3.73(2H,brs), 3.96(2H,d, J=7.2 Hz), 5.01(1H,brs), 6.99(1H,dd,J=8.9, 2.8 Hz), 7.20 (1H,d,J=9.1 Hz), 7.51(1H,d,J=3.0 Hz).

(Step 7)

T3P (8.35 mL, 14.04 mmol) was added to a solution of 4-amino-2-chlorobenzonitrile (1.190 g, 7.8 mmol), 4-(tert-butoxycarbonyl)morpholine-2-carboxylic acid (1.984 g, 8.58 mmol), DIEA (6.79 mL, 39.00 mmol) and DMAP (1.048 g, 8.58 mmol) in ethyl acetate (55 mL) at room temperature, and the mixture was stirred at 70° C. for 5 hr. To the reaction mixture was added water (150 mL), and the mixture was extracted 3 times with ethyl acetate. The organic layer was washed with 10% aqueous citric acid solution, aqueous sodium hydrogen carbonate solution and brine, dried over magnesium sulfate, and the solvent was evaporated under reduced pressure. The residue was purified by silica gel column chromatography (solvent gradient; 10→60% ethyl acetate/hexane) to give tert-butyl 2-((3-chloro-4-cyanophenyl)carbamoyl)morpholine-4-carboxylate (2.86 g, 7.82 mmol, 100%) as a pale-yellow solid.

$^1$H NMR (300 MHz, CDCl$_3$): δ 1.49(9H,s), 2.77-3.01(2H, m), 3.66(1H,td,J=11.6, 2.8 Hz), 3.93-4.10(3H,m), 4.37-4.48 (1H,m), 7.54(1H,dd), 7.62(1H,d), 7.93(1H,d,J=1.9 Hz), 8.50 (1H,s).

(Step 8)

4N Hydrogen chloride/CPME (48.9 mL, 195.46 mmol) solution was added to a solution of tert-butyl 2-((3-chloro-4-cyanophenyl)carbamoyl)morpholine-4-carboxylate (2.86 g, 7.82 mmol) in MeOH (20 mL) at room temperature, and the mixture was stirred at room temperature for 1.5 hr. The reaction mixture was concentrated under reduced pressure, and The precipitate was collected by filtration with EtOH-diethyl ether to give N-(3-chloro-4-cyanophenyl)morpholine-2-carboxamide hydrochloride (1.42 g, 4.70 mmol, 60.1%) as a grayish white solid.

$^1$H NMR (300 MHz, DMSO-d$_6$): δ 3.00-3.27(3H,m), 3.47(1H,dd,J=12.8, 2.3 Hz), 3.94(1H,td,J=11.8, 2.5 Hz), 4.07-4.15(1H,m), 4.59(1H,dd,J=10.4, 2.8 Hz), 7.83(1H,dd), 7.94(1H,d), 8.14(1H,d,J=1.9 Hz), 9.64(2H,brs), 10.79(1H, s).

(Step 9)

4-Nitrophenyl chloroformate (61.4 mg, 0.30 mmol) was added a solution of 6-amino-3-(cyclopropylmethyl)-1-isopropylquinazoline-2,4(1H, 3H)-dione (72.4 mg, 0.26 mmol) and pyridine (25 μL, 0.31 mmol) in THF (1 mL) at room temperature, and the mixture was stirred at room temperature for 2 hr. The reaction mixture was concentrated under reduced pressure, and the residue was dissolved in DMF (3 mL). Thereto were added N-(3-chloro-4-cyanophenyl)morpholine-2-carboxamide hydrochloride (80 mg, 0.26 mmol) and DIEA (115 μL, 0.66 mmol) at room temperature, and the mixture was stirred at room temperature for 1 hr. To the reaction mixture was added water (60 mL), and 2N hydrochloric acid was added up to pH 3. The mixture was extracted with ethyl acetate, and the organic layer was washed with brine, dried over magnesium sulfate, and the solvent was evaporated under reduced pressure. The residue was purified by silica gel column chromatography (solvent gradient; 30→100% ethyl acetate/hexane), and the precipitate was washed with IPE/hexane to give the title compound (111.7 mg, 0.198 mmol, 74.7%) as a white powder.

$^1$H NMR (300 MHz, CDCl$_3$): δ 0.42-0.49(4H,m), 1.26-1.35(1H,m), 1.61(6H,d,J=7.2 Hz), 3.18-3.33(2H,m), 3.74-3.84(1H,m), 3.93-4.03(3H,m), 4.05-4.12(1H,m), 4.22(2H, dd,J=9.8, 3.0 Hz), 5.04 (1H,brs), 6.99(1H,s), 7.33(1H,d, J=9.1 Hz), 7.57(1H, dd), 7.64(1H,d), 7.89-7.98(3H,m), 8.55 (1H,s).

Example 79

(2R)-N$^2$-(3-chloro-4-cyanophenyl)-N$^4$-(3-(cyclopropylmethyl)-1-isopropyl-2,4-dioxo-1,2,3,4-tetrahydroquinazolin-6-yl)morpholine-2,4-dicarboxamide (Step 1)

HATU (3.86 g, 10.14 mmol) was added to a solution of 4-amino-2-chlorobenzonitrile (1.19 g, 7.80 mmol), (R)-4-(tert-butoxycarbonyl)morpholine-2-carboxylic acid (1.984 g, 8.58 mmol) and DIEA (2.72 mL, 15.60 mmol) in DMF (40 mL) at room temperature, and the mixture was stirred at room temperature for 16 hr. To the reaction mixture was added aqueous sodium hydrogen carbonate solution (200 mL), and the mixture was extracted 3 times with ethyl acetate. The organic layer was washed with brine, dried over magnesium sulfate, and the solvent was evaporated under reduced pressure. The residue was purified by silica gel column chromatography (solvent gradient; 10→60% ethyl acetate/hexane) to give (R)-tert-butyl 2-((3-chloro-4-cyanophenyl)carbamoyl)morpholine-4-carboxylate (690 mg, 1.886 mmol, 24.2%) as a white amorphous solid.

$^1$H NMR (300 MHz, CDCl$_3$): δ 1.49(9H,s), 2.78-3.00(2H, m), 3.66(1H,td,J=11.7, 2.6 Hz), 3.95-4.09(3H,m), 4.36-4.47 (1H,m), 7.55-7.60(1H,dd like), 7.60-7.70(1H,d like), 7.93 (1H,d,J=1.9 Hz), 8.50(1H,s).

(Step 2)

4N Hydrogen chloride/ethyl acetate (57.4 mL, 229.63 mmol) was added to (R)-tert-butyl 2-((3-chloro-4-cyanophenyl)carbamoyl)morpholine-4-carboxylate (5.60 g, 15.31 mmol) at room temperature, and the mixture was stirred at room temperature for 3 hr. Crystallization from ethyl acetate gave (R)-N-(3-chloro-4-cyanophenyl)morpholine-2-carboxamide hydrochloride (4.50 g, 14.89 mmol, 97%) as a white solid.

¹H NMR (300 MHz, DMSO-d₆): δ 2.98-3.26(3H,m), 3.47(1H,dd,J=12.8, 2.3 Hz), 3.85-3.99(1H,m), 4.10(1H,d, J=12.8 Hz), 4.57(1H,dd,J=10.6, 2.6 Hz), 7.77-7.86(1H,m), 7.90-7.98(1H,m), 8.14(1H,d,J=1.9 Hz), 9.51(2H,brs), 10.76 (1H,s).
(Step 3)
4-Nitrophenyl chloroformate (61.4 mg, 0.30 mmol) was added to a solution of 6-amino-3-(cyclopropylmethyl)-1-isopropylquinazoline-2,4(1H, 3H)-dione (72.4 mg, 0.26 mmol) and pyridine (25 μL, 0.31 mmol) in THF (1 mL) at room temperature, and the mixture was stirred at room temperature for 2 hr. The reaction mixture was concentrated under reduced pressure. The residue was dissolved in DMF (3 mL), added to N-(3-chloro-4-cyanophenyl)morpholine-2-carboxamide hydrochloride (80 mg, 0.26 mmol) and DIEA (115 μL, 0.66 mmol), and the mixture was stirred at room temperature for 1 hr. To the reaction mixture was added water (60 mL), 2N hydrochloric acid was added up to pH 3, and the mixture was extracted with ethyl acetate. The organic layer was washed with water and brine, dried over magnesium sulfate, and the solvent was evaporated under reduced pressure. The residue was purified by silica gel column chromatography (solvent gradient; 30→100% ethyl acetate/hexane), and The precipitate was collected by filtration with IPE and hexane, and washed to give the title compound (111.7 mg, 0.198 mmol, 74.7%) as a white powder.
¹H NMR (300 MHz, CDCl₃): δ 0.42-0.49(4H,m), 1.26-1.35(1H,m), 1.61(6H,d,J=7.2 Hz), 3.18-3.33(2H,m), 3.74-3.84(1H,m), 3.93-4.03(3H,m), 4.05-4.12(1H,m), 4.22(2H, dd,J=9.8, 3.0 Hz), 5.04(1H,brs), 6.99(1H,s), 7.33(1H,d, J=9.1 Hz), 7.57(1H,dd), 7.64(1H,d), 7.89-7.98(3H,m), 8.55 (1H,s).

Example 81 benzyl 2-((3-chloro-4-cyanophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate (Step 1)
Benzyl carbonochloridate (6.43 mL, 45.03 mmol) was added to a solution of 1-tert-butyl 3-methyl piperazine-1,3-dicarboxylate (10 g, 40.94 mmol) and DIEA (14.30 mL, 81.87 mmol) in THF (100 mL) at 5° C., and the mixture was stirred at room temperature for 14 hr. The reaction mixture was added to water and ethyl acetate. The organic layer was washed with aqueous ammonium chloride solution, dried over magnesium sulfate, and the solvent was evaporated under reduced pressure. The residue was purified by silica gel column chromatography (solvent gradient; 5→20% ethyl acetate/hexane) to give 1-benzyl 4-tert-butyl 2-methyl piperazine-1,2,4-tricarboxylate (16.2 g, 42.8 mmol, 105%) as white crystals.
¹H NMR (300 MHz, CDCl₃): δ 1.44(9H,s), 2.63-3.48(3H, m), 3.74(3H,s), 4.11(2H,s), 4.44-4.86(2H,m), 5.08-5.26(2H, m), 7.22-7.42(5H,m).
(Step 2)
A solution of 1-benzyl 4-tert-butyl 2-methyl piperazine-1,2,4-tricarboxylate (3.7 g, 9.78 mmol) and 8N aqueous sodium hydroxide solution (5.01 mL, 40.09 mmol) in THF (20 mL) was stirred at room temperature for 14 hr, and neutralized with 6N hydrochloric acid (9 mL). The mixture was extracted twice with ethyl acetate, and the organic layer was washed with brine, dried over magnesium sulfate, and the solvent was evaporated under reduced pressure to give 1-((benzyloxy)carbonyl)-4-(tert-butoxycarbonyl) piperazine-2-carboxylic acid (3.9 g, 10.70 mmol, 109%) as a white solid.
¹H NMR (300 MHz, CDCl₃): δ 1.43(9H,s), 2.74-3.46(3H, m), 3.77-4.06(2H,m), 4.49-4.89(2H,m), 5.07-5.29(2H,m), 6.73-7.19(1H,m), 7.29-7.44(5H,m).
(Step 3)
T3P (8.77 mL, 14.75 mmol) was added to a solution of 1-((benzyloxy)carbonyl)-4-(tert-butoxycarbonyl)piperazine-2-carboxylic acid (1.970 g, 5.41 mmol), 4-amino-2-chlorobenzonitrile (0.75 g, 4.92 mmol), DMAP (0.661 g, 5.41 mmol) and DIEA (4.28 mL, 24.58 mmol) in ethyl acetate (20 mL) was stirred at 70° C. for 3 hr, and at 85° C. for 2 hr. The reaction mixture was added to an aqueous sodium hydrogen carbonate solution, and the mixture was extracted twice with ethyl acetate. The organic layer was washed with brine, dried over magnesium sulfate, and the solvent was evaporated under reduced pressure. The residue was purified by silica gel column chromatography (solvent gradient; 50→100% ethyl acetate/hexane) to give crude 1-benzyl 4-tert-butyl 2-((3-chloro-4-cyanophenyl)carbamoyl)piperazine-1,4-dicarboxylate (1.2 g, 2.405 mmol, 48.9%) as a colorless oil.
¹H NMR (300 MHz, CDCl₃): δ 1.43(9H,s), 2.90-3.54(3H, m), 3.77-4.06(2H,m), 4.35-4.94(2H,m), 5.22(2H,s), 7.35 (6H,s), 7.43-7.56(1H,m), 7.67-7.86(1H,m), 8.52-9.39(1H, m).
(Step 4)
4N Hydrogen chloride/ethyl acetate (0.349 mL, 1.40 mmol) was added to a solution of 1-benzyl 4-tert-butyl 2-((3-chloro-4-cyanophenyl)carbamoyl)piperazine-1,4-dicarboxylate (0.557 g, 1.40 mmol) in ethyl acetate (5 mL) at room temperature, and the mixture was stirred. The precipitate was collected by filtration with ethyl acetate to give benzyl 2-((3-chloro-4-cyanophenyl)carbamoyl)piperazine-1-carboxylate hydrochloride (0.55 g, 1.263 mmol, 90%) as a white powder.
¹H NMR (300 MHz, DMSO-d₆): δ 2.99(1H,d,J=3.4 Hz), 3.17-3.59(3H,m), 3.81-4.13(2H,m), 4.99(1H,brs), 5.15(2H, brs), 7.14-7.52(5H,m), 7.72(1H,dd,J=8.5, 2.1 Hz), 7.95(1H, d,J=8.7 Hz), 8.12(1H,brs), 8.90-9.67(2H,m), 11.26(1H,s).
(Step 5)
4-Nitrophenyl chloroformate (60.2 mg, 0.30 mmol) was added to a solution of 6-amino-3-(cyclopropylmethyl)-1-isopropylquinazoline-2,4(1H, 3H)-dione (71 mg, 0.26 mmol) and pyridine (0.024 mL, 0.30 mmol) in THF (1 mL) at room temperature, and the mixture was stirred at room temperature for 1 hr. The reaction mixture was concentrated under reduced pressure, and the residue was dissolved in DMF (3 mL). This solution was added to benzyl 2-((3-chloro-4-cyanophenyl)carbamoyl)piperazine-1-carboxylate hydrochloride (114 mg, 0.29 mmol) and DIEA (0.113 mL, 0.65 mmol), and the mixture was stirred at room temperature for 1 hr. To the reaction mixture were added water and aqueous ammonium chloride solution, and the mixture was extracted with ethyl acetate. The organic layer was washed with brine, dried over magnesium sulfate, and the solvent was evaporated under reduced pressure. The residue was treated by silica gel column chromatography (solvent gradient; 50→100% ethyl acetate/hexane) to give the title compound (0.212 g, 0.304 mmol, 117%) as a white powder.
¹H NMR (300 MHz, CDCl₃): δ 0.46(4H,s), 1.30-1.36(1H, m), 1.61(6H,d,J=6.8 Hz), 2.83-3.13(2H,m), 3.23-3.38(1H, m), 3.97(2H,d,J=7.2 Hz), 4.17-4.31(2H,m), 4.42-4.59(1H, m), 4.90-5.41(5H,m), 7.40(10H,s), 7.84-8.08(2H,m), 8.68-8.94(1H,m).

Example 82

N³-(3-chloro-4-cyanophenyl)-N¹-(3-(cyclopropylmethyl)-1-isopropyl-2,4-dioxo-1,2,3,4-tetrahydroquinazolin-6-yl)piperazine-1,3-dicarboxamide Iodotrimethylsilane (0.546 mL, 4.01 mmol) was added to a solution of benzyl 2-((3-chloro-4-cyanophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate (70 mg, 0.10 mmol) in acetonitrile (2 mL) at 5° C., and the mixture was stirred at 5° C. for 2 hr. The reaction mixture was added to an aqueous sodium hydroxide solution, and extracted twice with ethyl acetate. The organic layer was washed with brine, dried over magnesium sulfate, and the solvent was evaporated under reduced pressure. The residue was purified by silica gel column chromatography (solvent gradient; 0→10% MeOH/ethyl acetate) to give the title compound (52 mg, 0.092 mmol, 92%) as a pale-yellow powder.

$^1$H NMR (300 MHz, CDCl$_3$): δ 0.42-0.52(4H,m), 1.29-1.35(1H,m), 1.61(6H,d,J=6.8 Hz), 2.75-2.86(1H,m), 2.90-3.07(2H,m), 3.30-3.44(1H,m), 3.70-3.80(1H,m), 3.94-4.02(2H,m), 4.11(1H,s), 4.38-4.51(1H,m), 4.97-5.18(1H,m), 7.29-7.37(1H,m), 7.61-7.76(3H,m), 7.80-7.86(1H,m), 7.87-7.94(1H,m), 7.96-8.01(1H,m), 9.62-9.71(1H,m). (free amine 1H was not observed)

Example 88

3-((3-chloro-4-cyanobenzoyl)amino)-N-(3-(cyclopropylmethyl)-1-isopropyl-2,4-dioxo-1,2,3,4-tetrahydroquinazolin-6-yl)piperidine-1-carboxamide (Step 1)

A solution of 4-bromo-3-chlorobenzoic acid (24.5 g, 104.05 mmol) and concentrated sulfuric acid (11.09 mL, 208.10 mmol) in EtOH (245 mL) was heated under reflux overnight. The reaction mixture was cooled, and concentrated under reduced pressure. To the residue was added ethyl acetate, and the organic layer was washed with water, aqueous sodium hydrogen carbonate solution and brine. Then, the organic layer was dried over sodium sulfate, and the solvent was evaporated under reduced pressure to give ethyl 4-bromo-3-chlorobenzoate (26.6 g, 101 mmol, 97%) as a pale orange solid.

$^1$H NMR (300 MHz, CDCl$_3$): δ 1.40(3H,t,J=7.0 Hz), 4.38(2H,q,J=7.2 Hz), 7.59-7.73(1H,m), 7.74-7.87(1H,m), 8.11(1H,d,J=1.5 Hz).

(Step 2)

Copper(I) cyanide (18.11 g, 202.19 mmol) was added to a solution of ethyl 4-bromo-3-chlorobenzoate (26.64 g, 101.09 mmol) in DMF (200 mL) at room temperature, and the mixture was heated at 140° C. overnight. To the reaction mixture was added water, and the mixture was extracted with ethyl acetate. The organic layer was washed with water, dried over sodium sulfate, and the solvent was evaporated under reduced pressure. The residue was purified by silica gel column chromatography (solvent gradient; 5→15% ethyl acetate/hexane) to give ethyl 3-chloro-4-cyanobenzoate (16.37 g, 78 mmol, 77%) as a grayish white solid.

$^1$H NMR (300 MHz, CDCl$_3$): δ 1.42(3H,t,J=7.2 Hz), 4.43(2H,q,J=7.2 Hz), 7.76(1H,d,J=7.9 Hz), 8.02(1H,dd,J=7.9, 1.5 Hz), 8.17(1H,d,J=1.1 Hz).

(Step 3)

2N Aqueous sodium hydroxide solution (27.8 mL, 55.67 mmol) was added to a mixture of ethyl 3-chloro-4-cyanobenzoate (3.89 g, 18.56 mmol) in MeOH (56 mL) and THF (112 mL) at room temperature, and the mixture was stirred at room temperature overnight. The reaction mixture was concentrated under reduced pressure, and neutralized with 1N hydrochloric acid. The precipitate was collected by filtration, and washed with water to give 3-chloro-4-cyanobenzoic acid (3.36 g, 18.50 mmol, 100%) as a white solid.

$^1$H NMR (300 MHz, DMSO-d$_6$): δ 7.90-8.22(3H,m), 13.92(1H,brs).

(Step 4)

T3P (2.06 mL, 3.50 mmol) was added to a solution of tert-butyl 3-aminopiperidine-1-carboxylate (500 mg, 2.50 mmol), 3-chloro-4-cyanobenzoic acid (499 mg, 2.75 mmol) and DIEA (0.65 mL, 3.74 mmol) in ethyl acetate (12.5 mL) at room temperature, and the mixture was stirred at room temperature overnight. The reaction mixture was concentrated under reduced pressure, and the residue was purified by silica gel column chromatography (solvent gradient; 5→70% ethyl acetate/hexane) to give tert-butyl 3-(3-chloro-4-cyanobenzamido)piperidine-1-carboxylate (525 mg, 1.443 mmol, 57.8%).

MS(API): Calculated 363.8. Found 362.2 (M−H).

(Step 5)

4N Hydrogen chloride/ethyl acetate (5.4 mL, 21.66 mmol) was added to tert-butyl 3-(3-chloro-4-cyanobenzamido)piperidine-1-carboxylate (525.5 mg, 1.44 mmol) at room temperature, and the mixture was stirred at room temperature overnight. Ethyl acetate was added to allow for precipitation to give 3-chloro-4-cyano-N-(piperidin-3-yl)benzamide hydrochloride (356 mg, 1.186 mmol, 82%) as a white solid.

MS(API): Calculated 300.2. Found 264.2 (M−HCl+H).

(Step 6)

4-Nitrophenyl chloroformate (57.9 mg, 0.29 mmol) was added to a solution of 6-amino-3-(cyclopropylmethyl)-1-isopropylquinazoline-2,4(1H, 3H)-dione (75 mg, 0.27 mmol) and pyridine (25 μL, 0.31 mmol) in THF (0.63 mL) at room temperature, and the mixture was stirred at room temperature for 2 hr. The reaction mixture was concentrated under reduced pressure, and the residue was dissolved in DMF (1.9 mL). The solution was added to 3-chloro-4-cyano-N-(piperidin-3-yl)benzamide hydrochloride (75 mg, 0.25 mmol) and DIEA (109 μL, 0.62 mmol) at room temperature. The mixture was stirred at room temperature for 3 hr. To the reaction mixture was added water, and the mixture was extracted with ethyl acetate. The organic layer was washed with brine, dried over sodium sulfate, and the solvent was evaporated under reduced pressure. The residue was purified by silica gel column chromatography (solvent gradient; 5→100% ethyl acetate/hexane) to give the title compound (118 mg, 0.210 mmol, 84%) as a white amorphous solid.

$^1$H NMR (300 MHz, CDCl$_3$): δ 0.38-0.51(4H,m), 1.55-2.12(12H,m), 3.37-3.56(2H,m), 3.62-3.73(1H,m), 3.87-4.00(3H,m), 4.17(1H,d,J=8.3 Hz), 5.00(1H,brs), 7.22(1H,d, J=9.1 Hz), 7.59-7.71(2H,m), 7.75-7.84(2H,m), 7.86-7.93(2H,m).

Example 92

N³-(4-cyano-3-fluorophenyl)-N¹-(3-(cyclopropylmethyl)-1-isopropyl-2,4-dioxo-1,2,3,4-tetrahydroquinazolin-6-yl)piperazine-1,3-dicarboxamide hydrochloride (Step 1)

T3P (7.86 mL, 13.22 mmol) was added to a solution of 1-((benzyloxy)carbonyl)-4-(tert-butoxycarbonyl)piperazine-2-carboxylic acid (1.767 g, 4.85 mmol), 4-amino-2-fluorobenzonitrile (0.60 g, 4.41 mmol), DMAP (0.592 g, 4.85 mmol) and DIEA (3.84 mL, 22.04 mmol) in ethyl acetate (20 mL), and the mixture was stirred at 70° C. for 3 hr, and at 85° C. for 2 hr. To the reaction mixture was added water, and the mixture was extracted twice with ethyl acetate. The organic layer was washed with brine, dried over magnesium sulfate, and the solvent was evaporated under reduced pressure. The residue was purified by silica gel column chromatography (solvent gradient; 50→100% ethyl acetate/hexane) to give 1-benzyl 4-tert-butyl 2-((4-cyano-3-fluorophenyl)carbamoyl)piperazine-1,4-dicarboxylate (1.01 g, 2.093 mmol, 47.5%) as a colorless oil.

$^1$H NMR (300 MHz, CDCl$_3$): δ 1.44(9H,s), 2.98-3.35(3H, m), 3.80-4.06(2H,m), 4.45-4.95(2H,m), 5.15-5.30(2H,m), 7.06-7.23(1H,m), 7.36(5H,s), 7.44-7.54(1H,m), 7.56-7.71 (1H,m), 8.41-9.24(1H,m).

(Step 2)

A solution of 1-benzyl 4-tert-butyl 2-((4-cyano-3-fluorophenyl)carbamoyl)piperazine-1,4-dicarboxylate (1.01 g, 2.09 mmol) in TFA (5 mL) was stirred at 5° C. for 2 hr, and concentrated under reduced pressure. To the residue was added ethyl acetate, and the mixture was basified with aqueous sodium hydrogen carbonate solution and extracted twice with ethyl acetate. The organic layer was washed with brine, dried over magnesium sulfate, and the solvent was evaporated under reduced pressure. The residue was purified by silica gel column chromatography (solvent gradient; 0→10% MeOH/ethyl acetate) and treated with 4N hydrogen chloride/ethyl acetate (0.523 mL, 2.09 mmol) to give benzyl 2-((4-cyano-3-fluorophenyl)carbamoyl)piperazine-1-carboxylate hydrochloride (0.80 g, 1.910 mmol, 91%) as a white powder.

$^1$H NMR (300 MHz, CDCl$_3$): δ 2.73-3.15(4H,m), 3.46-3.59(1H,m), 3.92-4.18(2H,m), 4.67(1H,brs), 5.22(2H,brs), 7.11(1H,s), 7.31-7.43(5H,m), 7.49(1H,dd,J=8.7, 7.2 Hz), 7.59(1H,dd,J=11.1, 1.7 Hz), 8.92-9.24(1H,m).

(Step 3)

4-Nitrophenyl chloroformate (170 mg, 0.84 mmol) was added to a solution of 6-amino-3-(cyclopropylmethyl)-1-isopropylquinazoline-2,4(1H, 3H)-dione (200 mg, 0.73 mmol) and pyridine (0.068 mL, 0.84 mmol) in THF (1 mL) at room temperature, and the mixture was stirred at room temperature for 14 hr. The reaction mixture was concentrated under reduced pressure, and the residue was dissolved in DMF (3 mL), and the solution was added to benzyl 2-((4-cyano-3-fluorophenyl)carbamoyl)piperazine-1-carboxylate hydrochloride (306 mg, 0.73 mmol) and DIEA (0.319 mL, 1.83 mmol) at room temperature. The mixture was stirred at room temperature for 3 hr. To the reaction mixture were added water and aqueous ammonium chloride solution, and the mixture was extracted with ethyl acetate. The organic layer was washed with brine, dried over magnesium sulfate, and the solvent was evaporated under reduced pressure. The residue was purified by silica gel column chromatography (solvent gradient; 50→100% ethyl acetate/hexane) to give benzyl 2-((4-cyano-3-fluorophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate (0.458 g, 0.672 mmol, 92%) as a white powder.

$^1$H NMR (300 MHz, CDCl$_3$): δ 0.42-0.55 (m, 4H), 1.29-1.37 (m, 1H), 1.56-1.64 (m, 6H), 2.87-3.11 (m, 2H), 3.22-3.36 (m, 1H), 3.92-4.01 (m, 2H), 4.18-4.32 (m, 2H), 4.46-4.59 (m, 1H), 4.91-5.39 (m, 4H), 7.12-7.24 (m, 1H), 7.29-7.59 (m, 8H), 7.89 (dd, J=9.06, 2.64 Hz, 1H), 7.96-7.99 (m, 1H), 8.00-8.07 (m, 1H), 8.84-8.94 (m, 1H).

(Step 4)

A solution of benzyl 2-((4-cyano-3-fluorophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate (430 mg, 0.63 mmol) and 10% palladium-carbon (134 mg, 0.06 mmol, 50%, wet) in EtOH (1 mL) was stirred under a hydrogen atmosphere at 1 atm at room temperature for 2 hr. The catalyst was removed by filtration, and the filtrate was concentrated under reduced pressure. The residue was purified by silica gel column chromatography (solvent gradient; 0→10% MeOH/ethyl acetate) to give an oil.

$^1$H NMR (300 MHz, CDCl$_3$): δ 0.38-0.56(5H,m), 1.29-1.38(1H,m), 1.61(6H,d,J=7.2 Hz), 2.73-2.86(1H,m), 2.93-3.09(2H,m), 3.30-3.44(1H,m), 3.69-3.75(1H,m), 3.92-4.01 (2H,m), 4.01-4.07(1H,m), 4.34-4.49(1H,m), 4.87-5.16(1H, m), 7.29-7.35(1H,m), 7.38-7.45(1H,m), 7.56-7.64(1H,m), 7.66-7.70(1H,m), 7.71-7.78(1H,m), 7.86-7.93(1H,m), 7.97-8.01(1H,m), 9.66-9.75(1H,m). (free amine 1H was not observed)

The obtained oil was treated with 4N hydrogen chloride/ethyl acetate (0.158 mL, 0.63 mmol) to give the title compound (300 mg, 0.514 mmol, 81%) as a white powder.

Example 95

N$^2$-(3-chloro-4-cyanophenyl)-N$^4$-(3-(cyclopropylmethyl)-1-isopropyl-2,4-dioxo-1,2,3,4-tetrahydroquinazolin-6-yl)thiomorpholine-2,4-dicarboxamide (Step 1)

T3P (3.61 mL, 6.07 mmol) was added to a solution of 4-amino-2-chlorobenzonitrile (370 mg, 2.43 mmol), 4-(tert-butoxycarbonyl)thiomorpholine-2-carboxylic acid (500 mg, 2.02 mmol), DIEA (1.76 mL, 10.11 mmol) and DMAP (272 mg, 2.22 mmol) in ethyl acetate (10 mL) at room temperature, and the mixture was heated at 60° C. overnight. The reaction mixture was concentrated under reduced pressure, and the residue was purified by silica gel column chromatography (solvent gradient; 5→60% ethyl acetate/hexane) to give tert-butyl 2-((3-chloro-4-cyanophenyl)carbamoyl)thiomorpholine-4-carboxylate (765 mg, 2.003 mmol, 99%) as an orange oil.

$^1$H NMR (300 MHz, CDCl$_3$): δ 1.38-1.55(9H,m), 2.46-2.64(1H,m), 2.74-2.87(1H,m), 3.34-3.52(2H,m), 3.65(1H, dd,J=14.2, 2.8 Hz), 4.03-4.17(1H,m), 4.60(1H,dd,J=14.2, 4.0 Hz), 7.60(2H,d,J=3.8 Hz), 7.94(1H,s), 9.14(1H,brs).

(Step 2)

4N Hydrogen chloride/ethyl acetate (7.5 mL, 30.05 mmol) was added to tert-butyl 2-((3-chloro-4-cyanophenyl)carbamoyl)thiomorpholine-4-carboxylate (765.0 mg, 2.00 mmol), and the mixture was stirred at room temperature for 3 hr. Crystallization from ethyl acetate gave N-(3-chloro-4-cyanophenyl)thiomorpholine-2-carboxamide hydrochloride (575 mg, 1.806 mmol, 90%) as a pale-brown powder.

$^1$H NMR (300 MHz, DMSO-d$_6$): δ 2.95-3.06(2H,m), 3.30(2H,brs), 3.42-3.60(2H,m), 4.06-4.17(1H,m), 7.65(1H, dd,J=8.7, 1.9 Hz), 7.95(1H,d,J=8.7 Hz), 8.10(1H,d,J=1.9 Hz), 8.62(1H,brs), 9.66(1H,brs), 11.38(1H,s).

(Step 3)

4-Nitrophenyl chloroformate (219 mg, 1.08 mmol) was added to a solution of 6-amino-3-(cyclopropylmethyl)-1-isopropylquinazoline-2,4(1H, 3H)-dione (283 mg, 1.04 mmol) and pyridine (88 μL, 1.08 mmol) in THF (2.4 mL) at room temperature, and the mixture was stirred at room temperature for 2 hr. The reaction mixture was concentrated under reduced pressure, and the residue was dissolved in DMF (7.1 mL). The solution was added to N-(3-chloro-4- cyanophenyl)thiomorpholine-2-carboxamide hydrochloride (300 mg, 0.94 mmol) and DIEA (411 μL, 2.36 mmol) at room temperature, and the mixture was stirred at room temperature for 3 hr. To the reaction mixture was added water, and the mixture was extracted with ethyl acetate. The organic layer was washed with brine, dried over sodium sulfate, and the solvent was evaporated under reduced pressure. The residue was purified by silica gel column chromatography (solvent gradient; 5→100% ethyl acetate/hexane) to give the title compound (446 mg, 0.768 mmol, 81%) as a white amorphous solid.

$^1$H NMR (300 MHz, CDCl$_3$): δ 0.41-0.53(4H,m), 1.22-1.40(1H,m), 1.57-1.64(6H,m), 2.50-2.60(1H,m), 2.73-2.86(1H,m), 3.01-3.14(1H,m), 3.55-3.65(2H,m), 3.98(2H,d,J=7.2 Hz), 4.72-4.91(2H,m), 5.05(1H,brs), 7.32(1H,d,J=9.4 Hz), 7.66-7.83(3H,m), 7.90(1H,dd,J=9.3, 2.8 Hz), 8.01(1H,d,J=2.6 Hz), 8.17(1H,s), 9.55(1H,s).

Example 102

(2R)-N$^2$-(4-cyano-3-fluorophenyl)-N$^4$-(3-(cyclopropylmethyl)-1-isopropyl-2,4-dioxo-1,2,3,4-tetrahydroquinazolin-6-yl)morpholine-2,4-dicarboxamide 4-Nitrophenyl chloroformate (93 mg, 0.46 mmol) was added to a solution of 6-amino-3-(cyclopropylmethyl)-1-isopropylquinazoline-2,4(1H, 3H)-dione (115 mg, 0.42 mmol) and pyridine (37.3 μL, 0.46 mmol) in THF (1003 μL) at room temperature, and the mixture was stirred at room temperature for 2 hr. The reaction mixture was concentrated under reduced pressure. The residue was dissolved in DMF (3009 μL), and added to (R)-N-(4-cyano-3-fluorophenyl)morpholine-2-carboxamide hydrochloride (100 mg, 0.40 mmol) and DIEA (175 μL, 1.00 mmol), and the mixture was stirred at room temperature for 3 hr. To the reaction mixture was added water, and the mixture was extracted with ethyl acetate. The organic layer was washed with water and brine, dried over magnesium sulfate, and the solvent was evaporated under reduced pressure. The residue was purified by silica gel column chromatography and solidified with IPE to give the title compound (113 mg, 0.206 mmol, 51.4%) as a white solid.

$^1$H NMR (300 MHz, CDCl$_3$): δ 0.40-0.50(4H,m), 1.26-1.35(1H,m), 1.57-1.66(6H,m), 3.18-3.36(2H,m), 3.74-3.86(1H,m), 3.91-4.03(3H,m), 4.05-4.26(3H,m), 5.06(1H,brs), 6.98(1H,brs), 7.30-7.38(2H,m), 7.53-7.65(1H,m), 7.78(1H,dd,J=11.0, 1.9 Hz), 7.91-7.99(2H,m), 8.59(1H,s).

Example 103

(2R)-N$^2$-(6-cyano-5-fluoropyridin-3-yl)-N$^4$-(3-(cyclopropylmethyl)-1-isopropyl-2,4-dioxo-1,2,3,4-tetrahydroquinazolin-6-yl)morpholine-2,4-dicarboxamide (Step 1)
T3P (2.2 mL, 3.70 mmol) was added to a solution of (R)-4-(tert-butoxycarbonyl)morpholine-2-carboxylic acid (285 mg, 1.23 mmol), 5-amino-3-fluoropicolinonitrile (186.2 mg, 1.36 mmol), DIEA (1078 μL, 6.17 mmol) and DMAP (166 mg, 1.36 mmol) in ethyl acetate (6.2 mL), and the mixture was stirred at 80° C. overnight. T3P (2.2 mL, 3.70 mmol) was further added, and the mixture was stirred at 80° C. overnight. To the reaction mixture was added water, and the mixture was extracted with ethyl acetate. The organic layer was washed with water, dried over sodium sulfate, and the solvent was evaporated under reduced pressure. The residue was purified by silica gel column chromatography (NH, solvent gradient; 5→80% ethyl acetate/hexane) to give (R)-tert-butyl 2-((6-cyano-5-fluoropyridin-3-yl)carbamoyl)morpholine-4-carboxylate (343 mg, 0.980 mmol, 79%) as a white solid.

MS(API): Calculated 350.4. Found 349.2 (M–H).
(Step 2)
4N Hydrogen chloride/ethyl acetate (3.67 mL, 14.70 mmol) was added to (R)-tert-butyl 2-((6-cyano-5-fluoropyridin-3-yl)carbamoyl)morpholine-4-carboxylate (343.3 mg, 0.98 mmol), and the mixture was stirred at room temperature for 3 hr. The precipitate was collected by filtration with ethyl acetate to give (R)-N-(6-cyano-5-fluoropyridin-3-yl)morpholine-2-carboxamide hydrochloride (232 mg, 0.807 mmol, 82%) as a white solid.

$^1$H NMR (300 MHz, DMSO-d$_6$): δ 2.98-3.23(2H,m), 3.50(1H,d,J=12.1 Hz), 3.61-3.99(2H,m), 4.06-4.18(1H,m), 4.62(1H,dd,J=10.4, 2.8 Hz), 8.37(1H,dd,J=11.3, 1.9 Hz), 8.83-8.95(1H,m), 9.39(1H,brs), 9.63(1H,brs), 11.10(1H,s).
(Step 3)
4-Nitrophenyl chloroformate (69.5 mg, 0.34 mmol) was added to a solution of 6-amino-3-(cyclopropylmethyl)-1-isopropylquinazoline-2,4(1H, 3H)-dione (86 mg, 0.31 mmol) and pyridine (27.9 μL, 0.34 mmol) in THF (0.75 mL) at room temperature, and the mixture was stirred at room temperature for 2 hr. The reaction mixture was concentrated under reduced pressure, and the residue was dissolved in DMF (2.25 mL), and the solution was added to (R)-N-(6-cyano-5-fluoropyridin-3-yl)morpholine-2-carboxamide hydrochloride (75 mg, 0.30 mmol) and DIEA (131 μL, 0.75 mmol) at room temperature. The mixture was stirred at room temperature for 4 hr. To the reaction mixture was added water, and the mixture was extracted with ethyl acetate. The organic layer was washed with brine, dried over sodium sulfate, and the solvent was evaporated under reduced pressure, and the residue was crystallized from IPE to give the title compound (116 mg, 0.211 mmol, 70.4%) as white crystals.

$^1$H NMR (300 MHz, CDCl$_3$): δ 0.40-0.49(4H,m), 1.22-1.37(1H,m), 1.57-1.67(6H,m), 3.17-3.31(2H,m), 3.76-3.86(1H,m), 3.92-4.05(3H,m), 4.09-4.18(1H,m), 4.22-4.31(2H,m), 5.05(1H,brs), 6.90(1H,s), 7.34(1H,d,J=9.1 Hz), 7.90-8.00(2H,m), 8.41-8.48(2H,m), 8.79(1H,s).

Example 113 methyl 3-((1-((3-(cyclopropylmethyl)-1-isopropyl-2,4-dioxo-1,2,3,4-tetrahydroquinazolin-6-yl)carbamoyl)piperidin-3-yl)carbamoyl)benzoate (Step 1)
4-Nitrophenyl chloroformate (810 mg, 4.02 mmol) was added to a solution of 6-amino-3-(cyclopropylmethyl)-1-isopropylquinazoline-2,4(1H, 3H)-dione (955 mg, 3.50 mmol) and pyridine (325 μL, 4.02 mmol) in THF (8.7 mL) at room temperature, and the mixture was stirred at room temperature for 2 hr. The reaction mixture was concentrated under reduced pressure, and the residue was dissolved in DMF (2.6 mL). The solution was added to tert-butyl piperidin-3-ylcarbamate (700 mg, 3.50 mmol) and DIEA (1522 μL, 8.74 mmol) at room temperature. The mixture was stirred at room temperature for 1 hr. To the reaction mixture was added water, and the mixture was extracted with ethyl acetate. The organic layer was washed with brine, dried over sodium sulfate, and the solvent was evaporated under reduced pressure. The residue was purified by silica gel column chromatography to give tert-butyl (1-((3-(cyclopropylmethyl)-1-isopropyl-2,4-dioxo-1,2,3,4-tetrahydroquinazolin-6-yl)carbamoyl)piperidin-3-yl)carbamate (2427 mg, 4.86 mmol, 139%) as a pale-yellow oil.

MS(API): Calculated 499.6. Found 400.4 (M-Boc+H).

(Step 2)

4N Hydrogen chloride/ethyl acetate (13.13 mL, 52.50 mmol) was added to tert-butyl (1-((3-(cyclopropylmethyl)-1-isopropyl-2,4-dioxo-1,2,3,4-tetrahydroquinazolin-6-yl)carbamoyl)piperidin-3-yl)carbamate (1.749 g, 3.50 mmol), and the mixture was stirred at room temperature for 3 hr to give 3-amino-N-(3-(cyclopropylmethyl)-1-isopropyl-2,4-dioxo-1,2,3,4-tetrahydroquinazolin-6-yl)piperidine-1-carboxamide hydrochloride (2.65 g, 6.08 mmol, 174%) as a pale-orange oil.

MS(API): Calculated 435.95. Found 400.4 (M−HCl+H).

(Step 3)

T3P (1619 µL, 2.75 mmol) was added to a solution of 3-amino-N-(3-(cyclopropylmethyl)-1-isopropyl-2,4-dioxo-1,2,3,4-tetrahydroquinazolin-6-yl)piperidine-1-carboxamide hydrochloride (400 mg, 0.92 mmol), 3-(methoxycarbonyl)benzoic acid (248 mg, 1.38 mmol) and DIEA (801 µL, 4.59 mmol) in DMF (6.1 mL), and the mixture was stirred at room temperature for 4 hr. To the reaction mixture was added water, and the mixture was extracted with ethyl acetate. The organic layer was washed with brine, dried over sodium sulfate, and the solvent was evaporated under reduced pressure. The residue was purified by silica gel column chromatography (solvent; ethyl acetate/hexane) to give the title compound (50.6 mg, 0.090 mmol, 9.82%) as a white amorphous solid.

Example 122

(2R)-N²-(5-chloro-6-cyanopyridin-3-yl)-N⁴-(3-(cyclopropylmethyl)-1-isopropyl-2,4-dioxo-1,2,3,4-tetrahydroquinazolin-6-yl)morpholine-2,4-dicarboxamide (Step 1)

A mixture of 2,3-dichloro-5-nitropyridine (15.24 g, 78.97 mmol) and copper cyanide (28.3 g, 315.88 mmol) in NMP (128 mL) was stirred under microwave irradiation at 200° C. for 1 hr. The reaction mixture was added to 0.5 N HCl (1300 mL) and iron (III) chloride 6 hydrate (107 g, 394.84 mmol), and the mixture was stirred at room temperature for 40 min and extracted with ethyl acetate/hexane mixed solution (3:1). The organic layer was washed with water and brine, dried over magnesium sulfate, and the solvent was evaporated under reduced pressure. The residue was purified by silica gel column chromatography (solvent gradient; 2→10% ethyl acetate/hexane) to give 3-chloro-5-nitropicolinonitrile (4.76 g, 25.9 mmol, 32.8%) as a pale-yellow solid.

¹H NMR (300 MHz, CDCl₃): δ 8.68(1H,d,J=2.3 Hz), 9.40(1H,d,J=2.3 Hz).

(Step 2)

Iron powder (5.79 g, 103.73 mmol) was added to a mixture of 3-chloro-5-nitropicolinonitrile (4.76 g, 25.93 mmol) in MeOH (30 mL) and acetic acid (30 mL) at room temperature, and the mixture was stirred at 80° C. for 1 hr. The reaction mixture was added to an aqueous sodium hydrogen carbonate solution (400 mL), and the mixture was neutralized by carefully adding 8N aqueous sodium hydroxide solution and potassium carbonate. The mixture was extracted with ethyl acetate/THF mixed solution (3:1). Insoluble materials were filtered off. The organic layer was washed with water and brine, dried over sodium sulfate, and the solvent was evaporated under reduced pressure. The precipitate was collected by filtration with IPE/hexane. The precipitate was recrystallized from ethyl acetate/THF to give 5-amino-3-chloropicolinonitrile (2.59 g, 16.87 mmol, 65.0%) as pale-yellow prism crystals.

¹H NMR (300 MHz, DMSO-d₆): δ 6.78(2H,s), 7.06(1H, d,J=2.3 Hz), 7.94(1H,d,J=2.3 Hz).

(Step 3)

T3P (7.63 mL, 12.97 mmol) was added to a solution of (R)-4-(tert-butoxycarbonyl)morpholine-2-carboxylic acid (1.00 g, 4.32 mmol), 5-amino-3-chloropicolinonitrile (0.731 g, 4.76 mmol), DIEA (3.78 mL, 21.62 mmol) and DMAP (0.581 g, 4.76 mmol) in ethyl acetate (14.41 mL), and the mixture was stirred at 80° C. overnight. T3P (7.63 mL, 12.97 mmol) was further added, and the mixture was stirred at 80° C. for 2 hr. To the reaction mixture was added water, and the mixture was extracted with ethyl acetate. The organic layer was washed with water, dried over sodium sulfate, and the solvent was evaporated under reduced pressure. The residue was purified by silica gel column chromatography (solvent; ethyl acetate/hexane) to give (R)-tert-butyl 2-((5-chloro-6-cyanopyridin-3-yl)carbamoyl)morpholine-4-carboxylate (0.570 g, 1.554 mmol, 35.9%) as a white solid.

MS(API): Calculated 366.8. Found 366.2 (M−H).

(Step 4)

4N Hydrogen chloride/ethyl acetate (5.8 mL, 23.3 mmol) was added to (R)-tert-butyl 2-((5-chloro-6-cyanopyridin-3-yl)carbamoyl)morpholine-4-carboxylate (570 mg, 1.55 mmol), and the mixture was stirred at room temperature for 3 hr. The reaction mixture was concentrated under reduced pressure, and crystallization from ethyl acetate gave (R)-N-(5-chloro-6-cyanopyridin-3-yl)morpholine-2-carboxamide hydrochloride (453 mg, 1.493 mmol, 96%) as a white solid.

MS(API): Calculated 303.2. Found 267.1 (M−HCl+H).

(Step 5)

4-Nitrophenyl chloroformate (130 mg, 0.65 mmol) was added to a solution of 6-amino-3-(cyclopropylmethyl)-1-isopropylquinazoline-2,4(1H, 3H)-dione (161 mg, 0.59 mmol) and pyridine (52.3 µL, 0.65 mmol) in THF (1.4 mL) at room temperature, and the mixture was stirred at room temperature for 2 hr. The reaction mixture was concentrated under reduced pressure, and the residue was dissolved in DMF (4.2 mL). The solution was added to (R)-N-(5-chloro-6-cyanopyridin-3-yl)morpholine-2-carboxamide hydrochloride (150 mg, 0.56 mmol) and DIEA (245 µL, 1.41 mmol) at room temperature. The mixture was stirred at room temperature for 4 hr. To the reaction mixture was added water, and the mixture was extracted with ethyl acetate. The organic layer was washed with water and brine, dried over sodium sulfate, and the solvent was evaporated under reduced pressure. The residue was purified by silica gel column chromatography and crystallized from IPE to give the title compound (253 mg, 0.446 mmol, 79%) as white crystals.

¹H NMR (300 MHz, CDCl₃): δ 0.37-0.51 (m, 4H), 1.22-1.36 (m, 1H), 1.61 (d, J=7.09 Hz, 6H), 3.15-3.31 (m, 2H), 3.80 (td, J=11.25, 2.69 Hz, 1H), 3.92-4.05 (m, 3H), 4.07-4.18 (m, 1H), 4.21-4.36 (m, 2H), 5.05 (brs, 1H), 6.98 (s, 1H), 7.34 (d, J=9.05 Hz, 1H), 7.86-7.98 (m, 2H), 8.53-8.62 (m, 2H), 8.73 (s, 1H).

[α]$_D^{25}$ −55.5 (c 0.2530, MeOH)

Example 132 methyl 4-((1-((3-(cyclopropylmethyl)-1-isopropyl-2,4-dioxo-1,2,3,4-tetrahydroquinazolin-6-yl)carbamoyl)piperidin-3-yl)carbamoyl)benzoate (Step 1)

3-Amino-N-(3-(cyclopropylmethyl)-1-isopropyl-2,4-dioxo-1,2,3,4-tetrahydroquinazolin-6-yl)piperidine-1-carboxamide hydrochloride (1.0 g, 2.29 mmol) was added to aqueous sodium hydrogen carbonate solution and ethyl acetate. The organic layer was washed with water and brine, dried over sodium sulfate, and the solvent was evaporated under reduced pressure. The residue was purified by silica gel column chromatography (solvent; ethyl acetate/hexane), and crystallized from ethyl acetate/hexane to give 3-amino-N-(3-(cyclopropylmethyl)-1-isopropyl-2,4-dioxo-1,2,3,4-tetrahydroquinazolin-6-yl)piperidine-1-carboxamide (0.481 g, 1.204 mmol, 52.5%) as white crystals.

MS(API): Calculated 399.5. Found 400.4 (M+H).

(Step 2)

T3P (221 µL, 0.38 mmol) was added to a solution of 3-amino-N-(3-(cyclopropylmethyl)-1-isopropyl-2,4-dioxo-1,2,3,4-tetrahydroquinazolin-6-yl)piperidine-1-carboxamide (50 mg, 0.13 mmol), 4-(methoxycarbonyl)benzoic acid (27.1 mg, 0.15 mmol) and DIEA (109 µL, 0.63 mmol) in ethyl acetate (834 µL) at room temperature, and the mixture was stirred at room temperature overnight. The reaction mixture was concentrated under reduced pressure, and the residue was purified by silica gel column chromatography (solvent; ethyl acetate/hexane) and crystallized from IPE to give the title compound (6.30 mg, 0.011 mmol, 8.96%) as white crystals.

$^1$H NMR (300 MHz, CDCl$_3$): δ 0.41-0.49 (m, 4H), 1.26 (s, 1H), 1.55-2.03 (m, 10H), 3.48-3.81 (m, 4H), 3.89-4.01 (m, 5H), 4.11-4.20 (m, 1H), 5.04 (brs, 1H), 6.80 (d, J=4.91 Hz, 1H), 6.99 (s, 1H), 7.30 (d, J=9.06 Hz, 1H), 7.85 (d, J=8.31 Hz, 2H), 7.90-7.99 (m, 2H), 8.09 (d, J=8.31 Hz, 2H).

Example 135

N$^2$-(4-cyano-2,5-difluorophenyl)-N$^4$-(3-(cyclopropylmethyl)-1-isopropyl-2,4-dioxo-1,2,3,4-tetrahydroquinazolin-6-yl)morpholine-2,4-dicarboxamide (Step 1)

4-Nitrophenyl chloroformate (2.370 g, 11.76 mmol) was added to a solution of 6-amino-3-(cyclopropylmethyl)-1-isopropylquinazoline-2,4(1H, 3H)-dione (2.93 g, 10.73 mmol) and pyridine (0.951 mL, 11.76 mmol) in THF (25.6 mL) at room temperature, and the mixture was stirred at room temperature for 2 hr. The reaction mixture was concentrated under reduced pressure, and the residue was dissolved in DMF (77 mL). The solution was added to ethyl morpholine-2-carboxylate hydrochloride (2.00 g, 10.22 mmol) and DIEA (4.45 mL, 25.56 mmol) at room temperature. The mixture was stirred at room temperature for 3 hr. To the reaction mixture was added water, and the mixture was extracted with ethyl acetate. The organic layer was washed with brine, dried over sodium sulfate, and the solvent was evaporated under reduced pressure. The residue was purified by silica gel column chromatography to give crude ethyl 4-((3-(cyclopropylmethyl)-1-isopropyl-2,4-dioxo-1,2,3,4-tetrahydroquinazolin-6-yl)carbamoyl)morpholine-2-carboxylate (7.04 g, 15.35 mmol, 150%).

MS(API): Calculated 485.5. Found 459.4 (M+H).

(Step 2)

2N Aqueous sodium hydroxide solution (15.33 mL, 30.66 mmol) was added to a mixture of ethyl 4-((3-(cyclopropylmethyl)-1-isopropyl-2,4-dioxo-1,2,3,4-tetrahydroquinazolin-6-yl)carbamoyl)morpholine-2-carboxylate (4.69 g, 10.22 mmol) in THF (17.03 mL) and EtOH (8.52 mL) at room temperature, and the mixture was stirred at room temperature for 2 hr. The reaction mixture was neutralized with 2N hydrochloric acid, and extracted with ethyl acetate. The organic layer was washed with brine, dried over sodium sulfate, and the solvent was evaporated under reduced pressure. The residue was crystallized from ethyl acetate/hexane to give 4-((3-(cyclopropylmethyl)-1-isopropyl-2,4-dioxo-1,2,3,4-tetrahydroquinazolin-6-yl)carbamoyl)morpholine-2-carboxylic acid (2.60 g, 6.03 mmol, 59.0%) as white crystals.

$^1$H NMR (300 MHz, DMSO-d$_6$): δ 0.28-0.49(4H,m), 1.11-1.26(1H,m), 1.51(6H,d,J=6.8 Hz), 3.08-3.26(2H,m), 3.47-3.62(1H,m), 3.70-4.17(6H,m), 5.01(1H,brs), 7.58(1H, d,J=9.4 Hz), 7.89(1H,dd,J=9.3, 2.8 Hz), 8.19(1H,d,J=2.6 Hz), 8.90(1H,s), 13.01(1H,brs).

(Step 3)

T3P (0.410 mL, 0.70 mmol) was added to a solution of 4-((3-(cyclopropylmethyl)-1-isopropyl-2,4-dioxo-1,2,3,4-tetrahydroquinazolin-6-yl)carbamoyl)morpholine-2-carboxylic acid (100 mg, 0.23 mmol), 4-cyano-2,5-difluoroaniline (35.8 mg, 0.23 mmol), DIEA (0.203 mL, 1.16 mmol) and DMAP (31.2 mg, 0.26 mmol) in ethyl acetate (2.0 mL), and the mixture was stirred at 80° C. overnight. To the reaction mixture was added water, and the mixture was extracted 3 times with ethyl acetate. The organic layer was washed with 10% aqueous citric acid solution, aqueous sodium hydrogen carbonate solution and brine, dried over magnesium sulfate, and the solvent was evaporated under reduced pressure. The residue was purified by silica gel column chromatography (solvent; ethyl acetate/hexane) and crystallized from ethyl acetate/hexane to give the title compound (20.5 mg, 0.036 mmol, 15.58%) as white crystals.

$^1$H NMR (300 MHz, DMSO-d$_6$): δ 0.29-0.48(4H,m), 1.14-1.32(1H,m), 1.51(6H,d,J=7.2 Hz), 2.99-3.17(2H,m), 3.57-3.72(1H,m), 3.83(2H,d,J=7.2 Hz), 3.90-4.16(2H,m), 4.22-4.37(2H,m), 4.88-5.14(1H,m), 7.54-7.63(1H,m), 7.86-7.94(1H,m), 8.10(2H,m,J=10.2, 10.2, 6.0 Hz), 8.20(1H,d, J=2.6 Hz), 8.95(1H,s), 9.98(1H,s).

Example 146

N-(3-(cyclopropylmethyl)-1-isopropyl-2,4-dioxo-1,2,3,4-tetrahydroquinazolin-6-yl)-3-((phenylcarbamoyl)amino) piperidine-1-carboxamide A solution of phenylisocyanate (20.40 µL, 0.19 mmol) in THF (626 µL) was added to 3-amino-N-(3-(cyclopropylmethyl)-1-isopropyl-2,4-dioxo-1,2,3,4-tetrahydroquinazolin-6-yl)piperidine-1-carboxamide (50 mg, 0.13 mmol) and TEA (52.3 µL, 0.38 mmol) at room temperature, and the mixture was stirred at room temperature overnight. The reaction mixture was concentrated under reduced pressure, and the residue was purified by silica gel column chromatography (solvent; ethyl acetate/hexane) and crystallized from IPE to give the title compound (86 mg, 0.166 mmol, 133%) as white crystals.

$^1$H NMR (300 MHz, CDCl$_3$): δ 0.33-0.54 (m, 4H), 1.16-1.47 (m, 7H), 1.52-1.95 (m, 4H), 2.92-3.09 (m, 1H), 3.43 (d, J=13.22 Hz, 1H), 3.68-3.98 (m, 2H), 4.06-4.42 (m,

3H), 4.68 (brs, 1H), 6.16 (d, J=7.93 Hz, 1H), 6.78-6.91 (m, 1H), 6.91-7.11 (m, 5H), 7.35-7.56 (m, 2H), 7.66 (s, 1H), 8.11 (d, J=2.27 Hz, 1H).

Example 157

6-cyano-N-(1-((3-(cyclopropylmethyl)-1-isopropyl-2,4-dioxo-1,2,3,4-tetrahydroquinazolin-6-yl)carbamoyl)piperidin-3-yl) nicotinamide 6-Cyanonicotinic acid (0.160 mmol) was added to a solution of 3-amino-N-(3-(cyclopropylmethyl)-1-isopropyl-2,4-dioxo-1,2,3,4-tetrahydroquinazolin-6-yl)piperidine-1-carboxamide hydrochloride (0.035 g, 0.08 mmol), HATU (0.061 g, 0.160 mmol) and DIEA (0.056 mL, 0.320 mmol) in DMF (1 mL) at room temperature, and the mixture was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (34 mg, 64.2 μmol, 80%).

Example 168

(2R)-$N^2$-(4-cyano-2,5-difluorophenyl)-$N^4$-(3-(cyclopropylmethyl)-1-isopropyl-2,4-dioxo-1,2,3,4-tetrahydroquinazolin-6-yl)morpholine-2,4-dicarboxamide (Step 1)
T3P (10.68 mL, 18.16 mmol) was added to a solution of (R)-4-(tert-butoxycarbonyl)morpholine-2-carboxylic acid (1.4 g, 6.05 mmol), 4-amino-2,5-difluorobenzonitrile (1.026 g, 6.66 mmol), DIEA (5.29 mL, 30.27 mmol) and DMAP (0.814 g, 6.66 mmol) in ethyl acetate (30 mL), and the mixture was stirred at 80° C. overnight. To the reaction mixture was added water, and the mixture was extracted with ethyl acetate. The organic layer was dried over sodium sulfate, and the solvent was evaporated under reduced pressure. The residue was treated with ethyl acetate/hexane to filter off unreacted 4-amino-2,5-difluorobenzonitrile. The filtrate was concentrated under reduced pressure, and the residue was purified by silica gel column chromatography (solvent; ethyl acetate/hexane) to give (R)-tert-butyl 2-((4-cyano-2,5-difluorophenyl)carbamoyl)morpholine-4-carboxylate (350.3 mg, 16%) and crude (R)-tert-butyl 2-((4-cyano-2,5-difluorophenyl)carbamoyl)morpholine-4-carboxylate (910.1 mg) each as a white solid.
$^1$H NMR (300 MHz, CDCl$_3$): δ 1.50(9H,s), 2.77-3.07(2H, m), 3.60-3.74(1H,m), 3.94-4.18(3H,m), 4.30-4.59(1H,m), 7.36(1H,dd,J=9.8, 5.3 Hz), 8.47(1H,dd,J=10.6, 6.0 Hz), 8.87(1H,brs).
(Step 2)
4N Hydrogen chloride/ethyl acetate (5.0 mL, 20.00 mmol) was added to a solution of (R)-tert-butyl 2-((4-cyano-2,5-difluorophenyl)carbamoyl)morpholine-4-carboxylate (345 mg, 0.94 mmol) in ethyl acetate (5.0 mL), and the mixture was stirred at room temperature overnight. The reaction mixture was concentrated under reduced pressure, and the residue was crystallized from ethyl acetate to give (R)-N-(4-cyano-2,5-difluorophenyl)morpholine-2-carboxamide hydrochloride (246.9 mg, 0.813 mmol, 87%) as grayish white crystals.
MS(API): Calculated 303.7. Found 268.2 (M−HCl+H).

(Step 3)
4-Nitrophenyl chloroformate (85 mg, 0.42 mmol) was added to a solution of 6-amino-3-(cyclopropylmethyl)-1-isopropylquinazoline-2,4(1H, 3H)-dione (100 mg, 0.37 mmol) and pyridine (0.034 mL, 0.42 mmol) in THF (1 mL) at room temperature, and the mixture was stirred at room temperature for 1 hr. The reaction mixture was concentrated under reduced pressure, and the residue was dissolved in DMF (3 mL). The solution was added to (R)-N-(4-cyano-2,5-difluorophenyl)morpholine-2-carboxamide hydrochloride (111 mg, 0.37 mmol) and DIEA (0.159 mL, 0.91 mmol) at room temperature. The mixture was stirred at room temperature for 3 hr. To the reaction mixture was added water, and the mixture was extracted with ethyl acetate. The organic layer was washed with brine, dried over magnesium sulfate, and the solvent was evaporated under reduced pressure. The residue was purified by silica gel column chromatography (solvent gradient; 50→100% ethyl acetate/hexane) and crystallized from ethyl acetate/hexane to give the title compound (121.2 mg, 0.214 mmol, 58.5%) as white crystals.
$^1$H NMR (300 MHz, DMSO-d$_6$): δ 0.35(4H,s), 1.09-1.29 (1H,m), 1.51(6H,d,J=6.8 Hz), 3.00-3.17(2H,m), 3.56-3.71 (1H,m), 3.82(2H,d,J=6.8 Hz), 3.90-4.13(2H,m), 4.22-4.36 (2H,m), 5.01(1H,brs), 7.59(1H,d,J=9.1 Hz), 7.90(1H,dd, J=9.1, 2.6 Hz), 8.01-8.16(2H,m), 8.19(1H,d,J=2.6 Hz), 8.95 (1H,s), 9.98(1H,s).
$[\alpha]_D^{25}$ −21.0 (c 0.2525, MeOH)

Example 171

(2R)-$N^2$-(4-cyano-2,5-difluorophenyl)-$N^4$-(3-(cyclopropylmethyl)-7-fluoro-1-isopropyl-2,4-dioxo-1,2,3,4-tetrahydroquinazolin-6-yl)morpholine-2,4-dicarboxamide (Step 1)
A solution of aminomethylcyclopropane (5.01 g, 70.5 mmol), 2-amino-5-bromo-4-fluorobenzoic acid (15 g, 64.10 mmol) and DIEA (33.6 mL, 192.29 mmol) in DMF (200 mL) was stirred at room temperature for 15 min. HATU (29.2 g, 76.92 mmol) was added at room temperature, and the mixture was stirred at room temperature overnight. To the reaction mixture was added water, and the mixture was extracted with ethyl acetate. The organic layer was washed with water and brine, dried over magnesium sulfate, and the solvent was evaporated under reduced pressure. The residue was crystallized from IPE to give 2-amino-5-bromo-N-(cyclopropylmethyl)-4-fluorobenzamide (13.9 g, 48.4 mmol, 76%) as a brownish-red solid.
$^1$H NMR (300 MHz, CDCl$_3$): δ 0.22-0.31(2H,m), 0.50-0.63(2H,m), 0.93-1.13(1H,m), 3.25(2H,dd,J=7.2, 5.3 Hz), 5.72(2H,brs), 6.07(1H,brs), 6.43(1H,d,J=10.4 Hz), 7.49(1H, d,J=7.2 Hz).
(Step 2)
Bis(trichloromethyl)carbonate (9.63 g, 32.43 mmol) was added to a solution of 2-amino-5-bromo-N-(cyclopropylmethyl)-4-fluorobenzamide (13.9 g, 48.41 mmol) and TEA (14.84 mL, 106.50 mmol) in THF (200 mL) at room temperature, and the mixture was stirred at 65° C. for 2.5 hr. The reaction mixture was poured into ice water, brine was added thereto, and the mixture was extracted with ethyl acetate/THF. The organic layer was dried over magnesium sulfate, and the solvent was evaporated under reduced pressure. The precipitate was washed with IPE to give 6-bromo-3-(cyclopropylmethyl)-7-fluoroquinazoline-2,4 (1H, 3H)-dione (11.8 g, 37.7 mmol, 78%) as a brownish-red solid.

$^1$H NMR (300 MHz, CDCl$_3$): δ 0.39-0.58(4H,m), 1.22-1.40(1H,m), 3.96(2H,d,J=7.2 Hz), 6.87(1H,d,J=8.3 Hz), 8.37(1H,d,J=7.2 Hz), 9.54(1H,brs).

(Step 3)

2-Iodopropane (9.14 mL, 91.59 mmol) was added to a solution of 6-bromo-3-(cyclopropylmethyl)-7-fluoroquinazoline-2,4(1H, 3H)-dione (9.56 g, 30.53 mmol) and cesium carbonate (14.92 g, 45.80 mmol) in DMF (150 mL) at room temperature, and the mixture was stirred at 65° C. overnight. To the reaction mixture was added water, and the mixture was extracted with ethyl acetate. The organic layer was washed with water and brine, dried over magnesium sulfate, and the solvent was evaporated under reduced pressure. The residue was purified by silica gel column chromatography (solvent; ethyl acetate/hexane). A highly-polar product, 6-bromo-3-(cyclopropylmethyl)-7-fluoro-1-isopropylquinazoline-2,4(1H, 3H)-dione (3.81 g, 10.73 mmol, 35.1%), was obtained as a white solid.

$^1$H NMR (300 MHz, CDCl$_3$): δ 0.36-0.55(4H,m), 1.22-1.34(1H,m), 1.62(6H,d,J=6.8 Hz), 3.95(2H,d,J=7.2 Hz), 4.95(1H,brs), 7.14(1H,d,J=10.6 Hz), 8.44(1H,d,J=7.6 Hz).

(Step 4)

A solution of 6-bromo-3-(cyclopropylmethyl)-7-fluoro-1-isopropylquinazoline-2,4(1H, 3H)-dione (3.8 g, 10.70 mmol), cesium carbonate (8.71 g, 26.75 mmol), tert-butyl carbamate (1.755 g, 14.98 mmol), XPhos (0.510 g, 1.07 mmol) and Pd$_2$(dba)$_3$ (0.490 g, 0.53 mmol) in toluene (80 mL) was stirred at 80° C. overnight. To the reaction mixture was added water, and the mixture was extracted with ethyl acetate. The organic layer was washed with water and brine, dried over magnesium sulfate, and the solvent was evaporated under reduced pressure. The residue was purified by silica gel column chromatography (solvent gradient; 5→50% ethyl acetate/hexane, 0→10% MeOH/ethyl acetate) to give tert-butyl (3-(cyclopropylmethyl)-7-fluoro-1-isopropyl-2,4-dioxo-1,2,3,4-tetrahydroquinazolin-6-yl)carbamate (3.67 g, 9.38 mmol, 88%) as a pale-yellow solid.

$^1$H NMR (300 MHz, CDCl$_3$): δ 0.38-0.52(4H,m), 1.23-1.36(1H,m), 1.54(9H,s), 1.60(6H,d,J=7.2 Hz), 3.95(2H,d, J=7.2 Hz), 4.94(1H,brs), 6.56(1H,brs), 7.09(1H,d,J=13.2 Hz), 8.80(1H,d,J=8.3 Hz).

(Step 5)

4N Hydrogen chloride/ethyl acetate (35 mL, 9.38 mmol) was added to a solution of tert-butyl (3-(cyclopropylmethyl)-7-fluoro-1-isopropyl-2,4-dioxo-1,2,3,4-tetrahydroquinazolin-6-yl)carbamate (3.67 g, 9.38 mmol) in ethyl acetate (35 mL), and the mixture was stirred at room temperature for 5 hr. The reaction mixture was diluted with ethyl acetate, and The precipitate was collected by filtration with ethyl acetate to give 6-amino-3-(cyclopropylmethyl)-7-fluoro-1-isopropylquinazoline-2,4(1H, 3H)-dione hydrochloride (2.35 g, 7.17 mmol, 76%) as a grayish white solid.

$^1$H NMR (300 MHz, DMSO-d$_6$): δ 0.27-0.48 (m, 4H), 1.10-1.27 (m, 1H), 1.48 (d, J=6.80 Hz, 6H), 3.80 (d, J=7.18 Hz, 2H), 4.77-4.93 (m, 1H), 7.50 (d, J=13.60 Hz, 1H), 7.63 (d, J=9.44 Hz, 1H), 7.70-8.48 (m, 1H).

(Step 6)

4-Nitrophenyl chloroformate (255 mg, 1.26 mmol) and pyridine (0.221 mL, 2.75 mmol) were added to a solution of 6-amino-3-(cyclopropylmethyl)-7-fluoro-1-isopropylquinazoline-2,4(1H, 3H)-dione hydrochloride (360 mg, 1.10 mmol) in THF (4.0 mL) at room temperature, and the mixture was stirred at room temperature overnight. To the reaction mixture was added water, and the mixture was extracted with ethyl acetate. The organic layer was dried over magnesium sulfate, and the solvent was evaporated under reduced pressure to give crude 4-nitrophenyl (3-(cyclopropylmethyl)-7-fluoro-1-isopropyl-2,4-dioxo-1,2,3,4-tetrahydroquinazolin-6-yl)carbamate (342 mg) as a brown solid. This was directly used for the next step.

(Step 7)

DIEA (0.131 mL, 0.75 mmol) was added to a solution of (R)-N-(4-cyano-2,5-difluorophenyl)morpholine-2-carboxamide (100 mg, 0.37 mmol) and crude 4-nitrophenyl (3-(cyclopropylmethyl)-7-fluoro-1-isopropyl-2,4-dioxo-1,2,3, 4-tetrahydroquinazolin-6-yl)carbamate (342 mg) in DMF (2 mL) at room temperature, and the mixture was stirred at room temperature for 2 hr. To the reaction mixture was added water, and the mixture was extracted with ethyl acetate. The organic layer was dried over magnesium sulfate, and the solvent was evaporated under reduced pressure. The residue was purified by silica gel column chromatography (solvent; ethyl acetate/hexane) and crystallized from ethyl acetate/hexane to give the title compound (35.3 mg, 0.060 mmol, 16.14%) as white crystals.

$^1$H NMR (300 MHz, DMSO-d$_6$): δ 0.29-0.47(4H,m), 1.12-1.29(1H,m), 1.50(6H,d,J=6.4 Hz), 3.01-3.18(2H,m), 3.57-3.71(1H,m), 3.81(2H,d,J=6.8 Hz), 3.85-3.96(1H,m), 4.00-4.11(1H,m), 4.17-4.36(2H,m), 4.90(1H,brs), 7.60(1H, d,J=13.2 Hz), 8.01-8.17(3H,m), 8.69(1H,s), 9.99(1H,s).

$[α]_D^{25}$ −16.3 (c 0.1260, MeOH)

Example 172

(2R)-N$^2$-(4-cyano-3-fluorophenyl)-N$^4$-(3-(cyclopropylmethyl)-7-fluoro-1-isopropyl-2,4-dioxo-1,2,3,4-tetrahydroquinazolin-6-yl)morpholine-2,4-dicarboxamide (Step 1)

T3P (38.9 mL, 66.12 mmol) was added to a solution of (R)-4-(tert-butoxycarbonyl)morpholine-2-carboxylic acid (6.63 g, 28.65 mmol), 4-amino-2-fluorobenzonitrile (3.0 g, 22.04 mmol), DIEA (19.25 mL, 110.19 mmol) and DMAP (2.96 g, 24.24 mmol) in ethyl acetate (73.5 mL), and the mixture was stirred at 80° C. for 2 hr. To the reaction mixture was added water, and the mixture was extracted with ethyl acetate. The organic layer was washed with 10% aqueous citric acid solution, aqueous sodium hydrogen carbonate solution and brine, dried over sodium sulfate, and the solvent was evaporated under reduced pressure. The residue was purified by silica gel column chromatography (solvent; ethyl acetate/hexane) to give (R)-tert-butyl 2-((4-cyano-3-fluorophenyl)carbamoyl)morpholine-4-carboxylate (9.22 g, 26.4 mmol, 120%).

MS(API): Calculated 349.4. Found 348.8 (M−H).

(Step 2)

4N Hydrogen chloride/ethyl acetate (83 mL, 330.60 mmol) was added to (R)-tert-butyl 2-((4-cyano-3-fluorophenyl)carbamoyl)morpholine-4-carboxylate (7.70 g, 22.04 mmol), and the mixture was stirred at room temperature for 3 hr. The reaction product was concentrated under reduced pressure, and the residue was crystallized from ethyl acetate to give (R)-N-(4-cyano-3-fluorophenyl)morpholine-2-carboxamide hydrochloride (5.53 g, 19.36 mmol, 88%) as white crystals.

$^1$H NMR (300 MHz, DMSO-d$_6$): δ 2.95-3.29 (m, 3H), 3.48 (dd, J=12.84, 2.27 Hz, 1H), 3.89 (t, J=10.58 Hz, 1H), 4.11 (d, J=12.46 Hz, 1H), 4.54 (d, J=8.69 Hz, 1H), 7.69 (dd, J=8.69, 1.89 Hz, 1H), 7.81-7.98 (m, 2H), 9.36 (brs, 2H), 10.76 (s, 1H).

(Step 3)

DIEA (0.112 mL, 0.64 mmol) was added to a solution of (R)-N-(4-cyano-3-fluorophenyl)morpholine-2-carboxamide hydrochloride (80 mg, 0.32 mmol) and 4-nitrophenyl (3-(cyclopropylmethyl)-7-fluoro-1-isopropyl-2,4-dioxo-1,2,3,4-tetrahydroquinazolin-6-yl)carbamate (293 mg, 0.64 mmol) in DMF (2 mL) at room temperature, and the mixture was stirred at room temperature for 2 hr. To the reaction mixture was added water, and the mixture was extracted with ethyl acetate. The organic layer was washed with brine, dried over magnesium sulfate, and the solvent was evaporated under reduced pressure. The residue was purified by silica gel column chromatography (solvent; ethyl acetate/hexane) and crystallized from ethyl acetate/hexane to give the title compound (12.3 mg, 0.022 mmol, 6.76%) as white crystals.

$^1$H NMR (300 MHz, DMSO-d$_6$): δ 0.27-0.49(4H,m), 1.15-1.29(1H,m), 1.50(6H,d,J=6.8 Hz), 3.03-3.17(2H,m), 3.03-3.17(2H,m), 3.60-3.72(1H,m), 3.81(2H,d,J=7.2 Hz), 3.86-3.96(1H,m), 3.99-4.10(1H,m), 4.18-4.30(2H,m), 4.90 (1H,brs), 7.60(1H,d,J=13.6 Hz), 7.73(1H,dd,J=8.7, 1.9 Hz), 7.83-7.91(1H,m), 7.95(1H,dd,J=12.5, 1.9 Hz), 8.11(1H,d, J=9.1 Hz), 8.70(1H,brs), 10.55(1H,brs).

Example 176

N$^2$-(4-cyano-3-fluorophenyl)-N$^4$-(3-(cyclopropylmethyl)-1-isopropyl-2,4-dioxo-1,2,3,4-tetrahydroquinazolin-6-yl)morpholine-2,4-dicarboxamide T3P (410 μL, 0.70 mmol) was added to a solution of 4-((3-(cyclopropylmethyl)-1-isopropyl-2,4-dioxo-1,2,3,4-tetrahydroquinazolin-6-yl)carbamoyl)morpholine-2-carboxylic acid (100 mg, 0.23 mmol), 4-amino-2-fluorobenzonitrile (34.8 mg, 0.26 mmol), DIEA (203 μL, 1.16 mmol) and DMAP (31.2 mg, 0.26 mmol) in ethyl acetate (1162 μL), and the mixture was stirred at 80° C. overnight. To the reaction mixture was added water, and the mixture was extracted with ethyl acetate. The organic layer was washed with water, dried over magnesium sulfate, and the solvent was evaporated under reduced pressure. The residue was purified by silica gel column chromatography (solvent; ethyl acetate/hexane) and crystallized from IPE to give the title compound (48.0 mg, 0.088 mmol, 37.7%) as white crystals.

$^1$H NMR (300 MHz, CDCl$_3$): δ 0.37-0.52 (m, 4H), 1.25-1.45 (m, 1H), 1.51-1.71 (m, 6H), 3.17-3.37 (m, 2H), 3.62-3.89 (m, 1H), 3.90-4.28 (m, 6H), 5.05 (brs, 1H), 6.90-7.02 (m, 1H), 7.29-7.40 (m, 2H), 7.59 (dd, J=8.31, 7.18 Hz, 1H), 7.78 (dd, J=10.95, 1.89 Hz, 1H), 7.89-8.01 (m, 2H), 8.60 (s, 1H).

Example 180

3-((4-cyanobenzoyl)amino)-N-(3-(cyclopropylmethyl)-1-isopropyl-2,4-dioxo-1,2,3,4-tetrahydroquinazolin-6-yl)piperidine-1-carboxamide TEA (52.3 μL, 0.38 mmol) was added to a solution of 3-amino-N-(3-(cyclopropylmethyl)-1-isopropyl-2,4-dioxo-1,2,3,4-tetrahydroquinazolin-6-yl)piperidine-1-carboxamide (50 mg, 0.13 mmol) and 4-cyanobenzoyl chloride (31.1 mg, 0.19 mmol) in THF (626 μL) at room temperature, and the mixture was stirred at room temperature overnight. The reaction mixture was concentrated under reduced pressure, and the residue was purified by silica gel column chromatography (solvent; ethyl acetate/hexane) and crystallized from IPE to give the title compound (12.70 mg, 0.024 mmol, 19.20%) as white crystals.

$^1$H NMR (300 MHz, CDCl$_3$): δ 0.40-0.55 (m, 4H), 1.17-1.36 (m, 1H), 1.61-2.25 (m, 10H), 3.41-4.05 (m, 6H), 4.10-4.27 (m, 1H), 4.91-5.20 (m, 1H), 6.77-6.85 (m, 1H), 7.05-7.15 (m, 1H), 7.29-7.36 (m, 1H), 7.78 (s, 2H), 7.91 (s, 4H).

Example 218

(3R)-3-((4-cyanobenzoyl)amino)-N-(3-(cyclopropylmethyl)-1-isopropyl-2,4-dioxo-1,2,3,4-tetrahydroquinazolin-6-yl)piperidine-1-carboxamide (Step 1)

4-Nitrophenyl chloroformate (116 mg, 0.57 mmol) was added to a solution of 6-amino-3-(cyclopropylmethyl)-1-isopropylquinazoline-2,4(1H, 3H)-dione (143 mg, 0.52 mmol) and pyridine (46.4 μL, 0.57 mmol) in THF (1248 μL) at room temperature, and the mixture was stirred at room temperature for 2 hr. The reaction mixture was concentrated under reduced pressure, and the residue was dissolved in DMF (3745 μL). The solution was added to (R)-tert-butyl piperidin-3-ylcarbamate (100 mg, 0.50 mmol) and DIEA (217 μL, 1.25 mmol) at room temperature. The mixture was stirred at room temperature for 4 hr. To the reaction mixture was added water, and the mixture was extracted with ethyl acetate. The organic layer was washed with brine, dried over sodium sulfate, and the solvent was evaporated under reduced pressure. The residue was purified by silica gel column chromatography to give (R)-tert-butyl (1-((3-(cyclopropylmethyl)-1-isopropyl-2,4-dioxo-1,2,3,4-tetrahydroquinazolin-6-yl)carbamoyl)piperidin-3-yl)carbamate (191 mg, 0.382 mmol, 76%) as a white amorphous solid.

MS(API): Calculated 499.5. Found 498.3 (M−H).

(Step 2)

4N Hydrogen chloride/ethyl acetate (1431 μL, 5.72 mmol) was added to (R)-tert-butyl (1-((3-(cyclopropylmethyl)-1-isopropyl-2,4-dioxo-1,2,3,4-tetrahydroquinazolin-6-yl)carbamoyl)piperidin-3-yl)carbamate (190.6 mg, 0.38 mmol) at room temperature, and the mixture was stirred at room temperature for 3 hr. The reaction mixture was concentrated under reduced pressure to give crude (R)-3-amino-N-(3-(cyclopropylmethyl)-1-isopropyl-2,4-dioxo-1,2,3,4-tetrahydroquinazolin-6-yl)piperidine-1-carboxamide hydrochloride (166 mg, 0.380 mmol, 100%) as a white amorphous solid. The resultant product was used for the next step without further purification.

MS(API): Calculated 435.95. Found 400.4 (M−HCl+H).

(Step 3)

4N Hydrogen chloride/ethyl acetate (45.8 mL, 183.30 mmol) was added to (R)-tert-butyl (1-((3-(cyclopropylmethyl)-1-isopropyl-2,4-dioxo-1,2,3,4-tetrahydroquinazolin-6-yl)carbamoyl)piperidin-3-yl)carbamate (6.11 g, 12.22 mmol), and the mixture was stirred at room temperature for 3 hr. The reaction mixture was concentrated under reduced pressure, and ethyl acetate was added to the residue. The mixture was neutralized with aqueous sodium hydrogen carbonate solution. The organic layer was washed with water and brine, dried over sodium sulfate, and the solvent was evaporated under reduced pressure. The residue was purified by silica gel column chromatography (solvent; ethyl acetate/hexane) and crystallized from ethyl acetate/hexane to give (R)-3-amino-N-(3-(cyclopropylmethyl)-1-isopropyl-2,4-dioxo-1,2,3,4-tetrahydroquinazolin-6-yl)piperidine-1-carboxamide (3.61 g, 9.02 mmol, 73.8%) as white crystals.

¹H NMR (300 MHz, CDCl₃): δ 0.38-0.53 (m, 4H), 1.19-2.06 (m, 11H), 2.80-3.04 (m, 2H), 3.09-3.24 (m, 1H), 3.70 (dt, J=13.12, 4.39 Hz, 1H), 3.79-4.05 (m, 3H), 5.05 (brs, 1H), 6.77 (s, 1H), 7.32 (d, J=9.44 Hz, 1H), 7.80 (d, J=2.64 Hz, 1H), 8.05 (dd, J=9.06, 2.64 Hz, 1H).

(Step 4)

T3P (442 μL, 0.75 mmol) was added to a solution of (R)-3-amino-N-(3-(cyclopropylmethyl)-1-isopropyl-2,4-dioxo-1,2,3,4-tetrahydroquinazolin-6-yl)piperidine-1-carboxamide (100 mg, 0.25 mmol), 4-cyanobenzoic acid (73.7 mg, 0.50 mmol) and DIEA (219 μL, 1.25 mmol) in ethyl acetate (1669 μL) at room temperature, and the mixture was stirred at room temperature overnight. The reaction mixture was concentrated under reduced pressure, and the residue was purified by silica gel column chromatography (solvent; ethyl acetate/hexane) to give the title compound (92 mg, 0.175 mmol, 69.8%) as a white amorphous solid.

¹H NMR (300 MHz, CDCl₃): δ 0.39-0.54 (m, 4H), 1.21-1.37 (m, 1H), 1.55-1.75 (m, 7H), 1.76-2.16 (m, 3H), 3.42-3.70 (m, 3H), 3.80-4.01 (m, 3H), 4.10-4.21 (m, 1H), 5.04 (brs, 1H), 7.01 (s, 1H), 7.18 (d, J=5.67 Hz, 1H), 7.30 (d, J=9.06 Hz, 1H), 7.73 (d, J=8.31 Hz, 2H), 7.83-8.00 (m, 4H).

Example 219

(3R)-3-((4-cyano-2-fluorobenzoyl)amino)-N-(3-(cyclopropylmethyl)-1-isopropyl-2,4-dioxo-1,2,3,4-tetrahydroquinazolin-6-yl)piperidine-1-carboxamide T3P (442 μL, 0.75 mmol) was added to a solution of (R)-3-amino-N-(3-(cyclopropylmethyl)-1-isopropyl-2,4-dioxo-1,2,3,4-tetrahydroquinazolin-6-yl)piperidine-1-carboxamide (100 mg, 0.25 mmol), 4-cyano-2-fluorobenzoic acid (83 mg, 0.50 mmol) and DIEA (219 μL, 1.25 mmol) in ethyl acetate (1669 μL) at room temperature, and the mixture was stirred at room temperature overnight. The reaction mixture was concentrated under reduced pressure, and the residue was purified by silica gel column chromatography (solvent; ethyl acetate/hexane) and solidified with IPE to give the title compound (111 mg, 0.203 mmol, 81%) as a white solid.

¹H NMR (300 MHz, CDCl₃): δ 0.40-0.53 (m, 4H), 1.25-1.41 (m, 1H), 1.52-2.07 (m, 10H), 3.57 (t, J=5.48 Hz, 2H), 3.66-3.79 (m, 2H), 3.96 (d, J=7.18 Hz, 2H), 4.12-4.24 (m, 1H), 5.04 (brs, 1H), 6.77-6.92 (m, 1H), 7.02 (dd, J=12.09, 6.04 Hz, 1H), 7.31 (d, J=9.06 Hz, 1H), 7.46 (dd, J=10.95, 1.51 Hz, 1H), 7.58 (dd, J=7.93, 1.51 Hz, 1H), 7.86 (d, J=2.64 Hz, 1H), 7.98 (dd, J=9.25, 2.83 Hz, 1H), 8.24 (t, J=7.74 Hz, 1H).

Example 223

6-cyano-N-((3R)-1-((3-(cyclopropylmethyl)-1-isopropyl-2,4-dioxo-1,2,3,4-tetrahydroquinazolin-6-yl)carbamoyl)piperidin-3-yl)nicotinamide T3P (442 μL, 0.75 mmol) was added to a solution of (R)-3-amino-N-(3-(cyclopropylmethyl)-1-isopropyl-2,4-dioxo-1,2,3,4-tetrahydroquinazolin-6-yl)piperidine-1-carboxamide (100 mg, 0.25 mmol), 6-cyanonicotinic acid (74.2 mg, 0.50 mmol) and DIEA (219 μL, 1.25 mmol) in ethyl acetate (1669 μL) at room temperature, and the mixture was stirred at room temperature overnight. The reaction mixture was concentrated under reduced pressure, and the residue was purified by silica gel column chromatography (solvent; ethyl acetate/hexane) and solidified with IPE to give the title compound (100 mg, 0.188 mmol, 75%) as a white solid.

¹H NMR (300 MHz, CDCl₃): δ 0.39-0.54 (m, 4H), 1.23-1.38 (m, 1H), 1.55-2.20 (m, 10H), 3.35-3.53 (m, 2H), 3.65-3.79 (m, 1H), 3.92-4.07 (m, 3H), 4.23 (brs, 1H), 5.02 (brs, 1H), 6.95 (s, 1H), 7.30 (d, J=9.06 Hz, 1H), 7.63-7.93 (m, 4H), 8.29 (dd, J=7.93, 2.27 Hz, 1H), 9.08 (d, J=1.51 Hz, 1H).

Example 235

(2R)-N²-(3-chloro-4-cyanophenyl)-N⁴-(3-(cyclopropylmethyl)-7-fluoro-1-isopropyl-2,4-dioxo-1,2,3,4-tetrahydroquinazolin-6-yl)morpholine-2,4-dicarboxamide 4-Nitrophenyl chloroformate (70.7 mg, 0.35 mmol) was added to a solution of 6-amino-3-(cyclopropylmethyl)-7-fluoro-1-isopropylquinazoline-2,4(1H, 3H)-dione hydrochloride (100 mg, 0.31 mmol) and pyridine (0.062 mL, 0.76 mmol) in THF (2 mL) at room temperature, and the mixture was stirred at room temperature for 1 hr. The reaction mixture was concentrated under reduced pressure, and the residue was dissolved in DMF (3 mL). The solution was added to (R)-N-(3-chloro-4-cyanophenyl)morpholine-2-carboxamide hydrochloride (92 mg, 0.31 mmol) and DIEA (0.133 mL, 0.76 mmol) at room temperature. The mixture was stirred at room temperature for 3 hr. To the reaction mixture was added water, and the mixture was extracted with ethyl acetate. The organic layer was washed with brine, dried over magnesium sulfate, and the solvent was evaporated under reduced pressure. The residue was purified by silica gel column chromatography (solvent; ethyl acetate/hexane) to give the title compound (131 mg, 0.225 mmol, 73.8%) as a white solid.

¹H NMR (300 MHz, DMSO-d₆): δ 0.29-0.48(4H,m), 1.15-1.28(1H,m), 1.50(6H,d,J=6.4 Hz), 3.02-3.18(2H,m), 3.60-3.73(1H,m), 3.81(2H,d,J=7.2 Hz), 3.85-3.97(1H,m), 4.00-4.09(1H,m), 4.25(2H,s), 4.78-5.02(1H,m), 7.60(1H,d, J=13.2 Hz), 7.95(2H,s), 8.11(1H,d,J=8.7 Hz), 8.17(1H,d, J=1.9 Hz), 8.70(1H,brs), 10.48(1H,brs).

$[α]_D^{25}$ −40.5 (c 0.2510, MeOH)

Example 242

(3R)-N-(3-(cyclopropylmethyl)-1-isopropyl-2,4-dioxo-1,2,3,4-tetrahydroquinazolin-6-yl)-3-(((5-methyl-2-thienyl)carbonyl)amino)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 μL, 0.320 mmol) and 5-methyl-2-thiophenecarboxylic acid (0.16 mmol) in DMF (800 μL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (33.5 mg, 64 μmol, 80%).

Example 244

(3R)-N-(3-(cyclopropylmethyl)-1-isopropyl-2,4-dioxo-1,2,3,4-tetrahydroquinazolin-6-yl)-3-((4-methoxybenzoyl)amino)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 µL, 0.320 mmol) and 4-methoxybenzoic acid (0.16 mmol) in DMF (800 µL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (11.2 mg, 21 µmol, 26%).

Example 247

(3R)-3-((4-chlorobenzoyl)amino)-N-(3-(cyclopropylmethyl)-1-isopropyl-2,4-dioxo-1,2,3,4-tetrahydroquinazolin-6-yl)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 µL, 0.320 mmol) and 4-chlorobenzoic acid (0.16 mmol) in DMF (800 µL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (27.3 mg, 50.7 µmol, 63%).

Example 248

(3R)-3-((3-chlorobenzoyl)amino)-N-(3-(cyclopropylmethyl)-1-isopropyl-2,4-dioxo-1,2,3,4-tetrahydroquinazolin-6-yl)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 µL, 0.320 mmol) and 3-chlorobenzoic acid (0.16 mmol) in DMF (800 µL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (29.1 mg, 54.1 µmol, 67%).

Example 249

(3R)-3-((4-cyano-3-methylbenzoyl)amino)-N-(3-(cyclopropylmethyl)-1-isopropyl-2,4-dioxo-1,2,3,4-tetrahydroquinazolin-6-yl)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 µL, 0.320 mmol) and 4-cyano-3-methylbenzoic acid (0.16 mmol) in DMF (800 µL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (35.1 mg, 64.7 µmol, 81%).

Example 251

(3R)-N-(3-(cyclopropylmethyl)-1-isopropyl-2,4-dioxo-1,2,3,4-tetrahydroquinazolin-6-yl)-3-((2,3-dihydro-1-benzofuran-5-ylcarbonyl)amino)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 µL, 0.320 mmol) and 2,3-dihydrobenzo[b]furan-5-carboxylic acid (0.16 mmol) in DMF (800 µL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (17.1 mg, 31.3 µmol, 39%).

Example 259

(3R)-N-(3-(Cyclopropylmethyl)-1-isopropyl-2,4-dioxo-1,2,3,4-tetrahydroquinazolin-6-yl)-3-((2-fluoro-5-methylbenzoyl)amino)piperidine-1-carboxamide A solution of (R)-3-amino-N-(3-(cyclopropylmethyl)-1-isopropyl-2,4-dioxo-1,2,3,4-tetrahydroquinazolin-6-yl)piperidine-1-carboxamide (0.032 g, 0.080 mmol), HATU (61 mg, 0.16 mmol), DIEA (56 µL, 0.320 mmol) and 2-fluoro-5-methylbenzoic acid (0.16 mmol) in DMF (800 µL) was stirred at room temperature overnight. To the reaction mixture were added ethyl acetate (3 mL) and water (1 mL), and the mixture was stirred for 5 min. The mixture was filtered by Top-Phase Separation Filter Tube, and the filtrate was concentrated by blowing air at 60° C. The residue was purified by preparative HPLC (C18, mobile phase: water/acetonitrile (10 mM ammonium carbonate-containing solvent)). The fraction was concentrated by blowing air at 60° C. to give the title compound (34.1 mg, 63.7 µmol, 80%).

Example 264

4-cyano-N-((1S,2R)-2-((3-(cyclopropylmethyl)-1-isopropyl-2,4-dioxo-1,2,3,4-tetrahydroquinazolin-6-yl)carbamoyl)cyclopentyl)benzamide (Step 1)
T3P (1.937 mL, 3.29 mmol) was added to a solution of cis-2-((tert-butoxycarbonyl)amino)cyclopentane carboxylic acid (277 mg, 1.21 mmol), 6-amino-3-(cyclopropylmethyl)-1-isopropylquinazoline-2,4(1H, 3H)-dione (300 mg, 1.10 mmol), DIEA (0.958 mL, 5.49 mmol) and DMAP (147 mg, 1.21 mmol) in ethyl acetate (3 mL) at room temperature, and the mixture was stirred at room temperature overnight. To the reaction mixture was added water, and the mixture was extracted with ethyl acetate. The organic layer was washed with water and brine, dried over sodium sulfate, and the solvent was evaporated under reduced pressure. The residue was purified by silica gel column chromatography (solvent; ethyl acetate/hexane) to give tert-butyl (cis-2-((3-(cyclopropylmethyl)-1-isopropyl-2,4-dioxo-1,2,3,4-tetrahydroquinazolin-6-yl)carbamoyl)cyclopentyl)carbamate (400 mg, 0.826 mmol, 75%).

MS(API): Calculated 484.6. Found 483.1 (M−H).

(Step 2)

4N Hydrogen chloride/ethyl acetate (3102 μL, 12.41 mmol) was added to tert-butyl cis-2-((3-(cyclopropylmethyl)-1-isopropyl-2,4-dioxo-1,2,3,4-tetrahydroquinazolin-6-yl)carbamoyl)cyclopentyl)carbamate (400.8 mg, 0.83 mmol), and the mixture was stirred at room temperature for 3 hr. The reaction mixture was concentrated under reduced pressure. Crystallization from ethyl acetate gave cis-2-amino-N-(3-(cyclopropylmethyl)-1-isopropyl-2,4-dioxo-1,2,3,4-tetrahydroquinazolin-6-yl)cyclopentane carboxamide hydrochloride (298 mg, 0.707 mmol, 86%) as white crystals.

MS(API): Calculated 420.9. Found 385.3 (M−HCl+H).

(Step 3)

T3P (293 μL, 0.50 mmol) was added to a solution of cis-2-amino-N-(3-(cyclopropylmethyl)-1-isopropyl-2,4-dioxo-1,2,3,4-tetrahydroquinazolin-6-yl)cyclopentanecarboxamide hydrochloride (70 mg, 0.17 mmol), 4-cyanobenzoic acid (48.9 mg, 0.33 mmol) and DIEA (145 μL, 0.83 mmol) in ethyl acetate (1109 μL) at room temperature, and the mixture was stirred at room temperature overnight. The reaction mixture was concentrated under reduced pressure, and the residue was purified by silica gel column chromatography (solvent; ethyl acetate/hexane) and solidified with IPE to give the title compound (67.0 mg, 0.130 mmol, 78%) as a white solid.

$^1$H NMR (300 MHz, CDCl$_3$): δ 0.37-0.52 (m, 4H), 1.18-1.35 (m, 1H), 1.51-1.74 (m, 7H), 1.81-2.27 (m, 5H), 3.17 (q, J=7.93 Hz, 1H), 3.94 (d, J=7.18 Hz, 2H), 4.67 (quin, J=7.46 Hz, 1H), 5.02 (brs, 1H), 7.26-7.38 (m, 2H), 7.67 (d, J=8.31 Hz, 2H), 7.84 (d, J=8.31 Hz, 2H), 7.99 (dd, J=9.06, 2.64 Hz, 1H), 8.07 (d, J=2.64 Hz, 1H), 8.30 (s, 1H).

Example 266

(2R)-N$^2$-(5-chloro-6-cyanopyridin-3-yl)-N$^4$-(3-(cyclopropylmethyl)-7-fluoro-1-isopropyl-2,4-dioxo-1,2,3,4-tetrahydroquinazolin-6-yl)morpholine-2,4-dicarboxamide 4-Nitrophenyl chloroformate (70.7 mg, 0.35 mmol) was added to a solution of 6-amino-3-(cyclopropylmethyl)-7-fluoro-1-isopropylquinazoline-2,4(1H, 3H)-dione hydrochloride (100 mg, 0.31 mmol) and pyridine (0.062 mL, 0.76 mmol) in THF (2 mL) at room temperature, and the mixture was stirred at room temperature for 1 hr. The reaction mixture was concentrated under reduced pressure, and the residue was dissolved in DMF (3 mL). The solution was added to (R)-N-(5-chloro-6-cyanopyridin-3-yl)morpholine-2-carboxamide hydrochloride (92 mg, 0.31 mmol) and DIEA (0.133 mL, 0.76 mmol) at room temperature. The mixture was stirred at room temperature for 3 hr. To the reaction mixture was added water, and the mixture was extracted with ethyl acetate. The organic layer was washed with brine, dried over magnesium sulfate, and the solvent was evaporated under reduced pressure. The residue was purified by silica gel column chromatography (solvent gradient; 5→100% ethyl acetate/hexane) and solidified with ethyl acetate/hexane to give the title compound (87.8 mg, 0.150 mmol, 49.3%) as a white solid.

$^1$H NMR (300 MHz, DMSO-d$_6$): δ 0.29-0.48(4H,m), 1.12-1.29(1H,m), 1.50(6H,d,J=6.8 Hz), 3.04-3.19(2H,m), 3.62-3.76(1H,m), 3.81(2H,d,J=6.8 Hz), 3.85-3.97(1H,m), 4.00-4.12(1H,m), 4.17-4.34(2H,m), 4.90(1H,brs), 7.60(1H, d,J=13.2 Hz), 8.11(1H,d,J=9.1 Hz), 8.59(1H,d,J=2.3 Hz), 8.71(1H,s), 8.99(1H,d,J=2.3 Hz), 10.76(1H,s).

Example 274 tert-Butyl (4-(((3R)-1-((3-(cyclopropylmethyl)-1-isopropyl-2,4-dioxo-1,2,3,4-tetrahydroquinazolin-6-yl)carbamoyl)piperidin-3-yl)carbamoyl)benzyl) carbamate T3P (1.325 mL, 2.25 mmol) was added to a solution of (R)-3-amino-N-(3-(cyclopropylmethyl)-1-isopropyl-2,4-dioxo-1,2,3,4-tetrahydroquinazolin-6-yl)piperidine-1-carboxamide (300 mg, 0.75 mmol), 4-(((tert-butoxycarbonyl)amino)methyl)benzoic acid (283 mg, 1.13 mmol) and DIEA (0.656 mL, 3.75 mmol) in DMF (2 mL) at room temperature, and the mixture was stirred at room temperature for 2 days. To the reaction mixture was added an aqueous ammonium chloride solution, and the mixture was extracted with ethyl acetate. The organic layer was washed with brine, dried over magnesium sulfate, and the solvent was evaporated under reduced pressure. The residue was purified by silica gel column chromatography (solvent gradient; 5→25% ethyl acetate/hexane) to give the title compound (330 mg, 0.522 mmol, 69.4%) as a white amorphous solid.

$^1$H NMR (300 MHz, CDCl$_3$): δ 0.36-0.53 (m, 4H), 1.45 (s, 9H), 1.60 (d, J=7.18 Hz, 6H), 1.63-2.01 (m, 4H), 3.40-3.76 (m, 4H), 3.89-3.98 (m, 2H), 4.30-4.39 (m, 2H), 4.97-5.20 (m, 2H), 6.63-6.78 (m, 1H), 7.21-7.36 (m, 6H), 7.68-7.79 (m, 2H), 7.91 (s, 2H).

Example 282

(3R)-3-((5-chloro-2-fluorobenzoyl)amino)-N-(3-(cyclopropylmethyl)-7-fluoro-1-isopropyl-2,4-dioxo-1,2,3,4-tetrahydroquinazolin-6-yl)piperidine-1-carboxamide (Step 1)

4-Nitrophenyl chloroformate (0.707 g, 3.51 mmol) was added to a solution of 6-amino-3-(cyclopropylmethyl)-7-fluoro-1-isopropylquinazoline-2,4(1H, 3H)-dione hydrochloride (1.0 g, 3.05 mmol) and pyridine (0.531 mL, 6.56 mmol) in THF (7.63 mL) at room temperature, and the mixture was stirred at room temperature for 2 hr. The reaction mixture was concentrated under reduced pressure, and the residue was dissolved in DMF (22.88 mL). The solution was added to (R)-tert-butyl piperidin-3-ylcarbamate (0.672 g, 3.36 mmol) and DIEA (1.328 mL, 7.63 mmol) at room temperature. The mixture was stirred at room temperature overnight. To the reaction mixture was added water, and the mixture was extracted with ethyl acetate. The organic layer was washed with brine, dried over sodium sulfate, and the solvent was evaporated under reduced pressure. The residue was purified by silica gel column chromatography to give (R)-tert-butyl (1-((3-(cyclopropylmethyl)-7-fluoro-1-isopropyl-2,4-dioxo-1,2,3,4-tetrahydroquinazolin-6-yl)carbamoyl)piperidin-3-yl)carbamate (1.600 g, 3.09 mmol, 101%).

MS(API): Calculated 517.6. Found 416.2 (M-Boc).

(Step 2)

4N Hydrogen chloride/ethyl acetate (11.44 mL, 45.75 mmol) was added to (R)-tert-butyl (1-((3-(cyclopropylmethyl)-7-fluoro-1-isopropyl-2,4-dioxo-1,2,3,4-tetrahydroquinazolin-6-yl)carbamoyl)piperidin-3-yl)carbamate (1.579 g, 3.05 mmol), and the mixture was stirred at room temperature for 3 hr. The reaction mixture was concentrated under reduced pressure to give (R)-3-amino-N-(3-(cyclopropylmethyl)-7-fluoro-1-isopropyl-2,4-dioxo-1,2,3,4-tetrahydroquinazolin-6-yl)piperidine-1-carboxamide hydrochloride (1.385 g, 3.05 mmol, 100%) as a white amorphous solid.

MS(API): Calculated 453.9. Found 418.2 (M–HCl+H).

(Step 3)

4N Hydrogen chloride/ethyl acetate (20 mL) was added to (R)-tert-butyl (1-((3-(cyclopropylmethyl)-7-fluoro-1-isopropyl-2,4-dioxo-1,2,3,4-tetrahydroquinazolin-6-yl)carbamoyl)piperidin-3-yl)carbamate (4.45 g, 8.60 mmol), and the mixture was stirred at room temperature for 30 min. The reaction mixture was concentrated under reduced pressure, and ethyl acetate and 0.5N aqueous sodium hydroxide solution were added to the residue. The organic layer was dried over magnesium sulfate, and the solvent was evaporated under reduced pressure. The residue was purified by silica gel column chromatography (solvent gradient; 0→100% ethyl acetate/hexane), and crystallization from ethyl acetate gave (R)-3-amino-N-(3-(cyclopropylmethyl)-7-fluoro-1-isopropyl-2,4-dioxo-1,2,3,4-tetrahydroquinazolin-6-yl)piperidine-1-carboxamide (3.17 g, 88.0%) as white crystals.

MS(API): Calculated 417.5. Found 418.2 (M+H).

(Step 4)

T3P (0.143 g, 0.45 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (0.063 g, 0.15 mmol), 5-chloro-2-fluorobenzoic acid (0.031 g, 0.18 mmol), DIEA (0.097 g, 0.75 mmol) and DMAP (0.018 g, 0.15 mmol) in THF (2 mL), and the mixture was stirred at 70° C. for 6 hr. The reaction mixture was poured into ethyl acetate and water. The organic layer was dried over magnesium sulfate, and the solvent was evaporated under reduced pressure. The residue was purified by silica gel column chromatography (solvent gradient; 0→100% ethyl acetate/hexane) to give the title compound (0.049 g, 32.5%) as a white amorphous solid.

$^1$H NMR (300 MHz, CDCl$_3$): δ 0.40-0.48(4H,m), 1.22-1.32(1H,m), 1.59(6H,d,J=6.0 Hz), 1.60-2.10(4H,m), 3.50-3.68(2H,m), 3.67-3.72(2H,m), 3.93(2H,d,J=6.0 Hz), 4.15-4.22(1H,m), 4.92(1H,brs), 6.70(1H,brs), 6.94-7.02(1H,m), 7.06(1H,d,J=12.0 Hz), 7.11(1H,dd,J=9.0 Hz, 12.0 Hz), 7.36-7.43(1H,m), 7.95-8.00(1H,m), 8.56(1H,d,J=9.0 Hz).

Example 283

(3R)-N-(3-(cyclopropylmethyl)-7-fluoro-1-isopropyl-2,4-dioxo-1,2,3,4-tetrahydroquinazolin-6-yl)-3-((2-fluoro-5-methylbenzoyl)amino)piperidine-1-carboxamide T3P (0.143 g, 0.45 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (0.063 g, 0.15 mmol), 2-fluoro-5-methylbenzoic acid (0.028 g, 0.18 mmol), DIEA (0.097 g, 0.75 mmol) and DMAP (0.018 g, 0.15 mmol) in THF (2 mL) at room temperature, and the mixture was stirred at 70° C. for 2 hr. The reaction mixture was poured into ethyl acetate and water. The organic layer was dried over magnesium sulfate, and the solvent was evaporated under reduced pressure. The residue was purified by silica gel column chromatography (solvent gradient; 0→100% ethyl acetate/hexane) to give the title compound (0.029 g, 34.9%) as a white amorphous solid.

$^1$H NMR (300 MHz, CDCl$_3$): δ 0.39-0.49(4H,m), 1.22-1.36(1H,m), 1.59(6H,d,J=6.0 Hz), 1.70-1.90(3H,m), 1.98-2.08(1H,m), 2.34(3H,s), 3.45-3.55(1H,m), 3.58(1H,dd,J=6.0 Hz, 15.0 Hz), 3.60-3.70(1H,m), 3.79(1H,dd,J=3.0 Hz, 12.0 Hz), 3.94(2H,d,J=9.0 Hz), 4.12-4.22(1H,m), 4.93(1H,brs), 6.75(1H,brs), 6.86-6.94(1H,m), 7.02(1H,dd,J=9.0 Hz, 12.0 Hz), 7.06(1H,d,J=12.0 Hz), 7.32-7.38(1H,m), 7.84(1H,dd,J=3.0 Hz, 6.0 Hz), 8.57(1H,d,J=9.0 Hz).

Example 284

(3R)-3-((4-cyanobenzoyl)amino)-N-(3-(cyclopropylmethyl)-7-fluoro-1-isopropyl-2,4-dioxo-1,2,3,4-tetrahydroquinazolin-6-yl)piperidine-1-carboxamide T3P (0.143 g, 0.45 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (0.063 g, 0.15 mmol), 4-cyanobenzoic acid (0.026 g, 0.18 mmol), DIEA (0.097 g, 0.75 mmol) and DMAP (0.018 g, 0.15 mmol) in THF (2 mL) at room temperature, and the mixture was stirred at 70° C. for 2 hr. The reaction mixture was poured into ethyl acetate and water. The organic layer was dried over magnesium sulfate, and the solvent was evaporated under reduced pressure. The residue was purified by silica gel column chromatography (solvent gradient; 0→100% ethyl acetate/hexane) to give the title compound (0.032 g, 39.0%) as a white amorphous solid.

$^1$H NMR (300 MHz, CDCl$_3$): δ 0.40-0.52(4H,m), 1.23-1.33(1H,m), 1.48-1.56(1H,m), 1.60(6H,d,J=6.0 Hz), 1.78-1.98(2H,m), 2.17-2.27(1H,m), 3.37-3.47(2H,m), 3.70-3.77(1H,m), 3.96(2H,d,J=6.0 Hz), 4.03-4.10(1H,m), 4.20(1H,brs), 4.93(1H,brs), 6.71(1H,brs), 7.08(1H,d,J=12.0 Hz), 7.47(1H,brs), 7.77(2H,d,J=6.0 Hz), 7.95(2H,d,J=6.0 Hz), 8.57(1H,d,J=9.0 Hz).

Example 287

(3R)-N-(3-(cyclopropylmethyl)-7-fluoro-1-isopropyl-2,4-dioxo-1,2,3,4-tetrahydroquinazolin-6-yl)-3-((2,5-difluorobenzoyl)amino)piperidine-1-carboxamide T3P (0.143 g, 0.45 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (0.063 g, 0.15 mmol), 2,5-difluorobenzoic acid (0.028 g, 0.18 mmol), DIEA (0.097 g, 0.75 mmol) and DMAP (0.018 g, 0.15 mmol) in THF (2 mL) at room temperature, and the mixture was stirred at 70° C. for 6 hr. The reaction mixture was poured into ethyl acetate and water. The organic layer was dried over magnesium sulfate, and the solvent was evaporated under reduced pressure. The residue was purified by silica gel column chromatography (solvent gradient; 0→100% ethyl acetate/hexane) to give the title compound (0.033 g, 39.5%) as a white amorphous solid.

$^1$H NMR (300 MHz, CDCl$_3$): δ 0.42-0.48(4H,m), 1.23-1.29(1H,m), 1.59(6H,d,J=6.0 Hz), 1.65-2.05(4H,m), 3.48-3.62(2H,m), 3.64-3.78(2H,m), 3.94(2H,d,J=6.0 Hz), 4.16(1H,brs), 4.93(1H,brs), 6.60(1H,brs), 6.96-7.04(1H,m), 7.07(1H,d,J=15.0 Hz), 7.10-7.16(2H,m), 7.72-7.79(1H,m), 8.60(1H,d,J=9.0 Hz).

Example 291

(3R)-N-(3-(cyclopropylmethyl)-7-fluoro-1-isopropyl-2,4-dioxo-1,2,3,4-tetrahydroquinazolin-6-yl)-3-((2-fluoro-4-methoxybenzoyl)amino)piperidine-1-carboxamide T3P (296 μL, 0.50 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (70 mg, 0.17 mmol), 2-fluoro-4-methoxybenzoic acid (57.1 mg, 0.34 mmol) and DIEA (146 μL, 0.84 mmol) in ethyl acetate (1118 μL) at room temperature, and the mixture was stirred at room temperature overnight. The reaction mixture was concentrated under reduced pressure, and the residue was purified by silica gel column chromatography (solvent; ethyl acetate/hexane) and solidified with IPE to give the title compound (34.0 mg, 0.060 mmol, 35.6%) as a white solid.

$^1$H NMR (300 MHz, CDCl$_3$): δ 0.38-0.49(m,4H), 1.21-1.36(m,1H), 1.49-2.05(m,10H), 3.46-3.86(m,7H), 3.93(d, J=7.18 Hz,2H), 4.10-4.22(m,1H), 4.93(brs,1H), 6.58-6.92 (m,4H), 7.05(d,J=12.84 Hz,1H), 8.01(t,J=9.06 Hz,1H), 8.56 (d,J=9.06 Hz,1H).

Example 292

(3R)-3-(((5-cyano-2-thienyl)carbonyl)amino)-N-(3-(cyclopropylmethyl)-7-fluoro-1-isopropyl-2,4-dioxo-1,2,3,4-tetrahydroquinazolin-6-yl)piperidine-1-carboxamide T3P (194 μL, 0.33 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide hydrochloride (50 mg, 0.11 mmol), 5-cyanothiophene-2-carboxylic acid (33.7 mg, 0.22 mmol) and DIEA (96 μL, 0.55 mmol) in ethyl acetate (734 μL) at room temperature, and the mixture was stirred at room temperature overnight. The reaction mixture was concentrated under reduced pressure, and the residue was purified by silica gel column chromatography (solvent; ethyl acetate/hexane) and solidified with IPE to give the title compound (21.00 mg, 0.038 mmol, 34.5%) as a white solid.

$^1$H NMR (300 MHz, CDCl$_3$): δ 0.39-0.55 (m, 4H), 1.24-1.37 (m, 2H), 1.54-1.98 (m, 8H), 2.14-2.29 (m, 1H), 3.30-3.47 (m, 2H), 3.71-3.84 (m, 1H), 3.95 (d, J=7.18 Hz, 2H), 4.04-4.25 (m, 2H), 4.92 (brs, 1H), 6.68 (d, J=1.89 Hz, 1H), 7.08 (d, J=12.84 Hz, 1H), 7.48-7.67 (m, 3H), 8.55 (d, J=8.69 Hz, 1H).

Example 296

N-((3R)-1-((3-(cyclopropylmethyl)-7-fluoro-1-isopropyl-2,4-dioxo-1,2,3,4-tetrahydroquinazolin-6-yl) carbamoyl)piperidin-3-yl)-2-methyl-1,3-benzoxazole-5-carboxamide HATU (70.4 mg, 0.19 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide hydrochloride (70 mg, 0.15 mmol), 2-methylbenzo[d]oxazole-5-carboxylic acid (30.1 mg, 0.17 mmol) and DIEA (0.054 mL, 0.31 mmol) in DMF (2.0 mL) at room temperature, and the mixture was stirred at room temperature for 3 hr. To the reaction mixture was added water, and the mixture was extracted with ethyl acetate. The organic layer was washed with water and brine, dried over magnesium sulfate, and the solvent was evaporated under reduced pressure. The residue was purified by silica gel column chromatography (solvent; ethyl acetate/hexane) and crystallized from ethyl acetate/hexane to give the title compound (17.3 mg, 0.030 mmol, 19.46%) as a white solid.

$^1$H NMR (300 MHz, CDCl$_3$): δ 0.28-0.48 (4H, m), 1.10-1.27 (1H, m), 1.50 (6H, d, J=6.4 Hz), 1.52-1.67 (2H, m), 1.70-1.87 (1H, m), 1.88-2.04 (1H, m), 2.63 (3H, s), 2.83-2.99 (2H, m), 3.81 (2H, d, J=7.2 Hz), 3.85-4.00 (2H, m), 4.02-4.15 (1H, m), 4.89 (1H, brs), 7.56 (1H, d, J=13.2 Hz), 7.72 (1H, d, J=8.3 Hz), 7.88 (1H, dd, J=8.7, 1.9 Hz), 8.08 (1H, d, J=8.7 Hz), 8.15 (1H, d, J=1.1 Hz), 8.40 (1H, d, J=7.6 Hz), 8.50 (1H, s).

Example 303

(3R)—N-(3-(cyclopropylmethyl)-7-fluoro-1-isopropyl-2,4-dioxo-1,2,3,4-tetrahydroquinazolin-6-yl)-3-(6-methoxy-1-oxo-1,3-dihydro-2H-isoindol-2-yl) piperidine-1-carboxamide NaBH(OAc)$_3$ (142 mg, 0.67 mmol) was added to a mixture of 2-formyl-5-methoxybenzoic acid (60.4 mg, 0.34 mmol) and (R)-3-amino-N-(3-(cyclopropylmethyl)-7-fluoro-1-isopropyl-2,4-dioxo-1,2,3,4-tetrahydroquinazolin-6-yl)piperidine-1-carboxamide (70 mg, 0.17 mmol) in THF (762 μL) and acetic acid (76 μL) at room temperature, and the mixture was stirred at room temperature overnight. To the reaction mixture was added water, and the mixture was extracted with ethyl acetate. The organic layer was washed with water and brine, dried over magnesium sulfate, and the solvent was evaporated under reduced pressure. The residue was purified by silica gel column chromatography (solvent; ethyl acetate/hexane), and solidified with IPE to give the title compound (36.2 mg, 0.064 mmol, 38.3%) as a white solid.

$^1$H NMR (300 MHz, CDCl$_3$): δ 0.35-0.53 (m, 4H), 1.18-1.36 (m, 1H), 1.60 (d, J=7.18 Hz, 6H), 1.71-2.21 (m, 4H), 2.98 (t, J=10.95 Hz, 1H), 3.24 (dd, J=12.84, 10.20 Hz, 1H), 3.81-3.99 (m, 5H), 4.00-4.19 (m, 2H), 4.23-4.48 (m, 3H), 4.93 (brs, 1H), 6.93 (brs, 1H), 7.05-7.18 (m, 2H), 7.31-7.42 (m, 2H), 8.58 (d, J=9.06 Hz, 1H).

Example 315

4-(((3R)-1-((3-(cyclopropylmethyl)-7-fluoro-1-isopropyl-2,4-dioxo-1,2,3,4-tetrahydroquinazolin-6-yl) carbamoyl)piperidin-3-yl)carbamoyl)benzyl ethylcarbamate (Step 1)

A solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (0.209 g, 0.50 mmol), 4-(hydroxymethyl)benzoic acid (0.091 g, 0.60 mmol), HATU (0.570 g, 1.50 mmol), DIEA (0.323 g, 2.50 mmol) and DMAP (0.061 g, 0.50 mmol) in THF (5 mL) was stirred at room temperature for 1 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane), and crystallization from ethyl acetate gave (R)—N-(3-(cyclopropylmethyl)-7-fluoro-1-isopropyl-2,4-dioxo-1,2,3,4-tetrahydroquinazolin-6-yl)-3-(4-(hydroxymethyl) benzamide)piperidine-1-carboxamide (0.276 g, 100.0%) as a white powder.

¹H NMR (300 MHz, CDCl₃): δ 0.40-0.50 (4H, m), 1.24-1.32 (1H, m), 1.59 (6H, d, J=6.0 Hz), 1.65-2.10 (4H, m), 2.25 (1H, brs), 3.42-3.50 (1H, m), 3.55 (1H, dd, J=3.0 Hz, 12.0 Hz), 3.65-3.75 (1H, m), 3.85-3.95 (1H, m), 3.93 (2H, d, J=6.0 Hz), 4.16 (1H, brs), 4.74 (2H, s), 4.91 (1H, brs), 6.79 (1H, brs), 6.74-6.82 (1H, m), 7.07 (1H, d, J=12.0 Hz), 7.46 (2H, d, J=9.0 Hz), 7.79 (2H, d, J=9.0 Hz), 8.38 (1H, d, J=9.0 Hz).
(Step 2)

A mixture of (R)—N-(3-(cyclopropylmethyl)-7-fluoro-1-isopropyl-2,4-dioxo-1,2,3,4-tetrahydroquinazolin-6-yl)-3-(4-(hydroxymethyl)benzamido)piperidine-1-carboxamide (0.055 g, 0.10 mmol), ethyl isocyanate (0.014 g, 0.20 mmol) and DMAP (0.012 g, 0.10 mmol) in THF (2 mL) and DMF (0.5 mL) was stirred at room temperature for 24 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane) to give the title compound (0.062 g, 100.0%) as a white amorphous solid.

¹H NMR (300 MHz, CDCl₃): δ 0.41-0.49 (4H, m), 1.15 (3H, t, J=9.0 Hz), 1.24-1.32 (1H, m), 1.60 (6H, d, J=6.0 Hz), 1.65-1.75 (1H, m), 1.78-1.88 (1H, m), 1.90-2.05 (2H, m), 3.18-3.28 (2H, m), 3.55-3.65 (3H, m), 3.81 (1H, dd, J=3.0 Hz, 6.0 Hz), 3.95 (2H, d, J=9.0 Hz), 4.16 (1H, brs), 4.81 (1H, brs), 4.94 (1H, brs), 5.12 (2H, s), 6.66 (1H, brs), 6.67-6.73 (1H, m), 7.08 (1H, d, J=12.0 Hz), 7.42 (2H, d, J=6.0 Hz), 7.77 (2H, d, J=6.0 Hz), 8.61 (1H, d, J=9.0 Hz).

Example 319 tert-Butyl (4-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)benzyl)carbamate T3P (0.197 mL, 0.34 mmol) was added to a solution of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (70 mg, 0.17 mmol), 4-(((tert-butoxycarbonyl)amino)methyl)benzoic acid (50.6 mg, 0.20 mmol) and DIEA (0.090 mL, 0.50 mmol) in ethyl acetate (5 mL) at room temperature, and the mixture was stirred at room temperature overnight. To the reaction mixture was added brine, and the mixture was extracted with ethyl acetate. The organic layer was washed with brine, dried over magnesium sulfate, and the solvent was evaporated under reduced pressure. The residue was treated by silica gel column chromatography (solvent gradient; 30→100% ethyl acetate/hexane) to give the title compound (121 mg, 0.186 mmol, 111%) as a white solid.

¹H NMR (300 MHz, CDCl₃): δ 1.13 (d, J=6.04 Hz, 6H), 1.46 (s, 13H), 2.80 (s, 2H), 3.38-3.90 (m, 6H), 3.95 (d, J=7.18 Hz, 2H), 4.06-4.25 (m, 1H), 4.36 (d, J=6.04 Hz, 3H), 4.74-5.14 (m, 2H), 6.69 (brs, 2H), 7.08 (d, J=13.22 Hz, 1H), 7.37 (d, J=8.31 Hz, 3H), 7.76 (d, J=8.31 Hz, 2H), 8.03 (d, J=8.31 Hz, 1H), 8.48 (d, J=8.69 Hz, 1H).

Example 320

(3R)-3-((4-(aminomethyl)benzoyl)amino)-N-(3-(cyclopropylmethyl)-7-fluoro-1-isopropyl-2,4-dioxo-1,2,3,4-tetrahydroquinazolin-6-yl)piperidine-1-carboxamide hydrochloride A solution of tert-butyl (4-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)benzyl)carbamate (100 mg, 0.15 mmol) in TFA (3 mL) was stirred at room temperature for 30 min, and concentrated under reduced pressure. The residue was basified with 1N aqueous sodium hydroxide solution, and extracted with ethyl acetate. The organic layer was washed with brine, dried over magnesium sulfate, and the solvent was evaporated under reduced pressure to give the title compound (60.0 mg, 0.109 mmol, 70.9%) as a white solid.

¹H NMR (300 MHz, DMSO-d₆): δ 0.26-0.51 (4H, m), 1.39-1.70 (7H, m), 1.80 (1H, brs), 2.75-2.96 (1H, m), 3.73-4.21 (8H, m), 4.90 (1H, brs), 7.49-7.70 (4H, m), 7.82-8.14 (4H, m), 8.22-8.63 (5H, m).

Example 321 methyl (4-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)benzyl)carbamate A solution of (3R)-3-((4-(aminomethyl)benzoyl)amino)-N-(3-(cyclopropylmethyl)-7-fluoro-1-isopropyl-2,4-dioxo-1,2,3,4-tetrahydroquinazolin-6-yl)piperidine-1-carboxamide hydrochloride (58 mg, 0.10 mmol), methyl chlorocarbonate (0.011 mL, 0.15 mmol) and TEA (0.069 mL, 0.49 mmol) in THF (5 mL) was stirred at room temperature for 2 hr. To the reaction mixture was added brine, and the mixture was extracted with ethyl acetate. The organic layer was washed with brine, dried over magnesium sulfate, and the solvent was evaporated under reduced pressure. The residue was purified by silica gel column chromatography (solvent gradient; 50→100% ethyl acetate/hexane) to give the title compound (18.00 mg, 0.030 mmol, 29.9%) as a white solid.

¹H NMR (300 MHz, CDCl₃): δ 0.43 (brs, 4H), 0.95-1.43 (m, 3H), 1.73-2.47 (m, 6H), 3.29-4.52 (m, 13H), 4.92 (brs, 1H), 5.42 (brs, 1H), 6.52-7.18 (m, 4H), 7.35 (brs, 2H), 7.74 (d, J=5.67 Hz, 2H), 8.40 (d, J=6.42 Hz, 1H).

Example 323

(3R)-3-(6-cyano-1-oxo-1,3-dihydro-2H-isoindol-2-yl)-N-(3-(cyclopropylmethyl)-7-fluoro-1-isopropyl-2,4-dioxo-1,2,3,4-tetrahydroquinazolin-6-yl)piperidine-1-carboxamide DIEA (0.050 mL, 0.29 mmol) was added to a solution of methyl 2-(bromomethyl)-5-cyanobenzoate (73.0 mg, 0.29 mmol) and (R)-3-amino-N-(3-(cyclopropylmethyl)-7-fluoro-1-isopropyl-2,4-dioxo-1,2,3,4-tetrahydroquinazolin-6-yl)piperidine-1-carboxamide (100 mg, 0.24 mmol) in THF (30 mL) at room temperature. The mixture was stirred under a nitrogen gas atmosphere at 50° C. for 3 hr, and concentrated under reduced pressure. To the reaction mixture were added water and ethyl acetate. The organic layer was washed with brine, dried over sodium sulfate, and the solvent was evaporated under reduced pressure. The residue was purified by silica gel column chromatography (solvent; ethyl acetate/hexane), and solidified with IPE to give the title compound (49.3 mg, 0.088 mmol, 36.8%) as a white solid.

¹H NMR (300 MHz, CDCl₃): δ 0.37-0.53 (m, 4H), 1.25-1.36 (m, 1H), 1.49-2.21 (m, 10H), 3.00-3.18 (m, 1H), 3.36 (dd, J=13.03, 9.63 Hz, 1H), 3.86-4.13 (m, 4H), 4.25-4.38 (m, 1H), 4.57 (s, 2H), 4.94 (brs, 1H), 6.80 (s, 1H), 7.09

(d, J=13.22 Hz, 1H), 7.62 (d, J=7.93 Hz, 1H), 7.83 (dd, J=7.93, 1.51 Hz, 1H), 8.13 (s, 1H), 8.58 (d, J=8.69 Hz, 1H).

Example 324

(3R)-3-(7-cyano-4-oxoquinazoline-3(4H)-yl)-N-(3-(cyclopropylmethyl)-7-fluoro-1-isopropyl-2,4-dioxo-1,2,3,4-tetrahydroquinazolin-6-yl)piperidine-1-carboxamide (Step 1)

4-Nitrophenyl chloroformate (1.061 g, 5.26 mmol) was added to a solution of 6-amino-3-(cyclopropylmethyl)-7-fluoro-1-isopropylquinazoline-2,4(1H, 3H)-dione hydrochloride (1.5 g, 4.58 mmol) in THF (22.88 mL) at room temperature, and pyridine (0.923 mL, 11.44 mmol) was added thereto. The mixture was stirred at room temperature for 5 hr, and to the reaction mixture were added water and ethyl acetate. The organic layer was washed with water and brine, dried over sodium sulfate, and the solvent was evaporated under reduced pressure. The residue was purified by silica gel column chromatography (solvent; ethyl acetate/hexane) to give 4-nitrophenyl (3-(cyclopropylmethyl)-7-fluoro-1-isopropyl-2,4-dioxo-1,2,3,4-tetrahydroquinazolin-6-yl)carbamate (0.640 g, 1.402 mmol, 30.6%) as a white amorphous solid.

$^1$H NMR (300 MHz, CDCl$_3$): δ 0.40-0.53 (m, 4H), 1.25-1.35 (m, 1H), 1.60-1.67 (m, 6H), 3.95 (d, J=7.34 Hz, 2H), 4.96 (brs, 1H), 7.07-7.23 (m, 2H), 7.39-7.48 (m, 2H), 8.28-8.35 (m, 2H), 8.75-8.88 (m, 1H).

(Step 2)

HATU (12.49 g, 32.84 mmol) was added to a solution of (R)-tert-butyl 3-aminopiperidine-1-carboxylate (5.06 g, 25.26 mmol), 4-bromo-2-nitrobenzoic acid (6.22 g, 25.26 mmol) and DIEA (8.80 mL, 50.53 mmol) in DMF (120 mL) at room temperature, and the mixture was stirred at room temperature for 4 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 37→58% ethyl acetate/hexane) to give (R)-tert-butyl 3-(4-bromo-2-nitrobenzamido)piperidine-1-carboxylate (10.16 g, 23.72 mmol, 94%) as a pale-gray amorphous solid.

$^1$H NMR (300 MHz, CDCl$_3$): δ 1.44 (9H, s), 1.59-1.74 (2H, m), 1.88 (2H, brs), 3.26 (1H, brs), 3.44-3.64 (3H, m), 4.14-4.22 (1H, m), 6.03 (1H, brs), 7.41 (1H, d, J=7.9 Hz), 7.80 (1H, dd, J=7.9, 1.9 Hz), 8.20 (1H, d, J=1.5 Hz).

(Step 3)

Iron powder (6.62 g, 118.50 mmol) was added to a mixture of (R)-tert-butyl 3-(4-bromo-2-nitrobenzamido)piperidine-1-carboxylate (10.15 g, 23.70 mmol) and calcium chloride (2.63 g, 23.70 mmol) in EtOH (100 mL) and water (25 mL) at room temperature, and the mixture was stirred at 80° C. for 2.5 hr. To the reaction mixture was added aqueous sodium hydrogen carbonate solution, and the mixture was extracted 3 times with ethyl acetate. The organic layer was washed with water and brine, dried over magnesium sulfate, and the solvent was evaporated under reduced pressure to give (R)-tert-butyl 3-(2-amino-4-bromobenzamido)piperidine-1-carboxylate (9.16 g, 23.00 mmol, 97%) as a pale-yellow solid.

$^1$H NMR (300 MHz, CDCl$_3$): δ 1.46 (9H, s), 1.59-1.76 (2H, m), 1.84 (2H, brs), 3.24 (1H, t, J=9.1 Hz), 3.42-3.52 (1H, m), 3.60 (2H, dt, J=13.3, 4.7 Hz), 4.04-4.12 (1H, m), 5.64 (2H, brs), 6.23 (1H, brs), 6.73 (1H, dd, J=8.3, 1.9 Hz), 6.84 (1H, d, J=1.5 Hz), 7.13 (1H, d, J=8.7 Hz).

(Step 4)

N,N-Dimethylformamide dimethylacetal (61.0 mL, 458.96 mmol) was added to a solution of (R)-tert-butyl 3-(2-amino-4-bromobenzamido)piperidine-1-carboxylate (9.14 g, 22.95 mmol) in acetic acid (90 mL) at room temperature, and the mixture was stirred at 80° C. for 15 hr. To the reaction mixture were added ice and aqueous sodium hydrogen carbonate solution, and potassium carbonate was added to adjust the pH to 8. The mixture was extracted 3 times with ethyl acetate. The organic layer was washed with water and brine, dried over magnesium sulfate, and the solvent was evaporated under reduced pressure. The residue was purified by silica gel column chromatography (solvent gradient; 32→53% ethyl acetate/hexane) to give (R)-tert-butyl 3-(7-bromo-4-oxoquinazoline-3(4H)-yl)piperidine-1-carboxylate (6.89 g, 16.88 mmol, 73.5%) as a pale-yellow solid.

$^1$H NMR (300 MHz, CDCl$_3$): δ 1.47 (9H, s), 1.63-1.79 (1H, m), 1.81-2.03 (2H, m), 2.06-2.14 (1H, m), 2.87 (1H, t, J=11.3 Hz), 3.18 (1H, dd, J=12.5, 10.6 Hz), 4.01-4.10 (1H, m), 4.16-4.27 (1H, m), 4.70 (1H, brs), 7.61 (1H, dd, J=8.7, 1.9 Hz), 7.88 (1H, d, J=1.9 Hz), 8.08 (1H, s), 8.16 (1H, d, J=8.3 Hz).

(Step 5)

Under an argon gas atmosphere, a solution of (R)-tert-butyl 3-(7-bromo-4-oxoquinazoline-3(4H)-yl)piperidine-1-carboxylate (6.88 g, 16.85 mmol), zinc cyanide (5.94 g, 50.55 mmol) and Pd(PPh$_3$)$_4$ (1.947 g, 1.69 mmol) in DMF (60 mL) was stirred at 80° C. for 18 hr. To the reaction mixture was added 2.5% aqueous ammonia, and the mixture was extracted 3 times with ethyl acetate. The organic layer was washed with water and brine, dried over magnesium sulfate, and the solvent was evaporated under reduced pressure. The precipitate was collected by filtration with diethyl ether/hexane, and washed to give (R)-tert-butyl 3-(7-cyano-4-oxoquinazoline-3(4H)-yl)piperidine-1-carboxylate (4.82 g, 13.60 mmol, 81%) as a grayish white powder.

$^1$H NMR (300 MHz, CDCl$_3$): δ 1.47 (9H, s), 1.66-1.80 (1H, m), 1.82-2.16 (3H, m), 2.90 (1H, t, J=11.5 Hz), 3.21 (1H, dd, J=12.8, 10.6 Hz), 4.01-4.14 (1H, m), 4.22 (1H, d, J=11.0 Hz), 4.71 (1H, brs), 7.70 (1H, dd, J=7.9, 1.5 Hz), 8.03 (1H, d, J=1.1 Hz), 8.16 (1H, s), 8.40 (1H, d, J=8.3 Hz).

(Step 6)

4N Hydrogen chloride/CPME (70 mL, 280.00 mmol) was added to a solution of (R)-tert-butyl 3-(7-cyano-4-oxoquinazoline-3(4H)-yl)piperidine-1-carboxylate (4.81 g, 13.57 mmol) in MeOH (28 mL), and the mixture was stirred at room temperature for 50 min overnight. To the reaction mixture was added diethyl ether, and the precipitate was collected by filtration to give (R)-4-oxo-3-(piperidin-3-yl)-3,4-dihydroquinazoline-7-carbonitrile hydrochloride (4.47 g, 15.37 mmol, quant.) as a grayish white solid.

$^1$H NMR (300 MHz, DMSO-d$_6$): δ 1.81-2.06 (3H, m), 2.09-2.28 (1H, m), 2.86 (1H, q, J=11.8 Hz), 3.29 (1H, d, J=12.1 Hz), 3.37-3.51 (2H, m), 5.00-5.13 (1H, m), 7.93 (1H, dd, J=8.3, 1.5 Hz), 8.24 (1H, d, J=1.1 Hz), 8.29 (1H, d, J=8.3 Hz), 8.63 (1H, s), 9.47 (1H, brs), 9.92 (1H, d, J=10.2 Hz).

(Step 7)

DIEA (0.090 mL, 0.52 mmol) was added to a solution of (R)-4-oxo-3-(piperidin-3-yl)-3,4-dihydroquinazoline-7-carbonitrile hydrochloride (0.06 g, 0.21 mmol) and 4-nitrophenyl (3-(cyclopropylmethyl)-7-fluoro-1-isopropyl-2,4-dioxo-1,2,3,4-tetrahydroquinazolin-6-yl)carbamate (0.104 g, 0.23 mmol) in DMF (2.064 mL) at room temperature, and the mixture was stirred at room temperature overnight. To the reaction mixture was added water, and the mixture was extracted with ethyl acetate. The organic layer was washed with water and brine, dried over sodium sulfate, and the solvent was evaporated under reduced pressure. The residue was purified by silica gel column chromatography (solvent; ethyl acetate/hexane) and solidified with IPE to give the title compound (0.049 g, 0.085 mmol, 41.1%) as a white solid.

$^1$H NMR (300 MHz, CDCl$_3$): δ 0.38-0.51 (m, 4H), 1.25-1.35 (m, 1H), 1.60 (d, J=6.80 Hz, 6H), 1.77-2.28 (m, 4H), 2.98-3.14 (m, 1H), 3.31 (dd, J=12.84, 10.58 Hz, 1H), 3.94 (d, J=7.18 Hz, 2H), 4.14-4.24 (m, 1H), 4.32 (dd, J=13.22, 3.02 Hz, 1H), 4.62-4.76 (m, 1H), 4.96 (brs, 1H), 6.83 (brs, 1H), 7.11 (d, J=12.84 Hz, 1H), 7.72 (dd, J=8.12, 1.32 Hz, 1H), 8.05 (s, 1H), 8.21 (s, 1H), 8.40 (d, J=8.31 Hz, 1H), 8.61 (d, J=9.06 Hz, 1H).

Example 331

(2R)—N$^2$-(3-chloro-4-cyanophenyl)-N$^4$-(3-((2,2-difluorocyclopropyl)methyl)-7-fluoro-1-isopropyl-2,4-dioxo-1,2,3,4-tetrahydroquinazolin-6-yl)morpholine-2,4-dicarboxamide (Step 1)
A mixture of 2-amino-5-bromo-4-fluorobenzoic acid (10 g, 42.73 mmol), (4-methoxyphenyl)methanamine (6.45 g, 47.00 mmol), COMU (18.30 g, 42.73 mmol) and DIEA (11.05 g, 85.46 mmol) in DMF (200 mL) was stirred at room temperature overnight. To the reaction mixture was added water, and the mixture was extracted with ethyl acetate. The organic layer was washed with brine, dried over magnesium sulfate, and the solvent was evaporated under reduced pressure. The residue was purified by silica gel column chromatography (solvent gradient; 0→50% ethyl acetate/hexane) to give 2-amino-5-bromo-4-fluoro-N-(4-methoxybenzyl)benzamide (8 g, 22.65 mmol, 53.0%) as a brown solid.

$^1$H NMR (300 MHz, CDCl$_3$): δ 1.38-1.49 (m, 2H), 3.81 (s, 3H), 4.51 (d, J=5.29 Hz, 2H), 5.77 (brs, 2H), 6.12 (brs, 1H), 6.44 (d, J=10.20 Hz, 1H), 6.90 (d, J=8.69 Hz, 2H), 7.27-7.31 (m, 1H), 7.44 (d, J=7.18 Hz, 1H).

(Step 2)
A mixture of 2-amino-5-bromo-4-fluoro-N-(4-methoxybenzyl)benzamide (6.5 g, 18.40 mmol), bis(trichloromethyl) carbonate (3.66 g, 12.33 mmol) and TEA (5.64 mL, 40.49 mmol) in THF (40 mL) was stirred at room temperature for 5 hr. To the reaction mixture was added brine, and the mixture was extracted with ethyl acetate. The organic layer was washed with brine, dried over magnesium sulfate, and the solvent was evaporated under reduced pressure. The precipitate was collected by filtration to give 6-bromo-7-fluoro-3-(4-methoxybenzyl)quinazoline-2,4(1H, 3H)-dione (4.50 g, 11.87 mmol, 64.5%) as a white solid.

$^1$H NMR (300 MHz, DMSO-d$_6$): δ 3.71 (s, 3H), 4.99 (s, 2H), 6.70-6.92 (m, 2H), 7.07 (d, J=9.44 Hz, 1H), 7.27 (d, J=8.69 Hz, 2H), 8.16 (d, J=7.55 Hz, 1H), 11.73 (s, 1H).

(Step 3)
A mixture of 6-bromo-7-fluoro-3-(4-methoxybenzyl)quinazoline-2,4(1H, 3H)-dione (5 g, 13.19 mmol), 2-iodopropane (6.72 g, 39.56 mmol) and cesium carbonate (6.44 g, 19.78 mmol) in DMF (40 mL) was stirred at 70° C. for 4 hr. To the reaction mixture was added brine, and the mixture was extracted with ethyl acetate. The organic layer was washed with brine, dried over magnesium sulfate, and the solvent was evaporated under reduced pressure. The residue was purified by silica gel column chromatography (solvent gradient; 5→20% ethyl acetate/hexane) to give 6-bromo-7-fluoro-1-isopropyl-3-(4-methoxybenzyl)quinazoline-2,4(1H, 3H)-dione (1.600 g, 3.80 mmol, 28.8%) as a white solid.

$^1$H NMR (300 MHz, CDCl$_3$): δ 1.58 (d, J=7.18 Hz, 6H), 3.77 (s, 3H), 4.92 (brs, 1H), 5.16 (s, 2H), 6.71-6.91 (m, 2H), 7.10 (d, J=10.95 Hz, 1H), 7.46 (d, J=8.69 Hz, 2H), 8.35-8.61 (m, 1H).

(Step 4)
A mixture of 6-bromo-7-fluoro-1-isopropyl-3-(4-methoxybenzyl)quinazoline-2,4(1H, 3H)-dione (1.95 g, 4.63 mmol) and aluminum chloride (1.234 g, 9.26 mmol) in toluene (20 mL) was stirred at 50° C. for 30 min. To the reaction mixture was added brine, and the mixture was extracted with ethyl acetate. The organic layer was washed with brine, dried over magnesium sulfate, and the solvent was evaporated under reduced pressure. The precipitate was collected by filtration to give 6-bromo-7-fluoro-1-isopropylquinazoline-2,4(1H, 3H)-dione (1.140 g, 3.79 mmol, 82%) as a white solid.

$^1$H NMR (300 MHz, DMSO-d$_6$): δ 1.47 (d, J=6.80 Hz, 6H), 4.86 (brs, 1H), 7.72 (d, J=12.09 Hz, 1H), 8.18 (d, J=7.93 Hz, 1H), 11.32-11.79 (m, 1H).

(Step 5)
A mixture of 6-bromo-7-fluoro-1-isopropylquinazoline-2,4(1H, 3H)-dione (350 mg, 1.16 mmol), sodium iodide (261 mg, 1.74 mmol), cesium carbonate (568 mg, 1.74 mmol) and 2-(bromomethyl)-1,1-difluorocyclopropane (298 mg, 1.74 mmol) in DMF (10 mL) was stirred at 80° C. overnight. To the reaction mixture was added 1N hydrochloric acid, and the mixture was extracted with ethyl acetate. The organic layer was washed with brine, dried over magnesium sulfate, and the solvent was evaporated under reduced pressure. The residue was purified by silica gel column chromatography (solvent gradient; 0→20% ethyl acetate/hexane) to give 6-bromo-3-((2,2-difluorocyclopropyl)methyl)-7-fluoro-1-isopropylquinazoline-2,4(1H, 3H)-dione (429 mg, 1.097 mmol, 94%) as a pale-brown solid.

$^1$H NMR (300 MHz, CDCl$_3$): δ 1.34-1.49 (m, 3H), 1.61 (d, J=6.80 Hz, 7H), 2.05-2.21 (m, 1H), 3.97-4.39 (m, 3H), 4.93 (brs, 1H), 7.14 (d, J=10.95 Hz, 1H), 8.43 (d, J=7.93 Hz, 1H).

(Step 6)
A mixture of 6-bromo-3-((2,2-difluorocyclopropyl)methyl)-7-fluoro-1-isopropylquinazoline-2,4(1H, 3H)-dione (429 mg, 1.10 mmol), cesium carbonate (893 mg, 2.74 mmol), tert-butyl carbamate (180 mg, 1.54 mmol), Pd$_2$(dba)$_3$ (50.2 mg, 0.05 mmol) and XPhos (52.3 mg, 0.11 mmol) in toluene (10 mL) was stirred at 80° C. overnight. To the reaction mixture was added brine, and the mixture was extracted with ethyl acetate. The organic layer was washed with brine, dried over magnesium sulfate, and the solvent was evaporated under reduced pressure. The residue was purified by silica gel column chromatography (solvent gradient; 0→30% ethyl acetate/hexane) to give crude tert-butyl (3-((2,2-difluorocyclopropyl)methyl)-7-fluoro-1-isopropyl-2,4-dioxo-1,2,3,4-tetrahydroquinazolin-6-yl)carbamate (557 mg, 1.303 mmol, 119%) as a pale-brown oil.

$^1$H NMR (300 MHz, CDCl$_3$): δ 1.48-1.68 (m, 16H), 2.03-2.23 (m, 2H), 4.23-4.51 (m, 3H), 6.58 (brs, 1H), 7.10 (d, J=13.22 Hz, 1H), 8.59-9.11 (m, 1H).

(Step 7)
A mixture of crude tert-butyl (3-((2,2-difluorocyclopropyl)methyl)-7-fluoro-1-isopropyl-2,4-dioxo-1,2,3,4-tetrahydroquinazolin-6-yl)carbamate (557 mg, 1.30 mmol) and TFA (3 mL) was stirred at room temperature for 1 hr. To the reaction mixture was added aqueous sodium hydrogen carbonate solution, and the mixture was extracted with ethyl acetate. The organic layer was washed with brine, dried over magnesium sulfate, and the solvent was evaporated under reduced pressure to give 6-amino-3-((2,2-difluorocyclopropyl)methyl)-7-fluoro-1-isopropylquinazoline-2,4(1H, 3H)-dione (227 mg, 0.694 mmol, 53.2%) as a pale-yellow solid.

$^1$H NMR (300 MHz, CDCl$_3$): δ 1.31-1.49 (2H, m), 1.59 (6H, d, J=7.2 Hz), 2.04-2.22 (1H, m), 3.80 (2H, s), 4.11-4.29 (2H, m), 4.91 (1H, brs), 7.06 (1H, d, J=13.2 Hz), 7.62 (1H, d, J=9.8 Hz).

(Step 8)

4-Nitrophenyl chloroformate (42.5 mg, 0.21 mmol) was added to a mixture of 6-amino-3-((2,2-difluorocyclopropyl)methyl)-7-fluoro-1-isopropylquinazoline-2,4(1H, 3H)-dione (60 mg, 0.18 mmol) and pyridine (16.7 mg, 0.21 mmol) in THF (1 mL) at room temperature, and the mixture was stirred at room temperature for 2 hr. The reaction mixture was concentrated under reduced pressure, and the residue was dissolved in DMF (3 mL). The solution was added to (R)—N-(3-chloro-4-cyanophenyl) morpholine-2-carboxamide hydrochloride (55.4 mg, 0.18 mmol) and DIEA (52.1 mg, 0.40 mmol) at room temperature. The mixture was stirred at room temperature for 1 hr. To the reaction mixture was added water, the pH was adjusted to 3 with 2N hydrochloric acid, and the mixture was extracted with ethyl acetate. The organic layer was washed with water and brine, dried over magnesium sulfate, and the solvent was evaporated under reduced pressure. The residue was purified by silica gel column chromatography (solvent gradient; 30→100% ethyl acetate/hexane). The precipitate was collected by filtration with IPE/hexane to give the title compound (50.0 mg, 0.081 mmol, 44.1%) as a white powder.

$^1$H NMR (300 MHz, DMSO-d$_6$): δ 1.50 (d, J=6.80 Hz, 8H), 2.01-2.23 (m, 1H), 2.98-3.22 (m, 2H), 3.54-3.77 (m, 1H), 3.80-4.35 (m, 6H), 4.91 (brs, 1H), 7.62 (d, J=13.22 Hz, 1H), 7.80-7.99 (m, 2H), 8.08-8.22 (m, 2H), 8.70 (s, 1H), 10.47 (s, 1H).

Example 333

(2R)—N$^2$-(3-chloro-4-cyanophenyl)-N$^4$-(7-fluoro-1-isopropyl-2,4-dioxo-3-(tetrahydrofuran-2-ylmethyl)-1,2,3,4-tetrahydroquinazolin-6-yl)morpholine-2,4-dicarboxamide (Step 1)

A mixture of 6-bromo-7-fluoro-1-isopropylquinazoline-2,4(1H, 3H)-dione (0.301 g, 1.00 mmol), 2-(bromomethyl)tetrahydrofuran (0.248 g, 1.50 mmol), cesium carbonate (0.489 g, 1.50 mmol) and sodium iodide (0.225 g, 1.50 mmol) in DMF (2 mL) was stirred at 60° C. for 18 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane) to give 6-bromo-7-fluoro-1-isopropyl-3-((tetrahydrofuran-2-yl)methyl)quinazoline-2,4(1H, 3H)-dione (0.350 g, 91.0%) as a colorless oil.

$^1$H NMR (300 MHz, CDCl$_3$): δ 1.61 (6H, d, J=9.0 Hz), 1.60-1.70 (1H, m), 1.85-1.95 (1H, m), 1.95-2.10 (2H, m), 3.70-3.80 (1H, m), 3.88-3.98 (2H, m), 4.29-4.39 (2H, m), 4.91 (1H, brs), 7.11 (1H, d, J=12.0 Hz), 8.43 (1H, d, J=9.0 Hz).

(Step 2)

A mixture of 6-bromo-7-fluoro-1-isopropyl-3-((tetrahydrofuran-2-yl)methyl)quinazoline-2,4(1H, 3H)-dione (0.350 g, 91.0 mmol), tert-butyl carbamate (0.160 g, 1.36 mmol), XPhos (43 mg, 0.09 mmol), cesium carbonate (0.592 g, 1.82 mmol) and Pd$_2$(dba)$_3$ (0.042 g, 0.05 mmol) in toluene (2 mL) was stirred at 80° C. for 16 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane) to give tert-butyl (7-fluoro-1-isopropyl-2,4-dioxo-3-((tetrahydrofuran-2-yl)methyl)-1,2,3,4-tetrahydroquinazolin-6-yl)carbamate (0.373 g, 97.0%) as a pale-brown amorphous solid.

MS(API): Calculated 421.5. Found 422.1 (M+H).

(Step 3)

A mixture of 4N hydrogen chloride/ethyl acetate (5 mL) and tert-butyl (7-fluoro-1-isopropyl-2,4-dioxo-3-((tetrahydrofuran-2-yl)methyl)-1,2,3,4-tetrahydroquinazolin-6-yl)carbamate (0.373 g, 89.0 mmol) was stirred at room temperature for 1 hr. To the reaction mixture was added 0.1N aqueous sodium hydroxide solution, and the mixture was extracted with ethyl acetate. The organic layer was dried over magnesium sulfate, and the solvent was evaporated under reduced pressure to give 6-amino-7-fluoro-1-isopropyl-3-((tetrahydrofuran-2-yl)methyl)quinazoline-2,4(1H, 3H)-dione (0.284 g, quant.) as a pale-brown amorphous solid.

MS(API): Calculated 321.4. Found 322.1 (M+H).

(Step 4)

A mixture of 6-amino-7-fluoro-1-isopropyl-3-((tetrahydrofuran-2-yl)methyl)quinazoline-2,4(1H, 3H)-dione (64 mg, 0.20 mmol), 4-nitrophenyl chloroformate (44 mg, 0.22 mmol) and pyridine (17 mg, 0.22 mmol) in THF (2 mL) was stirred at 0° C. for 0.5 hr. The reaction mixture was concentrated under reduced pressure, and the residue was dissolved in DMF (2 mL). The solution was added to (R)—N-(3-chloro-4-cyanophenyl)morpholine-2-carboxamide hydrochloride (60 mg, 0.22 mmol) and DIEA (52 mg, 0.40 mmol) at 0° C. The mixture was stirred at 0° C. for 1 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane) and solidified with IPE to give the title compound (59 mg, 48.1%) as a white amorphous solid.

$^1$H NMR (300 MHz, CDCl$_3$): δ 1.59 (6H, d, J=6.0 Hz), 1.62-1.72 (1H, m), 1.82-1.92 (1H, m), 1.92-2.07 (2H, m), 3.18-3.38 (2H, m), 3.68-3.88 (2H, m), 3.90-4.05 (3H, m), 4.05-4.42 (5H, m), 4.90 (1H, brs), 6.70 (1H, d, J=1.5 Hz), 7.10 (1H, d, J=12.0 Hz), 7.57 (1H, dd, J=1.5 Hz, 12.0 Hz), 7.65 (1H, d, J=9.0 Hz), 7.92 (1H, d, J=1.5 Hz), 8.55 (1H, s), 8.61 (1H, d, J=9.0 Hz).

Example 335

(2R)—N$^2$-(3-chloro-4-cyanophenyl)-N$^4$-(7-fluoro-1-isopropyl-2,4-dioxo-3-(tetrahydrofuran-3-ylmethyl)-1,2,3,4-tetrahydroquinazolin-6-yl)morpholine-2,4-dicarboxamide (Step 1)

A mixture of 6-bromo-7-fluoro-1-isopropylquinazoline-2,4(1H, 3H)-dione (0.301 g, 1.00 mmol), (tetrahydrofuran-3-yl)methyl 4-methylbenzenesulfonate (0.248 g, 1.50 mmol), cesium carbonate (0.384 g, 1.50 mmol) and sodium iodide (0.225 g, 1.50 mmol) in DMF (2 mL) was stirred at 60° C. for 2 hr. To the reaction mixture was added water, and the mixture was extracted with ethyl acetate. The organic layer was dried over magnesium sulfate, and the solvent was evaporated under reduced pressure. The residue was purified by silica gel column chromatography (solvent gradient; 0→100% ethyl acetate/hexane) to give 6-bromo-7-fluoro-1-isopropyl-3-((tetrahydrofuran-3-yl)methyl)quinazoline-2,4(1H, 3H)-dione (0.350 g, 91.0%) as a white solid.

$^1$H NMR (300 MHz, CDCl$_3$): δ 1.60 (6H, d, J=6.0 Hz), 1.68-1.82 (1H, m), 1.92-2.06 (1H, m), 2.66-2.80 (1H, m), 3.60 (1H, dd, J=3.0 Hz, 12.0 Hz), 3.74-3.84 (2H, m), 3.91-3.99 (1H, m), 4.05 (1H, dd, J=6.0 Hz, 12.0 Hz), 4.17 (1H, dd, J=6.0 Hz, 12.0 Hz), 4.91 (1H, brs), 7.13 (1H, d, J=12.0 Hz), 8.43 (1H, d, J=9.0 Hz).

(Step 2)

A mixture of 6-bromo-7-fluoro-1-isopropyl-3-((tetrahydrofuran-3-yl)methyl)quinazoline-2,4(1H, 3H)-dione (0.350 g, 91.0 mmol), tert-butyl carbamate (0.160 g, 1.36 mmol), XPhos (43 mg, 0.09 mmol), cesium carbonate (0.592 g, 1.82 mmol) and Pd$_2$(dba)$_3$ (0.042 g, 0.05 mmol) in toluene (2 mL) was stirred at 80° C. for 16 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane) to give tert-butyl (7-fluoro-1-isopropyl-2,4-dioxo-3-((tetrahydrofuran-3-yl)methyl)-1,2,3,4-tetrahydroquinazolin-6-yl)carbamate (0.370 g, 97.0%) as a pale-brown amorphous solid.

MS(API): Calculated 421.5. Found 422.1 (M+H).

(Step 3)

A mixture of 4N hydrogen chloride/ethyl acetate (5 mL) and tert-butyl (7-fluoro-1-isopropyl-2,4-dioxo-3-((tetrahydrofuran-3-yl)methyl)-1,2,3,4-tetrahydroquinazolin-6-yl)carbamate (0.373 g, 89.0 mmol) was stirred at room temperature for 1 hr. To the reaction mixture was added 0.1N aqueous sodium hydroxide solution, and the mixture was extracted with ethyl acetate. The organic layer was dried over magnesium sulfate, and the solvent was evaporated under reduced pressure to give 6-amino-7-fluoro-1-isopropyl-3-((tetrahydrofuran-3-yl)methyl)quinazoline-2,4(1H, 3H)-dione (0.281 g, quant.) as a pale-brown amorphous solid.

(Step 4)

A mixture of 6-amino-7-fluoro-1-isopropyl-3-((tetrahydrofuran-3-yl)methyl)quinazoline-2,4(1H, 3H)-dione (64 mg, 0.20 mmol), 4-nitrophenyl chloroformate (44 mg, 0.22 mmol) and pyridine (17 mg, 0.22 mmol) in THF (2 mL) was stirred at 0° C. for 0.5 hr. The reaction mixture was concentrated under reduced pressure, and the residue was dissolved in DMF (2 mL). The solution was added to (R)—N-(3-chloro-4-cyanophenyl)morpholine-2-carboxamide hydrochloride (60 mg, 0.22 mmol) and DIEA (52 mg, 0.40 mmol) at 0° C. The mixture was stirred at 0° C. for 1 hr. To the reaction mixture was added water, and the mixture was extracted with ethyl acetate. The organic layer was concentrated under reduced pressure. The residue was purified by silica gel column chromatography (solvent gradient; 0→100% ethyl acetate/hexane) and solidified with IPE to give the title compound (61 mg, 49.8%) as a white amorphous solid.

$^1$H NMR (300 MHz, CDCl$_3$): δ 1.60 (6H, d, J=6.0 Hz), 1.68-1.80 (1H, m), 1.92-2.04 (1H, m), 2.68-2.80 (1H, m), 3.20-3.40 (2H, m), 3.60 (1H, dd, J=1.5 Hz, 9.0 Hz), 3.70-3.85 (3H, m), 3.88-4.20 (6H, m), 4.24 (1H, dd, J=3.0 Hz, 9.0 Hz), 4.90 (1H, brs), 6.75 (1H, brs), 7.12 (1H, d, J=12.0 Hz), 7.58 (1H, dd, J=1.5 Hz, 9.0 Hz), 7.65 (1H, d, J=9.0 Hz), 7.93 (1H, d, J=3.0 Hz), 8.56 (1H, s), 8.60 (1H, d, J=9.0 Hz).

Example 336

(3R)-3-(6-chloro-1-oxo-1,3-dihydro-2H-isoindol-2-yl)-N-(3-(cyclopropylmethyl)-7-fluoro-1-isopropyl-2,4-dioxo-1,2,3,4-tetrahydroquinazolin-6-yl)piperidine-1-carboxamide NaBH(OAc)$_3$ (424 mg, 2.00 mmol) was added to a mixture of 5-chloro-2-formylbenzoic acid (185 mg, 1.00 mmol) and (R)-3-amino-N-(3-(cyclopropylmethyl)-7-fluoro-1-isopropyl-2,4-dioxo-1,2,3,4-tetrahydroquinazolin-6-yl)piperidine-1-carboxamide (209 mg, 0.50 mmol) in THF (2.5 mL) and acetic acid (0.25 mL) at room temperature, and the mixture was stirred at room temperature for 6 hr. To the reaction mixture was added water, and the mixture was extracted with ethyl acetate. The organic layer was washed with water, dried over magnesium sulfate, and the solvent was evaporated under reduced pressure. The residue was purified by silica gel column chromatography (solvent gradient; 0→100% ethyl acetate/hexane), and solidified with IPE to give the title compound (56 mg, 19.7%) as a white amorphous solid.

$^1$H NMR (300 MHz, CDCl$_3$): δ 0.42-0.50 (4H, m), 1.21-1.31 (1H, m), 1.60 (6H, d, J=6.0 Hz), 1.72-1.82 (1H, m), 1.85-2.00 (2H, m), 2.10-2.20 (1H, m), 2.98-3.10 (1H, m), 3.32 (1H, dd, J=3.0 Hz, 12.0 Hz), 3.94 (2H, d, J=6.0 Hz), 4.04-4.12 (2H, m), 4.25-4.35 (1H, m), 4.45 (2H, s), 4.94 (1H, brs), 6.73 (1H, brs), 7.09 (1H, d, J=12.0 Hz), 7.41 (1H, d, J=9.0 Hz), 7.53 (1H, dd, J=1.5 Hz, 9.0 Hz), 7.83 (1H, d, J=3.0 Hz), 8.61 (1H, d, J=9.0 Hz).

Example 340 tert-butyl 6-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-3,4-dihydroisoquinoline-2 (1H)-carboxylate (Step 1)

NaBH$_4$ (3.46 g, 91.51 mmol) was slowly added to a mixture of 6-bromoisoquinoline (4.76 g, 22.88 mmol) and acetic acid (90 mL) at room temperature, and the mixture was stirred at room temperature for 1.5 hr. To the reaction mixture was added water, and the mixture was adjusted to pH 8 with 8N aqueous sodium hydroxide solution. The mixture was extracted 3 times with ethyl acetate/THF mixed solution (3:1). The organic layer was washed with water, dried over magnesium sulfate, and the solvent was evaporated under reduced pressure. The residue was purified by silica gel column chromatography (NH, solvent gradient; 20→90% ethyl acetate/hexane) to give 6-bromo-1,2,3,4-tetrahydroisoquinoline (3.26 g, 15.37 mmol, 67.2%) as a colorless oil.

$^1$H NMR (300 MHz, CDCl$_3$): δ 1.63 (1H, s), 2.77 (2H, t, J=6.0 Hz), 3.11 (2H, t, J=5.9 Hz), 3.95 (2H, s), 6.85-6.90 (1H, m), 7.21-7.26 (2H, m).

(Step 2)

Boc$_2$O (3.52 g, 16.14 mmol) was added to a solution of 6-bromo-1,2,3,4-tetrahydroisoquinoline (3.26 g, 15.37 mmol) in THF (45 mL) at room temperature, and the mixture was stirred at room temperature for 15 hr. The reaction mixture was concentrated under reduced pressure. The residue was purified by silica gel column chromatography (solvent gradient; 0→8% ethyl acetate/hexane) to give tert-butyl 6-bromo-3,4-dihydroisoquinoline-2 (1H)-carboxylate (5.05 g, 16.18 mmol, quant.) as a colorless oil.

$^1$H NMR (300 MHz, CDCl$_3$): δ 1.49 (9H, s), 2.80 (2H, t, J=5.9 Hz), 3.62 (2H, t, J=5.9 Hz), 4.51 (2H, s), 6.97 (1H, d, J=8.7 Hz), 7.28-7.32 (2H, m).
(Step 3)

A mixture of tert-butyl 6-bromo-3,4-dihydroisoquinoline-2 (1H)-carboxylate (5.04 g, 16.14 mmol), Pd(OAc)$_2$ (0.362 g, 1.61 mmol), 1,3-bis(diphenylphosphino)propane (0.666 g, 1.61 mmol) and TEA (6.75 mL, 48.43 mmol) in MeOH (35 mL) and DMSO (35 mL) was stirred under a carbon monoxide gas atmosphere (0.3 MPa) at 70° C. for 7.5 hr. The reaction mixture was filtered, water was added to the filtrate, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 4→25% ethyl acetate/hexane) to give 2-tert-butyl 6-methyl 3,4-dihydroisoquinoline-2,6(1H)-dicarboxylate (2.59 g, 8.89 mmol, 55.1%) as a white solid.

$^1$H NMR (300 MHz, CDCl$_3$): δ 1.50 (9H, s), 2.88 (2H, t, J=5.9 Hz), 3.66 (2H, t, J=5.9 Hz), 3.91 (3H, s), 4.62 (2H, s), 7.17 (1H, d, J=8.3 Hz), 7.81-7.86 (2H, m).
(Step 4)

3N Aqueous lithium hydroxide solution (17.78 mL, 53.34 mmol) was added to a mixture of 2-tert-butyl 6-methyl 3,4-dihydroisoquinoline-2,6(1H)-dicarboxylate (2.59 g, 8.89 mmol) in MeOH (21 mL) and THF (21 mL) at room temperature, and the mixture was stirred at room temperature for 2 hr. To the reaction mixture was added water, and the mixture was adjusted to pH 3 with 6N hydrochloric acid. The mixture was extracted 3 times with ethyl acetate. The organic layer was washed with water and brine, dried over magnesium sulfate, and the solvent was evaporated under reduced pressure. The precipitate was collected by filtration with IPE/hexane to give 2-(tert-butoxycarbonyl)-1,2,3,4-tetrahydroisoquinoline-6-carboxylic acid (2.18 g, 7.86 mmol, 88%) as a white powder.

$^1$H NMR (300 MHz, CDCl$_3$): δ 1.50 (9H, s), 2.90 (2H, t, J=5.7 Hz), 3.68 (2H, t, J=5.9 Hz), 4.64 (2H, s), 7.21 (1H, d, J=7.6 Hz), 7.89-7.94 (2H, m).
(Step 5)

HATU (213 mg, 0.56 mmol) was added to a mixture of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (180 mg, 0.43 mmol), 2-(tert-butoxycarbonyl)-1,2,3,4-tetrahydroisoquinoline-6-carboxylic acid (126 mg, 0.45 mmol) and DIEA (150 μL, 0.86 mmol) in DMF (2.2 mL) at room temperature, and the mixture was stirred at room temperature for 15 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 79→100% ethyl acetate/hexane) to give the title compound (262.6 mg, 0.388 mmol, 90%) as a white amorphous solid.

$^1$H NMR (300 MHz, CDCl$_3$): δ 0.41-0.49 (4H, m), 1.28-1.34 (1H, m), 1.49 (9H, s), 1.60 (6H, d, J=7.2 Hz), 1.65-2.02 (4H, m), 2.88 (2H, t, J=5.7 Hz), 3.49-3.68 (5H, m), 3.75-3.83 (1H, m), 3.94 (2H, d, J=7.2 Hz), 4.13-4.19 (1H, m), 4.59 (2H, s), 4.93 (1H, brs), 6.70-6.75 (2H, m), 7.08 (1H, d, J=12.8 Hz), 7.18 (1H, d, J=8.7 Hz), 7.56-7.62 (2H, m), 8.60 (1H, d, J=8.7 Hz).

Example 343 methyl 5-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-1,3-dihydro-2H-isoindole-2-carboxylate (Step 1)

1M Borane-THF complex (112 mL, 112.29 mmol) was slowly added to a mixture of 5-bromoisoindoline-1,3-dione (4.23 g, 18.71 mmol) in THF (50 mL) at 0° C., and the mixture was stirred at 60° C. for 15 hr. The mixture was cooled to 0° C., and MeOH (40 mL) and 2N hydrochloric acid (40 mL) were added. The mixture was stirred at 60° C. for 1 hr, and concentrated under reduced pressure to a half amount. Water was added to the mixture, and the mixture was adjusted to pH 8 with 8N aqueous sodium hydroxide solution. The mixture was extracted 3 times with ethyl acetate/THF mixed solution (3:1). The organic layer was washed with water, dried over magnesium sulfate, and the solvent was evaporated under reduced pressure. The residue was purified by silica gel column chromatography (NH, solvent gradient; 20→90% ethyl acetate/hexane) to give 5-bromoisoindoline-1,3-dione (2.24 g, 11.31 mmol, 60.4%) as a yellow solid.

$^1$H NMR (300 MHz, CDCl$_3$): δ 2.36 (1H, brs), 4.20 (4H, d, J=10.6 Hz), 7.11 (1H, d, J=7.9 Hz), 7.30-7.36 (1H, m), 7.38 (1H, s).
(Step 2)

Boc$_2$O (2.58 g, 11.82 mmol) was added to a mixture of 5-bromoisoindoline-1,3-dione (2.23 g, 11.26 mmol) in THF (35 mL) at room temperature, and the mixture was stirred at room temperature for 15 hr. The reaction mixture was concentrated under reduced pressure. The residue was purified by silica gel column chromatography (solvent gradient; 0→14% ethyl acetate/hexane) to give tert-butyl 5-bromoisoindoline-2-carboxylate (2.35 g, 7.88 mmol, 70.0%) as a white solid.

$^1$H NMR (300 MHz, CDCl$_3$): δ 1.51 (9H, s), 4.58-4.68 (4H, m), 7.07-7.17 (1H, m), 7.35-7.44 (2H, m).
(Step 3)

A mixture of tert-butyl 5-bromoisoindoline-2-carboxylate (2.35 g, 7.88 mmol), Pd(OAc)$_2$ (0.177 g, 0.79 mmol), 1,3-bis(diphenylphosphino)propane (0.325 g, 0.79 mmol) and TEA (3.30 mL, 23.64 mmol) in MeOH (20 mL) and DMSO (20 mL) was stirred under a carbon monoxide gas atmosphere (0.3 MPa) at 70° C. for 7.5 hr. The reaction mixture was filtered, water was added to the filtrate, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 7→28% ethyl acetate/hexane) to give 2-tert-butyl 5-methyl isoindoline-2,5-dicarboxylate (789 mg, 2.85 mmol, 36.1%) as a colorless oil.

$^1$H NMR (300 MHz, CDCl$_3$): δ 1.52 (9H, s), 3.92 (3H, s), 4.66-4.75 (4H, m), 7.27-7.36 (1H, m), 7.89-7.99 (2H, m).
(Step 4)

3N Aqueous lithium hydroxide solution (5.65 mL, 16.96 mmol) was added to a mixture of 2-tert-butyl 5-methyl isoindoline-2,5-dicarboxylate (784 mg, 2.83 mmol) in MeOH (6.8 mL) and THF (6.8 mL) at room temperature, and the mixture was stirred at room temperature for 2 hr. To the reaction mixture was added water, and the mixture was adjusted to pH 3 with 6N hydrochloric acid. The mixture was extracted 3 times with ethyl acetate. The organic layer was washed with water and brine, dried over magnesium sulfate, and the solvent was evaporated under reduced pressure. The precipitate was collected by filtration with IPE/hexane to give 2-(tert-butoxycarbonyl)isoindoline-5-carboxylic acid (594 mg, 2.256 mmol, 80%) as a white powder.

$^1$H NMR (300 MHz, CDCl$_3$): δ 1.53 (9H, s), 4.69-4.78 (4H, m), 7.31-7.41 (1H, m), 7.96-8.07 (2H, m).
(Step 5)

HATU (213 mg, 0.56 mmol) was added to a mixture of (R)-3-amino-N-(3-(cyclopropylmethyl)-7-fluoro-1-isopropyl-2,4-dioxo-1,2,3,4-tetrahydroquinazolin-6-yl)piperidine-1-carboxamide (180 mg, 0.43 mmol), 2-(tert-butoxycarbonyl)isoindoline-5-carboxylic acid (119 mg, 0.45 mmol) and DIEA (150 μL, 0.86 mmol) in DMF (2.2 mL) at room temperature, and the mixture was stirred at room temperature for 15 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 81→100% ethyl acetate/hexane) to give (R)-tert-butyl 5-((1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)isoindoline-2-carboxylate (244.8 mg, 0.369 mmol, 86%) as a white amorphous solid.

$^1$H NMR (300 MHz, CDCl$_3$): δ 0.41-0.48 (4H, m), 1.27-1.33 (1H, m), 1.52 (9H, s), 1.59 (6H, d, J=6.8 Hz), 1.65-2.03 (4H, m), 3.47-3.68 (3H, m), 3.83 (1H, dd, J=13.6, 5.3 Hz), 3.94 (2H, d, J=7.2 Hz), 4.13-4.20 (1H, m), 4.69 (4H, d, J=8.3 Hz), 4.93 (1H, brs), 6.70 (1H, d, J=1.9 Hz), 6.76 (1H, d, J=6.0 Hz), 7.08 (1H, d, J=12.8 Hz), 7.28-7.38 (1H, m), 7.65-7.73 (2H, m), 8.56 (1H, dd, J=8.9, 3.6 Hz).
(Step 6)

TFA (3 mL) was added to (R)-tert-butyl 5-((1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)isoindoline-2-carboxylate (175 mg, 0.26 mmol) at room temperature, and the mixture was stirred at room temperature for 20 min. To the reaction mixture was added aqueous sodium hydrogen carbonate solution, and the mixture was adjusted to pH 8 by adding potassium carbonate. Sodium chloride was added to the mixture, and the mixture was extracted 4 times with ethyl acetate/THF mixed solution (3:1, v/v). The organic layer was washed with brine, dried over magnesium sulfate, and the solvent was evaporated under reduced pressure to give (R)—N-(1-((3-(cyclopropylmethyl)-7-fluoro-1-isopropyl-2,4-dioxo-1,2,3,4-tetrahydroquinazolin-6-yl)carbamoyl)piperidin-3-yl)isoindoline-5-carboxamide (166 mg, 0.295 mmol, quant.) as a white amorphous solid.

$^1$H NMR (300 MHz, DMSO-d$_6$): 0.31-0.47 (4H, m), 1.13-1.22 (1H, m), 1.50 (6H, d, J=6.8 Hz), 1.54-1.62 (1H, m), 1.90-1.98 (1H, m), 2.18 (1H, s), 2.82-2.95 (2H, m), 3.34 (1H, brs), 3.81 (2H, d, J=7.2 Hz), 3.85-4.12 (3H, m), 4.24 (4H, s), 4.90 (1H, brs), 6.63-6.88 (1H, m), 7.37 (1H, d, J=7.9 Hz), 7.57 (1H, d, J=13.2 Hz), 7.74 (1H, dd like), 7.77 (1H, s), 8.08 (1H, d, J=9.1 Hz), 8.30 (1H, d, J=7.6 Hz), 8.51 (1H, s).
(Step 7)

Methyl chloroformate (16 μL, 0.21 mmol) was added to a solution of (R)—N-(1-((3-(cyclopropylmethyl)-7-fluoro-1-isopropyl-2,4-dioxo-1,2,3,4-tetrahydroquinazolin-6-yl)carbamoyl)piperidin-3-yl)isoindoline-5-carboxamide (77 mg, 0.14 mmol) and TEA (28.6 μL, 0.21 mmol) in THF (1.5 mL) at room temperature, and the mixture was stirred at room temperature for 3 hr. To the reaction mixture was added aqueous sodium hydrogen carbonate solution, and the mixture was extracted 3 times with ethyl acetate. The organic layer was washed with brine, dried over magnesium sulfate, and the solvent was evaporated under reduced pressure. The residue was purified by silica gel column chromatography (Diol, solvent gradient; 30→90% ethyl acetate/hexane) to give the title compound (40.9 mg, 0.066 mmol, 48.2%) as a white amorphous solid.

$^1$H NMR (300 MHz, CDCl$_3$): δ 0.41-0.49 (4H, m), 1.26-1.34 (1H, m), 1.60 (6H, d like), 1.69-2.10 (4H, m), 3.45-3.70 (3H, m), 3.79 (3H, s), 3.85 (1H, dd like), 3.94 (2H, d, J=7.2 Hz), 4.17 (1H, d, J=4.5 Hz), 4.75 (4H, d, J=12.5 Hz), 4.93 (1H, brs), 6.69 (1H, d, J=2.3 Hz), 6.76-6.90 (1H, m), 7.08 (1H, d, J=13.2 Hz), 7.35 (1H, dd, J=11.7, 8.3 Hz), 7.68-7.74 (2H, m), 8.56 (1H, dd, J=8.9, 7.0 Hz).

Example 347

(2R)—N$^2$-(5-chloro-4-cyano-2-fluorophenyl)-N$^4$-(3-(cyclopropylmethyl)-7-fluoro-1-isopropyl-2,4-dioxo-1,2,3,4-tetrahydroquinazolin-6-yl)morpholine-2,4-dicarboxamide (Step 1)

Copper(I) cyanide (3.99 g, 44.55 mmol) was added to a mixture of 4-bromo-5-chloro-2-fluoroaniline (5.0 g, 22.28 mmol) in DMF (30 mL) at room temperature, and the mixture was stirred at 150° C. for 5 hr. To the reaction mixture were added water and ethyl acetate, and the mixture was filtered. The organic layer was washed with water and brine, dried over magnesium sulfate, and the solvent was evaporated under reduced pressure. The residue was purified by silica gel column chromatography (ethyl acetate/hexane) to give 4-amino-2-chloro-5-fluorobenzonitrile (2.81 g, 16.47 mmol, 74.0%) as a grayish white solid.

$^1$H NMR (300 MHz, CDCl$_3$): δ 4.34 (2H, brs), 6.82 (1H, d, J=7.6 Hz), 7.21-7.29 (1H, m).
(Step 2)

T3P (19.38 mL, 32.95 mmol) was added to a mixture of (R)-4-(tert-butoxycarbonyl)morpholine-2-carboxylic acid (3.81 g, 16.47 mmol), 4-amino-2-chloro-5-fluorobenzonitrile (2.81 g, 16.47 mmol), DMAP (2.214 g, 18.12 mmol) and DIEA (14.39 mL, 82.37 mmol) in ethyl acetate (30 mL) at room temperature, and the mixture was stirred at 90° C. overnight. Ethyl acetate was added to the mixture, and the mixture was washed with water, dried over magnesium sulfate, and the solvent was evaporated under reduced pressure. The residue was purified by silica gel column chromatography (solvent; ethyl acetate/hexane) to give (R)-tert-butyl 2-((5-chloro-4-cyano-2-fluorophenyl)carbamoyl)morpholine-4-carboxylate (3.56 g, 9.28 mmol, 56.3%) as a white solid.

$^1$H NMR (300 MHz, CDCl$_3$): δ 1.50 (9H, s), 2.76-3.09 (2H, m), 3.60-3.74 (1H, m), 3.90-4.05 (1H, m), 4.09 (2H, dd, J=11.0, 3.0 Hz), 4.25-4.58 (1H, m), 7.42 (1H, d, J=10.2 Hz), 8.73 (1H, d, J=6.8 Hz), 8.81 (1H, brs).
(Step 3)

4N Hydrogen chloride/ethyl acetate (35 mL, 140.00 mmol) was added to a mixture of (R)-tert-butyl 2-((5-chloro-4-cyano-2-fluorophenyl)carbamoyl)morpholine-4-carboxylate (3.56 g, 9.28 mmol) in ethyl acetate (35 mL), and the mixture was stirred at room temperature overnight. The mixture was concentrated under reduced pressure, and solidified with ethyl acetate to give (R)—N-(5-chloro-4-cyano-2-fluorophenyl)morpholine-2-carboxamide hydrochloride (2.69 g, 8.40 mmol, 91%) as a white solid.

¹H NMR (300 MHz, DMSO-d₆): δ 2.99-3.27 (3H, m), 3.40-3.50 (1H, m), 3.83-3.97 (1H, m), 4.06-4.17 (1H, m), 4.62 (1H, dd, J=10.6, 3.0 Hz), 8.15 (1H, d, J=10.6 Hz), 8.26 (1H, d, J=6.4 Hz), 9.49 (2H, brs), 10.27 (1H, s).
(Step 4)

4-Nitrophenyl chloroformate (21.22 mg, 0.11 mmol) was added to a solution of 6-amino-3-(cyclopropylmethyl)-7-fluoro-1-isopropylquinazoline-2,4(1H, 3H)-dione hydrochloride (30 mg, 0.09 mmol) and pyridine (0.019 mL, 0.23 mmol) in THF (2 mL) at room temperature, and the mixture was stirred at room temperature for 1 hr. The reaction mixture was concentrated under reduced pressure, and the residue was dissolved in DMF (3 mL). The solution was added to (R)—N-(5-chloro-4-cyano-2-fluorophenyl)morpholine-2-carboxamide hydrochloride (29.3 mg, 0.09 mmol) and DIEA (0.040 mL, 0.23 mmol) at room temperature. The mixture was stirred at room temperature for 3 hr. To the reaction mixture was added water, and the mixture was extracted with ethyl acetate. The organic layer was washed with brine, dried over magnesium sulfate, and the solvent was evaporated under reduced pressure. The residue was purified by silica gel column chromatography (solvent; ethyl acetate/hexane), and solidified with ethyl acetate/hexane to give the title compound (18.8 mg, 0.031 mmol, 34.2%) as a white solid.

¹H NMR (300 MHz, DMSO-d₆): δ 0.29-0.47 (4H, m), 1.10-1.26 (1H, m), 1.50 (6H, d, J=6.8 Hz), 3.03-3.18 (2H, m), 3.57-3.72 (1H, m), 3.81 (2H, d, J=6.8 Hz), 3.85-3.96 (1H, m), 4.00-4.12 (1H, m), 4.18-4.27 (1H, m), 4.27-4.37 (1H, m), 4.79-5.01 (1H, m), 7.59 (1H, d, J=13.3 Hz), 8.08-8.17 (2H, m), 8.28 (1H, d, J=6.8 Hz), 8.69 (1H, s), 9.98 (1H, s).

Example 348

(2R)—N²-(5-chloro-4-cyano-2-fluorophenyl)-N⁴-(3-((2,2-difluorocyclopropyl)methyl)-7-fluoro-1-isopropyl-2,4-dioxo-1,2,3,4-tetrahydroquinazolin-6-yl)morpholine-2,4-dicarboxamide (mixture of two stereoisomers)

4-Nitrophenyl chloroformate (70.8 mg, 0.35 mmol) was added to a solution of 6-amino-3-((2,2-difluorocyclopropyl)methyl)-7-fluoro-1-isopropylquinazoline-2,4(1H, 3H)-dione (100 mg, 0.31 mmol) and pyridine (0.062 mL, 0.76 mmol) in THF (2 mL) at room temperature, and the mixture was stirred at room temperature for 1 hr. The reaction mixture was concentrated under reduced pressure, and the residue was dissolved in DMF (3 mL). The solution was added to (R)—N-(5-chloro-4-cyano-2-fluorophenyl)morpholine-2-carboxamide hydrochloride (98 mg, 0.31 mmol) and DIEA (0.133 mL, 0.76 mmol) at room temperature. The mixture was stirred at room temperature for 3 hr. To the reaction mixture was added water, and the mixture was extracted with ethyl acetate. The organic layer was washed with water and brine, dried over sodium sulfate, and the solvent was evaporated under reduced pressure. The residue was purified by silica gel column chromatography (solvent; ethyl acetate/hexane) to give the title compound (58.6 mg, 0.092 mmol, 30.1%) as a white solid.

¹H NMR (300 MHz, DMSO-d₆): δ 1.28-1.44 (1H, m), 1.50 (6H, d, J=6.8 Hz), 1.53-1.70 (1H, m), 2.00-2.20 (1H, m), 3.01-3.20 (2H, m), 3.58-3.73 (1H, m), 3.84-4.36 (6H, m), 4.77-5.02 (1H, m), 7.61 (1H, d, J=13.3 Hz), 8.06-8.19 (2H, m), 8.28 (1H, d, J=6.8 Hz), 8.70 (1H, s), 9.98 (1H, s).

Example 350

(2R)—N²-(3-chloro-4-cyanophenyl)-N⁴-(3-((3,3-difluorocyclobutyl)methyl)-7-fluoro-1-isopropyl-2,4-dioxo-1,2,3,4-tetrahydroquinazolin-6-yl)morpholine-2,4-dicarboxamide 4-Nitrophenyl chloroformate (60.3 mg, 0.30 mmol) was added to a solution of 6-amino-3-((3,3-difluorocyclobutyl)methyl)-7-fluoro-1-isopropylquinazoline-2,4(1H, 3H)-dione (89 mg, 0.26 mmol) and pyridine (24 μL, 0.30 mmol) in THF (1 mL) at room temperature, and the mixture was stirred at room temperature for 1 hr. The reaction mixture was concentrated under reduced pressure, and the residue was dissolved in DMF (3 mL). The solution was added to (R)—N-(3-chloro-4-cyanophenyl)morpholine-2-carboxamide hydrochloride (79 mg, 0.26 mmol) and DIEA (113 μL, 0.65 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with brine, dried over magnesium sulfate, and the solvent was evaporated under reduced pressure. The residue was purified by silica gel column chromatography (solvent gradient; 68→90% ethyl acetate/hexane) to give the title compound (116.5 mg, 0.184 mmol, 70.8%) as a white amorphous solid.

¹H NMR (300 MHz, CDCl₃): δ 1.60 (6H, d, J=7.2 Hz), 2.38-2.70 (5H, m), 3.22-3.39 (2H, m), 3.76-3.86 (1H, m), 3.99 (1H, d, J=13.6 Hz), 4.05-4.29 (5H, m), 4.89 (1H, brs), 6.74 (1H, d, J=1.9 Hz), 7.12 (1H, d, J=13.2 Hz), 7.57 (1H, dd), 7.65 (1H, d), 7.92 (1H, d, J=1.9 Hz), 8.55 (1H, s), 8.61 (1H, d, J=8.7 Hz).

Example 351

(2R)—N²-(5-chloro-4-cyano-2-fluorophenyl)-N⁴-(3-((3,3-difluorocyclobutyl)methyl)-7-fluoro-1-isopropyl-2,4-dioxo-1,2,3,4-tetrahydroquinazolin-6-yl)morpholine-2,4-dicarboxamide (Step 1)
HATU (2.459 g, 6.47 mmol) was added to a mixture of 2-amino-5-bromo-4-fluorobenzoic acid (1.164 g, 4.97 mmol), (3,3-difluorocyclobutyl)methanamine hydrochloride (0.784 g, 4.97 mmol) and DIEA (2.60 mL, 14.92 mmol) in DMF (15 mL) at room temperature. The mixture was stirred at room temperature for 15 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 9→30% ethyl acetate/hexane) to give 2-amino-5-bromo-N-((3,3-difluorocyclobutyl)methyl)-4-fluorobenzamide (1.21 g, 3.59 mmol, 72.1%) as a white solid.

¹H NMR (300 MHz, CDCl₃): δ 2.25-2.52 (3H, m), 2.63-2.80 (2H, m), 3.52 (2H, dd), 5.71 (2H, brs), 6.01 (1H, brs), 6.44 (1H, d, J=10.6 Hz), 7.44 (1H, d, J=7.2 Hz).
(Step 2)
Bis(trichloromethyl) carbonate (0.714 g, 2.40 mmol) was slowly added to a mixture of 2-amino-5-bromo-N-((3,3-difluorocyclobutyl)methyl)-4-fluorobenzamide (1.21 g, 3.59 mmol) and TEA (1.101 mL, 7.90 mmol) in THF (12 mL) at 0° C., and the mixture was stirred at 65° C. for 1.5 hr. To the reaction mixture was added ice water, and the mixture was extracted 3 times with ethyl acetate/THF mixed solution (3:1, v/v). The organic layer was washed with an aqueous sodium hydrogen carbonate solution, water and brine, dried over magnesium sulfate, and the solvent was evaporated under reduced pressure. The precipitate was collected by filtration with IPE/hexane to give 6-bromo-3-((3,3-difluorocyclobutyl)methyl)-7-fluoroquinazoline-2,4(1H, 3H)-dione (1.19 g, 3.28 mmol, 91%) as a pale-yellow solid.

$^1$H NMR (300 MHz, DMSO-d$_6$): δ 2.35-2.49 (2H, m), 2.52-2.74 (3H, m), 4.04 (2H, d, J=6.4 Hz), 7.05 (1H, d, J=9.4 Hz), 8.14 (1H, d, J=7.6 Hz), 11.69 (1H, s).

(Step 3)

2-Iodopropane (1.297 mL, 13.00 mmol) was added to a solution of 6-bromo-3-((3,3-difluorocyclobutyl)methyl)-7-fluoroquinazoline-2,4(1H, 3H)-dione (1.18 g, 3.25 mmol) and cesium carbonate (2.118 g, 6.50 mmol) in DMF (19 mL) at room temperature, and the mixture was stirred at 65° C. for 2 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 1→22% ethyl acetate/hexane) to give 6-bromo-3-((3,3-difluorocyclobutyl)methyl)-7-fluoro-1-isopropylquinazoline-2,4(1H, 3H)-dione (568 mg, 1.402 mmol, 43.1%) as a white solid.

$^1$H NMR (300 MHz, CDCl$_3$): δ 1.60 (6H, d, J=6.8 Hz), 2.40-2.72 (5H, m), 4.21 (2H, d, J=6.4 Hz), 4.90 (1H, brs), 7.13 (1H, d, J=10.6 Hz), 8.42 (1H, d, J=7.9 Hz).

(Step 4)

A mixture of 6-bromo-3-((3,3-difluorocyclobutyl)methyl)-7-fluoro-1-isopropylquinazoline-2,4(1H, 3H)-dione (560 mg, 1.38 mmol), tert-butyl carbamate (243 mg, 2.07 mmol), Pd$_2$(dba)$_3$ (63.3 mg, 0.07 mmol), XPhos (65.9 mg, 0.14 mmol), and cesium carbonate (901 mg, 2.76 mmol) in toluene (5 mL) was stirred under an argon gas atmosphere at 80° C. for 24 hr. To the reaction mixture was added water, and the mixture was extracted 3 times with ethyl acetate. The organic layer was concentrated under reduced pressure. The residue was purified by silica gel column chromatography (solvent gradient; 11→32% ethyl acetate/hexane) to give tert-butyl (3-((3,3-difluorocyclobutyl)methyl)-7-fluoro-1-isopropyl-2,4-dioxo-1,2,3,4-tetrahydroquinazolin-6-yl)carbamate (577 mg, 1.307 mmol, 95%) as a pale-yellow solid.

$^1$H NMR (300 MHz, CDCl$_3$): δ 1.54 (9H, s), 1.59 (6H, d, J=6.8 Hz), 2.41-2.68 (5H, m), 4.21 (2H, d, J=5.7 Hz), 4.88 (1H, brs), 6.57 (1H, brs), 7.09 (1H, d, J=13.2 Hz), 8.81 (1H, d, J=9.1 Hz).

(Step 5)

TFA (7.5 mL) was added to tert-butyl (3-((3,3-difluorocyclobutyl)methyl)-7-fluoro-1-isopropyl-2,4-dioxo-1,2,3,4-tetrahydroquinazolin-6-yl)carbamate (575 mg, 1.30 mmol) at room temperature, and the mixture was stirred at room temperature for 20 min. To the reaction mixture was added aqueous sodium hydrogen carbonate solution, and the mixture was adjusted to pH 8 by adding potassium carbonate. To the mixture was added sodium chloride, and the mixture was extracted 3 times with ethyl acetate. The organic layer was washed with brine, dried over magnesium sulfate, and the solvent was evaporated under reduced pressure. The precipitate was collected by filtration with hexane to give 6-amino-3-((3,3-difluorocyclobutyl)methyl)-7-fluoro-1-isopropylquinazoline-2,4(1H, 3H)-dione (388 mg, 1.137 mmol, 87%) as a grayish white solid.

$^1$H NMR (300 MHz, CDCl$_3$): δ 1.58 (6H, d, J=7.2 Hz), 2.40-2.70 (5H, m), 3.80 (2H, s), 4.20 (1H, d, J=6.0 Hz), 4.87 (1H, brs), 7.04 (1H, d, J=13.2 Hz), 7.61 (1H, d, J=9.8 Hz).

(Step 6)

4-Nitrophenyl chloroformate (60.3 mg, 0.30 mmol) was added to a solution of 6-amino-3-((3,3-difluorocyclobutyl)methyl)-7-fluoro-1-isopropylquinazoline-2,4(1H, 3H)-dione (89 mg, 0.26 mmol) and pyridine (24 μL, 0.30 mmol) in THF (1 mL) at room temperature, and the mixture was stirred at room temperature for 1 hr. The reaction mixture was concentrated under reduced pressure, and the residue was dissolved in DMF (3 mL). The solution was added to (R)—N-(5-chloro-4-cyano-2-fluorophenyl)morpholine-2-carboxamide hydrochloride (83 mg, 0.26 mmol) and DIEA (113 μL, 0.65 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 54→75% ethyl acetate/hexane), and The precipitate was collected by filtration with hexane to give the title compound (143.4 mg, 0.220 mmol, 85%) as a white powder.

$^1$H NMR (300 MHz, CDCl$_3$): δ 1.60 (6H, d, J=6.8 Hz), 2.41-2.68 (5H, m), 3.23-3.38 (2H, m), 3.83 (1H, td, J=11.0, 2.6 Hz), 3.98 (1H, d, J=13.6 Hz), 4.13 (1H, dt, J=11.5, 3.1 Hz), 4.16-4.24 (3H, m), 4.28 (1H, dd, J=9.4, 3.4 Hz), 4.89 (1H, brs), 6.68 (1H, d, J=2.3 Hz), 7.12 (1H, d, J=12.8 Hz), 7.44 (1H, d, J=9.8 Hz), 8.62 (1H, d, J=9.1 Hz), 8.70 (1H, d, J=6.8 Hz), 8.83 (1H, d, J=3.4 Hz).

Example 356

(2R)—N$^2$-(5-chloro-6-cyanopyridin-3-yl)-N$^4$-(3-((2,2-difluorocyclopropyl)methyl)-7-fluoro-1-isopropyl-2,4-dioxo-1,2,3,4-tetrahydroquinazolin-6-yl)morpholine-2,4-dicarboxamide (mixture of two stereoisomers)

4-Nitrophenyl chloroformate (35.4 mg, 0.18 mmol) was added to a solution of 6-amino-3-((2,2-difluorocyclopropyl)methyl)-7-fluoro-1-isopropylquinazoline-2,4(1H, 3H)-dione (50 mg, 0.15 mmol) and pyridine (13.90 mg, 0.18 mmol) in THF (1 mL) at room temperature, and the mixture was stirred at room temperature for 2 hr. The reaction mixture was concentrated under reduced pressure, and the residue was dissolved in DMF (3 mL). The solution was added to (R)—N-(5-chloro-6-cyanopyridin-3-yl)morpholine-2-carboxamide hydrochloride (46.3 mg, 0.15 mmol) and DIEA (43.4 mg, 0.34 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with brine, dried over sodium sulfate, and the solvent was evaporated under reduced pressure. The residue was purified by silica gel column chromatography (solvent gradient; 30→100% ethyl acetate/hexane), and The precipitate was collected by filtration with IPE/hexane to give the title compound (25.00 mg, 0.040 mmol, 26.4%) as a white powder.

$^1$H NMR (300 MHz, DMSO-d$_6$): δ 1.50 (d, J=6.80 Hz, 8H), 2.03-2.23 (m, 1H), 2.97-3.20 (m, 2H), 3.61-4.45 (m, 7H), 4.92 (brs, 1H), 7.62 (d, J=13.22 Hz, 1H), 8.13 (d, J=8.69 Hz, 1H), 8.58 (d, J=1.89 Hz, 1H), 8.72 (brs, 1H), 8.99 (d, J=2.27 Hz, 1H), 10.75 (brs, 1H).

Example 357

(2R)—N²-(3-chloro-4-cyanophenyl)-N⁴-(7-fluoro-1-isopropyl-2,4-dioxo-3-((2S)-tetrahydrofuran-2-ylmethyl)-1,2,3,4-tetrahydroquinazolin-6-yl)morpholine-2,4-dicarboxamide (Step 1)

HATU (5.23 g, 13.75 mmol) was added to a solution of 2-amino-5-bromo-4-fluorobenzoic acid (2.476 g, 10.58 mmol), (S)-(tetrahydrofuran-2-yl)methanamine (1.07 g, 10.58 mmol) and DIEA (3.69 mL, 21.16 mmol) in DMF (30 mL), and the mixture was stirred at room temperature for 15 hr. To the reaction mixture was added water, and the mixture was extracted 3 times with ethyl acetate. The organic layer was washed with water and brine, dried over magnesium sulfate, and the solvent was evaporated under reduced pressure. The precipitate was collected by filtration with IPE/hexane to give (S)-2-amino-5-bromo-4-fluoro-N-((tetrahydrofuran-2-yl)methyl)benzamide (2.97 g, 9.36 mmol, 89%) as a pale-brown solid.

$^1$H NMR (300 MHz, CDCl$_3$): δ 1.59-1.66 (1H, m), 1.88-2.10 (3H, m), 3.25 (1H, ddd, J=13.8, 7.7, 4.5 Hz), 3.68-3.84 (2H, m), 3.90 (1H, dt, J=8.4, 6.8 Hz), 4.06 (1H, qd, J=7.2, 3.2 Hz), 5.72 (2H, brs), 6.35 (1H, brs), 6.42 (1H, d, J=10.2 Hz), 7.49 (1H, d, J=7.2 Hz).

(Step 2)

Bis(trichloromethyl) carbonate (1.862 g, 6.27 mmol) was slowly added to a mixture of (S)-2-amino-5-bromo-4-fluoro-N-((tetrahydrofuran-2-yl)methyl)benzamide (2.97 g, 9.36 mmol) and TEA (2.87 mL, 20.60 mmol) in THF (31 mL) at 0° C., and the mixture was stirred at 65° C. for 1.5 hr. To the reaction mixture was added ice water, and the mixture was extracted 3 times with ethyl acetate/THF mixed solution (3:1, v/v). The organic layer was washed with an aqueous sodium hydrogen carbonate solution, water and brine, dried over magnesium sulfate, and the solvent was evaporated under reduced pressure. The precipitate was collected by filtration with IPE/hexane to give (S)-6-bromo-7-fluoro-3-((tetrahydrofuran-2-yl)methyl)quinazoline-2,4(1H, 3H)-dione (2.20 g, 6.41 mmol, 68.5%) as a pale-brown solid.

$^1$H NMR (300 MHz, DMSO-d$_6$): δ 1.57-1.68 (1H, m), 1.73-1.97 (3H, m), 3.56-3.65 (1H, m), 3.70-3.81 (2H, m), 4.03 (1H, dd), 4.11-4.20 (1H, m), 7.06 (1H, d, J=9.4 Hz), 8.15 (1H, d, J=7.2 Hz), 11.67 (1H, s).

(Step 3)

2-Iodopropane (2.55 mL, 25.53 mmol) was added to a solution of (S)-6-bromo-7-fluoro-3-((tetrahydrofuran-2-yl)methyl)quinazoline-2,4(1H, 3H)-dione (2.19 g, 6.38 mmol) and cesium carbonate (4.16 g, 12.76 mmol) in DMF (36 mL) at room temperature, and the mixture was stirred at 65° C. for 2 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 14→35% ethyl acetate/hexane) to give (S)-6-bromo-7-fluoro-1-isopropyl-3-((tetrahydrofuran-2-yl)methyl)quinazoline-2,4(1H, 3H)-dione (1.07 g, 2.78 mmol, 43.5%) as a white solid.

$^1$H NMR (300 MHz, CDCl$_3$): δ 1.60 (6H, d, J=7.2 Hz), 1.63-1.74 (1H, m), 1.83-2.10 (3H, m), 3.74 (1H, td, J=8.1, 6.0 Hz), 3.87-3.97 (2H, m), 4.26-4.40 (2H, m), 4.92 (1H, brs), 7.11 (1H, d, J=10.6 Hz), 8.43 (1H, d, J=7.6 Hz).

(Step 4)

A mixture of (S)-6-bromo-7-fluoro-1-isopropyl-3-((tetrahydrofuran-2-yl)methyl)quinazoline-2,4(1H, 3H)-dione (1.06 g, 2.75 mmol), tert-butyl carbamate (0.484 g, 4.13 mmol), Pd$_2$(dba)$_3$ (0.126 g, 0.14 mmol), XPhos (0.131 g, 0.28 mmol) and cesium carbonate (1.793 g, 5.50 mmol) in toluene (10 mL) was stirred under an argon gas atmosphere at 80° C. for 24 hr. To the reaction mixture was added water, and the mixture was extracted 3 times with ethyl acetate. The organic layer was concentrated under reduced pressure. The residue was purified by silica gel column chromatography (solvent gradient; 26→47% ethyl acetate/hexane) to give (S)-tert-butyl (7-fluoro-1-isopropyl-2,4-dioxo-3-((tetrahydrofuran-2-yl)methyl)-1,2,3,4-tetrahydroquinazolin-6-yl)carbamate (1.11 g, 2.63 mmol, 96%) as a pale-yellow amorphous solid.

$^1$H NMR (300 MHz, CDCl$_3$): δ 1.54 (9H, s), 1.59 (6H, d, J=7.2 Hz), 1.62-1.75 (1H, m), 1.79-2.03 (3H, m), 3.74 (1H, td, J=8.0, 5.9 Hz), 3.88-3.97 (2H, m), 4.26-4.42 (2H, m), 4.91 (1H, brs), 6.55 (1H, brs), 7.07 (1H, d, J=13.2 Hz), 8.79 (1H, d, J=9.1 Hz).

(Step 5)

TFA (14.5 mL) was added to (S)-tert-butyl (7-fluoro-1-isopropyl-2,4-dioxo-3-((tetrahydrofuran-2-yl)methyl)-1,2,3,4-tetrahydroquinazolin-6-yl)carbamate (1.11 g, 2.63 mmol) at room temperature, and the mixture was stirred at room temperature for 20 min. To the reaction mixture was added aqueous sodium hydrogen carbonate solution, and the mixture was adjusted to pH 8 by adding potassium carbonate. The mixture was extracted 3 times with ethyl acetate. The organic layer was washed with water and brine, dried over magnesium sulfate, and the solvent was evaporated under reduced pressure. The precipitate was collected by filtration with hexane to give (S)-6-amino-7-fluoro-1-isopropyl-3-((tetrahydrofuran-2-yl)methyl)quinazoline-2,4(1H, 3H)-dione (732 mg, 2.278 mmol, 86%) as a grayish white solid.

$^1$H NMR (300 MHz, CDCl$_3$): δ 1.58 (6H, d, J=6.8 Hz), 1.63-1.75 (1H, m), 1.80-2.08 (3H, m), 3.70-3.81 (3H, m), 3.89-3.98 (2H, m), 4.26-4.41 (2H, m), 4.89 (1H, brs), 7.02 (1H, d, J=13.2 Hz), 7.62 (1H, d, J=9.8 Hz).

(Step 6)

4-Nitrophenyl chloroformate (60.3 mg, 0.30 mmol) was added to a solution of (S)-6-amino-7-fluoro-1-isopropyl-3-((tetrahydrofuran-2-yl)methyl)quinazoline-2,4(1H, 3H)-dione (84 mg, 0.26 mmol) and pyridine (24 µL, 0.30 mmol) in THF (1 mL) at room temperature, and the mixture was stirred at room temperature for 1 hr. The reaction mixture was concentrated under reduced pressure, and the residue was dissolved in DMF (3 mL). The solution was added to (R)—N-(3-chloro-4-cyanophenyl)morpholine-2-carboxamide hydrochloride (79 mg, 0.26 mmol) and DIEA (113 µL, 0.65 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with brine, dried over magnesium sulfate, and the solvent was evaporated under reduced pressure. The residue was purified by silica gel column chromatography (solvent gradient; 81→100% ethyl acetate/hexane) to give the title compound (147.3 mg, 0.240 mmol, 92%) as a white amorphous solid.

$^1$H NMR (300 MHz, CDCl$_3$): δ 1.59 (6H, d, J=7.2 Hz), 1.65-1.74 (1H, m), 1.82-2.04 (3H, m), 3.20-3.37 (2H, m), 3.69-3.85 (2H, m), 3.87-4.02 (3H, m), 4.04-4.10 (1H, m), 4.15-4.40 (4H, m), 4.91 (1H, brs), 6.77 (1H, d, J=1.9 Hz), 7.09 (1H, d, J=13.2 Hz), 7.57 (1H, dd), 7.64 (1H, d), 7.92 (1H, d, J=1.9 Hz), 8.55-8.61 (2H, m).

Example 358

(2R)—N²-(5-chloro-4-cyano-2-fluorophenyl)-N⁴-(7-fluoro-1-isopropyl-2,4-dioxo-3-((2S)-tetrahydrofuran-2-ylmethyl)-1,2,3,4-tetrahydroquinazolin-6-yl)morpholine-2,4-dicarboxamide 4-Nitrophenyl chloroformate (60.3 mg, 0.30 mmol) was added to a solution of (S)-6-amino-7-fluoro-1-isopropyl-3-((tetrahydrofuran-2-yl)methyl)quinazoline-2,4(1H, 3H)-dione (84 mg, 0.26 mmol) and pyridine (24 µL, 0.30 mmol) in THF (1 mL) at room temperature, and the mixture was stirred at room temperature for 1 hr. The reaction mixture was concentrated under reduced pressure, and the residue was dissolved in DMF (3 mL). The solution was added to (R)—N-(5-chloro-4-cyano-2-fluorophenyl)morpholine-2-carboxamide hydrochloride (83 mg, 0.26 mmol) and DIEA (113 µL, 0.65 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with brine, dried over magnesium sulfate, and the solvent was evaporated under reduced pressure. The residue was purified by silica gel column chromatography (solvent gradient; 69→90% ethyl acetate/hexane) to give the title compound (148.6 mg, 0.235 mmol, 91%) as a white amorphous solid.

¹H NMR (300 MHz, CDCl₃): δ 1.57-1.61 (6H, m), 1.63-1.74 (1H, m), 1.79-2.03 (3H, m), 3.21-3.34 (2H, m), 3.68-4.02 (5H, m), 4.09-4.15 (1H, m), 4.17-4.40 (4H, m), 4.91 (1H, brs), 6.68 (1H, d, J=2.3 Hz), 7.10 (1H, d, J=13.2 Hz), 7.44 (1H, d, J=10.2 Hz), 8.60 (1H, d, J=8.7 Hz), 8.70 (1H, d, J=6.8 Hz), 8.83 (1H, d, J=3.4 Hz).

Example 360

(3R)-3-(7-cyano-4-oxoquinazoline-3(4H)-yl)-N-(3-((2,2-difluorocyclopropyl)methyl)-7-fluoro-1-isopropyl-2,4-dioxo-1,2,3,4-tetrahydroquinazolin-6-yl)piperidine-1-carboxamide (mixture of two stereoisomers)

4-Nitrophenyl chloroformate (35.4 mg, 0.18 mmol) was added to a solution of 6-amino-3-((2,2-difluorocyclopropyl)methyl)-7-fluoro-1-isopropylquinazoline-2,4(1H, 3H)-dione (50 mg, 0.15 mmol) and pyridine (13.90 mg, 0.18 mmol) in THF (1 mL) at room temperature, and the mixture was stirred at room temperature for 1 hr. The reaction mixture was concentrated under reduced pressure, and the residue was dissolved in DMF (3 mL). The solution was added to (R)-4-oxo-3-(piperidin-3-yl)-3,4-dihydroquinazoline-7-carbonitrile hydrochloride (44.4 mg, 0.15 mmol) and DIEA (43.4 mg, 0.34 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 60→100% ethyl acetate/hexane), and The precipitate was collected by filtration with IPE/hexane to give the title compound (30.0 mg, 0.049 mmol, 32.3%) as a white powder.

¹H NMR (300 MHz, DMSO-d₆): δ 1.24-1.74 (m, 8H), 1.81-2.25 (m, 5H), 2.93 (t, J=11.71 Hz, 1H), 3.89-4.40 (m, 5H), 4.67 (t, J=11.33 Hz, 1H), 4.91 (brs, 1H), 7.61 (d, J=13.22 Hz, 1H), 7.92 (dd, J=8.31, 1.51 Hz, 1H), 8.11 (d, J=9.06 Hz, 1H), 8.20-8.38 (m, 2H), 8.51-8.70 (m, 2H).

Example 363

(3R)-3-(7-cyano-4-oxoquinazoline-3(4H)-yl)-N-(3-((3,3-difluorocyclobutyl)methyl)-7-fluoro-1-isopropyl-2,4-dioxo-1,2,3,4-tetrahydroquinazolin-6-yl)piperidine-1-carboxamide (Step 1)

HATU (2.459 g, 6.47 mmol) was added to a solution of 2-amino-5-bromo-4-fluorobenzoic acid (1.164 g, 4.97 mmol), (3,3-difluorocyclobutyl)methanamine hydrochloride (0.784 g, 4.97 mmol) and DIEA (2.60 mL, 14.92 mmol) in DMF (15 mL), and the mixture was stirred at room temperature for 15 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 9→30% ethyl acetate/hexane) to give 2-amino-5-bromo-N-((3,3-difluorocyclobutyl)methyl)-4-fluorobenzamide (1.21 g, 3.59 mmol, 72.1%) as a white solid.

¹H NMR (300 MHz, CDCl₃): δ 2.25-2.52 (3H, m), 2.63-2.80 (2H, m), 3.52 (2H, dd), 5.71 (2H, brs), 6.01 (1H, brs), 6.44 (1H, d, J=10.6 Hz), 7.44 (1H, d, J=7.2 Hz).

(Step 2)

Bis(trichloromethyl) carbonate (0.714 g, 2.40 mmol) was slowly added to a mixture of 2-amino-5-bromo-N-((3,3-difluorocyclobutyl)methyl)-4-fluorobenzamide (1.21 g, 3.59 mmol) and TEA (1.101 mL, 7.90 mmol) in THF (12 mL) at 0° C., and the mixture was stirred at 65° C. for 1.5 hr. To the reaction mixture was added ice water, and the mixture was extracted 3 times with ethyl acetate/THF mixed solution (3:1, v/v). The organic layer was washed with an aqueous sodium hydrogen carbonate solution, water and brine, dried over magnesium sulfate, and the solvent was evaporated under reduced pressure. The precipitate was collected by filtration with IPE/hexane to give 6-bromo-3-((3,3-difluorocyclobutyl)methyl)-7-fluoroquinazoline-2,4(1H, 3H)-dione (1.19 g, 3.28 mmol, 91%) as a pale-yellow solid.

¹H NMR (300 MHz, DMSO-d₆): δ 2.35-2.49 (2H, m), 2.52-2.74 (3H, m), 4.04 (2H, d, J=6.4 Hz), 7.05 (1H, d, J=9.4 Hz), 8.14 (1H, d, J=7.6 Hz), 11.69 (1H, s).

(Step 3)

2-Iodopropane (1.297 mL, 13.00 mmol) was added to a solution of 6-bromo-3-((3,3-difluorocyclobutyl)methyl)-7-fluoroquinazoline-2,4(1H, 3H)-dione (1.18 g, 3.25 mmol) and cesium carbonate (2.118 g, 6.50 mmol) in DMF (19 mL) at room temperature, and the mixture was stirred at 65° C. for 2 hr. To the reaction mixture was added water, and the mixture was extracted 3 times with ethyl acetate. The organic layer was washed with water and brine, dried over magnesium sulfate, and the solvent was evaporated under reduced pressure. The residue was purified by silica gel column chromatography (solvent gradient; 1→22% ethyl acetate/hexane) to give 6-bromo-3-((3,3-difluorocyclobutyl)methyl)-7-fluoro-1-isopropylquinazoline-2,4(1H, 3H)-dione (568 mg, 1.402 mmol, 43.1%) as a white solid.

¹H NMR (300 MHz, CDCl₃): δ 1.60 (6H, d, J=6.8 Hz), 2.40-2.72 (5H, m), 4.21 (2H, d, J=6.4 Hz), 4.90 (1H, brs), 7.13 (1H, d, J=10.6 Hz), 8.42 (1H, d, J=7.9 Hz).

(Step 4)

A mixture of 6-bromo-3-((3,3-difluorocyclobutyl)methyl)-7-fluoro-1-isopropylquinazoline-2,4(1H, 3H)-dione (560 mg, 1.38 mmol), tert-butyl carbamate (243 mg, 2.07 mmol), Pd$_2$(dba)$_3$ (63.3 mg, 0.07 mmol), XPhos (65.9 mg, 0.14 mmol) and cesium carbonate (901 mg, 2.76 mmol) in toluene (5 mL) was stirred under an argon gas atmosphere at 80° C. for 24 hr. To the reaction mixture was added water, and the mixture was extracted 3 times with ethyl acetate. The organic layer was concentrated under reduced pressure. The residue was purified by silica gel column chromatography (solvent gradient; 11→32% ethyl acetate/hexane) to give tert-butyl (3-((3,3-difluorocyclobutyl)methyl)-7-fluoro-1-isopropyl-2,4-dioxo-1,2,3,4-tetrahydroquinazolin-6-yl)carbamate (577 mg, 1.307 mmol, 95%) as a pale-yellow amorphous solid.

$^1$H NMR (300 MHz, CDCl$_3$): δ 1.54 (9H, s), 1.59 (6H, d, J=6.8 Hz), 2.41-2.68 (5H, m), 4.21 (2H, d, J=5.7 Hz), 4.88 (1H, brs), 6.57 (1H, brs), 7.09 (1H, d, J=13.2 Hz), 8.81 (1H, d, J=9.1 Hz).

(Step 5)

TFA (7.5 mL) was added to tert-butyl (3-((3,3-difluorocyclobutyl)methyl)-7-fluoro-1-isopropyl-2,4-dioxo-1,2,3,4-tetrahydroquinazolin-6-yl)carbamate (575 mg, 1.30 mmol) at room temperature, and the mixture was stirred at room temperature for 20 min. To the reaction mixture was added aqueous sodium hydrogen carbonate solution, and the mixture was adjusted to pH 8 by adding potassium carbonate. The mixture was extracted 3 times with ethyl acetate. The organic layer was washed with water and brine, dried over magnesium sulfate, and the solvent was evaporated under reduced pressure. The precipitate was collected by filtration with hexane to give 6-amino-3-((3,3-difluorocyclobutyl)methyl)-7-fluoro-1-isopropylquinazoline-2,4(1H, 3H)-dione (388 mg, 1.137 mmol, 87%) as a grayish white solid.

$^1$H NMR (300 MHz, CDCl$_3$): δ 1.58 (6H, d, J=7.2 Hz), 2.40-2.70 (5H, m), 3.80 (2H, s), 4.20 (2H, d, J=6.0 Hz), 4.87 (1H, brs), 7.04 (1H, d, J=13.2 Hz), 7.61 (1H, d, J=9.8 Hz).

(Step 6)

4-Nitrophenyl chloroformate (60.3 mg, 0.30 mmol) was added to a solution of 6-amino-3-((3,3-difluorocyclobutyl)methyl)-7-fluoro-1-isopropylquinazoline-2,4(1H, 3H)-dione (89 mg, 0.26 mmol) and pyridine (24 μL, 0.30 mmol) in THF (1 mL) at room temperature, and the mixture was stirred at room temperature for 1 hr. The reaction mixture was concentrated under reduced pressure, and the residue was dissolved in DMF (3 mL). The solution was added to (R)-4-oxo-3-(piperidin-3-yl)-3,4-dihydroquinazoline-7-carbonitrile hydrochloride (83 mg, 0.29 mmol) and DIEA (113 μL, 0.65 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 77→100% ethyl acetate/hexane), and The precipitate was collected by filtration with IPE/hexane to give the title compound (138.9 mg, 0.223 mmol, 86%) as a white powder.

$^1$H NMR (300 MHz, CDCl$_3$): δ 1.60 (6H, d, J=6.8 Hz), 1.78-1.95 (1H, m), 2.00-2.10 (2H, m), 2.13-2.28 (2H, m), 2.39-2.69 (4H, m), 3.00-3.12 (1H, m), 3.30 (1H, dd, J=13.2, 10.6 Hz), 4.15-4.24 (3H, m), 4.32 (1H, dd, J=13.2, 3.4 Hz), 4.62-4.75 (1H, m), 4.90 (1H, brs), 6.83 (1H, d, J=2.3 Hz), 7.11 (1H, d, J=12.8 Hz), 7.72 (1H, dd, J=8.3, 1.5 Hz), 8.05 (1H, d, J=1.1 Hz), 8.20 (1H, s), 8.37-8.44 (1H, m), 8.64 (1H, d, J=8.7 Hz).

Example 366

(2R)—N$^2$-(3-chloro-4-cyanophenyl)-N$^4$-(3-(((1R or 1S)-2,2-difluorocyclopropyl)methyl)-7-fluoro-1-isopropyl-2,4-dioxo-1,2,3,4-tetrahydroquinazolin-6-yl)morpholine-2,4-dicarboxamide (one stereoisomer, quinazolinedione: derived from tR$_1$)

4-Nitrophenyl chloroformate (35.4 mg, 0.18 mmol) was added to a solution of 6-amino-3-((2,2-difluorocyclopropyl)methyl)-7-fluoro-1-isopropylquinazoline-2,4(1H, 3H)-dione (tR$_1$) (50 mg, 0.15 mmol) and pyridine (0.014 mL, 0.18 mmol) in THF (1 mL) at room temperature, and the mixture was stirred at room temperature for 2 hr. The reaction mixture was concentrated under reduced pressure, and the residue was dissolved in DMF (3 mL). The solution was added to (R)—N-(3-chloro-4-cyanophenyl)morpholine-2-carboxamide hydrochloride (46.2 mg, 0.15 mmol) and DIEA (0.067 mL, 0.38 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was treated by silica gel column chromatography (solvent gradient; 30→100% ethyl acetate/hexane), and The precipitate was collected by filtration with IPE/hexane to give the title compound (111.7 mg, 0.180 mmol, 118%) as a white powder.

$^1$H NMR (300 MHz, DMSO-d$_6$): δ 1.50 (8H, d, J=6.4 Hz), 1.99-2.23 (1H, m), 2.97-3.19 (2H, m), 3.81-4.31 (7H, m), 4.91 (1H, brs), 7.61 (1H, d, J=13.6 Hz), 7.75-8.02 (2H, m), 8.00-8.31 (2H, m), 8.70 (1H, brs), 10.48 (1H, brs).

Example 367

(3R)-3-(7-cyano-4-oxoquinazoline-3(4H)-yl)-N-(3-(((1R or 1S)-2,2-difluorocyclopropyl)methyl)-7-fluoro-1-isopropyl-2,4-dioxo-1,2,3,4-tetrahydroquinazolin-6-yl)piperidine-1-carboxamide (one stereoisomer, quinazolinedione: derived from tR$_1$)

(Step 1)

6-Amino-3-((2,2-difluorocyclopropyl)methyl)-7-fluoro-1-isopropylquinazoline-2,4(1H, 3H)-dione (645 mg) was optically resolved by chiral column chromatography. A preparative fraction with a shorter retention time was concentrated to give 6-amino-3-((2,2-difluorocyclopropyl)methyl)-7-fluoro-1-isopropylquinazoline-2,4(1H, 3H)-dione (tR$_1$) (284 mg, 44.0%, >99% ee), and a preparative fraction with a longer retention time was concentrated to give 6-amino-3-((2,2-difluorocyclopropyl)methyl)-7-fluoro-1-isopropylquinazoline-2,4(1H, 3H)-dione (tR$_2$) (287 mg, 44.5%, >99% ee) each as a grayish white solid.

Purification conditions by chiral column chromatography
    column: CHIRALCEL OD (NL001), 5 cm ID×50 cm L
    solvent: hexane/EtOH=80/20
    flow rate: 80 mL/min
    temperature: 30° C.
    detection method: UV 220 nm (Step 2)

4-Nitrophenyl chloroformate (35.4 mg, 0.18 mmol) was added to a solution of 6-amino-3-((2,2-difluorocyclopropyl)methyl)-7-fluoro-1-isopropylquinazoline-2,4(1H, 3H)-dione (tR$_1$) (50 mg, 0.15 mmol) and pyridine (13.90 mg, 0.18 mmol) in THF (1 mL) at room temperature, and the mixture was stirred at room temperature for 2 hr. The reaction mixture was concentrated under reduced pressure, and the residue was dissolved in DMF (3 mL). The solution was added to (R)-4-oxo-3-(piperidin-3-yl)-3,4-dihydroquinazoline-7-carbonitrile hydrochloride (44.4 mg, 0.15 mmol) and DIEA (43.4 mg, 0.34 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 60→100% ethyl acetate/hexane), and The precipitate was collected by filtration with IPE/hexane to give the title compound (54.3 mg, 0.089 mmol, 58.5%) as a white powder.

$^1$H NMR (300 MHz, DMSO-d$_6$): δ 1.26-1.72 (9H, m), 1.76-2.30 (4H, m), 2.93 (1H, t, J=11.7 Hz), 3.34-3.46 (1H, m), 3.90-4.32 (4H, m), 4.55-4.77 (1H, m), 4.91 (1H, brs), 7.61 (1H, d, J=13.2 Hz), 7.92 (1H, dd, J=7.9, 1.5 Hz), 8.11 (1H, d, J=8.7 Hz), 8.22-8.37 (2H, m), 8.51-8.73 (2H, m).

Example 368

(2R)—N$^2$-(3-chloro-4-cyanophenyl)-N$^4$-(3-(((1R or 1S)-2,2-difluorocyclopropyl)methyl)-7-fluoro-1-isopropyl-2,4-dioxo-1,2,3,4-tetrahydroquinazolin-6-yl)morpholine-2,4-dicarboxamide (one stereoisomer, quinazolinedione: derived from tR$_2$)

4-Nitrophenyl chloroformate (35.4 mg, 0.18 mmol) was added to a solution of 6-amino-3-((2,2-difluorocyclopropyl)methyl)-7-fluoro-1-isopropylquinazoline-2,4(1H, 3H)-dione (tR$_2$) (50 mg, 0.15 mmol) and pyridine (0.014 mL, 0.18 mmol) in THF (1 mL) at room temperature, and the mixture was stirred at room temperature for 2 hr. The reaction mixture was concentrated under reduced pressure, and the residue was dissolved in DMF (3 mL). The solution was added to (R)—N-(3-chloro-4-cyanophenyl)morpholine-2-carboxamide hydrochloride (46.2 mg, 0.15 mmol) and DIEA (0.067 mL, 0.38 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was treated by silica gel column chromatography (solvent gradient; 30→100% ethyl acetate/hexane), and The precipitate was collected by filtration with IPE/hexane to give the title compound (111.7 mg, 0.180 mmol, 118%) as a white powder.

$^1$H NMR (300 MHz, DMSO-d$_6$): δ 1.27-1.73 (9H, m), 2.02-2.21 (1H, m), 2.98-3.19 (2H, m), 3.81-4.34 (6H, m), 4.91 (1H, brs), 7.61 (1H, d, J=13.2 Hz), 7.79-8.01 (2H, m), 8.07-8.27 (2H, m), 8.70 (1H, brs), 10.47 (1H, brs).

Example 369

(3R)-3-(7-cyano-4-oxoquinazoline-3(4H)-yl)-N-(3-(((1R or 1S)-2,2-difluorocyclopropyl)methyl)-7-fluoro-1-isopropyl-2,4-dioxo-1,2,3,4-tetrahydroquinazolin-6-yl)piperidine-1-carboxamide (one stereoisomer, quinazolinedione: derived from tR$_2$)

4-Nitrophenyl chloroformate (35.4 mg, 0.18 mmol) was added to a solution of 6-amino-3-((2,2-difluorocyclopropyl)methyl)-7-fluoro-1-isopropylquinazoline-2,4(1H, 3H)-dione (tR$_2$) (50 mg, 0.15 mmol) and pyridine (13.90 mg, 0.18 mmol) in THF (1 mL) at room temperature, and the mixture was stirred at room temperature for 2 hr. The reaction mixture was concentrated under reduced pressure, and the residue was dissolved in DMF (3 mL). The solution was added to (R)-4-oxo-3-(piperidin-3-yl)-3,4-dihydroquinazoline-7-carbonitrile hydrochloride (44.4 mg, 0.15 mmol) and DIEA (43.4 mg, 0.34 mmol) at room temperature. The mixture was stirred at room temperature for 1 hr. To the reaction mixture was added water, and the mixture was adjusted to pH 3 with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 60→100% ethyl acetate/hexane), and The precipitate was collected by filtration with IPE/hexane to give the title compound (18.00 mg, 0.030 mmol, 19.39%) as a white powder.

$^1$H NMR (300 MHz, DMSO-d$_6$): δ 1.27-1.77 (9H, m), 1.80-2.40 (5H, m), 2.93 (1H, t, J=11.7 Hz), 3.81-4.37 (4H, m), 4.67 (1H, t, J=11.7 Hz), 4.91 (1H, brs), 7.61 (1H, d, J=13.2 Hz), 7.92 (1H, dd, J=8.3, 1.5 Hz), 8.11 (1H, d, J=9.1 Hz), 8.20-8.37 (2H, m), 8.49-8.72 (2H, m).

The compounds described in Examples 1-370 are as described below (Table 1-1-Table 1-37).

TABLE 1-1

| Ex. | IUPAC name | Structure | salt | MS |
|---|---|---|---|---|
| 1 | N-((1R,2S)-((1,3-bis(cyclopropyl-methyl)-2,4-dioxo-1,2,3,4-tetrahydroquinazolin-6-yl)carbamoyl)-cyclopentyl)-3-chloro-4-cyanobenzamide | 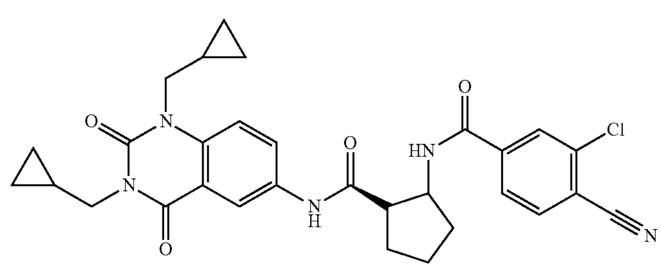 | | 560.2 (M + H) |

TABLE 1-1-continued

| Ex. | IUPAC name | Structure | salt | MS |
|---|---|---|---|---|
| 2 | 2-chloro-4-((1-((1,3-diethyl-2,4-dioxo-1,2,3,4-tetrahydroquinazolin-6-yl)carbonyl)piperidin-3-yl)methoxy)benzonitrile | 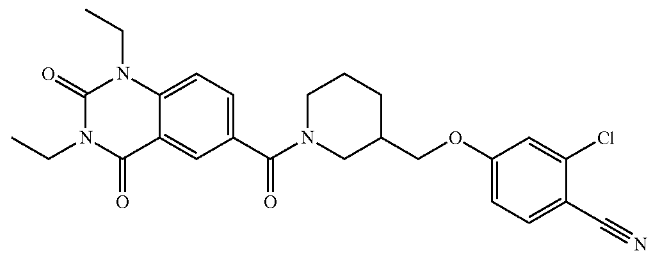 [SMILES: CCn1c(=O)c2cc(C(=O)N3CCCC(COc4ccc(C#N)c(Cl)c4)C3)ccc2n(CC)c1=O] | | 495.2 (M + H) |
| 3 | 5-chloro-6-cyano-N-(2-((1,3-diethyl-2,4-dioxo-1,2,3,4-tetrahydroquinazolin-6-yl)carbamoyl)cyclopentyl)nicotinamide | 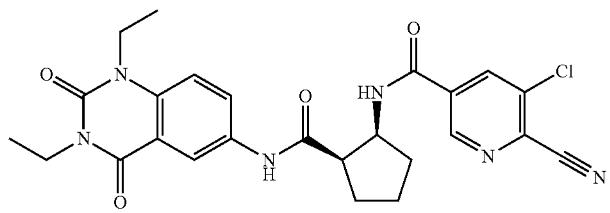 [SMILES: CCn1c(=O)c2cc(NC(=O)[C@@H]3CCC[C@@H]3NC(=O)c3cnc(C#N)c(Cl)c3)ccc2n(CC)c1=O] | | 509.2 (M + H) |
| 4 | 4-cyano-N-(cis-2-((1,3-diethyl-2,4-dioxo-1,2,3,4-tetrahydroquinazolin-6-yl)carbamoyl)cyclopentyl)-3-fluorobenzamide | 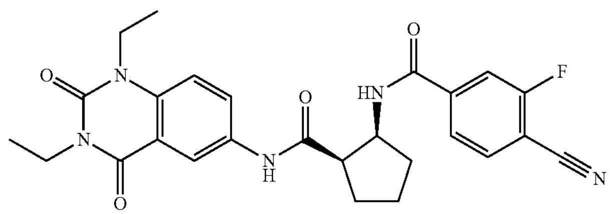 [SMILES: CCn1c(=O)c2cc(NC(=O)[C@@H]3CCC[C@@H]3NC(=O)c3ccc(C#N)c(F)c3)ccc2n(CC)c1=O] | | 492.2 (M + H) |
| 5 | Cis-N-(3-chloro-4-cyanophenyl)-N'-(1,3-diethyl-2,4-dioxo-1,2,3,4-tetrahydroquinazolin-6-yl)cyclopropane-1,2-dicarboxamide | 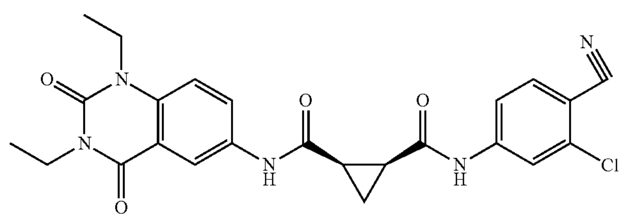 [SMILES: CCn1c(=O)c2cc(NC(=O)[C@@H]3C[C@@H]3C(=O)Nc3ccc(C#N)c(Cl)c3)ccc2n(CC)c1=O] | | 478.0 (M + H) |
| 6 | 2-((3-chloro-4-cyanophenoxy)methyl)-N-(3-(cyclopropylmethyl)-1-ethyl-2,4-dioxo-1,2,3,4-tetrahydroquinazolin-6-yl)pyrrolidine-1-carboxamide | 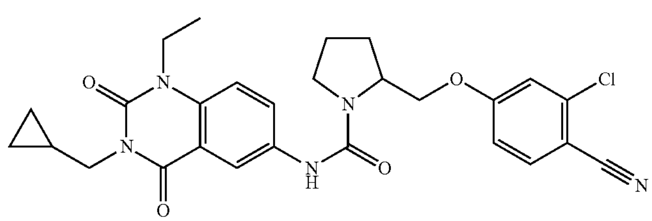 [SMILES: CCn1c(=O)n(CC2CC2)c(=O)c2cc(NC(=O)N3CCCC3COc3ccc(C#N)c(Cl)c3)ccc21] | | 522.2 (M + H) |
| 7 | 4-(3-chloro-4-cyanophenyl)-N-(3-(cyclopropylmethyl)-1-ethyl-2,4-dioxo-1,2,3,4-tetrahydroquinazolin-6-yl)-1,4-diazepane-1-carboxamide | 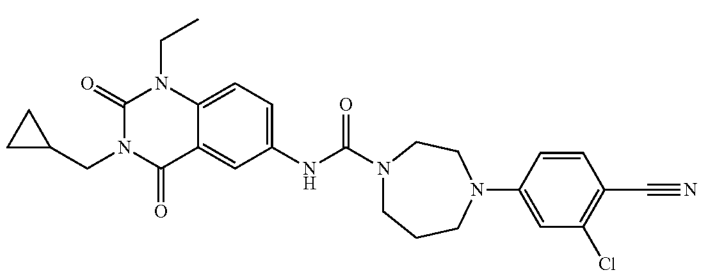 [SMILES: CCn1c(=O)n(CC2CC2)c(=O)c2cc(NC(=O)N3CCCN(c4ccc(C#N)c(Cl)c4)CC3)ccc21] | | 521.2 (M + H) |

TABLE 1-1-continued

| Ex. | IUPAC name | Structure | salt | MS |
|---|---|---|---|---|
| 8 | N-(3-chloro-4-cyanophenyl)-4-(1,3-diethyl-2,4-dioxo-1,2,3,4-tetrahydroquinazolin-6-yl)-1,4-diazepane-1-carboxamide | 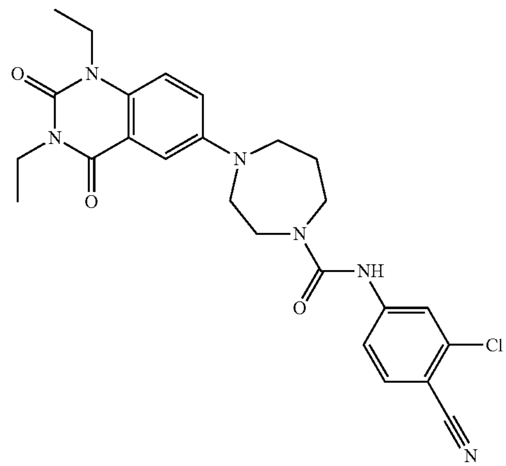 [SMILES: CCn1c(=O)c2cc(N3CCCN(C(=O)Nc4ccc(C#N)c(Cl)c4)CC3)ccc2n(CC)c1=O] | | 495.2 (M + H) |
| 9 | 2-((3-chloro-4-cyanophenoxy)methyl)-N-(3-(cyclopropylmethyl)-1-ethyl-2,4-dioxo-1,2,3,4-tetrahydroquinazolin-6-yl)piperidine-1-carboxamide | 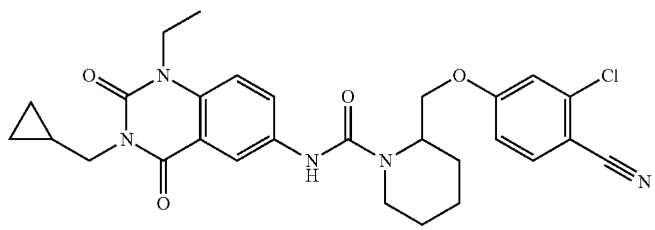 | | 536.2 (M + H) |
| 10 | 1,3-diethyl-2,4-dioxo-1,2,3,4-tetrahydroquinazolin-6-yl 2-(((3-chloro-4-cyanobenzoyl)amino)methyl)pyrrolidine-1-carboxylate | 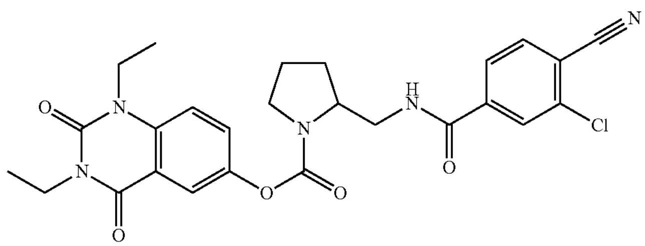 [SMILES: CCn1c(=O)c2cc(OC(=O)N3CCCC3CNC(=O)c3ccc(C#N)c(Cl)c3)ccc2n(CC)c1=O] | | 524.2 (M + H) |

TABLE 1-2

| Ex. | IUPAC name | Structure | salt | MS |
|---|---|---|---|---|
| 11 | 4-(3-chloro-4-cyanobenzoyl)-N-(3-(cyclopropylmethyl)-1-ethyl-2,4-dioxo-1,2,3,4-tetrahydroquinazolin-6-yl)-1,4-diazepane-1-carboxamide | 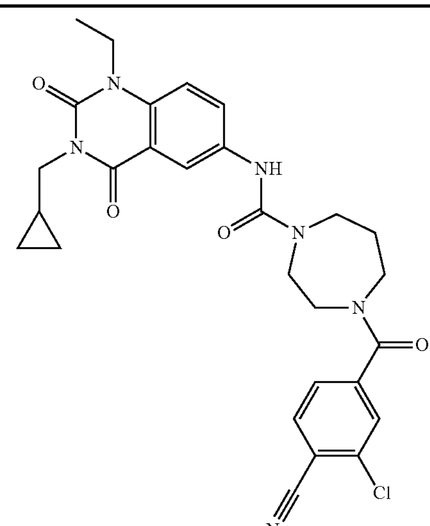 | | 549.1 (M + H) |

TABLE 1-2-continued

| Ex. | IUPAC name | Structure | salt | MS |
|---|---|---|---|---|
| 12 | 2-(((3-chloro-4-cyanobenzoyl)amino)-methyl)-N-(3-(cyclopropylmethyl)-1-ethyl-2,4-dioxo-1,2,3,4-tetrahydroquinazolin-6-yl)pyrrolidine-1-carboxamide | 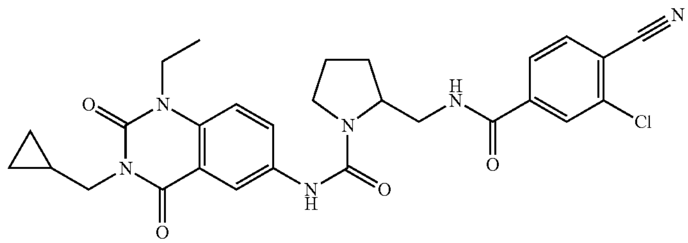 [SMILES: CCn1c(=O)n(CC2CC2)c(=O)c2cc(NC(=O)N3CCCC3CNC(=O)c3ccc(C#N)c(Cl)c3)ccc21] | | 549.2 (M + H) |
| 13 | N-((1-((3-chloro-4-cyanophenyl)carbamoyl)-pyrrolidin-2-yl)methyl)-1,3-diethyl-2,4-dioxo-1,2,3,4-tetrahydroquinazoline-6-carboxamide | 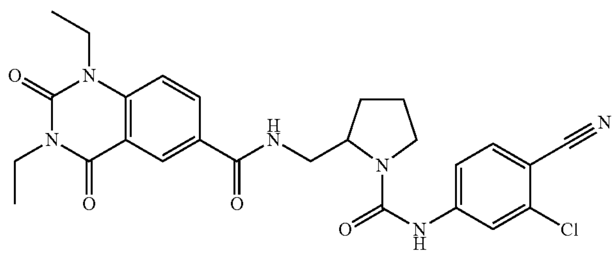 [SMILES: CCn1c(=O)c2cc(C(=O)NCC3CCCN3C(=O)Nc3ccc(C#N)c(Cl)c3)ccc2n(CC)c1=O] | | 523.2 (M + H) |
| 14 | 2-(((3-chloro-4-cyanobenzoyl)amino)-methyl)-N-(3-(cyclopropylmethyl)-1-ethyl-2,4-dioxo-1,2,3,4-tetrahydroquinazolin-6-yl)piperidine-1-carboxamide | 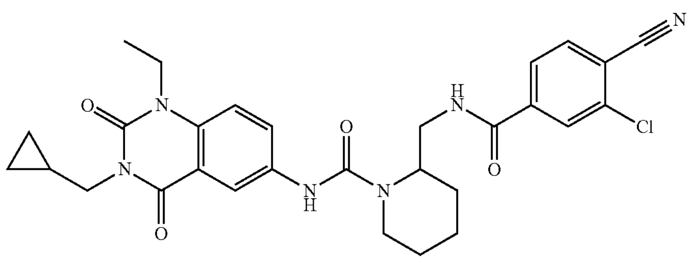 | | 563.2 (M + H) |
| 15 | 3-chloro-4-cyano-N-((1-((3-(cyclopropylmethyl)-1-ethyl-2,4-dioxo-1,2,3,4-tetrahydroquinazolin-6-yl)carbonyl)piperidin-2-yl)methyl)benzamide | 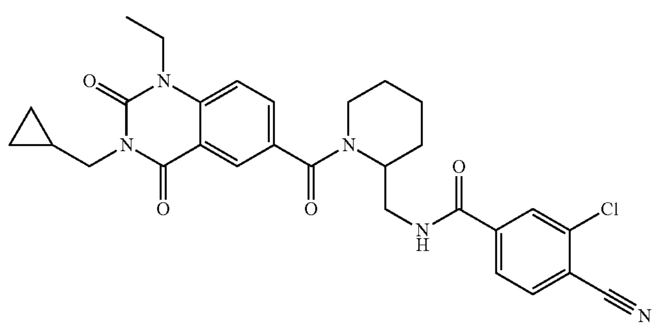 [SMILES: CCn1c(=O)n(CC2CC2)c(=O)c2cc(C(=O)N3CCCCC3CNC(=O)c3ccc(C#N)c(Cl)c3)ccc21] | | 548.2 (M + H) |
| 16 | 1,3-diethyl-2,4-dioxo-1,2,3,4-tetrahydroquinazolin-6-yl 2-((3-chloro-4-cyanobenzoyl)amino)methyl)-piperidine-1-carboxylate | 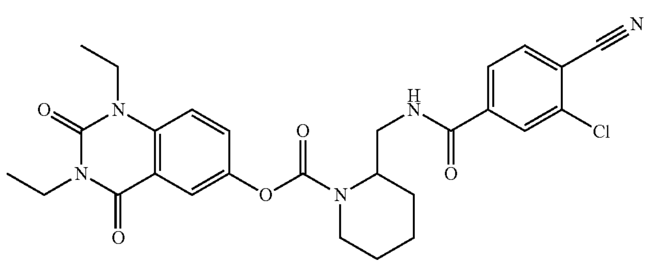 [SMILES: CCn1c(=O)c2cc(OC(=O)N3CCCCC3CNC(=O)c3ccc(C#N)c(Cl)c3)ccc2n(CC)c1=O] | | 538.2 (M + H) |

TABLE 1-2-continued

| Ex. | IUPAC name | Structure | salt | MS |
|---|---|---|---|---|
| 17 | 3-((3-chloro-4-cyanophenoxy)methyl)-N-(3-(cyclopropylmethyl)-1-ethyl-2,4-dioxo-1,2,3,4-tetrahydroquinazolin-6-yl)piperidine-1-carboxamide | 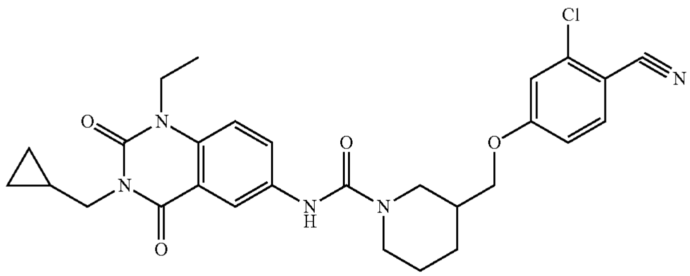 [SMILES: CCn1c(=O)n(CC2CC2)c(=O)c2cc(NC(=O)N3CCCC(COc4ccc(C#N)c(Cl)c4)C3)ccc21] | | 536.2 (M + H) |
| 18 | trans-N-(3-chloro-4-cyanophenyl)-N'-(1,3-diethyl-2,4-dioxo-1,2,3,4-tetrahydroquinazolin-6-yl)pyrrolidine-3,4-dicarboxamide hydrochloride | 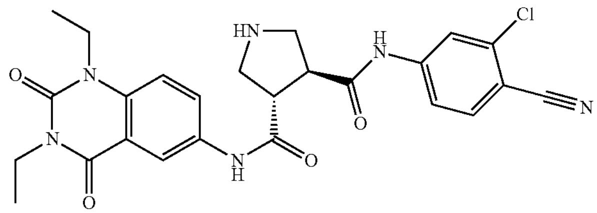 [SMILES: CCn1c(=O)c2cc(NC(=O)[C@@H]3CNC[C@H]3C(=O)Nc3ccc(C#N)c(Cl)c3)ccc2n(CC)c1=O] | HCl | 507.0 (M − HCl − H) |
| 19 | 3-((3-chloro-4-cyanophenoxy)methyl)-N-(3-(cyclopropylmethyl)-1-ethyl-2,4-dioxo-1,2,3,4-tetrahydroquinazolin-6-yl)morpholine-4-carboxamide | 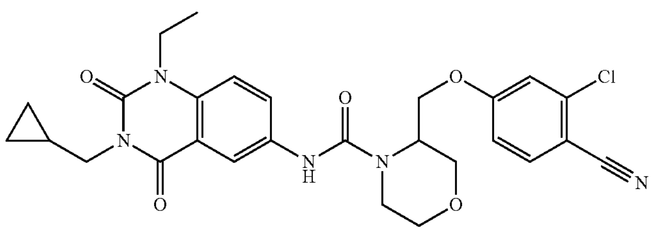 [SMILES: CCn1c(=O)n(CC2CC2)c(=O)c2cc(NC(=O)N3CCOCC3COc3ccc(C#N)c(Cl)c3)ccc21] | | 538.2 (M + H) |
| 20 | cis-N-(3-chloro-4-cyanophenyl)-N'-(1,3-diethyl-2,4-dioxo-1,2,3,4-tetrahydroquinazolin-6-yl)pyrrolidine-3,4-dicarboxamide hydrochloride | 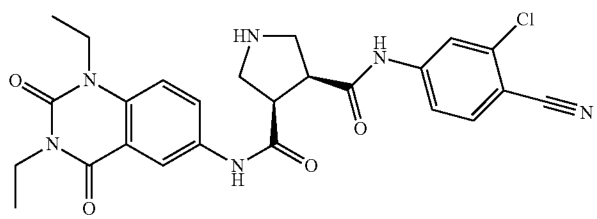 [SMILES: CCn1c(=O)c2cc(NC(=O)[C@H]3CNC[C@H]3C(=O)Nc3ccc(C#N)c(Cl)c3)ccc2n(CC)c1=O] | HCl | 507.1 (M − HCl − H) |

TABLE 1-3

| Ex. | IUPAC name | Structure | salt | MS |
|---|---|---|---|---|
| 21 | trans-N-(3-chloro-4-cyanophenyl)-N'-(1,3-diethyl-2,4-dioxo-1,2,3,4-tetrahydroquinazolin-6-yl)-1-methylpyrrolidine-3,4-dicarboxamide | 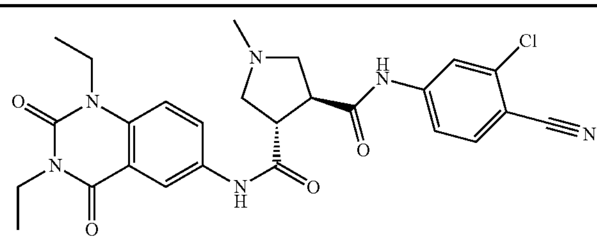 | | 521.1 (M − H) |
| 22 | cis-N-(3-chloro-4-cyanophenyl)-N'-(1,3-diethyl-2,4-dioxo-1,2,3,4-tetrahydroquinazolin-6-yl)-1-methylpyrrolidine-3,4-dicarboxamide | 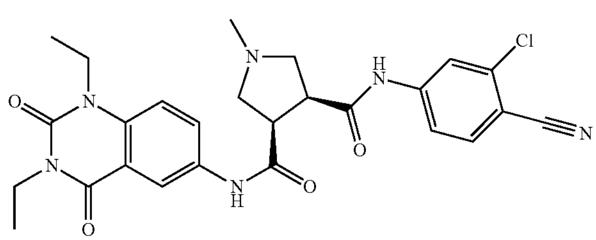 [SMILES: CCn1c(=O)c2cc(NC(=O)[C@H]3CN(C)C[C@H]3C(=O)Nc3ccc(C#N)c(Cl)c3)ccc2n(CC)c1=O] | | 521.1 (M − H) |

TABLE 1-3-continued

| Ex. | IUPAC name | Structure | salt | MS |
|---|---|---|---|---|
| 23 | trans-1-acetyl-N-(3-chloro-4-cyanophenyl)-N'-(1,3-diethyl-2,4-dioxo-1,2,3,4-tetrahydroquinazolin-6-yl)pyrrolidine-3,4-dicarboxamide | 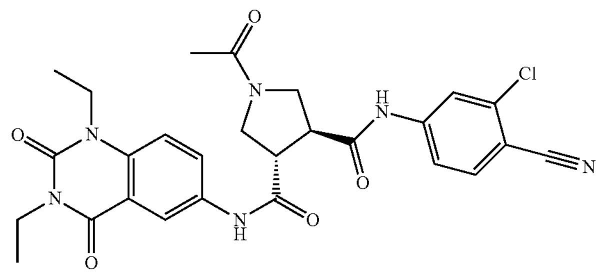 [SMILES: CCn1c(=O)c2cc(NC(=O)[C@@H]3CN(C(C)=O)C[C@H]3C(=O)Nc3ccc(C#N)c(Cl)c3)ccc2n(CC)c1=O] | | 549.1 (M − H) |
| 24 | cis-1-acetyl-N-(3-chloro-4-cyanophenyl)-N'-(1,3-diethyl-2,4-dioxo-1,2,3,4-tetrahydroquinazolin-6-yl)pyrrolidine-3,4-dicarboxamide | 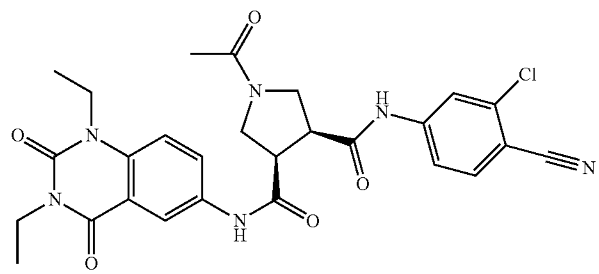 [SMILES: CCn1c(=O)c2cc(NC(=O)[C@H]3CN(C(C)=O)C[C@H]3C(=O)Nc3ccc(C#N)c(Cl)c3)ccc2n(CC)c1=O] | | 551.2 (M + H) |
| 25 | 3-(((3-chloro-4-cyanobenzoyl)amino)methyl)-N-(3-(cyclopropylmethyl)-1-ethyl-2,4-dioxo-1,2,3,4-tetrahydroquinazolin-6-yl)morpholine-6-carboxamide | 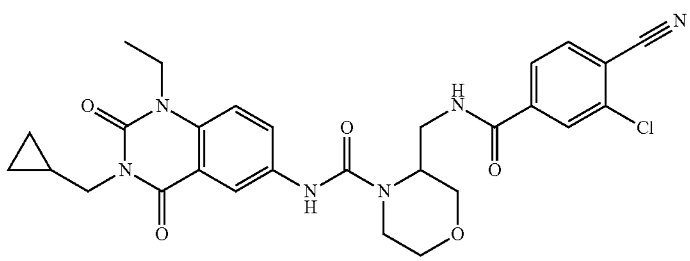 [SMILES: CCn1c(=O)n(CC2CC2)c(=O)c2cc(NC(=O)N3CCOCC3CNC(=O)c3ccc(C#N)c(Cl)c3)ccc21] | | 565.2 (M + H) |
| 26 | N$^4$-(3-chloro-4-cyanophenyl)-N$^3$-(3-(cyclopropylmethyl)-1-ethyl-2,4-dioxo-1,2,3,4-tetrahydroquinazolin-6-yl)morpholine-3,4-dicarboxamide | 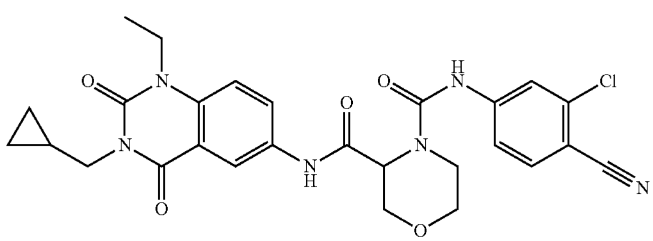 [SMILES: CCn1c(=O)n(CC2CC2)c(=O)c2cc(NC(=O)C3COCCN3C(=O)Nc3ccc(C#N)c(Cl)c3)ccc21] | | 551.1 (M + H) |
| 27 | N-(cis-2-((4-bromo-3-chlorophenyl)carbamoyl)cyclopentyl)-1,3-diethyl-2,4-dioxo-1,2,3,4-tetrahydroquinazoline-6-carboxamide | 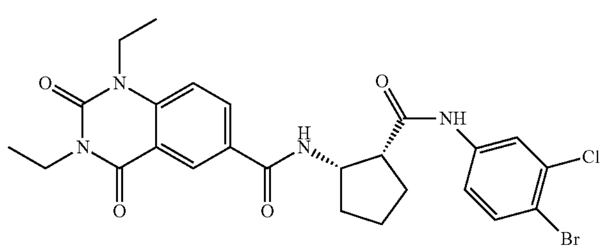 [SMILES: CCn1c(=O)c2cc(C(=O)N[C@H]3CCC[C@H]3C(=O)Nc3ccc(Br)c(Cl)c3)ccc2n(CC)c1=O] | | 561.1 (M + H) |
| 28 | trans-4-((3-chloro-4-cyanobenzoyl)amino)-N-(3-(cyclopropylmethyl)-1-ethyl-2,4-dioxo-1,2,3,4-tetrahydroquinazolin-6-yl)pyrrolidine-3-carboxamide hydrochloride | 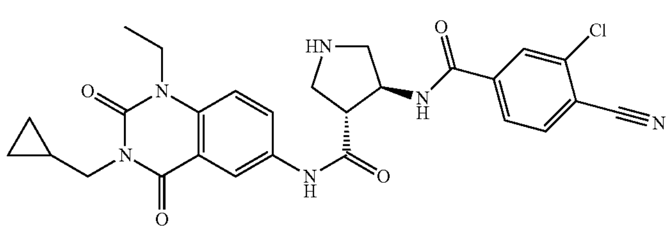 [SMILES: CCn1c(=O)n(CC2CC2)c(=O)c2cc(NC(=O)[C@@H]3CNC[C@H]3NC(=O)c3ccc(C#N)c(Cl)c3)ccc21] | HCl | 535.2 (M − HCl + H) |

TABLE 1-3-continued

| Ex. | IUPAC name | Structure | salt | MS |
|---|---|---|---|---|
| 29 | cis-4-((3-chloro-4-cyanobenzoyl)amino)-N-(3-(cyclopropylmethyl)-1-ethyl-2,4-dioxo-1,2,3,4-tetrahydroquinazolin-6-yl)pyrrolidine-3-carboxamide hydrochloride | 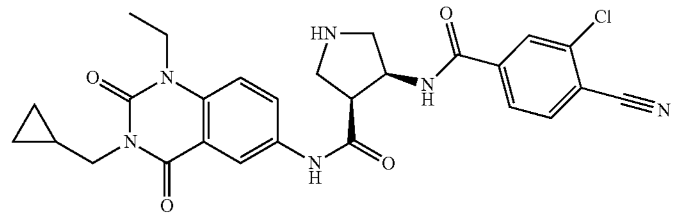 [SMILES: CCn1c(=O)n(CC2CC2)c(=O)c2cc(NC(=O)[C@H]3CNC[C@H]3NC(=O)c3ccc(C#N)c(Cl)c3)ccc21] | HCl | 535.2 (M − HCl + H) |
| 30 | trans-4-((3-chloro-4-cyanobenzoyl)amino)-N-(3-(cyclopropylmethyl)-1-ethyl-2,4-dioxo-1,2,3,4-tetrahydroquinazolin-6-yl)-1-methylpyrrolidine-3-carboxamide | 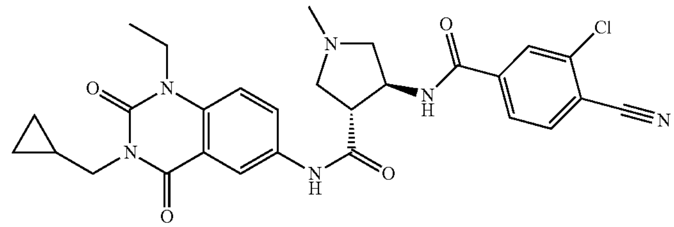 [SMILES: CCn1c(=O)n(CC2CC2)c(=O)c2cc(NC(=O)[C@@H]3CN(C)C[C@H]3NC(=O)c3ccc(C#N)c(Cl)c3)ccc21] | | 549.2 (M + H) |

TABLE 1-4

| Ex. | IUPAC name | Structure | salt | MS |
|---|---|---|---|---|
| 31 | cis-4-((3-chloro-4-cyanobenzoyl)amino)-N-(3-(cyclopropylmethyl)-1-ethyl-2,4-dioxo-1,2,3,4-tetrahydroquinazolin-6-yl)-1-methylpyrrolidine-3-carboxamide | 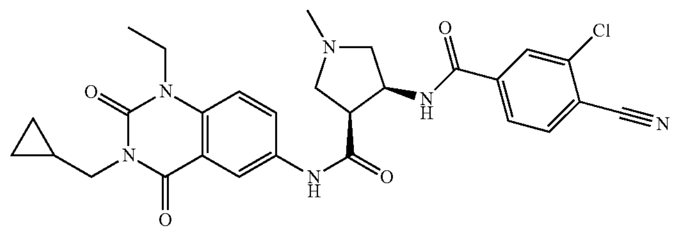 [SMILES: CCn1c(=O)n(CC2CC2)c(=O)c2cc(NC(=O)[C@H]3CN(C)C[C@H]3NC(=O)c3ccc(C#N)c(Cl)c3)ccc21] | | 549.2 (M + H) |
| 32 | N-(cis-2-((3-chloro-4-cyanophenyl)carbamoyl)cyclopentyl)-3-(cyclopropylmethyl)-1-ethyl-2,4-dioxo-1,2,3,4-tetrahydroquinazoline-6-carboxamide | 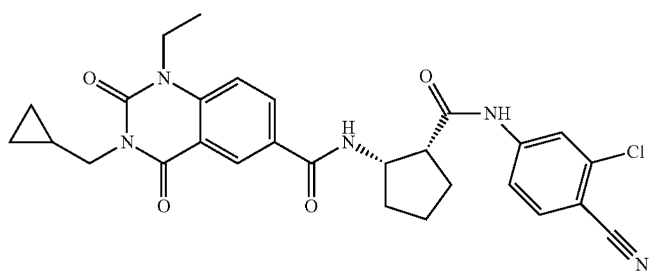 [SMILES: CCn1c(=O)n(CC2CC2)c(=O)c2cc(C(=O)N[C@H]3CCC[C@H]3C(=O)Nc3ccc(C#N)c(Cl)c3)ccc21] | | 534.2 (M + H) |
| 33 | N-(cis-2-((4-bromo-3-chlorophenyl)carbamoyl)cyclopentyl)-3-(cyclopropylmethyl)-1-ethyl-2,4-dioxo-1,2,3,4-tetrahydroquinazoline-6-carboxamide | 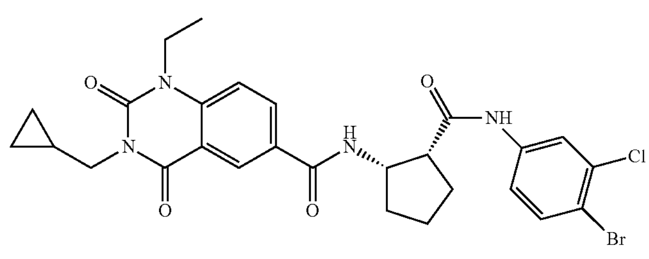 [SMILES: CCn1c(=O)n(CC2CC2)c(=O)c2cc(C(=O)N[C@H]3CCC[C@H]3C(=O)Nc3ccc(Br)c(Cl)c3)ccc21] | | 587.1 (M + H) |
| 34 | $N^3$-(3-chloro-4-cyanophenyl)-$N^1$-(3-(cyclopropylmethyl)-1-ethyl-2,4-dioxo-1,2,3,4-tetrahydroquinazolin-6-yl)piperidine-1,3-dicarboxamide | 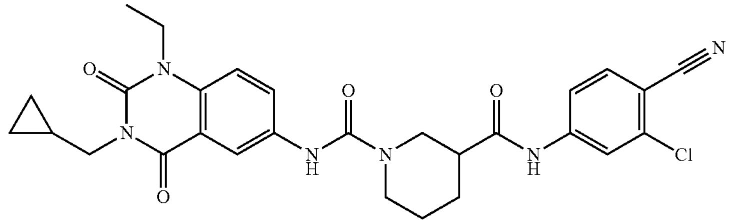 [SMILES: CCn1c(=O)n(CC2CC2)c(=O)c2cc(NC(=O)N3CCCC(C(=O)Nc4ccc(C#N)c(Cl)c4)C3)ccc21] | | 547.0 (M − H) |

TABLE 1-4-continued

| Ex. | IUPAC name | Structure | salt | MS |
|---|---|---|---|---|
| 35 | 3-chloro-4-cyano-N-(trans-2-((3-(cyclopropylmethyl)-1-ethyl-2,4-dioxo-1,2,3,4-tetrahydro-quinazolin-6-yl)-carbamoyl)cyclohexyl)-benzamide | 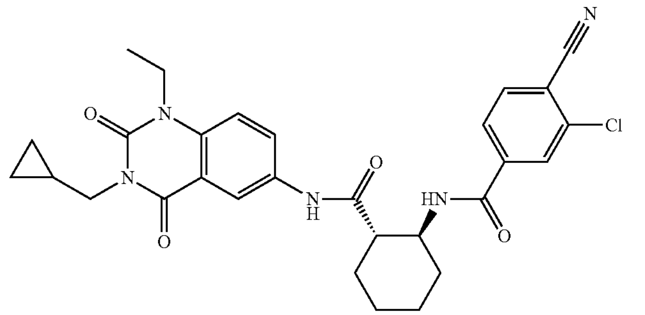 [SMILES: CCn1c(=O)n(CC2CC2)c(=O)c2cc(NC(=O)[C@H]3CCCC[C@@H]3NC(=O)c3ccc(C#N)c(Cl)c3)ccc21] | | 548.2 (M + H) |
| 36 | trans-1-acetyl-4-((3-chloro-4-cyanobenzoyl)amino)-N-(3-(cyclopropylmethyl)-1-ethyl-2,4-dioxo-1,2,3,4-tetrahydro-quinazolin-6-yl)pyrrolidine-3-carboxamide | 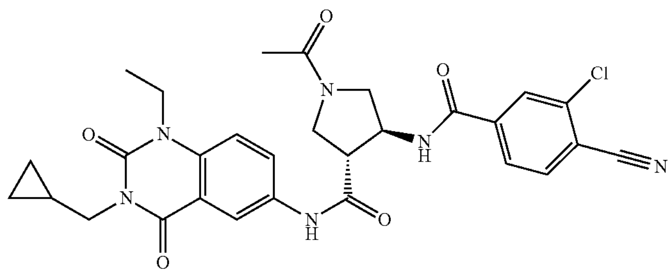 [SMILES: CCn1c(=O)n(CC2CC2)c(=O)c2cc(NC(=O)[C@@H]3CN(C(C)=O)C[C@H]3NC(=O)c3ccc(C#N)c(Cl)c3)ccc21] | | 575.1 (M − H) |
| 37 | cis-1-acetyl-4-((3-chloro-4-cyanobenzoyl)amino)-N-(3-(cyclopropylmethyl)-1-ethyl-2,4-dioxo-1,2,3,4-tetrahydro-quinazolin-6-yl)pyrrolidine-3-carboxamide | 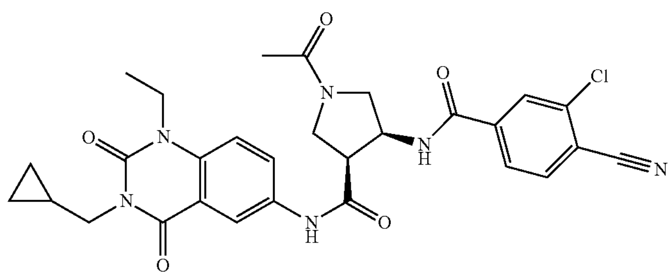 [SMILES: CCn1c(=O)n(CC2CC2)c(=O)c2cc(NC(=O)[C@H]3CN(C(C)=O)C[C@H]3NC(=O)c3ccc(C#N)c(Cl)c3)ccc21] | | 577.2 (M + H) |
| 38 | Cis-4-(((3-chloro-4-cyanophenyl)carbamoyl)amino)-N-(3-(cyclopropyl-methyl)-1-ethyl-2,4-dioxo-1,2,3,4-tetrahydroquinazolin-6-yl)tetrahydro-furan-3-carboxamide | 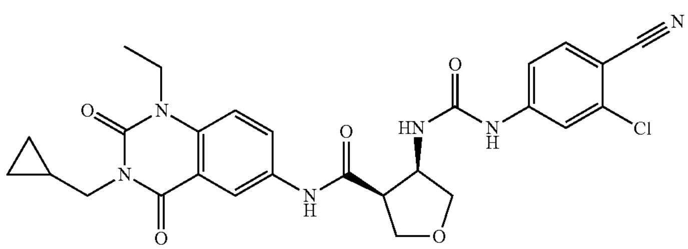 [SMILES: CCn1c(=O)n(CC2CC2)c(=O)c2cc(NC(=O)[C@@H]3COC[C@@H]3NC(=O)Nc3ccc(C#N)c(Cl)c3)ccc21] | | 551.1 (M + H) |
| 39 | Cis-4-((3-chloro-4-cyanobenzoyl)amino)-N-(3-(cyclopropylmethyl)-1-ethyl-2,4-dioxo-1,2,3,4-tetrahydro-quinazolin-6-yl)tetrahydrofuran-3-carboxamide | 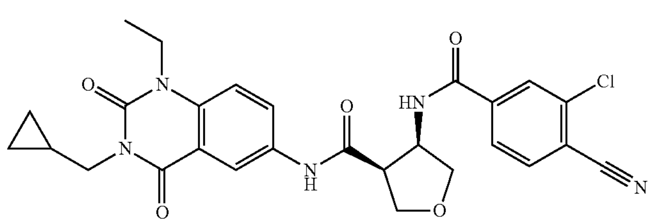 [SMILES: CCn1c(=O)n(CC2CC2)c(=O)c2cc(NC(=O)[C@@H]3COC[C@@H]3NC(=O)c3ccc(C#N)c(Cl)c3)ccc21] | | 536.1 (M + H) |
| 40 | (2S,4R)-$N^1$-(3-chloro-4-cyanophenyl)-$N^2$-(3-(cyclopropylmethyl)-1-ethyl-2,4-dioxo-1,2,3,4-tetrahydro-quinazolin-6-yl)-4-hydroxypyrrolidine-1,2-dicarboxamide | 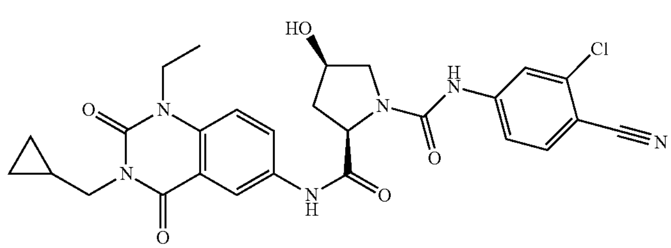 [SMILES: CCn1c(=O)n(CC2CC2)c(=O)c2cc(NC(=O)[C@H]3C[C@@H](O)CN3C(=O)Nc3ccc(C#N)c(Cl)c3)ccc21] | | 549.0 (M − H) |

TABLE 1-5

| Ex. | IUPAC name | Structure | salt | MS |
|---|---|---|---|---|
| 41 | N²-(3-chloro-4-cyanophenyl)-N⁴-(3-(cyclopropylmethyl)-1-ethyl-2,4-dioxo-1,2,3,4-tetrahydroquinazolin-6-yl)morpholine-2,4-dicarboxamide | 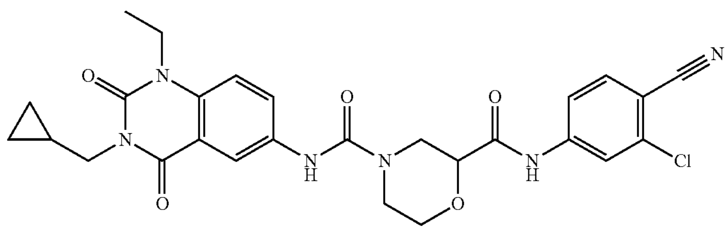 [SMILES: CCn1c(=O)n(CC2CC2)c(=O)c2cc(NC(=O)N3CCOC(C(=O)Nc4ccc(C#N)c(Cl)c4)C3)ccc21] | | 549.1 (M − H) |
| 42 | N-(cis-4-((3-chloro-4-cyanophenyl)carbamoyl)-tetrahydrofuran-3-yl)-3-(cyclopropylmethyl)-1-ethyl-2,4-dioxo-1,2,3,4-tetrahydroquinazoline-6-carboxamide | 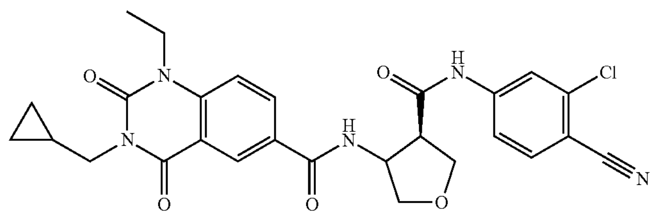 [SMILES: CCn1c(=O)n(CC2CC2)c(=O)c2cc(C(=O)NC3COC[C@@H]3C(=O)Nc3ccc(C#N)c(Cl)c3)ccc21] | | 536.1 (M + H) |
| 43 | trans-4-((3-chloro-4-cyanophenoxy)methyl)-N-(3-(cyclopropylmethyl)-1-ethyl-2,4-dioxo-1,2,3,4-tetrahydroquinazolin-6-yl)pyrrolidine-3-carboxamide hydrochloride | 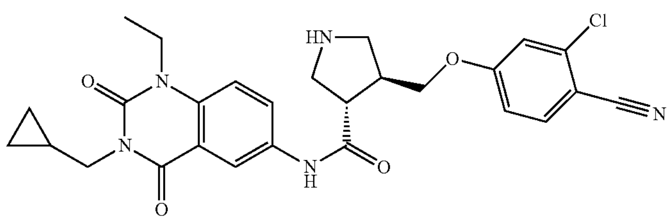 [SMILES: CCn1c(=O)n(CC2CC2)c(=O)c2cc(NC(=O)[C@@H]3CNC[C@H]3COc3ccc(C#N)c(Cl)c3)ccc21] | HCl | 520.1 (M − HCl − H) |
| 44 | cis-4-((3-chloro-4-cyanophenoxy)methyl)-N-(3-(cyclopropylmethyl)-1-ethyl-2,4-dioxo-1,2,3,4-tetrahydroquinazolin-6-yl)pyrrolidine-3-carboxamide hydrochloride | 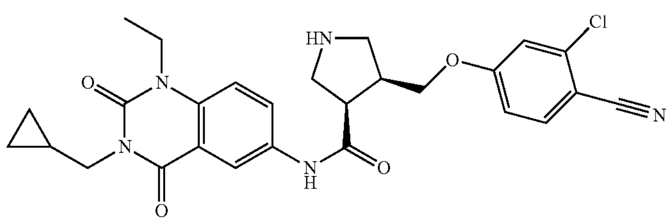 [SMILES: CCn1c(=O)n(CC2CC2)c(=O)c2cc(NC(=O)[C@H]3CNC[C@H]3COc3ccc(C#N)c(Cl)c3)ccc21] | HCl | 522.2 (M − HCl + H) |
| 45 | trans-4-((3-chloro-4-cyanophenoxy)methyl)-N-(3-(cyclopropylmethyl)-1-ethyl-2,4-dioxo-1,2,3,4-tetrahydroquinazolin-6-yl)-1-methylpyrrolidine-3-carboxamide | 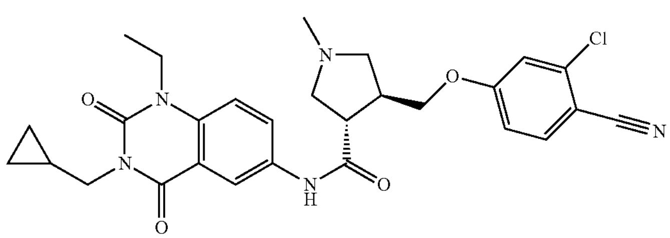 [SMILES: CCn1c(=O)n(CC2CC2)c(=O)c2cc(NC(=O)[C@@H]3CN(C)C[C@H]3COc3ccc(C#N)c(Cl)c3)ccc21] | | 536.2 (M + H) |
| 46 | cis-4-((3-chloro-4-cyanophenoxy)methyl)-N-(3-(cyclopropylmethyl)-1-ethyl-2,4-dioxo-1,2,3,4-tetrahydroquinazolin-6-yl)-1-methylpyrrolidine-3-carboxamide | 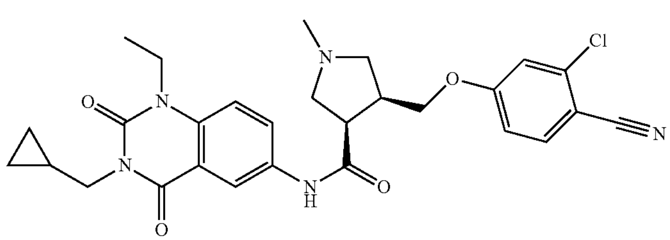 [SMILES: CCn1c(=O)n(CC2CC2)c(=O)c2cc(NC(=O)[C@H]3CN(C)C[C@H]3COc3ccc(C#N)c(Cl)c3)ccc21] | | 536.2 (M + H) |

TABLE 1-5-continued

| Ex. | IUPAC name | Structure | salt | MS |
|---|---|---|---|---|
| 47 | trans-1-acetyl-4-((3-chloro-4-cyanophenoxy)methyl)-N-(3-(cyclopropylmethyl)-1-ethyl-2,4-dioxo-1,2,3,4-tetrahydroquinazolin-6-yl)pyrrolidine-3-carboxamide | 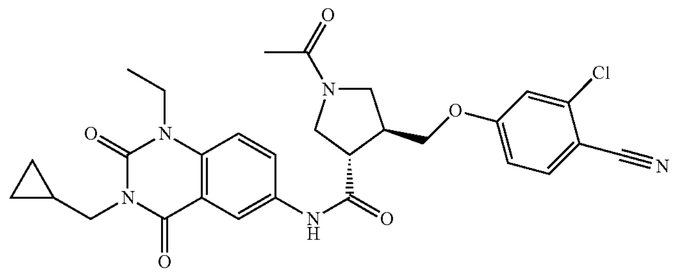 [SMILES: CCn1c(=O)n(CC2CC2)c(=O)c2cc(NC(=O)[C@@H]3CN(C(C)=O)C[C@H]3COc3ccc(C#N)c(Cl)c3)ccc21] | | 562.1 (M − H) |
| 48 | cis-1-acetyl-4-((3-chloro-4-cyanophenoxy)methyl)-N-(3-(cyclopropylmethyl)-1-ethyl-2,4-dioxo-1,2,3,4-tetrahydroquinazolin-6-yl)pyrrolidine-3-carboxamide | 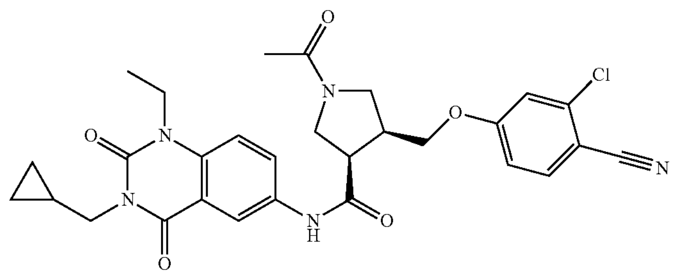 [SMILES: CCn1c(=O)n(CC2CC2)c(=O)c2cc(NC(=O)[C@H]3CN(C(C)=O)C[C@H]3COc3ccc(C#N)c(Cl)c3)ccc21] | | 564.2 (M + H) |
| 49 | 3-chloro-4-cyano-N-(cis-2-((3-(cyclopropylmethyl)-1-ethyl-2,4-dioxo-1,2,3,4-tetrahydroquinazolin-6-yl)carbamoyl)-cyclohexyl)benzamide | 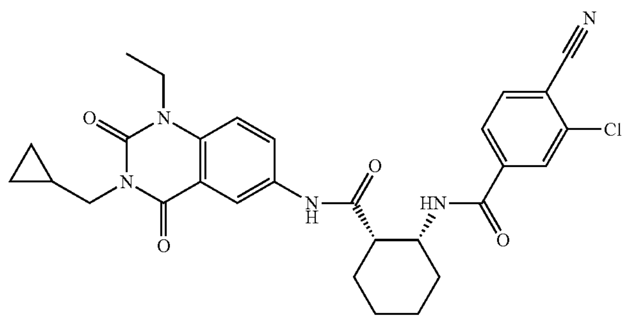 [SMILES: CCn1c(=O)n(CC2CC2)c(=O)c2cc(NC(=O)[C@H]3CCCC[C@H]3NC(=O)c3ccc(C#N)c(Cl)c3)ccc21] | | 548.2 (M + H) |
| 50 | 3-((3-chloro-4-cyanobenzoyl)amino)-N-(3-(cyclopropylmethyl)-1-ethyl-2,4-dioxo-1,2,3,4-tetrahydroquinazolin-6-yl)piperidine-1-carboxamide | 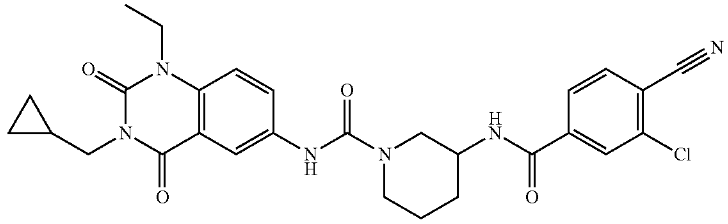 [SMILES: CCn1c(=O)n(CC2CC2)c(=O)c2cc(NC(=O)N3CCCC(NC(=O)c4ccc(C#N)c(Cl)c4)C3)ccc21] | | 549.2 (M + H) |

TABLE 1-6

| Ex. | IUPAC name | Structure | salt | MS |
|---|---|---|---|---|
| 51 | 3-(((3-chloro-4-cyanophenyl)acetyl)-amino)-N-(3-(cyclopropylmethyl)-1-ethyl-2,4-dioxo-1,2,3,4-tetrahydroquinazolin-6-yl)piperidine-1-carboxamide | 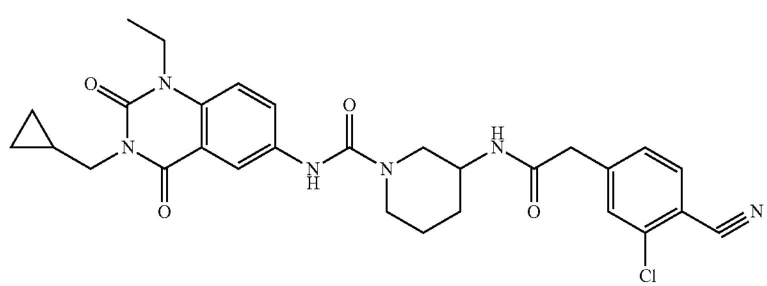 [SMILES: CCn1c(=O)n(CC2CC2)c(=O)c2cc(NC(=O)N3CCCC(NC(=O)Cc4ccc(C#N)c(Cl)c4)C3)ccc21] | | 563.2 (M + H) |

TABLE 1-6-continued

| Ex. | IUPAC name | Structure | salt | MS |
|---|---|---|---|---|
| 52 | 3-(((3-chloro-4-cyanobenzoyl)amino)-methyl)-N-(3-(cyclopropylmethyl)-1-ethyl-2,4-dioxo-1,2,3,4-tetrahydroquinazolin-6-yl)piperidine-1-carboxamide | 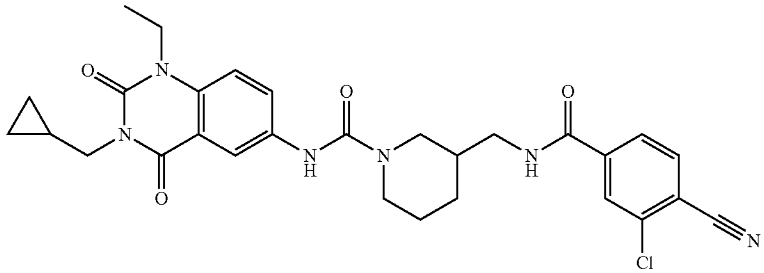 [SMILES: CCn1c(=O)n(CC2CC2)c(=O)c2cc(NC(=O)N3CCCC(CNC(=O)c4ccc(C#N)c(Cl)c4)C3)ccc21] | | 563.2 (M + H) |
| 53 | 1-(4-chloro-3-cyanophenyl)-3-(1-((3-(cyclopropylmethyl)-1-ethyl-2,4-dioxo-1,2,3,4-tetrahydroquinazolin-6-yl)carbonyl)piperidin-3-yl)urea | 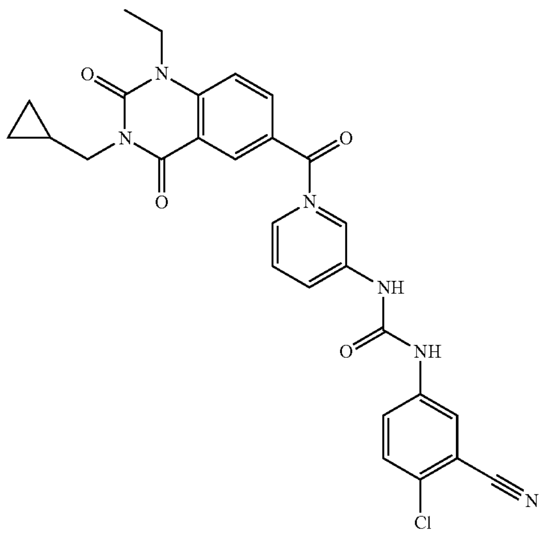 | | 549.2 (M + H) |
| 54 | 3-chloro-4-cyano-N-((4-((3-(cyclopropylmethyl)-1-ethyl-2,4-dioxo-1,2,3,4-tetrahydroquinazolin-6-yl)acetyl)morpholin-3-yl)methyl)benzamide | 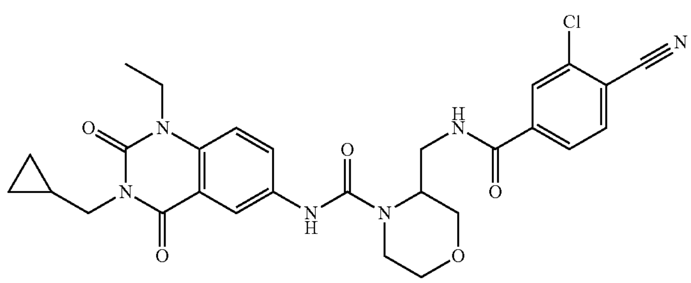 [SMILES: CCn1c(=O)n(CC2CC2)c(=O)c2cc(NC(=O)N3CCOCC3CNC(=O)c3ccc(C#N)c(Cl)c3)ccc21] | | 564.2 (M + H) |
| 55 | cis-2-(((3-chloro-4-cyanophenyl)carbamoyl)amino)-N-(1,3-diethyl-2,4-dioxo-1,2,3,4-tetra-hydroquinazolin-6-yl)-cyclopentanecarboxamide | 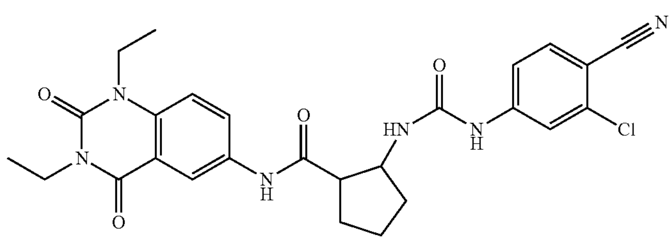 [SMILES: CCn1c(=O)c2cc(NC(=O)C3CCCC3NC(=O)Nc3ccc(C#N)c(Cl)c3)ccc2n(CC)c1=O] | | 523.2 (M + H) |
| 56 | cis-2-(((3-chloro-4-cyanophenyl)acetyl)amino)-N-(1,3-diethyl-2,4-dioxo-1,2,3,4-tetra-hydroquinazolin-6-yl)-cyclopentanecarboxamide | 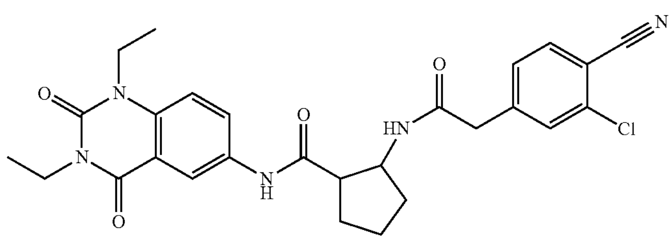 [SMILES: CCn1c(=O)c2cc(NC(=O)C3CCCC3NC(=O)Cc3ccc(C#N)c(Cl)c3)ccc2n(CC)c1=O] | | 522.2 (M + H) |

TABLE 1-6-continued

| Ex. | IUPAC name | Structure | salt | MS |
|---|---|---|---|---|
| 57 | 2-(((1-(3-chloro-4-cyanophenyl)-2,2,2-trifluoroethyl)amino)-methyl)-N-(3-(cyclopropylmethyl)-1-ethyl-2,4-dioxo-1,2,3,4-tetrahydroquinazolin-6-yl)piperidine-1-carboxamide (mixture of 4 stereoisomers) | 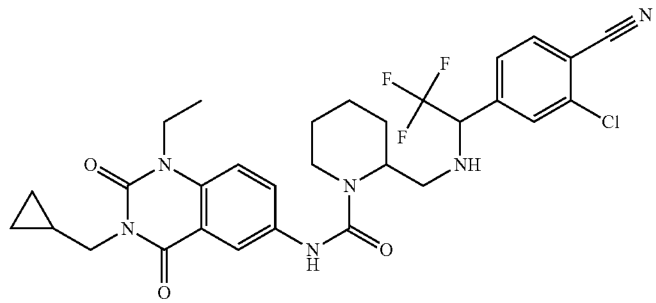 [SMILES: CCn1c(=O)n(CC2CC2)c(=O)c2cc(NC(=O)N3CCCCC3CNC(c3ccc(C#N)c(Cl)c3)C(F)(F)F)ccc21] | | 617.2 (M + H) |
| 58 | 2-((3-chloro-4-cyanophenoxy)methyl)-N-(3-(cyclopropylmethyl)-1-ethyl-2,4-dioxo-1,2,3,4-tetrahydroquinazolin-6-yl)morpholine-4-carboxamide | 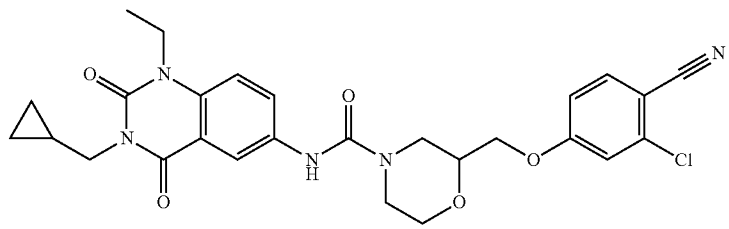 [SMILES: CCn1c(=O)n(CC2CC2)c(=O)c2cc(NC(=O)N3CCOC(COc4ccc(C#N)c(Cl)c4)C3)ccc21] | | 536.1 (M − H) |
| 59 | 2-chloro-4-((4-((3-(cyclopropylmethyl)-1-ethyl-2,4-dioxo-1,2,3,4-tetrahydroquinazolin-6-yl)acetyl)morpholin-2-yl)methoxy)benzonitrile | 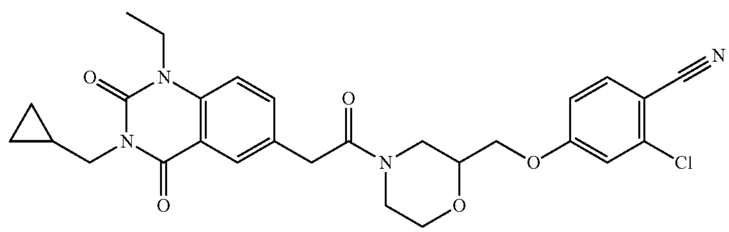 [SMILES: CCn1c(=O)n(CC2CC2)c(=O)c2cc(CC(=O)N3CCOC(COc4ccc(C#N)c(Cl)c4)C3)ccc21] | | 537.1 (M + H) |
| 60 | $N^4$-(1,3-bis(cyclopropylmethyl)-2,4-dioxo-1,2,3,4-tetrahydropyrido[2,3-d]pyrimidin-6-yl)-$N^2$-(3-chloro-4-cyanophenyl)morpholine-2,4-dicarboxamide | 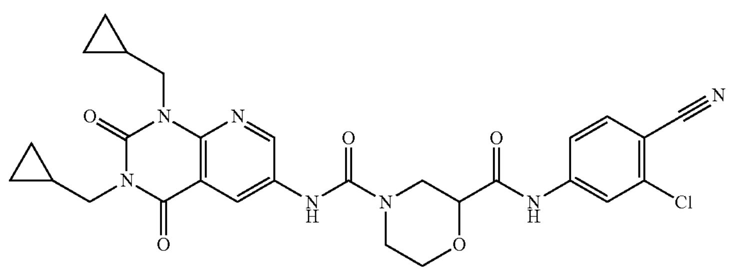 [SMILES: N#Cc1ccc(NC(=O)C2CN(C(=O)Nc3cnc4c(c3)c(=O)n(CC3CC3)c(=O)n4CC3CC3)CCO2)cc1Cl] | | 578.1 (M + H) |

TABLE 1-7

| Ex. | IUPAC name | Structure | salt | MS |
|---|---|---|---|---|
| 61 | N-(1,3-bis(cyclopropylmethyl)-2,4-dioxo-1,2,3,4-tetrahydropyrido[2,3-d]pyrimidin-6-yl)-2-((3-chloro-4-cyanophenoxy)methyl)morpholine-4-carboxamide | 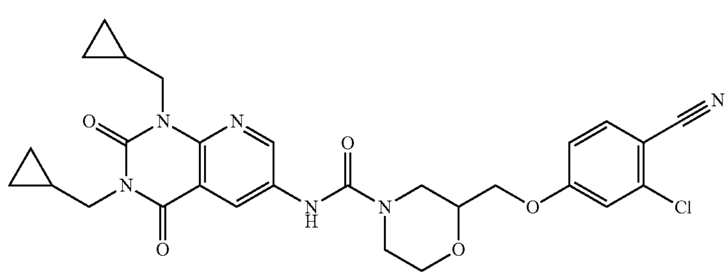 [SMILES: N#Cc1ccc(OCC2CN(C(=O)Nc3cnc4c(c3)c(=O)n(CC3CC3)c(=O)n4CC3CC3)CCO2)cc1Cl] | | 563.0 (M − H) |

TABLE 1-7-continued

| Ex. | IUPAC name | Structure | salt | MS |
|---|---|---|---|---|
| 62 | N⁴-(1,3-bis(cyclopropylmethyl)-2,4-dioxo-1,2,3,4-tetrahydropyrido[3,4-d]pyrimidin-6-yl)-N²-(3-chloro-4-cyanophenyl)morpholine-2,4-dicarboxamide | 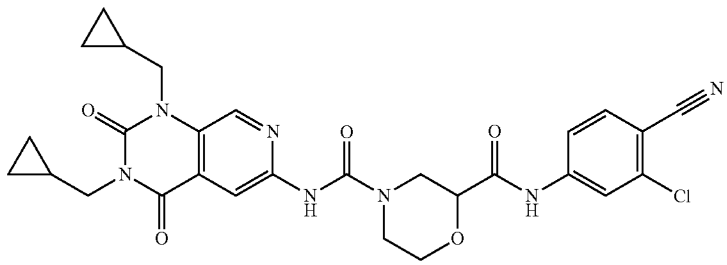 [SMILES: N#Cc1ccc(NC(=O)C2CN(C(=O)Nc3cc4c(=O)n(CC5CC5)c(=O)n(CC5CC5)c4cn3)CCO2)cc1Cl] | | 578.1 (M + H) |
| 63 | 3-((3-chloro-4-cyanophenoxy)methyl)-N-(3-(cyclopropylmethyl)-1-ethyl-2,4-dioxo-1,2,3,4-tetrahydroquinazolin-6-yl)morpholine-4-carboxamide (one stereoisomer, shorter retention time) | 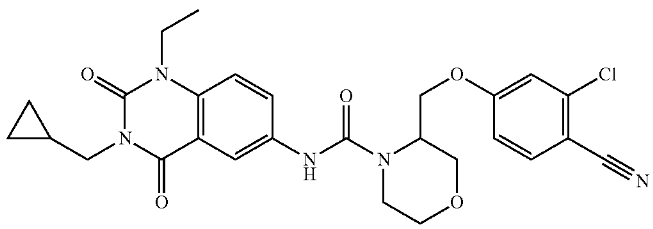 [SMILES: CCn1c(=O)n(CC2CC2)c(=O)c2cc(NC(=O)N3CCOCC3COc3ccc(C#N)c(Cl)c3)ccc21] | | 538.2 (M + H) |
| 64 | 3-((3-chloro-4-cyanophenoxy)methyl)-N-(3-(cyclopropylmethyl)-1-ethyl-2,4-dioxo-1,2,3,4-tetrahydro-quinazolin-6-yl)morpholine-4-carboxamide (one stereoisomer, longer retention time) | 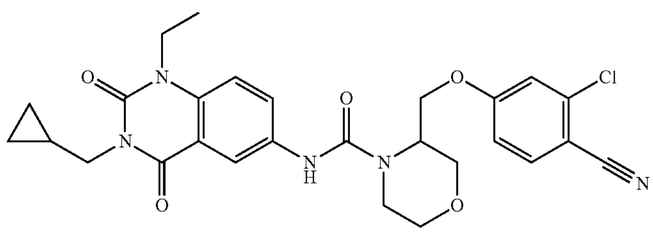 [SMILES: CCn1c(=O)n(CC2CC2)c(=O)c2cc(NC(=O)N3CCOCC3COc3ccc(C#N)c(Cl)c3)ccc21] | | 538.1 (M + H) |
| 65 | N⁴-(1,3-bis(cyclopropylmethyl)-2,4-dioxo-1,2,3,4-tetrahydroquinazolin-6-yl)-N²-(3-chloro-4-cyanophenyl)morpholine-2,4-dicarboxamide | 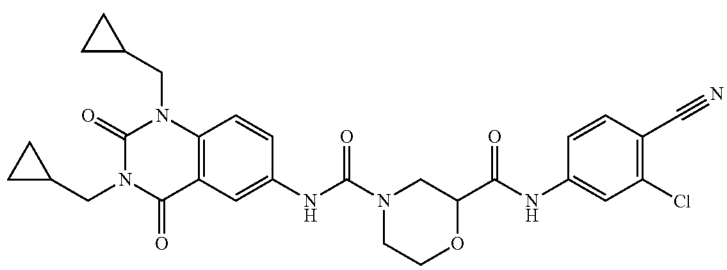 [SMILES: N#Cc1ccc(NC(=O)C2CN(C(=O)Nc3ccc4c(c3)c(=O)n(CC3CC3)c(=O)n4CC3CC3)CCO2)cc1Cl] | | 575.1 (M − H) |
| 66 | N²-(3-chloro-4-cyanophenyl)-N⁴-(3-(cyclopropylmethyl)-1-isobutyl-2,4-dioxo-1,2,3,4-tetrahydroquinazolin-6-yl)morpholine-2,4-dicarboxamide | 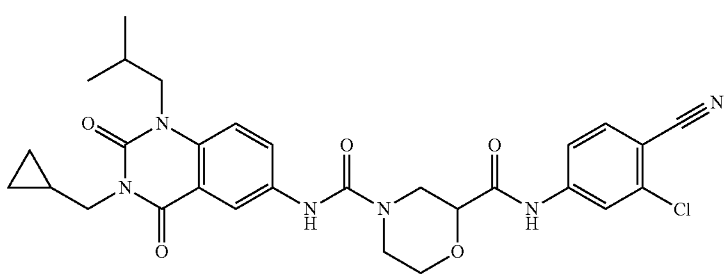 [SMILES: CC(C)Cn1c(=O)n(CC2CC2)c(=O)c2cc(NC(=O)N3CCOC(C(=O)Nc4ccc(C#N)c(Cl)c4)C3)ccc21] | | 577.1 (M − H) |
| 67 | N²-(3-chloro-4-cyanophenyl)-N⁴-(1-(cyclobutylmethyl)-3-(cyclopropylmethyl)-2,4-dioxo-1,2,3,4-tetrahydroquinazolin-6-yl)morpholine-2,4-dicarboxamide | 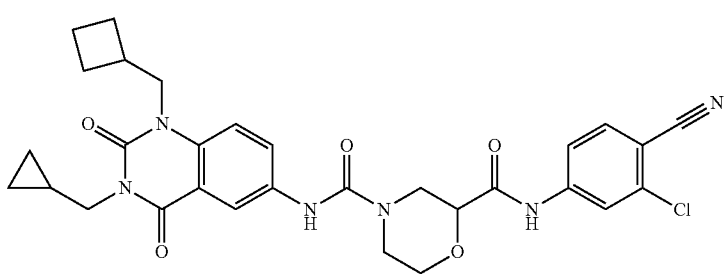 [SMILES: N#Cc1ccc(NC(=O)C2CN(C(=O)Nc3ccc4c(c3)c(=O)n(CC3CC3)c(=O)n4CC3CCC3)CCO2)cc1Cl] | | 589.1 (M − H) |

TABLE 1-7-continued

| Ex. | IUPAC name | Structure | salt | MS |
|---|---|---|---|---|
| 68 | N⁴-(1-sec-butyl-3-(cyclopropylmethyl)-2,4-dioxo-1,2,3,4-tetrahydroquinazolin-6-yl)-N²-(3-chloro-4-cyanophenyl)morpholine-2,4-dicarboxamide | 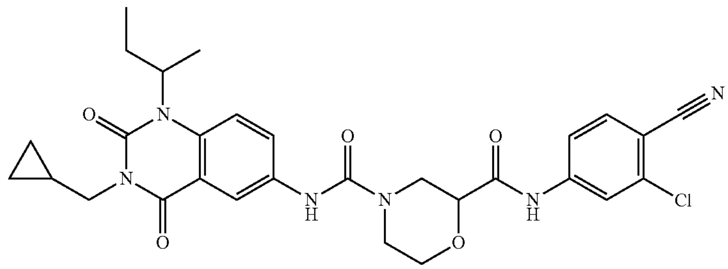 [SMILES: CCC(C)n1c(=O)n(CC2CC2)c(=O)c2cc(NC(=O)N3CCOC(C(=O)Nc4ccc(C#N)c(Cl)c4)C3)ccc21] | | 577.1 (M − H) |
| 69 | N²-(3-chloro-4-cyanophenyl)-N⁴-(3-(cyclopropylmethyl)-1-(2,2-dimethylpropyl)-2,4-dioxo-1,2,3,4-tetrahydroquinazolin-6-yl)morpholine-2,4-dicarboxamide | 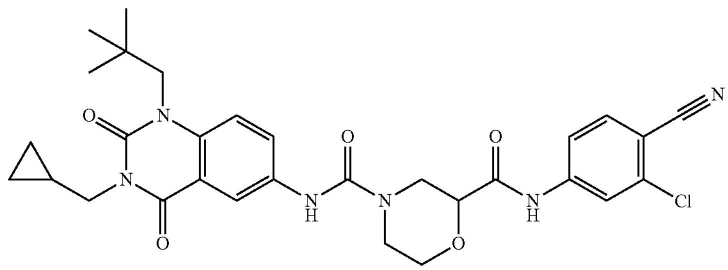 [SMILES: CC(C)(C)Cn1c(=O)n(CC2CC2)c(=O)c2cc(NC(=O)N3CCOC(C(=O)Nc4ccc(C#N)c(Cl)c4)C3)ccc21] | | 591.0 (M − H) |
| 70 | N⁴-(1,3-bis(cyclopropylmethyl)-7-fluoro-2,4-dioxo-1,2,3,4-tetrahydroquinazolin-6-yl)-N²-(3-chloro-4-cyanophenyl)morpholine-2,4-dicarboxamide | 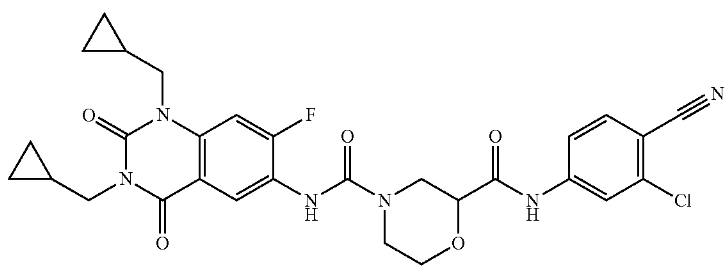 [SMILES: N#Cc1ccc(NC(=O)C2CN(C(=O)Nc3cc4c(=O)n(CC5CC5)c(=O)n(CC5CC5)c4cc3F)CCO2)cc1Cl] | | 594.9 (M + H) |

TABLE 1-8

| Ex. | IUPAC name | Structure | salt | MS |
|---|---|---|---|---|
| 71 | N²-(3-chloro-4-cyanophenyl)-N⁴-(3-(cyclopropylmethyl)-1-isopropyl-2,4-dioxo-1,2,3,4-tetrahydroquinazolin-6-yl)morpholine-2,4-dicarboxamide | 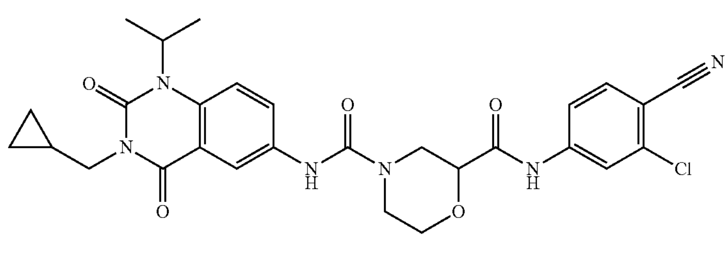 [SMILES: CC(C)n1c(=O)n(CC2CC2)c(=O)c2cc(NC(=O)N3CCOC(C(=O)Nc4ccc(C#N)c(Cl)c4)C3)ccc21] | | 565.1 (M + H) |
| 72 | N²-(3-chloro-4-cyanophenyl)-N⁴-(3-(cyclopropylmethyl)-1-(2,2-difluoroethyl)-2,4-dioxo-1,2,3,4-tetrahydroquinazolin-6-yl)morpholine-2,4-dicarboxamide | 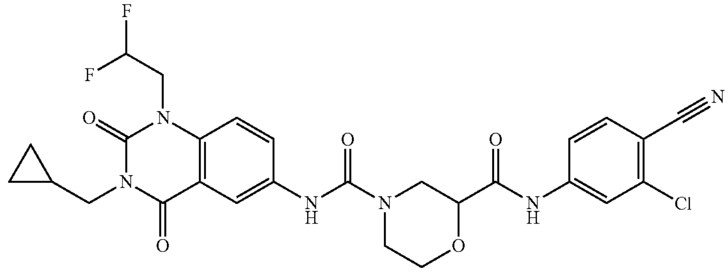 [SMILES: N#Cc1ccc(NC(=O)C2CN(C(=O)Nc3ccc4c(c3)c(=O)n(CC3CC3)c(=O)n4CC(F)F)CCO2)cc1Cl] | | 585.0 (M − H) |

| Ex. | IUPAC name | salt | MS |
|---|---|---|---|
| 73 | N²-(3-chloro-4-cyanophenyl)-N⁴-(3-(cyclopropylmethyl)-2,4-dioxo-1-(2,2,2-trifluoroethyl)-1,2,3,4-tetrahydroquinazolin-6-yl)morpholine-2,4-dicarboxamide | | 605.1 (M + H) |
| 74 | N²-(3-chloro-4-cyanophenyl)-N⁴-(3-(cyclopropylmethyl)-1-(3-methylbut-2-en-1-yl)-2,4-dioxo-1,2,3,4-tetrahydroquinazolin-6-yl)morpholine-2,4-dicarboxamide | | 589.1 (M − H) |
| 75 | N²-(3-chloro-4-cyanophenyl)-N⁴-(3-(cyclopropylmethyl)-1-(3-methylbutyl)-2,4-dioxo-1,2,3,4-tetrahydroquinazolin-6-yl)morpholine-2,4-dicarboxamide | | 591.0 (M − H) |
| 76 | N²-(5-chloro-6-cyanopyridin-3-yl)-N⁴-(3-(cyclopropylmethyl)-1-isopropyl-2,4-dioxo-1,2,3,4-tetrahydroquinazolin-6-yl)morpholine-2,4-dicarboxamide | | 566.1 (M + H) |
| 77 | N²-(3-chloro-4-cyanophenyl)-N⁴-(3-(cyclopropylmethyl)-1-ethyl-2,4-dioxo-1,2,3,4-tetrahydroquinazolin-6-yl)morpholine-2,4-dicarboxamide (one stereoisomer, shorter retention time) | | 549.0 (M − H) |
| 78 | N²-(3-chloro-4-cyanophenyl)-N⁴-(3-(cyclopropylmethyl)-1-ethyl-2,4-dioxo-1,2,3,4-tetrahydroquinazolin-6-yl)morpholine-2,4-dicarboxamide (one stereoisomer, longer retention time) | | 548.9 (M − H) |

TABLE 1-8-continued

| Ex. | IUPAC name | Structure | salt | MS |
|---|---|---|---|---|
| 79 | (2R)-N²-(3-chloro-4-cyanophenyl)-N⁴-(3-(cyclopropylmethyl)-1-isopropyl-2,4-dioxo-1,2,3,4-tetrahydroquinazolin-6-yl)morpholine-2,4-dicarboxamide | 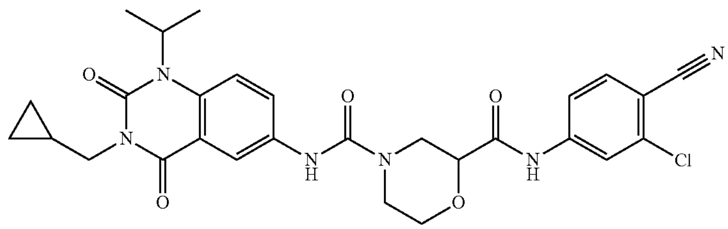 [SMILES: CC(C)n1c(=O)n(CC2CC2)c(=O)c2cc(NC(=O)N3CCOC(C(=O)Nc4ccc(C#N)c(Cl)c4)C3)ccc21] | | 565.1 (M − H) |
| 80 | (2S)-N²-(3-chloro-4-cyanophenyl)-N⁴-(3-(cyclopropylmethyl)-1-isopropyl-2,4-dioxo-1,2,3,4-tetrahydroquinazolin-6-yl)morpholine-2,4-dicarboxamide | 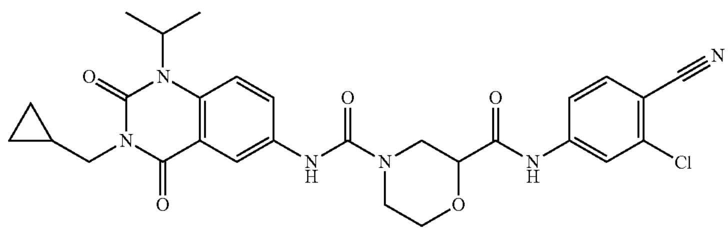 [SMILES: CC(C)n1c(=O)n(CC2CC2)c(=O)c2cc(NC(=O)N3CCOC(C(=O)Nc4ccc(C#N)c(Cl)c4)C3)ccc21] | | 563.0 (M − H) |

TABLE 1-9

| Ex. | IUPAC name | Structure | salt | MS |
|---|---|---|---|---|
| 81 | benzyl 2-((3-chloro-4-cyanophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate | 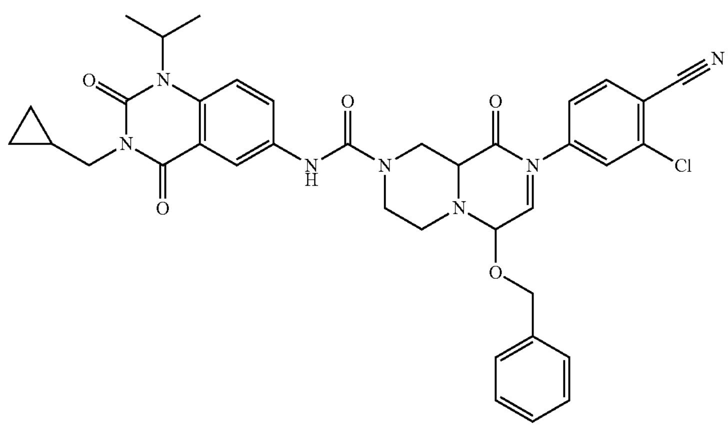 | | 696.1 (M − H) |
| 82 | N³-(3-chloro-4-cyanophenyl)-N¹-(3-(cyclopropylmethyl)-1-isopropyl-2,4-dioxo-1,2,3,4-tetrahydroquinazolin-6-yl)piperazine-1,3-dicarboxamide | 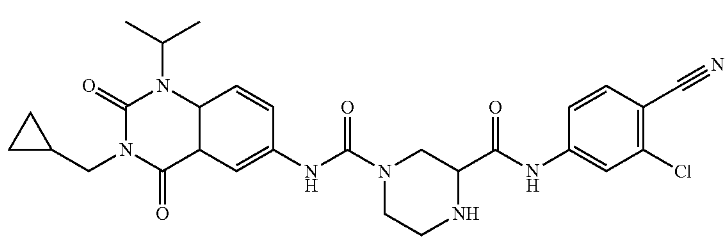 | | 562.0 (M − H) |

| Ex. | IUPAC name | Structure | salt | MS |
|---|---|---|---|---|
| 83 | 5-(2-((3-chloro-4-cyanophenyl)carbamoyl)-4-((3-(cyclopropylmethyl)-1-isopropyl-2,4-dioxo-1,2,3,4-tetrahydroquinazolin-6-yl)carbamoyl)piperazin-1-yl)-5-oxopentanoic acid | 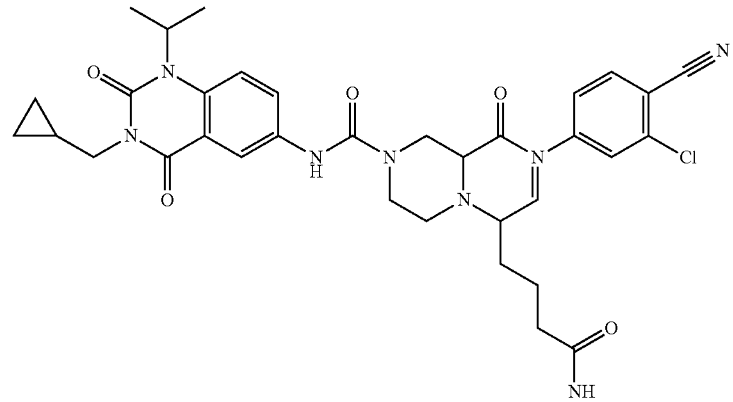 | | 676.1 (M − H) |
| 84 | N³-(3-chloro-4-cyanophenyl)-N¹-(3-(cyclopropylmethyl)-1-isopropyl-2,4-dioxo-1,2,3,4-tetrahydroquinazolin-6-yl)pyrrolidine-1,3-dicarboxamide | 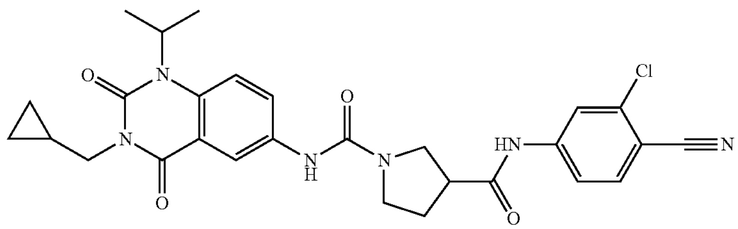 | | 546.9 (M − H) |
| 85 | N³-(4-cyano-3-fluorophenyl)-N¹-(3-(cyclopropylmethyl)-1-isopropyl-2,4-dioxo-1,2,3,4-tetrahydroquinazolin-6-yl)pyrrolidine-1,3-dicarboxamide | 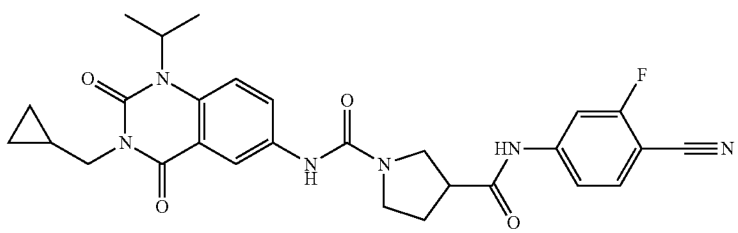 [SMILES: CC(C)n1c(=O)n(CC2CC2)c(=O)c2cc(NC(=O)N3CCC(C(=O)Nc4ccc(C#N)c(F)c4)C3)ccc21] | | 530.9 (M − H) |
| 86 | N⁴-(3-chloro-4-cyanophenyl)-N²-(3-(cyclopropylmethyl)-1-isopropyl-2,4-dioxo-1,2,3,4-tetrahydroquinazolin-6-yl)morpholine-2,4-dicarboxamide | 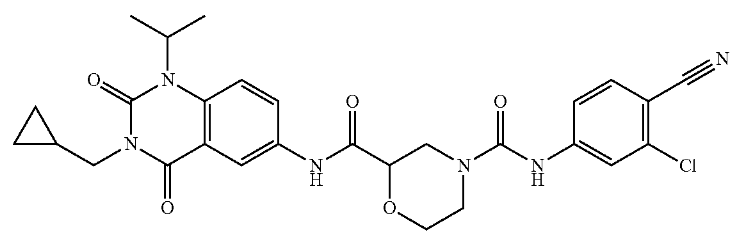 [SMILES: CC(C)n1c(=O)n(CC2CC2)c(=O)c2cc(NC(=O)C3CN(C(=O)Nc4ccc(C#N)c(Cl)c4)CCO3)ccc21] | | 563.2 (M − H) |
| 87 | N⁴-(5-chloro-6-cyanopyridin-3-yl)-N²-(3-(cyclopropylmethyl)-1-isopropyl-2,4-dioxo-1,2,3,4-tetrahydroquinazolin-6-yl)morpholine-2,4-dicarboxamide | 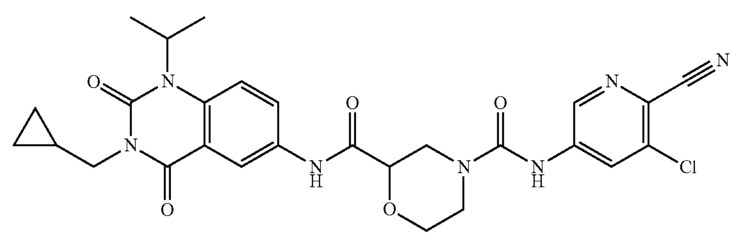 [SMILES: CC(C)n1c(=O)n(CC2CC2)c(=O)c2cc(NC(=O)C3CN(C(=O)Nc4cnc(C#N)c(Cl)c4)CCO3)ccc21] | | 563.9 (M − H) |
| 88 | 3-((3-chloro-4-cyanobenzoyl)amino)-N-(3-(cyclopropylmethyl)-1-isopropyl-2,4-dioxo-1,2,3,4-tetrahydroquinazolin-6-yl)piperidine-1-carboxamide | 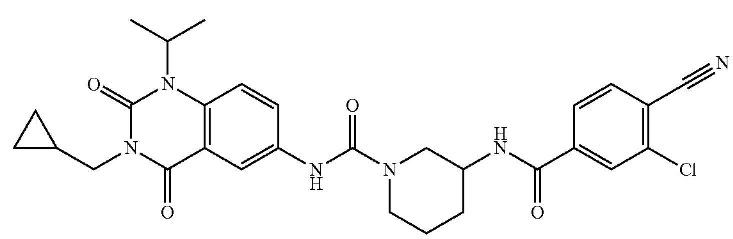 [SMILES: CC(C)n1c(=O)n(CC2CC2)c(=O)c2cc(NC(=O)N3CCCC(NC(=O)c4ccc(C#N)c(Cl)c4)C3)ccc21] | | 563.0 (M + H) |

TABLE 1-9-continued

| Ex. | IUPAC name | Structure | salt | MS |
|---|---|---|---|---|
| 89 | 3-chloro-4-cyano-N-((1S,3R)-3-((3-(cyclopropylmethyl)-1-isopropyl-2,4-dioxo-1,2,3,4-tetrahydro-quinazolin-6-1)-carbamoyl)cyclohexyl)-benzamide | 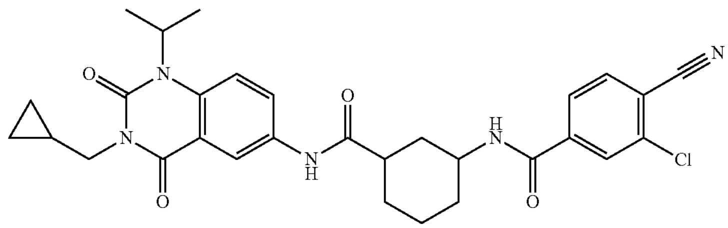 [SMILES: CC(C)n1c(=O)n(CC2CC2)c(=O)c2cc(NC(=O)C3CCCC(NC(=O)c4ccc(C#N)c(Cl)c4)C3)ccc21] | | 562.0 (M + H) |
| 90 | 3-chloro-4-cyano-N-((1R,3S)-3-((3-(cyclopropylmethyl)-1-isopropyl-2,4-dioxo-1,2,3,4-tetrahydro-quinazolin-6-yl)-carbamoyl)cyclohexyl)-benzamide | 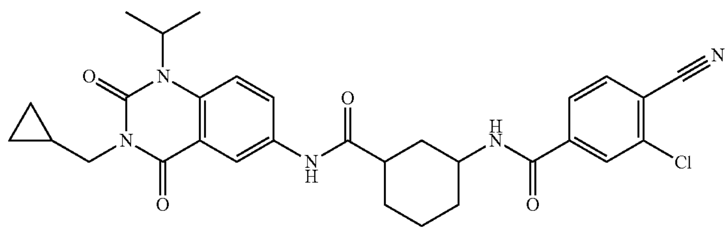 [SMILES: CC(C)n1c(=O)n(CC2CC2)c(=O)c2cc(NC(=O)C3CCCC(NC(=O)c4ccc(C#N)c(Cl)c4)C3)ccc21] | | 562.0 (M + H) |

TABLE 1-10

| Ex. | IUPAC name | Structure | salt | MS |
|---|---|---|---|---|
| 91 | benzyl 2-((4-cyano-3-fluorophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate | 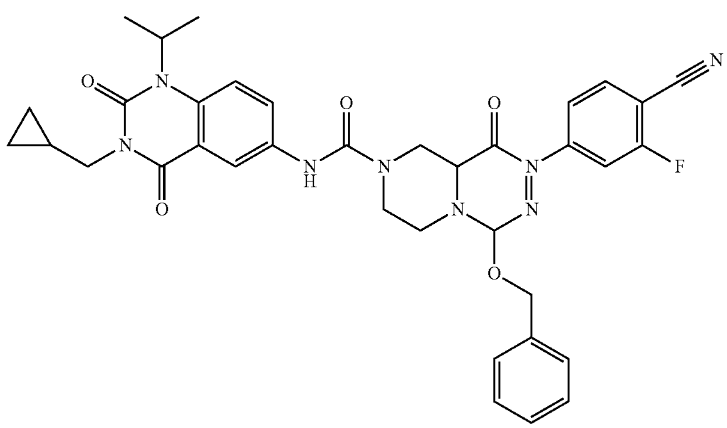 | | 680.1 (M − H) |
| 92 | N³-(4-cyano-3-fluorophenyl)-N¹-(3-(cyclopropylmethyl)-1-isopropyl-2,4-dioxo-1,2,3,4-tetrahydroquinazolin-6-yl)piperazine-1,3-dicarboxamide hydrochloride | 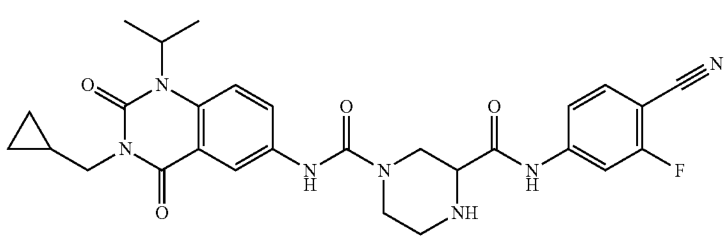 [SMILES: CC(C)n1c(=O)n(CC2CC2)c(=O)c2cc(NC(=O)N3CCNC(C(=O)Nc4ccc(C#N)c(F)c4)C3)ccc21] | HCl | 546.0 (M − HCl − H) |

TABLE 1-10-continued

| Ex. | IUPAC name | Structure | salt | MS |
|---|---|---|---|---|
| 93 | 2-(benzyloxy)-2-oxoethyl 2-((4-cyano-3-fluorophenyl)carbamoyl)-4-((3-(cyclopropylmethyl)-1-isopropyl-2,4-dioxo-1,2,3,4-tetrahydroquinazolin-6-yl)carbamoyl)piperazine-1-carboxylate | 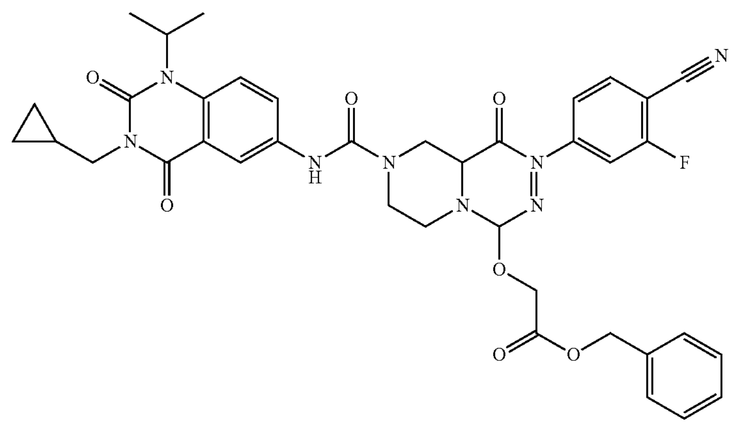 | | 738.1 (M − H) |
| 94 | (((2-((4-cyano-3-fluorophenyl)carbamoyl)-4-((3-(cyclopropylmethyl)-1-isopropyl-2,4-dioxo-1,2,3,4-tetrahydroquinazolin-6-yl)carbamoyl)piperazin-1-yl)carbonyl)oxy)acetic acid | 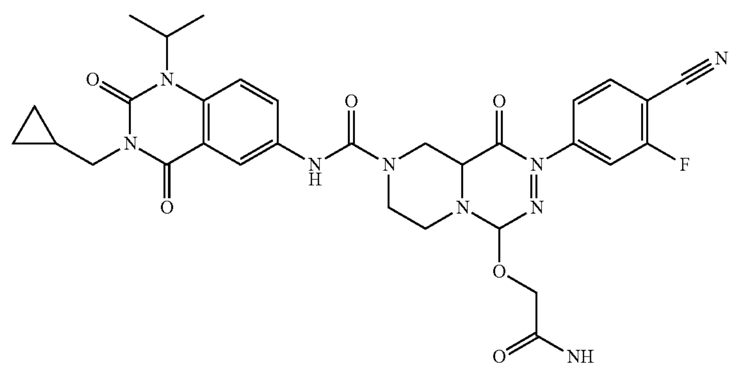 | | 650.0 (M + H) |
| 95 | $N^2$-(3-chloro-4-cyanophenyl)-$N^4$-(3-(cyclopropylmethyl)-1-isopropyl-2,4-dioxo-1,2,3,4-tetrahydroquinazolin-6-yl)thiomorpholine-2,4-dicarboxamide | 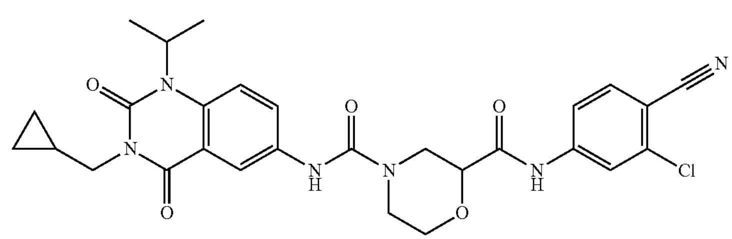 [SMILES: CC(C)n1c(=O)n(CC2CC2)c(=O)c2cc(NC(=O)N3CCOC(C(=O)Nc4ccc(C#N)c(Cl)c4)C3)ccc21] | | 578.9 (M − H) |
| 96 | $N^2$-(3-chloro-4-cyanophenyl)-$N^4$-(3-(cyclopropylmethyl)-1-isopropyl-2,4-dioxo-1,2,3,4-tetrahydroquinazolin-6-yl)thiomorpholine-2,4-dicarboxamide 1,1-dioxide | 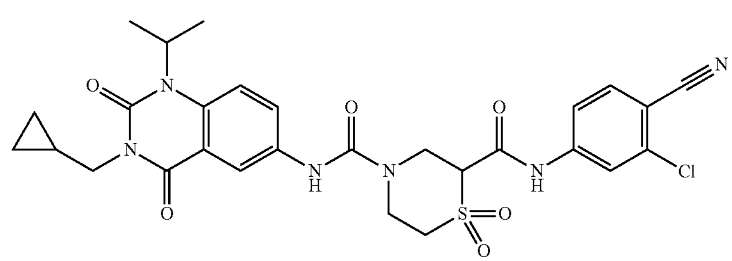 [SMILES: CC(C)n1c(=O)n(CC2CC2)c(=O)c2cc(NC(=O)N3CCS(=O)(=O)C(C(=O)Nc4ccc(C#N)c(Cl)c4)C3)ccc21] | | 613.0 (M + H) |
| 97 | N-(3-chloro-4-cyanophenyl)-N'-trans-(3-(cyclopropylmethyl)-1-isopropyl-2,4-dioxo-1,2,3,4-tetrahydroquinazolin-6-yl)cyclohexane-1,3-dicarboxamide | 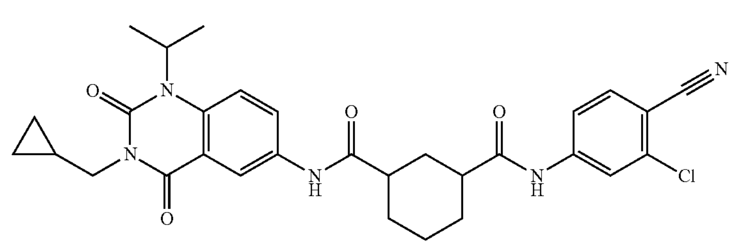 [SMILES: CC(C)n1c(=O)n(CC2CC2)c(=O)c2cc(NC(=O)C3CCCC(C(=O)Nc4ccc(C#N)c(Cl)c4)C3)ccc21] | | 559.9 (M − H) |

TABLE 1-10-continued

| Ex. | IUPAC name | Structure | salt | MS |
|---|---|---|---|---|
| 98 | 4-acetyl-N³-(4-cyano-3-fluorophenyl)-N¹-(3-(cyclopropylmethyl)-1-isopropyl-2,4-dioxo-1,2,3,4-tetrahydroquinazolin-6-yl)piperazine-1,3-dicarboxamide | 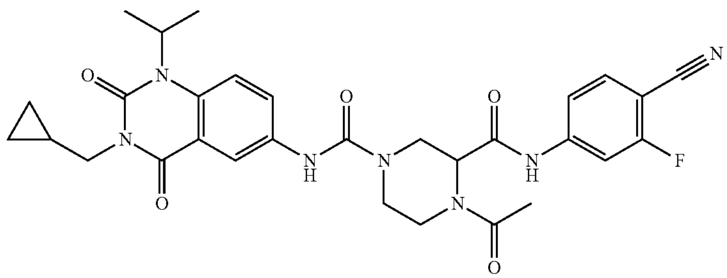 [SMILES: CC(=O)N1CCN(C(=O)Nc2ccc3c(c2)c(=O)n(CC2CC2)c(=O)n3C(C)C)CC1C(=O)Nc1ccc(C#N)c(F)c1] | | 588.3 (M − H) |
| 99 | N³-(4-cyano-3-fluorophenyl)-N¹-(3-(cyclopropylmethyl)-1-isopropyl-2,4-dioxo-1,2,3,4-tetrahydroquinazolin-6-yl)-4-(methylsulfonyl)piperazine-1,3-dicarboxamide | 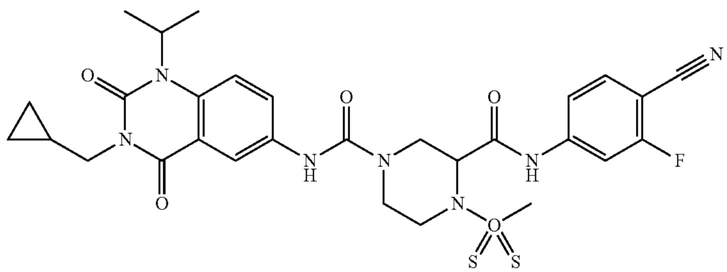 | | 624.3 (M − H) |
| 100 | N³-(4-cyano-3-fluorophenyl)-N¹-(3-(cyclopropylmethyl)-1-isopropyl-2,4-dioxo-1,2,3,4-tetrahydroquinazolin-6-yl)-4-methylpiperazine-1,3-dicarboxamide | 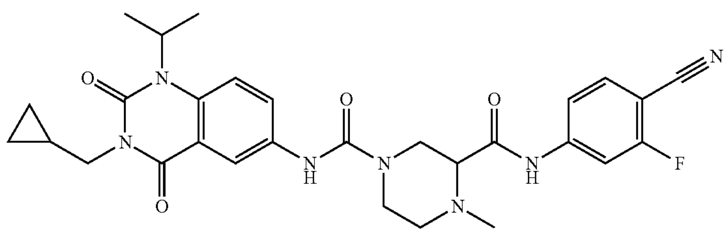 [SMILES: CC(C)n1c(=O)n(CC2CC2)c(=O)c2cc(NC(=O)N3CCN(C)C(C(=O)Nc4ccc(C#N)c(F)c4)C3)ccc21] | | 560.2 (M − H) |

TABLE 1-11

| Ex. | IUPAC name | Structure | salt | MS |
|---|---|---|---|---|
| 101 | 3-((3-chloro-4-cyanophenoxy)methyl)-N-(3-(cyclopropylmethyl)-1-isopropyl-2,4-dioxo-1,2,3,4-tetrahydroquinazolin-6-yl)morpholine-4-carboxamide | 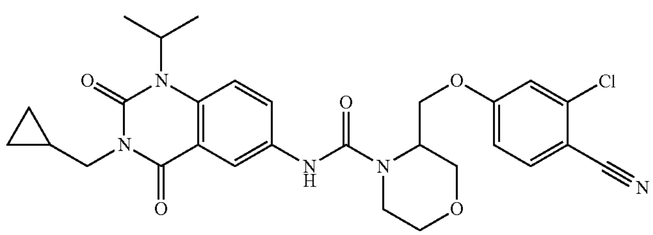 [SMILES: CC(C)n1c(=O)n(CC2CC2)c(=O)c2cc(NC(=O)N3CCOCC3COc3ccc(C#N)c(Cl)c3)ccc21] | | 552.2 (M + H) |
| 102 | (2R)-N²-(4-cyano-3-fluorophenyl)-N⁴-(3-(cyclopropylmethyl)-1-isopropyl-2,4-dioxo-1,2,3,4-tetrahydroquinazolin-6-yl)morpholine-2,4-dicarboxamide | 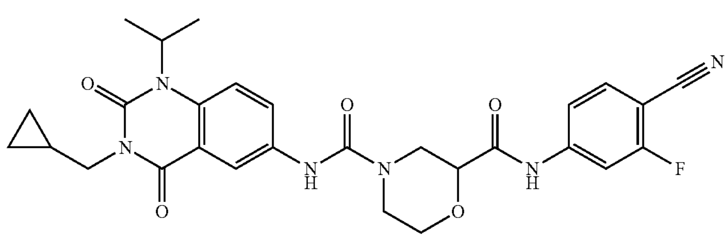 | | 547.2 (M − H) |

TABLE 1-11-continued

| Ex. | IUPAC name | Structure | salt | MS |
|---|---|---|---|---|
| 103 | (2R)-N²-(6-cyano-5-fluoropyridin-3-yl)-N⁴-(3-(cyclopropylmethyl)-1-isopropyl-2,4-dioxo-1,2,3,4-tetrahydroquinazolin-6-yl)morpholine-2,4-dicarboxamide | 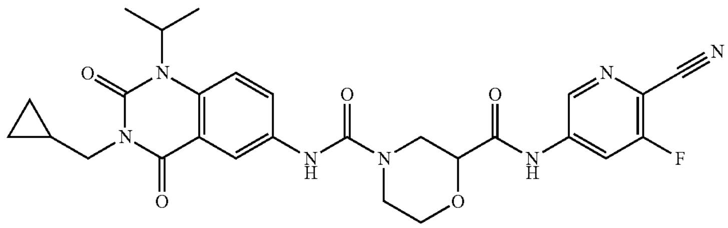 | | 548.2 (M − H) |
| 104 | N-(3-(cyclopropyl-methyl)-1-isopropyl-2,4-dioxo-1,2,3,4-tetrahydroquinazolin-6-yl)-3-((4-(methyl-sulfonyl)benzoyl)amino)-piperidine-1-carboxamide | 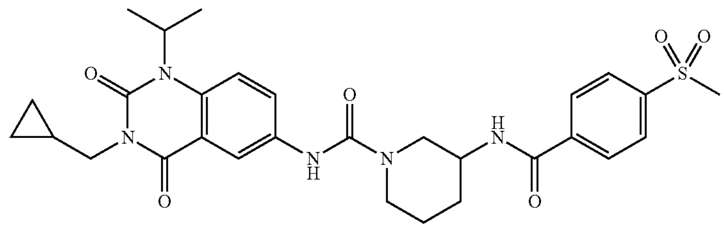 [SMILES: CC(C)n1c(=O)n(CC2CC2)c(=O)c2cc(NC(=O)N3CCCC(NC(=O)c4ccc(S(C)(=O)=O)cc4)C3)ccc21] | | 580.2 (M − H) |
| 105 | N-(3-(cyclopropyl-methyl)-1-isopropyl-2,4-dioxo-1,2,3,4-tetrahydroquinazolin-6-yl)-3-((3-(methyl-sulfonyl)benzoyl)amino)-piperidine-1-carboxamide | 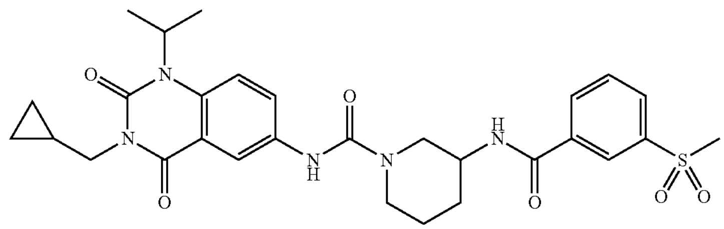 [SMILES: CC(C)n1c(=O)n(CC2CC2)c(=O)c2cc(NC(=O)N3CCCC(NC(=O)c4cccc(S(C)(=O)=O)c4)C3)ccc21] | | 582.3 (M + H) |
| 106 | methyl cis-5-((3-chloro-4-cyanophenyl)-carbamoyl)-1-((3-(cyclopropylmethyl)-1-isopropyl-2,4-dioxo-1,2,3,4-tetrahydro-quinazolin-6-yl)carbamoyl)piperidine-3-carboxylate | 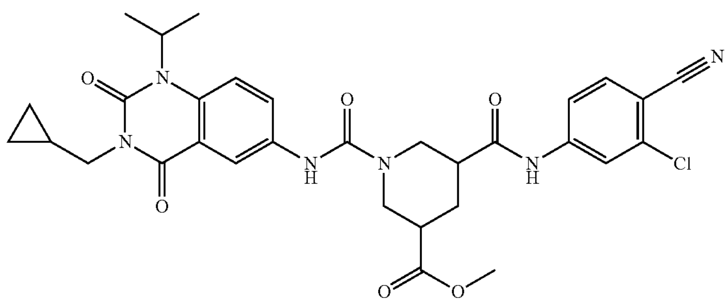 [SMILES: COC(=O)C1CC(C(=O)Nc2ccc(C#N)c(Cl)c2)CN(C(=O)Nc2ccc3c(c2)c(=O)n(CC2CC2)c(=O)n3C(C)C)C1] | | 619.3 (M − H) |
| 107 | cis-5-((3-chloro-4-cyanophenyl)carbamoyl)-1-((3-(cyclopropylmethyl)-1-isopropyl-2,4-dioxo-1,2,3,4-tetrahydroquinazolin-6-yl)carbamoyl)piperidine-3-carboxylic acid | 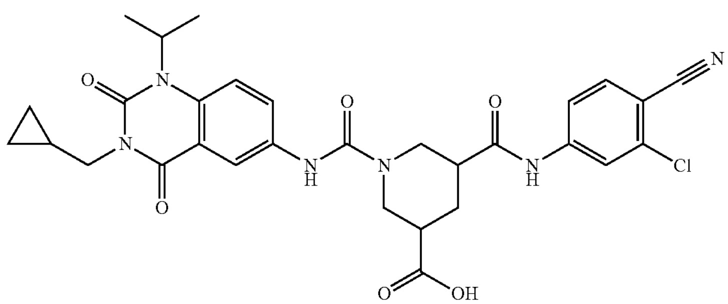 [SMILES: CC(C)n1c(=O)n(CC2CC2)c(=O)c2cc(NC(=O)N3CC(C(=O)O)CC(C(=O)Nc4ccc(C#N)c(Cl)c4)C3)ccc21] | | 605.3 (M − H) |
| 108 | cis-N³-(3-chloro-4-cyanophenyl)-N¹-(3-(cyclopropylmethyl)-1-isopropyl-2,4-dioxo-1,2,3,4-tetrahydroquinazolin-6-yl)piperidine-1,3,5-tricarboxamide | 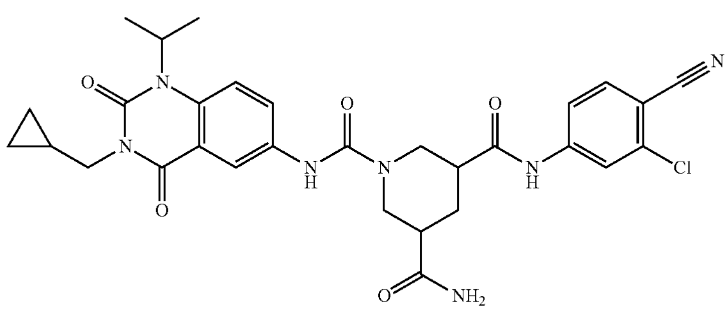 [SMILES: CC(C)n1c(=O)n(CC2CC2)c(=O)c2cc(NC(=O)N3CC(C(N)=O)CC(C(=O)Nc4ccc(C#N)c(Cl)c4)C3)ccc21] | | 604.3 (M − H) |

TABLE 1-11-continued

| Ex. | IUPAC name | Structure | salt | MS |
|---|---|---|---|---|
| 109 | tert-butyl (3S,5R)-3-((3-chloro-4-cyanobenzoyl)amino)-5-((3-(cyclopropylmethyl)-1-isopropyl-2,4-dioxo-1,2,3,4-tetrahydroquinazolin-6-yl)carbamoyl)piperidine-1-carboxylate | 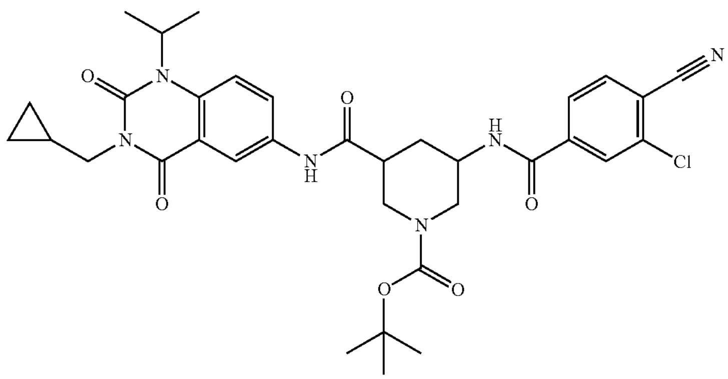 [SMILES: CC(C)n1c(=O)n(CC2CC2)c(=O)c2cc(NC(=O)C3CC(NC(=O)c4ccc(C#N)c(Cl)c4)CN(C(=O)OC(C)(C)C)C3)ccc21] | | 661.4 (M − H) |
| 110 | (3R,5S)-5-((3-chloro-4-cyanobenzoyl)amino)-N-(3-(cyclopropylmethyl)-1-isopropyl-2,4-dioxo-1,2,3,4-tetrahydroquinazolin-6-yl)-piperidine-3-carboxamide hydrochloride | 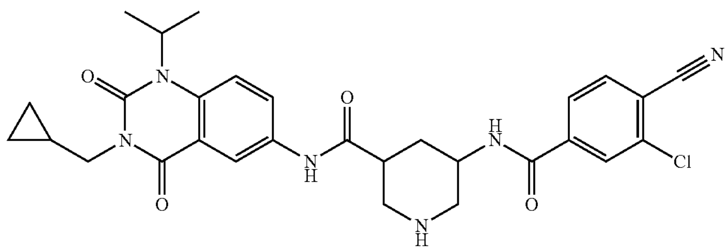 [SMILES: CC(C)n1c(=O)n(CC2CC2)c(=O)c2cc(NC(=O)C3CNCC(NC(=O)c4ccc(C#N)c(Cl)c4)C3)ccc21] | HCl | 563.2 (M − HCl + H) |

TABLE 1-12

| Ex. | IUPAC name | Structure | salt | MS |
|---|---|---|---|---|
| 111 | (3R,5S)-1-acetyl-5-((3-chloro-4-cyanobenzoyl)amino)-N-(3-(cyclopropylmethyl)-1-isopropyl-2,4-dioxo-1,2,3,4-tetrahydroquinazolin-6-yl)piperidine-3-carboxamide | 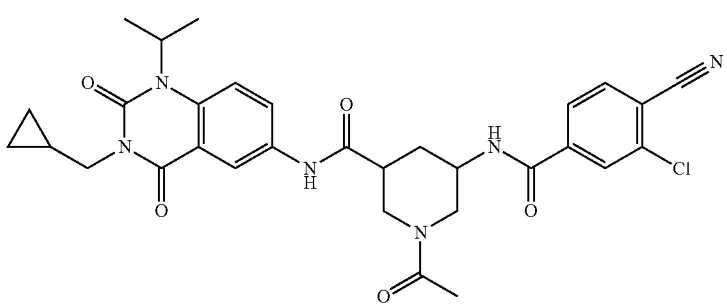 [SMILES: CC(=O)N1CC(NC(=O)c2ccc(C#N)c(Cl)c2)CC(C(=O)Nc2ccc3c(c2)c(=O)n(CC2CC2)c(=O)n3C(C)C)C1] | | 603.2 (M − H) |
| 112 | (3R,5S)-5-((3-chloro-4-cyanobenzoyl)amino)-N-(3-(cyclopropylmethyl)-1-isopropyl-2,4-dioxo-1,2,3,4-tetrahydroquinazolin-6-yl)-1-(methylsulfonyl)-piperidine-3-carboxamide | 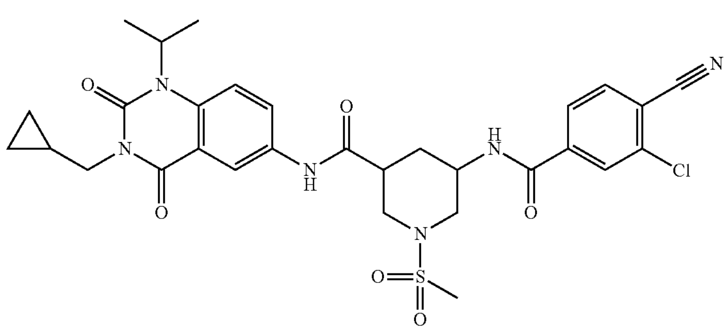 [SMILES: CC(C)n1c(=O)n(CC2CC2)c(=O)c2cc(NC(=O)C3CC(NC(=O)c4ccc(C#N)c(Cl)c4)CN(S(C)(=O)=O)C3)ccc21] | | 641.2 (M + H) |

TABLE 1-12-continued

| Ex. | IUPAC name | Structure | salt | MS |
|---|---|---|---|---|
| 113 | methyl 3-((1-((3-(cyclopropylmethyl)-1-isopropyl-2,4-dioxo-1,2,3,4-tetrahydroquinazolin-6-yl)carbamoyl)piperidin-3-yl)carbamoyl)benzoate | 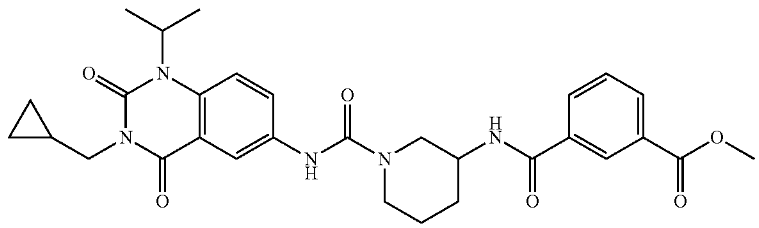 [SMILES: COC(=O)c1cccc(C(=O)NC2CCCN(C(=O)Nc3ccc4c(c3)c(=O)n(CC3CC3)c(=O)n4C(C)C)C2)c1] | | 562.2 (M + H) |
| 114 | N-(3-(cyclopropylmethyl)-1-isopropyl-2,4-dioxo-1,2,3,4-tetrahydroquinazolin-6-yl)-3-((3-vinylbenzoyl)amino)piperidine-1-carboxamide | 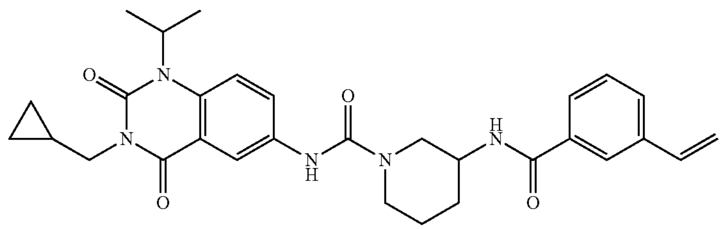 [SMILES: C=Cc1cccc(C(=O)NC2CCCN(C(=O)Nc3ccc4c(c3)c(=O)n(CC3CC3)c(=O)n4C(C)C)C2)c1] | | 530.2 (M + H) |
| 115 | $N^4$-(3-(cyclopropylmethyl)-1-isopropyl-2,4-dioxo-1,2,3,4-tetrahydroquinazolin-6-yl)-$N^2$-(3,4-dicyanophenyl)morpholine-2,4-dicarboxamide | 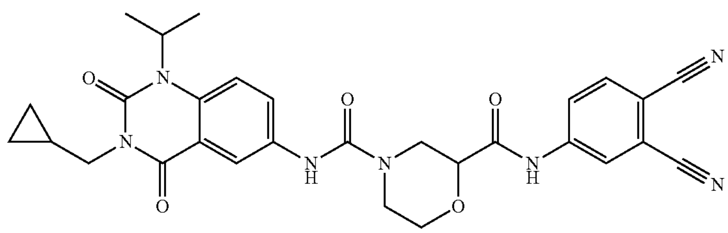 [SMILES: CC(C)n1c(=O)n(CC2CC2)c(=O)c2cc(NC(=O)N3CCOC(C(=O)Nc4ccc(C#N)c(C#N)c4)C3)ccc21] | | 556.2 (M + H) |
| 116 | ethyl 3-(((4-((3-(cyclopropylmethyl)-1-isopropyl-2,4-dioxo-1,2,3,4-tetrahydroquinazolin-6-yl)carbamoyl)morpholin-2-yl)carbonyl)amino)benzoate | 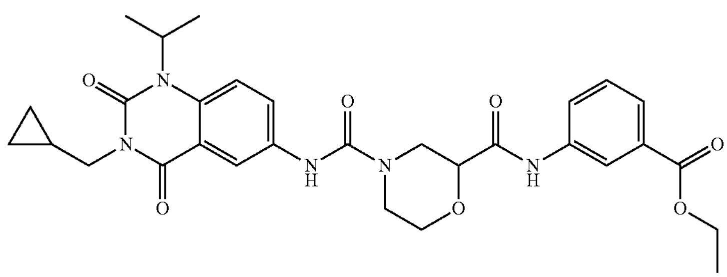 [SMILES: CCOC(=O)c1cccc(NC(=O)C2CN(C(=O)Nc3ccc4c(c3)c(=O)n(CC3CC3)c(=O)n4C(C)C)CCO2)c1] | | 578.2 (M + H) |
| 117 | $N^4$-(3-(cyclopropylmethyl)-1-isopropyl-2,4-dioxo-1,2,3,4-tetrahydroquinazolin-6-yl)-$N^2$-(3-vinylphenyl)morpholine-2,4-dicarboxamide | 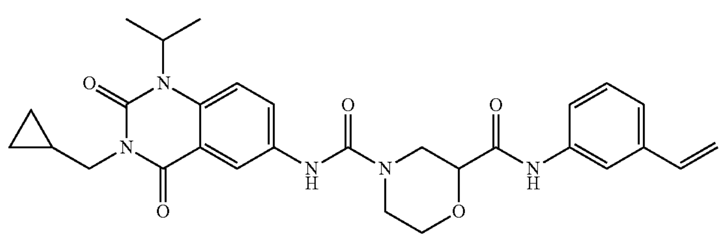 [SMILES: C=Cc1cccc(NC(=O)C2CN(C(=O)Nc3ccc4c(c3)c(=O)n(CC3CC3)c(=O)n4C(C)C)CCO2)c1] | | 532.2 (M + H) |
| 118 | $N^4$-(3-(cyclopropylmethyl)-1-isopropyl-2,4-dioxo-1,2,3,4-tetrahydroquinazolin-6-yl)-$N^2$-(3-(oxiran-2-yl)phenyl)morpholine-2,4-dicarboxamide | 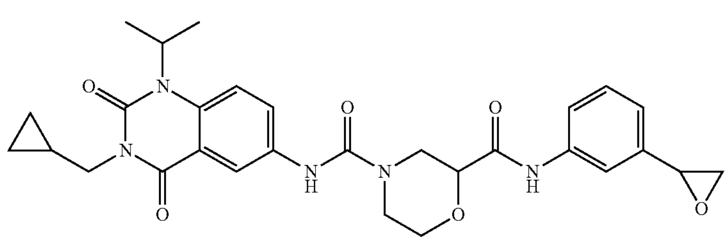 [SMILES: CC(C)n1c(=O)n(CC2CC2)c(=O)c2cc(NC(=O)N3CCOC(C(=O)Nc4cccc(C5CO5)c4)C3)ccc21] | | 546.2 (M − H) |

TABLE 1-12-continued

| Ex. | IUPAC name | Structure | salt | MS |
|---|---|---|---|---|
| 119 | (1R,3S)-N-(3-chloro-4-cyanophenyl)-N'-(3-(cyclopropylmethyl)-1-isopropyl-2,4-dioxo-1,2,3,4-tetrahydroquinazolin-6-yl)cyclohexane-1,3-dicarboxamide | 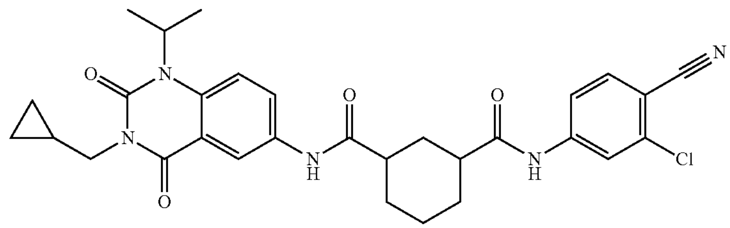 [SMILES: CC(C)n1c(=O)n(CC2CC2)c(=O)c2cc(NC(=O)C3CCCC(C(=O)Nc4ccc(C#N)c(Cl)c4)C3)ccc21] | | 560.2 (M − H) |
| 120 | 3-((3-chloro-4-cyanophenoxy)methyl)-N-(3-(cyclopropylmethyl)-1-isopropyl-2,4-dioxo-1,2,3,4-tetrahydroquinazolin-6-yl)-4-hydroxypiperidine-1-carboxamide | 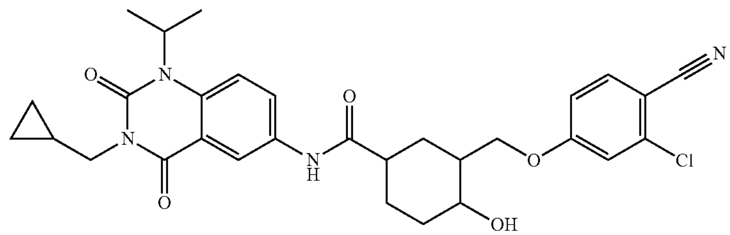 [SMILES: CC(C)n1c(=O)n(CC2CC2)c(=O)c2cc(NC(=O)C3CCC(O)C(COc4ccc(C#N)c(Cl)c4)C3)ccc21] | | 566.2 (M + H) |

TABLE 1-13

| Ex. | IUPAC name | Structure | salt | MS |
|---|---|---|---|---|
| 121 | 4-(3-chloro-4-cyanophenoxy)-N-(3-(cyclopropylmethyl)-1-isopropyl-2,4-dioxo-1,2,3,4-tetrahydroquinazolin-6-yl)-3-(hydroxymethyl)-piperidine-1-carboxamide | 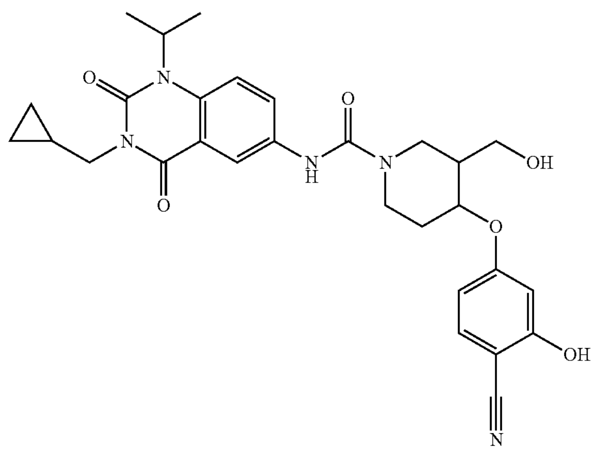 | | 566.2 (M + H) |
| 122 | (2R)-$N^2$-(5-chloro-6-cyanopyridin-3-yl)-$N^4$-(3-(cyclopropylmethyl)-1-isopropyl-2,4-dioxo-1,2,3,4-tetrahydroquinazolin-6-yl)morpholine-2,4-dicarboxamide | 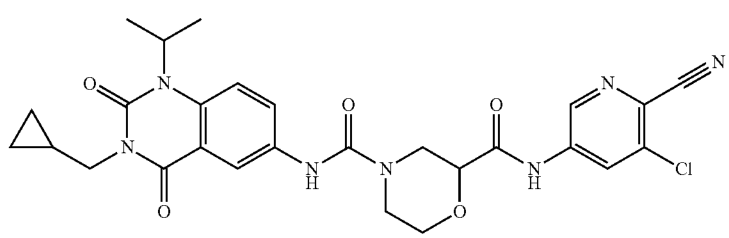 [SMILES: CC(C)n1c(=O)n(CC2CC2)c(=O)c2cc(NC(=O)N3CCOC(C(=O)Nc4cnc(C#N)c(Cl)c4)C3)ccc21] | | 564.1 (M − H) |
| 123 | 3-(benzoylamino)-N-(3-(cyclopropylmethyl)-1-isopropyl-2,4-dioxo-1,2,3,4-tetrahydroquinazolin-6-yl)piperidine-1-carboxamide | 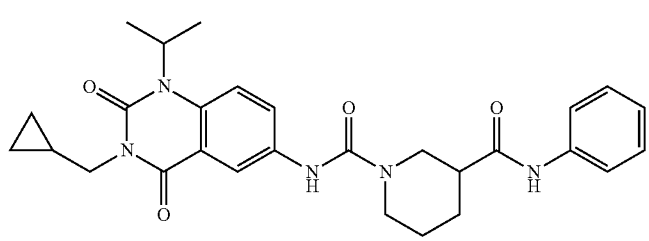 [SMILES: CC(C)n1c(=O)n(CC2CC2)c(=O)c2cc(NC(=O)N3CCCC(C(=O)Nc4ccccc4)C3)ccc21] | | 504.2 (M + H) |

TABLE 1-13-continued

| Ex. | IUPAC name | Structure | salt | MS |
|---|---|---|---|---|
| 124 | N-(3-(cyclopropylmethyl)-1-isopropyl-2,4-dioxo-1,2,3,4-tetrahydro-quinazolin-6-yl)-3-((3-methylbenzoyl)amino)-piperidine-1-carboxamide | 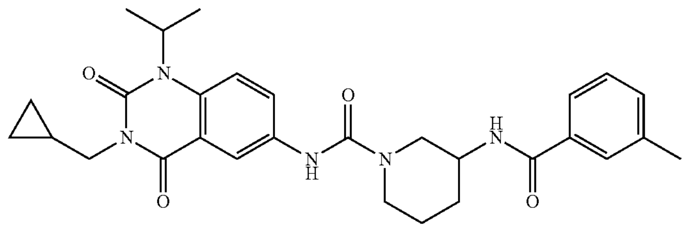 [SMILES: Cc1cccc(C(=O)NC2CCCN(C(=O)Nc3ccc4c(c3)c(=O)n(CC3CC3)c(=O)n4C(C)C)C2)c1] | | 518.2 (M + H) |
| 125 | 3-((3-cyclopropyl-benzoyl)amino)-N-(3-(cyclopropylmethyl)-1-isopropyl-2,4-dioxo-1,2,3,4-tetrahydroquinazolin-6-yl)piperidine-1-carboxamide | 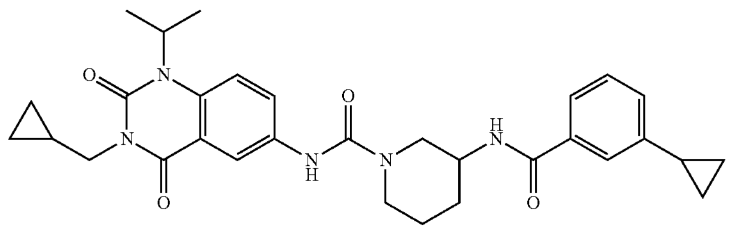 [SMILES: CC(C)n1c(=O)n(CC2CC2)c(=O)c2cc(NC(=O)N3CCCC(NC(=O)c4cccc(C5CC5)c4)C3)ccc21] | | 544.3 (M + H) |
| 126 | ethyl 3-(((1-((3-(cyclopropylmethyl)-1-isopropyl-2,4-dioxo-1,2,3,4-tetrahydroquinazolin-6-yl)carbamoyl)piperidin-3-yl)carbonyl)-amino)benzoate | 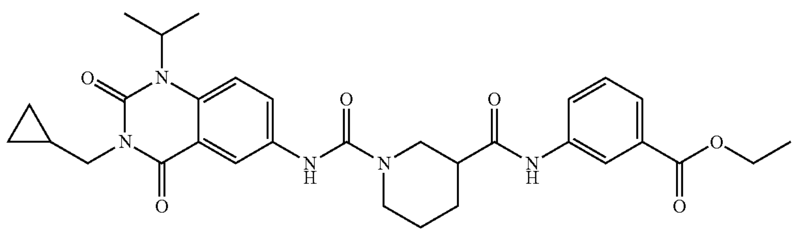 [SMILES: CCOC(=O)c1cccc(NC(=O)C2CCCN(C(=O)Nc3ccc4c(c3)c(=O)n(CC3CC3)c(=O)n4C(C)C)C2)c1] | | 576.2 (M + H) |
| 127 | $N^1$-(3-(cyclopropyl-methyl)-1-isopropyl-2,4-dioxo-1,2,3,4-tetrahydroquinazolin-6-yl)-$N^3$-(3-vinylphenyl)piperidine-1,3-dicarboxamide | 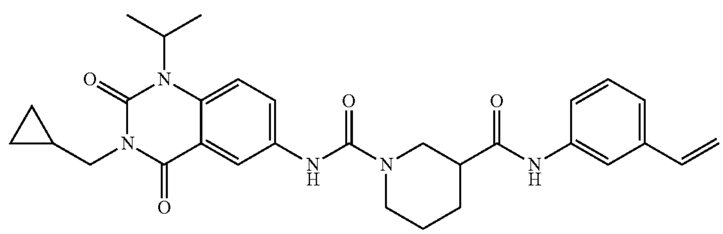 [SMILES: C=Cc1cccc(NC(=O)C2CCCN(C(=O)Nc3ccc4c(c3)c(=O)n(CC3CC3)c(=O)n4C(C)C)C2)c1] | | 530.2 (M + H) |
| 128 | methyl 3-(((1-((3-(cyclopropylmethyl)-1-isopropyl-2,4-dioxo-1,2,3,4-tetrahydroquinazolin-6-yl)carbamoyl)piperidin-2-yl)methyl)-carbamoyl)benzoate | 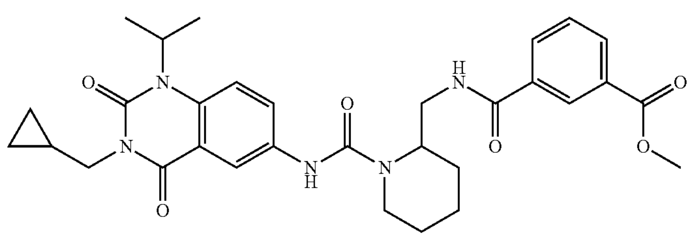 [SMILES: COC(=O)c1cccc(C(=O)NCC2CCCCN2C(=O)Nc2ccc3c(c2)c(=O)n(CC2CC2)c(=O)n3C(C)C)c1] | | 576.2 (M + H) |
| 129 | methyl 3-(((4-((3-(cyclopropylmethyl)-1-isopropyl-2,4-dioxo-1,2,3,4-tetrahydroquinazolin-6-yl)carbamoyl)morpholin-3-yl)methyl)-carbamoyl)benzoate | 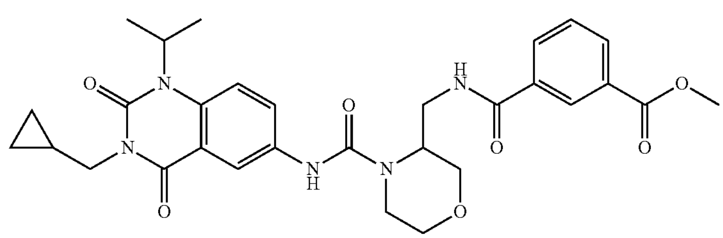 [SMILES: COC(=O)c1cccc(C(=O)NCC2COCCN2C(=O)Nc2ccc3c(c2)c(=O)n(CC2CC2)c(=O)n3C(C)C)c1] | | 578.2 (M + H) |

TABLE 1-13-continued

| Ex. | IUPAC name | Structure | salt | MS |
|---|---|---|---|---|
| 130 | methyl 3-((1-((3-(cyclopropylmethyl)-1-isopropyl-2,4-dioxo-1,2,3,4-tetrahydroquinazolin-6-yl)carbamoyl)piperidin-3-yl)methoxy)benzoate | 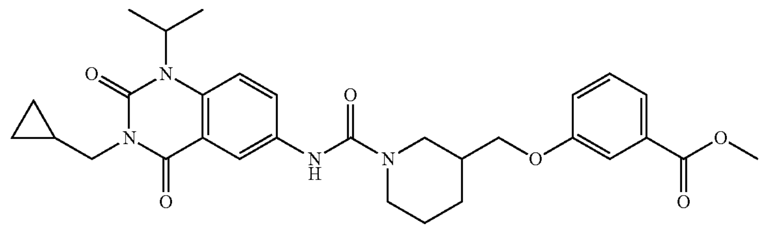 [SMILES: COC(=O)c1cccc(OCC2CCCN(C(=O)Nc3ccc4c(c3)c(=O)n(CC3CC3)c(=O)n4C(C)C)C2)c1] | | 549.3 (M + H) |

TABLE 1-14

| Ex. | IUPAC name | Structure | salt | MS |
|---|---|---|---|---|
| 131 | 3-((1-((3-(cyclopropylmethyl)-1-isopropyl-2,4-dioxo-1,2,3,4-tetrahydroquinazolin-6-yl)carbamoyl)piperidin-3-yl)carbamoyl)benzoic acid | 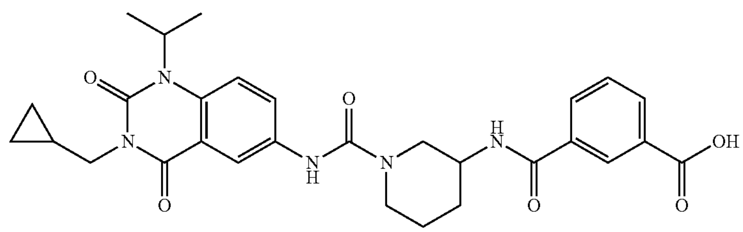 [SMILES: CC(C)n1c(=O)n(CC2CC2)c(=O)c2cc(NC(=O)N3CCCC(NC(=O)c4cccc(C(=O)O)c4)C3)ccc21] | | 548.2 (M + H) |
| 132 | methyl 4-((1-((3-(cyclopropylmethyl)-1-isopropyl-2,4-dioxo-1,2,3,4-tetrahydroquinazolin-6-yl)carbamoyl)piperidin-3-yl)carbamoyl)benzoate | 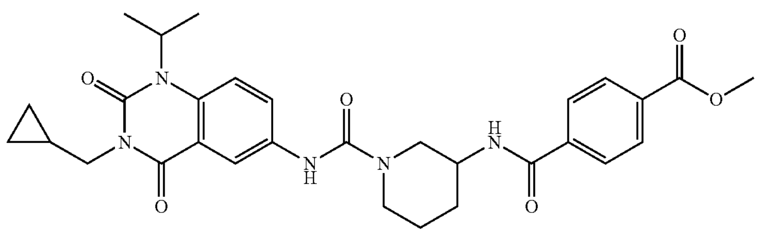 [SMILES: COC(=O)c1ccc(C(=O)NC2CCCN(C(=O)Nc3ccc4c(c3)c(=O)n(CC3CC3)c(=O)n4C(C)C)C2)cc1] | | 562.2 (M + H) |
| 133 | N-(3-(cyclopropyl-methyl)-1-isopropyl-2,4-dioxo-1,2,3,4-tetrahydroquinazolin-6-yl)-3-((4-vinylbenzoyl)-amino)piperidine-1-carboxamide | 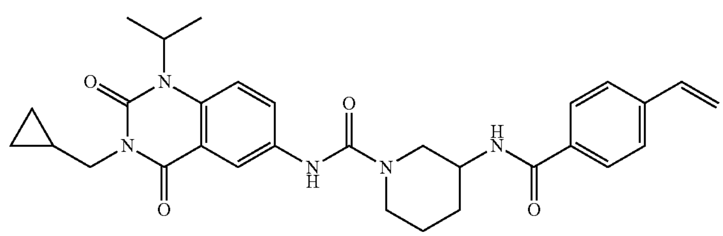 [SMILES: C=Cc1ccc(C(=O)NC2CCCN(C(=O)Nc3ccc4c(c3)c(=O)n(CC3CC3)c(=O)n4C(C)C)C2)cc1] | | 530.2 (M + H) |
| 134 | $N^2$-(3-chloro-4-cyano-2-fluorophenyl)-$N^4$-(3-(cyclopropylmethyl)-1-isopropyl-2,4-dioxo-1,2,3,4-tetrahydroquinazolin-6-yl)morpholine-2,4-dicarboxamide | 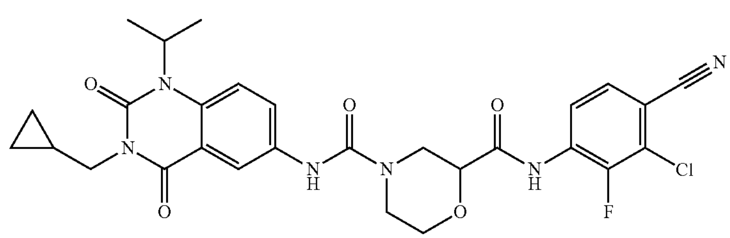 [SMILES: CC(C)n1c(=O)n(CC2CC2)c(=O)c2cc(NC(=O)N3CCOC(C(=O)Nc4ccc(C#N)c(Cl)c4F)C3)ccc21] | | 583.2 (M + H) |
| 135 | $N^2$-(4-cyano-2,5-difluorophenyl)-$N^4$-(3-(cyclopropylmethyl)-1-isopropyl-2,4-dioxo-1,2,3,4-tetrahydroquinazolin-6-yl)morpholine-2,4-dicarboxamide | 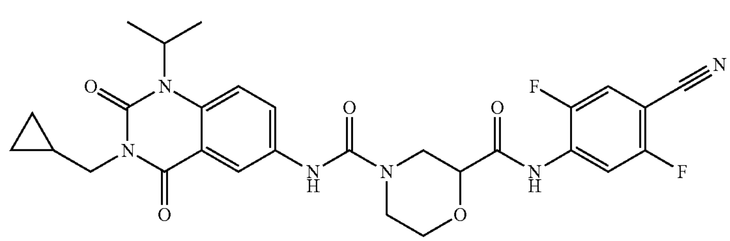 [SMILES: CC(C)n1c(=O)n(CC2CC2)c(=O)c2cc(NC(=O)N3CCOC(C(=O)Nc4cc(F)c(C#N)cc4F)C3)ccc21] | | 567.2 (M + H) |

TABLE 1-14-continued

| Ex. | IUPAC name | Structure | salt | MS |
|---|---|---|---|---|
| 136 | (3R)-3-(benzoylamino)-N-(3-(cyclopropylmethyl)-1-isopropyl-2,4-dioxo-1,2,3,4-tetrahydroquinazolin-6-yl)piperidine-1-carboxamide | 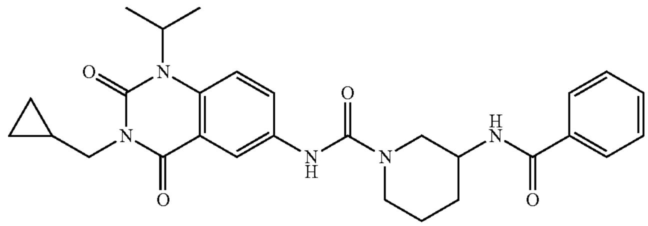 [SMILES: CC(C)n1c(=O)n(CC2CC2)c(=O)c2cc(NC(=O)N3CCCC(NC(=O)c4ccccc4)C3)ccc21] | | 504.2 (M + H) |
| 137 | N²-(4-cyano-3,5-difluorophenyl)-N⁴-(3-(cyclopropylmethyl)-1-isopropyl-2,4-dioxo-1,2,3,4-tetrahydroquinazolin-6-yl)morpholine-2,4-dicarboxamide | 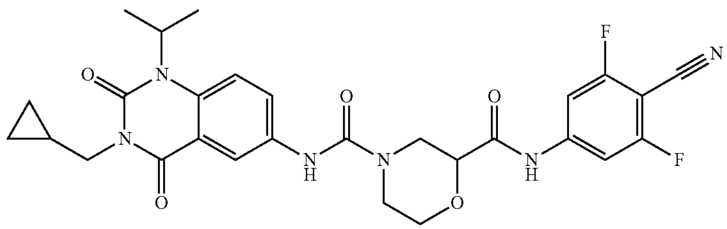 [SMILES: CC(C)n1c(=O)n(CC2CC2)c(=O)c2cc(NC(=O)N3CCOC(C(=O)Nc4cc(F)c(C#N)c(F)c4)C3)ccc21] | | 565.2 (M − H) |
| 138 | N-((1R,3S)-3-((3-(cyclopropylmethyl)-1-isopropyl-2,4-dioxo-1,2,3,4-tetrahydro-quinazolin-6-yl)-carbamoyl)cyclohexyl)-benzamide | 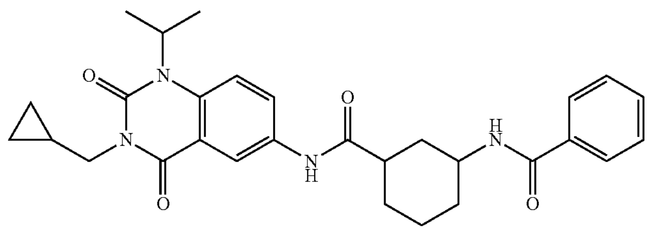 [SMILES: CC(C)n1c(=O)n(CC2CC2)c(=O)c2cc(NC(=O)C3CCCC(NC(=O)c4ccccc4)C3)ccc21] | | 503.2 (M + H) |
| 139 | N-(cis-2-((3-(cyclopropylmethyl)-1-isopropyl-2,4-dioxo-1,2,3,4-tetrahydro-quinazolin-6-yl)-carbamoyl)cyclopentyl)-benzamide | 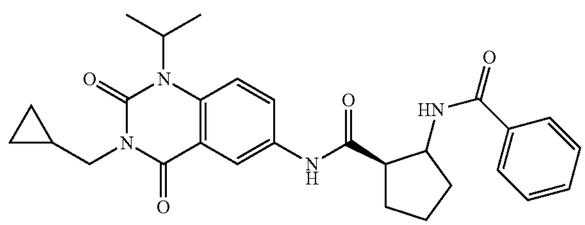 [SMILES: CC(C)n1c(=O)n(CC2CC2)c(=O)c2cc(NC(=O)[C@@H]3CCCC3NC(=O)c3ccccc3)ccc21] | | 489.2 (M + H) |
| 140 | cis-N-(3-(cyclopropylmethyl)-1-isopropyl-2,4-dioxo-1,2,3,4-tetrahydro-quinazolin-6-yl)-2-((phenylcarbamoyl)amino)cyclopentanecarboxamide | 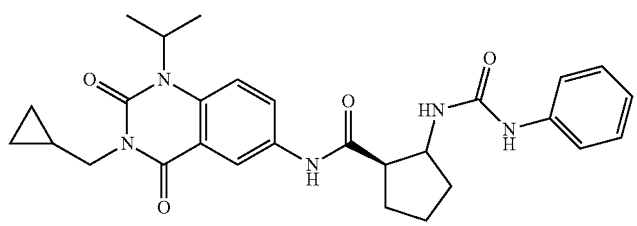 [SMILES: CC(C)n1c(=O)n(CC2CC2)c(=O)c2cc(NC(=O)[C@@H]3CCCC3NC(=O)Nc3ccccc3)ccc21] | | 504.3 (M + H) |

TABLE 1-15

| Ex. | IUPAC name | Structure | salt | MS |
|---|---|---|---|---|
| 141 | N²-(4-cyano-2,3-difluorophenyl)-N⁴-(3-(cyclopropylmethyl)-1-isopropyl-2,4-dioxo-1,2,3,4-tetrahydroquinazolin-6-yl)morpholine-2,4-dicarboxamide | 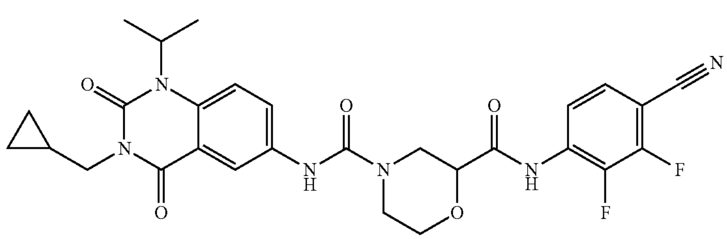 | | 567.2 (M + H) |

TABLE 1-15-continued

| Ex. | IUPAC name | Structure | salt | MS |
|---|---|---|---|---|
| 142 | 2-(5-cyano-1H-benzimidazol-2-yl)-N-(3-(cyclopropylmethyl)-1-isopropyl-2,4-dioxo-1,2,3,4-tetrahydroquinazolin-6-yl)morpholine-4-carboxamide | 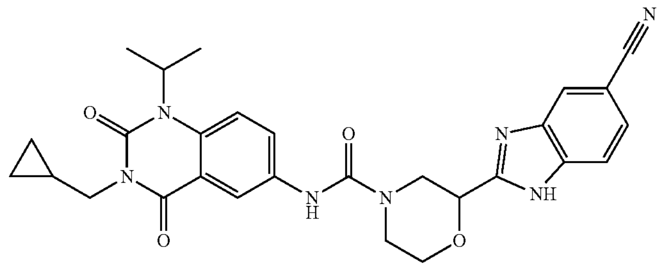 [SMILES: CC(C)n1c(=O)n(CC2CC2)c(=O)c2cc(NC(=O)N3CCOC(c4nc5cc(C#N)ccc5[nH]4)C3)ccc21] | | 526.2 (M − H) |
| 143 | N-(3-(cyclopropylmethyl)-1-isopropyl-2,4-dioxo-1,2,3,4-tetrahydroquinazolin-6-yl)-3-(1-oxo-1,3-dihydro-2H-isoindol-2-yl)piperidine-1-carboxamide | 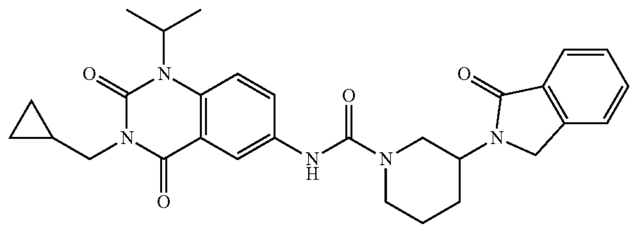 [SMILES: CC(C)n1c(=O)n(CC2CC2)c(=O)c2cc(NC(=O)N3CCCC(N4Cc5ccccc5C4=O)C3)ccc21] | | 516.3 (M + H) |
| 144 | N-(3-(cyclopropyl-methyl)-1-isopropyl-2,4-dioxo-1,2,3,4-tetra-hydroquinazolin-6-yl)-3-(5-phenyl-1,3,4-oxadiazol-2-yl)-piperidine-1-carboxamide | 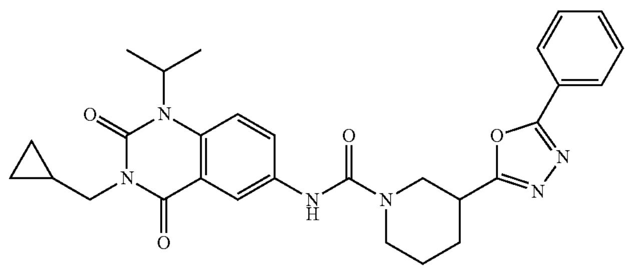 [SMILES: CC(C)n1c(=O)n(CC2CC2)c(=O)c2cc(NC(=O)N3CCCC(c4nnc(-c5ccccc5)o4)C3)ccc21] | | 529.2 (M + H) |
| 145 | N-(3-(cyclopropylmethyl)-1-isopropyl-2,4-dioxo-1,2,3,4-tetrahydroquinazolin-6-yl)-3-((phenylsulfonyl)amino)piperidine-1-carboxamide | 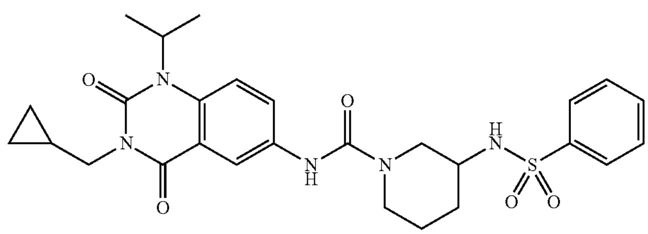 [SMILES: CC(C)n1c(=O)n(CC2CC2)c(=O)c2cc(NC(=O)N3CCCC(NS(=O)(=O)c4ccccc4)C3)ccc21] | | 538.2 (M − H) |
| 146 | N-(3-(cyclopropyl-methyl)-1-isopropyl-2,4-dioxo-1,2,3,4-tetrahydroquinazolin-6-yl)-3-((phenyl-carbamoyl)amino)piperidine-1-carboxamide | 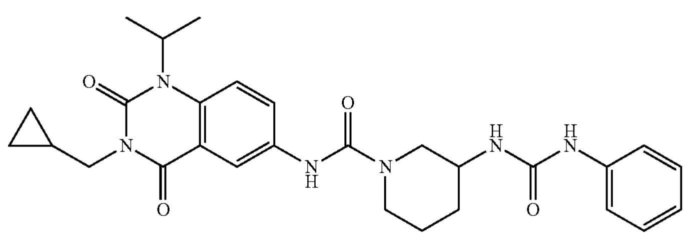 | | 519.2 (M + H) |
| 147 | (2R)-N$^2$-(4-cyano-3-fluorophenyl)-N$^4$-(1-isopropyl-3-(2-methoxyethyl)-2,4-dioxo-1,2,3,4-tetrahydroquinazolin-6-yl)morpholine-2,4-dicarboxamide | 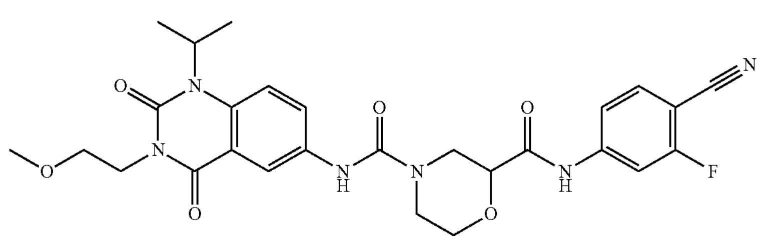 [SMILES: COCCn1c(=O)c2cc(NC(=O)N3CCOC(C(=O)Nc4ccc(C#N)c(F)c4)C3)ccc2n(C(C)C)c1=O] | | 553.2 (M + H) |

TABLE 1-15-continued

| Ex. | IUPAC name | Structure | salt | MS |
|---|---|---|---|---|
| 148 | N-(1-((3-(cyclopropylmethyl)-1-isopropyl-2,4-dioxo-1,2,3,4-tetrahydroquinazolin-6-yl)carbonyl)piperidin-3-yl)benzamide | 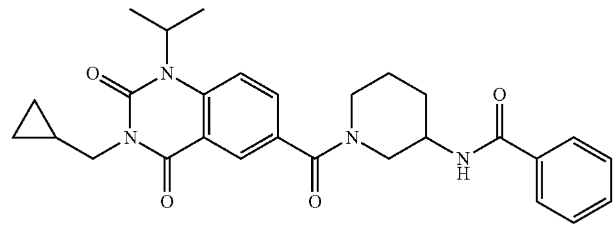 [SMILES: CC(C)n1c(=O)n(CC2CC2)c(=O)c2cc(C(=O)N3CCCC(NC(=O)c4ccccc4)C3)ccc21] | | 489.2 (M + H) |
| 149 | N-(3-(cyclopropylmethyl)-1-isopropyl-2,4-dioxo-1,2,3,4-tetrahydroquinazolin-6-yl)-3-(5-phenyl-1,3-oxazol-2-yl)piperidine-1-carboxamide | 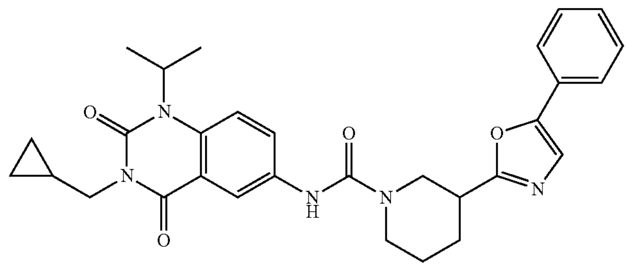 [SMILES: CC(C)n1c(=O)n(CC2CC2)c(=O)c2cc(NC(=O)N3CCCC(c4ncc(-c5ccccc5)o4)C3)ccc21] | | 528.2 (M + H) |
| 150 | N-(3-(cyclopropyl-methyl)-1-isopropyl-2,4-dioxo-1,2,3,4-tetrahydroquinazolin-6-yl)-3-((tetrahydro-2H-pyran-4-ylcarbonyl)-amino)piperidine-1-carboxamide | 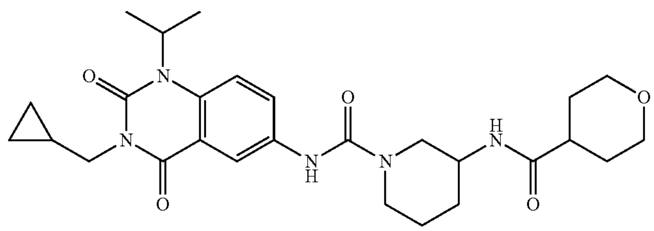 [SMILES: CC(C)n1c(=O)n(CC2CC2)c(=O)c2cc(NC(=O)N3CCCC(NC(=O)C4CCOCC4)C3)ccc21] | | 512.2 (M + H) |

TABLE 1-16

| Ex. | IUPAC name | Structure | salt | MS |
|---|---|---|---|---|
| 151 | N-(1-((3-(cyclopropylmethyl)-1-isopropyl-2,4-dioxo-1,2,3,4-tetrahydroquinazolin-6-yl)carbamoyl)piperidin-3-yl)-6-methylpyridine-2-carboxamide | 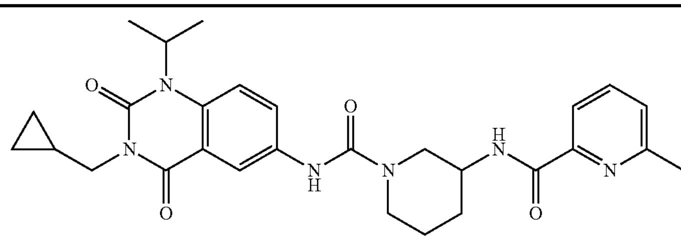 | | 519.2 (M + H) |
| 152 | N-(1-((3-(cyclopropylmethyl)-1-isopropyl-2,4-dioxo-1,2,3,4-tetrahydroquinazolin-6-yl)carbamoyl)piperidin-3-yl)-2-methylisonicotinamide | 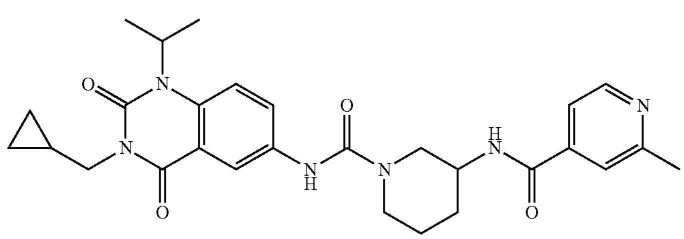 [SMILES: Cc1cc(C(=O)NC2CCCN(C(=O)Nc3ccc4c(c3)c(=O)n(CC3CC3)c(=O)n4C(C)C)C2)ccn1] | | 519.2 (M + H) |
| 153 | N-(1-((3-(cyclopropylmethyl)-1-isopropyl-2,4-dioxo-1,2,3,4-tetrahydroquinazolin-6-yl)carbamoyl)piperidin-3-yl)-5-methylnicotinamide | 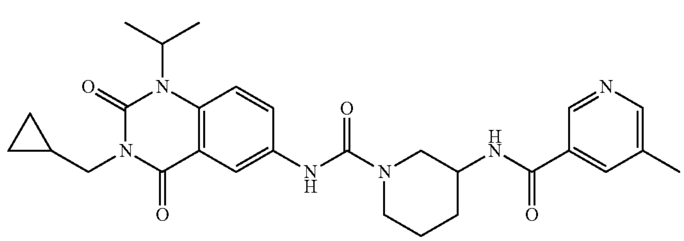 [SMILES: Cc1cncc(C(=O)NC2CCCN(C(=O)Nc3ccc4c(c3)c(=O)n(CC3CC3)c(=O)n4C(C)C)C2)c1] | | 519.3 (M + H) |

TABLE 1-16-continued

| Ex. | IUPAC name | Structure | salt | MS |
|---|---|---|---|---|
| 154 | N-(1-((3-(cyclopropylmethyl)-1-isopropyl-2,4-dioxo-1,2,3,4-tetrahydroquinazolin-6-yl)carbamoyl)piperidin-3-yl)-4-methylpyridine-2-carboxamide | 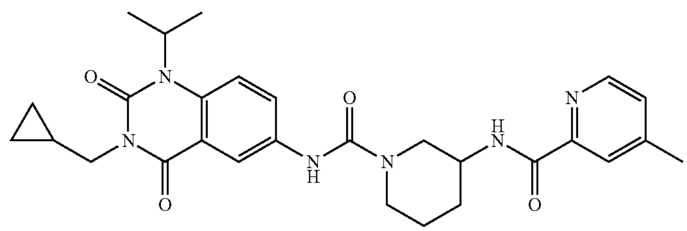 [SMILES: Cc1ccnc(C(=O)NC2CCCN(C(=O)Nc3ccc4c(c3)c(=O)n(CC3CC3)c(=O)n4C(C)C)C2)c1] | | 519.2 (M + H) |
| 155 | N-(1-((3-(cyclopropylmethyl)-1-isopropyl-2,4-dioxo-1,2,3,4-tetrahydroquinazolin-6-yl)carbamoyl)piperidin-3-yl)-6-hydroxynicotinamide | 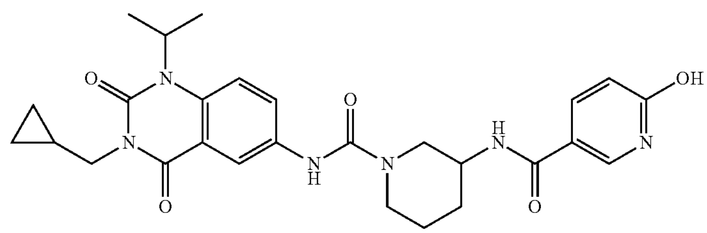 [SMILES: CC(C)n1c(=O)n(CC2CC2)c(=O)c2cc(NC(=O)N3CCCC(NC(=O)c4ccc(O)nc4)C3)ccc21] | | 521.2 (M + H) |
| 156 | N-(1-((3-(cyclopropylmethyl)-1-isopropyl-2,4-dioxo-1,2,3,4-tetrahydroquinazolin-6-yl)carbamoyl)piperidin-3-yl)-6-hydroxypyridine-2-carboxamide | 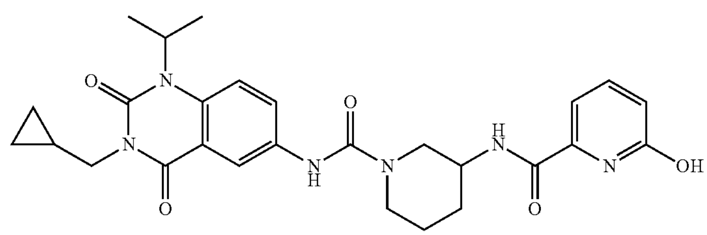 [SMILES: CC(C)n1c(=O)n(CC2CC2)c(=O)c2cc(NC(=O)N3CCCC(NC(=O)c4cccc(O)n4)C3)ccc21] | | 521.2 (M + H) |
| 157 | 6-cyano-N-(1-((3-(cyclopropylmethyl)-1-isopropyl-2,4-dioxo-1,2,3,4-tetrahydroquinazolin-6-yl)carbamoyl)piperidin-3-yl)nicotinamide | 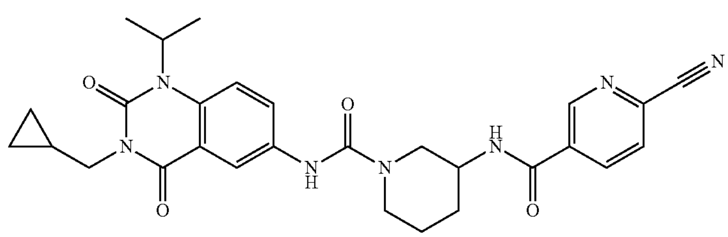 [SMILES: CC(C)n1c(=O)n(CC2CC2)c(=O)c2cc(NC(=O)N3CCCC(NC(=O)c4ccc(C#N)nc4)C3)ccc21] | | 530.2 (M + H) |
| 158 | N-(3-(cyclopropylmethyl)-1-isopropyl-2,4-dioxo-1,2,3,4-tetrahydroquinazolin-6-yl)-3-((hydroxy-(phenyl)acetyl)amino)-piperidine-1-carboxamide (mixture of 4 stereoisomers) | 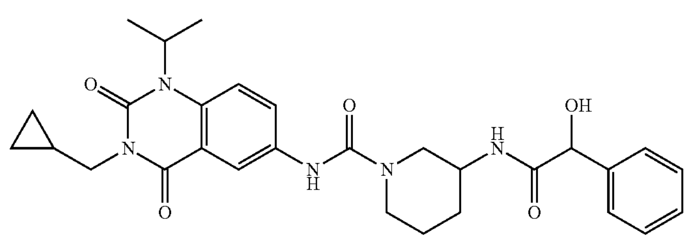 [SMILES: CC(C)n1c(=O)n(CC2CC2)c(=O)c2cc(NC(=O)N3CCCC(NC(=O)C(O)c4ccccc4)C3)ccc21] | | 534.3 (M + H) |
| 159 | N-(1-((3-(cyclopropylmethyl)-1-isopropyl-2,4-dioxo-1,2,3,4-tetrahydroquinazolin-6-yl)carbamoyl)piperidin-3-yl)-1-methyl-6-oxo-1,6-dihydropyridine-3-carboxamide | 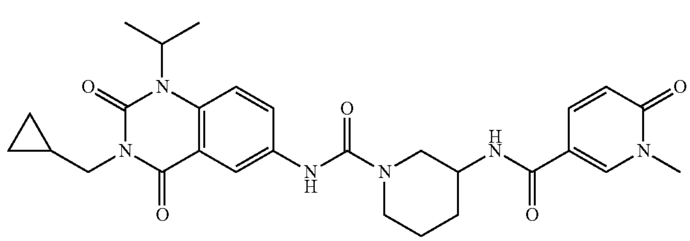 [SMILES: CC(C)n1c(=O)n(CC2CC2)c(=O)c2cc(NC(=O)N3CCCC(NC(=O)c4ccc(=O)n(C)c4)C3)ccc21] | | 535.2 (M + H) |

TABLE 1-16-continued

| Ex. | IUPAC name | Structure | salt | MS |
|---|---|---|---|---|
| 160 | 4-((1-((3-(cyclopropylmethyl)-1-isopropyl-2,4-dioxo-1,2,3,4-teterahydroquinazolin-6-yl)carbamoyl)piperidin-3-yl)carbamoyl)benzoic acid | 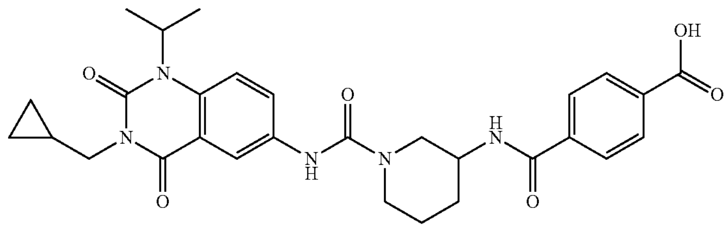 [SMILES: CC(C)n1c(=O)n(CC2CC2)c(=O)c2cc(NC(=O)N3CCCC(NC(=O)c4ccc(C(=O)O)cc4)C3)ccc21] | | 548.2 (M + H) |

TABLE 1-17

| Ex. | IUPAC name | Structure | salt | MS |
|---|---|---|---|---|
| 161 | 3-(((1-acetylpiperidin-4-yl)carbonyl)amino)-N-(3-(cyclopropylmethyl)-1-isopropyl-2,4-dioxo-1,2,3,4-tetrahydroquinazolin-6-yl)piperidine-1-carboxamide | 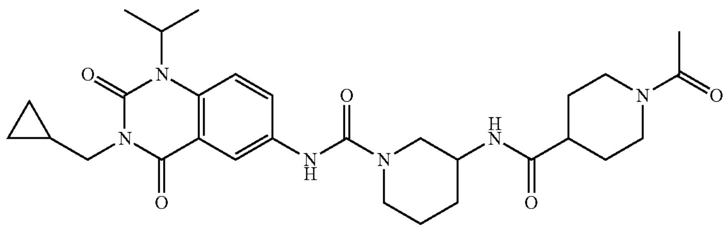 [SMILES: CC(=O)N1CCC(C(=O)NC2CCCN(C(=O)Nc3ccc4c(c3)c(=O)n(CC3CC3)c(=O)n4C(C)C)C2)CC1] | | 553.3 (M + H) |
| 162 | N-(3-(cyclopropyl-methyl)-1-isopropyl-2,4-dioxo-1,2,3,4-tetrahydroquinazolin-6-yl)-3-((3-(3-hydroxy-1,2-oxazol-5-yl)-propanoyl)amino)-piperidine-1-carboxamide | 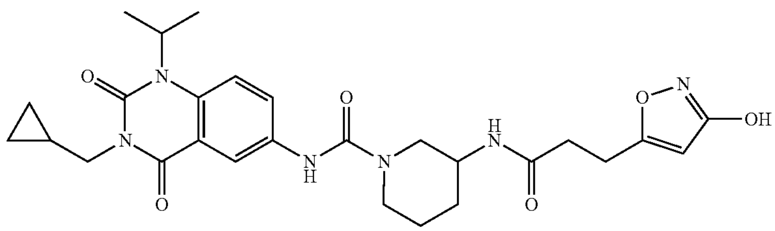 [SMILES: CC(C)n1c(=O)n(CC2CC2)c(=O)c2cc(NC(=O)N3CCCC(NC(=O)CCc4cc(O)no4)C3)ccc21] | | 539.3 (M + H) |
| 163 | 6-acetyl-N-(1-((3-(cyclopropylmethyl)-1-isopropyl-2,4-dioxo-1,2,3,4-tetrahydro-quinazolin-6-yl)carbamoyl)piperidin-3-yl)pyridine-2-carboxamide | 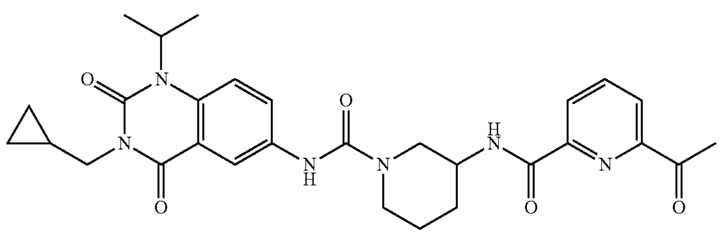 [SMILES: CC(=O)c1cccc(C(=O)NC2CCCN(C(=O)Nc3ccc4c(c3)c(=O)n(CC3CC3)c(=O)n4C(C)C)C2)n1] | | 547.2 (M + H) |
| 164 | N-(1-((4-cyano-3-fluorophenyl)carbamoyl)-piperidin-3-yl)-3-(cyclopropylmethyl)-1-isopropyl-2,4-dioxo-1,2,3,4-tetrahydroquinazoline-6-carboxamide | 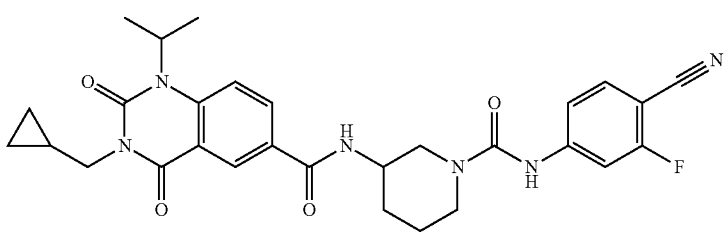 [SMILES: CC(C)n1c(=O)n(CC2CC2)c(=O)c2cc(C(=O)NC3CCCN(C(=O)Nc4ccc(C#N)c(F)c4)C3)ccc21] | | 547.2 (M + H) |
| 165 | N-((2R)-2-((3-chloro-4-cyanophenyl)carbamoyl)-morpholin-4-yl)-3-(cyclopropylmethyl)-1-isopropyl-2,4-dioxo-1,2,3,4-tetrahydro-quinazoline-6-carboxamide | 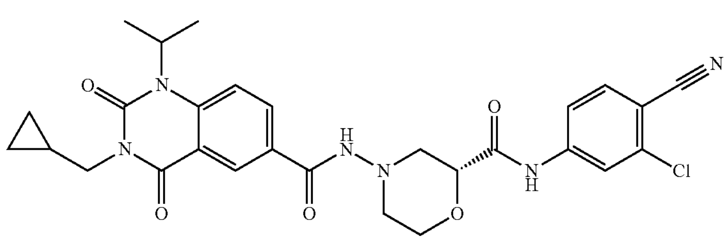 [SMILES: CC(C)n1c(=O)n(CC2CC2)c(=O)c2cc(C(=O)NN3CCO[C@@H](C(=O)Nc4ccc(C#N)c(Cl)c4)C3)ccc21] | | 565.2 (M + H) |

TABLE 1-17-continued

| Ex. | IUPAC name | Structure | salt | MS |
|---|---|---|---|---|
| 166 | N-(3-(cyclopropyl-methyl)-1-isopropyl-2,4-dioxo-1,2,3,4-tetrahydroquinazolin-6-yl)-3-(1-oxo-3,4-dihydroisoquinolin-2(1H)-yl)piperidine-1-carboxamide | 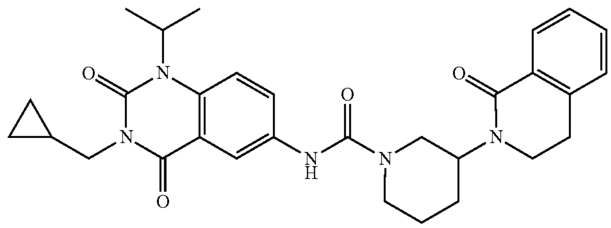 [SMILES: CC(C)n1c(=O)n(CC2CC2)c(=O)c2cc(NC(=O)N3CCCC(N4CCc5ccccc5C4=O)C3)ccc21] | | 530.2 (M + H) |
| 167 | (2R)-$N^2$-(4-cyano-3-fluorophenyl)-$N^4$-(3-(2,2-difluoroethyl)-1-isopropyl-2,4-dioxo-1,2,3,4-tetrahydro-quinazolin-6-yl)morpholine-2,4-dicarboxamide | 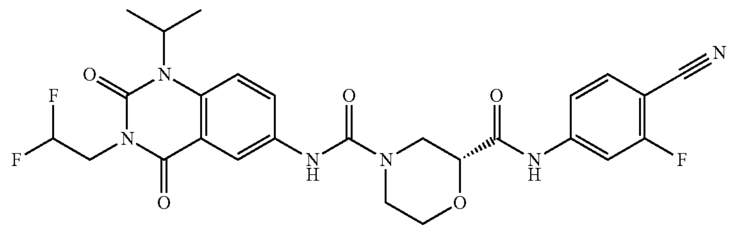 [SMILES: CC(C)n1c(=O)n(CC(F)F)c(=O)c2cc(NC(=O)N3CCO[C@@H](C(=O)Nc4ccc(C#N)c(F)c4)C3)ccc21] | | 559.1 (M − H) |
| 168 | (2R)-$N^2$-(4-cyano-2,5-difluorophenyl)-$N^4$-(3-(cyclopropylmethyl)-1-isopropyl-2,4-dioxo-1,2,3,4-tetrahydroquinazolin-6-yl)morpholine-2,4-dicarboxamide | 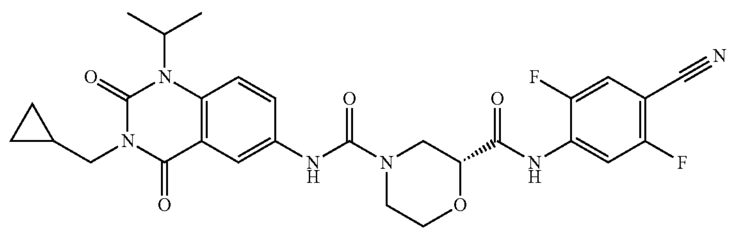 [SMILES: CC(C)n1c(=O)n(CC2CC2)c(=O)c2cc(NC(=O)N3CCO[C@@H](C(=O)Nc4cc(F)c(C#N)cc4F)C3)ccc21] | | 567.2 (M + H) |
| 169 | (2R)-$N^2$-(4-cyano-3-fluorophenyl)-$N^4$-(3-ethyl-7-fluoro-1-isopropyl-2,4-dioxo-1,2,3,4-tetrahydroquinazolin-6-yl)morpholine-2,4-dicarboxamide | 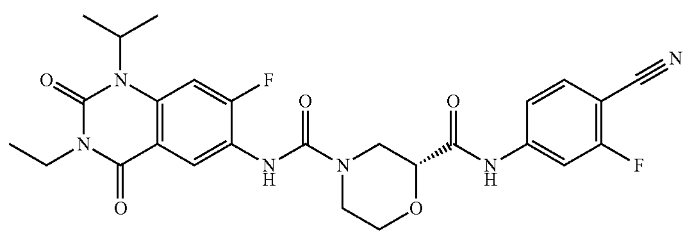 [SMILES: CCn1c(=O)c2cc(NC(=O)N3CCO[C@@H](C(=O)Nc4ccc(C#N)c(F)c4)C3)c(F)cc2n(C(C)C)c1=O] | | 541.2 (M + H) |
| 170 | (2R)-$N^2$-(4-cyano-2,5-difluorophenyl)-$N^4$-(3-ethyl-7-fluoro-1-isopropyl-2,4-dioxo-1,2,3,4-tetrahydroquinazolin-6-yl)morpholine-2,4-dicarboxamide | 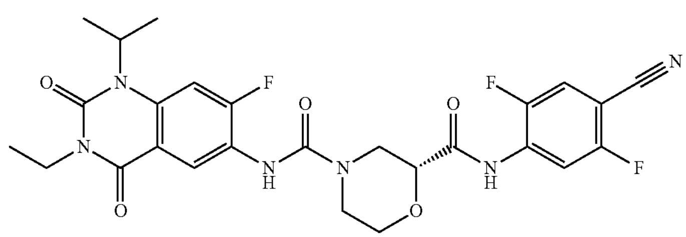 [SMILES: CCn1c(=O)c2cc(NC(=O)N3CCO[C@@H](C(=O)Nc4cc(F)c(C#N)cc4F)C3)c(F)cc2n(C(C)C)c1=O] | | 559.1 (M + H) |

TABLE 1-18

| Ex. | IUPAC name | Structure | salt | MS |
|---|---|---|---|---|
| 171 | (2R)-$N^2$-(4-cyano-2,5-difluorophenyl)-$N^4$-(3-(cyclopropylmethyl)-7-fluoro-1-isopropyl-2,4-dioxo-1,2,3,4-tetrahydroquinazolin-6-yl)morpholine-2,4-dicarboxamide | 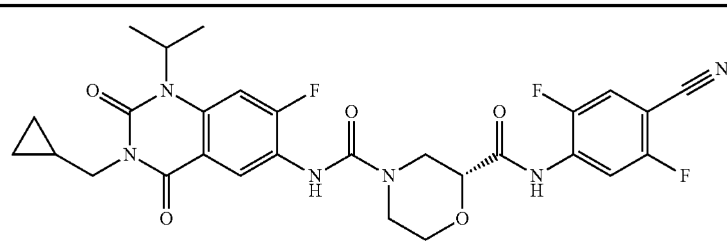 | | 585.2 (M + H) |

TABLE 1-18-continued

| Ex. | IUPAC name | Structure | salt | MS |
|---|---|---|---|---|
| 172 | (2R)-N²-(4-cyano-3-fluorophenyl)-N⁴-(3-(cyclopropylmethyl)-7-fluoro-1-isopropyl-2,4-dioxo-1,2,3,4-tetrahydroquinazolin-6-yl)morpholine-2,4-dicarboxamide | 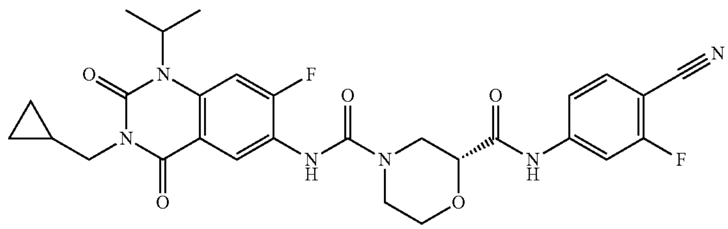 | | 565.2 (M − H) |
| 173 | (2R)-N-(4-cyano-3-fluorophenyl)-4-((3-(cyclopropylmethyl)-1-isopropyl-2,4-dioxo-1,2,3,4-tetrahydroquinazolin-6-yl)acetyl)morpholine-2-carboxamide | 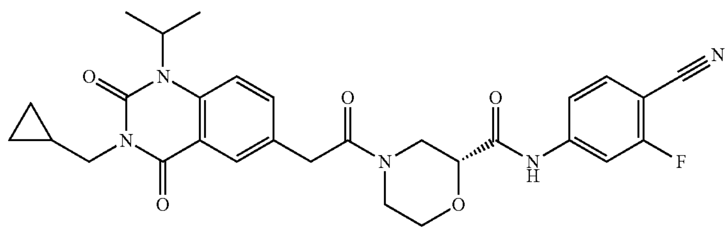 [SMILES: CC(C)n1c(=O)n(CC2CC2)c(=O)c2cc(CC(=O)N3CCO[C@@H](C(=O)Nc4ccc(C#N)c(F)c4)C3)ccc21] | | 546.2 (M − H) |
| 174 | N-(3-(cyclopropylmethyl)-1-isopropyl-2,4-dioxo-1,2,3,4-tetrahydroquinazolin-6-yl)-3-(((1-methyl-1H-pyrazol-3-yl)carbonyl)amino)piperidine-1-carboxamide | 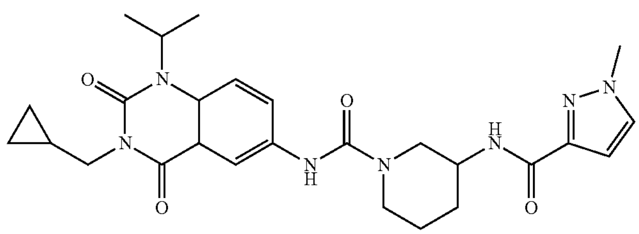 [SMILES: CC(C)N1C(=O)N(CC2CC2)C(=O)C2C=C(NC(=O)N3CCCC(NC(=O)c4ccn(C)n4)C3)C=CC21] | | 508.3 (M + H) |
| 175 | N-(3-(cyclopropylmethyl)-1-isopropyl-2,4-dioxo-1,2,3,4-tetrahydroquinazolin-6-yl)-3-(((1-methyl-1H-pyrazol-4-yl)carbonyl)amino)piperidine-1-carboxamide | 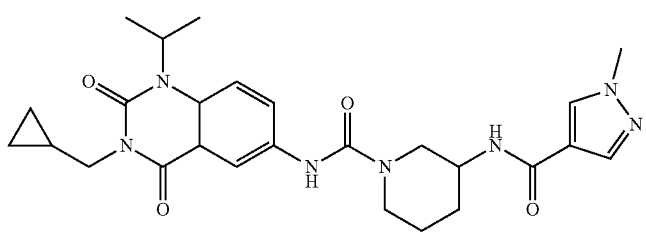 [SMILES: CC(C)N1C(=O)N(CC2CC2)C(=O)C2C=C(NC(=O)N3CCCC(NC(=O)c4cnn(C)c4)C3)C=CC21] | | 508.3 (M + H) |
| 176 | N²-(4-cyano-3-fluorophenyl)-N⁴-(3-(cyclopropylmethyl)-1-isopropyl-2,4-dioxo-1,2,3,4-tetrahydroquinazolin-6-yl)morpholine-2,4-dicarboxamide | 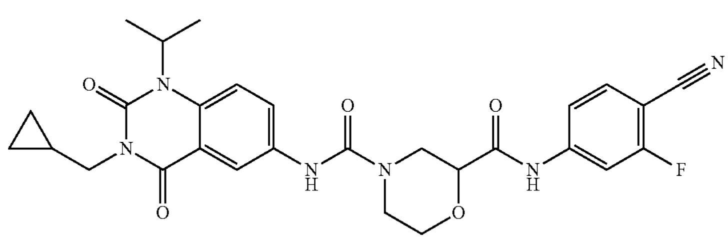 [SMILES: CC(C)n1c(=O)n(CC2CC2)c(=O)c2cc(NC(=O)N3CCOC(C(=O)Nc4ccc(C#N)c(F)c4)C3)ccc21] | | 547.2 (M − H) |
| 177 | N⁴-(3-(cyclopropylmethyl)-1-isopropyl-2,4-dioxo-1,2,3,4-tetrahydroquinazolin-6-yl)-N²-phenylmorpholine-2,4-dicarboxamide | 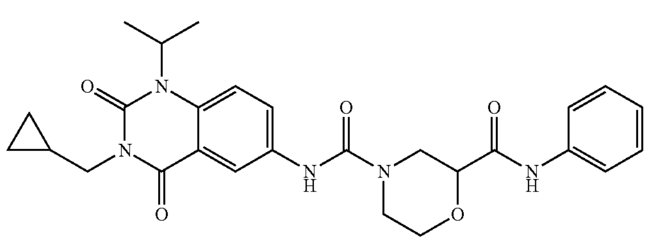 [SMILES: CC(C)n1c(=O)n(CC2CC2)c(=O)c2cc(NC(=O)N3CCOC(C(=O)Nc4ccccc4)C3)ccc21] | | 506.2 (M + H) |

TABLE 1-18-continued

| Ex. | IUPAC name | Structure | salt | MS |
|---|---|---|---|---|
| 178 | 3-((benzoylamino)methyl)-N-(3-(cyclopropylmethyl)-1-isopropyl-2,4-dioxo-1,2,3,4-tetrahydroquinazolin-6-yl)piperidine-1-carboxamide | 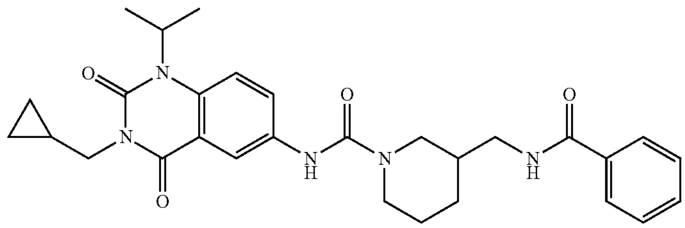 [SMILES: CC(C)n1c(=O)n(CC2CC2)c(=O)c2cc(NC(=O)N3CCCC(CNC(=O)c4ccccc4)C3)ccc21] | | 518.2 (M + H) |
| 179 | 3-(2-anilino-2-oxoethyl)-N-(3-(cyclopropylmethyl)-1-isopropyl-2,4-dioxo-1,2,3,4-tetrahydroquinazolin-6-yl)piperidine-1-carboxamide | 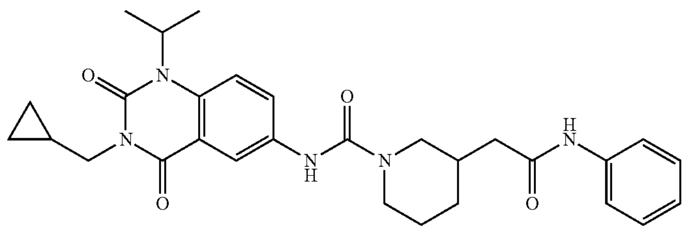 [SMILES: CC(C)n1c(=O)n(CC2CC2)c(=O)c2cc(NC(=O)N3CCCC(CC(=O)Nc4ccccc4)C3)ccc21] | | 518.2 (M + H) |
| 180 | 3-((4-cyanobenzoyl)amino)-N-(3-(cyclopropylmethyl)-1-isopropyl-2,4-dioxo-1,2,3,4-tetrahydroquinazolin-6-yl)piperidine-1-carboxamide | 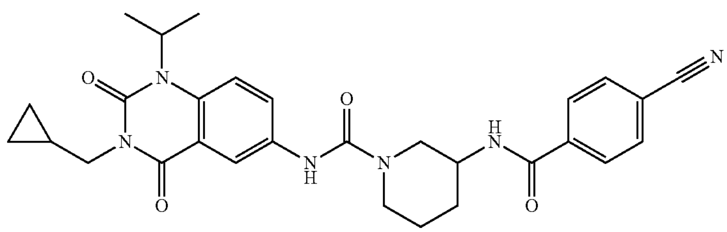 [SMILES: CC(C)n1c(=O)n(CC2CC2)c(=O)c2cc(NC(=O)N3CCCC(NC(=O)c4ccc(C#N)cc4)C3)ccc21] | | 527.2 (M − H) |

TABLE 1-19

| Ex. | IUPAC name | Structure | salt | MS |
|---|---|---|---|---|
| 181 | 4-(benzoylamino)-N-(3-(cyclopropylmethyl)-1-isopropyl-2,4-dioxo-1,2,3,4-tetrahydroquinazolin-6-yl)morpholine-2-carboxamide | 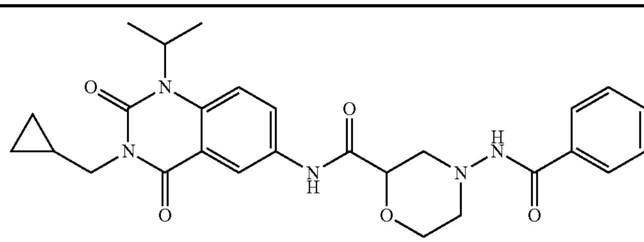 | | 506.2 (M + H) |
| 182 | N-(1-((5-chloro-6-cyanopyridin-3-yl)carbamoyl)piperidin-3-yl)-3-(cyclopropylmethyl)-1-isopropyl-2,4-dioxo-1,2,3,4-tetrahydroquinazoline-6-carboxamide | 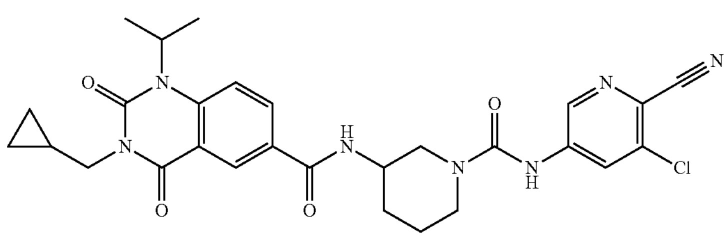 [SMILES: CC(C)n1c(=O)n(CC2CC2)c(=O)c2cc(C(=O)NC3CCCN(C(=O)Nc4cnc(C#N)c(Cl)c4)C3)ccc21] | | 564.1 (M + H) |
| 183 | 3-(cyclopropylmethyl)-1-isopropyl-2,4-dioxo-N-(1-(phenylcarbamoyl)piperidin-3-yl)-1,2,3,4-tetrahydroquinazoline-6-carboxamide | 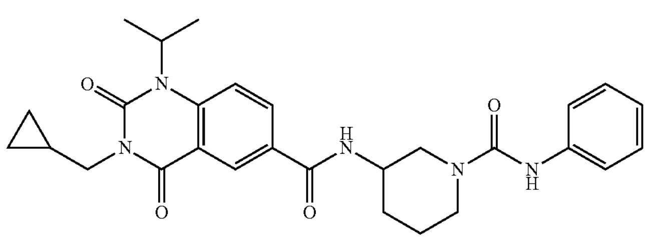 [SMILES: CC(C)n1c(=O)n(CC2CC2)c(=O)c2cc(C(=O)NC3CCCN(C(=O)Nc4ccccc4)C3)ccc21] | | 504.2 (M + H) |

TABLE 1-19-continued

| Ex. | IUPAC name | Structure | salt | MS |
|---|---|---|---|---|
| 184 | N-(3-(cyclopropylmethyl)-1-isopropyl-2,4-dioxo-1,2,3,4-tetrahydroquinazolin-6-yl)-4-phenyl-1,4-diazepane-1-carboxamide | 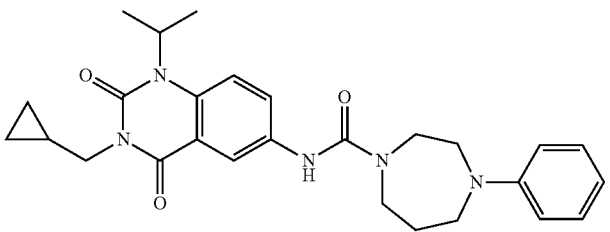 [SMILES: CC(C)n1c(=O)n(CC2CC2)c(=O)c2cc(NC(=O)N3CCCN(c4ccccc4)CC3)ccc21] | | 476.3 (M + H) |
| 185 | N-(3-(cyclopropyl-methyl)-1-isopropyl-2,4-dioxo-1,2,3,4-tetrahydroquinazolin-6-yl)-N'-phenyl-1,4-diazepane-1,4-dicarboxamide | 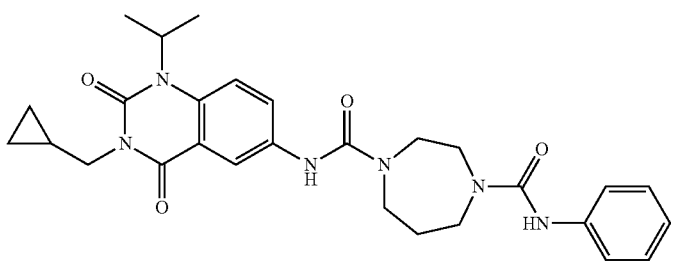 [SMILES: CC(C)n1c(=O)n(CC2CC2)c(=O)c2cc(NC(=O)N3CCCN(C(=O)Nc4ccccc4)CC3)ccc21] | | 519.3 (M + H) |
| 186 | N-(cis-2-((3-(cyclopropylmethyl)-1-isopropyl-2,4-dioxo-1,2,3,4-tetrahydro-quinazolin-6-yl)-carbamoyl)cyclohexyl)-benzamide | 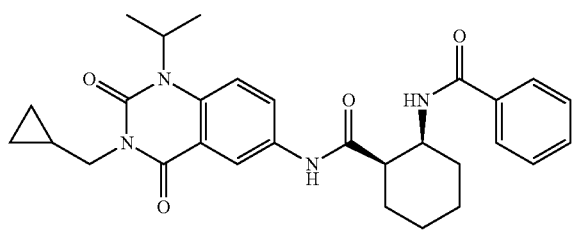 [SMILES: CC(C)n1c(=O)n(CC2CC2)c(=O)c2cc(NC(=O)[C@@H]3CCCC[C@@H]3NC(=O)c3ccccc3)ccc21] | | 503.3 (M + H) |
| 187 | cis-N-(3-(cyclopropyl-methyl)-1-isopropyl-2,4-dioxo-1,2,3,4-tetrahydroquinazolin-6-yl)-2-((phenyl-carbamoyl)amino)-cyclohexanecarboxamide | 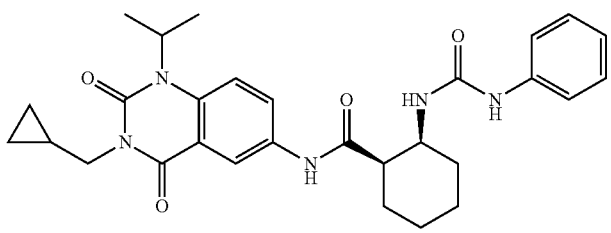 [SMILES: CC(C)n1c(=O)n(CC2CC2)c(=O)c2cc(NC(=O)[C@@H]3CCCC[C@@H]3NC(=O)Nc3ccccc3)ccc21] | | 518.3 (M + H) |
| 188 | N-(trans-2-((3-(cyclopropylmethyl)-1-isopropyl-2,4-dioxo-1,2,3,4-tetrahydro-quinazolin-6-yl)-carbamoyl)cyclohexyl)-benzamide | 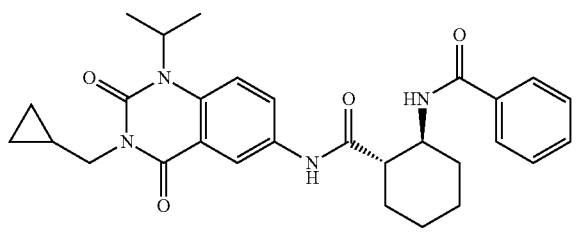 [SMILES: CC(C)n1c(=O)n(CC2CC2)c(=O)c2cc(NC(=O)[C@H]3CCCC[C@@H]3NC(=O)c3ccccc3)ccc21] | | 503.3 (M + H) |
| 189 | trans-N-(3-(cyclopropylmethyl)-1-isopropyl-2,4-dioxo-1,2,3,4-tetrahydroquinazolin-6-yl)-2-((phenyl-carbamoyl)amino)-cyclohexanecarboxamide | 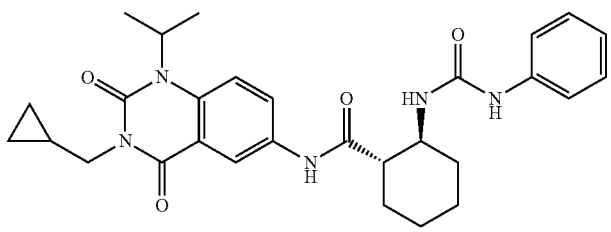 [SMILES: CC(C)n1c(=O)n(CC2CC2)c(=O)c2cc(NC(=O)[C@H]3CCCC[C@@H]3NC(=O)Nc3ccccc3)ccc21] | | 518.3 (M + H) |

TABLE 1-19-continued

| Ex. | IUPAC name | Structure | salt | MS |
|---|---|---|---|---|
| 190 | N-((2S)-2-((3-chloro-4-cyanophenyl)carbamoyl)-morpholin-4-yl)-3-(cyclopropylmethyl)-1-isopropyl-2,4-dioxo-1,2,3,4-tetrahydro-quinazoline-6-carboxamide | 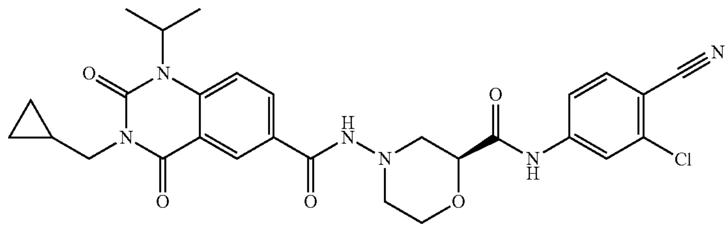 [SMILES: CC(C)n1c(=O)n(CC2CC2)c(=O)c2cc(C(=O)NN3CCO[C@H](C(=O)Nc4ccc(C#N)c(Cl)c4)C3)ccc21] | | 565.3 (M + H) |

TABLE 1-20

| Ex. | IUPAC name | Structure | salt | MS |
|---|---|---|---|---|
| 191 | trans-N-(3-(cyclo-propylmethyl)-1-isopropyl-2,4-dioxo-1,2,3,4-tetrahydro-quinazolin-6-yl)-2-((phenylcarbamoyl)amino)cyclopentanecarboxamide | 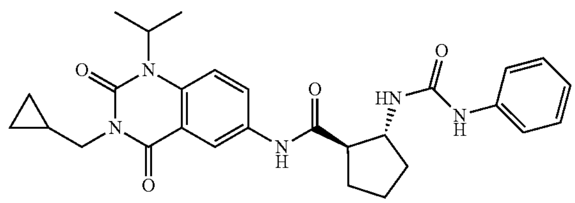 | | 504.3 (M + H) |
| 192 | (2R)-N$^2$-(4-cyano-2,5-difluorophenyl)-N$^4$-(3-(cyclopropylmethyl)-5-fluoro-1-isopropyl-2,4-dioxo-1,2,3,4-tetrahydroquinazolin-6-yl)morpholine-2,4-dicarboxamide | 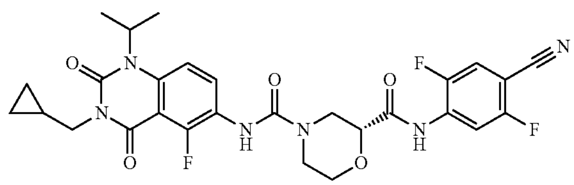 [SMILES: CC(C)n1c(=O)n(CC2CC2)c(=O)c2c(F)c(NC(=O)N3CCO[C@@H](C(=O)Nc4cc(F)c(C#N)cc4F)C3)ccc21] | | 585.2 (M + H) |
| 193 | (2R)-N$^2$-(4-cyano-3-fluorophenyl)-N$^4$-(3-(cyclopropylmethyl)-5-fluoro-1-isopropyl-2,4-dioxo-1,2,3,4-tetrahydroquinazolin-6-yl)morpholine-2,4-dicarboxamide | 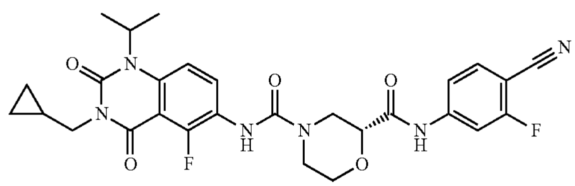 [SMILES: CC(C)n1c(=O)n(CC2CC2)c(=O)c2c(F)c(NC(=O)N3CCO[C@@H](C(=O)Nc4ccc(C#N)c(F)c4)C3)ccc21] | | 567.2 (M + H) |
| 194 | N-(3-(cyclopropylmethyl)-1-isopropyl-2,4-dioxo-1,2,3,4-tetrahydro-quinazolin-6-yl)-3-((3-(oxiran-2-yl)benzoyl)-amino)piperidine-1-carboxamide | 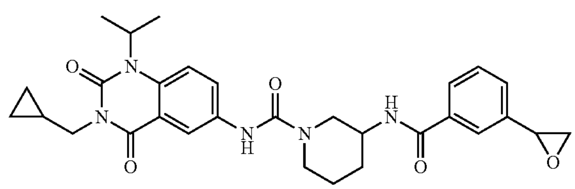 [SMILES: CC(C)n1c(=O)n(CC2CC2)c(=O)c2cc(NC(=O)N3CCCC(NC(=O)c4cccc(C5CO5)c4)C3)ccc21] | | 546.3 (M + H) |
| 195 | N-((3R)-1-((4-cyano-3-fluorophenyl)carbamoyl)-piperidin-3-yl)-3-(cyclopropylmethyl)-1-isopropyl-2,4-dioxo-1,2,3,4-tetrahydroquinazoline-6-carboxamide | 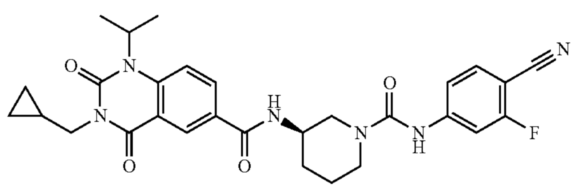 [SMILES: CC(C)n1c(=O)n(CC2CC2)c(=O)c2cc(C(=O)N[C@@H]3CCCN(C(=O)Nc4ccc(C#N)c(F)c4)C3)ccc21] | | 545 3 (M − H) |
| 196 | N-((3S)-1-((4-cyano-3-fluorophenyl)carbamoyl)-piperidin-3-yl)-3-(cyclopropylmethyl)-1-isopropyl-2,4-dioxo-1,2,3,4-tetrahydroquinazoline-6-carboxamide | 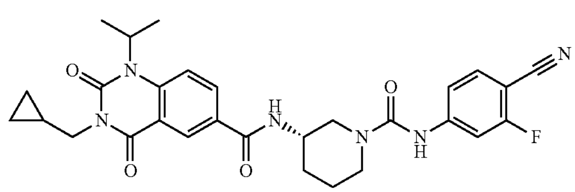 [SMILES: CC(C)n1c(=O)n(CC2CC2)c(=O)c2cc(C(=O)N[C@H]3CCCN(C(=O)Nc4ccc(C#N)c(F)c4)C3)ccc21] | | 547.3 (M + H) |

TABLE 1-20-continued

| Ex. | IUPAC name | Structure | salt | MS |
|---|---|---|---|---|
| 197 | N-(1-((4-cyanophenyl)-acetyl)piperidin-3-yl)-3-(cyclopropylmethyl)-1-isopropyl-2,4-dioxo-1,2,3,4-tetrahydroquinazoline-6-carboxamide | 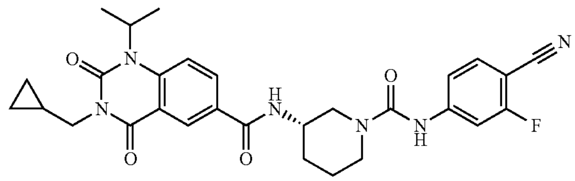 | | 528.3 (M + H) |
| 198 | 2-((benzoylamino)-methyl)-N-(3-(cyclopropylmethyl)-1-isopropyl-2,4-dioxo-1,2,3,4-tetrahydroquinazolin-6-yl)pyrrolidine-1-carboxamide | 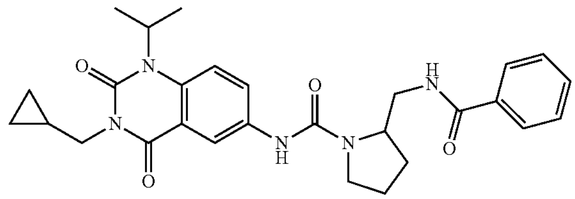 [SMILES: CC(C)n1c(=O)n(CC2CC2)c(=O)c2cc(NC(=O)N3CCCC3CNC(=O)c3ccccc3)ccc21] | | 504.3 (M + H) |
| 199 | N-(3-(cyclopropyl-methyl)-1-isopropyl-2,4-dioxo-1,2,3,4-tetrahydroquinazolin-6-yl)-2-(((phenyl-carbamoyl)amino)methyl)-pyrrolidine-1-carboxamide | 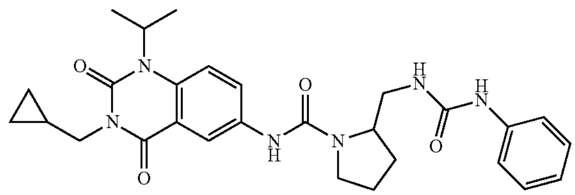 [SMILES: CC(C)n1c(=O)n(CC2CC2)c(=O)c2cc(NC(=O)N3CCCC3CNC(=O)Nc3ccccc3)ccc21] | | 519.3 (M + H) |
| 200 | trans-3-(benzoylamino)-N-(3-(cyclopropylmethyl)-1-isopropyl-2,4-dioxo-1,2,3,4-tetrahydroquinazolin-6-yl)-4-hydroxypiperidine-1-carboxamide | 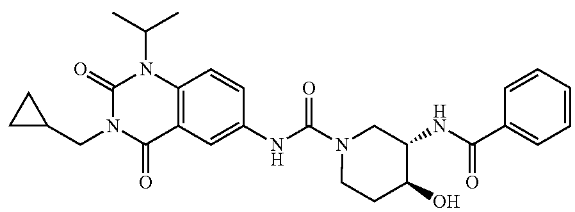 [SMILES: CC(C)n1c(=O)n(CC2CC2)c(=O)c2cc(NC(=O)N3CC[C@H](O)[C@@H](NC(=O)c4ccccc4)C3)ccc21] | | 520.3 (M + H) |

TABLE 1-21

| Ex. | IUPAC name | Structure | salt | MS |
|---|---|---|---|---|
| 201 | (2R)-N²-(4-cyano-2-fluorophenyl)-N⁴-(3-(cyclopropylmethyl)-1-isopropyl-2,4-dioxo-1,2,3,4-tetrahydroquinazolin-6-yl)morpholine-2,4-dicarboxamide | 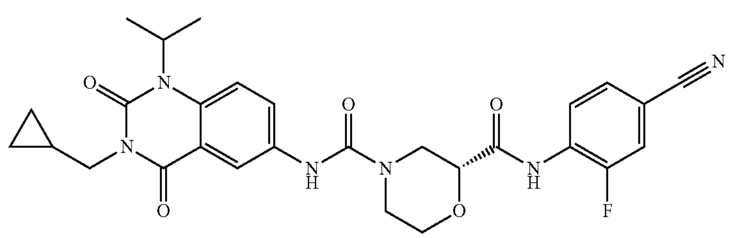 [SMILES: CC(C)n1c(=O)n(CC2CC2)c(=O)c2cc(NC(=O)N3CCO[C@@H](C(=O)Nc4ccc(C#N)cc4F)C3)ccc21] | | 549.2 (M + H) |
| 202 | (2R)-N²-(4-cyano-2,5-difluorophenyl)-N⁴-(1-isopropyl-3-(2-methoxyethyl)-2,4-dioxo-1,2,3,4-tetrahydroquinazolin-6-yl)morpholine-2,4-dicarboxamide | 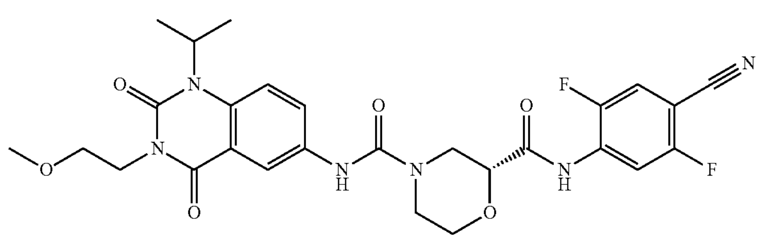 [SMILES: COCCn1c(=O)c2cc(NC(=O)N3CCO[C@@H](C(=O)Nc4cc(F)c(C#N)cc4F)C3)ccc2n(C(C)C)c1=O] | | 571.1 (M + H) |

TABLE 1-21-continued

| Ex. | IUPAC name | Structure | salt | MS |
|---|---|---|---|---|
| 203 | (2R)-N²-(4-cyano-2,5-difluorophenyl)-N⁴-(3-(2,2-difluoroethyl)-1-isopropyl-2,4-dioxo-1,2,3,4-tetrahydroquinazolin-6-yl)morpholine-2,4-dicarboxamide | 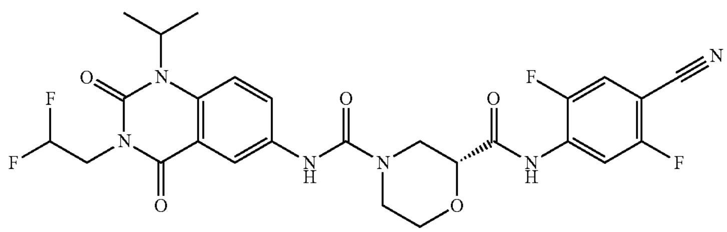 [SMILES: CC(C)n1c(=O)n(CC(F)F)c(=O)c2cc(NC(=O)N3CCO[C@@H](C(=O)Nc4cc(F)c(C#N)cc4F)C3)ccc21] | | 577.0 (M + H) |
| 204 | (3R)-N-(3-(cyclopropyl-methyl)-1-isopropyl-2,4-dioxo-1,2,3,4-tetra-hydroquinazolin-6-yl)-3-((3-((1E)-3-oxobut-1-en-1-yl)benzoyl)amino)-piperidine-1-carboxamide | 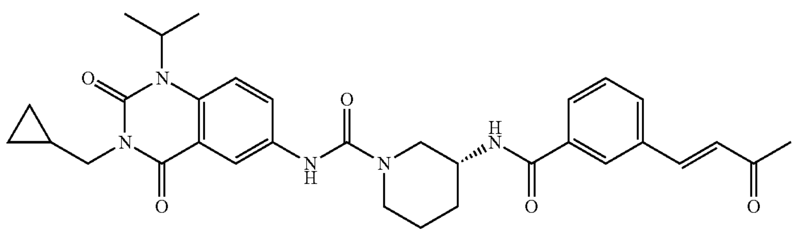 [SMILES: CC(=O)/C=C/c1cccc(C(=O)N[C@@H]2CCCN(C(=O)Nc3ccc4c(c3)c(=O)n(CC3CC3)c(=O)n4C(C)C)C2)c1] | | 572.3 (M + H) |
| 205 | N-((1R,2S)-2-(((4-cyano-3-fluorophenyl)-carbamoyl)amino)-cyclohexyl)-3-(cyclopropylmethyl)-1-isopropyl-2,4-dioxo-1,2,3,4-tetrahydroquinazoline-6-carboxamide | 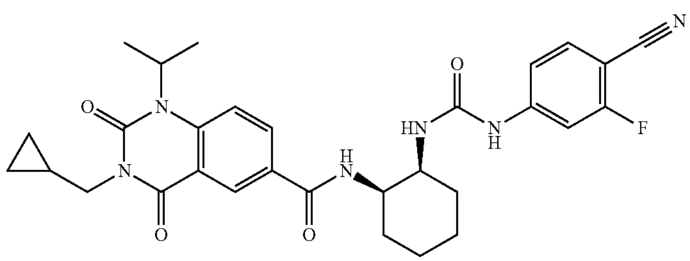 [SMILES: CC(C)n1c(=O)n(CC2CC2)c(=O)c2cc(C(=O)N[C@@H]3CCCC[C@@H]3NC(=O)Nc3ccc(C#N)c(F)c3)ccc21] | | 561.2 (M + H) |
| 206 | N-((1S,2R)-2-(((4-cyano-3-fluorophenyl)-carbamoyl)amino)cyclo-hexyl)-3-(cyclopropyl-methyl)-1-isopropyl-2,4-dioxo-1,2,3,4-tetrahydroquinazoline-6-carboxamide | 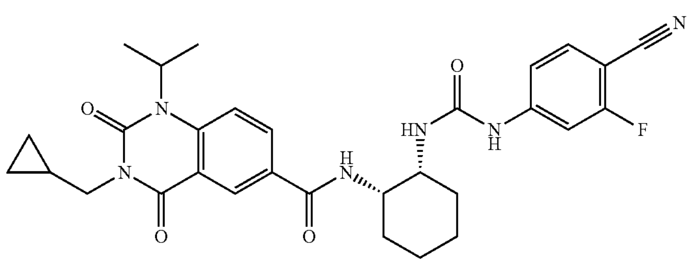 [SMILES: CC(C)n1c(=O)n(CC2CC2)c(=O)c2cc(C(=O)N[C@H]3CCCC[C@H]3NC(=O)Nc3ccc(C#N)c(F)c3)ccc21] | | 561.3 (M + H) |
| 207 | N-((1R,2R)-2-(((4-cyano-3-fluorophenyl)-carbamoyl)amino)cyclo-hexyl)-3-(cyclopropyl-methyl)-1-isopropyl-2,4-dioxo-1,2,3,4-tetrahydroquinazoline-6-carboxamide | 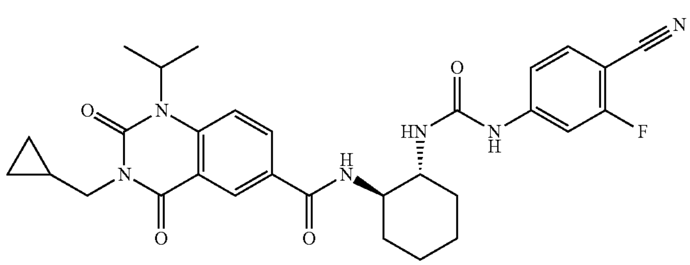 [SMILES: CC(C)n1c(=O)n(CC2CC2)c(=O)c2cc(C(=O)N[C@@H]3CCCC[C@H]3NC(=O)Nc3ccc(C#N)c(F)c3)ccc21] | | 561.3 (M + H) |
| 208 | N-((1S,2S)-2-(((4-cyano-3-fluorophenyl)-carbamoyl)amino)cyclo-hexyl)-3-(cyclopropylmethyl)-1-isopropyl-2,4-dioxo-1,2,3,4-tetrahydroquinazoline-6-carboxamide | 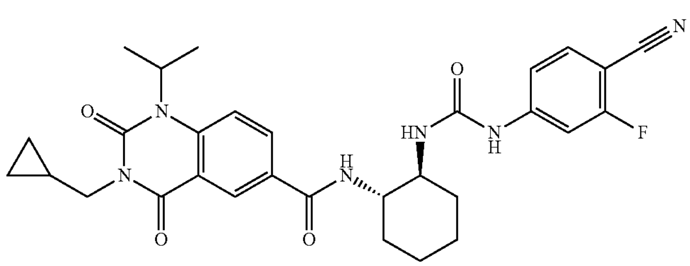 [SMILES: CC(C)n1c(=O)n(CC2CC2)c(=O)c2cc(C(=O)N[C@H]3CCCC[C@@H]3NC(=O)Nc3ccc(C#N)c(F)c3)ccc21] | | 561.3 (M + H) |

TABLE 1-21-continued

| Ex. | IUPAC name | Structure | salt | MS |
|---|---|---|---|---|
| 209 | N-((1R,2R)-2-((4-cyano-3-fluorobenzoyl)-amino)cyclohexyl)-3-(cyclopropylmethyl)-1-isopropyl-2,4-dioxo-1,2,3,4-tetrahydroquinazoline-6-carboxamide | 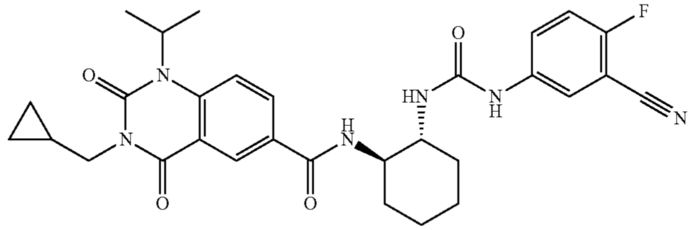 | | 546.2 (M + H) |
| 210 | N-((1S,2S)-2-((4-cyano-3-fluorobenzoyl)amino)-cyclohexyl)-3-(cyclopropylmethyl)-1-isopropyl-2,4-dioxo-1,2,3,4-tetrahydro-quinazoline-6-carboxamide | 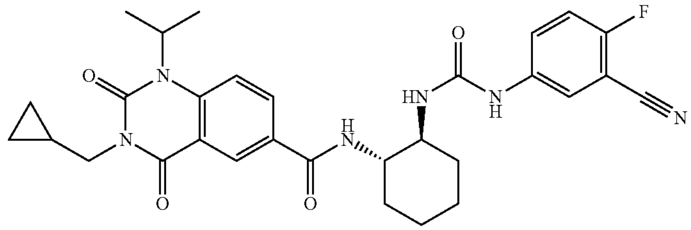 | | 546.3 (M + H) |

TABLE 1-22

| Ex. | IUPAC name | Structure | salt | MS |
|---|---|---|---|---|
| 211 | N-((1R,3S)-3-((4-cyano-3-fluorophenyl)-carbamoyl)cyclohexyl)-3-(cyclopropylmethyl)-1-isopropyl-2,4-dioxo-1,2,3,4-tetrahydroquinazoline-6-carboxamide | 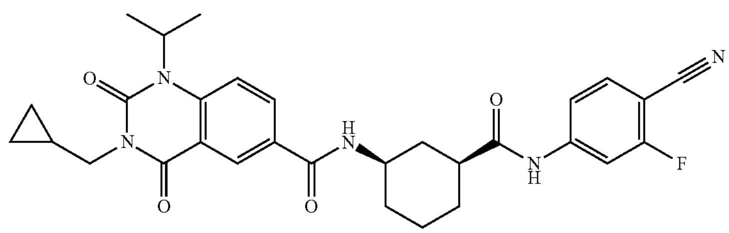 [SMILES: CC(C)n1c(=O)n(CC2CC2)c(=O)c2cc(C(=O)N[C@@H]3CCC[C@H](C(=O)Nc4ccc(C#N)c(F)c4)C3)ccc21] | | 546.1 (M + H) |
| 212 | (3R)-3-((4-(2-bromo-ethyl)benzoyl)amino)-N-(3-(cyclopropylmethyl)-1-isopropyl-2,4-dioxo-1,2,3,4-tetrahydroquinazolin-6-yl)piperidine-1-carboxamide | 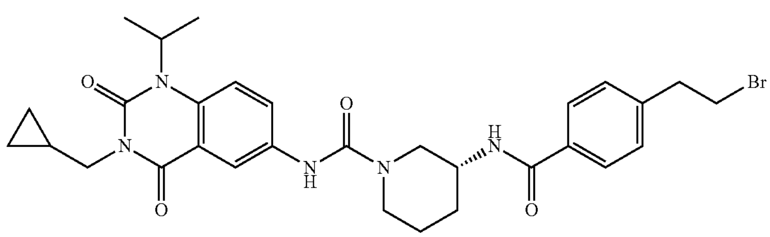 [SMILES: CC(C)n1c(=O)n(CC2CC2)c(=O)c2cc(NC(=O)N3CCC[C@@H](NC(=O)c4ccc(CCBr)cc4)C3)ccc21] | | 610.4 (M + H) |
| 213 | N²-(5-cyanopyridin-2-yl)-N⁴-(3-(cyclopropylmethyl)-1-isopropyl-2,4-dioxo-1,2,3,4-tetrahydroquinazolin-6-yl)morpholine-2,4-dicarboxamide | 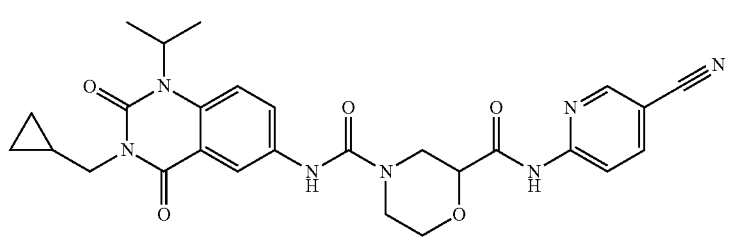 [SMILES: CC(C)n1c(=O)n(CC2CC2)c(=O)c2cc(NC(=O)N3CCOC(C(=O)Nc4ccc(C#N)cn4)C3)ccc21] | | 532.2 (M + H) |

TABLE 1-22-continued

| Ex. | IUPAC name | Structure | salt | MS |
|---|---|---|---|---|
| 214 | tert-butyl (2-(((3R)-1-((3-(cyclopropylmethyl)-1-isopropyl-2,4-dioxo-1,2,3,4-tetrahydroquinazolin-6-yl)carbamoyl)piperidin-3-yl)carbamoyl)phenyl)carbamate | 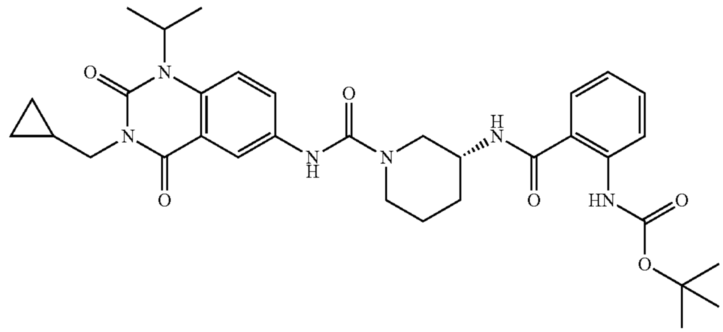 [SMILES: CC(C)n1c(=O)n(CC2CC2)c(=O)c2cc(NC(=O)N3CCC[C@@H](NC(=O)c4ccccc4NC(=O)OC(C)(C)C)C3)ccc21] | | 617.5 (M − H) |
| 215 | tert-butyl (4-(((3R)-1-((3-(cyclopropylmethyl)-1-isopropyl-2,4-dioxo-1,2,3,4-tetrahydroquinazolin-6-yl)carbamoyl)piperidin-3-yl)carbamoyl)phenyl)carbamate | 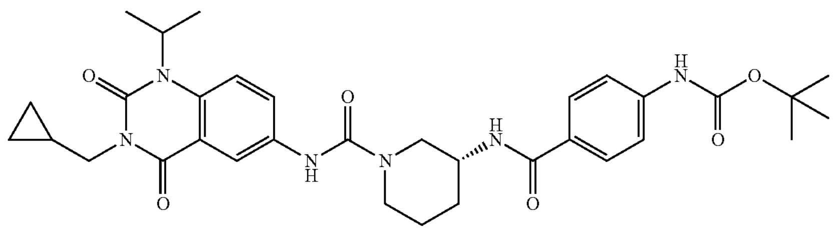 [SMILES: CC(C)n1c(=O)n(CC2CC2)c(=O)c2cc(NC(=O)N3CCC[C@@H](NC(=O)c4ccc(NC(=O)OC(C)(C)C)cc4)C3)ccc21] | | 619.3 (M + H) |
| 216 | (3R)-3-((2-aminobenzoyl)amino)-N-(3-(cyclopropylmethyl)-1-isopropyl-2,4-dioxo-1,2,3,4-tetrahydroquinazolin-6-yl)piperidine-1-carboxamide | 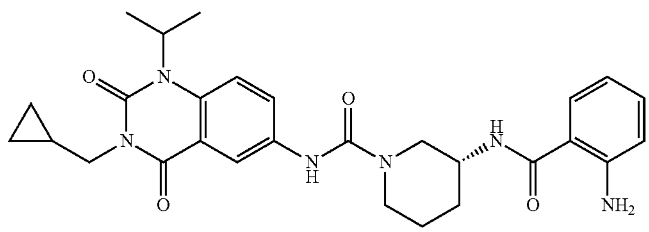 [SMILES: CC(C)n1c(=O)n(CC2CC2)c(=O)c2cc(NC(=O)N3CCC[C@@H](NC(=O)c4ccccc4N)C3)ccc21] | | 519.3 (M + H) |
| 217 | (3R)-3-((4-aminobenzoyl)amino)-N-(3-(cyclopropylmethyl)-1-isopropyl-2,4-dioxo-1,2,3,4-tetrahydroquinazolin-6-yl)piperidine-1-carboxamide | 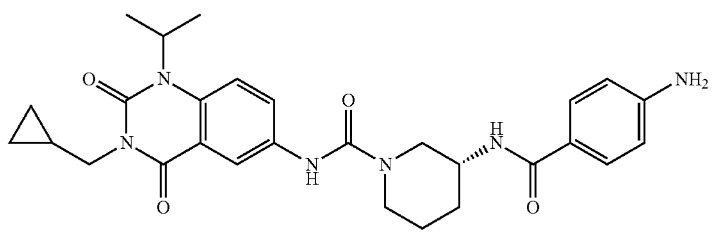 [SMILES: CC(C)n1c(=O)n(CC2CC2)c(=O)c2cc(NC(=O)N3CCC[C@@H](NC(=O)c4ccc(N)cc4)C3)ccc21] | | 519.3 (M + H) |
| 218 | (3R)-3-((4-cyanobenzoyl)amino)-N-(3-(cyclopropylmethyl)-1-isopropyl-2,4-dioxo-1,2,3,4-tetrahydroquinazolin-6-yl)piperidine-1-carboxamide | 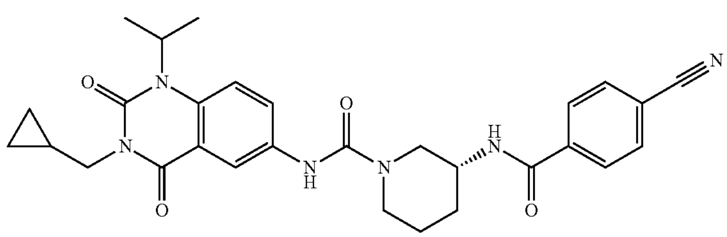 [SMILES: CC(C)n1c(=O)n(CC2CC2)c(=O)c2cc(NC(=O)N3CCC[C@@H](NC(=O)c4ccc(C#N)cc4)C3)ccc21] | | 529.2 (M + H) |
| 219 | (3R)-3-((4-cyano-2-fluorobenzoyl)amino)-N-(3-(cyclopropylmethyl)-1-isopropyl-2,4-dioxo-1,2,3,4-tetrahydroquinazolin-6-yl)piperidine-1-carboxamide | 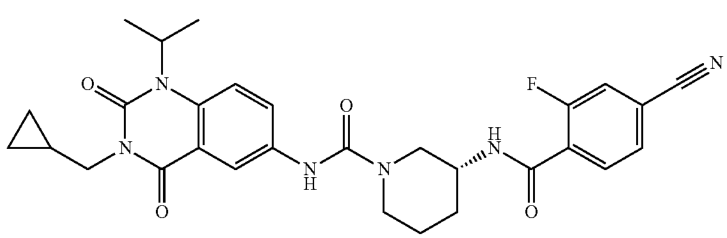 [SMILES: CC(C)n1c(=O)n(CC2CC2)c(=O)c2cc(NC(=O)N3CCC[C@@H](NC(=O)c4ccc(C#N)cc4F)C3)ccc21] | | 547.2 (M + H) |

TABLE 1-22-continued

| Ex. | IUPAC name | Structure | salt | MS |
|---|---|---|---|---|
| 220 | (3R)-3-((2-(acryloyl-amino)benzoyl)amino)-N-(3-(cyclopropylmethyl)-1-isopropyl-2,4-dioxo-1,2,3,4-tetrahydroquinazolin-6-yl)piperidine-1-carboxamide | 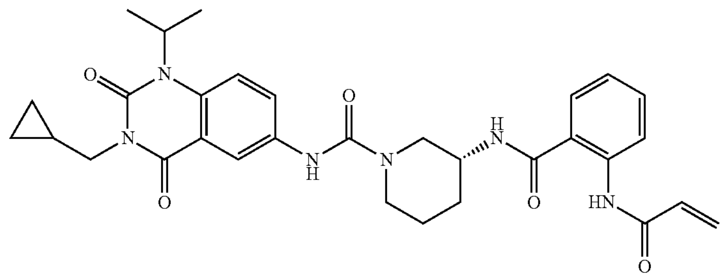 [SMILES: C=CC(=O)Nc1ccccc1C(=O)N[C@@H]1CCCN(C(=O)Nc2ccc3c(c2)c(=O)n(CC2CC2)c(=O)n3C(C)C)C1] | | 573.4 (M + H) |

TABLE 1-23

| Ex. | IUPAC name | Structure | salt | MS |
|---|---|---|---|---|
| 221 | (3R)-3-((4-(acryloyl-amino)benzoyl)amino)-N-(3-(cyclopropylmethyl)-1-isopropyl-2,4-dioxo-1,2,3,4-tetrahydroquinazolin-6-yl)piperidine-1-carboxamide | 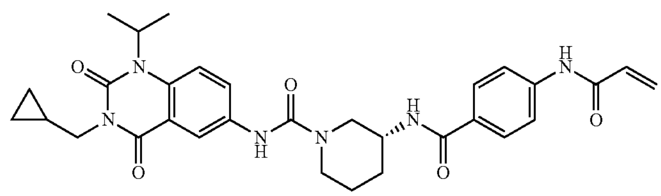 [SMILES: C=CC(=O)Nc1ccc(C(=O)N[C@@H]2CCCN(C(=O)Nc3ccc4c(c3)c(=O)n(CC3CC3)c(=O)n4C(C)C)C2)cc1] | | 573.4 (M + H) |
| 222 | (3R)-N-(3-(cyclopropylmethyl)-1-isopropyl-2,4-dioxo-1,2,3,4-tetrahydro-quinazolin-6-yl)-3-((2-(propionylamino)benzoyl)amino)piperidine-1-carboxamide | 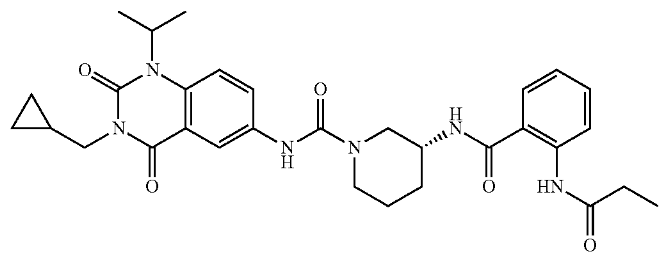 [SMILES: CCC(=O)Nc1ccccc1C(=O)N[C@@H]1CCCN(C(=O)Nc2ccc3c(c2)c(=O)n(CC2CC2)c(=O)n3C(C)C)C1] | | 575.2 (M + H) |
| 223 | 6-cyano-N-((3R)-1-((3-(cyclopropylmethyl)-1-isopropyl-2,4-dioxo-1,2,3,4-tetrahydroquinazolin-6-yl)carbamoyl)piperidin-3-yl)nicotinamide | 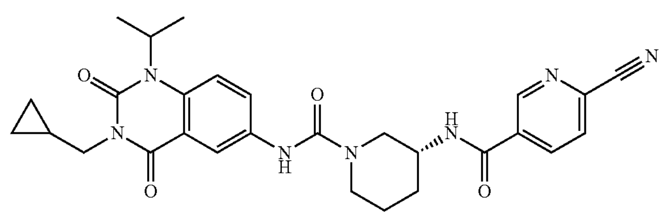 [SMILES: CC(C)n1c(=O)n(CC2CC2)c(=O)c2cc(NC(=O)N3CCC[C@@H](NC(=O)c4ccc(C#N)nc4)C3)ccc21] | | 530.2 (M + H) |
| 224 | (3R)-N-(3-(cyclopropylmethyl)-1-isopropyl-2,4-dioxo-1,2,3,4-tetrahydroquinazolin-6-yl)-3-((4-(propionyl-amino)benzoyl)amino)-piperidine-1-carboxamide | 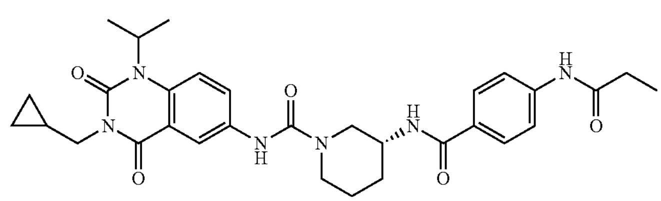 [SMILES: CCC(=O)Nc1ccc(C(=O)N[C@@H]2CCCN(C(=O)Nc3ccc4c(c3)c(=O)n(CC3CC3)c(=O)n4C(C)C)C2)cc1] | | 575.3 (M + H) |
| 225 | 5-cyano-N-((3R)-1-((3-(cyclopropylmethyl)-1-isopropyl-2,4-dioxo-1,2,3,4-tetrahydroquinazolin-6-yl)carbamoyl)piperidin-3-yl)pyridine-2-carboxamide | 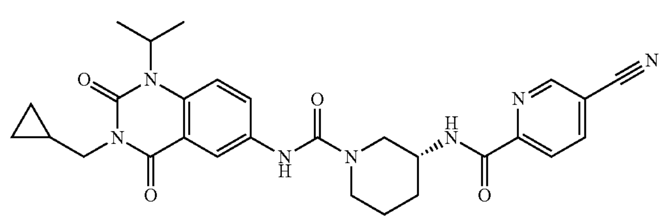 [SMILES: CC(C)n1c(=O)n(CC2CC2)c(=O)c2cc(NC(=O)N3CCC[C@@H](NC(=O)c4ccc(C#N)cn4)C3)ccc21] | | 530.2 (M + H) |

TABLE 1-23-continued

| Ex. | IUPAC name | Structure | salt | MS |
|---|---|---|---|---|
| 226 | 3-(benzoyl(methyl)amino)-N-(3-(cyclopropylmethyl)-1-isopropyl-2,4-dioxo-1,2,3,4-tetrahydroquinazolin-6-yl)piperidine-1-carboxamide | 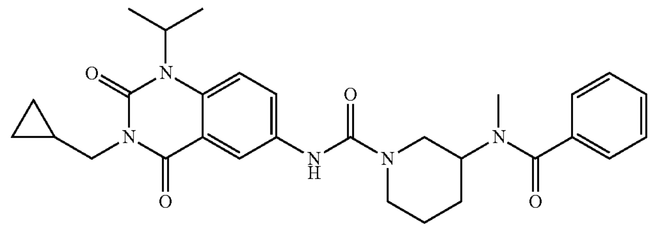 [SMILES: CC(C)n1c(=O)n(CC2CC2)c(=O)c2cc(NC(=O)N3CCCC(N(C)C(=O)c4ccccc4)C3)ccc21] | | 518.3 (M + H) |
| 227 | N²-(4-cyano-2,5-difluorophenyl)-N⁴-(3-(cyclopropylmethyl)-1-isopropyl-2,4-dioxo-1,2,3,4-tetrahydroquinazolin-6-yl)-N²-methylmorpholine-2,4-dicarboxamide | 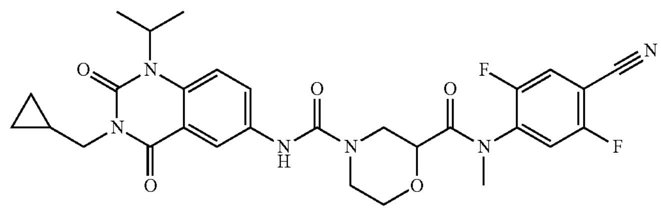 [SMILES: CC(C)n1c(=O)n(CC2CC2)c(=O)c2cc(NC(=O)N3CCOC(C(=O)N(C)c4cc(F)c(C#N)cc4F)C3)ccc21] | | 581.3 (M + H) |
| 228 | (3R)-3-((3-aminobenzoyl)amino)-N-(3-(cyclopropylmethyl)-1-isopropyl-2,4-dioxo-1,2,3,4-tetrahydroquinazolin-6-yl)piperidine-1-carboxamide | 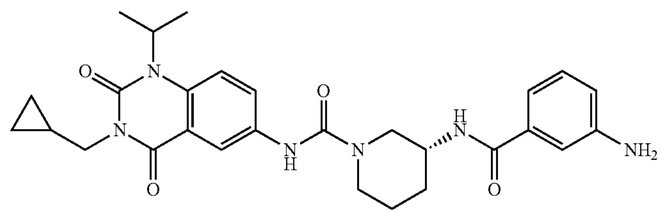 [SMILES: CC(C)n1c(=O)n(CC2CC2)c(=O)c2cc(NC(=O)N3CCC[C@@H](NC(=O)c4cccc(N)c4)C3)ccc21] | | 519.3 (M + H) |
| 229 | 1-((3-(cyclopropylmethyl)-1-isopropyl-2,4-dioxo-1,2,3,4-tetrahydroquinazolin-6-yl)carbamoyl)piperidin-3-yl phenylcarbamate | 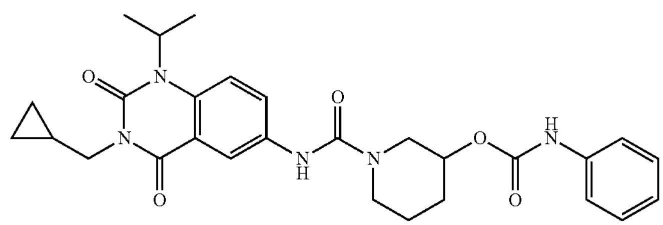 [SMILES: CC(C)n1c(=O)n(CC2CC2)c(=O)c2cc(NC(=O)N3CCCC(OC(=O)Nc4ccccc4)C3)ccc21] | | 520.2 (M + H) |
| 230 | (3R)-3-((3-(acryloyl-amino)benzoyl)amino)-N-(3-(cyclopropylmethyl)-1-isopropyl-2,4-dioxo-1,2,3,4-tetrahydroquinazolin-6-yl)piperidine-1-carboxamide | 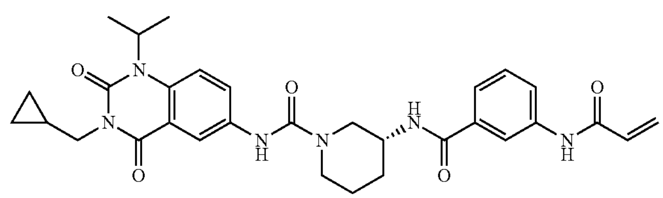 [SMILES: C=CC(=O)Nc1cccc(C(=O)N[C@@H]2CCCN(C(=O)Nc3ccc4c(c3)c(=O)n(CC3CC3)c(=O)n4C(C)C)C2)c1] | | 573.4 (M + H) |

TABLE 1-24

| Ex. | IUPAC name | Structure | salt | MS |
|---|---|---|---|---|
| 231 | (3R)-3-((3-((chloroacetyl)amino)-benzoyl)amino)-N-(3-(cyclopropylmethyl)-1-isopropyl-2,4-dioxo-1,2,3,4-tetrahydroquinazolin-6-yl)piperidine-1-carboxamide | 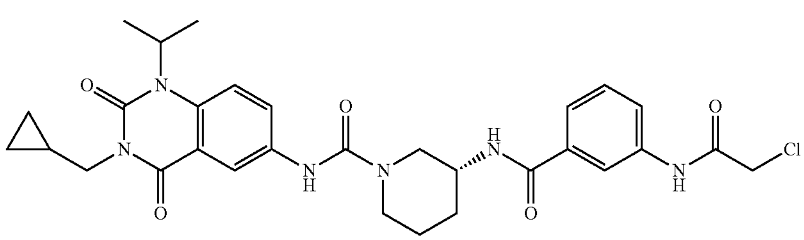 [SMILES: CC(C)n1c(=O)n(CC2CC2)c(=O)c2cc(NC(=O)N3CCC[C@@H](NC(=O)c4cccc(NC(=O)CCl)c4)C3)ccc21] | | 595.3 (M + H) |

TABLE 1-24-continued

| Ex. | IUPAC name | Structure | salt | MS |
|---|---|---|---|---|
| 232 | N-((3R)-1-((3-(cyclopropylmethyl)-1-isopropyl-2,4-dioxo-1,2,3,4-tetrahydroquinazolin-6-yl)carbamoyl)piperidin-3-yl)-1,3-benzothiazole-6-carboxamide | 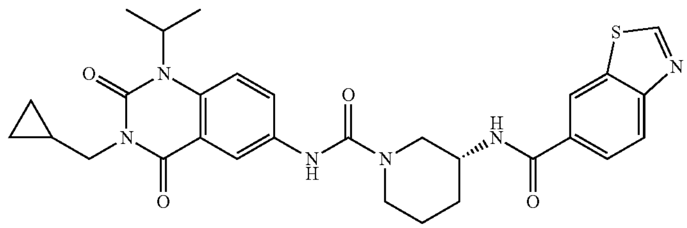 [SMILES: CC(C)n1c(=O)n(CC2CC2)c(=O)c2cc(NC(=O)N3CCC[C@@H](NC(=O)c4ccc5ncsc5c4)C3)ccc21] | | 561.2 (M + H) |
| 233 | (3R)-N-(3-(cyclopropylmethyl)-1-isopropyl-2,4-dioxo-1,2,3,4-tetrahydro-quinazolin-6-yl)-3-((3-((vinylsulfonyl)amino)-benzoyl)amino)piperidine-1-carboxamide | 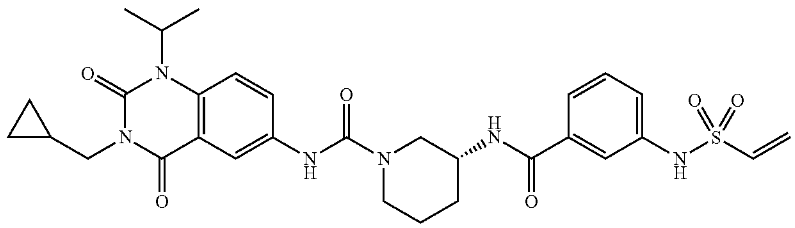 [SMILES: C=CS(=O)(=O)Nc1cccc(C(=O)N[C@@H]2CCCN(C(=O)Nc3ccc4c(c3)c(=O)n(CC3CC3)c(=O)n4C(C)C)C2)c1] | | 607.3 (M − H) |
| 234 | N-((3R)-1-((3-(cyclopropylmethyl)-1-isopropyl-2,4-dioxo-1,2,3,4-tetrahydroquinazolin-6-yl)carbamoyl)piperidin-3-yl)-2-methyl-1,3-benzothiazole-6-carboxamide | 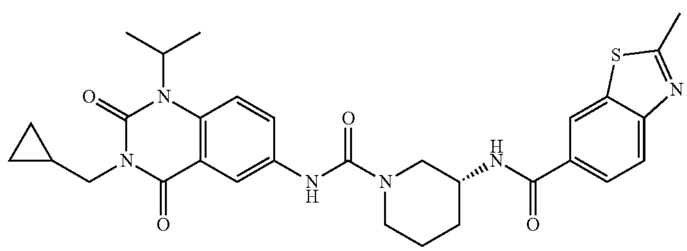 [SMILES: Cc1nc2ccc(C(=O)N[C@@H]3CCCN(C(=O)Nc4ccc5c(c4)c(=O)n(CC4CC4)c(=O)n5C(C)C)C3)cc2s1] | | 575.2 (M + H) |
| 235 | (2R)-$N^2$-(3-chloro-4-cyanophenyl)-$N^4$-(3-(cyclopropylmethyl)-7-fluoro-1-isopropyl-2,4-dioxo-1,2,3,4-tetrahydroquinazolin-6-yl)morpholine-2,4-dicarboxamide | 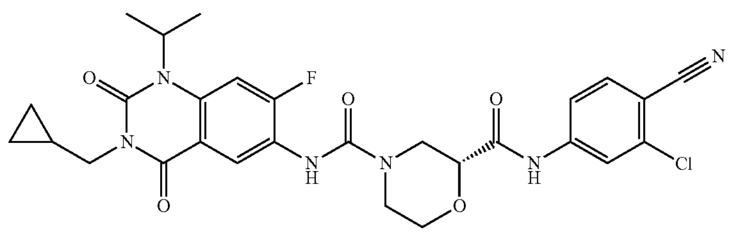 | | 583.2 (M + H) |
| 236 | (2R)-$N^2$-(6-cyano-5-fluoropyridin-3-yl)-$N^4$-(3-(cyclopropylmethyl)-7-fluoro-1-isopropyl-2,4-dioxo-1,2,3,4-tetrahydroquinazolin-6-yl)morpholine-2,4-dicarboxamide | 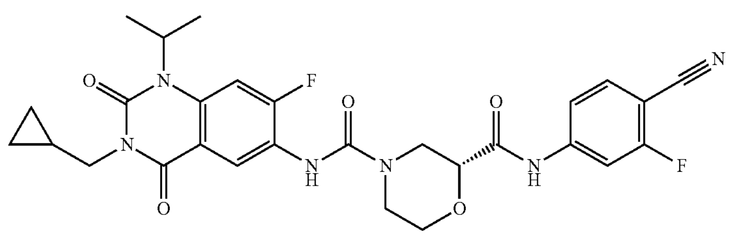 | | 568.2 (M + H) |
| 237 | N-((3R)-1-((3-(cyclopropylmethyl)-1-isopropyl-2,4-dioxo-1,2,3,4-tetrahydroquinazolin-6-yl)carbamoyl)piperidin-3-yl)pyridine-2-carboxamide | 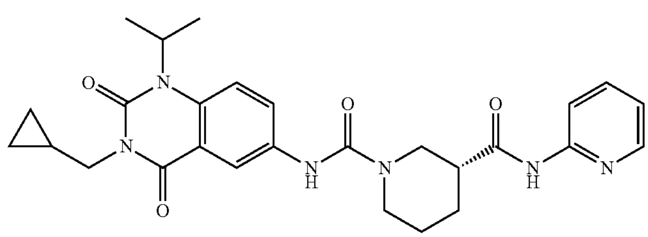 [SMILES: CC(C)n1c(=O)n(CC2CC2)c(=O)c2cc(NC(=O)N3CCC[C@@H](C(=O)Nc4ccccn4)C3)ccc21] | | 505.2 (M + H) |

TABLE 1-24-continued

| Ex. | IUPAC name | Structure | salt | MS |
|---|---|---|---|---|
| 238 | (3R)-N-(3-(cyclopropylmethyl)-1-isopropyl-2,4-dioxo-1,2,3,4-tetrahydroquinazolin-6-yl)-3-((5-methyl-2-furoyl)amino)piperidine-1-carboxamide | 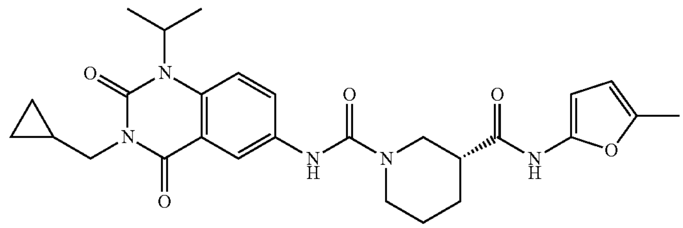 [SMILES: Cc1ccc(NC(=O)[C@@H]2CCCN(C(=O)Nc3ccc4c(c3)c(=O)n(CC3CC3)c(=O)n4C(C)C)C2)o1] | | 508.2 (M + H) |
| 239 | N-((3R)-1-((3-(cyclopropylmethyl)-1-isopropyl-2,4-dioxo-1,2,3,4-tetrahydroquinazolin-6-yl)carbamoyl)piperidin-3-yl)-5-methylpyridine-2-carboxamide | 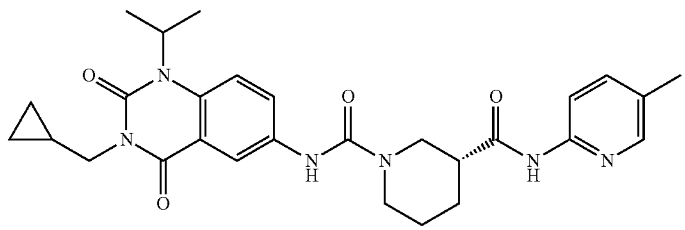 [SMILES: Cc1ccc(NC(=O)[C@@H]2CCCN(C(=O)Nc3ccc4c(c3)c(=O)n(CC3CC3)c(=O)n4C(C)C)C2)nc1] | | 519.2 (M + H) |
| 240 | 3-amino-N-((3R)-1-((3-(cyclopropylmethyl)-1-isopropyl-2,4-dioxo-1,2,3,4-tetrahydroquinazolin-6-yl)carbamoyl)piperidin-3-yl)pyridine-2-carboxamide | 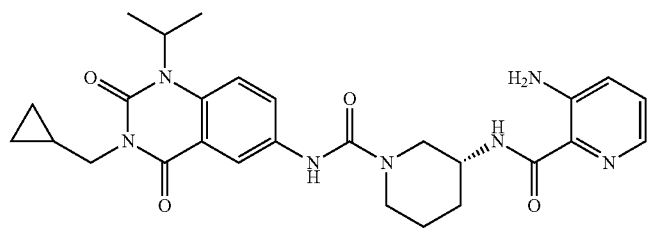 [SMILES: CC(C)n1c(=O)n(CC2CC2)c(=O)c2cc(NC(=O)N3CCC[C@@H](NC(=O)c4ncccc4N)C3)ccc21] | | 520.2 (M + H) |

TABLE 1-25

| Ex. | IUPAC name | Structure | salt | Ms |
|---|---|---|---|---|
| 241 | (3R)-N-(3-(cyclopropylmethyl)-1-isopropyl-2,4-dioxo-1,2,3,4-tetrahydro-quinazolin-6-yl)-3-(((1,5-dimethyl-1H-pyrazol-3-yl)carbonyl)amino)piperidine-1-carboxamide | 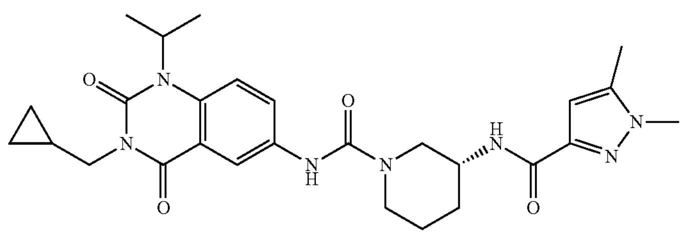 [SMILES: Cc1cc(C(=O)N[C@@H]2CCCN(C(=O)Nc3ccc4c(c3)c(=O)n(CC3CC3)c(=O)n4C(C)C)C2)nn1C] | | 522.3 (M + H) |
| 242 | (3R)-N-(3-(cyclopropylmethyl)-1-isopropyl-2,4-dioxo-1,2,3,4-tetrahydroquinazolin-6-yl)-3-(((5-methyl-2-thienyl)carbonyl)amino)-piperidine-1-carboxamide | 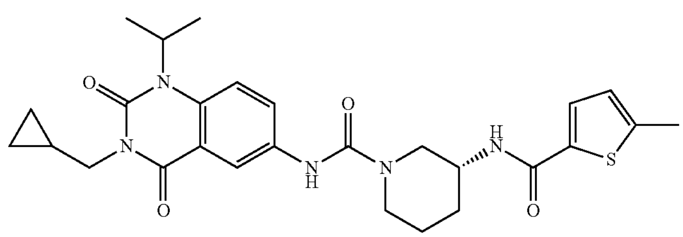 [SMILES: Cc1ccc(C(=O)N[C@@H]2CCCN(C(=O)Nc3ccc4c(c3)c(=O)n(CC3CC3)c(=O)n4C(C)C)C2)s1] | | 524.3 (M + H) |
| 243 | (3R)-3-((3-cyanobenzoyl)amino)-N-(3-(cyclopropylmethyl)-1-isopropyl-2,4-dioxo-1,2,3,4-tetrahydroquinazolin-6-yl)piperidine-1-carboxamide | 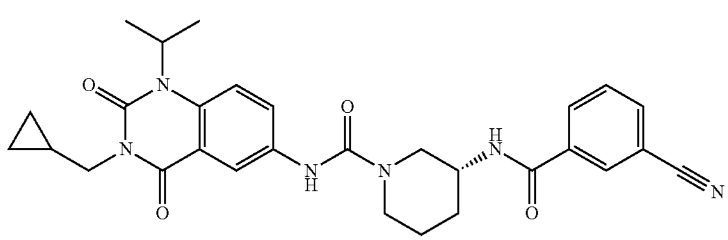 [SMILES: CC(C)n1c(=O)n(CC2CC2)c(=O)c2cc(NC(=O)N3CCC[C@@H](NC(=O)c4cccc(C#N)c4)C3)ccc21] | | 529.2 (M + H) |

TABLE 1-25-continued

| Ex. | IUPAC name | Structure | salt | Ms |
|---|---|---|---|---|
| 244 | (3R)-N-(3-(cyclopropylmethyl)-1-isopropyl-2,4-dioxo-1,2,3,4-tetrahydro-quinazolin-6-yl)-3-((4-methoxybenzoyl)amino)-piperidine-1-carboxamide | 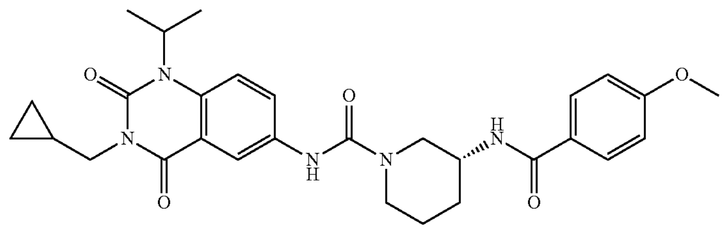 [SMILES: COc1ccc(C(=O)N[C@@H]2CCCN(C(=O)Nc3ccc4c(c3)c(=O)n(CC3CC3)c(=O)n4C(C)C)C2)cc1] | | 534.2 (M + H) |
| 245 | (3R)-N-(3-(cyclopropylmethyl)-1-isopropyl-2,4-dioxo-1,2,3,4-tetrahydro-quinazolin-6-yl)-3-((3-methoxybenzoyl)amino)-piperidine-1-carboxamide | 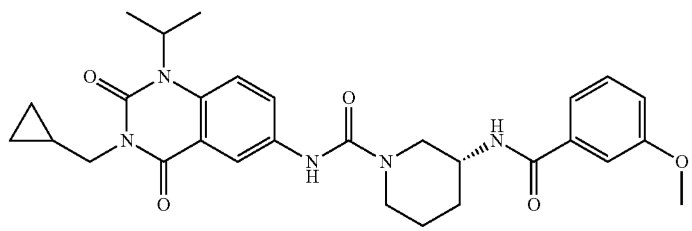 [SMILES: COc1cccc(C(=O)N[C@@H]2CCCN(C(=O)Nc3ccc4c(c3)c(=O)n(CC3CC3)c(=O)n4C(C)C)C2)c1] | | 534.2 (M + H) |
| 246 | (3R)-N-(3-(cyclopropylmethyl)-1-isopropyl-2,4-dioxo-1,2,3,4-tetrahydroquinazolin-6-yl)-3-(((2-methyl-1,3-thiazol-5-yl)carbonyl)amino)piperidine-1-carboxamide | 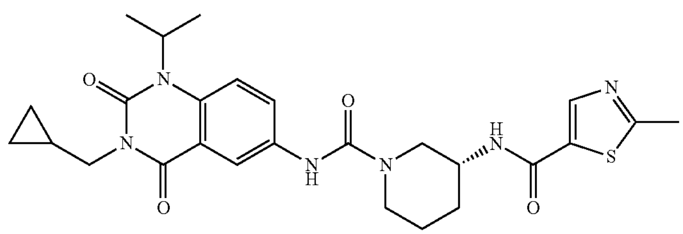 [SMILES: Cc1ncc(C(=O)N[C@@H]2CCCN(C(=O)Nc3ccc4c(c3)c(=O)n(CC3CC3)c(=O)n4C(C)C)C2)s1] | | 523.3 (M − H) |
| 247 | (3R)-3-((4-chlorobenzoyl)amino)-N-(3-(cyclopropylmethyl)-1-isopropyl-2,4-dioxo-1,2,3,4-tetrahydroquinazolin-6-yl)piperidine-1-carboxamide | 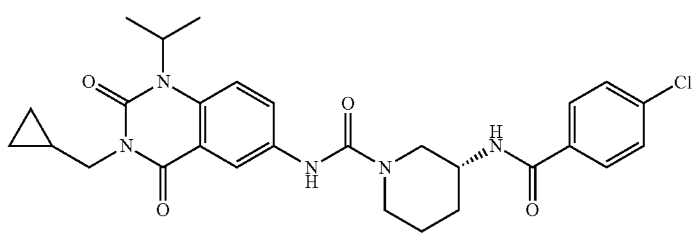 [SMILES: CC(C)n1c(=O)n(CC2CC2)c(=O)c2cc(NC(=O)N3CCC[C@@H](NC(=O)c4ccc(Cl)cc4)C3)ccc21] | | 538.2 (M + H) |
| 248 | (3R)-3-((3-chlorobenzoyl)amino)-N-(3-(cyclopropylmethyl)-1-isopropyl-2,4-dioxo-1,2,3,4-tetrahydroquinazolin-6-yl)piperidine-1-carboxamide | 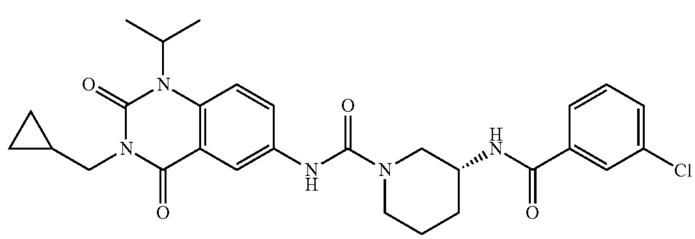 [SMILES: CC(C)n1c(=O)n(CC2CC2)c(=O)c2cc(NC(=O)N3CCC[C@@H](NC(=O)c4cccc(Cl)c4)C3)ccc21] | | 538.2 (M + H) |
| 249 | (3R)-3-((4-cyano-3-methylbenzoyl)amino)-N-(3-(cyclopropylmethyl)-1-isopropyl-2,4-dioxo-1,2,3,4-tetrahydroquinazolin-6-yl)piperidine-1-carboxamide | 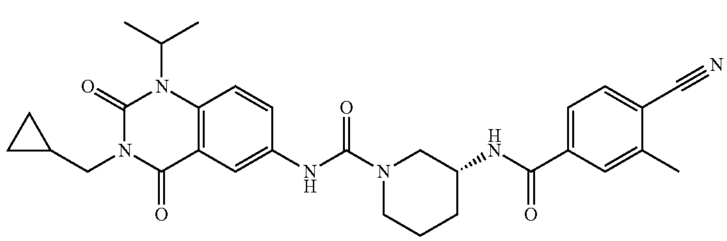 [SMILES: Cc1cc(C(=O)N[C@@H]2CCCN(C(=O)Nc3ccc4c(c3)c(=O)n(CC3CC3)c(=O)n4C(C)C)C2)ccc1C#N] | | 541.3 (M − H) |

TABLE 1-25-continued

| Ex. | IUPAC name | Structure | salt | Ms |
|---|---|---|---|---|
| 250 | (3R)-3-((4-(cyanomethyl)benzoyl)-amino)-N-(3-(cyclopropylmethyl)-1-isopropyl-2,4-dioxo-1,2,3,4-tetrahydroquinazolin-6-yl)piperidine-1-carboxamide | 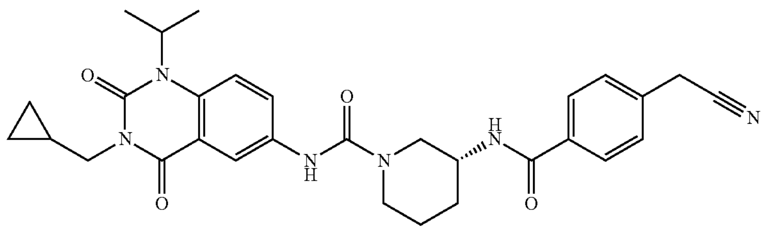 [SMILES: CC(C)n1c(=O)n(CC2CC2)c(=O)c2cc(NC(=O)N3CCC[C@@H](NC(=O)c4ccc(CC#N)cc4)C3)ccc21] | | 543.2 (M + H) |

TABLE 1-26

| Ex. | IUPAC name | Structure | salt | MS |
|---|---|---|---|---|
| 251 | (3R)-N-(3-(cyclopropylmethyl)-1-isopropyl-2,4-dioxo-1,2,3,4-tetrahydro-quinazolin-6-yl)-3-((2,3-dihydro-1-benzofuran-5-ylcarbonyl)amino)-piperidine-1-carboxamide | 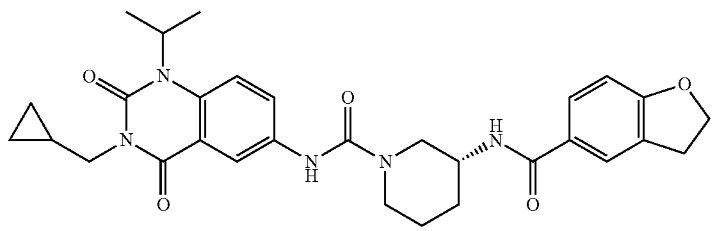 [SMILES: CC(C)n1c(=O)n(CC2CC2)c(=O)c2cc(NC(=O)N3CCC[C@@H](NC(=O)c4ccc5c(c4)CCO5)C3)ccc21] | | 546.3 (M + H) |
| 252 | (3R)-N-(3-(cyclopropylmethyl)-1-isopropyl-2,4-dioxo-1,2,3,4-tetrahydro-quinazolin-6-yl)-3-(((1-oxo-2,3-dihydro-1H-inden-5-yl)carbonyl)-amino)piperidine-1-carboxamide | 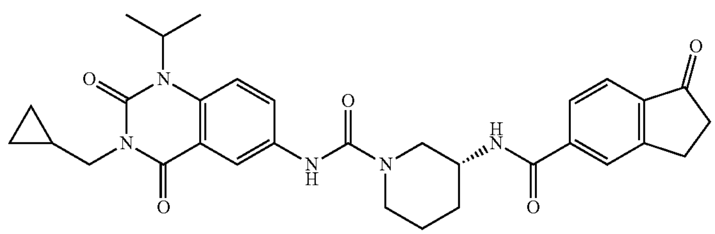 [SMILES: CC(C)n1c(=O)n(CC2CC2)c(=O)c2cc(NC(=O)N3CCC[C@@H](NC(=O)c4ccc5c(c4)CCC5=O)C3)ccc21] | | 558.3 (M + H) |
| 253 | N-((3R)-1-((3-(cyclopropylmethyl)-1-isopropyl-2,4-dioxo-1,2,3,4-tetrahydroquinazolin-6-yl)carbamoyl)piperidin-3-yl)-2-oxoindoline-5-carboxamide | 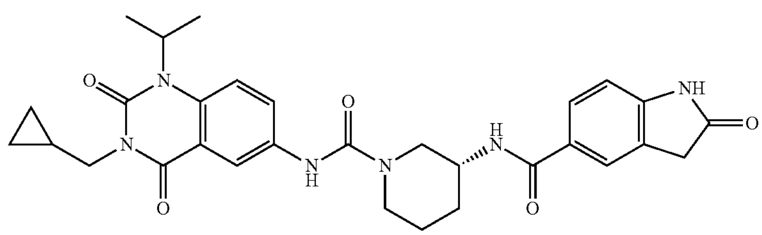 [SMILES: CC(C)n1c(=O)n(CC2CC2)c(=O)c2cc(NC(=O)N3CCC[C@@H](NC(=O)c4ccc5c(c4)CC(=O)N5)C3)ccc21] | | 559.3 (M + H) |
| 254 | (3R)-3-((4-acetamido-benzoyl)amino)-N-(3-(cyclopropylmethyl)-1-isopropyl-2,4-dioxo-1,2,3,4-tetrahydroquinazolin-6-yl)piperidine-1-carboxamide | 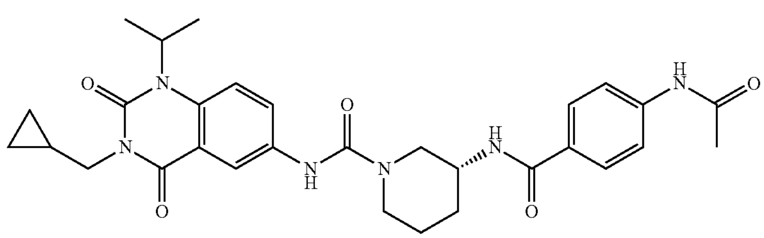 [SMILES: CC(=O)Nc1ccc(C(=O)N[C@@H]2CCCN(C(=O)Nc3ccc4c(c3)c(=O)n(CC3CC3)c(=O)n4C(C)C)C2)cc1] | | 561.2 (M + H) |
| 255 | (3R)-3-((3-acetamidobenzoyl)amino)-N-(3-(cyclopropylmethyl)-1-isopropyl-2,4-dioxo-tetrahydroquinazolin-6-yl)piperidine-1-carboxamide | 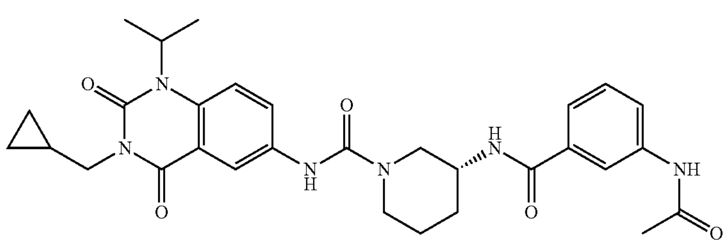 [SMILES: CC(=O)Nc1cccc(C(=O)N[C@@H]2CCCN(C(=O)Nc3ccc4c(c3)c(=O)n(CC3CC3)c(=O)n4C(C)C)C2)c1] | | 561.2 (M + H) |

TABLE 1-26-continued

| Ex. | IUPAC name | Structure | salt | MS |
|---|---|---|---|---|
| 256 | N-((3R)-1-((3-(cyclopropylmethyl)-1-isopropyl-2,4-dioxo-1,2,3,4-tetrahydroquinazolin-6-yl)carbamoyl)piperidin-3-yl)-5-(trifluoro-methyl)pyridine-2-carboxamide | 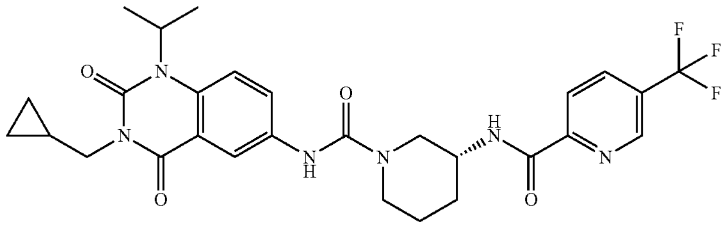 [SMILES: CC(C)n1c(=O)n(CC2CC2)c(=O)c2cc(NC(=O)N3CCC[C@@H](NC(=O)c4ccc(C(F)(F)F)cn4)C3)ccc21] | | 573.3 (M + H) |
| 257 | N-((3R)-1-((3-(cyclopropylmethyl)-1-isopropyl-2,4-dioxo-1,2,3,4-tetrahydro-quinazolin-6-yl)carbamoyl)piperidin-3-yl)-4-(trifluoro-methyl)pyridine-2-carboxamide | 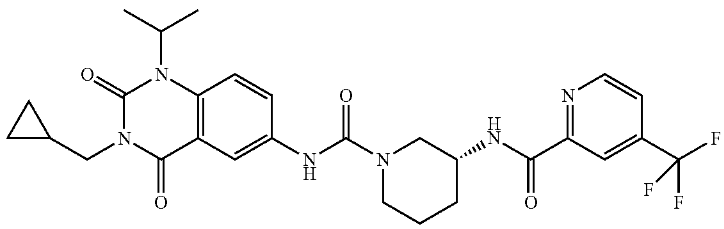 [SMILES: CC(C)n1c(=O)n(CC2CC2)c(=O)c2cc(NC(=O)N3CCC[C@@H](NC(=O)c4cc(C(F)(F)F)ccn4)C3)ccc21] | | 573.5 (M + H) |
| 258 | N-((3R)-1-((3-(cyclopropylmethyl)-1-isopropyl-2,4-dioxo-1,2,3,4-tetrahydroquinazolin-6-yl)carbamoyl)piperidin-3-yl)-5-fluoropyridine-2-carboxamide | 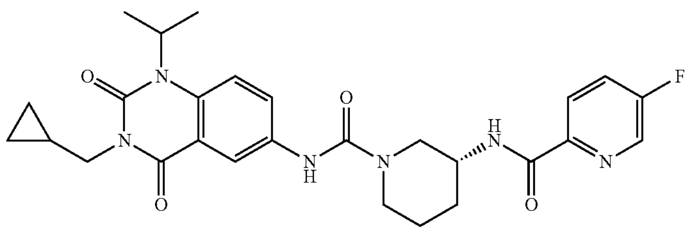 [SMILES: CC(C)n1c(=O)n(CC2CC2)c(=O)c2cc(NC(=O)N3CCC[C@@H](NC(=O)c4ccc(F)cn4)C3)ccc21] | | 523.2 (M + H) |
| 259 | (3R)-N-(3-(cyclopropylmethyl)-1-isopropyl-2,4-dioxo-1,2,3,4-tetrahydro-quinazolin-6-yl)-3-((2-fluoro-5-methylbenzoyl)-amino)piperidine-1-carboxamide | 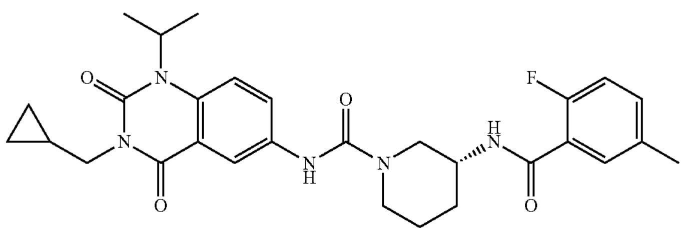 [SMILES: Cc1ccc(F)c(C(=O)N[C@@H]2CCCN(C(=O)Nc3ccc4c(c3)c(=O)n(CC3CC3)c(=O)n4C(C)C)C2)c1] | | 536.2 (M + H) |
| 260 | (3R)-N-(3-(cyclopropylmethyl)-1-isopropyl-2,4-dioxo-1,2,3,4-tetrahydro-quinazolin-6-yl)-3-((2-fluorobenzoyl)amino)-piperidine-1-carboxamide | 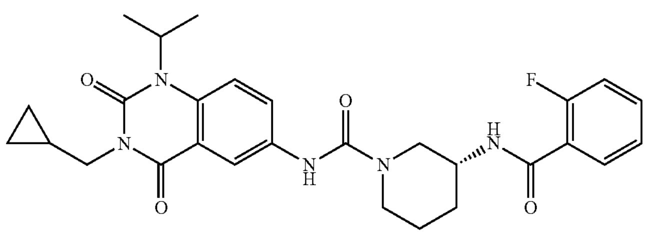 [SMILES: CC(C)n1c(=O)n(CC2CC2)c(=O)c2cc(NC(=O)N3CCC[C@@H](NC(=O)c4ccccc4F)C3)ccc21] | | 522.2 (M + H) |

TABLE 1-27

| Ex. | IUPAC name | Structure | salt | MS |
|---|---|---|---|---|
| 261 | (3R)-3-((3-acryloyl-benzoyl)amino)-N-(3-(cyclopropylmethyl)-1-isopropyl-2,4-dioxo-1,2,3,4-tetrahydro-quinazolin-6-yl)-piperidine-1-carboxamide | 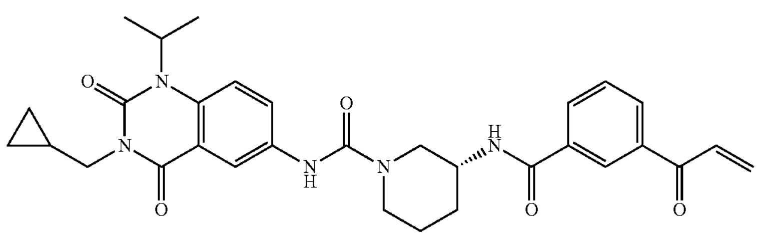 [SMILES: C=CC(=O)c1cccc(C(=O)N[C@@H]2CCCN(C(=O)Nc3ccc4c(c3)c(=O)n(CC3CC3)c(=O)n4C(C)C)C2)c1] | | 558.2 (M + H) |

TABLE 1-27-continued

| Ex. | IUPAC name | Structure | salt | MS |
|---|---|---|---|---|
| 262 | N-((1R,2R)-2-((4-cyano-3-fluorophenyl)-carbamoyl)cyclohexyl)-3-(cyclopropylmethyl)-1-isopropyl-2,4-dioxo-1,2,3,4-tetrahydro-quinazoline-6-carboxamide | 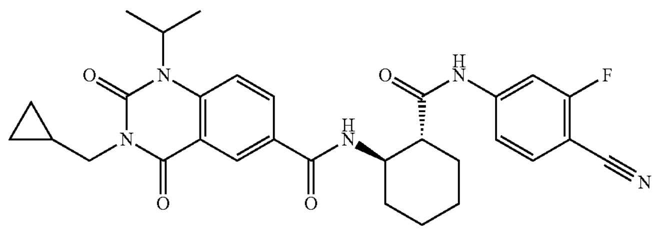 [SMILES: CC(C)n1c(=O)n(CC2CC2)c(=O)c2cc(C(=O)N[C@@H]3CCCC[C@H]3C(=O)Nc3ccc(C#N)c(F)c3)ccc21] | | 544.2 (M − H) |
| 263 | N-((1R,2S)-2-((4-cyano-3-fluorophenyl)-carbamoyl)cyclohexyl)-3-(cyclopropylmethyl)-1-isopropyl-2,4-dioxo-1,2,3,4-tetrahydroquinazoline-6-carboxamide | 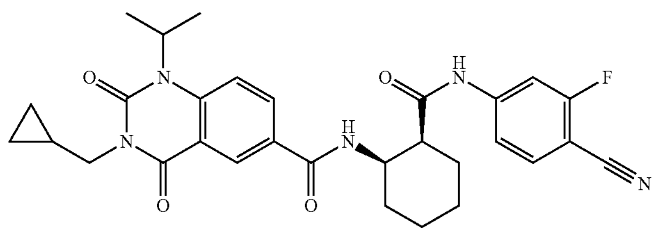 [SMILES: CC(C)n1c(=O)n(CC2CC2)c(=O)c2cc(C(=O)N[C@@H]3CCCC[C@@H]3C(=O)Nc3ccc(C#N)c(F)c3)ccc21] | | 544.2 (M − H) |
| 264 | 4-cyano-N-((1S,2R)-2-((3-(cyclopropylmethyl)-1-isopropyl-2,4-dioxo-1,2,3,4-tetrahydro-quinazolin-6-yl)-carbamoyl)cyclopentyl)-benzamide | 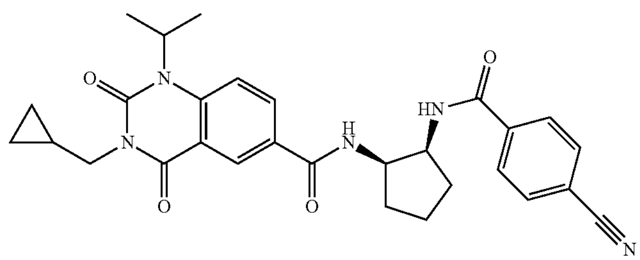 [SMILES: CC(C)n1c(=O)n(CC2CC2)c(=O)c2cc(C(=O)N[C@@H]3CCC[C@@H]3NC(=O)c3ccc(C#N)cc3)ccc21] | | 514.1 (M + H) |
| 265 | (3R)-3-(benzoylamino)-N-(3-(cyclopropylmethyl)-7-fluoro-1-isopropyl-2,4-dioxo-1,2,3,4-tetrahydroquinazolin-6-yl)piperidine-1-carboxamide | 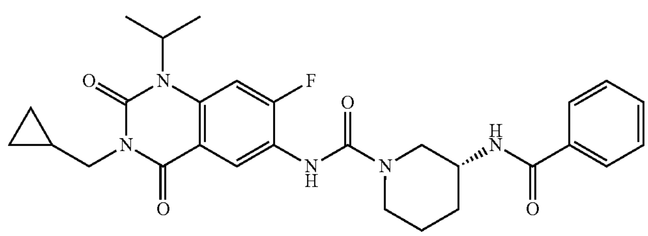 [SMILES: CC(C)n1c(=O)n(CC2CC2)c(=O)c2cc(NC(=O)N3CCC[C@@H](NC(=O)c4ccccc4)C3)c(F)cc21] | | 522.2 (M + H) |
| 266 | (2R)-N$^2$-(5-chloro-6-cyanopyridin-3-yl)-N$^4$-(3-(cyclopropylmethyl)-7-fluoro-1-isopropyl-2,4-dioxo-1,2,3,4-tetrahydroquinazolin-6-yl)morpholine-2,4-dicarboxamide | 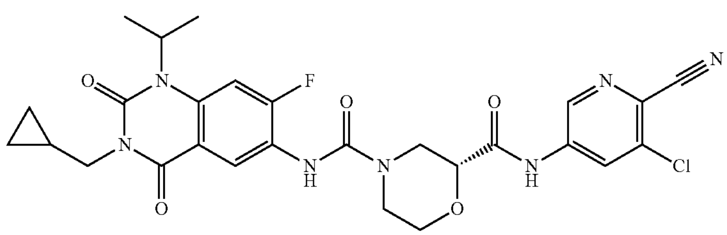 [SMILES: CC(C)n1c(=O)n(CC2CC2)c(=O)c2cc(NC(=O)N3CCO[C@@H](C(=O)Nc4cnc(C#N)c(Cl)c4)C3)c(F)cc21] | | 582.2 (M − H) |
| 267 | (2R)-N$^2$-(4-cyanophenyl)-N$^4$-(3-(cyclopropylmethyl)-7-fluoro-1-isopropyl-2,4-dioxo-1,2,3,4-tetrahydroquinazolin-6-yl)morpholine-2,4-dicarboxamide | 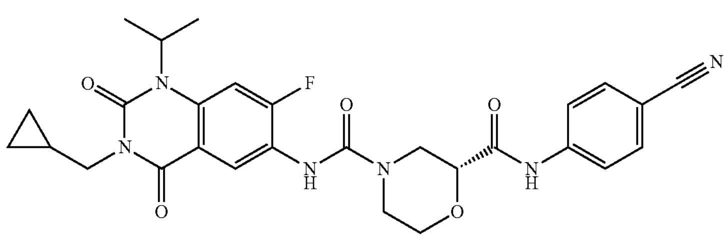 [SMILES: CC(C)n1c(=O)n(CC2CC2)c(=O)c2cc(NC(=O)N3CCO[C@@H](C(=O)Nc4ccc(C#N)cc4)C3)c(F)cc21] | | 549.1 (M + H) |

TABLE 1-27-continued

| Ex. | IUPAC name | Structure | salt | MS |
|---|---|---|---|---|
| 268 | N-((3R)-1-((3-(cyclopropylmethyl)-1-isopropyl-2,4-dioxo-1,2,3,4-tetrahydroquinazolin-6-yl)carbamoyl)piperidin-3-yl)-2-methylimidazo[1,2-a]pyridine-6-carboxamide | 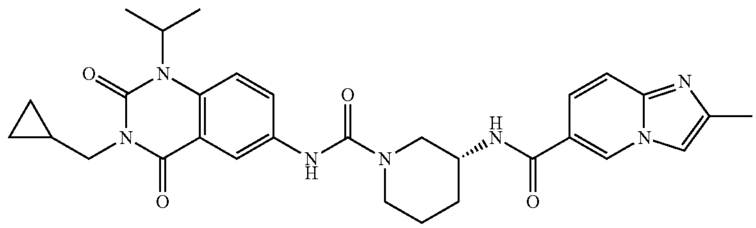 [SMILES: Cc1cn2cc(C(=O)N[C@@H]3CCCN(C(=O)Nc4ccc5c(c4)c(=O)n(CC4CC4)c(=O)n5C(C)C)C3)ccc2n1] | | 558.2 (M + H) |
| 269 | (2R)-N²-(4-cyano-2-fluorophenyl)-N⁴-(3-(cyclopropylmethyl)-7-fluoro-1-isopropyl-2,4-dioxo-1,2,3,4-tetrahydroquinazolin-6-yl)morpholine-2,4-dicarboxamide | 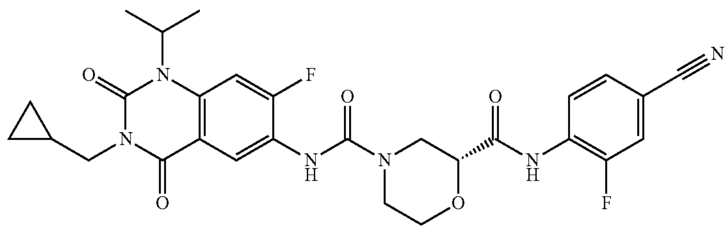 | | 567.1 (M + H) |
| 270 | (3R)-N-(3-(cyclopropylmethyl)-7-fluoro-1-isopropyl-2,4-dioxo-1,2,3,4-tetrahydroquinazolin-6-yl)-3-(1-oxo-1,3-dihydro-2H-isoindol-2-yl)piperidine-1-carboxamide | 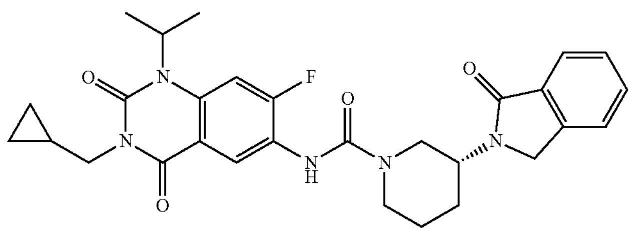 [SMILES: CC(C)n1c(=O)n(CC2CC2)c(=O)c2cc(NC(=O)N3CCC[C@@H](N4Cc5ccccc5C4=O)C3)c(F)cc21] | | 534.1 (M + H) |

TABLE 1-28

| Ex. | IUPAC name | Structure | salt | MS |
|---|---|---|---|---|
| 271 | cis-4-(benzoylamino)-N-3-(cyclopropylmethyl)-1-isopropyl-2,4-dioxo-1,2,3,4-tetrahydroquinazolin-6-yl)tetrahydrofuran-3-carboxamide | 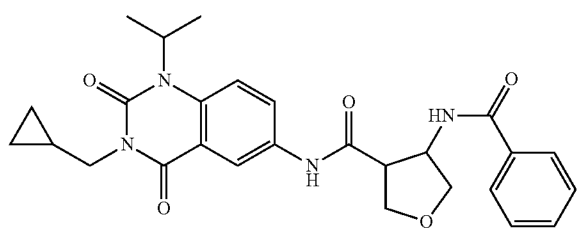 | | 491.2 (M + H) |
| 272 | cis-4-(benzoylamino)-N-(3-(cyclopropylmethyl)-7-fluoro-1-isopropyl-2,4-dioxo-1,2,3,4-tetrahydroquinazolin-6-yl)tetrahydrofuran-3-carboxamide | 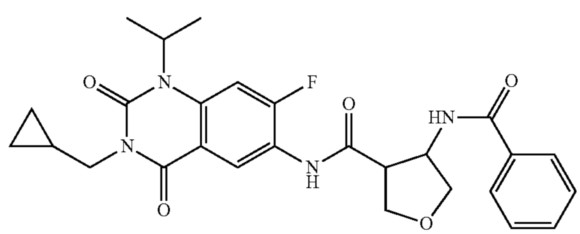 [SMILES: CC(C)n1c(=O)n(CC2CC2)c(=O)c2cc(NC(=O)C3COCC3NC(=O)c3ccccc3)c(F)cc21] | | 509.1 (M + H) |
| 273 | (3R)-N-(3-(cyclopropylmethyl)-1-isopropyl-2,4-dioxo-1,2,3,4-tetrahydroquinazolin-6-yl)-3-((3-(((2E)-4-(dimethylamino)but-2-enoyl)amino)benzoyl)-amino)piperidine-1-carboxamide | 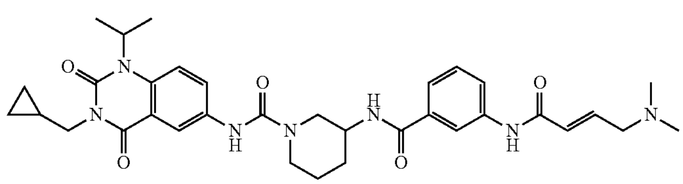 [SMILES: CC(C)n1c(=O)n(CC2CC2)c(=O)c2cc(NC(=O)N3CCCC(NC(=O)c4cccc(NC(=O)/C=C/CN(C)C)c4)C3)ccc21] | | 630.3 (M + H) |

TABLE 1-28-continued

| Ex. | IUPAC name | salt | MS |
|---|---|---|---|
| 274 | tert-butyl (4-(((3R)-1-((3-(cyclopropylmethyl)-1-isopropyl-2,4-dioxo-1,2,3,4-tetrahydroquinazolin-6-yl)carbamoyl)piperidin-3-yl)carbamoyl)-benzyl)carbamate | | 631.4 (M − H) |
| 275 | (3R)-3-((4-(aminomethyl)benzoyl)-amino)-N-(3-(cyclopropylmethyl)-1-isopropyl-2,4-dioxo-1,2,3,4-tetrahydroquinazolin-6-yl)piperidine-1-carboxamide | | 533.2 (M + H) |
| 276 | (3R)-3-((4-((acryloylamino)methyl)-benzoyl)amino)-N-(3-(cyclopropylmethyl)-1-isopropyl-2,4-dioxo-1,2,3,4-tetrahydroquinazolin-6-yl)piperidine-1-carboxamide | | 587.2 (M + H) |
| 277 | (3R)-3-((4-(((chloroacetyl)amino)-methyl)benzoyl)amino)-N-(3-(cyclopropylmethyl)-1-isopropyl-2,4-dioxo-1,2,3,4-tetrahydroquinazolin-6-yl)piperidine-1-carboxamide | | 609.2 (M + H) |
| 278 | N-(1-((4-cyano-3-fluorophenyl)carbamoyl)-azepan-4-yl)-3-(cyclopropylmethyl)-1-isopropyl-2,4-dioxo-1,2,3,4-tetrahydroquinazoline-6-carboxamide | | 561.2 (M + H) |
| 279 | N-(1-(4-cyano-3-fluorobenzoyl)azepan-4-yl)-3-(cyclopropyl-methyl)-1-isopropyl-2,4-dioxo-1,2,3,4-tetrahydroquinazoline-6-carboxamide | | 546.0 (M + H) |
| 280 | N-(1-((4-cyano-3-fluorophenyl)acetyl)-azepan-4-yl)-3-(cyclopropylmethyl)-1-isopropyl-2,4-dioxo-1,2,3,4-tetrahydroquinazoline-6-carboxamide | | 560.1 (M + H) |

TABLE 1-29

| Ex. | IUPAC name | Structure | salt | MS |
|---|---|---|---|---|
| 281 | (3R)-N-(3-(cyclopropyl-methyl)-7-fluoro-1-isopropyl-2,4-dioxo-1,2,3,4,-tetrahydro-quinazolin-6-yl)-3-((2-fluoro-5-(trifluoro-methyl)benzoyl)amino)-piperidine-1-carboxamide | 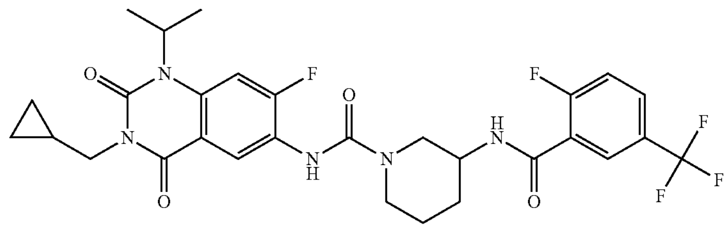 [SMILES: CC(C)n1c(=O)n(CC2CC2)c(=O)c2cc(NC(=O)N3CCCC(NC(=O)c4cc(C(F)(F)F)ccc4F)C3)c(F)cc21] | | 608.2 (M + H) |
| 282 | (3R)-3-((5-chloro-2-fluorobenzoyl)amino)-N-(3-(cyclopropylmethyl)-7-fluoro-1-isopropyl-2,4-dioxo-1,2,3,4-tetrahydroquinazolin-6-yl)piperidine-1-carboxamide | 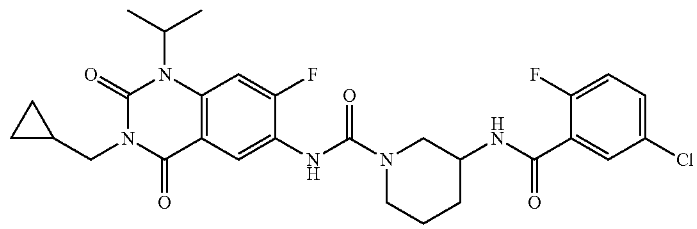 [SMILES: CC(C)n1c(=O)n(CC2CC2)c(=O)c2cc(NC(=O)N3CCCC(NC(=O)c4cc(Cl)ccc4F)C3)c(F)cc21] | | 574.1 (M + H) |
| 283 | (3R)-N-(3-(cyclopropylmethyl)-7-fluoro-1-isopropyl-2,4-dioxo-1,2,3,4-tetrahydroquinazolin-6-yl)-3-((2-fluoro-5-methylbenzoyl)amino)-piperidine-1-carboxamide | 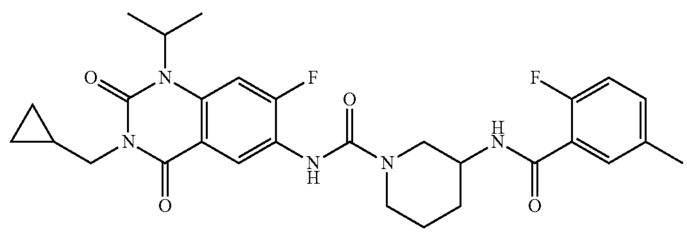 [SMILES: Cc1ccc(F)c(C(=O)NC2CCCN(C(=O)Nc3cc4c(=O)n(CC5CC5)c(=O)n(C(C)C)c4cc3F)C2)c1] | | 553.9 (M + H) |
| 284 | (3R)-3-((4-cyanobenzoyl)amino)-N-(3-(cyclopropylmethyl)-7-fluoro-1-isopropyl-2,4-dioxo-1,2,3,4-tetrahydroquinazolin-6-yl)piperidine-1-carboxamide | 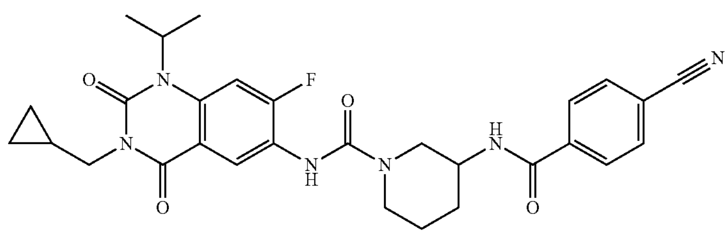 [SMILES: CC(C)n1c(=O)n(CC2CC2)c(=O)c2cc(NC(=O)N3CCCC(NC(=O)c4ccc(C#N)cc4)C3)c(F)cc21] | | 547.1 (M + H) |
| 285 | (3R)-N-(3-(cyclopropylmethyl)-7-fluoro-1-isopropyl-2,4-dioxo-1,2,3,4-tetrahydroquinazolin-6-yl)-3-((2,3-dihydro-1-benzofuran-5-ylcarbonyl)amino)-piperidine-1-carboxamide | 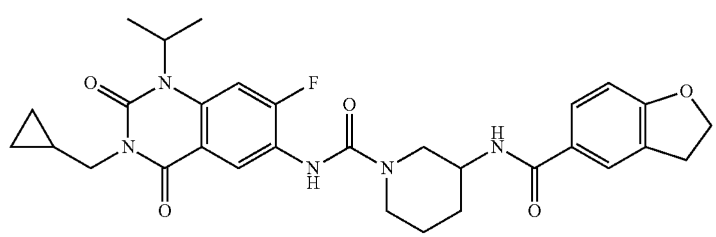 [SMILES: CC(C)n1c(=O)n(CC2CC2)c(=O)c2cc(NC(=O)N3CCCC(NC(=O)c4ccc5c(c4)CCO5)C3)c(F)cc21] | | 564.1 (M + H) |
| 286 | (3R)-N-(3-(cyclopropyl-methyl)-7-fluoro-1-isopropyl-2,4-dioxo-1,2,3,4-tetrahydro-quinazolin-6-yl)-3-((2-fluoro-4-(trifluoro-methyl)benzoyl)amino)-piperidine-1-carboxamide | 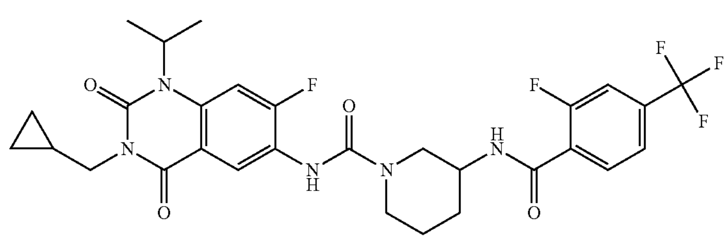 [SMILES: CC(C)n1c(=O)n(CC2CC2)c(=O)c2cc(NC(=O)N3CCCC(NC(=O)c4ccc(C(F)(F)F)cc4F)C3)c(F)cc21] | | 608.1 (M + H) |

TABLE 1-29-continued

| Ex. | IUPAC name | Structure | salt | MS |
|---|---|---|---|---|
| 287 | (3R)-N-(3-(cyclopropylmethyl)-7-fluoro-1-isopropyl-2,4-dioxo-1,2,3,4-tetrahydroquinazolin-6-yl)-3-((2,5-difluorobenzoyl)amino)-piperidine-1-carboxamide | 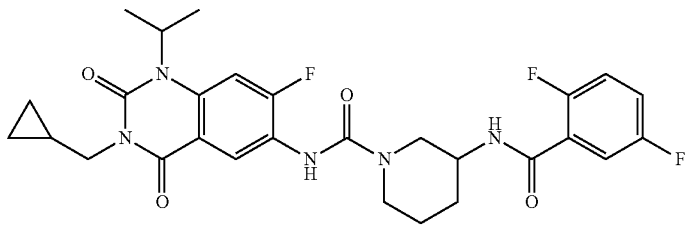 | | 558.1 (M + H) |
| 288 | N-((1-((3-(cyclopropylmethyl)-1-isopropyl-2,4-dioxo-1,2,3,4-tetrahydro-quinazolin-6-yl)-carbamoyl)cyclopropyl)-methyl)benzamide | 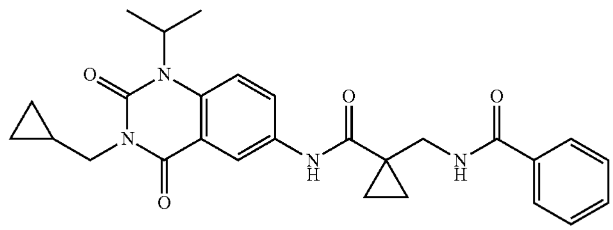 [SMILES: CC(C)n1c(=O)n(CC2CC2)c(=O)c2cc(NC(=O)C3(CNC(=O)c4ccccc4)CC3)ccc21] | | 475.2 (M + H) |
| 289 | 4-cyano-N-((1-((3-(cyclopropylmethyl)-1-isopropyl-2,4-dioxo-1,2,3,4-tetrahydro-quinazolin-6-yl)-carbamoyl)cyclopropyl)-methyl)benzamide | 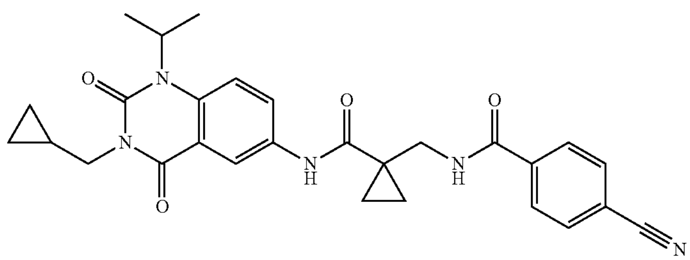 [SMILES: CC(C)n1c(=O)n(CC2CC2)c(=O)c2cc(NC(=O)C3(CNC(=O)c4ccc(C#N)cc4)CC3)ccc21] | | 500.1 (M + H) |
| 290 | (3R)-N-(3-(cyclopropylmethyl)-7-fluoro-1-isopropyl-2,4-dioxo-1,2,3,4-tetrahydroquinazolin-6-yl)-3-((2,4-difluoro-benzoyl)amino)-piperidine-1-carboxamide | 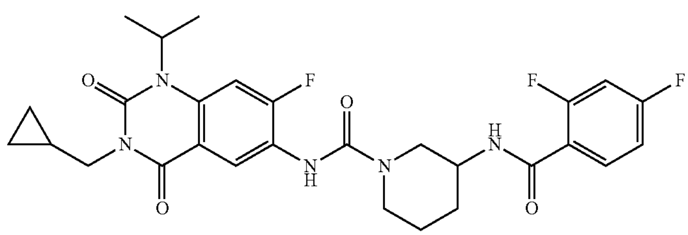 [SMILES: CC(C)n1c(=O)n(CC2CC2)c(=O)c2cc(NC(=O)N3CCCC(NC(=O)c4ccc(F)cc4F)C3)c(F)cc21] | | 558.1 (M + H) |

TABLE 1-30

| Ex. | IUPAC name | Structure | salt | MS |
|---|---|---|---|---|
| 291 | (3R)-N-(3-(cyclopropylmethyl)-7-fluoro-1-isopropyl-2,4-dioxo-1,2,3,4-tetrahydroquinazolin-6-yl)-3-((2-fluoro-4-methoxybenzoyl)amino)-piperidine-1-carboxamide | 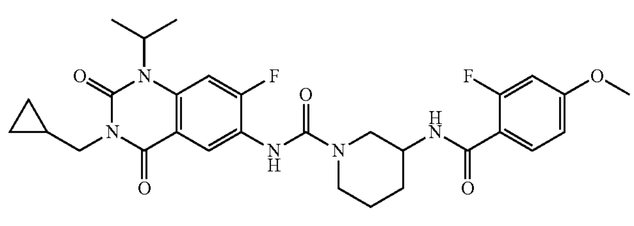 [SMILES: COc1ccc(C(=O)NC2CCCN(C(=O)Nc3cc4c(=O)n(CC5CC5)c(=O)n(C(C)C)c4cc3F)C2)c(F)c1] | | 570.2 (M + H) |
| 292 | (3R)-3-(((5-cyano-2-thienyl)carbonyl)amino)-N-(3-(cyclopropylmethyl)-7-fluoro-1-isopropyl-2,4-dioxo-1,2,3,4-tetrahydroquinazolin-6-yl)piperidine-1-carboxamide | 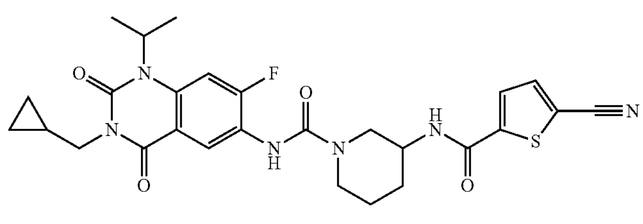 [SMILES: CC(C)n1c(=O)n(CC2CC2)c(=O)c2cc(NC(=O)N3CCCC(NC(=O)c4ccc(C#N)s4)C3)c(F)cc21] | | 553.1 (M + H) |

TABLE 1-30-continued

| Ex. | IUPAC name | Structure | salt | MS |
|---|---|---|---|---|
| 293 | cis-4-((4-cyanobenzoyl)amino)-N-(3-(cyclopropylmethyl)-7-fluoro-1-isopropyl-2,4-dioxo-1,2,3,4-tetrahydroquinazolin-6-yl)tetrahydrofuran-3-carboxamide | 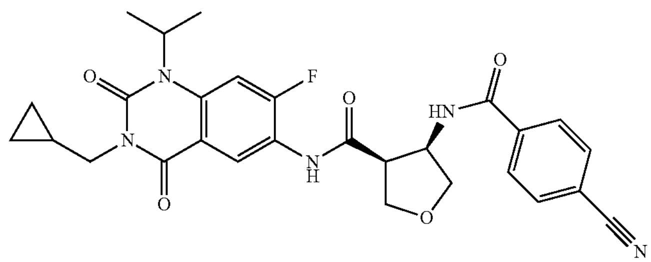 [SMILES: CC(C)n1c(=O)n(CC2CC2)c(=O)c2cc(NC(=O)[C@@H]3COC[C@@H]3NC(=O)c3ccc(C#N)cc3)c(F)cc21] | | 534.1 (M + H) |
| 294 | cis-N-(3-(cyclopropylmethyl)-7-fluoro-1-isopropyl-2,4-dioxo-1,2,3,4-tetrahydroquinazolin-6-yl)-4-(1-oxo-1,3-dihydro-2H-isoindol-2-yl)tetrahydrofuran-3-carboxamide | 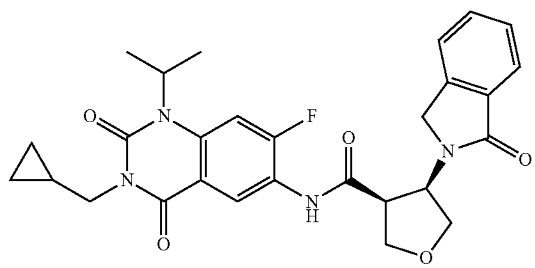 [SMILES: CC(C)n1c(=O)n(CC2CC2)c(=O)c2cc(NC(=O)[C@@H]3COC[C@@H]3N3Cc4ccccc4C3=O)c(F)cc21] | | 521.1 (M + H) |
| 295 | (3R)-N-(3-(cyclopropylmethyl)-7-fluoro-1-isopropyl-2,4-dioxo-1,2,3,4-tetrahydroquinazolin-6-yl)-3-(1,3-dioxo-3,4-dihydroisoquinolin-2(1H)-yl)piperidine-1-carboxamide | 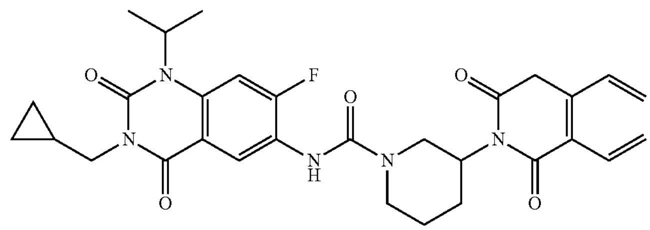 [SMILES: C=CC1=C(C=C)C(=O)N(C2CCCN(C(=O)Nc3cc4c(=O)n(CC5CC5)c(=O)n(C(C)C)c4cc3F)C2)C(=O)C1] | | 562.1 (M + H) |
| 296 | N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-2-methyl-1,3-benzoxazole-5-carboxamide | 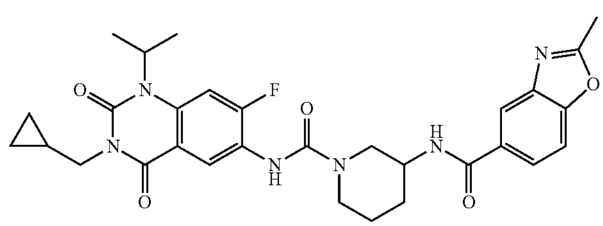 [SMILES: Cc1nc2cc(C(=O)NC3CCCN(C(=O)Nc4cc5c(=O)n(CC6CC6)c(=O)n(C(C)C)c5cc4F)C3)ccc2o1] | | 577.1 (M + H) |
| 297 | N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-2-methyl-1H-benzimidazole-5-carboxamide | 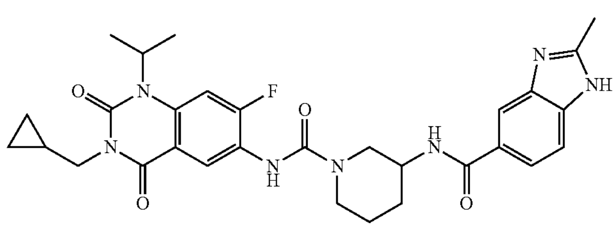 [SMILES: Cc1nc2cc(C(=O)NC3CCCN(C(=O)Nc4cc5c(=O)n(CC6CC6)c(=O)n(C(C)C)c5cc4F)C3)ccc2[nH]1] | | 576.2 (M + H) |
| 298 | N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-2-(trifluoromethyl)-1H-benzimidazole-5-carboxamide | 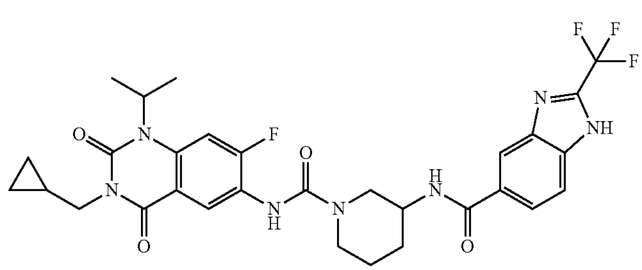 [SMILES: CC(C)n1c(=O)n(CC2CC2)c(=O)c2cc(NC(=O)N3CCCC(NC(=O)c4ccc5[nH]c(C(F)(F)F)nc5c4)C3)c(F)cc21] | | 630.2 (M + H) |

TABLE 1-30-continued

| Ex. | IUPAC name | Structure | salt | MS |
|---|---|---|---|---|
| 299 | N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-2-methyl-2H-indazole-5-carboxamide | 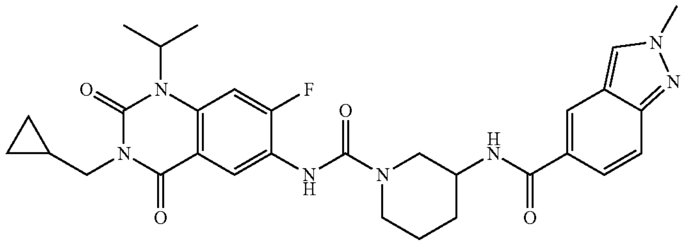 [SMILES: CC(C)n1c(=O)n(CC2CC2)c(=O)c2cc(NC(=O)N3CCCC(NC(=O)c4ccc5nn(C)cc5c4)C3)c(F)cc21] | | 576.2 (M + H) |
| 300 | N-((3R)-1-((3-(cloproylmethyl)-7-fluoro-1-isopropyl-2,4-dioxo-1,2,3,4-tetrahydroquinazolin-6-yl)carbamoyl)piperidin-3-yl)-2-methyl-2H-indazole-6-carboxamide | 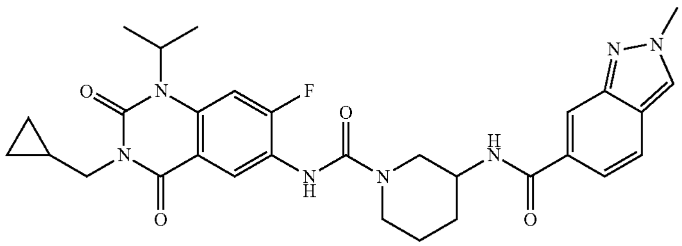 [SMILES: CC(C)n1c(=O)n(CC2CC2)c(=O)c2cc(NC(=O)N3CCCC(NC(=O)c4ccc5cn(C)nc5c4)C3)c(F)cc21] | | 576.1 (M + H) |

TABLE 1-31

| Ex. | IUPAC name | Structure | salt | MS |
|---|---|---|---|---|
| 301 | (3R)-N-(3-(cyclopropylmethyl)-7-fluoro-1-isopropyl-2,4-dioxo-1,2,3,4-tetrahydroquinazolin-6-yl)-3-(2,4-dioxo-1,4-dihydroquinazolin-3(2H)-yl)piperidine-1-carboxamide | 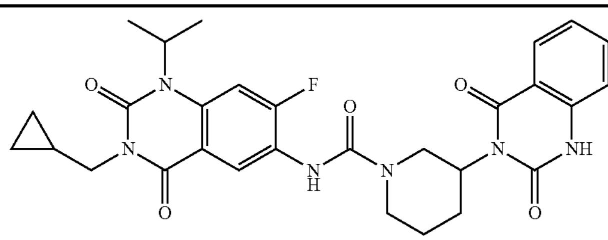 | | 563.2 (M + H) |
| 302 | (3R)-N-(3-(cyclopropylmethyl)-7-fluoro-1-isopropyl-2,4-dioxo-1,2,3,4-tetrahydroquinazolin-6-yl)-3-(4-oxoquinazolin-3(4H)-yl)piperidine-1-carboxamide | 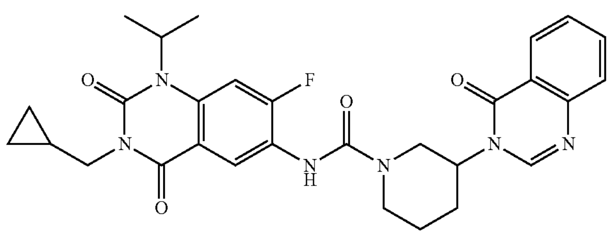 [SMILES: CC(C)n1c(=O)n(CC2CC2)c(=O)c2cc(NC(=O)N3CCCC(n4cnc5ccccc5c4=O)C3)c(F)cc21] | | 547.1 (M + H) |
| 303 | (3R)-N-(3-(cyclopropylmethyl)-7-fluoro-1-isopropyl-2,4-dioxo-1,2,3,4-tetrahydroquinazolin-6-yl)-3-(6-methoxy-1-oxo-1,3-dihydro-2H-isoindol-2-yl)piperidine-1-carboxamide | 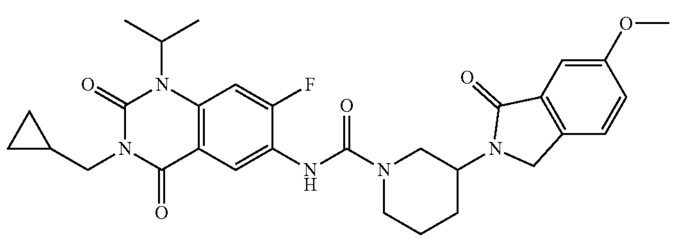 [SMILES: COc1ccc2c(c1)C(=O)N(C1CCCN(C(=O)Nc3cc4c(=O)n(CC5CC5)c(=O)n(C(C)C)c4cc3F)C1)C2] | | 564.1 (M + H) |
| 304 | (3R)-N-(3-(cyclopropylmethyl)-1-ethyl-2,4-dioxo-1,2,3,4-tetrahydroquinazolin-6-yl)-3-(1-oxo-1,3-dihydro-2H-isoindol-2-yl)piperidine-1-carboxamide | 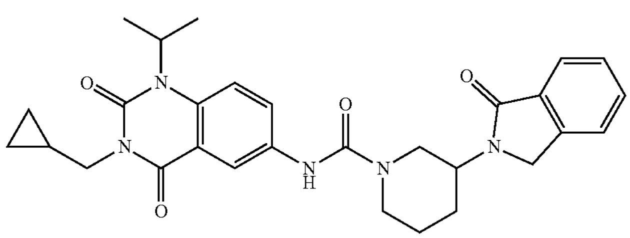 | | 502.0 (M + H) |

TABLE 1-31-continued

| Ex. | IUPAC name | Structure | salt | MS |
|---|---|---|---|---|
| 305 | (3R)-N-(3-(cyclopropylmethyl)-1-(2,2-difluoroethyl)-2,4-dioxo-1,2,3,4-tetrahydroquinazolin-6-yl)-3-(1-oxo-1,3-dihydro-2H-isoindol-2-yl)piperidine-1-carboxamide | 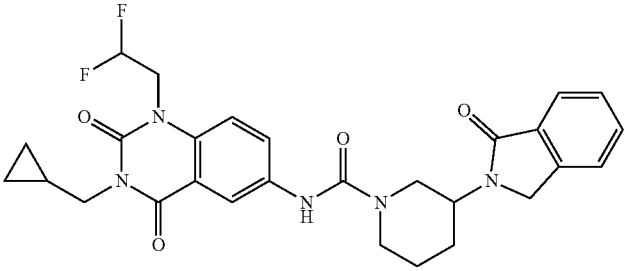 [SMILES: O=C(Nc1ccc2c(c1)c(=O)n(CC1CC1)c(=O)n2CC(F)F)N1CCCC(N2Cc3ccccc3C2=O)C1] | | 538.1 (M + H) |
| 306 | (3R)-N-(3-(cyclopropylmethyl)-2,4-dioxo-1-(2,2,2-trifluoroethyl)-1,2,3,4-tetrahydroquinazolin-6-yl)-3-(1-oxo-1,3-dihydro-2H-isoindol-2-yl)piperidine-1-carboxamide | 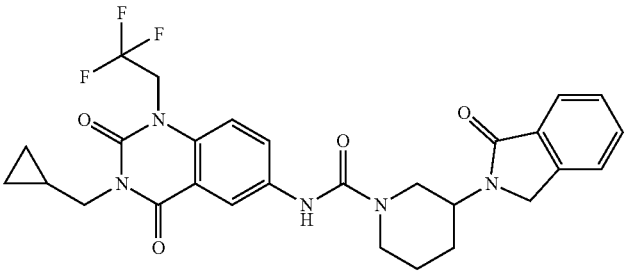 [SMILES: O=C(Nc1ccc2c(c1)c(=O)n(CC1CC1)c(=O)n2CC(F)(F)F)N1CCCC(N2Cc3ccccc3C2=O)C1] | | 556.2 (M + H) |
| 307 | (3R)-N-(3-(cyclopropylmethyl)-1-(3-methylbutyl)-2,4-dioxo-1,2,3,4-tetrahydroquinazolin-6-yl)-3-(1-oxo-1,3-dihydro-2H-isoindol-2-yl)piperidine-1-carboxamide | 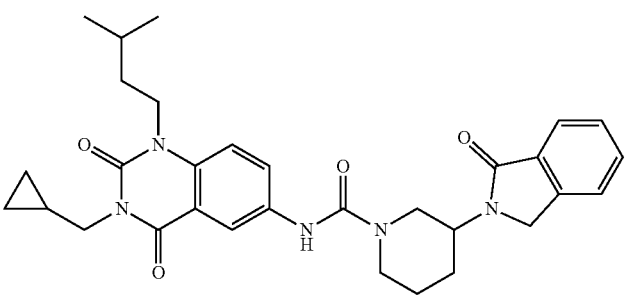 [SMILES: CC(C)CCn1c(=O)n(CC2CC2)c(=O)c2cc(NC(=O)N3CCCC(N4Cc5ccccc5C4=O)C3)ccc21] | | 544.1 (M + H) |
| 308 | N-((1R,2S)-2-((3-(cyclopropylmethyl)-1-isopropyl-2,4-dioxo-1,2,3,4-tetrahydro-quinazolin-6-yl)-carbamoyl)cyclopentyl)-benzamide | 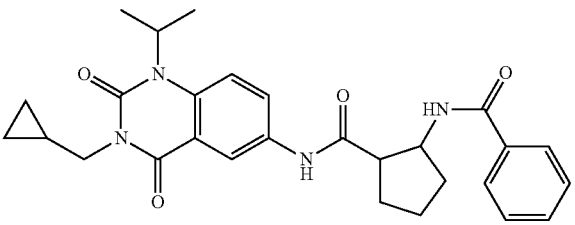 [SMILES: CC(C)n1c(=O)n(CC2CC2)c(=O)c2cc(NC(=O)C3CCCC3NC(=O)c3ccccc3)ccc21] | | 489.1 (M + H) |
| 309 | N-((1S,2R)-2-((3-(cyclopropylmethyl)-1-isopropyl-2,4-dioxo-1,2,3,4-tetrahydro-quinazolin-6-yl)-carbamoyl)cyclopentyl)-benzamide | 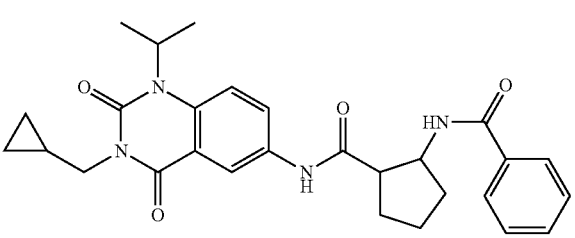 [SMILES: CC(C)n1c(=O)n(CC2CC2)c(=O)c2cc(NC(=O)C3CCCC3NC(=O)c3ccccc3)ccc21] | | 489.1 (M + H) |
| 310 | N-(1-(2-((3-(cyclopropylmethyl)-7-fluoro-1-isopropyl-2,4-dioxo-1,2,3,4-tetrahydroquinazolin-6-yl)amino)-2-oxoethyl)cyclopentyl)-benzamide | 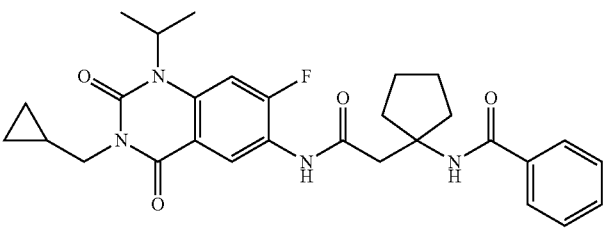 [SMILES: CC(C)n1c(=O)n(CC2CC2)c(=O)c2cc(NC(=O)CC3(NC(=O)c4ccccc4)CCCC3)c(F)cc21] | | 521.1 (M + H) |

TABLE 1-32

| Ex. | IUPAC name | Structure | salt | MS |
|---|---|---|---|---|
| 311 | 4-cyano-N-(1-(2-((3-(cyclopropylmethyl)-7-fluoro-1-isopropyl-2,4-dioxo-1,2,3,4-tetrahydroquinazolin-6-yl)amino)-2-oxoethyl)cyclopentyl)benzamide | 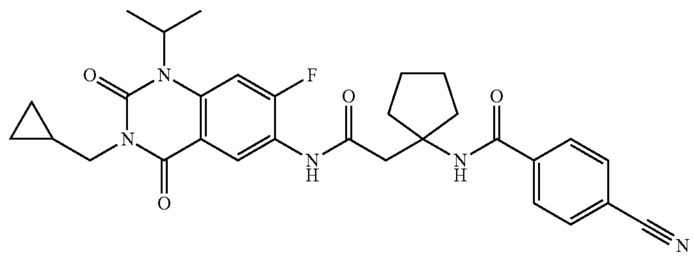 [SMILES: CC(C)n1c(=O)n(CC2CC2)c(=O)c2cc(NC(=O)CC3(NC(=O)c4ccc(C#N)cc4)CCCC3)c(F)cc21] | | 546.1 (M + H) |
| 312 | (3R)-N-(3-(cyclopropylmethyl)-7-fluoro-1-isopropyl-2,4-dioxo-1,2,3,4-tetrahydroquinazolin-6-yl)-3-((4-(hydroxymethyl)benzoyl)amino)piperidine-1-caroxamide | 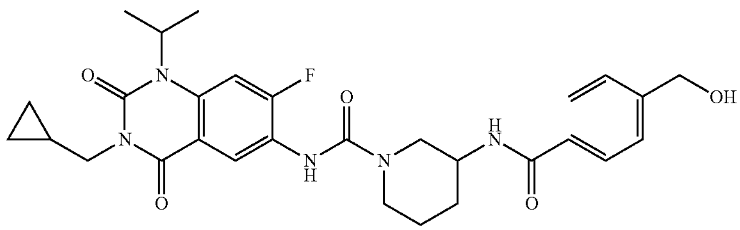 [SMILES: C=C/C(=C\C=C\C(=O)NC1CCCN(C(=O)Nc2cc3c(=O)n(CC4CC4)c(=O)n(C(C)C)c3cc2F)C1)CO] | | 552.1 (M + H) |
| 313 | (3R)-3-((2-chloro-5-(trifluoromethyl)benzoyl)amino)-N-(3-(cyclopropylmethyl)-7-fluoro-1-isopropyl-2,4-dioxo-1,2,3,4-tetrahydroquinazolin-6-yl)piperidine-1-carboxamide | 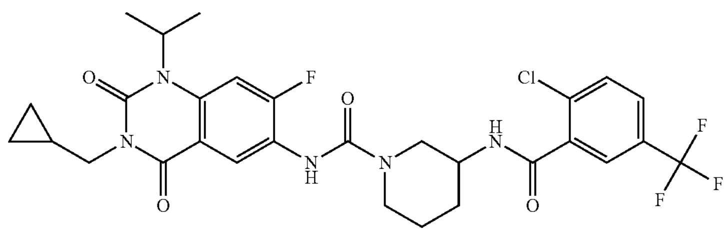 | | 624.1 (M + H) |
| 314 | (3R)-3-((2-chloro-5-fluorobenzoyl)amino)-N-(3-(cyclopropylmethyl)-7-fluoro-1-isopropyl-2,4-dioxo-1,2,3,4-tetrahydroquinazolin-6-yl)piperidine-1-carboxamide | 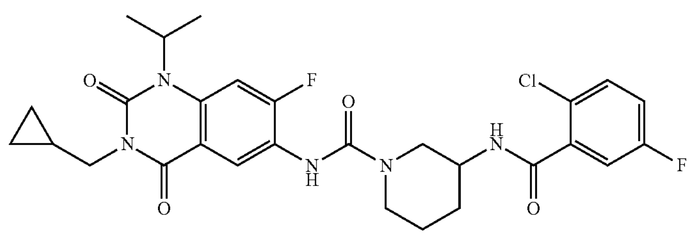 | | 574.1 (M + H) |
| 315 | 4-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)benzyl ethylcarbamate | 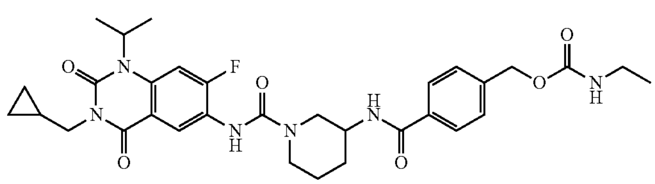 [SMILES: CCNC(=O)OCc1ccc(C(=O)NC2CCCN(C(=O)Nc3cc4c(=O)n(CC5CC5)c(=O)n(C(C)C)c4cc3F)C2)cc1] | | 623.1 (M + H) |
| 316 | (3R)-N-(3-(cyclopropylmethyl)-7-fluoro-1-isopropyl-2,4-dioxo-1,2,3,4-tetrahydroquinazolin-6-yl)-3-((4-(difluoromethoxy)benzoyl)amino)piperidine-1-carboxamide | 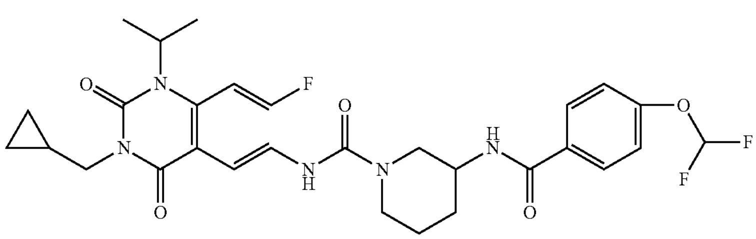 [SMILES: CC(C)n1c(/C=C/F)c(/C=C/NC(=O)N2CCCC(NC(=O)c3ccc(OC(F)F)cc3)C2)c(=O)n(CC2CC2)c1=O] | | 588.2 (M + H) |

TABLE 1-32-continued

| Ex. | IUPAC name | Structure | salt | MS |
|---|---|---|---|---|
| 317 | N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-6-(trifluoromethyl)nicotinamide | 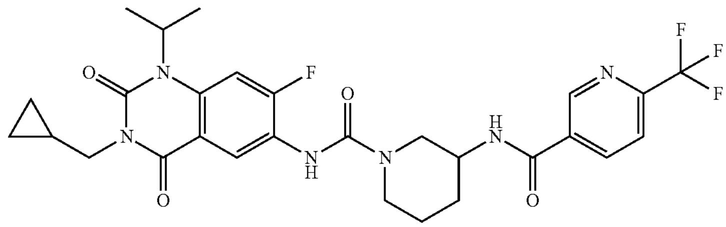 [SMILES: CC(C)n1c(=O)n(CC2CC2)c(=O)c2cc(NC(=O)N3CCCC(NC(=O)c4ccc(C(F)(F)F)nc4)C3)c(F)cc21] | | 591.1 (M + H) |
| 318 | (3R)-N-(3-(cyclopropylmethyl)-7-fluoro-1-isopropyl-2,4-dioxo-1,2,3,4-tetrahydroquinazolin-6-yl)-3-((2,3-dihydro-1-benzofuran-6-ylcarbonyl)amino)-piperidine-1-carboxamide | 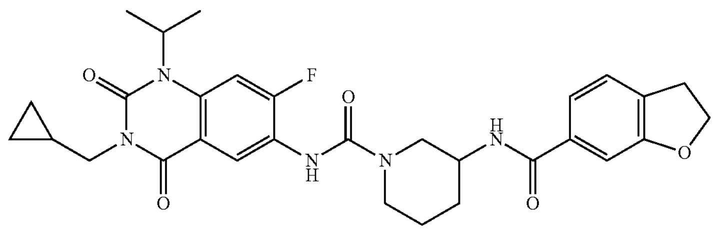 [SMILES: CC(C)n1c(=O)n(CC2CC2)c(=O)c2cc(NC(=O)N3CCCC(NC(=O)c4ccc5c(c4)OCC5)C3)c(F)cc21] | | 564.2 (M + H) |
| 319 | tert-butyl (4-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-benzyl)carbamate | 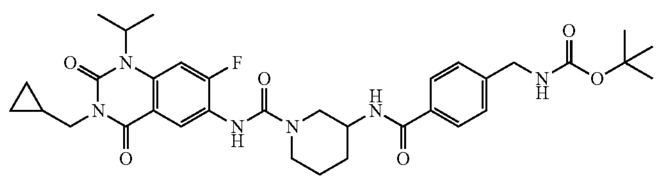 | | 649.4 (M − H) |
| 320 | (3R)-3-((4-(aminoethyl)benzoyl)-amino)-N-(3-(cyclopropylmethyl)-7-fluoro-1-isopropyl-2,4-dioxo-1,2,3,4-tetrahydroquinazolin-6-yl)piperidine-1-carboxamide hydrochloride | 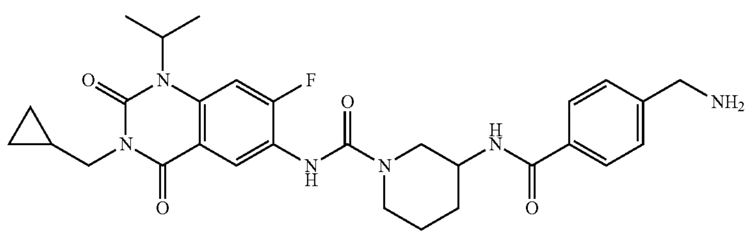 [SMILES: CC(C)n1c(=O)n(CC2CC2)c(=O)c2cc(NC(=O)N3CCCC(NC(=O)c4ccc(CN)cc4)C3)c(F)cc21] | HCl | 551.2 (M − HCl + H) |

TABLE 1-33

| Ex. | IUPAC name | Structure | salt | MS |
|---|---|---|---|---|
| 321 | methyl (4-(((3R)-1-((3-(cyclopropylmethyl-7-fluoro-1-isopropyl-2,4-dioxo-1,2,3,4-tetrahydroquinazolin-6-yl)carbamoyl)piperidin-3-yl)carbamoyl)-benzyl)carbamate | 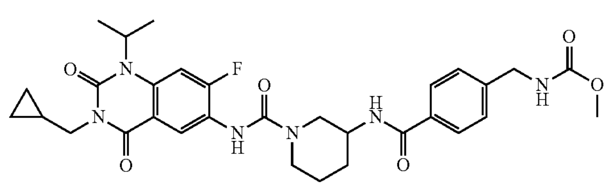 [SMILES: COC(=O)NCc1ccc(C(=O)NC2CCCN(C(=O)Nc3cc4c(=O)n(CC5CC5)c(=O)n(C(C)C)c4cc3F)C2)cc1] | | 609.1 (M + H) |
| 322 | N$^1$-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-2-fluoroterephthalamide | 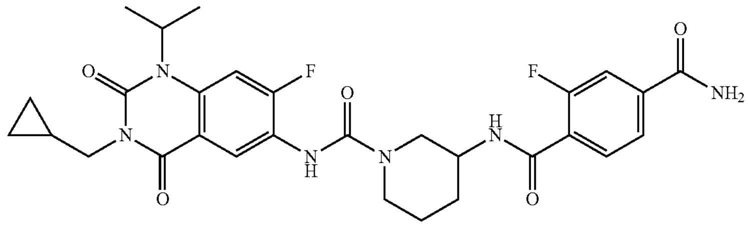 [SMILES: CC(C)n1c(=O)n(CC2CC2)c(=O)c2cc(NC(=O)N3CCCC(NC(=O)c4ccc(C(N)=O)cc4F)C3)c(F)cc21] | | 583.1 (M + H) |

TABLE 1-33-continued

| Ex. | IUPAC name | Structure | salt | MS |
|---|---|---|---|---|
| 323 | (3R)-3-(6-cyano-1-oxo-1,3-dihydro-2H-isoindol-2-yl)-N-(3-(cyclopropylmethyl)-7-fluoro-1-isopropyl-2,4-dioxo-1,2,3,4-tetrahydroquinazolin-6-yl)piperidine-1-carboxamide | 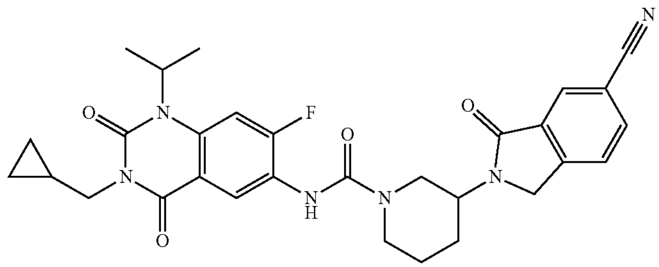 [SMILES: CC(C)n1c(=O)n(CC2CC2)c(=O)c2cc(NC(=O)N3CCCC(N4Cc5ccc(C#N)cc5C4=O)C3)c(F)cc21] | | 559.1 (M + H) |
| 324 | (3R)-3-(7-cyano-4-oxoquinazolin-3(4H)-yl)-N-(3-(cyclopropylmethyl)-7-fluoro-1-isopropyl-2,4-dioxo-1,2,3,4-tetrahydroquinazolin-6-yl)piperidine-1-carboxamide | 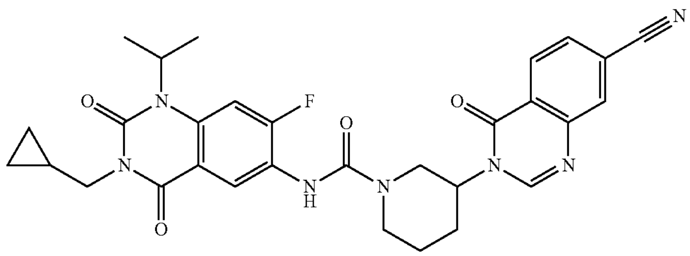 [SMILES: CC(C)n1c(=O)n(CC2CC2)c(=O)c2cc(NC(=O)N3CCCC(n4cnc5cc(C#N)ccc5c4=O)C3)c(F)cc21] | | 572.2 (M + H) |
| 325 | (3R)-N-(3-(cyclopropylmethyl)-7-fluoro-1-isopropyl-2,4-dioxo-1,2,3,4-tetrahydroquinazolin-6-yl)-3-((4-(methoxymethyl)benzoyl)-amino)piperidine-1-carboxamide | 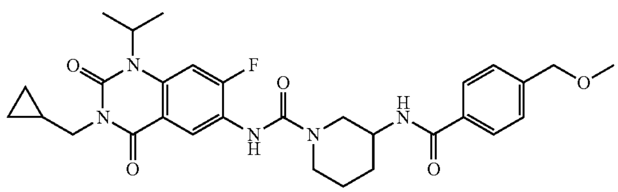 [SMILES: COCc1ccc(C(=O)NC2CCCN(C(=O)Nc3cc4c(=O)n(CC5CC5)c(=O)n(C(C)C)c4cc3F)C2)cc1] | | 566.2 (M + H) |
| 326 | (3R)-N-(3-(cyclopropylmethyl)-7-fluoro-1-isoproypl-2,4-dioxo-1,2,3,4-tetrahydroquinazolin-6-yl)-3-((4-(2-methoxyethoxy)benzoyl)-amino)piperidine-1-carboxamide | 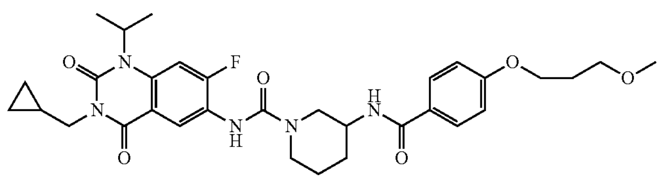 | | 596.1 (M + H) |
| 327 | (3R)-N-(3-(cyclopropylmethyl)-7-fluoro-1-isopropyl-2,4-dioxo-1,2,3,4-tetrahydroquinazolin-6-yl)-3-((5-methyl-1,3-thiazol-2-yl)carbonyl)amino)-piperidine-1-carboxamide | 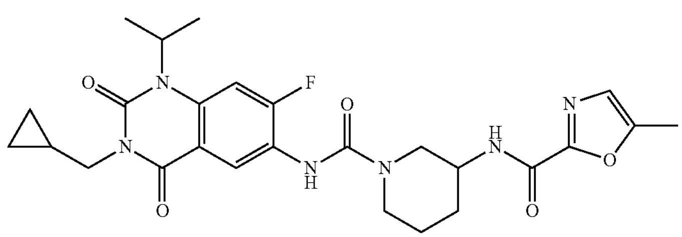 | | 543.0 (M + H) |
| 328 | (3R)-3-(5-cyano-1-oxo-1,3-dihydro-2H-isoindol-2-yl)-N-(3-(cyclopropylmethyl)-7-fluoro-1-isopropyl-2,4-dioxo-1,2,3,4-tetrahydroquinazolin-6-yl)piperidine-1-carboxamide | 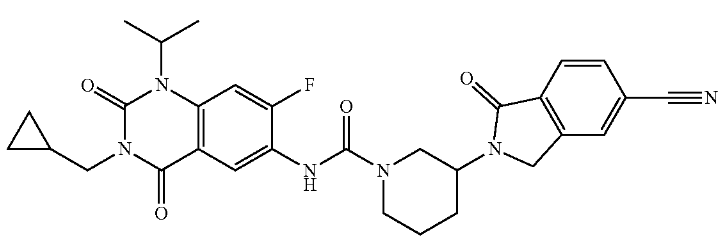 [SMILES: CC(C)n1c(=O)n(CC2CC2)c(=O)c2cc(NC(=O)N3CCCC(N4Cc5cc(C#N)ccc5C4=O)C3)c(F)cc21] | | 559.1 (M + H) |

TABLE 1-33-continued

| Ex. | IUPAC name | Structure | salt | MS |
|---|---|---|---|---|
| 329 | (2R)-N²-(3-chloro-4-cyanophenyl)-N⁴-(1-isopropyl-3-(2-methoxyethyl)-2,4-dioxo-1,2,3,4-tetrahydroquinazolin-6-yl)morpholine-2,4-dicarboxamide | 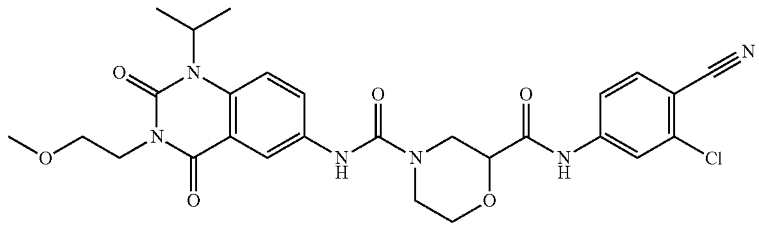 [SMILES: COCCn1c(=O)c2cc(NC(=O)N3CCOC(C(=O)Nc4ccc(C#N)c(Cl)c4)C3)ccc2n(C(C)C)c1=O] | | 569.1 (M + H) |
| 330 | (3R)-N-(1-isopropyl-3-(2-methoxyethyl)-2,4-dioxo-1,2,3,4-tetrahydroquinazolin-6-yl)-3-(1-oxo-1,3-dihydro-2H-isoindol-2-yl)piperidine-1-carboxamide | 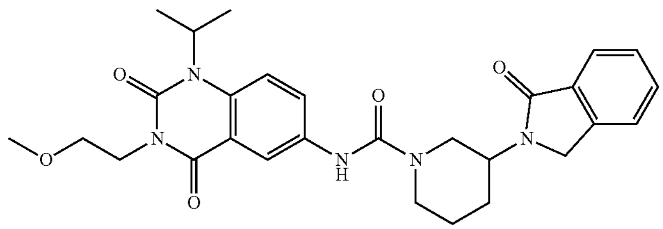 [SMILES: COCCn1c(=O)c2cc(NC(=O)N3CCCC(N4Cc5ccccc5C4=O)C3)ccc2n(C(C)C)c1=O] | | 520.1 (M + H) |

TABLE 1-34

| Ex. | IUPAC name | Structure | salt | MS |
|---|---|---|---|---|
| 331 | (2R)-N²-(3-chloro-4-cyanophenyl)-N⁴-(3-((2,2-difluorocyclopropyl)methyl)-7-fluoro-1-isopropyl-2,4-dioxo-1,2,3,4-tetrahydroquinazolin-6-yl)morpholine-2,4-dicarboxamide | 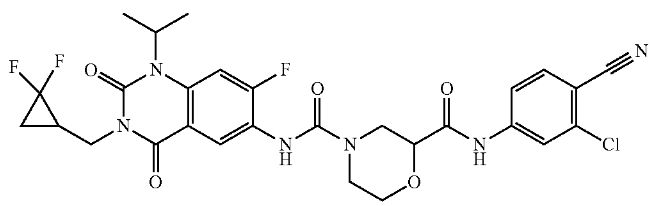 [SMILES: CC(C)n1c(=O)n(CC2CC2(F)F)c(=O)c2cc(NC(=O)N3CCOC(C(=O)Nc4ccc(C#N)c(Cl)c4)C3)c(F)cc21] | | 619.1 (M + H) |
| 332 | (3R)-N-(7-fluoro-1-isopropyl-2,4-dioxo-3-(tetrahydrofuran-2-ylmethyl)-1,2,3,4-tetrahydroquinazolin-6-yl)-3-(1-oxo-1,3-dihydro-2H-isoindol-2-yl)piperidine-1-carboxamide | 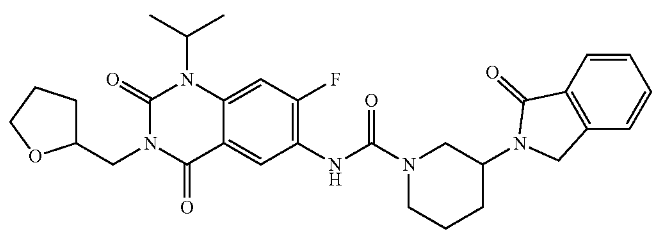 [SMILES: CC(C)n1c(=O)n(CC2CCCO2)c(=O)c2cc(NC(=O)N3CCCC(N4Cc5ccccc5C4=O)C3)c(F)cc21] | | 564.2 (M + H) |
| 333 | (2R)-N²-(3-chloro-4-cyanophenyl)-N⁴-(7-fluoro-1-isopropyl-2,4-dioxo-3-(tetrahydrofuran-2-ylmethyl)-1,2,3,4-tetrahydroquinazolin-6-yl)morpholine-2,4-dicarboxamide | 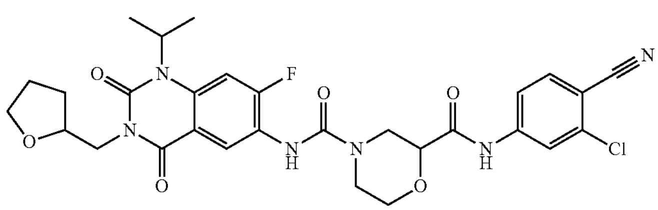 [SMILES: CC(C)n1c(=O)n(CC2CCCO2)c(=O)c2cc(NC(=O)N3CCOC(C(=O)Nc4ccc(C#N)c(Cl)c4)C3)c(F)cc21] | | 613.1 (M + H) |
| 334 | (3R)-N-(7-fluoro-1-isopropyl-2,4-dioxo-3-(tetrahydrofuran-3-ylmethyl)-1,2,3,4-tetrahydroquinazolin-6-yl)-3-(1-oxo-1,3-dihydro-2H-isoindol-2-yl)piperidine-1-carboxamide | 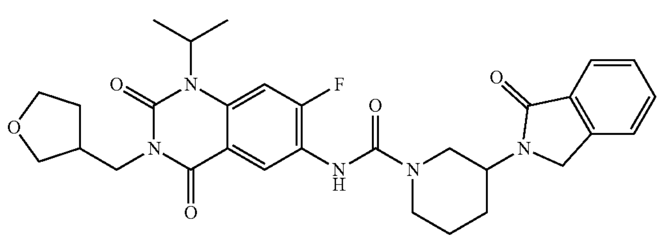 [SMILES: CC(C)n1c(=O)n(CC2CCOC2)c(=O)c2cc(NC(=O)N3CCCC(N4Cc5ccccc5C4=O)C3)c(F)cc21] | | 564.1 (M + H) |

TABLE 1-34-continued

| Ex. | IUPAC name | Structure | salt | MS |
|---|---|---|---|---|
| 335 | (2R)-N²-(3-chloro-4-cyanophenyl)-N⁴-(7-fluoro-1-isopropyl-2,4-dioxo-3-(tetrahydrofuran-3-ylmethyl)-1,2,3,4-tetrahydroquinazolin-6-yl)morpholine-2,4-dicarboxamide | 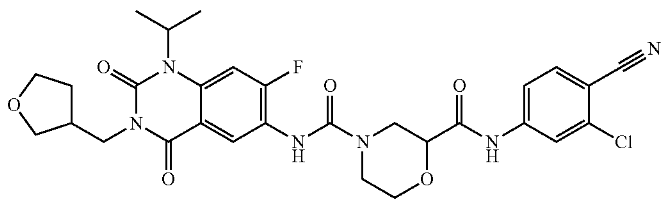 [SMILES: CC(C)n1c(=O)n(CC2CCOC2)c(=O)c2cc(NC(=O)N3CCOC(C(=O)Nc4ccc(C#N)c(Cl)c4)C3)c(F)cc21] | | 613.0 (M + H) |
| 336 | (3R)-3-(6-chloro-1-oxo-1,3-dihydro-2H-isoindol-2-yl)-N-(3-(cyclopropylmethyl)-7-fluoro-1-isopropyl-2,4-dioxo-1,2,3,4-tetrahydroquinazolin-6-yl)piperidine-1-carboxamide | 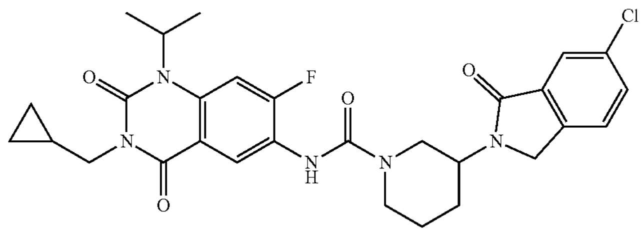 [SMILES: CC(C)n1c(=O)n(CC2CC2)c(=O)c2cc(NC(=O)N3CCCC(N4Cc5ccc(Cl)cc5C4=O)C3)c(F)cc21] | | 568.1 (M + H) |
| 337 | (3R)-N-(3-((2,2-difluorocyclopropyl)methyl)-7-fluoro-1-isopropyl-2,4-dioxo-1,2,3,4-tetrahydroquinazolin-6-yl)-3-(1-oxo-1,3-dihydro-2H-isoindol-2-yl)piperidine-1-carboxamide | 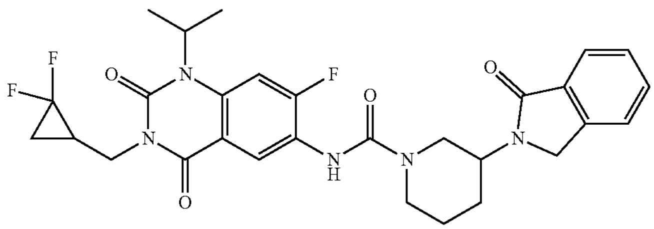 [SMILES: CC(C)n1c(=O)n(CC2CC2(F)F)c(=O)c2cc(NC(=O)N3CCCC(N4Cc5ccccc5C4=O)C3)c(F)cc21] | | 570.1 (M + H) |
| 338 | (3R)-3-(6-cyano-4-oxoquinazolin-3(4H)-yl)-N-(3-(cyclopropylmethyl)-7-fluoro-1-isopropyl-2,4-dioxo-1,2,3,4-tetrahydroquinazolin-6-yl)piperidine-1-carboxamide | 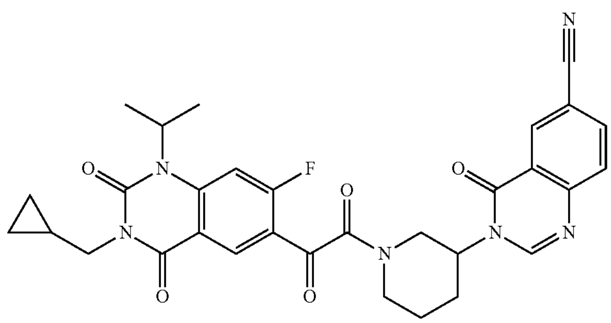 [SMILES: CC(C)n1c(=O)n(CC2CC2)c(=O)c2cc(C(=O)C(=O)N3CCCC(n4cnc5ccc(C#N)cc5c4=O)C3)c(F)cc21] | | 570.3 (M − H) |
| 339 | tert-butyl 5-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-1,3-dihydro-2H-isoindole-2-carboxylate | 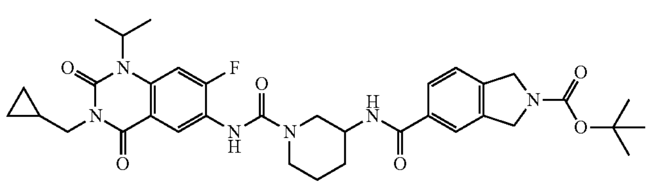 [SMILES: CC(C)n1c(=O)n(CC2CC2)c(=O)c2cc(NC(=O)N3CCCC(NC(=O)c4ccc5c(c4)CN(C(=O)OC(C)(C)C)C5)C3)c(F)cc21] | | 661.4 (M − H) |
| 340 | tert-butyl 6-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-3,4-dihydroisoquinoline-2(1H)-carboxylate | 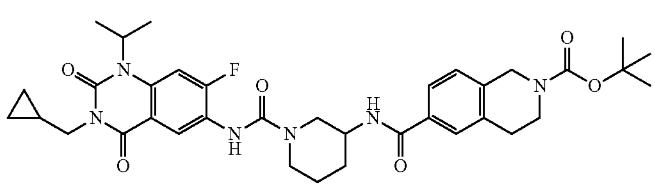 [SMILES: CC(C)n1c(=O)n(CC2CC2)c(=O)c2cc(NC(=O)N3CCCC(NC(=O)c4ccc5c(c4)CCN(C(=O)OC(C)(C)C)C5)C3)c(F)cc21] | | 675.3 (M − H) |

TABLE 1-35

| Ex. | IUPAC name | Structure | salt | MS |
|---|---|---|---|---|
| 341 | 2-acetyl-N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)isoindoline-5-carboxamide | 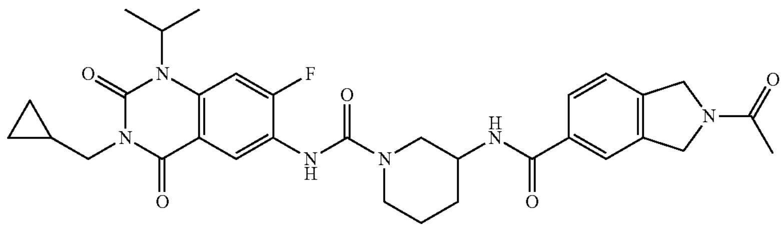 [SMILES: CC(=O)N1Cc2ccc(C(=O)NC3CCCN(C(=O)Nc4cc5c(=O)n(CC6CC6)c(=O)n(C(C)C)c5cc4F)C3)cc2C1] | | 605.2 (M + H) |
| 342 | 2-acetyl-N-((3R)-1-((3-(cyclopropylmethyl)-7-fluoro-1-isopropyl-2,4-dioxo-1,2,3,4-tetrahydroquinazolin-6-yl)carbamoyl)piperidin-3-yl)-1,2,3,4-tetrahydroisoquinoline-6-carboxamide | 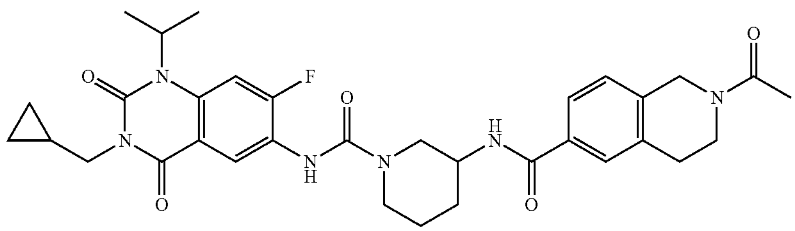 [SMILES: CC(=O)N1CCc2cc(C(=O)NC3CCCN(C(=O)Nc4cc5c(=O)n(CC6CC6)c(=O)n(C(C)C)c5cc4F)C3)ccc2C1] | | 619.3 (M + H) |
| 343 | methyl 5-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-1,3-dihydro-2H-isoindole-2-carboxylate | 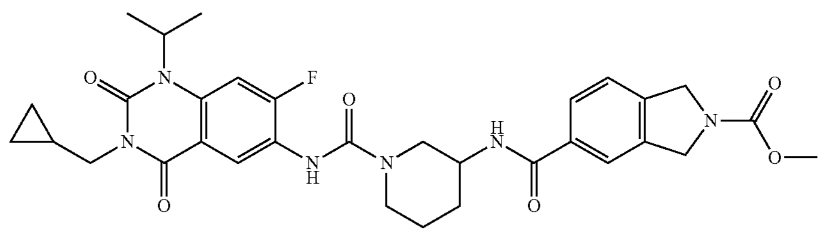 [SMILES: COC(=O)N1Cc2ccc(C(=O)NC3CCCN(C(=O)Nc4cc5c(=O)n(CC6CC6)c(=O)n(C(C)C)c5cc4F)C3)cc2C1] | | 621.2 (M + H) |
| 344 | methyl 6-(((3R)-1-((3-(cyclopropylmethyl)-7-fluoro-1-isopropyl-2,4-dioxo-1,2,3,4-tetrahydroquinazolin-6-yl)carbamoyl)piperidin-3-yl)carbamoyl)-3,4-dihydroisoquinoline-2(1H)-carboxylate | 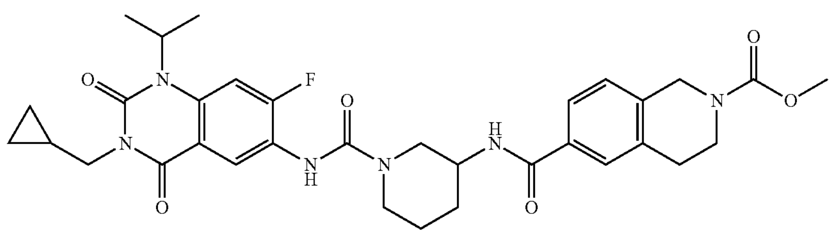 [SMILES: COC(=O)N1CCc2cc(C(=O)NC3CCCN(C(=O)Nc4cc5c(=O)n(CC6CC6)c(=O)n(C(C)C)c5cc4F)C3)ccc2C1] | | 635.2 (M + H) |
| 345 | 4-cyano-N-(1-(2-((3-(cyclopropylmethyl)-7-fluoro-1-isopropyl-2,4-dioxo-1,2,3,4-tetrahydroquinazolin-6-yl)amino)-2-oxoethyl)cyclohexyl)benzamide | 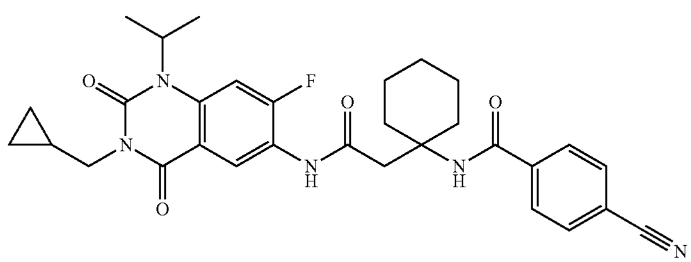 | | 560.2 (M + H) |
| 346 | 4-cyano-N-(4-(2-((3-(cyclopropylmethyl)-7-fluoro-1-isopropyl-2,4-dioxo-1,2,3,4-tetrahydroquinazolin-6-yl)amino)-2-oxoethyl)tetrahydro-2H-pyran-4-yl)benzamide | 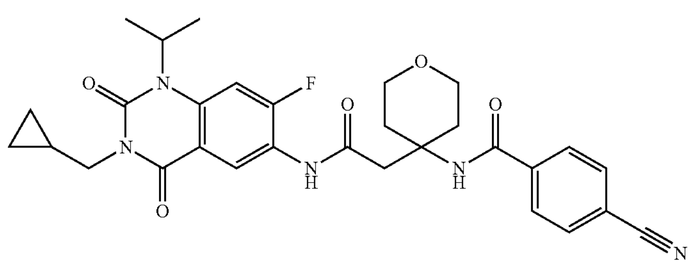 [SMILES: CC(C)n1c(=O)n(CC2CC2)c(=O)c2cc(NC(=O)CC3(NC(=O)c4ccc(C#N)cc4)CCOCC3)c(F)cc21] | | 560.2 (M − H) |

TABLE 1-35-continued

| Ex. | IUPAC name | Structure | salt | MS |
|---|---|---|---|---|
| 347 | (2R)-N²-(5-chloro-4-cyano-2-fluorophenyl)-N⁴-(3-(cyclopropylmethyl)-7-fluoro-1-isopropyl-2,4-dioxo-1,2,3,4-tetrahydroquinazolin-6-yl)morpholine-2,4-dicarboxamide | 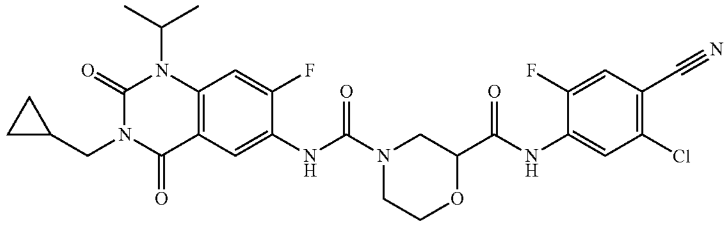 [SMILES: CC(C)n1c(=O)n(CC2CC2)c(=O)c2cc(NC(=O)N3CCOC(C(=O)Nc4cc(Cl)c(C#N)cc4F)C3)c(F)cc21] | | 601.1 (M + H) |
| 348 | (2R)-N²-(5-chloro-4-cyano-2-fluorophenyl)-N⁴-(3-((2,2-difluorocyclopropyl)methyl)-7-fluoro-1-isopropyl-2,4-dioxo-1,2,3,4-tetrahydroquinazolin-6-yl)morpholine-2,4-dicarboxamide (mixture of two stereoisomers) | 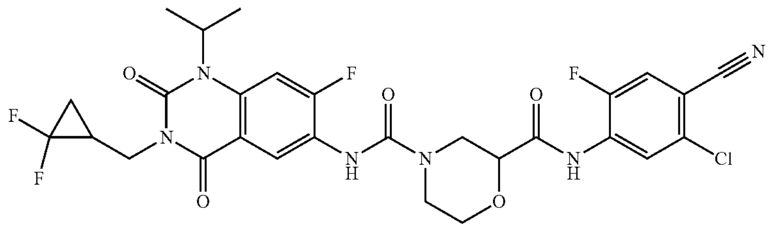 [SMILES: CC(C)n1c(=O)n(CC2CC2(F)F)c(=O)c2cc(NC(=O)N3CCOC(C(=O)Nc4cc(Cl)c(C#N)cc4F)C3)c(F)cc21] | | 637.1 (M + H) |
| 349 | tert-butyl 3-(6-((((2R)-2-((3-chloro-4-cyanophenyl)carbamoyl)-morpholin-4-yl)carbonyl)amino)-7-fluoro-1-isopropyl-2,4-dioxo-1,4-dihydroquinazolin-3(2H)-yl)propanoate | 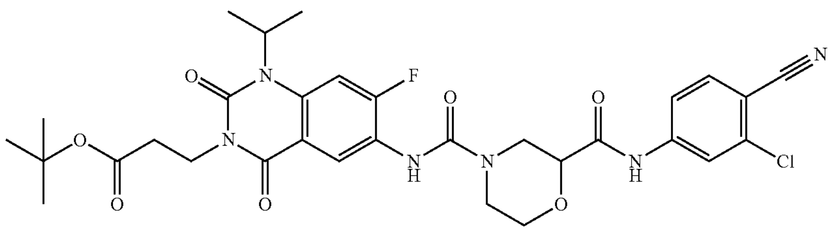 [SMILES: CC(C)n1c(=O)n(CCC(=O)OC(C)(C)C)c(=O)c2cc(NC(=O)N3CCOC(C(=O)Nc4ccc(C#N)c(Cl)c4)C3)c(F)cc21] | | 655.3 (M − H) |
| 350 | (2R)-N²-(3-chloro-4-cyanophenyl)-N⁴-(3-((3,3-difluorocyclobutyl)methyl)-7-fluoro-1-isopropyl-2,4-dioxo-1,2,3,4-tetrahydroquinazolin-6-yl)morpholine-2,4-dicarboxamide | 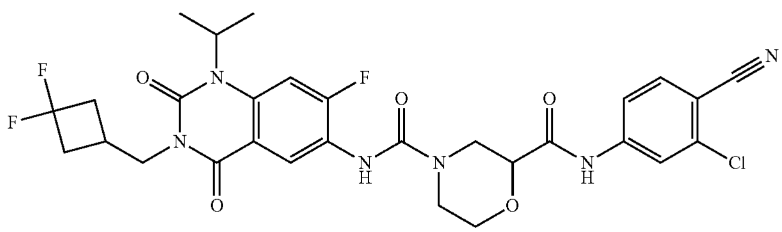 [SMILES: CC(C)n1c(=O)n(CC2CC(F)(F)C2)c(=O)c2cc(NC(=O)N3CCOC(C(=O)Nc4ccc(C#N)c(Cl)c4)C3)c(F)cc21] | | 633.0 (M + H) |

TABLE 1-36

| Ex. | IUPAC name | Structure | salt | MS |
|---|---|---|---|---|
| 351 | (2R)-N²-(5-chloro-4-cyano-2-fluorophenyl)-N⁴-(3-((3,3-difluorocyclobutyl)methyl)-7-fluoro-1-isopropyl-2,4-dioxo-1,2,3,4-tetrahydroquinazolin-6-yl)morpholine-2,4-dicarboxamide | 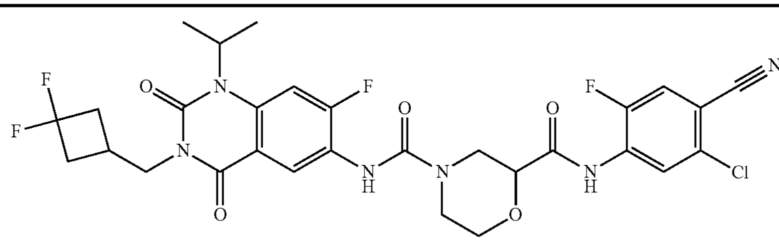 | | 651.1 (M + H) |
| 352 | (3R)-N-(3-((3,3-difluorocyclobutyl)methyl)-7-fluoro-1-isopropyl-2,4-dioxo-1,2,3,4-tetrahydroquinazolin-6-yl)-3-(1-oxo-1,3-dihydro-2H-isoindol-2-yl)-piperidine-1-carboxamide | 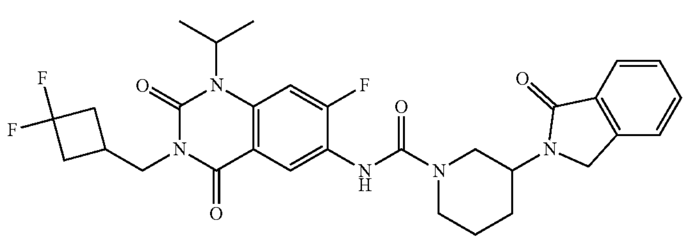 [SMILES: CC(C)n1c(=O)n(CC2CC(F)(F)C2)c(=O)c2cc(NC(=O)N3CCCC(N4Cc5ccccc5C4=O)C3)c(F)cc21] | | 584.2 (M + H) |

TABLE 1-36-continued

| Ex. | IUPAC name | Structure | salt | MS |
|---|---|---|---|---|
| 353 | (2R)-N²-(3-chloro-4-cyanophenyl)-N⁴-(7-fluoro-1-isopropyl-2,4-dioxo-3-((2R)-tetrahydrofuran-2-ylmethyl)-1,2,3,4-tetrahydroquinazolin-6-yl)morpholine-2,4-dicarboxamide | 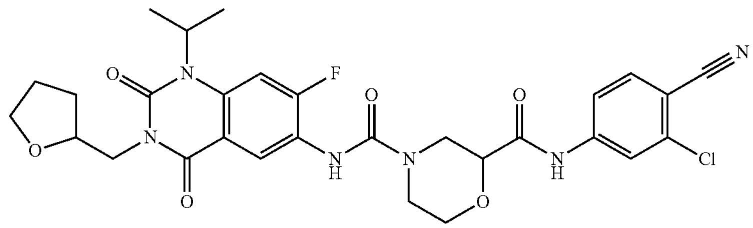 [SMILES: CC(C)n1c(=O)n(CC2CCCO2)c(=O)c2cc(NC(=O)N3CCOC(C(=O)Nc4ccc(C#N)c(Cl)c4)C3)c(F)cc21] | | 613.1 (M + H) |
| 354 | (2R)-N²-(5-chloro-4-cyano-2-fluorophenyl)-N⁴-(7-fluoro-1-isopropyl-2,4-dioxo-3-((2R)-tetrahydrofuran-2-ylmethyl)-1,2,3,4-tetrahydroquinazolin-6-yl)morpholine-2,4-dicarboxamide | 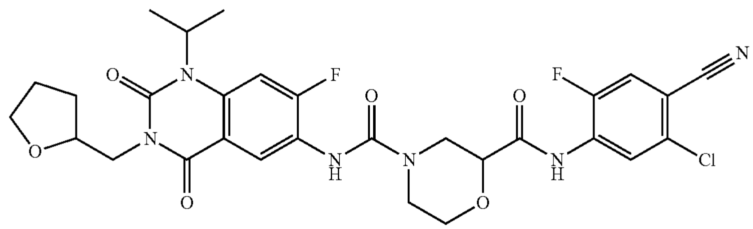 [SMILES: CC(C)n1c(=O)n(CC2CCCO2)c(=O)c2cc(NC(=O)N3CCOC(C(=O)Nc4cc(Cl)c(C#N)cc4F)C3)c(F)cc21] | | 631.1 (M + H) |
| 355 | (3R)-N-(7-fluoro-1-isopropyl-2,4-dioxo-3-((2R)-tetrahydrofuran-2-ylmethyl)-1,2,3,4-tetrahydroquinazolin-6-yl)-3-(1-oxo-1,3-dihydro-2H-isoindol-2-yl)piperidine-1-carboxamide | 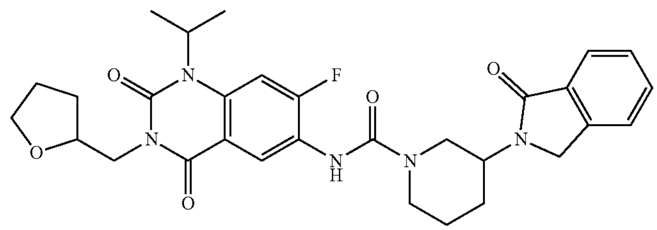 [SMILES: CC(C)n1c(=O)n(CC2CCCO2)c(=O)c2cc(NC(=O)N3CCCC(N4Cc5ccccc5C4=O)C3)c(F)cc21] | | 564.2 (M + H) |
| 356 | (2R)-N²-(5-chloro-6-cyanopyridin-3-yl)-N⁴-(3-((2,2-difluorocyclopropyl)methyl)-7-fluoro-1-isopropyl-2,4-dioxo-1,2,3,4-tetrahydroquinazolin-6-yl)morpholine-2,4-dicarboxamide (mixture of two stereoisomers) | 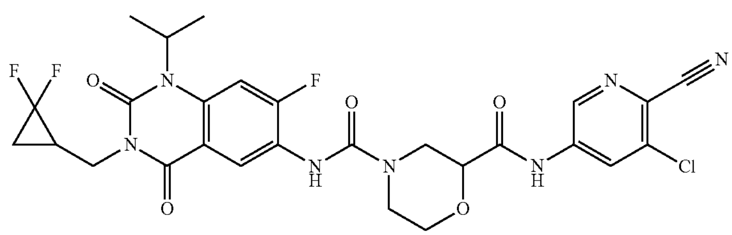 [SMILES: CC(C)n1c(=O)n(CC2CC2(F)F)c(=O)c2cc(NC(=O)N3CCOC(C(=O)Nc4cnc(C#N)c(Cl)c4)C3)c(F)cc21] | | 620.1 (M + H) |
| 357 | (2R)-N²-(3-chloro-4-cyanophenyl)-N⁴-(7-fluoro-1-isopropyl-2,4-dioxo-3-((2S)-tetrahydrofuran-2-ylmethyl)-1,2,3,4-tetrahydroquinazolin-6-yl)morpholine-2,4-dicarboxamide | 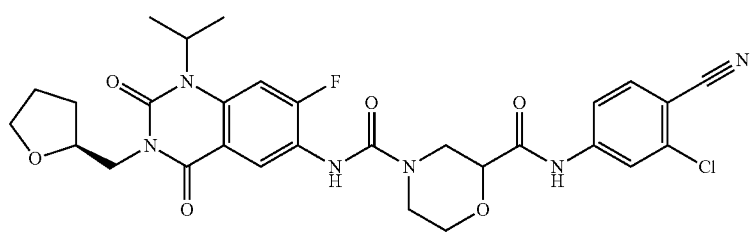 [SMILES: CC(C)n1c(=O)n(C[C@@H]2CCCO2)c(=O)c2cc(NC(=O)N3CCOC(C(=O)Nc4ccc(C#N)c(Cl)c4)C3)c(F)cc21] | | 613.1 (M + H) |
| 358 | (2R)-N²-(5-chloro-4-cyano-2-fluorophenyl)-N⁴-(7-fluoro-1-isopropyl-2,4-dioxo-3-((2S)-tetrahydrofuran-2-ylmethyl)-1,2,3,4-tetrahydroquinazolin-6-yl)morpholine-2,4-dicarboxamide | 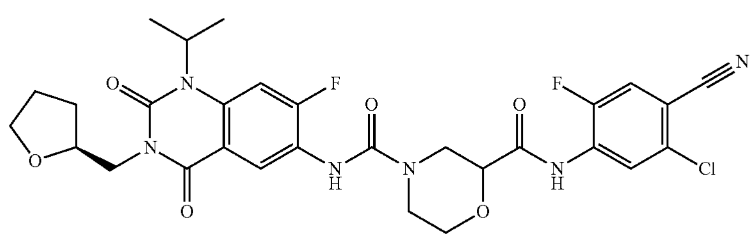 [SMILES: CC(C)n1c(=O)n(C[C@@H]2CCCO2)c(=O)c2cc(NC(=O)N3CCOC(C(=O)Nc4cc(Cl)c(C#N)cc4F)C3)c(F)cc21] | | 631.1 (M + H) |

TABLE 1-36-continued

| Ex. | IUPAC name | Structure | salt | MS |
|---|---|---|---|---|
| 359 | (3R)-N-(7-fluoro-1-isopropyl-2,4-dioxo-3-((2S)-tetrahydrofuran-2-ylmethyl)-1,2,3,4-tetrahydroquinazolin-6-yl)-3-(1-oxo-1,3-dihydro-2H-isoindol-2-yl)piperidine-1-carboxamide | 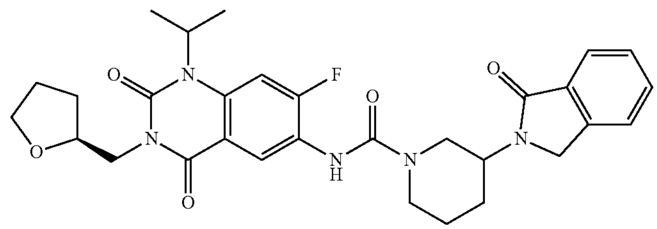 [SMILES: CC(C)n1c(=O)n(C[C@@H]2CCCO2)c(=O)c2cc(NC(=O)N3CCCC(N4Cc5ccccc5C4=O)C3)c(F)cc21] | | 564.2 (M + H) |
| 360 | (3R)-3-(7-cyano-4-oxoquinazolin-3(4H)-yl)-N-(3-((2,2-difluoro-cyclopropyl)methyl)-7-fluoro-1-isopropyl-2,4-dioxo-1,2,3,4-tetrahydroquinazolin-6-yl)piperidine-1-carboxamide (mixture of two stereoisomers) | 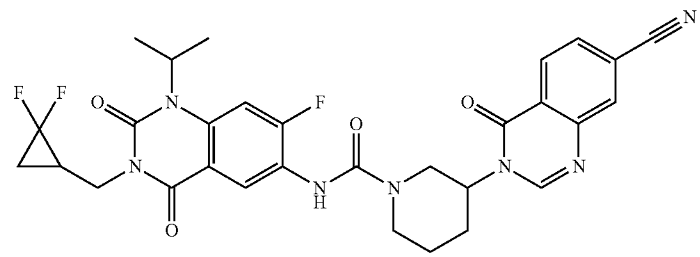 [SMILES: CC(C)n1c(=O)n(CC2CC2(F)F)c(=O)c2cc(NC(=O)N3CCCC(n4cnc5cc(C#N)ccc5c4=O)C3)c(F)cc21] | | 606.2 (M − H) |

TABLE 1-37

| Ex. | IUPAC name | Structure | salt | MS |
|---|---|---|---|---|
| 361 | 4-cyano-N-(1-(2-((3-(cyclopropylmethyl)-7-fluoro-1-isopropyl-2,4-dioxo-1,2,3,4-tetrahydroquinazolin-6-yl)amino)-2-oxoethyl)-cyclohexyl)-3-fluorobenzamide | 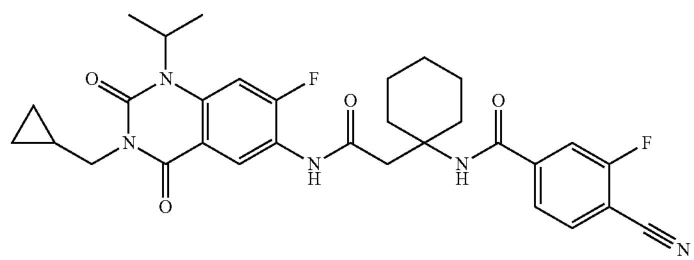 [SMILES: CC(C)n1c(=O)n(CC2CC2)c(=O)c2cc(NC(=O)CC3(NC(=O)c4ccc(C#N)c(F)c4)CCCCC3)c(F)cc21] | | 576.2 (M − H) |
| 362 | 4-cyano-N-(4-(2-((3-(cyclopropylmethyl)-7-fluoro-1-isopropyl-2,4-dioxo-1,2,3,4-tetrahydroquinazolin-6-yl)amino)-2-oxoethyl)-tetrahydro-2H-pyran-4-yl)-3-fluorobenzamide | 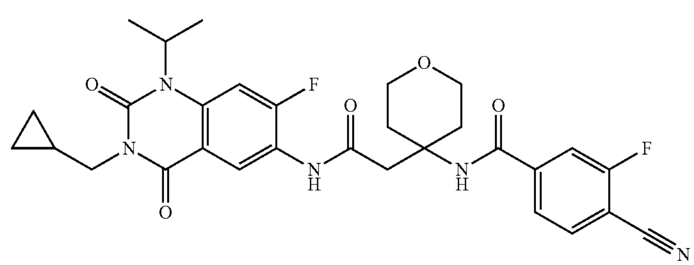 [SMILES: CC(C)n1c(=O)n(CC2CC2)c(=O)c2cc(NC(=O)CC3(NC(=O)c4ccc(C#N)c(F)c4)CCOCC3)c(F)cc21] | | 578.1 (M − H) |
| 363 | (3R)-3-(7-cyano-4-oxoquinazolin-3(4H)-yl)-N-(3-((3,3-difluoro-cyclobutyl)methyl)-7-fluoro-1-isopropyl-2,4-dioxo-1,2,3,4-tetrahydroquinazolin-6-yl)piperidine-1-carboxamide | 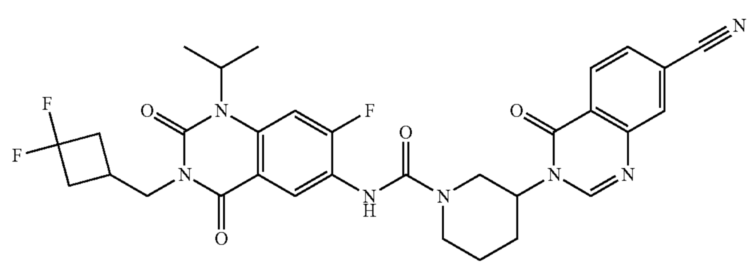 [SMILES: CC(C)n1c(=O)n(CC2CC(F)(F)C2)c(=O)c2cc(NC(=O)N3CCCC(n4cnc5cc(C#N)ccc5c4=O)C3)c(F)cc21] | | 620.3 (M − H) |

TABLE 1-37-continued

| Ex. | IUPAC name | Structure | salt | MS |
|---|---|---|---|---|
| 364 | (3R)-3-(7-cyano-4-oxoquinazolin-3(4H)-yl)-N-(7-fluoro-1-isopropyl-2,4-dioxo-3-((2R)-tetrahydrofuran-2-ylmethyl)-1,2,3,4-tetrahydroquinazolin-6-yl)piperidine-1-carboxamide (mixture of one stereoisomer) | 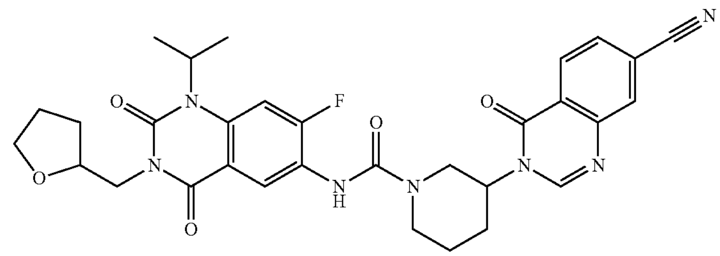 [SMILES: CC(C)n1c(=O)n(CC2CCCO2)c(=O)c2cc(NC(=O)N3CCCC(n4cnc5cc(C#N)ccc5c4=O)C3)c(F)cc21] | | 600.3 (M − H) |
| 365 | (3R)-3-(7-cyano-4-oxoquinazolin-3(4H)-yl)-N-(7-fluoro-1-isopropyl-2,4-dioxo-3-((2S)-tetrahydrofuran-2-ylmethyl)-1,2,3,4-tetrahydroquinazolin-6-yl)piperidine-1-carboxamide | 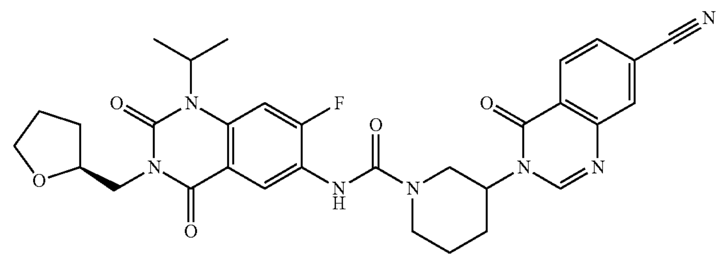 [SMILES: CC(C)n1c(=O)n(C[C@@H]2CCCO2)c(=O)c2cc(NC(=O)N3CCCC(n4cnc5cc(C#N)ccc5c4=O)C3)c(F)cc21] | | 600.2 (M − H) |
| 366 | (2R)-N$^2$-(3-chloro-4-cyanophenyl)-N$^4$-(3-(((1R)-2,2-difluorocyclopropyl)methyl)-7-fluoro-1-isopropyl-2,4-dioxo-1,2,3,4-tetrahydroquinazolin-6-yl)morpholine-2,4-dicarboxamide (one stereoisomer, quinazolinedione: derived from tR$_1$) | 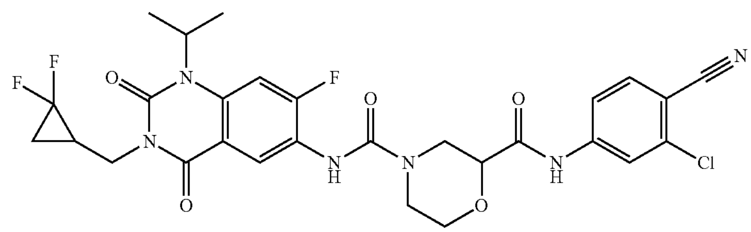 [SMILES: CC(C)n1c(=O)n(CC2CC2(F)F)c(=O)c2cc(NC(=O)N3CCOC(C(=O)Nc4ccc(C#N)c(Cl)c4)C3)c(F)cc21] | | 619.1 (M + H) |
| 367 | (3R)-3-(7-cyano-4-oxoquinazolin-3(4H)-yl)-N-(3-(((1R)-2,2-difluorocyclopropyl)methyl)-7-fluoro-1-isopropyl-2,4-dioxo-1,2,3,4-tetrahydroquinazolin-6-yl)piperidine-1-carboxamide (one stereoisomer, quinazolinedione: derived from tR$_1$ | 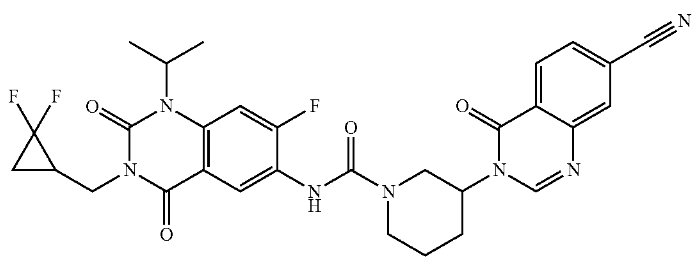 [SMILES: CC(C)n1c(=O)n(CC2CC2(F)F)c(=O)c2cc(NC(=O)N3CCCC(n4cnc5cc(C#N)ccc5c4=O)C3)c(F)cc21] | | 606.2 (M − H) |
| 368 | (2R)-N$^2$-(3-chloro-4-cyanophenyl)-N$^4$-(3-(((1R or 1S)-2,2-difluorocyclopropyl)methyl)-7-fluoro-1-isopropyl-2,4-dioxo-1,2,3,4-tetrahydroquinazolin-6-yl)morpholine-2,4-dicarboxamide (one stereoisomer, quinazolinedione: derived from tR$_2$) | 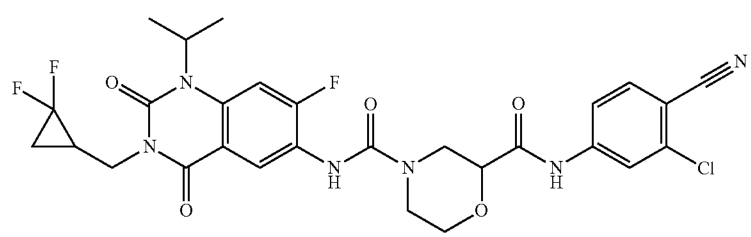 [SMILES: CC(C)n1c(=O)n(CC2CC2(F)F)c(=O)c2cc(NC(=O)N3CCOC(C(=O)Nc4ccc(C#N)c(Cl)c4)C3)c(F)cc21] | | 619.1 (M + H) |
| 369 | (3R)-3-(7-cyano-4-oxoquinazolin-3(4H)-yl)-N-(3-(((1R or 1S)-2,2-difluorocyclopropyl)methyl)-7-fluoro-1-isopropyl-2,4-dioxo-1,2,3,4-tetrahydroquinazolin-6-yl)piperidine-1-carboxamide (one stereoisomer, quinazolinedione: derived from tR$_2$) | 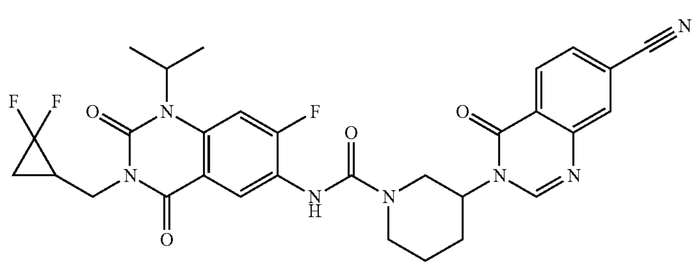 [SMILES: CC(C)n1c(=O)n(CC2CC2(F)F)c(=O)c2cc(NC(=O)N3CCCC(n4cnc5cc(C#N)ccc5c4=O)C3)c(F)cc21] | | 606.2 (M − H) |

| Ex. | IUPAC name | Structure | salt | MS |
|---|---|---|---|---|
| 370 | 3-chloro-4-cyano-N-(4-(2-((3-(cyclopropyl-methyl)-7-fluoro-1-isopropyl-2,4-dioxo-1,2,3,4-tetrahydro-quinazolin-6-yl)amino)-2-oxoethyl)tetrahydro-2H-pyran-4-yl)benzamide | 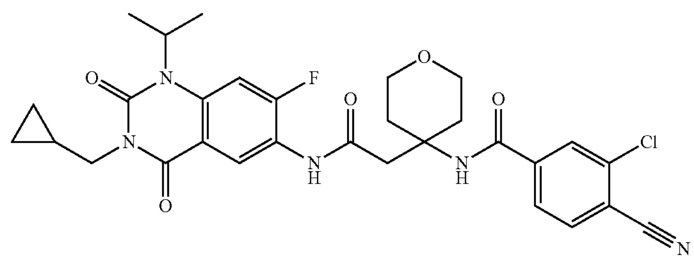 | | 594.2 (M − H) |

The compounds described in Examples 2-78, 80, 83-87, 89-91, 93, 94, 96-101, 104-112, 114-121, 123-131, 133-134, 136-145, 147-156, 158-167, 169, 170, 173-175, 177-179, 181-217, 220-222, 224-234, 236-241, 243, 245, 246, 250, 252-258, 260-263, 265, 267-273, 275-281, 285, 286, 288-290, 293-295, 297-302, 304-314, 316-318, 322, 325-330, 332, 334, 337-339, 341, 342, 344-346, 349, 352-355, 359, 361, 362, 364, 365 and 370 were synthesized by reaction and purification in the same manner as in the methods described in the above-mentioned Examples.

Example 371

(2R)-N²-(3-chloro-4-cyanophenyl)-N⁴-(3-(cyclopropylmethyl)-1-(1,1-difluoropropan-2-yl)-7-fluoro-2,4-dioxo-1,2,3,4-tetrahydroquinazolin-6-yl)morpholine-2,4-dicarboxamide (one stereoisomer, quinazolinedione: derived from tR₁)

(Step 1)
Cesium carbonate (46.85 g, 143.77 mmol) and methyl 2-bromopropanoate (4.8 mL, 43.13 mmol) were added to a solution of 6-bromo-3-(cyclopropylmethyl)-7-fluoroquinazoline-2,4(1H, 3H)-dione (9.0 g, 28.75 mmol) in DMF (50 mL) at room temperature, and the mixture was stirred at room temperature for 3 hr. To the reaction mixture was added water (100 mL), and the mixture was extracted twice with ethyl acetate (60 mL). The organic layer was washed with water (2×60 mL) and brine (50 mL), dried over sodium sulfate, and the solvent was evaporated under reduced pressure. The residue was purified by silica gel column chromatography (solvent gradient; 10→15% ethyl acetate/hexane) to give methyl 2-(6-bromo-3-(cyclopropylmethyl)-7-fluoro-2,4-dioxo-3,4-dihydroquinazoline-1 (2H)-yl)propanoate (7.5 g, 65%) as a white solid.

¹H NMR (300 MHz, DMSO-d₆): δ 0.31-0.35 (2H, m), 0.42-0.44 (2H, m), 1.12-1.18 (1H, m), 1.51 (3H, d, J=6.6 Hz), 3.63 (3H, s), 3.71-3.79 (1H, m), 3.82-3.87 (1H, m), 5.37-5.42 (1H, m), 7.79 (1H, d, J=11.2 Hz), 8.30 (1H, d, J=7.6 Hz).

(Step 2)
A solution of lithium hydroxide (822 mg, 20.05 mmol) in water (10 mL) was added to a solution of methyl 2-(6-bromo-3-(cyclopropylmethyl)-7-fluoro-2,4-dioxo-3,4-dihydroquinazoline-1 (2H)-yl)propanoate (2.0 g, 5.01 mmol) in THF (30 mL) at 0° C., and the mixture was stirred at room temperature for 5 hr. The reaction mixture was concentrated under reduced pressure, water (25 mL) was added to the residue, and the mixture was washed with diethyl ether (2×25 mL). The aqueous layer was acidified with 2N hydrochloric acid, and the organic product was extracted with ethyl acetate (2×25 mL). The organic layer was washed with water (30 mL) and brine (20 mL), dried over sodium sulfate, and the solvent was evaporated under reduced pressure to give crude 2-(6-bromo-3-(cyclopropylmethyl)-7-fluoro-2,4-dioxo-3,4-dihydroquinazoline-1 (2H)-yl)propanoic acid (1.6 g) as a grayish white solid. The resultant product was used for the next step without purification.

(Step 3)
1M Borane-THF complex (20 mL, 20.0 mmol) was added to a solution of crude 2-(6-bromo-3-(cyclopropylmethyl)-7-fluoro-2,4-dioxo-3,4-dihydroquinazoline-1 (2H)-yl)propanoic acid (1.6 g, 4.16 mmol) in THF (10 mL) at 0° C., and the mixture was stirred at room temperature for 20 hr. To the reaction mixture was added MeOH (20 mL), and the mixture was heated under reflux for 1 hr, and concentrated under reduced pressure. The residue was purified by silica gel column chromatography (solvent gradient; 10→15% ethyl acetate/hexane) to give 6-bromo-3-(cyclopropylmethyl)-7-fluoro-1-(1-hydroxypropan-2-yl)quinazoline-2,4(1H, 3H)-dione (900 mg, 49%, 2 steps) as a white solid.

MS(API): Calculated 370. Found 371.0 (M+H).

¹H NMR (300 MHz, DMSO-d₆): δ 0.33-0.39 (2H, m), 0.41-0.45 (2H, m), 1.14-1.20 (1H, m), 1.41 (3H, d, J=6.8 Hz), 3.59-3.76 (1H, m), 3.78-3.85 (2H, m), 4.03-4.09 (1H, m), 4.72 (1H, brs), 4.87 (1H, t, J=5.6 Hz), 7.79 (1H, d, J=11.8 Hz), 8.24 (1H, d, J=7.9 Hz).

(Step 4)
Molecular sieves 3 Å (500 mg) and Dess-Martin periodinane (4.86 g, 11.46 mmol) were added to a mixture of 6-bromo-3-(cyclopropylmethyl)-7-fluoro-1-(1-hydroxypropan-2-yl)quinazoline-2,4(1H, 3H)-dione (1.7 g, 4.58 mmol) in dichloromethane (50 mL) at room temperature, and the mixture was stirred in the dark at room temperature for 3 hr. To the reaction mixture was added 10% aqueous sodium thiosulfate solution, and organic substances were extracted with dichloromethane (2×40 mL). The organic layer was dried over sodium sulfate, and the solvent was evaporated under reduced pressure. The residue was purified by silica gel column chromatography (solvent; 10% ethyl acetate/hexane) to give 2-(6-bromo-3-(cyclopropylmethyl)-7-fluoro-2,4-dioxo-3,4-dihydroquinazoline-1 (2H)-yl)propanal (1.2 g, 71%) as a white solid.

MS(API): Calculated 368. Found 369.1 (M+H).

¹H NMR (300 MHz, DMSO-d₆): δ 0.33-0.37 (2H, m), 0.43-0.46 (2H, m), 1.12-1.19 (1H, m), 1.40 (3H, d, J=6.5 Hz), 3.75-3.85 (2H, m), 4.98-5.03 (1H, m), 7.80 (1H, d, J=11.2 Hz), 8.31 (1H, d, J=7.7 Hz), 9.48 (1H, s).

(Step 5)
(Diethylamino)sulfur trifluoride (1.04 g, 6.44 mmol) was added to a solution of 2-(6-bromo-3-(cyclopropylmethyl)-7-fluoro-2,4-dioxo-3,4-dihydroquinazoline-1 (2H)-yl)propanal (950 mg, 2.58 mmol) in 1,2-dichloroethane (30 mL) at room temperature, and the mixture was stirred at 60° C. for 12 hr. To the reaction mixture was added saturated aqueous sodium hydrogen carbonate solution, and the mixture was extracted with dichloromethane (2×30 mL). The organic layer was washed with saturated aqueous sodium hydrogen carbonate solution, water and brine, dried over sodium sulfate, and the solvent was evaporated under reduced pressure. The residue was purified by silica gel column chromatography (solvent; 5% ethyl acetate/hexane) to give 6-bromo-3-(cyclopropylmethyl)-1-(1,1-difluoropropan-2-yl)-7-fluoroquinazoline-2,4(1H, 3H)-dione (750 mg, 74%) as a grayish white solid.

MS(API): Calculated 390. Found 390.8 (M+H).

$^1$H NMR (300 MHz, DMSO-$d_6$): δ 0.34-0.35 (2H, m), 0.38-0.45 (2H, m), 1.17 (1H, brs), 1.52 (3H, d, J=6.6 Hz), 3.81 (2H, d, J=7.1 Hz), 4.93 (1H, brs), 6.65 (1H, dt, J=6.2, 57.9 Hz), 8.00 (1H, d, J=11.4 Hz), 8.29 (1H, d, J=7.8 Hz).

(Step 6)

In a sealed tube reaction vessel, tert-butyl carbamate (493.8 mg, 4.21 mmol) and cesium carbonate (2.29 g, 7.02 mmol) were added to 6-bromo-3-(cyclopropylmethyl)-1-(1,1-difluoropropan-2-yl)-7-fluoroquinazoline-2,4(1H, 3H)-dione (1.2 g, 2.81 mmol) in 1,4-dioxane (30 mL), and XPhos (268 mg, 0.56 mmol) and Pd$_2$(dba)$_3$ (258 mg, 0.27 mmol) were added under an argon atmosphere. The mixture was stirred at 100° C. for 20 hr and, after cooling, filtered through celite, and the filtrate was concentrated under reduced pressure. The residue was purified by silica gel column chromatography (solvent gradient; 10→20% ethyl acetate/hexane) to give tert-butyl (3-(cyclopropylmethyl)-1-(1,1-difluoropropan-2-yl)-7-fluoro-2,4-dioxo-1,2,3,4-tetrahydroquinazolin-6-yl)carbamate (1.0 g, 83%) as a brown solid.

MS(API): Calculated 427. Found 428.1 (M+H).

(Step 7)

To a solution of tert-butyl (3-(cyclopropylmethyl)-1-(1,1-difluoropropan-2-yl)-7-fluoro-2,4-dioxo-1,2,3,4-tetrahydroquinazolin-6-yl)carbamate (1.0 g, 2.32 mmol) in dichloromethane (25 mL) was added trifluoroacetic acid (10 mL) at 0° C., and the mixture was stirred at said temperature for 2 hr. The reaction mixture was concentrated under reduced pressure, and ethyl acetate (60 mL) was added to the residue. The organic layer was washed with saturated aqueous sodium hydrogen carbonate solution (2×30 mL), water (40 mL) and brine (30 mL), dried over sodium sulfate, and the solvent was evaporated under reduced pressure to give crude 6-amino-3-(cyclopropylmethyl)-1-(1,1-difluoropropan-2-yl)-7-fluoroquinazoline-2,4(1H, 3H)-dione.

(Step 8)

Crude 6-amino-3-(cyclopropylmethyl)-1-(1,1-difluoropropan-2-yl)-7-fluoroquinazoline-2,4(1H, 3H)-dione (700 mg) was subjected to preparative chiral SFC to separate stereoisomer (optical isomer). A preparative fraction with a shorter retention time was concentrated to give 6-amino-3-(cyclopropylmethyl)-1-(1,1-difluoropropan-2-yl)-7-fluoroquinazoline-2,4(1H, 3H)-dione (tR$_1$) (200 mg, 26%, optical purity 99.36%) as a pale-yellow solid.

Purification conditions by preparative chiral SFC
apparatus: Thar SFC PREP 80
column: Chiralcel OJ-H (250×21 mm), 5 μm
solvent: A=CO$_2$, B=MeOH (A: 70%, B: 30%)
flow rate: 30 g/min
temperature: 35° C.
Analysis conditions by chiral SFC
apparatus: Thar SFC Method Station
column: Chiralcel OJ-H (250×4.6 mm), 5 μm
solvent: A=CO$_2$, B=MeOH (A: 80%, B: 20%)
flow rate: 2.0 mL/min
temperature: 35° C.

MS(API): Calculated 327.3. Found 328.1 (M+H).

$^1$H NMR (400 MHz, DMSO-$d_6$): δ 0.33-0.34 (2H, m), 0.41-0.43 (2H, m), 1.15-1.17 (1H, m), 1.49 (3H, d, J=6.6 Hz), 3.80 (2H, d, J=7.1 Hz), 4.82 (1H, brs), 5.43 (2H, s), 6.64 (1H, dt, J=6.3, 58.1 Hz), 7.48 (1H, d, J=9.8 Hz), 7.64 (1H, d, J=13.5 Hz).

(Step 9)

4-Nitrophenyl carbonochloridate (43.9 mg, 0.22 mmol) was added to a mixture of 6-amino-3-(cyclopropylmethyl)-1-(1,1-difluoropropan-2-yl)-7-fluoroquinazoline-2,4(1H, 3H)-dione (tR$_1$) (62 mg, 0.19 mmol) and pyridine (0.018 mL, 0.22 mmol) in THF (1 mL) at room temperature, and the mixture was stirred at room temperature for 2 hr. The reaction mixture was concentrated under reduced pressure, DMF (3 mL) was added to the residue, and then (R)-N-(3-chloro-4-cyanophenyl)morpholine-2-carboxamide hydrochloride (63.0 mg, 0.21 mmol) and DIEA (24.48 mg, 0.19 mmol) were added thereto at room temperature, and the mixture was stirred at room temperature for 1 hr. To the reaction mixture was added water, and the mixture was acidified with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 30→100% ethyl acetate/hexane) to give the title compound (111.7 mg, 0.180 mmol, 95%) as white crystals.

$^1$H NMR (300 MHz, DMSO-$d_6$): δ 0.25-0.53 (4H, m), 1.09-1.32 (1H, m), 1.53 (3H, d, J=6.4 Hz), 3.00-3.20 (2H, m), 3.60-3.74 (1H, m), 3.76-3.96 (3H, m), 3.96-4.12 (1H, m), 4.14-4.35 (2H, m), 4.93 (1H, brs), 6.33-6.89 (1H, m), 7.75-7.98 (3H, m), 8.09-8.23 (2H, m), 8.77 (1H, brs), 10.52 (1H, brs).

Example 372

(3R)-3-(7-cyano-4-oxoquinazoline-3(4H)-yl)-N-(3-(cyclopropylmethyl)-1-(1,1-difluoropropan-2-yl)-7-fluoro-2,4-dioxo-1,2,3,4-tetrahydroquinazolin-6-yl) piperidine-1-carboxamide (one stereoisomer, quinazolinedione: derived from tR$_1$)

4-Nitrophenyl carbonochloridate (43.9 mg, 0.22 mmol) was added to a mixture of 6-amino-3-(cyclopropylmethyl)-1-(1,1-difluoropropan-2-yl)-7-fluoroquinazoline-2,4(1H, 3H)-dione (tR$_1$) (62 mg, 0.19 mmol) and pyridine (0.018 mL, 0.22 mmol) in THF (1 mL) at room temperature, and the mixture was stirred at room temperature for 2 hr. The reaction mixture was concentrated under reduced pressure, DMF (3 mL) was added to the residue, (R)-4-oxo-3-(piperidin-3-yl)-3,4-dihydroquinazoline-7-carbonitrile hydrochloride (60.6 mg, 0.21 mmol) and DIEA (49.0 mg, 0.38 mmol) were added thereto at room temperature, and the mixture was stirred at room temperature for 1 hr. To the reaction mixture was added water, and the mixture was acidified with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 30→100% ethyl acetate/hexane), and The precipitate was collected by filtration with IPE/hexane to give the title compound (63.0 mg, 0.104 mmol, 54.7%) as white crystals.

¹H NMR (300 MHz, DMSO-d₆): δ 0.24-0.55 (4H, m), 1.06-1.27 (1H, m), 1.52 (3H, d, J=6.4 Hz), 1.58-1.76 (1H, m), 1.79-2.08 (2H, m), 2.10-2.31 (1H, m), 2.93 (1H, t, J=12.5 Hz), 3.34-3.45 (1H, m), 3.82 (2H, d, J=6.8 Hz), 4.03-4.34 (2H, m), 4.52-4.78 (1H, m), 4.92 (1H, brs), 6.30-7.03 (1H, m), 7.82 (1H, d, J=13.2 Hz), 7.93 (1H, dd, J=8.3, 1.5 Hz), 8.14 (1H, d, J=8.7 Hz), 8.22-8.37 (2H, m), 8.63 (2H, s).

Example 373

(2R)-N²-(3-chloro-4-cyanophenyl)-N⁴-(3-(cyclopropylmethyl)-1-(1,1-difluoropropan-2-yl)-7-fluoro-2,4-dioxo-1,2,3,4-tetrahydroquinazolin-6-yl)morpholine-2,4-dicarboxamide (one stereoisomer, quinazolinedione: derived from tR₂)

(Step 1)
Crude 6-amino-3-(cyclopropylmethyl)-1-(1,1-difluoropropan-2-yl)-7-fluoroquinazoline-2,4(1H, 3H)-dione (700 mg) was subjected to preparative chiral SFC to separate stereoisomer (optical isomer). A preparative fraction with a longer retention time was concentrated to give 6-amino-3-(cyclopropylmethyl)-1-(1,1-difluoropropan-2-yl)-7-fluoroquinazoline-2,4(1H, 3H)-dione (tR₂) (218 mg, 28%, optical purity 98.12%) as a pale-yellow solid.
Purification conditions by preparative chiral SFC
apparatus: Thar SFC PREP 80
column: Chiralcel OJ-H (250×21 mm), 5 μm
solvent: A=CO₂, B=MeOH (A: 70%, B: 30%)
flow rate: 30 g/min
temperature: 35° C.
Analysis conditions by chiral SFC
apparatus: Thar SFC Method Station
column: Chiralcel OJ-H (250×4.6 mm), 5 μm
solvent: A=CO₂, B=MeOH (A: 80%, B: 20%)
flow rate: 2.0 mL/min
temperature: 35° C.
MS(API): Calculated 327.3. Found 328.1 (M+H).
¹H NMR (400 MHz, DMSO-d₆): δ 0.33-0.34 (2H, m), 0.39-0.43 (2H, m), 1.15-1.19 (1H, m), 1.49 (3H, d, J=6.5 Hz), 3.80 (2H, d, J=7.1 Hz), 4.82 (1H, brs), 5.44 (2H, s), 6.64 (1H, dt, J=6.4, 58.2 Hz), 7.48 (1H, d, J=9.8 Hz), 7.64 (1H, d, J=13.6 Hz).
(Step 2)
4-Nitrophenyl carbonochloridate (35.4 mg, 0.18 mmol) was added to a mixture of 6-amino-3-(cyclopropylmethyl)-1-(1,1-difluoropropan-2-yl)-7-fluoroquinazoline-2,4(1H, 3H)-dione (tR₂) (50 mg, 0.15 mmol) and pyridine (0.014 mL, 0.18 mmol) in THF (1 mL) at room temperature, and the mixture was stirred at room temperature for 2 hr. The reaction mixture was concentrated under reduced pressure, DMF (3 mL) was added to the residue, (R)-N-(3-chloro-4-cyanophenyl)morpholine-2-carboxamide hydrochloride (50.8 mg, 0.17 mmol) and DIEA (19.74 mg, 0.15 mmol) were added thereto at room temperature, and the mixture was stirred at room temperature for 1 hr. To the reaction mixture was added water, and the mixture was acidified with 2N hydrochloric acid. The mixture was extracted with ethyl acetate. The organic layer was washed with water and brine, dried over magnesium sulfate, and the solvent was evaporated under reduced pressure. The residue was purified by silica gel column chromatography (solvent gradient; 30→100% ethyl acetate/hexane), and The precipitate was collected by filtration with IPE/hexane to give the title compound (55.0 mg, 0.089 mmol, 58.2%) as white crystals.

¹H NMR (300 MHz, DMSO-d₆): δ 0.25-0.54 (4H, m), 1.08-1.30 (2H, m), 1.53 (3H, d, J=6.4 Hz), 2.99-3.23 (2H, m), 3.66-3.73 (1H, m), 3.73-4.12 (4H, m), 4.12-4.36 (2H, m), 4.93 (1H, brs), 7.74-7.99 (3H, m), 8.11-8.21 (2H, m), 8.75 (1H, brs), 10.49 (1H, brs).

Example 374

(3R)-3-(7-cyano-4-oxoquinazoline-3(4H)-yl)-N-(3-(cyclopropylmethyl)-1-(1,1-difluoropropan-2-yl)-7-fluoro-2,4-dioxo-1,2,3,4-tetrahydroquinazolin-6-yl)piperidine-1-carboxamide (one stereoisomer, quinazolinedione: derived from tR₂)

4-Nitrophenyl carbonochloridate (41.1 mg, 0.20 mmol) was added to a mixture of 6-amino-3-(cyclopropylmethyl)-1-(1,1-difluoropropan-2-yl)-7-fluoroquinazoline-2,4(1H, 3H)-dione (tR₂) (58 mg, 0.18 mmol) and pyridine (0.016 mL, 0.20 mmol) in THF (5 mL) at room temperature, and the mixture was stirred at room temperature for 1 hr. The reaction mixture was concentrated under reduced pressure, DMF (5 mL) was added to the residue, (R)-4-oxo-3-(piperidin-3-yl)-3,4-dihydroquinazoline-7-carbonitrile hydrochloride (56.7 mg, 0.19 mmol) and DIEA (45.8 mg, 0.35 mmol) were added thereto at room temperature, and the mixture was stirred at room temperature for 1 hr. To the reaction mixture was added water, and the mixture was extracted with ethyl acetate. The organic layer was washed with water and brine, dried over magnesium sulfate, and the solvent was evaporated under reduced pressure. The residue was purified by silica gel column chromatography (solvent gradient; 70→100% ethyl acetate/hexane), and The precipitate was collected by filtration with IPE to give the title compound (40.0 mg, 0.066 mmol, 37.2%) as white crystals.
¹H NMR (300 MHz, DMSO-d₆): δ 0.23-0.55 (4H, m), 1.18 (1H, dd, J=8.7, 3.8 Hz), 1.53 (3H, d, J=6.8 Hz), 1.58-2.32 (4H, m), 2.63-3.06 (1H, m), 3.39 (1H, d, J=11.7 Hz), 3.83 (2H, d, J=6.8 Hz), 4.03-4.36 (2H, m), 4.68 (1H, t, J=11.3 Hz), 4.93 (1H, brs), 6.29-6.97 (1H, m), 7.81 (1H, d, J=13.2 Hz), 7.92 (1H, dd, J=8.1, 1.7 Hz), 8.14 (1H, d, J=8.7 Hz), 8.20-8.38 (2H, m), 8.63 (2H, s).

Example 375

3-(7-cyano-4-oxoquinazoline-3(4H)-yl)-N-(3-(cyclopropylmethyl)-7-fluoro-1-isopropyl-2,4-dioxo-1,2,3,4-tetrahydroquinazolin-6-yl)-4,4-difluoropiperidine-1-carboxamide (one stereoisomer, piperidine: derived from tR₁)

(Step 1)
m-Chloroperbenzoic acid (11.9 g, 229.19 mmol) was added to a solution of tert-butyl 3,6-dihydropyridine-1(2H)-carboxylate (30 g, 163.71 mmol) in dichloromethane (150 mL) at 0° C., and the mixture was stirred under a nitrogen gas atmosphere at room temperature for 16 hr. To the reaction mixture was added ice water (500 mL), and the mixture was extracted with ethyl acetate (2×500 mL). The organic layer was washed with an aqueous sodium hydrogen carbonate solution, brine, dried over sodium sulfate, and the solvent was evaporated under reduced pressure. The residue was purified by silica gel column chromatography (solvent gradient; 15→20% ethyl acetate/hexane) to give tert-butyl 7-oxa-3-azabicyclo[4.1.0]heptane-3-carboxylate (21 g, 64%) as a pale-yellow oil.

¹H NMR (400 MHz, CDCl₃): δ 1.43 (9H, s), 1.85-1.92 (1H, m), 2.02 (1H, m), 3.09 (1H, t, J=8.9 Hz), 3.19 (1H, br s), 3.27 (1H, s), 3.41 (1H, br s), 3.68 (1H, br s), 3.81-3.95 (1H, m).

(Step 2)

A mixture of sodium azide (16.24 g, 94.1 mmol) and acetone-water (2:1, v/v, 48 mL) was added to a solution of tert-butyl 7-oxa-3-azabicyclo[4.1.0]heptane-3-carboxylate (12.5 g, 62.73 mmol) in DMF (50 mL), and the mixture was stirred at 80° C. for 16 hr. The reaction mixture was cooled, and water (100 mL) and ethyl acetate (150 mL) were added thereto. The organic layer was separated, washed with water and brine, dried over sodium sulfate, and the solvent was evaporated under reduced pressure. The residue was purified by silica gel column chromatography (solvent gradient; 15→20% ethyl acetate/hexane) to give tert-butyl 3-azido-4-hydroxypiperidine-1-carboxylate (1.8 g, 12%) as a yellow oil.

¹H NMR (400 MHz, CDCl₃): δ 1.47-1.55 (10H, m), 1.93-1.97 (1H, m), 2.33 (1H, br s), 2.79-2.85 (2H, m), 3.24-3.30 (1H, m), 3.54 (1H, br s), 3.95-3.99 (1H, m), 4.21 (1H, br s).

(Step 3)

Dess-Martin periodinane (3.68 g, 8.67 mmol) was added to a solution of tert-butyl 3-azido-4-hydroxypiperidine-1-carboxylate (1.75 g, 7.22 mmol) in dichloromethane (15 mL), and the mixture was stirred at room temperature for 16 hr. To the reaction mixture was added dichloromethane (50 mL), and the solution was filtered through celite. The filtrate was washed with an aqueous sodium hydrogen carbonate solution and water, dried over sodium sulfate, and the solvent was evaporated under reduced pressure. The residue was purified by silica gel column chromatography (solvent gradient; 30→40%% ethyl acetate/hexane) to give tert-butyl 3-azido-4-oxopiperidine-1-carboxylate (1.52 g, 87%) as a white gummy substance.

¹H NMR (400 MHz, CDCl₃): δ 1.46-1.49 (9H, m), 2.51-2.55 (2H, m), 2.98 (1H, br s), 3.11-3.19 (1H, m), 3.97 (1H, br s), 4.26 (2H, br s).

(Step 4)

(Diethylamino)sulfur trifluoride (0.06 mL, 0.45 mmol) was added to a solution of tert-butyl 3-azido-4-oxopiperidine-1-carboxylate (50 mg, 0.21 mmol) in 1,2-dichloroethane (2 mL) under a nitrogen gas atmosphere at 0° C., and the mixture was stirred at room temperature for 16 hr. The reaction mixture was cooled to 0° C., saturated aqueous sodium hydrogen carbonate solution (10 mL) was added, and the mixture was extracted with ethyl acetate (2×50 mL). The organic layer was washed with water and brine, dried over sodium sulfate, and the solvent was evaporated under reduced pressure. The residue was purified by silica gel column chromatography (solvent gradient; 20→25% ethyl acetate/hexane) to give tert-butyl 3-azido-4,4-difluoropiperidine-1-carboxylate (30 mg, 55%) as a colorless oil.

¹H NMR (400 MHz, CDCl₃): δ 1.46 (9H, s), 1.89 (1H, br s), 2.13-2.16 (1H, m), 3.36 (1H, br s), 3.58-3.66 (4H, m).

(Step 5)

To a solution of tert-butyl 3-azido-4,4-difluoropiperidine-1-carboxylate (120 mg, 0.46 mmol) in MeOH (5.0 mL) was added 10% palladium-carbon (12 mg), and the mixture was stirred under a hydrogen atmosphere at 1 atm at room temperature for 16 hr. The catalyst was removed by filtration, and the filtrate was concentrated under reduced pressure to give crude tert-butyl 3-amino-4,4-difluoropiperidine-1-carboxylate (80 mg, 74%) as a colorless oil. The resultant product was used for the next step without further purification.

¹H NMR (400 MHz, CDCl₃): δ 1.40 (9H, s), 1.79-1.85 (3H, m), 2.08-2.13 (1H, m), 2.88-3.02 (2H, m), 3.14-3.20 (1H, t, J=10.0 Hz), 3.59-3.68 (2H, m).

(Step 6)

HATU (837 mg, 2.20 mmol), N-methylmorpholine (0.65 mL, 5.93 mmol) and 4-bromo-2-nitro-benzoic acid (625 mg, 2.54 mmol) was added to a solution of crude tert-butyl 3-amino-4,4-difluoropiperidine-1-carboxylate (400 mg, 1.69 mmol) in DMF (5 mL), and the mixture was stirred under a nitrogen gas atmosphere at room temperature for 16 hr. To the reaction mixture were added ethyl acetate (50 mL) and water (10 mL), and the organic layer was separated. The organic layer was washed with water, saturated aqueous sodium hydrogen carbonate solution and brine, dried over sodium sulfate, and the solvent was evaporated under reduced pressure. The residue was purified by silica gel column chromatography (solvent gradient; 30→35% ethyl acetate/hexane) to give tert-butyl 3-[(4-bromo-2-nitrobenzoyl)amino]-4,4-difluoropiperidine-1-carboxylate (510 mg, 65%) as a white solid.

¹H NMR (400 MHz, CDCl₃): δ 1.47 (9H, s), 1.99-2.17 (2H, m), 3.00 (1H, t, J=11.1 Hz), 3.11 (1H, t, J=12.2 Hz), 4.02 (1H, br s), 4.27-4.30 (1H, m), 4.46-4.48 (1H, m), 6.04 (1H, d, J=8.6 Hz), 7.42 (1H, d, J=8.08 Hz), 7.81 (1H, dd, J=1.6, 8.1 Hz), 8.24 (1H, s).

(Step 7)

Iron powder (337 mg, 6.03 mmol) and ammonium chloride (231 mg, 4.31 mmol) were added to a mixed solution of tert-butyl 3-[(4-bromo-2-nitrobenzoyl)amino]-4,4-difluoropiperidine-1-carboxylate (400 mg, 0.86 mmol) in THF-EtOH-water (4:2:1, v/v, 5 mL), and the mixture was stirred at 50° C. for 16 hr. After cooling, ethyl acetate (50 mL) was added to the mixture, and the solution was filtered through celite. The filtrate was washed with water and aqueous sodium hydrogen carbonate solution, dried over sodium sulfate, and the solvent was evaporated under reduced pressure. The residue was purified by silica gel column chromatography (solvent gradient; 25→30% ethyl acetate/hexane) to give tert-butyl 3-[(2-amino-4-bromobenzoyl)amino]-4,4-difluoropiperidine-1-carboxylate (300 mg, 80%) as a grayish white solid.

¹H NMR (400 MHz, CDCl₃): δ 1.46 (9H, s), 1.99-2.16 (2H, m), 3.03 (1H, t, J=11.6 Hz). 3.18 (1H, t, J=9.8 Hz), 3.96 (1H, br s), 4.10-4.14 (1H, m), 4.43 (1H, br s), 5.62 (2H, s), 6.13 (1H, d, J=7.5 Hz), 6.76 (1H, dd, J=1.4, 8.4 Hz), 6.85 (1H, d, J=1.4 Hz), 7.17 (1H, d, J=8.4 Hz).

(Step 8)

In a sealed tube reaction vessel, a mixture of tert-butyl 3-[(2-amino-4-bromobenzoyl)amino]-4,4-difluoropiperidine-1-carboxylate (490 mg, 1.13 mmol) in triethyl orthoformate (5 mL) was stirred at 120° C. for 72 hr. The reaction mixture was cooled, and concentrated under reduced pressure. The residue was purified by silica gel column chromatography (solvent gradient; 20→25% ethyl acetate/hexane) to give tert-butyl 3-(7-bromo-4-oxoquinazoline-3(4H)-yl)-4,4-difluoropiperidine-1-carboxylate (320 mg, 64%) as a white solid.

¹H NMR (400 MHz, CDCl₃): δ 1.47 (9H, s), 2.10-2.26 (2H, m), 3.09 (1H, br s), 3.35 (1H, br s), 4.31 (2H, br s), 5.36-5.45 (1H, m), 7.62 (1H, d, J=8.6 Hz), 7.89 (1H, s), 8.15-8.17 (2H, m).

(Step 9)

Zinc cyanide (54 mg, 0.46 mmol) was added to a solution of tert-butyl 3-(7-bromo-4-oxoquinazoline-3(4H)-yl)-4,4-difluoropiperidine-1-carboxylate (200 mg, 0.46 mmol) in DMF (2 mL), and the mixture was stirred under an argon gas atmosphere for 15 min. Then, Pd(PPh₃)₄ (53 mg, 0.046 mmol) was added, and the mixture was stirred under microwave irradiation at 140° C. for 30 min. The reaction mixture was cooled, and ethyl acetate (20 mL) was added thereto. The organic layer was washed with water and aqueous sodium hydrogen carbonate solution, dried over sodium sulfate, and the solvent was evaporated under reduced pressure. The residue was purified by silica gel column chromatography (solvent gradient; 25→30% ethyl acetate/hexane) to give tert-butyl 3-(7-cyano-4-oxoquinazoline-3(4H)-yl)-4,4-difluoropiperidine-1-carboxylate. This was subjected to preparative chiral SFC to separate stereoisomer (optical isomer). A preparative fraction with a shorter retention time was concentrated to give tert-butyl 3-(7-cyano-4-oxoquinazoline-3(4H)-yl)-4,4-difluoropiperidine-1-carboxylate ($tR_1$) (30 mg, 17%) as a white solid.
Purification conditions by preparative chiral SFC
apparatus: Thar SFC PREP 80
column: AD-H (250×21 mm), 5 μm
solvent: A=$CO_2$, B=MeOH (A: 52%, B: 48%)
flow rate: 25 g/min
temperature: 35° C.
$^1$H NMR (400 MHz, $CDCl_3$): δ 1.50 (9H, s), 2.19-2.31 (2H, m), 3.12 (1H, br s), 3.38 (1H, br s), 4.35 (2H, br s), 5.32-5.44 (1H, m), 7.75 (1H, d, J=7.0 Hz), 8.06 (1H, s), 8.24 (1H, s), 8.44 (1H, d, J=8.2 Hz).
(Step 10)
To a solution of tert-butyl 3-(7-cyano-4-oxoquinazoline-3(4H)-yl)-4,4-difluoropiperidine-1-carboxylate ($tR_1$) (22 mg, 0.06 mmol) in ethyl acetate (2 mL) was added 4N hydrogen chloride/ethyl acetate (2 mL, 8.00 mmol), and the mixture was stirred at room temperature overnight. The reaction mixture was concentrated under reduced pressure, and IPE was added to the residue. The precipitate was collected by filtration to give 3-(4,4-difluoropiperidin-3-yl)-4-oxo-3,4-dihydroquinazoline-7-carbonitrile hydrochloride (one stereoisomer, piperidine: derived from $tR_1$) (18.00 mg, 0.055 mmol, 98%) as a white solid.
MS(API): Calculated 326.1. Found 291.2 (M+H—HCl).
(Step 11)
4-Nitrophenyl carbonochloridate (13.75 mg, 0.07 mmol) was added to a mixture of 6-amino-3-(cyclopropylmethyl)-7-fluoro-1-isopropylquinazoline-2,4(1H, 3H)-dione hydrochloride (18.07 mg, 0.06 mmol) and pyridine (5.52 μL, 0.07 mmol) in THF (1 mL) at room temperature, and the mixture was stirred at room temperature for 2 hr. The reaction mixture was concentrated under reduced pressure, DMF (1 mL) was added to the residue, 3-(4,4-difluoropiperidin-3-yl)-4-oxo-3,4-dihydroquinazoline-7-carbonitrile hydrochloride (one stereoisomer, piperidine: derived from $tR_1$) (18 mg, 0.06 mmol) and DIEA (0.022 mL, 0.12 mmol) were added to the mixture at room temperature, and the mixture was stirred at room temperature for 1 hr. The reaction mixture was concentrated under reduced pressure, water was added to the reaction mixture, and the mixture was acidified with 2N hydrochloric acid and extracted with ethyl acetate. The organic layer was washed with water and brine, dried over magnesium sulfate, and the solvent was evaporated under reduced pressure. The residue was purified by silica gel column chromatography (solvent gradient; 30→60% ethyl acetate/hexane), and The precipitate was collected by filtration with IPE/hexane to give the title compound (9.70 mg, 0.016 mmol, 25.7%) as a white solid.
$^1$H NMR (300 MHz, DMSO-$d_6$): δ 0.26-0.52 (4H, m), 0.78-0.92 (1H, m), 1.50 (6H, d, J=6.8 Hz), 2.16-2.45 (2H, m), 3.17 (1H, t, J=10.6 Hz), 3.72-3.93 (3H, m), 4.22-4.50 (2H, m), 4.91 (1H, brs), 5.19-5.53 (1H, m), 7.61 (1H, d, J=13.2 Hz), 7.97 (1H, dd, J=7.9, 1.5 Hz), 8.16 (1H, d, J=9.1 Hz), 8.26-8.39 (2H, m), 8.52-8.62 (1H, m), 8.84 (1H, s).

Example 376

3-(7-cyano-4-oxoquinazoline-3(4H)-yl)-N-(3-(cyclopropylmethyl)-7-fluoro-1-isopropyl-2,4-dioxo-1,2,3,4-tetrahydroquinazolin-6-yl)-4,4-difluoropiperidine-1-carboxamide.trifluoroacetic acid mixture (one stereoisomer, piperidine: derived from $tR_2$)

(Step 1)
tert-Butyl 3-(7-cyano-4-oxoquinazoline-3(4H)-yl)-4,4-difluoropiperidine-1-carboxylate was subjected to preparative chiral SFC to separate stereoisomer (optical isomer). A preparative fraction with a longer retention time was concentrated to give tert-butyl 3-(7-cyano-4-oxoquinazoline-3(4H)-yl)-4,4-difluoropiperidine-1-carboxylate ($tR_2$) (27 mg, 15%) as a white solid.
Purification conditions by preparative chiral SFC
apparatus: Thar SFC PREP 80
column: AD-H (250×21 mm), 5 μm
solvent: A=$CO_2$, B=MeOH (A: 52%, B: 48%)
flow rate: 25 g/min
temperature: 35° C.
$^1$H NMR (300 MHz, $CDCl_3$): δ 1.47 (9H, s), 2.11-2.28 (2H, m), 3.10 (1H, br s), 3.36 (1H, br s), 4.34 (2H, br s), 5.29-5.44 (1H, m), 7.72 (1H, d, J=8.1 Hz), 8.04 (1H, s), 8.21 (1H, s), 8.41 (1H, d, J=8.2 Hz).
(Step 2)
To a solution of tert-butyl 3-(7-cyano-4-oxoquinazoline-3(4H)-yl)-4,4-difluoropiperidine-1-carboxylate ($tR_2$) (20 mg, 0.05 mmol) in ethyl acetate (2 mL) was added 4N hydrogen chloride/ethyl acetate (2 mL, 8.00 mmol), and the mixture was stirred at room temperature overnight. The reaction mixture was concentrated under reduced pressure, and IPE was added to the residue. The precipitate was collected by filtration to give 3-(4,4-difluoropiperidin-3-yl)-4-oxo-3,4-dihydroquinazoline-7-carbonitrile hydrochloride (one stereoisomer, piperidine: derived from $tR_2$) (10.40 mg, 0.032 mmol, 62.1%) as a white solid.
MS(API): Calculated 326.1. Found 291.2 (M+H—HCl).
(Step 3)
4-Nitrophenyl carbonochloridate (7.40 mg, 0.04 mmol) was added to a mixture of 6-amino-3-(cyclopropylmethyl)-7-fluoro-1-isopropylquinazoline-2,4(1H, 3H)-dione hydrochloride (10.70 mg, 0.04 mmol) and pyridine (2.97 μL, 0.04 mmol) in THF (2 mL) at 0° C., and the mixture was stirred at 0° C. for 2 hr. The reaction mixture was concentrated under reduced pressure, DMF (2 mL) was added to the residue, 3-(4,4-difluoropiperidin-3-yl)-4-oxo-3,4-dihydroquinazoline-7-carbonitrile hydrochloride (one stereoisomer, piperidine: derived from $tR_2$) (10 mg, 0.03 mmol) and DIEA (9.89 mg, 0.08 mmol) were added to the mixture at room temperature, and the mixture was stirred at room temperature for 2 hr. The reaction mixture was concentrated under reduced pressure, water was added to the reaction mixture, and the mixture was extracted with ethyl acetate. The organic layer was washed with water and brine, dried over magnesium sulfate, and the solvent was evaporated under reduced pressure. The residue was purified by silica gel column chromatography (solvent gradient; 30→100% ethyl acetate/hexane). The residue was purified by preparative HPLC (L-Column 2 ODS, mobile phase: water/acetonitrile (0.01% TFA-containing solvent)) to give the title compound (5.00 mg, 6.93 μmol, 22.64%).

$^1$H NMR (300 MHz, CD$_3$OD): δ 0.26-0.63 (4H, m), 1.09-1.41 (1H, m), 1.58 (6H, d, J=6.8 Hz), 2.20-2.52 (2H, m), 3.33-3.54 (1H, m), 3.68-4.03 (3H, m), 4.26-4.58 (2H, m), 4.86-4.99 (2H, m), 5.33-5.78 (1H, m), 7.43 (1H, d, J=13.2 Hz), 7.83 (1H, dd, J=8.3, 1.5 Hz), 8.08 (1H, d, J=1.1 Hz), 8.24 (1H, d, J=8.7 Hz), 8.39 (1H, d, J=8.3 Hz), 8.49 (1H, d, J=2.3 Hz).

The compounds described in Examples 371-376 are as described below (Tables 1-38).

TABLE 1-38

| Ex. No. | IUPAC name | Structure | salt | MS |
|---|---|---|---|---|
| 371 | (2R)-N$^2$-(3-chloro-4-cyanophenyl)-N$^4$-(3-(cyclopropylmethyl)-1-(1,1-difluoropropan-2-yl)-7-fluoro-2,4-dioxo-1,2,3,4-tetrahydro-quinazolin-6-yl)-morpholine-2,4-dicarboxamide (one stereoisomer, quinazolinedione: derived from tR$_1$) | 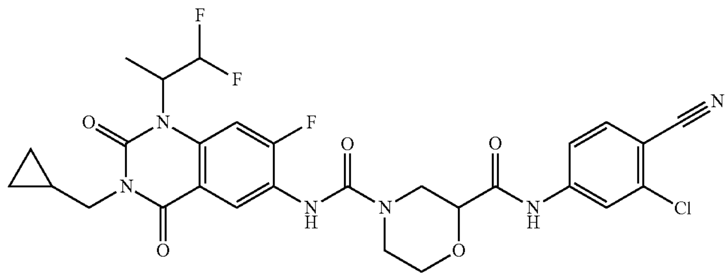 [SMILES: CC(C(F)F)n1c(=O)n(CC2CC2)c(=O)c2cc(NC(=O)N3CCOC(C(=O)Nc4ccc(C#N)c(Cl)c4)C3)c(F)cc21] | | 619.2 (M + H) |
| 372 | (3R)-3-(7-cyano-4-oxoquinazoline-3(4H)-yl)-N-(3-(cyclopropylmethyl)-1-(1,1-difluoropropan-2-yl)-7-fluoro-2,4-dioxo-1,2,3,4-tetrahydro-quinazolin-6-yl)piperidine-1-carboxamide (one stereoisomer, quinazolinedione: derived from tR$_1$) | 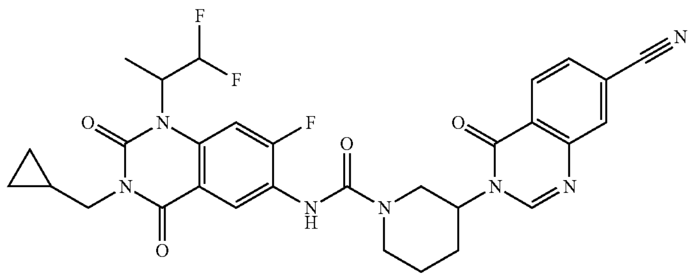 [SMILES: CC(C(F)F)n1c(=O)n(CC2CC2)c(=O)c2cc(NC(=O)N3CCCC(n4cnc5cc(C#N)ccc5c4=O)C3)c(F)cc21] | | 608.2 (M + H) |
| 373 | (2R)-N$^2$-(3-chloro-4-cyanophenyl)-N$^4$-(3-(cyclopropylmethyl)-1-(1,1-difluoropropan-2-yl)-7-fluoro-2,4-dioxo-1,2,3,4-tetrahydro-quinazolin-6-yl)morpholine-2,4-dicarboxamide (one stereoisomer, quinazolinedione: derived from tR$_2$) | 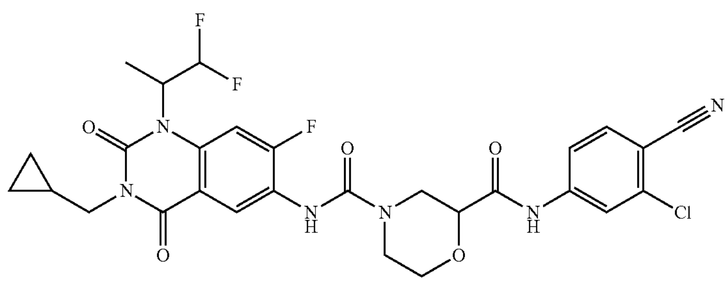 [SMILES: CC(C(F)F)n1c(=O)n(CC2CC2)c(=O)c2cc(NC(=O)N3CCOC(C(=O)Nc4ccc(C#N)c(Cl)c4)C3)c(F)cc21] | | 619.2 (M + H) |
| 374 | (3R)-3-(7-cyano-4-oxoquinazoline-3(4H)-yl)-N-(3-(cyclopropylmethyl)-1-(1,1-difluoropropan-2-yl)-7-fluoro-2,4-dioxo-1,2,3,4-tetrahydro-quinazolin-6-yl)piperidine-1-carboxamide (one stereoisomer, quinazolinedione: derived from tR$_2$) | 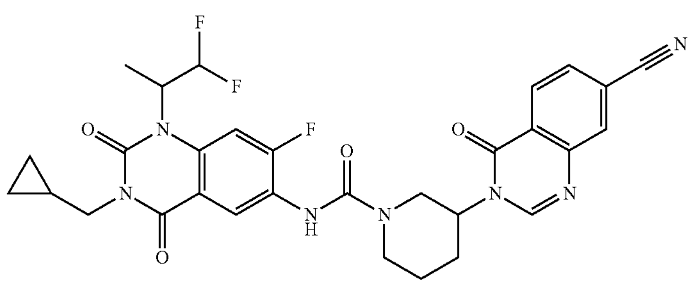 [SMILES: CC(C(F)F)n1c(=O)n(CC2CC2)c(=O)c2cc(NC(=O)N3CCCC(n4cnc5cc(C#N)ccc5c4=O)C3)c(F)cc21] | | 608.3 (M + H) |
| 375 | 3-(7-cyano-4-oxoquinazoline-3(4H)-yl)-N-(3-(cyclopropylmethyl)-7-fluoro-1-isopropyl-2,4-dioxo-1,2,3,4-tetrahydro-quinazolin-6-yl)-4,4-difluoropiperidine-1-carboxamide (one stereoisomer, piperidine: derived from tR$_1$) | 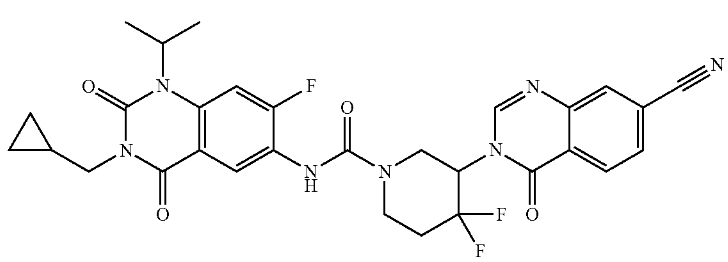 [SMILES: CC(C)n1c(=O)n(CC2CC2)c(=O)c2cc(NC(=O)N3CCC(F)(F)C(n4cnc5cc(C#N)ccc5c4=O)C3)c(F)cc21] | | 608.2 (M + H) |

TABLE 1-38-continued

| Ex. No. | IUPAC name | Structure | salt | MS |
|---|---|---|---|---|
| 376 | 3-(7-cyano-4-oxoquina-zoline-3(4H)-yl)-N-(3-(cyclopropylmethyl)-7-fluoro-1-isopropyl-2,4-dioxo-1,2,3,4-tetra-hydroquinazolin-6-yl)-4,4-difluoropiperidine-1-carboxamide•trifluoro-acetic acid mixture (one stereoisomer, piperidine: derived from tR$_2$) | 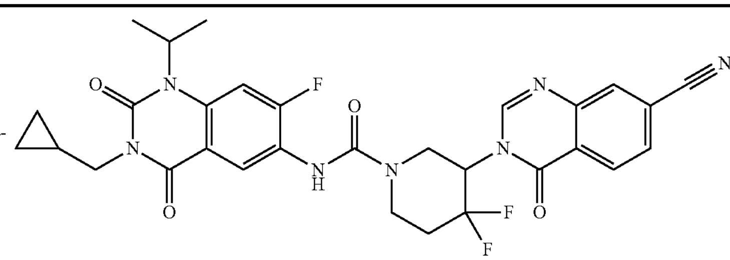 | CF$_3$CO$_2$H | 608.2 (M − CF$_3$CO$_2$H + H) |

Experimental Example 1

RORγt Binding Test Using Fluorescent-Labeled Synthetic Ligand

Fluorescent-labeled synthetic ligand was synthesized as follows.

(Step 1)

A solution of (4-(methoxymethyl)phenyl)boronic acid (999 mg, 6.02 mmol), glyoxylic acid monohydrate (554 mg, 6.02 mmol) and diallylamine (0.741 mL, 6.02 mmol) in acetonitrile (12 mL) was stirred at 60° C. for 5 hr. The reaction mixture was concentrated under reduced pressure. The obtained residue was purified by silica gel column chromatography (Diol, solvent; ethyl acetate), and crystallized from ethyl acetate to give 2-(diallylamino)-2-(4-(methoxymethyl)phenyl)acetic acid (200 mg, 0.726 mmol, 12.07%) as white crystals.

$^1$H NMR (300 MHz, DMSO-d$_6$): δ 3.04-3.46 (7H, m), 4.39 (2H, s), 4.43 (1H, s), 5.04-5.23 (4H, m), 5.78 (2H, ddt, J=16.9, 10.5, 6.3 Hz), 7.23-7.40 (4H, m).

(Step 2)

To a solution of 3,5-difluoro-4-(trimethylsilyl)aniline (5 g, 24.84 mmol), 2-(diallylamino)-2-(4-(methoxymethyl)phenyl)acetic acid (8.21 g, 29.81 mmol), DMAP (3.34 g, 27.32 mmol) and DIEA (21.69 mL, 124.20 mmol) in ethyl acetate (150 mL) was added T3P (29.2 mL, 49.68 mmol), and the mixture was stirred at 80° C. for 2 hr. To the reaction mixture were added water and ethyl acetate, and the organic layer was separated. The organic layer was washed with brine, dried over magnesium sulfate, and the solvent was evaporated under reduced pressure. The obtained residue was purified by silica gel column chromatography (solvent gradient; 0→10% ethyl acetate/hexane) to give 2-(diallylamino)-N-(3,5-difluoro-4-(trimethylsilyl)phenyl)-2-(4-(methoxymethyl)phenyl)acetamide (6.79 g, 14.81 mmol, 59.6%) as a pale-yellow oil.

(Step 3)

A solution of 2-(diallylamino)-N-(3,5-difluoro-4-(trimethylsilyl)phenyl)-2-(4-(methoxymethyl)phenyl)acetamide (6.79 g, 14.81 mmol), 1,3-dimethylbarbituric acid (4.85 g, 31.09 mmol) and Pd(PPh$_3$)$_4$ (0.684 g, 0.59 mmol) in THF (120 mL) was stirred under an argon gas atmosphere at room temperature overnight. The obtained residue was purified by silica gel column chromatography (NH, solvent gradient; 50→100% ethyl acetate/hexane) to give crude 2-amino-N-(3,5-difluoro-4-(trimethylsilyl)phenyl)-2-(4-(methoxymethyl)phenyl)acetamide (8.49 g) as a pale-yellow oil.

(Step 4)

To a solution of crude 2-amino-N-(3,5-difluoro-4-(trimethylsilyl)phenyl)-2-(4-(methoxymethyl)phenyl)acetamide (9.07 mg, 0.02 mmol) in DMF (0.5 mL) was added 1-((5-((2Z)-2-((1-(difluoroboryl)-3,5-dimethyl-1H-pyrrol-2-yl)methylene)-2H-pyrrol-5-yl)pentanoyl)oxy)pyrrolidine-2,5-dione (BODIPY (registered trade mark) FL-C5 succinimidyl ester) (5.0 mg, 0.01 mmol) at room temperature, and the mixture was stirred at room temperature for 3 hr. To the reaction mixture was added water, and the mixture was extracted with ethyl acetate. The organic layer was washed with brine, dried over magnesium sulfate, and the solvent was evaporated under reduced pressure. The obtained residue was purified by silica gel column chromatography (solvent; ethyl acetate/hexane), and further by preparative HPLC (C18, mobile phase: water/acetonitrile (0.1% TFA-containing solvent)) to give a fluorescent-labeled synthetic ligand, 5-((2Z)-2-((1-(difluoroboryl)-3,5-dimethyl-1H-pyrrol-2-yl)methylene)-2H-pyrrol-5-yl)-N-(2-((3,5-difluoro-4-(trimethylsilyl)phenyl)amino)-1-(4-(methoxymethyl)phenyl)-2-oxoethyl)pentanamide (3.8 mg, 5.58 μmol, 46.6%) as an orange solid.

$^1$H NMR (300 MHz, CDCl$_3$): δ 0.31 (9H, t, J=1.3 Hz), 1.71-1.87 (4H, m), 2.25 (3H, s), 2.32-2.42 (2H, m), 2.53 (3H, s), 2.91-3.03 (2H, m), 3.35 (3H, s), 4.40 (2H, s), 5.71 (1H, d, J=7.2 Hz), 6.09 (1H, s), 6.23 (1H, d, J=4.2 Hz), 6.80-6.90 (2H, m), 6.90-6.99 (2H, m), 7.06 (1H, s), 7.23-7.31 (2H, m), 7.33-7.42 (2H, m), 8.63 (1H, s).

MS(API): Calculated 680.6. Found 679.3 (M−H).

The binding activity of the test compound to RORγt was measured by a time resolved fluorescence resonance energy transfer (TR-FRET) utilizing histidine-tagged RORγt, fluorescent-labeled synthetic ligand, and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 μL. Then, RORγt diluted with an assay buffer to 240 nM was added by 3 μL, after which fluorescent-labeled synthetic ligand diluted with the assay buffer to 12 μM was added by 3 μL, and the mixture was stood at room temperature for 20 min. Thereafter, a terbium-labeled anti-histidine tag antibody diluted with the assay buffer to 8 nM was added by 3 μL. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled synthetic ligand to RORγt at test compound 1 μM) measured by the above-mentioned method are shown in Table 2.

Experimental Example 2

Cofactor Recruitment Test

Cofactor recruitment test was performed by Alpha Screen (Histidine Detection Kit, PerkinElmer) method. First, a test compound was diluted with an assay buffer (50 mM Tris-HCl (pH 7.5), 50 mM KCl, 1 mM DTT, 0.1% BSA) and added to a 384 well plate by 5 μL. Then, RORγt diluted with an assay buffer to 125 nM was added by 10 μL each, after which solutions of 25 nM biotinylated SRC-1 peptide (biotin-CLTARHKILHRLLQEGSPSD), 12.5 μg/mL acceptor beads and 12.5 μg/mL donor beads prepared with the assay buffer were added by 10 μL each. The mixture was stood in a dark place for 1 hr, and the signal value was measured by Envision (PerkinElmer).

The results (signal value inhibitory rate at test compound 1 μM) measured by the above-mentioned method are shown in Table 2.

Experimental Example 3

Jurkat Reporter Test

The Jurkat cells used for the reporter test were cultured in a culture medium (RPMI (Invitrogen), 10% FCS (AusGeneX), 100 U/mL penicillin, 100 μg/mL streptomycin). On the day of the test, $4\times10^7$ cells were recovered by a centrifugal operation (1000 rpm, for 5 min) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector 53 μg wherein a human IL-17 ROR response element was inserted into the upstream of luciferase of pGL 4.28 (Promega), and a vector (27 μg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 μg/mL streptomycin, 5 μM lovastatin), and plated in a 96 well plate by 90 μL. A test compound diluted with the reaction medium was added by 10 μL, and the cells were cultured overnight in an incubator. Bright-Glo (Promega) was added by 100 μL, and the mixture was stirred at room temperature for 10 min, and the luminescence level was measured by Envision (PerkinElmer).

The results (luminescence level inhibitory rate at test compound 3 μM) measured by the above-mentioned method are shown in Table 2.

TABLE 2

| Ex. No. | Experimental Example 1 binding inhibitory rate (%) of fluorescent-labeled synthetic ligand to RORγt at test compound 1 μM | Experimental Example 2 signal value inhibitory rate (%) at test compound 1 μM | Experimental Example 3 luminescence level inhibitory rate (%) at test compound 3 μM |
|---|---|---|---|
| 71 | 101% | 102% | 103% |
| 79 | 102% | 102% | 102% |
| 82 | 101% | 103% | 102% |
| 88 | 102% | 102% | 102% |
| 92 | 102% | 103% | 103% |
| 95 | 102% | 102% | 103% |
| 102 | 101% | 102% | 104% |
| 103 | 101% | 102% | 103% |
| 113 | 102% | 109% | 102% |
| 122 | 101% | 112% | 103% |
| 132 | 102% | 112% | 100% |
| 135 | 102% | 113% | 99% |
| 146 | 102% | 103% | 101% |
| 157 | 102% | 109% | 102% |
| 168 | 102% | 108% | 102% |
| 171 | 101% | 107% | 103% |
| 172 | 102% | 111% | 105% |
| 176 | 101% | 111% | 100% |
| 180 | 102% | 111% | 101% |
| 218 | 102% | 111% | 103% |
| 219 | 102% | 110% | 101% |
| 223 | 102% | 111% | 102% |
| 235 | 102% | 109% | 103% |
| 242 | 102% | 105% | 103% |
| 244 | 102% | 105% | 104% |
| 247 | 102% | 107% | 103% |
| 248 | 102% | 104% | 104% |
| 249 | 102% | 110% | 103% |
| 251 | 102% | 105% | 102% |
| 259 | 102% | 102% | 102% |
| 264 | 102% | 110% | 102% |
| 266 | 102% | 108% | 103% |
| 274 | 102% | 89% | 101% |
| 282 | 102% | 108% | 102% |
| 283 | 102% | 108% | 101% |
| 284 | 102% | 112% | 102% |
| 287 | 102% | 111% | 100% |
| 291 | 102% | 107% | 101% |
| 292 | 102% | 112% | 101% |
| 296 | 102% | 108% | 102% |
| 303 | 102% | 107% | 102% |
| 315 | 102% | 94% | 108% |
| 319 | 101% | 95% | 103% |
| 321 | 101% | 105% | 101% |
| 323 | 102% | 108% | 103% |
| 324 | 102% | 106% | 103% |
| 331 | 102% | 109% | 103% |
| 333 | 101% | 107% | 106% |
| 335 | 101% | 108% | 106% |
| 336 | 102% | 106% | 106% |
| 340 | 98% | 92% | 107% |
| 343 | 101% | 107% | 108% |
| 347 | 102% | 107% | 107% |
| 348 | 102% | 107% | 107% |
| 350 | 102% | 108% | 107% |
| 351 | 101% | 108% | 106% |
| 356 | 102% | 108% | 107% |
| 357 | 101% | 107% | 106% |
| 358 | 101% | 107% | 106% |
| 360 | 101% | 105% | 107% |
| 363 | 102% | 106% | 107% |
| 366 | 102% | 105% | 108% |
| 367 | 102% | 105% | 110% |
| 368 | 102% | 105% | 108% |
| 369 | 102% | 105% | 110% |
| 371 | 95% | NT | NT |
| 372 | 101% | NT | NT |
| 373 | 97% | NT | NT |
| 374 | 102% | NT | NT |
| 375 | 95% | NT | NT |

(NT: not tested)

Formulation Example 1 (Production of Capsule)

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2 (Production of Tablet)

| | |
|---|---|
| 1) compound of Example 1 | 30 g |
| 2) lactose | 50 g |
| 3) cornstarch | 15 g |
| 4) carboxymethylcellulose calcium | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Formulation Example 3 (Production of Ointment)

| | |
|---|---|
| 1) compound of Example 1 | 0.5 g |
| 2) liquid paraffin | 1 g |
| 3) white petrolatum | 98.5 g |
| Total | 100 g |

1), 2) are mixed well in a mortar, 3) is gradually added with kneading to the total amount of 100 g. The obtained product is distribution filled in a tube to give an ointment.

INDUSTRIAL APPLICABILITY

The compound of the present invention has an RORγt inhibitory action, and is useful as a prophylactic or therapeutic agent for psoriasis, inflammatory bowel disease, ulcerative colitis, Crohn's disease, rheumatoid arthritis, multiple sclerosis, uveitis, asthma, ankylopoietic spondylarthritis, systemic lupus erythematosus, chronic obstructive pulmonary disease or the like.

This application is based on a patent application No. 2014-184778 filed in Japan (filing date: Sep. 11, 2014), the contents of which are incorporated in full herein.

The invention claimed is:

1. A compound represented by the following formula (I):

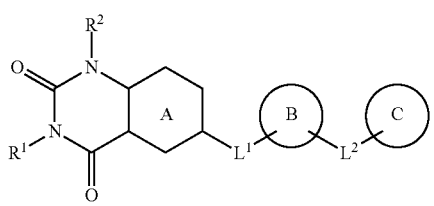

(I)

wherein $R^1$ and $R^2$ are each independently (1) a methyl group substituted by one substituent selected from (a) an optionally substituted $C_{3-6}$ cycloalkyl group and (b) an optionally substituted 5- or 6-membered non-aromatic heterocyclic group, (2) an optionally substituted $C_{2-6}$ alkyl group, or (3) an optionally substituted $C_{2-6}$ alkenyl group;

ring A is an optionally further substituted 6-membered aromatic ring;

$L^1$ is a bond, or a spacer having a main chain having 1-2 atoms;

ring B is a non-aromatic ring optionally further substituted by 1 to 3 substituents selected from the group consisting of: (a) an acyl group, (b) an optionally substituted $C_{1-6}$ alkyl group, (c) an optionally substituted $C_{1-6}$ alkoxy group, (d) a hydroxy group, (e) a halogen atom, and (f) an oxo group;

$L^2$ is a bond, or a spacer having a main chain having 1-4 atoms; and ring C is a optionally further substituted ring, or a salt thereof.

2. The compound according to claim 1, wherein $R^2$ is an optionally substituted $C_{3-6}$ alkyl group or an optionally substituted $C_{3-6}$ alkenyl group, each of which is branched at a carbon atom bonded to a nitrogen atom, or a salt thereof.

3. The compound according to claim 1, wherein $R^1$ is (1) a methyl group substituted by one substituent selected from the group consisting of (a) a $C_{3-6}$ cycloalkyl group optionally substituted by 1 to 3 halogen atoms and (b) a 5- or 6-membered non-aromatic heterocyclic group, or (2) a $C_{2-6}$ alkyl group optionally substituted by 1 to 3 substituents selected from the group consisting of a halogen atom, a $C_{1-6}$ alkoxy group, and a $C_{1-6}$ alkoxy-carbonyl group;

$R^2$ is (1) a methyl group substituted by a $C_{3-6}$ cycloalkyl group, (2) a $C_{2-6}$ alkyl group optionally substituted by 1 to 3 halogen atoms, or (3) a $C_{2-6}$ alkenyl group;

ring A is (1) a benzene ring optionally further substituted by 1 to 3 halogen atoms, or (2) 6-membered aromatic heterocycle;

$L^1$ is a bond, —C(=O)—, —O—C(=O)—, —CH$_2$—C(=O)—, —C(=O)—NH—, or —NH—C(=O)—;

ring B is $C_{3-10}$ cycloalkane or non-aromatic heterocycle, each of which is optionally further substituted by 1 to 3 substituents selected from the group consisting of (a) an acyl group selected from the group consisting of (i) a carboxy group, (ii) a $C_{1-6}$ alkyl-carbonyl group optionally substituted by a carboxy group, (iii) a $C_{1-6}$ alkoxy-carbonyl group optionally substituted by a carboxy group or a $C_{7-16}$ aralkyloxy-carbonyl group, (iv) a $C_{7-16}$ aralkyloxy-carbonyl group, (v) a carbamoyl group, and (vi) a $C_{1-6}$ alkyl-sulfonyl group, (b) a $C_{1-6}$ alkyl group optionally substituted by a hydroxy group, (c) a hydroxy group, and (d) an oxo group;

$L^2$ is a bond, —O—, —C(=O)—, —CH$_2$—O—, —C(=O)—CH$_2$—, —C(=O)—NH— optionally substituted by a $C_{1-6}$ alkyl group optionally substituted by 1 to 3 halogen atoms, —NH—C(=O)— optionally substituted by a $C_{1-6}$ alkyl group optionally substituted by 1 to 3 halogen atoms, —NH—S(=O)$_2$—, —CH$_2$—C(=O)—NH—, —CH$_2$—NH—C(=O)—, —O—C(=O)—NH—, —NH—C(=O)—NH—, —NH—C(=O)—CH$_2$— optionally substituted by a hydroxy group, —CH$_2$—NH—CH$_2$— optionally substituted by a $C_{1-6}$ alkyl group optionally substituted by 1 to 3 halogen atoms, —NH—C(=O)—CH$_2$—CH$_2$— or —CH$_2$—NH—C(=O)—NH—; and ring C is a $C_{6-14}$ aromatic hydrocarbon ring, a 5- or 6-membered monocyclic aromatic heterocycle, a 8- to 14-membered fused polycyclic aromatic heterocycle, a 3- to 8-membered monocyclic non-aromatic heterocycle or a 9- to 14-membered fused polycyclic non-aromatic heterocycle, each of which is optionally further substituted by 1 to 3 substituents selected from the group consisting of (1) a cyano group, (2) a hydroxy group, (3) an oxo group, (4) a halogen atom, (5) a $C_{1-6}$ alkyl group optionally substituted by 1 to 3 substituents selected from the group consisting of a cyano group, a hydroxy group, a halogen atom, a $C_{1-6}$ alkoxy group, an amino group, a $C_{1-6}$ alkoxy-carbonylamino group, a $C_{1-6}$ alkyl-carbonylamino group optionally substituted by a halogen atom, a $C_{2-6}$ alkenyl-carbonylamino group, and a $C_{1-6}$ alkyl-aminocarbonyloxy group, (6) a $C_{2-6}$ alkenyl group optionally substituted by a $C_{1-6}$ alkyl-carbonyl group, (7) a $C_{3-6}$ cycloalkyl group, (8) a $C_{6-14}$ aryl group, (9) a $C_{1-6}$ alkoxy group optionally substituted by 1 to 3 substituents selected from the group consisting of a halogen atom and a $C_{1-6}$ alkoxy group, (10) a $C_{1-6}$ alkyl-carbonyl group, (11) a carboxy group, (12) a $C_{2-6}$ alkenyl-carbonyl group, (13) a $C_{1-6}$ alkoxy-carbonyl group, (14) a carbamoyl group, (15) an amino group, (16) a $C_{1-6}$ alkyl-carbonylamino group optionally substituted by a halogen atom, (17) a $C_{1-6}$ alkoxy-carbonylamino group, (18) a $C_{1-6}$ alkyl-sulfonyl group, (19) a $C_{2-6}$ alkenyl-carbonylamino group optionally substituted by a mono- or di-$C_{1-6}$ alkylamino group, (20) a $C_{2-6}$ alkenyl-sulfonylamino group, and (21) a 3- to 8-membered monocyclic non-aromatic heterocycle; or a salt thereof.

4. The compound according to claim 1, wherein
$R^1$ is a methyl group substituted by one substituent selected from the group consisting of (a) a $C_{3-6}$ cycloalkyl group optionally substituted by 1 to 3 halogen atoms and (b) a 5- or 6-membered non-aromatic heterocyclic group;
$R^2$ is a $C_{2-6}$ alkyl group;
ring A is a benzene ring optionally further substituted by 1 to 3 halogen atoms;
$L^1$ is —NH—C(=O)—;
ring B is a $C_{3-10}$ cycloalkane or a 3- to 8-membered monocyclic non-aromatic heterocycle;
$L^2$ is a bond, —C(=O)—NH—, —NH—C(=O)— or —NH—C(=O)—NH—; and
ring C is a $C_{6-14}$ aromatic hydrocarbon ring, a 5- or 6-membered monocyclic aromatic heterocycle, a 8- to 14-membered fused polycyclic aromatic heterocycle or a 9- to 14-membered fused polycyclic non-aromatic heterocycle, each of which is optionally further substituted by 1 to 3 substituents selected from the group consisting of (1) a cyano group, (2) an oxo group, (3) a halogen atom, (4) a $C_{1-6}$ alkyl group optionally substituted by 1 to 3 substituents selected from the group consisting of a $C_{1-6}$ alkoxy-carbonylamino group and a $C_{1-6}$ alkyl-aminocarbonyloxy group, (5) a $C_{1-6}$ alkoxy group, and (6) a $C_{1-6}$ alkoxy-carbonyl group; or a salt thereof.

5. (2R)-$N^2$-(3-chloro-4-cyanophenyl)-$N^4$-(3-(cyclopropylmethyl)-7-fluoro-1-isopropyl-2,4-dioxo-1,2,3,4-tetrahydroquinazolin-6-yl)morpholine-2,4-dicarboxamide or a salt thereof.

6. (3R)-3-(7-cyano-4-oxoquinazolin-3(4H)-yl)-N-(3(cyclopropylmethyl)-7-fluoro-1-isopropyl-2,4-dioxo-1,2,3,4-tetrahydroquinazolin-6-yl)piperidine-1-carboxamide or a salt thereof.

7. 4-Cyano-N-((1S,2R)-2-((3-(cyclopropylmethyl)-1-isopropyl-2,4-dioxo-1,2,3,4-tetrahydroquinazolin-6-yl)carbamoyl)cyclopentyl)benzamide or a salt thereof.

8. (3R)-3-(benzoylamino)-N-(3-(cyclopropylmethyl)-1-isopropyl-2,4-dioxo-1,2,3,4-tetrahydroquinazolin-6-yl)piperidine-1-carboxamide or a salt thereof.

9. (3R)-N-(3-(cyclopropylmethyl)-7-fluoro-1-isopropyl-2,4-dioxo-1,2,3,4-tetrahydroquinazolin-6-yl)-3-((2,5-difluorobenzoyl)amino)piperidine-1-carboxamide or a salt thereof.

10. (3R)-N-(3-((3,3-difluorocyclobutyl)methyl)-7-fluoro-1-isopropyl-2,4-dioxo-1,2,3,4-tetrahydroquinazolin-6-yl)-3-(1-oxo-1,3-dihydro-2H-isoindol-2-yl)piperidine-1-carboxamide or a salt thereof.

11. A medicament comprising the compound according to claim 1 or a salt thereof.

12. A method of inhibiting RORγt, comprising administering an effective amount of the compound according to claim 1 or a salt thereof to a mammal.

13. A method for the treatment of psoriasis, inflammatory bowel disease, ulcerative colitis, Crohn's disease, rheumatoid arthritis, multiple sclerosis, uveitis, asthma, ankylopoietic spondylarthritis, systemic lupus erythematosus or chronic obstructive pulmonary disease, comprising administering an effective amount of the compound according to claim 1 or a salt thereof to a mammal.

* * * * *

UNITED STATES PATENT AND TRADEMARK OFFICE
CERTIFICATE OF CORRECTION

PATENT NO.       : 10,000,488 B2
APPLICATION NO.  : 15/510225
DATED            : June 19, 2018
INVENTOR(S)      : Satoshi Yamamoto et al.

It is certified that error appears in the above-identified patent and that said Letters Patent is hereby corrected as shown below:

In the Claims

In Column 290, Line 4, of issued Claim 1, "$_{3-6}$" should read --$C_{3-6}$--.

Signed and Sealed this
Eighth Day of January, 2019

Andrei Iancu
*Director of the United States Patent and Trademark Office*